US010577248B2

(12) United States Patent
Harper, Jr.

(10) Patent No.: US 10,577,248 B2
(45) Date of Patent: Mar. 3, 2020

(54) METHODS AND SYSTEMS FOR LARGE SCALE CARBON DIOXIDE UTILIZATION FROM LAKE KIVU VIA A $CO_2$ INDUSTRIAL UTILIZATION HUB INTEGRATED WITH ELECTRIC POWER PRODUCTION AND OPTIONAL CRYO-ENERGY STORAGE

(71) Applicant: Harper Biotech LLC, Villanova, PA (US)

(72) Inventor: Charles L. Harper, Jr., Villanova, PA (US)

(73) Assignee: HARPER BIOTECH LLC, Villanova, PA (US)

( * ) Notice: Subject to any disclaimer, the term of this patent is extended or adjusted under 35 U.S.C. 154(b) by 0 days.

(21) Appl. No.: 15/603,670

(22) Filed: May 24, 2017

(65) Prior Publication Data
US 2017/0341942 A1    Nov. 30, 2017

Related U.S. Application Data

(60) Provisional application No. 62/340,818, filed on May 24, 2016.

(51) Int. Cl.
| | | |
|---|---|---|
| *C01B 31/20* | (2006.01) | |
| *C01B 32/50* | (2017.01) | |
| *C02F 9/00* | (2006.01) | |
| *C12M 1/00* | (2006.01) | |
| *C05D 7/00* | (2006.01) | |
| *F01K 7/16* | (2006.01) | |
| *F01K 25/10* | (2006.01) | |
| *F25J 3/02* | (2006.01) | |
| *C12M 1/107* | (2006.01) | |
| *F25J 3/04* | (2006.01) | |
| *C02F 1/20* | (2006.01) | |
| *C02F 3/32* | (2006.01) | |
| *C02F 1/66* | (2006.01) | |

(Continued)

(52) U.S. Cl.
CPC ............. *C01B 32/50* (2017.08); *C02F 9/00* (2013.01); *C05D 7/00* (2013.01); *C12M 21/04* (2013.01); *C12M 43/06* (2013.01); *C12M 43/08* (2013.01); *F01K 7/16* (2013.01); *F01K 25/103* (2013.01); *F25J 3/0209* (2013.01); *F25J 3/0233* (2013.01); *F25J 3/0266* (2013.01); *F25J 3/04533* (2013.01); *F25J 3/04563* (2013.01); *C02F 1/008* (2013.01); *C02F 1/20* (2013.01); *C02F 1/66* (2013.01); *C02F 3/322* (2013.01); *C02F 2101/10* (2013.01); *C02F 2101/32* (2013.01); *C02F 2103/007* (2013.01); *C02F 2301/046* (2013.01); *C02F 2303/10* (2013.01); *F25J 2205/20* (2013.01); *F25J 2210/66* (2013.01); *F25J 2215/04* (2013.01); *F25J 2260/30* (2013.01); *F25J 2260/44* (2013.01); *F25J 2260/80* (2013.01); *Y02C 10/12* (2013.01); *Y02E 50/343* (2013.01); *Y02P 20/152* (2015.11); *Y02W 10/30* (2015.05); *Y02W 10/33* (2015.05); *Y02W 10/37* (2015.05)

(58) Field of Classification Search
CPC ....................................................... C01B 32/50
See application file for complete search history.

(56) References Cited

U.S. PATENT DOCUMENTS

| | | |
|---|---|---|
| 1,896,689 A | 2/1933 | Spencer |
| 2,138,758 A | 11/1938 | Eastman |

(Continued)

FOREIGN PATENT DOCUMENTS

| | | |
|---|---|---|
| BE | 531780 A1 | 9/1954 |
| DE | 42487 C | 5/1887 |

OTHER PUBLICATIONS

Ausubel, J., (2004). Big green energy machines. Industrial Physicist, Oct./Nov., 2004., p. 20-24. Online: https://phe.rockefeller.edu/docs/BigGreen.pdf.
Bocin-Dimitru, A., et al., (2013). European Union JRC Scientific and Policy Reports. Carbon Capture and Utilization Workshop. p. 1-77. Online: http://publications.jrc.ec.europa.eu/repository/bitstream/JRC86324/co2%20re-use%20workshop%20report_isbn_online_eur_pages.pdf.
Chaves, R. B., (1996). Geothermal gases as a source of commercial CO2 in Miravalles, Costa Rica and Haedarendi, Iceland. United Nations University Geothermal Training Programme, Reports 1996, No. 3, p. 23-44.

(Continued)

*Primary Examiner* — Stuart L Hendrickson
(74) *Attorney, Agent, or Firm* — Caesar Rivise, PC

(57) ABSTRACT

Lake Kivu contains ~50 million tonnes (MT) dissolved biomethane. Efficient use is problematic from massive associated $CO_2$: ~600 MT. Conventional extraction scrubs $CO_2$ with ~50% overall $CH_4$ loss, and returns ~80% $CO_2$ into the deep lake, preserving a catastrophe hazard threatening >2 M people. Methods and systems are disclosed coupling: (1) efficient $CH_4+CO_2$ degassing; (2) optional oxyfuel power generation and $CO_2$ power cycle technologies; and (3) $CO_2$ capture, processing, storage and use in a utilization hub. The invention optimally allows power production with >2× improved efficiency plus cryo-energy storage and large-scale greentech industrialization. $CO_2$-utilizing products can include: Mg-cements/building materials, algal products/biofuels, urea, bioplastics and recycled materials, plus $CO_2$ for greenhouse agriculture, $CO_2$-EOR/CCS, off-grid cooling, fumigants, solvents, carbonation, packaging, ores-, biomass-, and agro-processing, cold pasteurization, frack and geothermal fluids, and inputs to produce methanol, DME, CO, syngas, formic acid, bicarbonate and other greentech chemicals, fuels, fertilizers and carbon products.

26 Claims, 9 Drawing Sheets

(51) Int. Cl.
*C02F 101/10* (2006.01)
*C02F 101/32* (2006.01)
*C02F 103/00* (2006.01)
*C02F 1/00* (2006.01)

(56) References Cited

U.S. PATENT DOCUMENTS

| | | | |
|---|---|---|---|
| 4,441,555 | A | 4/1984 | Shu |
| 5,112,610 | A | 5/1992 | Kienle |
| 5,518,540 | A | 5/1996 | Jones, Jr. |
| 6,477,841 | B1 | 11/2002 | Yantovsky |
| 7,041,327 | B2 | 5/2006 | Hotchkiss et al. |
| 7,255,794 | B2 * | 8/2007 | Max .......................... A23L 2/08 210/711 |
| 7,347,896 | B2 | 3/2008 | Harrison |
| 7,906,559 | B2 | 3/2011 | Olah et al. |
| 8,563,067 | B2 | 10/2013 | Hagemeyer et al. |
| 8,596,075 | B2 | 12/2013 | Allam et al. |
| 8,715,401 | B2 | 5/2014 | Baxter |
| 8,764,885 | B2 | 7/2014 | Baxter et al. |
| 8,906,219 | B2 | 12/2014 | Lubomirsky et al. |
| 8,963,347 | B2 | 2/2015 | Baxter |
| 8,991,510 | B2 | 3/2015 | Saar et al. |
| 9,028,789 | B2 | 5/2015 | Brito Da Silva Correia |
| 9,133,084 | B2 | 9/2015 | Urakawa et al. |
| 9,410,736 | B2 | 8/2016 | Baxter |
| 9,718,702 | B2 | 8/2017 | Harper, Jr. |
| 9,732,671 | B2 | 8/2017 | Harper, Jr. |
| 2011/0100002 | A1 | 5/2011 | Muir et al. |
| 2011/0226010 | A1 | 9/2011 | Baxter |
| 2012/0115965 | A1 | 5/2012 | Olah et al. |
| 2013/0139543 | A1 | 6/2013 | Baxter |

OTHER PUBLICATIONS

Cockerill, R., (2015). Linde Gaz Turkey brings CO2 plant on-stream. GasWorld Magazine, Nov. 20, 2015, p. 1-2. Online: https://www.gasworld.com/linde-gaz-turkey-brings-co2-plant-on-stream/2009603.article.

Designimations (2012). CES OFT900. Transcript and screenshots from Youtube video available online at https://www.youtube.com/watch?v=-53170uf7nM.

Gao, C., et al., (2013). Heavy oil production by carbon dioxide injection. Greenhouse Gases Science and Technology, 1-11.

General Electric (2014). GE Power & Water: Distributed Power. Growing your greenhouse business faster with gas engines. p. 1-9. Online brochure: https://www.gepower.com/content/dam/gepower-pgdp/global/en_US/distributed-power-downloads/documents/asgreenhouseonlinejan2014.pdf.

Glennon, J. A., et al. (2004). The operation and geography of carbon-dioxide-driven, cold-water "geysers." GOSA Transactions, vol. IX: 184-192. Online: https://pdfs.semanticscholar.org/57b3/1748382bfb9176d580fb69c5a0ft7ed8b6e0.pdf.

Indala, S., (2004). Development and integration of new processes consuming carbon dioxide in multi-plant chemical production complexes. LSU Master's Thesis, 3907. Online: https://digitalcommons.lsu.edu/cgi/viewcontent.cgi?referer=https://www.google.com/&httpsredir=1&article=4906&context=gradschool_theses.

Kapteijn, P., et al., (2012). A breakthrough oxy-fuel technology for cost-effective enhanced oil recovery. SPE International, SPE 162541 (Conference presentation report). p. 1-9.

Li, F.-F., et al. (2015). A one-pot synthesis of hydrogen and carbon fuels from water and carbon dioxide. Adv. Energy Mats., 5: 1401791, p. 1-7.

Licht, S., et al., (2016). Carbon nanotubes produced from ambient carbon dioxide for environmentally sustainable lithium-ion and sodium-ion battery anodes. ACS Central Science, 2(3): 162-168.

Making Lewes (2014). Eco-Industrial Parks & Industrial Ecology. Eco-Industrial Parks. Retrieved online from https://makinglewes.org/tag/eco-industrial-parks/.

Meylan, F. D., et al., (2015). CO2 utilization in the perspective of industrial ecology: An overview. J. CO2 Utilization. p. 1-8. Online: https://www.researchgate.net/publication/279070295_CO2_utilization_in_the_perspective_of_industrial_ecology_an_overview.

Mikkelsen, M., et al. (2010). The teraton challenge. A review of fixation and transformation of carbon dioxide. Energy Environ. Sci., 3: 43-81.

Norstebo, S., et al., (2012). Use of natural gas with high CO2 content in an integrated industrial park. ISIJ Int'l, 52(8): 1439-1446, Online: https://www.jstage.jst.go.jp/article/isijinternational/52/8/52_1439/_pdf.

Nuhoff-Isakhanyan, G., et al., (2015). Section 7.1 "Biopark Terneuzen" and Section 7.2 ""Agropark A7" in Synergy parks: collaborative strategies to valorize side streams between companies." Case study report. ARBOR. p. 31-35. Online: https://www.researchgate.net/publication/286921762_Synergy_Parks_collaborative_strategies_to_valorise_side_streams_between_companies.

Osterdijk, H., et al. (2012). Lake Kivu: Turning a threat into prosperity. TCE, The Chemical Engineer, issue 852, Jun. 2012, pp. 32-35. Online: http://www.infrassure.com/images/uploads/user/TCE852kivuenergy.pdf.

Rotterdam Climate Initiative (2011). CO2 Capture and Storage in Rotterdam: A Network Approach. p. 1-32. Online: http://www.rotterdamclimateinitiative.nl/documents/2015-en-ouder/CCS_brochure_compleet%20def.versie%20dd%2009-09-2010.pdf.

Suzuki, T., et al., (2013). Conceptual design of CO2 transportation system for CCS. Energy Procedia, 37: 2989-2996. Online: https://ac.els-cdn.com/S1876610213004281/1-s2.0-S1876610213004281-main.pdf?_tid=spdf-68dad9fb-d088-4ffd-9517-634e6fb4ff3d&acdnat=1519407329_857e6403530be6b11a49ac6de67856ea.

Tietze, K. (2007). Basic plan for monitoring, regulating and steering exploitation of the unique methane gas deposit in Lake Kivu: Safely, environmentally soundly and with optimal yield. Copyright, PDT GmbH / Dr Klaus Tietze, Celle, Germany. p. 1-201.

Wallace et al. (2015). A review of the CO2 pipeline infrastructure in the U.S. DOE/NETL Report: DOE/NETL-2014/1681. p. i-44. Online: https://energy.gov/sites/prod/files/2015/04/f22/QER%20Analysis%20-%20A%20Review%20of%20the%20CO2%20Pipeline%20Infrastructure%20in%20the%20U.S_0.pdf.

Wallace, M. et al. (2014). Near-Term Projections of CO2 Utilization for Enhanced Oil Recovery Report: DOE/NETL-2014/1648, p. i-23. Online: www.netl.doe.gov/energy-analyses/temp/FY14_NearTermProjectionsofCO2UtilizationforEnhancedOilRecovery_040114.pdf.

Xu et al., (2005). Development and integration of new processes consuming carbon dioxide in multi-plant chemical production complexes. Clean Tech. Environ Policy, 7: 97-115. Online: https://pdfs.semanticscholar.org/9cf3/ea0fd2a5b3bf02c4ddce3034f00c744d660a.pdf.

Yantovski, E. I., (2008). The solar energy conversion through seaweed photosynthesis and zero emissions power generation. Electronic material processing, (2): 73-82.

Yantovsky, E. I., et al., (2009). Chapter 8: "Solar Energy Conversion through Photosynthesis and Zero Emissions Oxy-Fuel Combustion." in Zero Emissions Power Cycles. CRC Press, Taylor & Francis Group, Boca Raton. (pp. 177-195).

* cited by examiner

METHODS AND SYSTEMS FOR LARGE SCALE CARBON DIOXIDE UTILIZATION FROM LAKE KIVU VIA A CO₂ INDUSTRIAL UTILIZATION HUB INTEGRATED WITH ELECTRIC POWER PRODUCTION AND OPTIONAL CRYO-ENERGY STORAGE

BACKGROUND OF THE INVENTION

1. Field of Invention

The invention relates to methods, systems and apparatus for safe, efficient, environmentally responsible extraction and utilization of Lake Kivu deepwater resources, particularly deployed for power generation from biogas directly combined with "green" industrial utilization of massive associated $CO_2$ to secure local safety, generate employment, accelerate regional economic growth, build a global R&D network hub for Rwanda, and create a globally significant demonstration of the business viability of very large scale $CO_2$ "Carbon Capture and Utilization" (CCU).

2. Description of Related Art

A major challenge of the contemporary age is to halt the continuing increase in the $CO_2$ concentration of the Earth's atmosphere. Important related agendas are to develop new large-scale ways to utilize $CO_2$ commercially with economic viability. For example, it is desirable to recycle $CO_2$ rather than to continue to utilize drilled flows of subterranean $CO_2$ for use in Enhanced Oil Recovery (EOR) operations. These flows amount to roughly 60 millions of tonnes $CO_2$ per year in the US (Wallace and Kuuskraa, 2014). Mostly they are obtained from drilling wells that tap high-purity $CO_2$ reserves present in large trapped geo-pressurized accumulations analogous to those of natural gas (methane, NG, $CH_4$).

The huge amount of dissolved $CO_2$ (~600 million tonnes) trapped at depth in Lake Kivu stands in a different category. It presents a mortal threat in the region as well as to the ecosystem of Lake Kivu. It is only temporarily trapped in the deep lake. It will be released to the atmosphere by a catastrophic natural process of runaway convective release within a century or two unless preventative action is taken to degas a substantial fraction of the reserve.

Two options have been considered and debated between scientific experts, engineers and governmental leaders engaged in planning for large-scale utilization of Lake Kivu's deepwater biomethane resource. Like the $CO_2$, this resource is present as dissolved gas. It amounts to ~50 million tonnes of $CH_4$. The two options are: (i) an environmentally unattractive option to degas Lake Kivu's $CO_2$ and, in parallel with utilization of its biomethane, to vent the degassed $CO_2$ to the atmosphere, or (ii) return extracted $CO_2$ to the depths of the lake employing a simple process broadly within the design space of the type of extraction system first developed by Belgian engineers in the 1950s (for the first methane fueled powerplant developed on Lake Kivu in ~1960). The second option extends the risk faced by the local population of a possible mass catastrophe. In its maximal extent, such a catastrophe has the potential to asphyxiate more than two million people. Therefore, neither choice is attractive.

Related art is described in three categories. The first is directly related art. This comprises two pending patent applications by the inventor focused on solving specific problems of Lake Kivu deepwater resources utilization. US 2015/0354451 A1 relates to a method for safe, efficient, economically productive, environmentally responsible, extraction and utilization of dissolved gases in deep waters of a lake susceptible to limnic eruptions in which methane is accompanied by abundant carbon dioxide. This method applies a technology known as oxyfuel combustion in combination with an innovative modality of degassing of Lake Kivu deepwater gas. Oxyfuel combustion has been developed as a way to develop drilled acid- and sour-gas reserves, yielding power and a stream of exhaust comprised of water vapor plus nominally pure $CO_2$. The inventor's disclosure in US 2015/0354451 A1 shows how Lake Kivu deepwater gas can be developed by an innovative modified method that obtains gas dissolved in deepwater by extraction within an upward flow of water, degasses it, and then produces three outputs. These are: (i) power; (ii) an exhaust of water vapor plus nominally pure $CO_2$; and (iii) a stream of degassed nutrient-rich deepwater utilizable in various valuable ways. U.S. Patent Application Publication No. 20160257577 A1 relates to a method for treating nutrient-rich dense deepwater from Lake Kivu. Also of broadly-related interest is the patent of Evgeny Yantovsky, 2002. U.S. Pat. No. 6,477,841, "Closed Cycle Power Plant" which concerns the connection of a lake to a zero emissions power plant (Yantovsky and McGovern, 2006; Yantovsky, 2008, 2009; Yantovsky et al., 2009, chapter 8).

The second category of related art is industrial $CO_2$ production from drilled sources. Lake Kivu is not a drilled source. The extraction of $CO_2$ from Lake Kivu deepwater is based on pipe extraction within an open body of water. $CO_2$ flows upwards in pipes or risers in a dissolved state in water. A brief description is provided in following describing the development of industrial $CO_2$ capture from drilled artesian well sources in the late $19^{th}$ century. These sources combine drilling-based access to the resource with $CO_2$ flowing upwards in water in a dissolved state. Brief mention also is made of the development of very large $CO_2$ drilled gas well reservoirs exploited mostly in the Western USA. These are gas wells. Carbon dioxide rises upwards in the wells without being dissolved in water. Such discussions provide pertinent background covering the extraction of $CO_2$ by methods and systems using drilling to access the resource.

The third category is contextually related art. This type of related art covers a wide range of aspects of $CO_2$ utilization for industrial purposes such as variously are, or may be, contained within embodiments of the invention, involving carbon dioxide utilization. Related art involving $CO_2$ utilization is presented at extended length herein. Doing so is appropriate for describing related art in order to promote clear understanding of three aspects of pertinent knowledge. These are: (i) the nested set of quite different problems the invention has been created to solve; (ii) the nature of a core aspect of the invention which is open to, and seeks, incorporation of many highly diverse technologies for $CO_2$ utilization, and related "greentech" industrial production activities; and (iii) a wide and diverse background to the inventive art involved, knowledge of which provides a teaching to facilitate practice of the invention.

Carbon dioxide has never been sourced for industrial utilization from a dissolved source present in a lake. Lake sources of concentrated dissolved $CO_2$ that potentially are utilizable as $CO_2$ sources in large flows (greater than 100,000 tonnes per year) over extended periods of time are unknown in the world, with one exception only: that being the focus of the present disclosure. Also, whereas methane has been obtained and utilized from a dissolved source in a lake (Lake Kivu), carbon dioxide has never been sourced from a lake in a manner wherein associated dissolved methane also is co-extracted and utilized within an efficiently coordinated process such that neither $CO_2$ nor methane is wasted. In general, $CO_2$-dominated hyper-"acid" natural gas occurrences of the type present in Lake Kivu's deepwater are widely considered to be unattractive to develop. For example, Indonesia's $CO_2$-rich (~71% mole fraction $CO_2$) offshore "East Natuna" giant field has been known since 1970, but has been left undeveloped (Wikipedia: East Natuna Gas Field; Batubara et al., 2014. Estimated recoverable methane: ~46 Trillion Cubic Feet, TCF).

Neither Government overseeing the development of Lake Kivu's deepwater resources has expressed potential utility for the $CO_2$ present in the lake (e.g., Expert Working Group on Lake Kivu Extraction, 2009, 2010; Ndimubanzi, 2014). Carbon dioxide is not considered to be a resource in the common document called "Management Prescriptions for the Development of Lake Kivu Resources," (Expert Working Group on Lake Kivu Extraction, 2009, 2010). Lake Kivu's $CO_2$ has been considered to be a threat, an environmental nuisance, and an obstacle to be overcome for obtaining power efficiently from the dissolved methane that is present.

In East Africa, $CO_2$ is supplied for industrial use, especially beverage carbonation (including beer), by the Kenyan company Carbacid ($CO_2$) Limited (http://www.carbacid.co.ke). Carbacid obtains its $CO_2$ from a Kereita Forest spring source. This source has been developed by drilling to create an artesian well that exsolves $CO_2$ upon depressurization as the flow approaches the surface. Uncapped, it provides a fountaining jet of water and $CO_2$. (See photo of the initial fountain jet in: http://www.carbacid.co.ke/about/). Carbon dioxide is upwelling in the crust in the region as a consequence of rift tectonics and associated active volcanism (cf, Lee et al., 2016). Carbacid's source of $CO_2$ is identical in design with that of the world's first large-scale industrial $CO_2$ capture plant developed in Herste Germany in the late $19^{th}$ century in an area of mineral springs near Paderborn, (Muller, undated). The Herste source was drilled and developed for $CO_2$ capture in 1894-5 by Carl Gustav Rommenholler, founder of Kohlensaurewerke C. G. Rommenholler GmbH (Schwedt, 2015: Quinn and Jones, 1936). Rommenholler patented his artesian well $CO_2$ extraction and capture method with E. Leehrmann in 1887 (Almqvist, 2003; Wender, 1901)

Both Carbacid's and Rommenholler's sources of $CO_2$ are equivalent in design to those drilled by the founders of the German sparkling mineral water company Gerolsteiner, operating since 1888 (www.gerolsteinder.de) in the German town of Gerolstein. Gerolsteiner extracts the mineral water, and the $CO_2$ it uses to re-carbonate it, from a drilled artesian well fountaining water and $CO_2$. Initially, Gerolsteiner's first source in 1888 fountained a jet of water and $CO_2$ to a height of over 50 meters. (See photos in: https://www.gerolsteiner.de/de/gerolsteiner-brunnen/historie/; http://www.eat-drink-etc.com/showcase/Gerolsteiner; Gerolsteiner, 2013, 2015). Gerolsteiner's present day sources are similar to the nearby $CO_2$-exsolving "cold geysers" drilled in the region in the village of Wallenborn bei Gerolstein (Menhert, 2016), and also in Andernach in the Geopark Vulkanland Eifel nearby (Wikipedia: Andernach Geser). Several such drilled cold geysers exist in the USA (Kaushik, 2015). (Glennon et al., 2004 provides a worldwide inventory of both natural and man-made cold geysers). Carbon dioxide in the volcanic Eifel region of Germany bubbles up in large amounts from the bottom of a volcanic crater lake, the Laacher See, but is not captured for use (Goepel et al., 2014). Artificially created cold geysers historically associated with carbonated mineral water bottling and German-style $CO_2$ capture operations include those in Saratoga Springs N.Y. (Quinn and Jones, 1936; Millet, 2015; Sarasota Springs Heritage Area Visitor Center, 2009; Stoddard, 1895). Carbon dioxide is captured for the carbonation of many well-known mineral waters by methods identical to that practiced by Carbacid and Gerolsteiner. It is separated from the depressurization flows of artesian wells and redissolved under pressure into mineral waters during the bottling process. Prominent examples of bottled sparkling mineral waters obtained by this method include: Appolinaris and Selters (Germany), Perrier and Badoit (France), San Pelligrino and Ferrarelle (Italy), Walsdquelle (Austria), and Borsec (Romania), (LaMoreaux and Tanner, 2002).

Well sources used for bottling mineral waters with $CO_2$ capture from upflow degassing are non-polluting. They typically do not contain dissolved substances that cause eutrophication when released into surface water river flows. The design of extraction systems therefore does not involve engineering to avoid surface water pollution. Such sources also are selected for a high purity of $CO_2$ emission thereby avoiding the need to refine the gas to remove contaminating gases such as methane, nitrogen and hydrogen sulfide. Separating minor (<30% molar) amounts of methane from major amounts of $CO_2$ is a capital- and energy-intensive process (e.g., ExxonMobil's Controlled Freeze Zone™ CFZ™, process. Thomas and Denton, 1988; Northrop and Valencia, 2009; Kelley et al., 2011; Herbertson et al., 2011; Parker et al., 2011; Boschee, 2012; Condon and Kelman, 2012; Finn and O'Brian, 2014; Denton et al., 2015; Lang et al., 2015).

On Lake Kivu, the standard separation process in use (described herein) is wasteful of methane (in total >~40% is wasted). As practiced, it also uses up a substantial fraction of produced power (~>12%) for gas-cleaning operations ($CO_2$ removal).

Other natural sources of $CO_2$ include drilled wells in historical areas of $CO_2$ emission in Kizildere Turkey (Wikipedia: Kizildere Geothermal Power Plant), in Machachi Ecuador ("Agua y Gas de Sillunchi," Thorhallsson, 1997), in and near Repcelak, Hungary, and in the Becej area of Serbia. The $CO_2$-specialized industrial gases company Linde has built $CO_2$ capture plants in all three areas. Locations of shallow-drilled artesian jet-type $CO_2$ wells used for dry ice production include Ashland Oreg. USA (Klicktat Mineral Springs; Schafer, 1955; Wagner, 1959: Buckhorn Springs, 2015), the Salton Volcanic Domes of Imperial Valley, Calif. (Calvin and Pace, 2016), and Ankavan, Armenia (Hennenberger et al., 2000).

Commercial plants for obtaining $CO_2$ from geothermal sources of hot water/steam linked with geothermal power production include: Kizildere, Turkey (noted above), Miravalles, Costa Rica, and Haedarendi, Iceland (Chaves, 1996). The production of $CO_2$ in these plants requires separation of hydrogen sulfide.

The world's largest natural sources for $CO_2$ utilized industrially are deep-drilled gas wells in the USA in the states of New Mexico, Utah, Colorado, Wyoming and Missouri (Broadhead et al., 2009; Johnson, 2011; DiPietro et al., 2012; Allis et al., undated; DOE/NETL, 2015b). Mostly these sources yield high grade $CO_2$. There is no separation of $CO_2$ gas from water in production from these deep gas wells.

Apart from drilled wells, major sources of industrially utilized $CO_2$ include: natural gas cleaning/purification plants, ethanol plants, breweries, distilleries, hydrogen plants (using natural gas inputs), ammonia plants (also using natural gas inputs), ethylene glycol plants, biogas cleaning operations, cement plants, refineries and fossil fuel-burning powerplants. (For overview perspectives, see: Garvey and Turley, 2011; Cockerill, 2016).

Rwanda is a dynamic East African nation with strong economic growth and an agenda to double the national per capita GDP growth rate, averaging ~4% per annum in constant dollar terms. The nation has made impressive strides forward building a lawful order with expanding peace and prosperity in the interval since it experienced a catastrophic genocidal disaster in 1994. Rwanda's Parliament and executive leadership have created a set of well-defined national goals in "Rwanda 2020" and associated "EDPRS2" documents (see: "Government of Rwanda" in references). Reaching these goals requires a new phase of rapid industrialization. Rapid industrialization is necessary to create new modalities of economic livelihood with increased productivity for the large fraction of Rwanda's citizens living mostly by traditional agriculture. At present, more than 80% of Rwanda's total population of ~11 million people live in rural situations. Their main economic activity is traditional forms of agriculture and husbandry (plantain/banana, corn/maize, cassava, soy and green beans, millet, rice, potatoes, sweet potatoes, sorghum, carrots, tomatoes, sugar cane, coffee, tea, goats, sheep, chickens, pigs, dairy and beef cattle, etc.). Most live predominantly without access to electricity or to self-owned motorized equipment. Industrialization in Rwanda appropriately will involve several million people diversifying their activity into new types of jobs utilizing modern technologies.

According to the Executive Secretary of the UN Economic Commission for Africa, Carlos Lopes, optimally advantageous industrialization in Rwanda and other countries in Sub-Saharan Africa (SSA) should include three characteristics. They are: (i) substantial value addition to natural resources prior to export; (ii) industrialization leap-frogging to utilize new clean "greentech" technologies; and (iii) expansion of trade between the nations within Sub-Saharan Africa's rapidly growing markets (Lopes, 2015b).

Rural electrification with a low cost of power is a clear and obvious agenda. Low cost power is necessary to accelerate economic growth. Low-cost engine fuels also are necessary for rapid industrialization. Low cost electricity and low-cost engine fuels together provide a critical foundation for industrialization to build upon. However, Rwanda is in a situation of high cost electricity (>US$0.20/kWh) and high cost engine fuels (>US$1.2/liter). This situation is preventing realization of the country's economic goals.

Rwanda possesses an unusual and abundant energy resource: 50% of a large reserve of natural biogas (methane: $CH_4$), ~50 million tonnes (MT). This biogas is dissolved in the depths of a large lake, Lake Kivu. Lake Kivu is shared geographically ~50:50 between Rwanda and the Democratic Republic of Congo (DRC). The gas exists together in Lake Kivu's deepwater with an extremely high amount of associated carbon dioxide, ~600 MT. Also present are abundant dissolved Mg—Na—K—Ca bicarbonates plus dissolved NP (nitrogen and phosphorus) and other trace element fertilizers.

Lake Kivu deepwater methane has been used for electric power production since the 1950s, but many problems exist and many substantial opportunities for additional resource utilization have not been realized.

Lake Kivu's reserve of dissolved $CO_2$ is deep-sourced in the mantle and crust. It is geothermally injected into the deep lake. A large upward flux of $CO_2$ is associated with the active volcanic province adjacent to the lake's northern boundary and situated within the structure of the Albertine rift. Lake Kivu's deepwater acts as a trap for this ascending $CO_2$. Gases build-up over time. They are released catastrophically in irregularly periodic convective runaway events called "limnic eruptions." Artificial extraction of deepwater $CO_2$ changes the dynamics from all-at-once events to a steady rate of removal over time. However, artificial $CO_2$ extraction does not increase the overall $CO_2$ emission rate averaged over a timescale of hundreds of years. The overall $CO_2$ flux from the crust into the atmosphere in the region is set by underlying natural processes of tectono-magmatic transport. These transport processes make the northern Lake Kivu sector one of the largest natural emission sources of $CO_2$ in the world. (For the same reason, geothermal energy producing nations avoid accounting for $CO_2$ emissions associated with geothermal energy. See: Arnannsson, 2003, 2005.) Time-averaged emission from the Nyiragongo volcano alone is estimated to be the highest flux in the world for any volcano: ~19 million tonnes of $CO_2$ per annum (MTA), (Burton et al., 2013).

The presence of so much geothermally-derived $CO_2$ associated with biogas creates a major technical challenge to efficient extraction and use of Lake Kivu's biomethane. In US 2015/0354451 A1, the inventor disclosed a method and system for creating both efficient power and long-term lake safety by "total degassing" ($CH_4$ and $CO_2$ together) of Lake Kivu deepwater. The invention utilizes feeding of both gases, unseparated, into an oxyfuel combustor supplied with oxygen gas via an Air Separation Unit (ASU). It also organizes return flow of the deepwater into the lake in a fully degassed state. One aspect of the output of this power production method is that it generates a post-combustion exhaust comprised of a mixture of condensable steam plus nearly pure $CO_2$.

In U.S. Patent Application Publication No. 20160257577 A1, the inventor further disclosed a method and system for total degassing with treatment of the return flow of degassed water in such a way to decrease its density by creating abundant photosynthetic bioproducts and precipitated magnesium hydroxide [brucite: $Mg(OH)_2$]. This allows replacement of degassed and de-densified water just below the base of the lake's biozone, thereby optimizing long-term lake safety, capturing a very large component of valuable methane otherwise lost, and creating useful products in the de-densification process. Production of precipitated brucite then allows large scale production of eco-concrete and related building materials by utilizing $CO_2$ and steam to carbonate and hydrate Mg-cement and Mg-cement-pozzolan compositions. The bioprocessing of return flow water additionally produces very large quantities of algal biomass and associated products. Overall, the method offers ~×2.5 factor increase in electricity production per unit of methane present in Lake Kivu, relative to standard technologies. The method also adds a large factor multiplier to overall industrial productivity by production of bioproducts and eco-concretes and related building materials with value greatly exceeding that of electricity. In this method, however, deepwater bicarbonate ion provides the main carbon source for photosynthetic bioproduction, rather than $CO_2$.

None of these disclosures have addressed how optimally to utilize the full scale of the massive quantities of deepwater $CO_2$ released by a "total degassing" process. Environmental stewardship as well as industrialization opportunity makes $CO_2$ utilization a vital unsolved problem and inventive challenge. The scale of the potential flux, ranging up to ~20 million tonnes per year $CO_2$ in total for a 30 year extraction time, makes Lake Kivu the world's most dynamic opportunity for developing advanced industrialized $CO_2$ utilization on a large scale. Many technologies exist matched with attractive market opportunities in the region and beyond. Meeting such a challenge in the situation of Lake Kivu in the center of Africa is non-trivial. It requires inventive new technology in several different types combined together.

Industrializing systems of innovative machines are necessary to a long-term better economic future for hundreds of millions of people in Sub-Saharan Africa (SSA). Long-term economic development is a consequence of "market creating" industrialization: the creation of systems of innovative machines managed with the capability to allow people to transform basic resources into valuable and exportable products efficiently, on a large scale, with market competitiveness, thereby creating new high-value trade, high-value employment and widespread prosperity (Economic Commission for Africa, 2014, 2015; Lopes, 2015a,b; Arkhangelskaya and Taylor, 2014; Taylor, 2014a,b; African Transformation Report, 2014; Christensen, 2014; Mezue et al., 2015). Industrialization based on industrial technology transfer creating a basis for production and export trade has long been the core driver of spectacular economic growth in rapidly developing countries over the past 50 years. The dynamic of successful $20^{th}$ century industrialization has operated through various modes of change including entrepreneurship, new scientific and engineering insights, capital investment, government policies and wartime emergencies (Maddison, 2001, 2005, 2007, 2008). Underneath all of these aspects of understanding, it can be useful to recognize that growth in employment and prosperity fundamentally is built upon mechanical productivity: that is machines. Innovative systems of machines drive enhancements in human productivity. (Typically these are factories. However, systems of machines also include IT-based coordinated productivity.) Machines provide the basic nexus for the multiplication of output per person of goods and services. Machines are the sine qua non, the without-which-nothing, whereby human activity is multiplied drastically in economic productivity, thereby advancing prosperity (Lewis, 2004).

The creation of systems of industrial machines to produce low-cost power is a doubly foundational aspect of industrialization. Electricity is one of the basic forms of industrial power. Yet roughly 600 million citizens in SSA are disconnected from access to electricity needed to power machines necessary to leverage economic productivity.

The Manufacturing Value Added (MVA) percentage of GDP is an index for accessing national performance in industrial productivity (UNIDO, undated). MVA has fallen drastically in SSA over the past 40 years: from ~18% to ~10%, while simultaneously MVA has expanded massively in East Asia (Rowden, 2013). Per capita manufacturing value addition in Rwanda, a country with massive gains in governance and growth but still mainly exporting commodity dried coffee beans, tea leaves and raw minerals, was ~$30 per person per year in 2014 (with MVA at 6% of GDP). This may be compared to ~$1,900 for China, ~$6,000 for the USA and ~$10,000 for Singapore (UNIDO, 2015; GlobalEconomy.com, undated). Such statistics indicate a massive industrialization gap consistent with Rwanda scoring as one of the world's least industrialized societies in UNIDO reports (UNIDO, 2013, 2015). An estimated 83% of Rwandans inhabit rural regions where they live mostly by farming activity (NISR, 2014; de la Victoire, 2014), working with their hands using baskets and hoes as their major form of technology leverage. Rwanda has outstanding potential from its many reforms, thriving capital city and rapidly rising per capita GDP. Its low industrialization represents one of the greatest opportunities in the world for rapid human betterment. Rwandan leaders are aware of this challenge and opportunity. They have established a policy to encourage very rapid growth in the industrial economy (Economic Commission for Africa, 2015b; Ministry of Trade and Industry, 2011). Turning policies into realities, however, will require installing systems of industrial machines on a large scale through private enterprise and governmental joint ventures with the private sector. Future growth depends especially on "moving up the value chain" (Kaberuka, 2015) by both processing traditional products such as coffee, tea and minerals to add value, and by creating completely new modes of production for export. Overall, sustained development of Rwanda and other countries in Sub-Saharan Africa depends on success in accelerating industrialization in energy, manufacturing and technologically modernized agriculture (Economic Commission for Africa, 2015a; African Transformation Report, 2014).

Systems of industrial machines require both policy support and intrinsic profitability to grow rapidly through initial capital investment with follow-on investment pursuing demonstrated success. Areas of particular promise will demonstrate industrial clustering potential from the presence of abundant low-cost resources and associated opportunities to transform these resources into locally useful and/or exportable products possessing substantial value-addition. Successful cluster development, however, additionally requires attracting many highly innovative technically trained people (Porter, 1998; Wadhwa, 201). That sometimes is not easy in Africa, though Rwanda benefits from a very impressive returning diaspora. While resource extraction productivity can operate in isolation, as in the case of offshore oil platforms, and whereas broadband Internet communications now can create global virtual video-community networks easily, the development of clustering sufficient for industrial-economic take-off, and the rapid growth of knowledge capital more generally (Hanushek and Woessmann, 2015, 2016), still requires the ability to attract many high-talent people to a region.

Lake Kivu is one of the most elegantly beautiful and climatologically attractive regions in the world. Though relatively little known, its future holds tremendous potential (Kivu Belt, 2013).

Systems of industrial machines are a key to greentech transformation to achieve "green economy" environmental goals (UNEP, 2014, 2015). The increase of carbon dioxide ($CO_2$) in the atmosphere from industrial activity is widely considered to have generated a substantial global risk from the possibility of major climatic system instabilities (IPCC, 2015). Accordingly, one of the challenges of the age is to find solutions to address this risk. Talented people all over the world are focused on this task. Attractive solutions especially will avoid constraining economic growth, in particular growth that benefits emerging market economies where the need for development is great, as in Sub-Saharan Africa. One agenda being widely pursued is to develop ways to create power, fuels and industrial products in ways that absorb, utilize and recycle, rather than emit, $CO_2$, and that do so with superior performance in the competitive economic marketplace. Despite intense research and many impressive scientific-technological breakthroughs, only limited substantially scaled examples exist in industry. The largest quantities of utilized $CO_2$ are injected into oil wells via $CO_2$-based Enhanced Oil Recovery ($CO_2$-EOR, Meyer, 2007; Al-Mjeni et al., 2010/2011; Muggeridge et al., 2015). Most of this $CO_2$, however, is not recycled. It is obtained from natural wells.

The agenda to create new industries based on industrial $CO_2$ recovery and utilization recycling (Benson, 2015) is described by the terms "carbon capture utilization" (CCU) and "carbon dioxide utilization" (CDU, Styring et al., 2011). In recent years, huge international effort has been invested to develop new scientific insights and technologies pertinent to $CO_2$ utilization. A large quantity of literature exists on CCU/CDU (hereafter: CCU). It includes an industry overview (Prize Capital, L L C, 2011) plus many books (Goosmann, 1906; Aresta and Forti, 1987/2011; DOE, 1993; Halman, 1993; Sullivan et al., 1993; Inui et al., 1998; National Academy of Sciences, 2001; Creutz and Fujita, 2001; Song et al., 2002; Aresta 2003, 2010; DeSimone and Tumas, 2003; Liu and Mallinson, 2003; Olah and Goeppert, 2006; Hu, 2011; Yang et al., 2012; Suib, 2013; De Falco et al., 2013; Anastas et al., 2014; Aresta and van Eldik, 2014; Bhanage and Arai, 2014; Centi and Parathoner, 2014; Styring and Quadrelli, 2014; Aresta and Dibenedetto, 2015; Aresta et al., 2015; Jin et al., 2015; Morreale and Shi, 2015; Surampalli et al., 2015). The field includes a dedicated research journal publishing articles since 2013, the Journal of $CO_2$ Utilization (JCOU). It includes several annual conference series, including the International Conference on $CO_2$ Utilization (ICCDU), (Aresta, 2015), the Carbon Capture, Utilization and Storage Conference series organized by the United States Energy Association, USEA (USEA, undated), the Conference on Carbon Dioxide as Feedstock for Fuels, Chemicals and Polymers series (http://co2-chemistry.eu/past), the Carbon Dioxide Utilization Summit series organized by Active Communications International (ACI), the European Carbon Capture and Storage conferences, and the Guangdong International Carbon Capture Utilization and Storage Conference series (http://www.gdccus.org). The literature of CCU includes an abundance of technical review papers, for example: Behr, 1987, 1988; Mortensen, 1987; Braunstein et al., 1988; Darensbourg and Holtcamp, 1996; Leitner, 1996; Shaikh and Sivaram, 1996; Kendal et al., 1999; Taylor et al., 2000; Arekawa et al., 2001; Creutz and Fujita, 2001; Song, 2002; Beckman, 2003, 2004; Mazzotti et al., 2005; Aresta, 2006; Omae, 2006, 2012; Sugimoto and Inoue, 2006; Aresta and Dibenedetto, 2007; Darensbourg, 2007; Jitaru, 2007; Haring, 2008; Sakakura et al., 2007; Benson et al., 2009; He et al., 2009, 2010; Munshi and Bhaduri, 2009; Ramsey et al., 2009; Glueck et al., 2010; Riduan and Zhang, 2010; Jiang et al., 2010; Dai et al., 2010; Darensbourg, 2010, 2014; Mikkelsen et al., 2010; Darensbourg et al., 2010; CCUS-China, 2011; Cokoja et al., 2011, 2015; Global CCS Institute/Parsons Brinckerhoff, 2011; Yang et al., 2011; Centi et al., 2011, 2013; Quadrelli et al., 2011; Mohamed and Eastoe, 2011; Peters et al., 2011; Savile and Lalonde, 2011; Viswanathan, 2011/2014; Wang et al., 2011; Darensbourg and Wilson, 2012; Fukuoka, 2012; Lu and Darensbourg, 2012; Holscher et al., 2012; Jessop et al., 2012; Jin et al., 2012; Kumar et al., 2012; Laumb et al., 2012; Pearson et al., 2012; Sumida, 2012; Tsuji and Fujihara, 2012; Ackiewicz et al., 2013; Appel et al., 2013; Aresta et al., 2013, 2014; 2015; Bocin-Dimitru et al., 2013; Costentin et al., 2013; Gao et al., 2013; Yang et al., 2012; Hawkins, 2013; Harriman, 2013; Hendriks et al., 2013; Oman et al., 2013; Kondratenko et al., 2013; Geerlings and Zevenhoven, 2013; Power et al., 2013; Zakkour, 2013; ADEME, 2014; Araujo et al., 2014; Centi and Perathoner, 2014; Huang and Tan, 2014; Matthessen et al., 2014; Patel et al., 2014; Sanna et al., 2014; Silva and Meireles, 2014; Ravanchi and Sahebdelfar, 2014; Shi et al., 2015; Taherimehr and Pescarmona, 2014; Urakawa and Sa, 2014; Alissandratos and Easton, 2015; Behrens, 2015; Demirel et al., 2015; Wang et al., 2015; Cuellar-Franca and Azapagic, 2015; Durre and Eikmanns, 2015; Lee et al., 2015; Liu, Q., et al., 2015; Luca and Fenwick, 2015; Ampelli et al., 2015; Alvarez-Guerra et al., 2015; Kenis, 2015; Kortlever et al., 2015; Lim, 2015; Shi et al., 2015; Romanov et al., 2015; Su et al., 2015; Theulen, 2015; Wang et al., 2015; White et al., 2015; Wuppertal Institute, 2015; Xin et al., 2015; and Porosoff et al., 2016. The field of CCU includes long-established industrial examples such as: sodium bicarbonate production (Wikipedia: Solvay process), salycilic acid production (Rocke, 1993), and carbon monoxide production (from coal reacting with $CO_2$, Hunt at al., 2013), used in mineral ores smelting and cyclic organocarbonates production (North, 2012). Long established examples also include: urea production from ammonia; neutralization of industrial alkaline residues including high-pH alkaline wastewaters (Linde, undated; Garmo and Escudero, 2014; Gomes et al., 2016); production of precipitated fine calcium carbonate white pigment used in paper making and many other industries (Lopez-Periago et al., 2010); chemicals production based on Grignard reagent carboxylations (Silverman and Rakita, 2005; Wu et al., 2014); and carbonation-precipitation of $CaCO_3$ as a purification step in sugar refining (Moodley et al., 2002; Varelius, 2014). The field of CCU also includes various direct $CO_2$ uses such as, for example: dry ice, insecticidal fumigants, fire extinguishing gas (Makowa/NAFED, undated), refrigerant gas (Bodinus, 1999), supercritical $CO_2$ solvent and reaction medium applications, food preservation/storage gas, and horticultural plant feeding employing the $CO_2$ fertilization effect applied in commercial greenhouses (Mortensen, 1987; Allen et al., 1996; Blom, 2015). The field of CCU also includes developments with recent rapid industrial growth on a large scale: $CO_2$-based Enhanced Oil Recovery (EOR) as well as the use of $CO_2$ as a fracking fluid or as a component in fracking fluids. It includes power storage technologies for stabilizing intermittent renewable electric power input via "power-to-gas" methanization of $CO_2$ using hydrogen generated by water electrolysis, operating commercially in Germany (Schiermeier, 2013; Wikipedia: Power to gas; Hydrogenics, undated; ETOGAS, 2015; Schlumberger, 2014; Prokofyeva, 2014). It includes industrial "green chemistry" with many possibilities, amongst which a prominent commercial example is polyurethane foam manufacture by the German manufacturing giant Bayer using $CO_2$ input to create "$CO_2$-polyols" (Langanke et al., 2014; Prokofyeva and Gurtler, 2015a,b; see also: www.novomer.com, and additionally Chapman et al., 2015 describing similar activity by the UK company Econic). Another related example is a promising effort to industrialize large-scale production of industrially useful glycerol carbonate from $CO_2$ reacting with industrially abundant glycerol (North et al., 2010; CyclicCO$_2$R, undated; North, 2012; Sonatti et al., 2013; Castro-Osma et al., 2014). Recent breakthroughs in CCU include a new mode of cement and concrete manufacture based on $Mg(OH)_2$ rather than $CaCO_3$. This technology incorporates $CO_2$ rather than releases it (www.tececo.com; Harrison, 2013; Al Tabbaa, 2013). CCU also includes an embryonic technology revolution developing many new technologies for artificial photosynthesis to produce "electrofuels," "solar fuels," and other industrial "solar chemicals" from inputs of $CO_2$, water and light (Goodson, 2015).

Also, wherever algae species are grown commercially and under photoautotrophic conditions, $CO_2$ typically is utilized as an input carbon source. Examples include the US-based algae companies Earthrise (www.earthrise.com), Cyanotech, (www.cyanotech.com; www.nutrex.com), Algenol (www.algenol.com), Sapphire Energy (www.sapphireenergy.com), Heliae (www.heliae.com), Aurora Algae (www.aurorainc.com), Cellana (www.cellana.com), Algae-2-Omega (www.Algae2Omega.com), Qualitas-Health (www.qualitas-health.com), Bioprocess Algae (www.bioprocessalgae.com), Algae Systems (www.algaesystems.com), the Israeli companies NBT (https://www.d-factoryalgae.eu/42-eng-nbt.html) and Algatech (www.algatech.com), FEBICO in Taiwan, (http://www.febico.com/en/page/Facility/facility.html), Yaeyama *Chlorella* in Japan (www.yaeyamachlorella.com), Parry Nutraceuticals in India (www.parrynutraceuticals.com), and Roquette Klotze in Germany (www.algomed.de), (ABO, 2015; Burlew, 1953; Benemann et al., 1987; Benemann and Oswald, 1996; Benemann, 1997, 2003; Anderson, 2005; Gershwin and Belay, 2008; Linde, 2010; Liu and Hu, 2013; Richmond and Hu, 2013; Borowitzka and Borowitzka, 1988; Borowitzka and Moheimani, 2013; Carr, 2015; Sapphire, 2015; Woods, 2015; Anton, 2015; Legere, 2015; Global CCS Institute, 2011-Appendix E; Lundquist et al., 2010; Craggs et al., 2012: Ben-Amotz, 2011; Boussiba, 2015).

For applicability of CCU in Sub-Saharan Africa, a key to future success will be the development and demonstration of large-scale profitable examples. Early examples will require special circumstances. Ideally, these will include: (i) freely available and nearly pure $CO_2$; (ii) high-value product options; (iii) strong market demand such products at a high price point; (iv) strong long-term rapid growth potential (v), a favorable business environment for investment, and (vi) industrial cluster-forming potential. A strategic factor of special interest for cluster-forming potential is the world-historic significance of CCU. The prospect of developing major components of a carbon-recycling economy creates a powerful attractor for entrepreneurs, investors and high-talent engineers and scientists as well as to institutions involved in research and development towards a green economy. This factor adds another aspect of attraction to already attractive arena of being involved in transforming the lives of hundreds of millions of people Sub-Saharan Africa towards prosperity.

Human industrial and agricultural activities release ~35 gigatonnes of $CO_2$ into the Earth's atmosphere each year, about half of which accumulates. At present anthropogenic release of $CO_2$ is causing an annual increase in the $CO_2$ concentration of the Earth's atmosphere of ~0.5% per year. Pre-industrial $CO_2$ prior to ~1750 was about 280 ppm. Today it is ~400 ppm. Growth is ~2 ppm per annum, with an accelerating growth trend as developing countries rapidly industrialize. Carbon dioxide is a radiation-trapping "greenhouse" gas. Increase in its atmospheric abundance generates a climatological warming tendency. It also generates ocean acidification from increased $CO_2$ uptake into seawater. A worldwide coalition of governments is concerned about risks from climate change and ocean acidification. This coalition is seeking to decrease the flux of $CO_2$ released by human activities into the atmosphere. However, the rapid industrial development of developing countries, a vital matter for the alleviation of mass poverty, drives accelerating growth in world $CO_2$ output. Hence a conundrum exists. Strategies that encourage the persistence of mass poverty are unlikely to succeed. Therefore a key challenge is to transform new industrialization, especially in developing countries, from standard high-$CO_2$ modes to "greentech" modes. A key focus for this agenda relates to the combustion of the ~4 billion tonnes of coal mined each year (BP, 2015), almost all of the carbon (12 grams per mole) of which is converted to $CO_2$ (44 grams per mole).

One aspect of this agenda is industrialization of $CO_2$ utilization technologies: to invert the situation of $CO_2$ being a waste into $CO_2$ being a carbon source input into industrial production. To be useful for environmental purposes, industrial $CO_2$ utilization requires the development of profitable uses for $CO_2$ in large quantities, especially involving, wherever possible, carbon recycling as well as inputs of renewable sources of power (Olah et al., 2011). Scale matters. To make a substantial impact on atmospheric carbon accumulation, overall $CO_2$ utilization targets worldwide should sum to at least, say, 10% of the human $CO_2$ emissions rate of ~35 billion tonnes ($35 \times 10^9$ T) per year (=~10 billion tonnes elemental carbon per year). The agenda and challenge is to inaugurate a new mode of dynamic industrialization wherein new modes of $CO_2$ utilization contribute substantially to economic growth. This requires new forms of industrial production at a total $CO_2$ utilization scale of several billion tonnes per year. This challenge therefore unavoidably must be focused predominantly on products in areas of very large-scale production in terms of mass. Such arenas include agriculture and wood production, mining and metallurgy, fuels extraction and production, plastics manufacture, and the production of cement-based building materials and aggregate such as provide the inputs into the production of concrete. Concrete (cement+aggregate+water), for example, is produced on a global scale of roughly 30 billion tonnes per annum (Smil, 2013; Armstrong, 2013). For comparison, world liquid transport fuels production is about 5 BTA, (USEIA, 2015; BP, 2015), world iron ore production is about 3 BTA (USGS, 2015), world roundwood production is about 1.5 BTA (FAO, 2014), world plastics production is about 0.3 BTA (Gourmelon, 2015) and world aluminum ore bauxite production and processing is about 0.25 MTA (USGS, 2015). Examples of industrial $CO_2$ utilization linking with these large scale forms of production include: (i) structural capture into cements and concretes; (ii) sequestering $CO_2$ underground via processes of enhanced oil recovery, EOR (NETL/DOE, 2010), (iii) utilizing $CO_2$ as a carbon source for energy storage in transportation fuels by $CO_2$ reduction with hydrogen obtained from renewable sources by water electrolysis; (iv) creating $CO_2$-sourced replacement for petrochemicals in plastics manufacture such as for example polyethylene and polyurethane; (v) increasing agricultural productivity both by $CO_2$ plant feeding and high-yield sustainable forest management; and (vi) developing low-cost mining and ore processing technologies extracting major industrial metals such as iron and/or nickel and/or aluminum using processes that mineralize carbon.

A major challenge moving forward is to create economically viable examples of conglomerated $CO_2$ utilization industrial networks. In such networks, waste $CO_2$ would create a basis for industrialization across a range of specific modes of $CO_2$ utilization. This task has not been achieved. No examples exist. The world's largest mode of industrial $CO_2$ utilization, $CO_2$-EOR, is dominated by $CO_2$ pipeline networks in the United States (NETL/DOE, 2010; Department of Energy, 2015). And the $CO_2$ used in EOR in the United States is predominantly derived from $CO_2$ wells and not from recycling of industrial waste $CO_2$ sources.

The X-Prize Foundation (www.xprize.org) launched the US$20 million "NRG Cosia Carbon X-Prize" in 2015 to incentivise major breakthroughs in large scale $CO_2$ utilization (http://carbon.xprize.org; Lim, 2015).

Lake Kivu possesses a density-stratified convectively stable ("meromictic") structure. A relatively shallow oxygenated convecting "bio-zone" exists from the surface down to 30 to 70 meters, varying according to seasonality and storm intensity. Below ~100 meters, trapped gases are present in a stack of anoxic layers known collectively as the "monimolimnion." In these, the water density increases in a stepwise manner down to a maximum depth of 485 meters. Lake Kivu's main methane reserve is below 250 meters. It contains a total amount of dissolved methane ($CH_4$) of about 32 million tons (approximately 1.5 trillion cubic feet, TCF). Dissolved $CO_2$ also is present: about 423 million tons (Capart and Kuffrath, 1956; Schmitz and Kuffrath, 1955; Tietze, 1978, 1980a,b; 2000, 2007 Wuest et al., 2009, 2012; Tassi et al. 2009). The dissolved deepwater gas below Lake Kivu's density discontinuity at 250 meters has a molar ratio: $CO_2/CH_4$~4.8. Lake Kivu's deepwater also is nutrient-rich (Tassi et al. 2009). Descy et al., (2012) provides comprehensive overview perspectives on Lake Kivu.

Pipes originating in the depths of Lake Kivu below 250 meters connecting to the surface can auto-siphon, transporting expanding bubbly flows upwards without a necessity for pumping (Halbwachs, website; Tassi et al., 2009).

The deepest and most methane-rich resource zone in Lake Kivu is called the "Main Resource Zone" (MRZ). The trapped gas resource in the MRZ, ~32 million tonnes of methane, has the capability, in principle, to provide approximately 1,000 megawatts continuous power over a period of 30 years if extracted and combusted with high efficiency.

The presence of an estimated approximately 500 million tonnes of associated $CO_2$ trapped at depth in Lake Kivu in the MRZ and PRZ presents a major efficiency challenge. Methane typically cannot be combusted efficiently for power production in the presence of large amounts of $CO_2$. Pre-combustion separation of $CO_2$ by various differential extraction and gas-cleaning technologies requires substantial power production efficiency loss as well as large capital investment in equipment.

A staged system based on the differential gas solubility of $CH_4$ and $CO_2$ in water at different pressures has been used in Lake Kivu by all power projects. The design was developed and patented by the company L'Union Chimique Belge in 1953-1962 (Patent: 1954, published 1957: Kingdom of Belgium patent 531780, l'UNION CHIMIQUE BELGE S. A., "PROCEDE D'EXPLOITATION DE GAZ DISSOUS DANS DES EAUX PROFONDES. Related references: Capart, 1954, 1960; Borgniez, 1960; Capart et al, 1957/8; Capart and Kufferath, 1956, 1962; Tietze and Maier-Reimer, 1977; Williams Brothers Engineering Company/USAID, 1979; Descy et al., 2012; Halbwachs, 2011: European patent application: EP 2 357 318 A1). The design was developed using the limnological data of Damas (1937a,b), Capart and Kufferath, (1956), Verbeke (1957), and others. The design and principles are detailed on the website of Dr. Michel Halbwachs (Halbwachs, website) and elsewhere (Tietze and Maier-Reimer, 1977; Williams Brothers Engineering Company/USAID, 1979; Maj/YLEC Consultants, 2009; Antares Offshore LLC website, undated; Tietze 1980b, 2000, 2007; Wuest et al., 2009, 2012; Osterdijk and Heencamp, 2012).

The main engineering challenge of separating the extreme amount of $CO_2$ associated with methane can be overcome with oxyfuel combustion technology linked with a total degassing process. This technology has the capability to combust Lake Kivu's $CO_2$-rich gas directly, yielding power with high thermal efficiency and without loss of methane and energy from $CO_2$ separation processing. This solution is described the inventor's U.S. Patent Application Publications Nos. 20150354451 A1 and 20160257577 A1.

The presence of so much $CO_2$ trapped at depth in Lake Kivu presents a serious threat of mass asphyxiation of the ~2M people living in close proximity to the lake within its basin (Baxter et al., 1989; Costa and Chiodini, 2015). The danger is from the possibility of very large scale convective runaway gas release "limnic eruption" (Sigurdsson et al., 1987; Kling et al., (1987); Tietze, (1992); Zhang, (1996); Halbwachs et al., (2004); Schmid et al., (2004, 2005); Zhang and Kling, (2006); Halbwachs, (2014); and Vaselli et al. (2015). Mass asphyxiations from much smaller scale limnic eruptions that occurred in small volcanic lakes in Cameroon in the 1980s have been described by Baxter et al., (1989); Tietze (1992); Eby et al., (2006); Costa and Chiodini, (2015); and Kling, (undated). A future event in Lake Kivu likely would be triggered by lake bottom volcanism in the northern sector of the lake. Bathymetric surveys have revealed the presence of several volcanogenic cones on the deep lake bottom. The natural quasi-periodicity of convective runaway events is approximately every 1,000 years. The last event occurred ~900 years ago. This is known from studies of sediment cores from Lake Kivu which reveal evidence of past convective runaway events in the lake. All appear to have been triggered by volcanic activity according to the evidence found in these cores (Haberyan and Hecky, 1987; Ross, 2013a,b; Hecky and Reinthal, 2010; Ross et al., 2013, 2014, 2015. However, see also: Zhang et al., 2014). Wauthier et al., (2012, 2015) presented evidence connecting Lake Kivu's continental rift environment to the extensive volcanism adjacent to it in the north and by rift-related fracturing and deep magmatic dike intrusion to the various volcanic cones present at depths below 300 meters in the northern sector. Volcanic plumbing in this system was activated in the 2002 eruption near to the shore of the lake, but fortunately not underneath it. The recent work of Ross and Wauthier and their colleagues has illuminated important aspects of Lake Kivu's danger. These insights suggest degassing removal of $CO_2$ from the deep lake will be urgently prudent to protect both human populations and Lake Kivu's ecosystem.

Commercially viable industrial utilization of $CO_2$ in large-scale flows (that is, exceeding ~100,000 tonnes per year) must connect sources to sinks in an economically efficient manner, either by adjacent proximity or pipeline systems. Long distance transport of $CO_2$ can be expensive, adding a cost in the range of US$15 to $35 per tonne for compression and transport on the scale of about 500 km (Kuang et al., 2015. For detailed analysis, see: Doctor et al., 2005). Long distance $CO_2$ pipeline systems exist only in certain areas of the US and Canada (Noothout et al., 2014; Denbury, 2011; IPCC, 2005 chapter 4; Ortiz et al., 2013; Department of Energy, 2015). The world's most extensive $CO_2$ pipeline system includes almost 3,000 miles of pipeline. It connects through Denver City, NW Texas. Denver City is the world's largest $CO_2$ distribution hub (Clark, 2014). Its pipeline network connects into another pipeline network to the south coordinated via the McCamey hub in McCamey, Tex. These interconnected networks distribute $CO_2$ for enhanced oil recovery throughout the Permian Basin (EOR, Muggeridge et al., 2015; Al-Mjeni et al., 2010/2011). The Denver City hub distributes about 30 million tonnes (MTA) of $CO_2$ per annum for EOR injection into old low-productivity oilfields to rejuvenate oil extraction (Powerplantccs, undated; Kuuskraa and Wallace, 2014; Wallace and Kuuskraa, 2014). This $CO_2$ mostly is obtained from natural wells: Sheep Mountain, McElmo Dome and Doe Canyon in Colorado, and Bravo Dome in New Mexico. In 2010 and 2012, a major new source of industrial $CO_2$ came on line via Occidental petroleum's Century Gas Processing Plant located in Fort Stockton Tex. located about 160 miles south of Denver City. The Century plant added a $CO_2$ extraction capacity exceeding 8 MTA into the hub system (Century Plant Fact Sheet, 2014; ZeroCO2, undated). This added to other industrially-sourced $CO_2$ input into West Texas regional pipeline systems from a network of five $CO_2$ sources from ammonia production and natural gas "sweetening" ($CO_2$- and $H_2S$-removal) plants developed in ~1972. These include the Pikes Peak, Grey Ranch, Puckett, Mitchell, and Terell gas sweetening plants, plus the Val Verde ammonia plant. This network provided the first basis for using $CO_2$ on a large commercial-scale for EOR in the USA (Meyer, 2007; Gao et al., 2013). Ever since, this system has piped purified $CO_2$, between 1 and 2 million tonnes per year, 132 km to a Val Verde Tex. distribution hub for distribution for EOR use (Benson, 2015; MIT, 2015). Detailed maps of these Permian Basin collection and distribution systems are provided by Moore (2005), Melzer (2007), Husted (2009) and Department of Energy (2015). Beginning in 1976, supercritical $CO_2$ was pumped ~100 km from an ammonia plant to the Lick Creek oilfield in southern Arkansas for immiscible $CO_2$-EOR flooding in a depleted heavy oil field (Reid et al., 1981). An additional system utilizing anthropogenic $CO_2$ exists in Texas near Houston. About 1 MTA waste $CO_2$ is captured from an industrial steam reformer hydrogen plant within the Valero refinery in Port Arthur. This $CO_2$ is piped 159 km for EOR injection into the Hastings oil field near Houston (Haszeldine, 2015).

$CO_2$ utilization for greenhouse fertilization is widespread. Greenfield Specialty Alcohols (www.gfsa.com) of Chatham, Ontario (Canada) operates in a local industrial symbiosis with the greenhouse tomato grower Truly Green Farms (http://www.trulygreenfarms.ca). Ethanol production provides waste heat and $CO_2$ to the greenhouses (Jessen, 2013; GreenEnergyFutures, 2014). A similar situation exists in Sweden linking a distillery with a tomato grower (Advantage Environment, 2013). In 2015, the company Linde Gas Turkey commissioned a $CO_2$ purification and liquefaction plant to capture geothermal $CO_2$ from the Zorlu Energy geothermal power plant near Denizli in order to supply an initiative to create an "Organized Greenhousing Zone" in the region (Cockerill, 2015).

Close proximity allows $CO_2$ to be routed efficiently between sources and utilizers without the need to purchase land use rights, construct transport pipeline systems and pay energy costs for compressing $CO_2$ for extended transfer. Proximity-based industrial collaborations linking $CO_2$ producers and users are reviewed briefly in following. Most involve urea production. The industrial production of ammonia ($NH_3$) creates $CO_2$ waste via the process of methane reforming. Most of it can be cycled into the production of urea (for example: Agrium, 2015; Wikipedia: Urea; Perez-Fortes et al., 2014). Urea is produced by combining ammonia and $CO_2$ to form ammonium carbamate via an exothermic reaction, $2NH_3+CO_2 \rightarrow H_2NCOONH_4$, followed by an endothermic "urea conversion" dehydration reaction: $H_2NCOONH_4 \rightarrow (NH_2)_2CO+H_2O$. Natural gas is the dominant hydrogen source input into the Haber-Bosch (Smil, 2000) and Bosch-Meiser processes for ammonia and urea production, respectively. The carbon present in the input natural gas is mostly transformed into $CO_2$ in the process of industrial hydrogen production. Ammonia ($NH_3$) is produced using the resulting hydrogen ($H_2$). This is done by fixing nitrogen ($N_2$) obtained from air via Haber-Bosch synthesis: $3H_2+N_2 \rightarrow 2NH_3$.

The Saudi Arabia Basic Industries Corporation (SABIC) is creating the world's largest $CO_2$ purification and liquefaction plant in Jubail Industrial City, Saudi Arabia (Linde, 2013a; World of Chemicals, 2013). This plant will pipe $CO_2$ waste from two ethylene glycol plants to be utilized in nearby urea and methanol plants. It is planned that most of the $CO_2$ eventually will be used for $CO_2$-EOR. Additional examples of plans for proximity CCU in heavy industry under development include: (i) Masdar City in the UAE (Masdar/Al Reyadah, undated), and (ii) possibly the Jurong Island Eco-Industrial Park in Singapore (Pan et al., 2015; For an overview analysis see: Singapore report, 2014).

A team of Louisiana State University engineers focused on CCU examined the US lower Mississippi River Corridor (MRC) complex of large-scale heavy industries in chemicals and energy. Their aim was to understand and promote opportunities for large-scale CCU implementation (Hertwig et al., 2002; Xu et al., 2003, 2005; and Indala, 2004). This group concluded there was substantial potential for profitability from CCU implementation coordinating $CO_2$ flows between producers and users. They especially noted possibilities for future development based on new CCU-favorable modes of industrial chemicals production. This hoped-for development has not yet taken place. Nonetheless, development of networked CCU in the wider region has grown hugely by connection with $CO_2$-EOR. In 2011, Denbury (www.denbury.com; Schnacke, 2015) completed its ~700 km US$1B $CO_2$ "Green pipeline" network crossing the MRC. The "Green" pipeline links a natural $CO_2$ source, Jackson Dome in central Mississippi State to EOR locations in and near Houston, Tex. (Denbury 2009a,b; Denbury, 2011). At present, $CO_2$ from the Geismar La. ammonia plant owned by Potash Corporation/PCS Nitrogen adds to $CO_2$ flow into this pipeline. Additional anthropogenic industrial $CO_2$ inputs are planned and in development (Kuuskraa and Wallace, 2014; Wallace and Kuuskraa, 2014; Kuuskraa, 2014). These include an expected ~3 million tonnes per year (MTA) of $CO_2$ to be captured from the integrated gasification combined cycle (IGCC) clean coal "Kemper Project" ~500 MW power plant in Mississippi expected. This plant is expected to start-up in 2016 (www.kemperproject.org; Wikipedia: Kemper Project; Sarkus, 2015; Wilson, 2015).

Denbury's "Green" $CO_2$ pipeline from mid-state in Mississippi to Houston Tex. follows a $CO_2$-EOR-focused business model. Hasan et al., (2014) evaluated the technology and economics of CCU industrial ecology. These authors estimated a cost basis for $CO_2$ of ~US$40 per tonne "captured and managed" in the US with predominant $CO_2$-EOR utilization. Subground $CO_2$ storage management in the US and Canada is beginning to link with $CO_2$-EOR, as there is potential for favorable economics extracting large quantities of oil left behind after conventional extraction flows have dried up (Carter, 2012; Godec et al., 2013; Kuuskraa et al., 2013: OECD/IEA, 2015; IEA, 2015, 2016). A prominent well-studied example that combines $CO_2$-EOR and $CO_2$-sequestration is the "IEA GHG Weyburn-Midale $CO_2$ Monitoring and Storage Project." $CO_2$ from the Great Plains Synfuel Plant in Beulah, N. Dak. (USA) is piped 323 km for injection into the Weyburn and Midale oilfields in Saskatchewan, Canada (Wikipedia entry: Weyburn-Midale Carbon Dioxide Project; Whittaker et al., 2011; NETL/DOE, 2015; PTRC, undated; Cenovus Energy, undated; Apache, undated). More than 25 million tonnes of injected anthropogenic $CO_2$ already have been stored in these oilfields via $CO_2$-EOR stimulation of oil production. The average rate of injection has been ~3 million tonnes (MT) $CO_2$ per year. About 40 to 60 MT $CO_2$ is expected to be sequestered in the course of extracting approximately 215 million barrels of excess oil production overall (Whittaker et al., 2011). $CO_2$-EOR with associated $CO_2$ sequestration is a relatively well-developed technology in the USA. The an overall injection rate for US $CO_2$-EOR is about 60 million tonnes $CO_2$ per year (MTA), circa 2015 (Hill et al., 2013). This generates in excess of 100 million barrels per year of incremental crude oil production (NETL/DOE, 2010; Hill et al., 2013. See Jaramillo et al., 2009, Azzolina et al., 2015 and Cooney et al., 2015, for $CO_2$ Life Cycle Analysis, LCA, of $CO_2$ EOR). At present, however, for viable industrial production processes other than $CO_2$-EOR and natural gas-based urea production, special circumstances and innovation appear to be required to bring together captured $CO_2$ output availability at low cost with value-creating CCU on a large scale.

Plentiful rift-based oils are present in the Albertine graben in Western Uganda bordering the Eastern DRC (Lirong et al., 2004a,b; Gao, 2012; Abeinomugisha and Kasande, 2012; Karp et al., 2012). Substantial reserves have been proven on the eastern shore of Lake Albert. A total of ~6.5 billion barrels is estimated for Uganda in this area (Nakhle, 2015; OIES, 2015). Recoverable reserves are estimated at roughly 1.5 to 2 billion barrels (OIES, 2015; Nakhle, 2015; Jarrett, 2014; Powell, 2014). Exploration blocks to the south near Rwanda bordering Lake Edward also have been drilled with substantial oils reserves discovered (URN, 2010). Discussions of pipeline technologies for the possibility of the transport of the Albertine rift's crude to the distant East African coast indicate most oils are heavy (API ~19 to 33), viscous (cP ~40), and wax-rich (~19%). Heating and/or solvent addition is required both for extraction and pipeline transport of this type of crude. Reports suggest the oils pour only above 40° C., and will flow efficiently in pipes only above 60° C. (Jarvie et al., 2007: Deep Earth, 2015; Ochan and Amusugut, 2012; Open Oil, 2012). Operational problems in producing and transporting such oils include precipitative clogging by wax and asphaltene precipitation both of the reservoir during extraction, as well as pipeline clogging above ground. Oils of this type are expensive to extract and trade at a discount. Efficient production requires specialized technologies (Oil in Uganda, 2014).

Oil reservoir rocks in the Albertine Graben in the region of Lake Albert typically are sandstones, often with calcium carbonate pore cementing (Ochan and Amusugut, 2012; Karp et al., 2012).

Hard-to-produce heavy oils are abundant worldwide. They exist in amounts exceeding the scale of all conventional reserves prior to extraction. Heavy oils represent a major focus of effort for development of economically viable extractive technologies (Chopra et al., 2010; Alboudwarej et al., 2006). $CO_2$-EOR typically is considered to be a technique restricted to non-heavy oils (NETL/DOE, 2010; Shell, 2012). However, injected $CO_2$ has long been used successfully to pressurize depleted heavy oil fields via immiscible $CO_2$ flooding (Gao et al., 2013; Emadi et al., 2011). Prominent examples reviewed by Gao et al., (2013) include the Lick Creek Field in Southern Arkansas (USA, Reid and Robinson, 1981), the Wilmington Field near Los Angeles, the Bati Raman field in SE Turkey (See also: Kok and Ors, 2012; Ansarizadeh et al., 2015), the Liaohe Field in NE China, and the Forest and Oropouche fields in Trinidad. In most $CO_2$-EOR operations, a substantial fraction of $CO_2$ remains sequestered in the formation. And $CO_2$ co-produced with oil can be separated and recycled into continuing $CO_2$-EOR injection. Consequently, efforts are being made to develop efficient heavy oil extraction technologies to expand use of $CO_2$ in heavy oil production combining extractive efficiency goals with environmental $CO_2$ sequestration goals (Whittaker, 2015; Emadi et al., 2011; Gao et al., 2013).

One such strategy is known as VAPEX (vapor extraction). VAPEX has been extensively piloted in the field. It is based on phase transformation for vapor extraction without a necessity for heat addition (Butler and Mokrys, 1991; Upreti et al., 2007). As VAPEX technologies have developed, $CO_2$ addition has become prominent. VAPEX operates by the solvent action of horizontally injected solvent-gas "vapor chambers." These mobilize heavy oils on their expanding peripheries. This creates flow conditions for solvent-mobilized oil migration into adjacent horizontal extraction well systems. Efficient VAPEX injection schemes include $CO_2$ admixed with depressurization-recoverable light hydrocarbon gas co-solvents such as propane. Recent results have refined understanding of this method for field applications. In particular, recent research has found $CO_2$ to be an optimal co-solvent with propane (Tchambak et al., 2012; Torabi et al., 2012; Jahaveri, 2013; Bayat et al., 2015a,b,c; Mohammadpoor and Torabi, 2014, 2015a,b). A general advantage of $CO_2$ injection under both miscible and immiscible conditions is $CO_2$ absorption into heavy oil causing viscosity decrease and volumetric swelling. This creates reservoir pressurization and oil mobilization, increasing extraction performance (Klins, 1982; Sahin et al., 2007, 2012; Gao et al., 2013). Future developments are likely to utilize $CO_2$ across a range of cost-minimized injection technologies that simultaneously sequester $CO_2$ while producing heavy oils efficiently. $CO_2$ already can be utilized across a range of circumstances and technologies in heavy, waxy and asphaltene-rich oil production. A key economic factor apart from the market price of oil is the availability large quantities of pipeline-accessible low-cost $CO_2$ (Wei et al., 2015; Advanced Research International, 2006).

Examples of further innovations utilizing $CO_2$ in EOR include: (i) Carbonated Water Injection (Shu, 1982: U.S. Pat. No. 4,441,555, "Carbonated waterflooding for viscous oil recovery"; Perez et al., 1992; Sohrabi et al., 2011; Gao et al., 2013; Zuo and Benson, 2013; Mosavat, 2014; Seyyedi and Sohrabi, 2015); (ii) surfactant-generated $CO_2$ foams (Enik and Olsen, 2011; Sohrabi, 2012, 2013; Daraei et al., 2015; Sagir et al., 2015); and (iii) alkali (including sodium carbonate) stabilization of $CO_2$ foams (Farzaneh and Sohrabi, 2015). Carbonated Water Injection (CWI) has long been known to be a means of increasing reservoir porosity in carbonate host rock oil reservoirs (Holm, 1959). Success in oil recovery enhancement from $CO_2$ dissolving of carbonate host rock to increase porosity is well demonstrated in the Bati Raman field of SE Turkey (Sahin et al., 2007). CWI can be a useful method for liberating oil in low porosity reservoir sandstones cemented by calcium carbonate (Qiao et al., 2015).

$CO_2$ increasingly is being used as a fracking fluid to promote "tight" oil production from low-porosity sources. $CO_2$ and $CO_2$-admixed fluids used in such advanced fracking efforts exhibit certain advantages in some rock types for both gas and oil extraction (Schlumberger, undated; Praxair, undated; Song, 2013; Jacobs, 2014; Sorensen et al., 2014; Geiver, 2015; Fergus, 2015; Gong and Yu, 2015; Jung et al., 2015; Middleton et al., 2015; Yu et al., 2015).

$CO_2$ is utilized for enhanced recovery of natural gas. Enhanced Gas Recovery (EGR) proceeds by injection of $CO_2$ into gas fields for the purpose of re-pressurizing natural gas flow into extraction wells. The field has been researched for over 15 years (Oldenburg and Benson, 2001; Oldenberg, et al., 2001; Oldenberg, 2003a,b). It couples increased resource extraction with $CO_2$ sequestration. The basic process seeks to avoid mixing of natural gas with injected $CO_2$. The role of $CO_2$ is to pressurize methane along a moving front of expanding $CO_2$ from injection sites towards extraction wells (TNO, 2008; van der Meer et al., 2009; Hughes et al., 2012; Hussen et al., 2012; Honari et al., 2013, 2015; Kuhn et al., 2012, 2013; Khan et al., 2013a,b; Gou et al., 2014; Leeuwenburgh et al., 2014; Klimkowski et al., 2015; Kuhn, 2015). EGR research suggests it will be extended for use in the arena of "tight gas" (fracking-based extraction), (Li and Ellsworth, 2014; Kulga et al., 2014).

$CO_2$ similarly can be utilized by injection into deep coalbed deposits as a means of enhancing the extraction fraction of coalbed methane (CBM) while simultaneously sequestering $CO_2$ in a "$CO_2$-ECBM" process (Busch and Gensterblum, 2011; Godec et al., 2014; Li and Fang, 2014; Litynski et al., 2014). The technology has been shown to be effective, especially with special reservoir development involving co-injected nitrogen and involving other technologies to avoid porosity closure due to coal swelling from $CO_2$ absorption. Commercial takeoff of this form of $CO_2$ utilization, however, appears to require a carbon tax environment with sequestration credit payments (Sloss, 2015).

The European $CO_2$ Test Centre Mongstad ($CO_2$-TCM) is located near Bergen Norway on the site of Norway's largest oil refinery. A natural gas power plant is present within the industrial complex. The $CO_2$-TCM is one of the world's largest industrial joint ventures for development of large-scale $CO_2$ capture technologies (MIT, 2015b). CCU, however, was not a component of the venture until development of the "$CO_2$ to Bio Project" in 2011-2012 ($CO_2$BIO, 2012). $CO_2$BIO is focused on utilizing $CO_2$ as carbon source food input into photosynthetic algal biocultures to produce aquaculture feeds rich in the long-chain omega-3 lipids DHA and EPA. $CO_2$BIO project produced a report (Kleivdal et al., 2012) and a start-up company, $CO_2$BIO AS (www.co2bio.no). The initial agenda of the company is to create a piloting project at Mongstad. Norway is the world's leading nation in production and innovation in salmon aquaculture. Scientists and fisheries and government leaders recognize an important long-term strategic necessity for the development of very large-scale business-viable production of algae-derived omega-3-rich aquaculture feeds, especially for salmon. This is necessary to replace unsustainable and escalating use of forage fish for feeds. Escalating use of wild-caught forage fish for aquaculture/mariculture feeds is grossly harmful to the sustainability of world forage fish populations and their associated fisheries (Sorensen et al., 2011; Kleivdal et al., 2013; BlueBio, 2013; Reitan, 2013. See also: SARF, 2014). The Norwegian Parliament has granted US$1M to $CO_2$BIO in a research consortium to create a 350 square meter greenhouse pilot testing facility adjacent to the Mongstad $CO_2$-TCM. Construction was scheduled to begin in 2015 (Holm, 2015; Kleivdal, 2015). However, $CO_2$BIO perhaps is unlikely to create large-scale algal production operations adjacent to Mongstad. Mongstad therefore is not an example of a CCU-focused industrial eco-park.

Eco-Industrial Parks (EIPs, see Wikipedia entry and, Making Lewes, undated) are a widespread mode of industrial aggregation focused on systematic recycling of waste outputs into production inputs, often described by the term "industrial ecology" (Garner and Keoleian, 1995). To date, no EIP has been developed with a core focus on carbon capture utilization (CCU). A few examples exist of "industrial symbiosis" between paired companies. The Ulsan Eco-Industrial Park in Korea includes a linkage between a zinc plant producing waste $CO_2$ and steam, and a paper plant using $CO_2$ and steam. These plants are connected by a 3.8 km pipeline (Park, 2013). The Herdersbrug eco-industrial park in Belgium has qualified itself as "carbon neutral." However, it does not incorporate any CCU industrial activities (Block et al., 2011). The "Industrial Estate Moerdijk," in the Netherlands, includes an "Experimental Garden." This eco-park section connects $CO_2$-produced in a sewage incinerator with $CO_2$ use by the Swiss company, Omya. Omya produces precipitated fine calcium carbonate sold into the paper industry as a whitener pigment (GreenPort, 2009). Shell Chemicals also supplies waste $CO_2$ to Omya at this location (Royston, 2012). "Bioport Terneuzen" is an eco-park located in the Dutch port of Zeeland, between Antwerp and Rotterdam. It includes a coordinated $CO_2$ industrial symbiosis between several $CO_2$ and heat producers, including a Yara fertilizer plant, and a network of adjacent commercial greenhouses, "Glastuinbouw Terneuzen" (WarmCO$_2$, undated; Rijckaert, 2009; Nuhoff-Isakhanyan et al., 2015). Iceland's Svartsengi Geothermal Resource Park combines geothermal power and district heating operations connected with Carbon Recycling International's "George Olah $CO_2$ to Renewable Methanol Plant" (Prakash, 2013, 2014). CRI's methanol plant utilizes electrolytic hydrogen (using geothermal power) and geothermally-derived $CO_2$ flux from the powerplant (Hettinga, 2013; Sigurbjornsson, 2013). Industrial ecology parks based on $CO_2$ production linked with diversified utilization have been strategized (Meylan, 2015), and modeled (Norstebo et al., 2012). However, none thus far have been specifically designed.

$CO_2$ hubs may be defined as industrial methods, designs and realizations having three main components interlinked to each other. The first is one or more $CO_2$ sources. Sources may be natural, such as extraction from a drilled $CO_2$ well. Or they may be from natural source via an industrial separation process such as removal from natural gas in natural gas upgrading. Or $CO_2$ sources may capture $CO_2$ from industrial waste gas streams, for example by capture-separation of $CO_2$ from post-combustion exhaust of a powerplant. Sources inputting $CO_2$ into a hub system may involve combinations of any or all of these source types. The second component is that which connects the first component to the third component focused on utilization of $CO_2$. This second is the core of the hub. It is that which distributes and, if necessary beforehand separates and purifies $CO_2$, and if necessary stores and variously, as needed, compresses and/or refrigerates, the $CO_2$ obtained from sources. This is a system of tanks, pumps, compressors, gas treatment facilities, valve systems and pipelines. The third component is the sink for $CO_2$ utilization and/or sequestration. This involves methods, designs and realizations which sequester and/or utilize $CO_2$. Utilization involves industrial and/or agricultural and/or aquacultural use for purposes gaining economic utility from consuming a supply of $CO_2$. Thus far, all $CO_2$ hubs, strategized, planned or realized, principally are focused on $CO_2$ sequestration, $CO_2$-EOR, or greenhouse horticulture, or urea or methanol production. With the exception of the Green Pipeline system (which is geographically dispersed over a very long distance and is not per se a hub), no $CO_2$ hubs yet exist where the principle focus for $CO_2$ distribution involves a gathering together of industrial activities assembled for the purpose of waste $CO_2$ utilization different from providing supply for $CO_2$-EOR alone, or for greenhouse horticulture alone, or for $CO_2$-EOR and greenhouse horticulture in combination (as planned for the Port of Rotterdam), or for urea production alone, or for methanol production alone, or for calcium carbonate production alone. (For a partial global summary, see: Der, 2014, slide #9 and Haszeltine, 2015, slide 38.)

Rotterdam provides a city-centered model of a $CO_2$ hub linking captured $CO_2$ outputs from refinery and bioethanol production waste to agricultural use of $CO_2$ in greenhouse culture of flowers and vegetables (Rotterdam Climate Initiative, 2011; OCAP, 2012; van Engelenburg, 2012; Linde, 2013b, 2014; Ros et al., 2014; Port of Rotterdam, undated). The Port of Rotterdam's distribution network handles ~0.5 MTA $CO_2$. It supplies almost 600 greenhouses via a ~300 km network of pipelines. Greenhouse demand for the $CO_2$, however, is seasonal whereas $CO_2$ source output is roughly constant over time. Plans remain uncertain for a possible major scale-up called the ROAD project. ROAD aims to integrate the existing $CO_2$ hub with a new pipeline network for offshore subsea $CO_2$ storage linked with offshore $CO_2$-EOR (Carbon Capture Journal, 2014; Read et al., 2014; Read 2015a,b; Tillema, 2015). The City of Rotterdam's agenda is to develop the largest-scale $CO_2$ hub in Europe. The plan involves a network of companies called "CINTRA," an acronym for "Carbon In Transport," (CINTRA Factsheet, 2011). CINTRA is part of the ROAD initiative. ROAD is an acronym in Dutch for: "Rotterdam capture and storage demonstration." It is a sub-unit of the Rotterdam Climate Initiative (Tillema, 2015; Read, 2015a,b; van Tongeren, 2011; Radgen, 2015; Read et al., 2014; Neele et al., 2014; Singh and Haines, 2014; www.rotterdamclimateinitiative.nl; IEAGHG, 2015). The agenda for the CINTRA consortium is: (i) to create the Port of Rotterdam $CO_2$ hub linking incoming $CO_2$ from a network of onshore pipelines into a network of subsea offshore $CO_2$ pipelines, and (ii) also to create a capacity for loading of liquified $CO_2$ onto transport ships docking in the Port of Rotterdam (Loeve et al., 2013), and into the tanks of tanker trucks for road deliveries.

Creation of the type of capacity the Port of Rotterdam plans for diversified $CO_2$ delivery requires a compression pumping station with temporary storage for pressurized $CO_2$, as well as a refrigeration-liquefaction plant and adjacent storage tanks for liquid $CO_2$ sufficient in volume to allow rapid loading onto transport ships (Groensmit, 2010; van der Ben, 2011; de Wolff et al., 2013). An engineering overview for a $CO_2$ hub operating in a port is provided by Suzuki et al., (2013).

The Belgian Port of Antwerp is developing plans to reproduce Rotterdams's example. Antwerp hosts the largest integrated refinery complex in Europe (Callebaut, 2015). Most other European initiatives for large-scale CCU, are focused on CCS, variously linking North Sea $CO_2$ sequestration-storage together with $CO_2$-EOR opportunities. These efforts are reviewed by Kjarstad et al., (2014), Brownsort et al., (2015), and Scottish Enterprise—SCCS, (undated).

Links between $CO_2$ emitters and $CO_2$ utilization for greenhouse fertilization are widespread. Greenfield Specialty Alcohols (www.gfsa.com) of Chatham, Ontario (Canada) operates in a local industrial symbiosis with the greenhouse tomato grower Truly Green Farms (http://www.trulygreenfarms.ca). Ethanol production provides waste heat and $CO_2$ to the greenhouses (Jessen, 2013; GreenEnergyFutures, 2014). A similar situation exists in Sweden linking a distillery with a tomato grower (Advantage Environment, 2013). In 2015, the company Linde Gas Turkey commissioned a $CO_2$ purification and liquefaction plant to capture geothermal $CO_2$ from the Zorlu Energy geothermal power plant near Denizli to supply an initiative to create an "Organized Greenhousing Zone" in the region (Cockerill, 2015).

Temporary $CO_2$ storage associated with utilization is required for "dry fracking" of oil and gas extraction wells with $CO_2$. Injections of $CO_2$ to dry frack a single well may require up to 6,000 tonnes of $CO_2$ (Sears and Feve, 2014). Stored $CO_2$, if in refrigerated liquid form, typically is reheated before subterranean injection (Liebscher et al., 2013).

Capabilities for cryogenic capture and storage of gases can be an important mode in advanced powerplant operations. Cryogenic capturing of $CO_2$ can be useful for purification of input natural gas containing associated $CO_2$ in addition to being an effective means of capturing $CO_2$ in post-combustion exhaust. Cryocapture and storage of various gases, including $O_2$, $N_2$, $CO_2$, $CH_4$ and air, can be used as a means of high-efficiency power storage via Cryogenic Energy Storage, CES (see: Wikipedia entry: Cryogenic Energy Storage; www.highview-power.com; Highview Power Storage, 2014, 2017; www.dearman.co.uk; Center for Low Carbon Futures, 2013; Strahan, 2013; Brett and Barnett, 2014; Abdo et al., 2015; Morgan et al., 2015; Starns et al., 2015; Liquid Air Energy Network, undated; Tweed, 2015; www.keukaenergy.com; Zhang et al., 2015a,b; Chen et al., 2009; www.sesinnovation.com; Baxter, 2015, 2015 video, 2016a,b; Baxter et al., 2016; Safdarnejad et al., 2015; U.S. Pat. No. 9,410,736, Baxter, 2011, "System and Methods For Integrated Energy Storage And Cryogenic Carbon Capture"; Jensen, 2015; Ebahimzadeh, 2016; Fazlollahi, 2016; Fazlollahi and Baxter, 2015). Cryogenic production of such liquified gases by an Air Separation Unit (ASU) equipped with adjunct CES power generators can allow a powerplant to store and release energy as needed in order to vary its sales electricity output over time while producing power from its main power source at a continuous rate of output, if desired. If a powerplant operates with air cryoprocessing, as for example an oxyfuel powerplant does to provide $O_2$ gas into combustion, then such a powerplant can use CES to modulate its disposition of electric power over time. The plant uses its power output "internally" to build-up stored cryoenergy reserves. It then converts these cryoenergy reserves in times of high demand (and high prices) in order to maximize sales of electric power. CES systems store cryogenically liquified gases in one or more thermally insulated reservoirs. Additionally, a powerplant with cryogenic energy storage capacities can provide valuable grid-balancing services both for power intake and output. These can be useful especially for incorporation of renewable power inputs into an electric power grid. Wind and solar inputs, as well as small- and micro-hydropower inputs, often are highly irregular and unpredictable in time and scale.

Both liquefied oxygen and nitrogen are produced by an ASU if it is of the cryogenic type. Both gases can be sold as pressurized bottled and/or cryogenic gas products. Both can be utilized for cryogenic energy storage for electric power output modulation. Uses for pressurized or liquefied oxygen are many. Uses for pressurized and/or cold liquefied $N_2$ also are many. They include: (i) cooling-refrigeration, such as of a data center, or for transportation cooling food storage in trucks; (ii) fumigation of stored crops or of horticultural greenhouses overnight (by blowing-in an $N_2$ or $N_2$—$CO_2$ atmosphere to asphyxiate oxygen-respiring pests) with or without cooling; (ii) $N_2$-EOR, "waterless" $N_2$-fracking, and "waterless" $N_2$ cryogenic fracking (Higgins, 2015; Cai et al., 2015; Cha et al., 2015; Crawford, 2015); (iii) solvent switching in switchable ionic liquids using $CO_2$ as a switching gas and N$_2$ for return; (iv) canopy gas for algal biomass production in situations where avoidance of atmospheric O$_2$ is desired; (v) sparging gas for removal of O$_2$ and/or CO$_2$ from solution (Al-Mashhadani et al., 2012); (vi) numerous medical and laboratory uses; (vii) rapid deep freezing of foods; (viii) a carrier gas for chemically reducing uses of carbon monoxide, for example tin smelting; (ix) input into the production of chemicals, for example ammonia and urea; (x) for humane animal slaughter, (xi) pressurizing gas input for beer preparation, and (xii) cryogenic energy storage (CES).

Both gaseous and liquefied nitrogen gas (LN$_2$) is a byproduct of air separation by cryogenic air separation units used to obtain separated oxygen for purposes such as oxyfuel combustion. In the process of air separation, liquefied nitrogen is used to cool incoming air via heat exchange processes. This recycles cryo-energy and creates waste flows of pure N$_2$ gas that can be utilized. Excess liquid nitrogen also is created as a waste in so far as it does not need to be saved for use in oxycombustion. It can be vented to the atmosphere. This can be done as a means of generating electricity, utilizing cryo-energy. A power-generating turbine based on LN$_2$ runs by the expansion of liquid nitrogen into gas consequent of heat exchange with the ambient atmosphere. It uses the same logic and design as liquid air engines and power generators (https://en.wikipedia.org/wiki/Cryogenic_energy_storage; www.dearman.co.uk; https://en.wikipedia.org/wiki/Liquid_nitrogenvehicle). Additional efficiency-boosting aspects of integration of ASU nitrogen with an oxyfuel powerplant are described in Aneke and Wang, (2015).

Professor Larry L. Baxter of Brigham Young University, and several university collaborators and co-workers in a start-up company, SES Innovation (www.sesinnovation.com), have developed commercialized technologies for efficient cryogenic capture of CO$_2$ from coal-based power plant flue gases. Baxter's technologies connect CO$_2$ capture and storage with powerplant cryogenic energy storage. They allow the powerplant to operate with an efficient stable power output over 24 hour cycles while maximizing the sale of electricity at times of high demand (and higher sales price), minimizing electricity sales at times of lower demand (and lower sales prices). Such output variability can be supported by using electricity internally to build-up cryogenic coolant reserves at times of lower demand within the 24 hour cycle. Stored cryogenic reserves of cryo-energy then are utilized to produce power at times of high demand. Systems designed by SES Innovation also allow dry ice production, refrigeration of natural gas into LNG, and utilization of liquid nitrogen for power production in the case of power plants linked with Air Separation Units (ASUs) such as oxyfuel power plants (Baxter, 2015, 2016a, b; Safdarnejad et al., 2015; Fazlollahi et al., 2015; Ebrahimzadeh, 2016; Ebrahimzadeh, et al., 2016; a,b; Fazlollahi, 2016; Jensen et al., 2015; http://www.sesinnovation.com/technology/carbon_capture/ES/; Baxter, U.S. Pat. No. 8,715,401 B2, "Methods and systems for condensable vapors from gases"; Baxter, US 2013/0139543 A1, "Systems and methods for integrated energy storage and cryogenic carbon capture"; Baxter and Bence, U.S. Pat. No. 8,764,885 B2, "Systems and methods for separating condensable vapors from gases by direct-contact heat exchange"; Baxter, US 2011/0226010 A1, "Carbon dioxide capture from flue gas"; Baxter, U.S. Pat. No. 8,963,347 B2, "Methods and systems for generating power from a turbine using pressurized nitrogen"; Baxter: WO2013062922A1, "System and Methods For Integrated Energy And Cryogenic Carbon Capture"; Fazlollahi and Baxter, 2017; Fazlollahi et al., 2016a,b) The energy cost for CO$_2$ capture in Baxter and colleagues' latest model for application of their (bolt-on) technology to a coal-fired power plant is: 0.74MJe/kgCO$_2$ (Jensen et al., 2015). Cryogenic separation of associated CO$_2$ from natural gas also is a function that can be coupled with the cryogenic capacities noted above developed by Baxter and colleagues. Round trip efficiency for cryo-energy storage by LNG is expected to be able to exceed 95% (Park et al., 2017).

Cryogenic separation is the standard technology for obtaining large quantities of oxygen gas for industrial purposes such as oxyfuel combustion. However, another technology exists approaching large-scale commercial applicability. This is Ion Transport Membrane technology (ITM). The US company Air Products (www.airproducts.com) has developed and piloted a modular ITM technology. Progress to date suggests it may be capable of being scaled to a minimum ~2000 TPD output size module needed for clean coal oxyfuel powerplants (Repasky et al., 2012, 2013a,b, 2014; Anderson et al., 2011, 2015).

CCU is well developed in the greenhouse horticulture industry. It provides the carbon feed source for accelerated photosynthesis at enhanced CO$_2$ concentrations, typically 2× to 3× the present atmospheric concentration of 400 ppm (dry air molecular mole fraction). In the interval 1998 and 2003, the Dutch company Ecofys developed a "closed" greenhouse model incorporating a powerplant within the greenhouse system producing electric power, heat and CO$_2$ (Opdam et al., 2005; et al., 2005; Gelder et al., 2005). This created a CCU business model based on combining CO$_2$ production for horticulture with natural gas electric power generation using small powerplants installed individually within greenhouse complexes. The new mode of high-efficiency greenhouse horticulture spread rapidly (van der Veen, 2012). General Electric (GE), Cummins Engine, and Rolls Royce all offer natural gas-powered combined heat and power (CHP) generator systems for greenhouse use. These systems generate electrical power for greenhouse and heating and lighting and other operations. They also provide CO$_2$ from the engine's exhaust plus waste heat. Engine exhaust is cleaned of CO and nitrogen oxides (GE, undated; Commercial Greenhouse Grower, 2012). In the Netherlands, greenhouse businesses using CHP systems sell excess power locally or into the grid (Tasin, 2005; Campernolle et al., 2011; Clarke Energy, undated; Yates, 2012; De Wit, 2014; Power Engineering, 2014; GE, undated). CHP exemplifies profitable CCU. At cold times of the year when greenhouses need heat and often use artificial lighting, systems can have close to 100% utilization of the total chemical energy of the natural gas utilized by the CHP engine power generator. One example of a CHP user is the Dutch tomato growers cooperative "Prominent Growers" (District Energy, 2015). Another is the very large Thanet Earth greenhouse complex in SE England. Thanet Earth combines three different greenhouse companies, together utilizing GE CHP systems for combined power, heat and CO$_2$ (WSGA, undated). Another example is greenhouse tomato grower Springhill Nursery near Evesham in England. Springhill powers its CHP powerplant with biogas from on-site anaerobic digestion (HDC, 2014). Wright Salads, Ltd., of the Isle of Wight is another UK-based greenhouse grower using CHP systems (36 MW), (Bower, 2013). A prominent example in the USA and Canada is Houweling's Tomatoes. Howelings operates GE CHP-based greenhouses in Southern California (Yates, 2012) and BC Canada (Houwelings, undated). In 2014, Houwelings built a third high-tech greenhouse in Mona, Utah. This greenhouse is linked with power, waste CO$_2$ and heat from an adjacent power plant burning natural gas (Houweling's, 2014, undated; Abcarian, 2015). None of these systems, however, offer multi-product CCU platforming beyond horticultural products.

"Agriport A7" (http://www.agriporta7.nl; http://www.b-ezoekagriport.nl/en/home-2) is a Dutch coordinated private association cluster of greenhouse growers and related packaging and logistics companies operating on a very large scale: >1000 hectares. Agriport utilizes several GE CHP systems (Nuhoff-Isakhanyan et al., 2015; Smits, 2014; Buurma and Ruijs, 2011; Neville, 2009; Vale, 2008). It has expanded to include associated livestock, dairy and fish production. Agriport A7 additionally includes a 38-hectare Microsoft data center utilizing local electricity produced from natural gas. It provides waste heat into the greenhouse complex. Moreover, Agriport A7 has accreted a business park (Metropolitan Food Clusters, 2013). However, CCU has not been developed at Agriport A7 beyond the core industrial symbiosis connecting CHP systems with greenhouses.

The urban vertical greenhouse design company Plantagon offers an urban vision for greenhouse-linked CHP (Plantagon, undated, 2015).

$CO_2$ began to be used as a refrigerant system thermodynamic fluid in the 1850s. It became the dominant refrigerant for 100 years (Kim at al., 2004; Pearson, 2005; Austin and Sumathy, 2011; Harris, 2014). For over 75 years it has been known that heat engine $CO_2$ power cycles (that is, heat engines using $CO_2$ as a thermodynamic "working fluid") are potentially hyper-efficient and have great potential (Hochstein, 1940; Angelino, 1968; Feher, 1968; Yantovskii et al., 1993, 2009; Wall et al., 1995; Ausubel, 1999, 2004; Dostal et al., 2004; Bahamonde Noriega, 2012; Kim et al., 2012; DOE/NETL, 2012; Wright, 2012). Possibilities include fossil-fueled open system turbine power. Closed-cycle heat engine applications of $CO_2$ power cycle technology include solar-thermal power converters, nuclear power systems, geothermal power systems, hyper-efficient jet engines, and solar-electric propulsion (Brown, 2000; Ahn et al., 2015; Ausubel, 2004; Daniels, 2015; Colonna, 2016; Schuwer, 2015; Neises and Turchi, 2014; Rochau, 2011, 2014; Cleanenergyauthority, 2012; Lee et al., 2012; Wright, 2012; Wright et al., 2012; http://energy.sandia.gov/energy/renewable-energy/supercritical-co2/; McClung et al., 2014; Tahil, 2014; Yeom, 2015; USDOE, undated). The expected advantages of commercial development of $CO_2$ power cycle heat engines using supercritical $CO_2$ are astonishing. They include powerplant thermal efficiency boosting to ~70% with radical reduction in the volumetric size and complexity, hence cost, of turbo machinery. The volume of space taken up by machinery can be decreased by roughly a factor of ~100. This is consequent of a much higher density of the jetting supercritical fluid that transfers its flow momentum into the extracted rotational power of spinning turbine blade systems. Cost reduction scaling eventually should be by a factor of ~x0.1 or better (Rochau, 2014; Wright, 2012). Environmental advantages also are impressive via the possibility of compact Zero Emissions Power Plants (ZEPPs). These provide streams of nearly pure $CO_2$ waste for utilization and sequestration without any necessity for complicated, costly and energy-absorbing "$CO_2$ capture" from powerplant exhaust (Yantovskii et al., 1993; Ausubel, 1999; 2004; Foy and Yantovski, 2006; Yantovsky et al., 2009). In an oxyfueled ZEPP, whether using a supercritical $CO_2$ power cycle or not, the exhaust is a mixture of $CO_2$ and condensable water such that "$CO_2$ capture" is unnecessary. Only $CO_2$ sequestration or utilization is needed.

Commercialization of a closed $CO_2$ cycle system has been accomplished by the US company Echogen (www.echogen.com) for power production utilizing waste heat. Echogen supercritical $CO_2$ cycle systems add a second heat engine onto power systems to capture waste heat. This boosts efficiency via bolt-on Combined Cycle Power (CCP). The resulting output boosting is about one third on a constant fuel input basis (Persichilli et al., 2012; Held, 2014; Echogen, 2012, 2014. See also: www.tharenergyllc.com and Chordia, 2015).

Three start-up companies appear to be creating additional commercial supercritical $CO_2$ closed cycle heat engines. Peregrine Turbine Technologies, LLC, (www.Peregrineturbine.com), based in the State of Maine, USA, appears to be creating a compact power-generating multi-fuel turbine heat engine based on a closed supercritical $CO_2$ power cycle (Fishell, 2015; Valigra, 2015; Young, 2015). Supercritical Technologies, Inc., (www.supercritical.tech) based near Seattle, in the state of Washington, USA, appears to be creating a waste heat recovery unit with a diurnal load-balancing energy storage capability using the freezing and melting of water ice (Wright et al., 2014). Infinity Turbine (www.infinityturbine.com) appears to be developing a waste heat capturing heat engine.

The technology giant GE (General Electric) is developing a supercritical $CO_2$ power cycle turbine system. Initially, this development activity is focused in the area of converting solar-thermal energy into electricity (Allhart, 2016; Kalra et al., 2014; Hofer, 2016; Apr. 13, 2016 online video, "May carbon dioxide turbine address clean power generation?": https://www.youtube.com/watch?v=MsyUX4Qr5Vw).

Oxyfuel combustion technology has been developed for open cycle turbine power production fueled by natural gas (Foy and Yantovski, 2006; Jerica and Fesharski, 1995; Clean Energy Systems, 2006; Hammer et al., 2009; Revzani et al., 2009; Woolat and Franco, 2009; Yantovsky et al., 2009; Thimsen, 2014; Daniels, 2015; Hu and Yan, 2015; Stanger et al., 2015). Modern commercialized oxyfuel turbines burning natural gas can have high overall energy conversion (fuel to electricity) efficiencies approaching 60%, including the energy used to obtain oxygen, typically via an air separation unit, ASU. This high efficiency is retained with intake of fuel gas containing extremely high associated $CO_2$. Carbon dioxide then acts as the primary carrier gas or "working fluid" in the absence of the $N_2$ intake that accompanies air as the source of oxygen feeding into combustion. An oxyfuel turbine system burning natural gas with very high associated $CO_2$ and highly compressed intake represents an open supercritical $CO_2$ power cycle system. (NB: a non-combusting working fluid is needed to keep turbine temperatures low enough to be within an operational range. For combustion of pure methane with pure oxygen, the "flame" is too hot for containment and momentum transfer by flow through turbine fan blades.) The $CO_2$ concentration in methane fuel input gas in high thermal efficiency operations may exceed 93% by mass in a two-component fueling mixture. Water vapor also operates as an effective working liquid. Oxyfuel turbines utilizing an infeed of $O_2$ plus a $CH_4+(CO_2+H_2O)$ fuel mix exhaust a hot mixture of $CO_2$+steam. This may be used for various purposes directly or with various degrees of condensation of the water vapor.

Oxyfuel turbine systems operating commercially in the oil and gas arena have been developed by the US company Clean Energy Systems (www.CleanEnergySystems.com) in partnership with the German technology giant Siemens, and in concert with sales and field implementation by the Danish oil and gas production company Maersk Oil (Anderson, 2001; Anderson and Bischoff, 2003; Anderson et al., 2004, 2008, 2009, 2010, 2014; Siemens and Clean Energy Systems, 2006, 2012; Husted, 2009; Devanna, 2007, 2011, 2012, 2013; MacAdam and Anderson, 2007; MacAdam et al., 2007; Kapteijn et al., 2011, 2012; Clean Energy Systems, 2012; Hollis et al., 2012; Peters, 2012; Hende and Bek-Pedersen, 2012; Pronske, 2013; Alford, 2014; Maersk Oil, 2012, 2013; Maslin, 2014; Henni, 2014; Maersk Oil and CES, undated; www.cleanenergysystems.com; Several presentations and videos may be viewed at http://trigen.propeoplelabs.com). Maersk's initial "Trigen" system is a modified 43 MW Siemens turbine. Its power rating has been increased to ~150 MW running in oxyfuel mode with high-$CO_2$ fuel gas. The modified turbine is known as an "OFT900" (Clean Energy Systems, 2012 video).

A turbine system for power generation combining oxyfuel combustion with a supercritical $CO_2$ power cycle (hence with a highly compressed $CO_2$-rich fuel infeed) is being developed for application for various fuels, including natural gas, by a consortium including NET Power (https://netpower.com), 8 Rivers Capital, CB&I, Exelon, and the turbine-specialized Japanese technology giant Toshiba (Lu, 2014; Isles, 2014; Dodge, 2014; NET Power, 2013, 2015; Toshiba, 2013, 2014; Sasaki, 2014; Davison, 2015; 8 Rivers, 2015; Lignite Energy Council, 2015; Iwai and Itoh, 2015; Iwai et al., 2015). The technology is known as the "Allam cycle." It was developed by the British inventor Rodney John Allam, OBE, winner of the 2012 Global Energy Prize (Allam, 2013; Allam et al., 2013, 2014; Allam et al., 2013: U.S. Pat. No. 8,596,075, System and method for high efficiency power generation using a carbon dioxide circulating working fluid; Global Energy Prize, 2012, 2013; BBC, 2013). Allam cycle heat engines represent a massive breakthrough innovation for power generation efficiency, system cost, and environmental advantages. The Allam cycle uses $CO_2$ inflow as a powerful efficiency advantage. It therefore inverts the usual problem that high $CO_2$ inflow with methane fuel causes a decrease of power generation efficiency. Allam cycle power generating systems include two design types: (i) a single turbine version (Allam et al., 2013) and (ii) a double turbine version (Allam et al., 2014). Several additional patents by Allam and colleagues have been granted under 8 Rivers Capital, LLC as assignee. The design recycles exhaust $CO_2$ into the oxyfueled infeed gas flow. Thermal efficiency for natural gas fueling (including oxygen generation) with this exhaust recycling is expected to be ~59% (Tata, 2015). While Allam cycle technology is novel and advanced, capital costs for powerplants are expected to decrease because of the simplification and miniaturization effects of the supercritical $CO_2$ power cycle on turbine components.

Supercritical $CO_2$ power cycle heat engines are a promising new technology with wide application and a high technological readiness level. Echogen's line of closed-cycle engines entered the commercial power sector in ~2014. Field testing of Toshiba's 50 MW natural gas Allam cycle turbine engine is scheduled for ~2016. Toshiba's system, if successful, will offer $CO_2$ outputs suitable for Carbon Capture Sequestration (CCS) and Carbon Capture Utilization (CCU), —a winning combination. Supercritical $CO_2$ cycle heat engines offers participants entry into a new greentech power economy via a fundamentally superior technology relative to the classic use of steam in heat engines that has energized the industrialization revolution for over 300 years (Irfan, 2015). Linked with CCS and CCU, supercritical $CO_2$ power cycle technologies offer the possibility of widescale success of strategies developed in the EU over the past decade to develop ZEPPs: zero emissions electric power plants burning fossil fuels (cf., http://www.zeroemissionsplatform.eu/about-zep.html; ZEP, 2006, 2007; Hage, 2007). These technologies also represent a key step towards practical CCS in the US power generation sector. They have been recognized accordingly in overviews of the US Department of Energy's most recent Technology Readiness Assessment (DOE/NETL, 2015), and in its latest Quadrennial Technology Review (DOE, 2015a,b; Daniels, 2015; Orr, 2015; http://www.netl.doe.gov/research/coal/energy-systems/turbines/supercritical-co2-power-cycles; http://energy.gov/supercritical-co2-tech-team). The USDOE has supported the commercial realization of innovative oxyfuel turbine technologies since 2000 (Siemens, 2006; MacAdam and Anderson, 2007; Dennis, 2014). A global overview of research activities on supercritical $CO_2$ power cycles is provided in the PhD thesis of Monge (2014).

Additional modes of $CO_2$ utilization are many and varied.

$CO_2$ can be utilized to increase the value of coffee exports using a $CO_2$ packaging atmosphere. In comparison with green coffee stored in the traditional way in jute bags, bagging in sealed $CO_2$-filled bags has been demonstrated to increase quality evaluation scores for green coffee. Evaluation was made for specialty grade status after 12 months storage in hermetically sealed bags injected with $CO_2$ (Borem et al., 2013; Ribero et al., 2011).

$CO_2$ has long been used as an asphyxiating and poisoning agent for insect pests. It is especially useful as a non-pesticide "organic" agent for fumigation of silos and other harvest storage containers (Jay, 1971; Jay & Pearman, 1973; Ryan, 2008a; Timlick, 2014). $CO_2$ is applied either directly as an asphyxiant, or together with low $O_2$ (Neven 2003), or in combination with other specific poisoning agents such as phosphine ($ECO_2FUME$: Wilson, 2001; Cytec, undated; Valizadegan et al., 2014), ethyl formate (Vapormate™: Ryan and Bishop, 2003; Linde, undated), ethanol vapor (Arevalo-Galarza et al., 2010) and various insecticides (ENVIROSOL, Ryan, 2008b). $CO_2$ is widely used in Thailand as a storage insecticide applied to plastic-sealed bag stacks of rice (FFTC, 2004). This method also has been tested with excellent results in Spain (Rudevets et al., 2009; Pons et al., 2010) and Portugal (Carvalho et al., 2012). Grain storage utilizing $CO_2$ pest-control is practiced in China on large scale (Daolin et al., 2007), especially in combination with phosphine (Boaxing, 2008). Plastic silo bags are the world's newest grain storage technology. The world's largest storage facility using this technology is in Sudan. Silo bags are advertised to be pest-resistant. This is because grain respiration inside them uses up oxygen which is transformed into $CO_2$. This automatically creates a gas environment that kills insects (GrainSaver, undated). However, this process does not stop early infestations before $CO_2$ build-up. Direct injection of a $CO_2$ atmosphere into grain-filled silo bags before sealing has been demonstrated to be a successful insecticidal method by Milanesio, (2010, cited in Cardoso et al., 2012).

Vapormate™ is a combination of $CO_2$ with ethyl formate, noted above. It is widely used for insecticidal treatment of fresh fruit, vegetables and other commodities prepared for export (Linde, 2014). $ECO_2FUME$ is fumigant gas comprised of $CO_2$ with 2% phosphine gas (Cytec, undated).

$CO_2$ also has been developed as a solvent-propellent for outdoor industrial spraying of pyrethrum as a natural biological insecticide (Trade names: Pestigas, Turbocide, SupaPy. Ryan et al., 2015; www.supagas.com.au). This use was pioneered by the Tasmanian company Botanical Resources Australia, BRA. BRA is the world's largest pyrethrum grower (Ryan et al., 2015; http://www.botanicalra.com.au). CO$_2$ utilization relates to pyrethrum-based organic insecticide production in three ways. First, growth of Pryrethrum *chrysanthemum* plants (*Tanacetum cinerariifolium*) is enhanced substantially by CO$_2$ addition, with increased pyrethrin yield per plant and shortened the period of growth to harvest (Suraweera et al., 2015). Second, high-pressure CO$_2$ is used for extraction and refining of the insecticidal components in the dried flowers (details provided below). Third, pyrethrum insecticides may be purveyed in bottles of pressurized CO$_2$ acting as both a solvent and propellant, as noted above.

CO$_2$ has been proposed and tested as an overnight insecticidal fumigant for greenhouse horticulture in concentrations up to ~10% without harm to tomatoes. This method has demonstrated a ~50% kill rate on aphids (Goerke et al., 2005). It can be used in combination with N$_2$ for atmospheric replacement to exclude oxygen. This method has been used for fumigation to kill snails in orchid greenhouse culture (Pontaweesap et al., 2011). It is likely to be highly potent more generally for insecticidal fumigation.

CO$_2$ can be used for cold sterilization of milk, beer and juices by "cold pasteurization" (Garcia-Gonzalez et al., 2007; Spilimbergo et al., 2011; King, 2014). This method functions by means of "dense phase" CO$_2$ chemical interaction under high-pressure and without heat addition. High pressure dense phase CO$_2$ destroys the cell membranes of bacteria and/or yeast. The method was developed and tested for cold pasteurization of beer by the research group of Murat Balaban at the University of Florida (Folkes, 2004; Dagan and Balaban, 2006; Balaban: U.S. Pat. No. 6,994, 878B2; Balaban and Ferrentino, 2012). Balaban's work was done in association with commercialization by Praxair of a nearly identical method for cold-pasteurizing orange juice under process trademark "Better Than Fresh™" (Connery et al., 2005; Kincal et al., 2005; Fabroni et al. 2010). Taste testing showed no distinguishable taste differences from unpasteurized beer.

Many studies have validated the use of dense phase CO$_2$ for sterilization-pasteurization of milk without application of heat (Hotchkiss et al 2006: U.S. Pat. No. 7,041,327 B2; Werner and Hotchkiss, 2006; Hotchkiss et al., 2006; Damar and Balaban, 2006; Di Giacomo et al., 2009; Singh et al., 2011; Hongmai et al., 2014; Zhou et al., 2015; Bonnaillie and Tomasula, 2015; Ceni et al., 2016). This technology is fully ready for industrial application in situations where large quantities of food grade CO$_2$ are available at low cost (Hagemeyer et al., 2013: U.S. Pat. No. 8,563,067 B2). Low pressure CO$_2$ also is used as a milk preservative both for refrigerated raw milk (de los Reyes-Gavilan et al., 2005). It also is used in modified atmosphere packaging (MAP) to extend the shelf-life of pasteurized milk (Hotchkiss et al., 1999; Singh et al., 2011). CO$_2$ is a superior input for optimization-modification of the pH of milk for cheesemaking (Air Liquide, undated), Apple juice (Ferrintio et al., 2009; Yuk et al., 2010), carrot juice (Park et al., 2002) coconut water (Damar et al., 2009) and tomato paste (Parton et al., 2007) similarly can be sterilized by cold processing under pressure with dense phase CO$_2$.

Low-pressure CO$_2$ is utilized as a packing preservative in modified atmosphere packaging (MAP) of many types of food (Linde, undated; WITT, undated; Wikipedia: Modified atmosphere). Modified Atmosphere Packaging (MAP) utilizes CO$_2$ to extend the freshness timescale of various fruits and vegetables, often in combination with low O$_2$ (Mattos et al., 2012). Two examples where packaging in a CO$_2$-enriched (and low-O$_2$) atmosphere is known to add substantially to shelf-life and flavor development are mangos (Galvis et al., 2005; Ullah et al., 2009) and avocados (Kassim et al., 2013). Enhanced CO$_2$ is believed to suppress Krebs cycle enzyme reactions in these and other fruits (Kader, 1986).

CO$_2$ is a well-developed plant fertilizer input in greenhouse horticulture (Enoch and Kimball, 1986; Atwell et al., 1999; BOC, undated; Jablonski et al., 2002; De Gelder et al., 2012, 2014; Bishop et al., 2014; Rodriguez et al., 2015). The scale of the effect of CO$_2$ enhancement depends broadly on whether the plant utilizes a C3 or a C4 photosynthetic system (Taub, 2010; Sage and Zhu, 2011). Gains in C3 plants tend to be large. Sometimes they exceed a ×2 yield doubling. Gains from CO$_2$ use in typical greenhouse-grown C3 crop yields range from about a third for cucumbers and tomatoes (Atwell et al., 1999; Dannehl at al., 2013) to 60% for roses (BOC, undated; Beeson and Graham, 1991). Greenhouse technology gains, especially the development of low-ventilation quasi-closed systems, have driven a yield increase trend over decades. The trend is due to gains from growth under enhanced CO$_2$. Yields for tomatoes in Dutch greenhouses, for example, have more than doubled in two decades between 1983 and 2013: from ~280 tonnes of fresh tomatoes per hectare per year to ~625 tonnes (de Gelder et al., 2012, 2014; Selina, 2015). C3 tubers are expected to have an especially strong root crop yield response to enhanced CO$_2$ (Miglietta et al., 2000). For example, cassava root dry mass more than doubles with exposure to CO$_2$~1.5× atmospheric (Rosenthal et al., 2012). Other C3 tubers, such as Irish potatoes also respond to CO$_2$ fertilization with strongly enhanced growth (Haverkort et al., 2013; Miglietta et al., 2000), sometimes as high as ×2 (NIPCC, 2014). Sweet potato enhancements can be doubled (Czeck, 2014). Carrots, radishes and turnips exhibit tuber mass yield increases up to doubling (Idso and Kimball, 1989; Azam et al., 2013). Cotton (*Gossypium hirsutum* L.), a C3 plant, yields increase by more than 40% (Mauney et al., 1994). Ginger root (rhizome) mass more than doubles (Gaasemzadeh and Jaafar, 2011). The yield of the herb thyme (*Thymus vulgaris*) is more than doubled when grown under enhanced CO$_2$ (Tisserat, 2002). Thyme's active herbal substance thymol, when grown in air with ultra-highly enriched CO$_2$, exhibited 317× the concentration of thymol compared to thyme shoots grown in identical conditions except under normal atmospheric CO$_2$ (Tisserat and Vaughn, 2001). Yields from orange trees (C3) double (Kimball, 2013). Dutch growers claim eggplant (C3) yields are doubled (Rijckaert, 2009). Common beans (C3) exhibit yield gains of 77% under enhanced CO$_2$ (Bunce, 2014). Onion crops exhibit increases from 32% to 44% (Daymondi et al., 1997). Grape (C3) yields increase 36% (Kurooka et al., 1990). Orchid horticulture utilizes CO$_2$ in various special ways relating to the specialized ways orchids use CO$_2$ biologically via Crassulacean Acid Metabolism, CAM, with nocturnal carbon uptake (Gouk et al., 1997, 1999; Yong et al., 1999; Drennan and Nobel, 2000; Hew and Yong, 2004; Texiera da Silva, 2013). Some growth increase effects in orchids from extreme CO$_2$ enrichment have been observed to exceed a factor of twenty (Norikane et al., 2013). Vanilla (*Vanila planifolia*) is an orchid crop with obligate CAM metabolism. It is grown extensively in Uganda and Madagascar. Rice, a C3 plant, exhibits enhancements of ~20 to 35% with strong variability by both cultivar and temperature condition (Wang et al., 2015; Hasegawa et al., 2013; Baker et al., 1990). Some US strains have shown crop yield increases as high as 71% with elevated CO$_2$ (Baker, 2004). C4 corn/maize yield enhancements are substantial only in relation to increased drought resistance and fertilizer levels (Bunce, 2014). Enhanced sugar production from sugar cane (C4) with enhanced $CO_2$ is in in the range of ~20 to 30% (Madan et al., 2014). Banana and plantain (C3) biomass gains increase very strongly with $CO_2$ enrichment (Schaeffer at al., 1996, 1999). However, no detailed studies of fruit yields are published. The C3 bamboo species *Aulonemia aristulata* exhibits a very strong $CO_2$ effect with approximate doubling of biomass growth (Grambone-Guarantini et al., 2013). Seedlings of the C3 tree species *Eucalyptus grandis* and *Eucalyptus cladocalyx* F. Muell., also exhibit approximate doubling of biomass accretion with enhanced $CO_2$ (Conroy et al., 1992; Gleadow et al., 1998). Similarly, oil palm seedlings show very strong biomass growth response to excess $CO_2$. Photosynthesis rates are observed to triple with 3× atmospheric $CO_2$ (Ibrahim et al., 2010; Jaafar and Ibrahim, 2012; Ibrahim and Jaafar, 2012). Banana, for which waste can be used for paper production (Hussain and Tarar, 2014), is now grown commercially in greenhouses on a scale from 100 to 5,000 hectares per country in: the Canary Islands, Morocco, South Africa, Spain, Turkey, Israel and Cyprus (Gubbuk and Pekmezci, 2004).

Spain's large complex of greenhouses on the Mediterranean coast linked with a desalination plant near Almeria exemplifies the development of economic clustering dynamics in greenhouse horticulture (Perez-Mesa et al., 2015; Pardossi et al., 2004; FAO, 2013). About 30,000 hectares are under greenhouse cultivation adjacent to Almeria (Jackson, 2015; Pardossi et al., 2004). Annual revenues average about US$90,000 per hectare (Hortidaily, 2014). Greenhouse horticulture has a long record of success in boosting economic development in the Almeria region (Aznar-Sanchez et al., 2011). Greenhouse horticulture also has been a source of agro-industrialization in developing countries. Columbia is well known for a landmark early success in developing flower exports (McQuaid, 2011). Columbia's example has been followed by Mexico, Morocco, Kenya, and Ethiopia. Kenya now has three agri-export clusters: fish, coffee and greenhouse-grown flowers. Mexico has developed three fruit clusters in avocados, lemons and pineapples in addition to extensive greenhouse cultivation of tomatoes (Galvez-Nogales, 2010; Selina, 2015). China has been the most rapid large-scale developer of greenhouse production for food production. Almost 4 million hectares are estimated to be under some form of greenhouse protection in China (Yang, 2015). Ghana is considering developing high intensity greenhouse vegetables production with advisory assistance from Dutch expertise of Wageningen University (Saavedra et al., 2014). South Africa and Australia are also building-up their agriculture sectors in greenhouse production by collaboration with Dutch experts (de Visser and Dijkxhoorn, 2011; Bundock, 2010). Burney et al., (2010) have advocated agricultural intensification as an excellent strategy for $CO_2$ utilization for mitigation of atmospheric $CO_2$ build-up. Greenhouse horticulture, especially using $CO_2$ fertilization into new closed system air handling technologies, is potentially an attractive way to utilize $CO_2$ while simultaneously boosting food security and exports in developing countries. Greenhouse horticulture also can offer an attractive mode of labor market industrialization for farmers who have an innate appreciation for, and understanding of, plant cultivation. However, low-cost $CO_2$ typically is unavailable in developing countries.

The amount of $CO_2$ input for use in greenhouse horticulture relates to several variables. These include especially the desired degree of enhancement over atmospheric concentration and the rate of ventilation of air into and out of the greenhouse (Nederhoff, 2004). Some rough numbers are: (i) from the OCAP distribution network in Rotterdam (OCAP, 2012): ~400,000 tonnes $CO_2$ in a year supplied ~2,000 heactares of greenhouses for an average utilization of ~200 tonnes per hectare per year; and (ii) from Nederhoff (2004) in New Zealand: ~7.5 grams $CO_2$ per square meter per hour averaged over a 24-hour basis with a high-productivity focus: ~660 tonnes per hectare per year. Therefore, for 10,000 hectares, (a square: 10 km×10 km), an intermediate usage of ~400 tonnes $CO_2$ per hectare per year sums to ~4 million tonnes $CO_2$ utilization per year. Edwards (2008) provides a detailed treatment of $CO_2$ utilization in greenhouses based on the bio-intake basis of plant photosynthesis.

The use of $CO_2$ in the cultivation of medicinal ginseng root demonstrates a different type of biotechnological horticulture focused on very high value products. North American ginseng root takes several years to grow in the wild or under cultivation. It sells wholesale to Asian processors for a price exceeding US$2,000 per kilogram (Maher, 2014). Ali et al., (2005) demonstrated rapid growth of ginseng root tips in $CO_2$-enriched bioreactors, with strong increase in production of the specific phenolic substances desired for medicinal use. Ginseng also has been grown industrially in cell culture suspensions since the 1990s (Yesil-Celiktas et al., 2010; Thanh et al., 2014). $CO_2$ used in this manner acts as a stressor rather than as a photosynthetic carbon source in ginseng root growth in bioreactors (Kim et al., 2002).

Coffee plantlets have been grown in mass culture in enhanced $CO_2$ photoautotrophic conditions (Afreen et al. 2002), for example in temporary root immersion bioreactors by the company Nestle (Ducos wt al., 2007).

The anti-malarial drug artemisinin is produced by the plant, *Artemisia annua* L. Mass propagations of high-producing clones of this plant use an acclimatization step involving photoautotrophic growth with $CO_2$-enriched air (Supaibulwattana et al., 2011). The use of $CO_2$ in photoautotrophic micropropagation of plants is a well-known horticultural biotechnology (e.g., Hayadhi et al., 1993; Xiao et al., 2011). This technology uses $CO_2$-enriched air for transitioning and "hardening" young plants to survive post the changeover from heterotrophy to photoautotrophy. This can be done in so-called mist bioreactors. These bioreactors create rooted plantlets on a mass scale from liquid mass cultures of cell-derived plant embryo clones (Fei and Weathers, 2014). An example of a company producing agricultural products via this method is Rootec (www.rootec.com).

Potentially a very large scale use for $CO_2$ is as a carbon source in the production of microalgae (both prokaryotic cyanobacterial algae and eukaryotic algae, both microalgae and macroalgae). Algae is produced for various uses ranging from biofertilizer and beneficial crop innoculant (Benemann, 1979; Connelly, 2014; Wang et al., 2015; Prasanna et al., 2015; Rana et al., 2015; Renuka et al., 2015), to bioplastics input (Zeller et al., 2013), to bio-asphalt (Audo et al., 2015), to high-protein "superfood" (Hug and Von Der Weid, 2011; www.cyanotech.com; www.earthrise.com), to biofuel (Brennan and Owende, 2010; Lundquist et al., 2010; Benemann, 2013; E4Tech, 2014), to high-value nutraceuticals and pharmaceuticals (Fichtali and Senanayake, 2010; Cuellar-Bermudez et al., 2014; Stefan and Boussiba, 2014). $CO_2$ typically is diffused by bubbling in photobioreactors or into downflow bubble-diffuser trenches in circulating open pond systems of the Oswald type (Oswald, 1962, 1988; Richmond and Hu, 2013; Weissman and Goebel, 1987). Alternately, for pH above ~10, $CO_2$ input can be coupled with a cyclic pH-swing process. This process absorbs $CO_2$ by converting dissolved sodium carbonate into dissolved sodium bicarbonate. This is operated in a diurnal cycle that balances the pH decrease of $CO_2$ addition at night with the opposite process of pH increase driven by algal photosynthesis during the day (Chi et al., 2011, 2013).

Algal biomass processing can utilize $CO_2$ in various ways. Lee et al., (2015) have demonstrated a method for pressurized $CO_2$ to be used as a coagulation agent for algal harvesting. Supercritical and other forms of $CO_2$ can be used for product extractions from algal biomass (for example: Aresta et al., 2005; Soh and Zimmerman, 2011, 2012; Soh et al., 2014; Du et al., 2015; Goto et al., 2015). Of particular interest, low-energy-cost $CO_2$ switchable solvent systems have been proposed by Boyd et al., (2012) and Du et al., (2013, 2015) for lipids extraction from wet algal biomass.

$CO_2$ can be utilized industrially as a thermal energy transport fluid for efficient geothermal energy extraction. Low viscosity and a strong thermosiphon convective plume effect are the key physical advantages. $CO_2$ is injected in supercritical (deep pressurized) conditions as the working fluid for geothermal heat extraction, sometimes creating mixtures with circulating geothermal waters (Brown, 2000; Preuss 2006, 2008; Atrens et al., 2009a,b,c, 2010a,b, 2011a, b, 2014; Atrens and Gurgenci, 2013; Randolph, 2011; Randolph and Saar, 2010, 2011a,b,c, 2013; Global CCS Institute, 2011; Eastman and Muir, 2012, 2013; US 2011/0100002 A1; U.S. Pat. No. 8,991,510 B2; Randolph et al., 2013; Garapati et al., 2014; Eastman, 2014; Adams et al., 2014, 2015a,b; Ismail, 2013; Carroll and Stillman, 2014; Mohan et al., 2015; Xu et al., 2015; Plaksina and White, 2016). Attractively, this technology can be linked with geological sequestration of $CO_2$. Two US start-up companies are developing this technology: (i) Green Fire Energy (www.greenfireenergy.com) and (ii) Heat Mining Company LLC, apparently renamed TerraCOH Inc. (www.terracohage.com). Plans are afoot for possible future application in Australia (Xu et al., 2015). A first field trial has been made via a USDOE-funded partnership between the Lawrence Berkeley National Laboratory and the sc-$CO_2$ power cycle heat engine company Echogen. This trial tested geothermal energy extraction by $CO_2$-injection in the SECARB Cranfield CCS site in Mississippi (Krotz, 2011; Freifield et al., 2013, undated).

East Africa is a prime location for geothermal power in the context of continental rifting and volcanism. Kenya has ~600 MW of installed and operating geothermal power (https://en.wikipedia.org/wiki/Geothermal_power in Kenya). Kenya also has been utilizing geothermally associated $CO_2$ in its greenhouse horticulture industry, with waste heat utilized in pyrethrum drying (Mangi, 2013; Omeda and Simiyu, 2015). Rwanda aims to develop its geothermal energy resources.

$CO_2$ is used very widely in industry as a supercritical solvent (Srinivas and King, 2010; Peach and Eastoe, 2014; Hellivan, 2012; King, 2014). $CO_2$ has vast potential for future "tuned solvent" development used in combination with ionic liquids (Keskin et al., 2007). Supercritical $CO_2$ is an environmentally benign reaction medium for many forms of chemical synthesis (Tanchoux and Leitner, 2002). For example, botanical extractions using supercritical $CO_2$ (sc-$CO_2$) include: tea and coffee decaffeination (U.S. Pat. No. 4,260,639; Zosel, 1978; Lack and Seidlitz, 2012), extraction and refining of vanilla oleoresin and vanillin from vanilla beans (Nguyen et al., 1991; Castillo-Ruz et al., 2011; Runco, 2015), extracting insecticidal pyrethrum components (pyrethrin I & II) and oleoresin from dried pyrethrum flowers (Pan et al., 1995; Ryan et al., undated; Botanical Resources Australia Pty. Ltd., undated; Kiriamiti et al., 2003a,b, 2006), extracting hops flavor extraction from hops for use in the beer brewing industry (Schmidt et al., undated), extracting rose oil from roses (https://en.wikipedia.org/wiki/Rose_oil), extracting thymol from the herb thyme (Prado et al., 2009), extracting onion flavor oil from onion, extracting ginger flavor oleoresin from ginger root, extracting the anti-malarial drug artemisinin from the plant *Artemisia annua* (Padayatchi, 2004), extracting mango butter from waste mango kernels (Yimsiri et al., 2011; Jahurul et al., 2014), extracting and/or refining the high-value nutraceutical astaxanthin as an oleoresin from algal biomass (Cyanotech, 2015; King, 2013), as well as from krill and crustacean and copepod waste (Sanchez-Camargo et al., 2011, 2012, 2014; Ali-Nehari et al., 2012), extracting and purifying high-value omega-3 nutraceutical oils and anti-oxidant carotenoids from algal biomass (Natex, undated; Shen et al., 2011; King, 2013), extracting medicinal and nutraceutical triterpanoid-rich extracts from bamboo (Jiao et al., 2007; Lu et al., 2010; Nirmala and Bisht, 2015; Zhang et al., U.S. Pat. No. 7,811,997 B2, "Composition containing total triterpanoid sapogenins extracted from bamboo, and the preparation method and use thereof."), and extracting and purifying the blood-pressure-reducing flavonoid nutraceutical epicatechin from tea leaves (Bermejo et al., 2015), and cacao beans (Murga et al., 2000; Sarmento et al., 2008; Gadkari and Balaramanm 2015 King and Srivivas, 2014). Supercritical $CO_2$ can be used as a basis for simplified palm oil and palm kernel oil refining (Manan et al., 2009; Akanda et al., 2012; Mursillo and Bolanos, 2013; Setapar et al., 2014; Zaidul et al., 2007). Sc—$CO_2$ also allows extraction of valuable substances from palm oil such as beta-carotene, alpha-tocopherol (Setapar et al., 2014; Murcillo and Bolanos, 2013), and squalene (Stavroulias and Panayioyou, 2005; Popa et al., 2014, 2015).

Squalene ($C_{30}H_{60}$) is a bioactive nutraceutical (a triterpenic hydrocarbon) present in olive oil and palm oil and in the waste materials from processing of both (Ramirez-Torrez wt al., 2010). It is particularly enriched in amaranth seed oil: ~3 to 10% (He and Corke, 2003; Caselato-Sousa and Amaya-Farfan, 2012; Rodas and Bressani, 2009). Squalene has been shown to be extractable efficiently from palm oil, palm oil waste and from amaranth seeds using supercritical $CO_2$ (He et al., 2002; He and Corke, 2003; He et al., 2003; Westerman et al., 2006; May et al., 2009; Czaplicki et al., 2012; Norhidayah et al., 2012; Akgun et al., 2013; Wejnerowska et al., 2013; Yunus, 2015; Brunner et al. 2011: U.S. Pat. No. 8,048,462 B2, "Process for production of highly enriched fractions of natural compounds from palm oil with supercritical and near critical fluids"). Squalene appears to be a substantially beneficial dietary supplement (Spanova and Daum, 2011; Popa et al. 2014, 2015). It has a long history in traditional and neo-traditional medicine in Japan where it is obtained as shark liver oil. Squalene has been widely discussed as a likely causative agent involved in epidemiologically detected benefits of the "Mediterranean diet" via its presence in olive oil (Strandberg et al., 1990). In direct examination, it exhibits moderately well demonstrated cardiac and cancer prevention effects in humans (Spanova and Daum, 2011). For example, dietary supplementation has been demonstrated by clinical trial to have a similar scale of beneficial effect to conventional medical statin therapy, (substantially reducing bulk cholesterol and LDL, while increasing HDL). Dietary supplementation of squalene was found to act well in combination with statin therapy, generating a substantially synergistic effect on blood chemistry (Chen et al., 1996. See also: Hamadate et al., 2015).

"Amaranth" describes a plant genus with many species and varieties worldwide. As in the case of quinoa, agricultural use of amaranth seed began in pre-Columbian South America as a traditional food staple. Amaranth leaves are also cooked as a kind of spinach. Amaranth recently has become a part of a major trend in demand for gluten-free alternatives to wheat (Maisto, 2011; Caselato-Sousa and Amaya-Farfan, 2012; Coles, 2014; Wikipedia: "Amaranth grain"). The plant is abundant in Africa (Cernansky, 2015), especially in Rwanda. Due to its rapid growth and abundantly leafy form (often as a weed), it is known there as "the plant from the gods" and goes by the name "dodo" (Todd, 2013). The food company Innovesca (www.innovesca.com) has initiated efforts to industrialize Rwandan amaranth. Squalene extraction from amaranth seed is an example of ways supercritical $CO_2$ can be utilized strategically in new market creation. Extracting high-value nutraceutical oil from amaranth seed leaves behind a defatted protein-rich secondary product.

Supercritical $CO_2$ can be used as a solvent for tire recycling by devulcanization of tire-derived "crumb" rubber particles containing the carbon black component added to manufacture tires (Zhang, 2002; Zhang and Tzoganakis, 2004; Tzoganakis, undated; Meysami and Tzoganakis, 2009; Meysoumi, 2012; McCoy, 2015; U.S. Pat. No. 7,189,762 B2, Tzoganakis, "Method of modifying crosslinked rubber"). This process has been industrialized by the Canadian company Tyromer (www.tyromer.com) in a partnership with the rubber supplier Airboss Rubber Compounding (CNW Group, 2015). Industrial routinization of this technology may offer the possibility to manufacture new tires using components of recycled material.

Supercritical $CO_2$ can be used to recycle polystyrene waste such as styrofoam packaging material. Polystyrene recycling can use waste polystyrene to create new molded styrofoam packaging materials. The production of many packaged exports requires the availability of use-specific molded styrofoam packaging. The new technology is described in the PhD thesis of Cristina Munoz Gutierrez of the University of Castilla-La Mancha, Cuidad Real, Spain (Gutierrez, 2014), and in several associated papers (Gutierrez et al., 2010, 2012, 2013a,b,c, 2014a,b,c, 2015). The technology has four main process stages. Polystyrene waste is first dissolved in limonene to separate it from associated non-dissolving waste. Second, supercritical $CO_2$ is used as an anti-solvent to remove most of the limonene from polystyrene, (which precipitates with some admixed limonene). Third, $CO_2$ is used as a foam-forming blowing agent to form new molded polystyrene foam parts by pressure absorption and depressurization. Fourth, $CO_2$ is used as a wash to clean remnant limonene from the polystyrene foam.

Supercritical $CO_2$ extraction is a high-yield, low-waste, energy-efficient method to obtain limonene from citrus peel wastes (Read, 2009; McKenzie et al., 2004; Atti-Santos et al., 2005; Ferhat et al., 2007; Suetsuga et al., 2013). Limonene is a widely produced natural product. It has well-known uses in cosmetics, perfumes, as a natural biocide, and as an input into a wide variety of chemical synthesis reactions in the new bioeconomy (Ciriminna et al., 2014).

Limonene oxide is produced by reaction of limonene with $O_2$ in supercritical $CO_2$ as reaction medium (Corazza et al., 2003; Lima et al., 2005). Limonine oxide and $CO_2$, in turn, are copolymerizable into the high-quality CCU bioplastic, limonene polycarbonate (Byrne et al., 2004; Yang et al., 2005; Scott, 2006; Bahr et al., 2012; Hauenstein et al., 2015).

A new mode of biorefinery uses high-pressure $CO_2$ as a biosolvent and bioprocessing liquid in various combinations, also in mixtures with water and ethanol (King and Srinivas, 2014; King, 2014; Schievano et al., 2015). Prominent supercritical $CO_2$ specialized companies pioneering such uses include: (i) Evonik (Evonik, undated website materials), the company that pioneered tea decaffeination, (ii) NATECO$_2$ (www.nateco2.de), which pioneered extraction of hops extracts for the beer industry, and (iii) Fayecon (www.fayecon.com), which has pioneered a wide range of industrial uses of supercritical $CO_2$. Supercritical $CO_2$ offers a way to separate foodstuff substances "toxin-free" in the absence of residual organosolvent toxins (commonly hexane). This allows both the extracted and residual components to be marketable on this basis, as noted above for amaranth seed. Further examples include: (i) decaffeination of tea and coffee to provide decaffeinated products as well as marketable natural caffeine used in the caffeination of beverages, and (ii) defatting of whole macadamia nuts to provide macadamia oil and diet macadamia nuts (Silva et al., 2008). Separated caffeine has market value. It is a natural biopesticide. It is especially effective against slugs, snails and frogs (Hollingsworth et al., 2002, 2003; Kim et al., 2010; Raloff, undated). Supercritical $CO_2$ also can be used to separate whey protein isolate from whey waste from cheese-making (Bonnaillie and Tomasula, 2012; Yver at al., 2012). Whey protein isolates are popular protein additives to high-nutrition health drinks. Rice can be processed with milling and sc-$CO_2$ treatments into a main component of ultra-purified white rice (RiceMate, undated). Supercritical $CO_2$ processing can produce several bran-based biproducts including rice bran oil, fiber- and protein-rich defatted bran, and the nutraceuticals γ-oryzanol and tocopherol (King, 2014; Natex, undated; Tomita et al., 2014).

$CO_2$ is utilized as a non-CFC-based heat transfer refrigerant fluid in cooling systems (Belman-Flores et al., 2014; Sarkar, 2012; Cavallini, 2004; Evans, 2010). This technology is being extensively commercialized in the supermarket refrigeration sector.

$CO_2$ is utilized commercially as a cryogenic refrigerant. Dry ice allows $CO_2$ to be utilized as a cargo transport coolant. Dry ice can provide off-grid refrigeration linked with the delivery of kegs of beer and other beverages. Dry ice chilling therefore can allow draft dispensing from kegs, thereby avoiding the expense of bottles and bottling on off-grid locations. Cold liquified $CO_2$ also is used as a refrigeration coolant in the trucking sector (Tassou et al., undated). This method has ecological and cost advantages over diesel engine-based refrigeration systems if liquid $CO_2$ is captured from industrial exhaust, and if it is purified/compressed/cooled efficiently (Thermo King, undated; Sustania 100, 2013).

Solidified $CO_2$ or "dry ice" has been commercialized since 1925 and has many uses. It can be useful as a way to provide refrigeration to off-grid locations connected with periodic delivery of food and beverage supplies requiring cool storage (FPA, 2006; http://www.dryicesouthafrica.co.za). Typically, dry ice is manufactured from pressurized liquid $CO_2$ by Joule-Thompson depressurization cooling (Rusli et al., 2014). This is wasteful of both energy and $CO_2$ unless recycled. An alternate efficient method is to manufacture dry ice blocks by cooling liquid $CO_2$ in block molds (Eastman, U.S. Pat. No. 2,138,758, "Manufacture of carbon dioxide ice"). This method can be practiced in locations where large-scale cryogenic facilities are available.

Compressed $CO_2$ is utilized as for industrial blasting in situations of flammability danger such as coal mines and silo blockages. The company "Cardox" manufactures systems for these purposes (Cardox. Undated).

Liquid/supercritical $CO_2$ is used for water-free, waste-free dry cleaning of clothing using a variety of surfactant additives and mechanical washing modes (www.solvaircleaning-.com; www.tersussolutions.com; Taylor et al., 2000; DeSimone, 2002; Stewart, 2003; van Roosmalen, 2003; van Roosmalen et al., 2003a,b; Sutanto, 2014; Sutanto et al., 2014a,b; CompanyWeek, 2015). This technology was patented and industrialized in the 1990s (Taylor et al., 2000; DeSimone et al., U.S. Pat. No. 5,783,082, "Cleaning process using carbon dioxide as a solvent and employing molecularly engineered surfactants." Iliff et al., U.S. Pat. No. 5,412,958, "Liquid/supercritical carbon dioxide/dry cleaning system.").

Supercritical $CO_2$ is used industrially for water-free and waste-free dying of textiles (www.dyecoo.com; Knittel et al., 1993; Saus et al., 1993; Montero et al., 2000; Bach et al., 2002; van der Kraan, 2005; DyeCoo, 2010; Liao and Chang, 2012; Yeh Group, undated; Huntsman, 2013).

Supercritical $CO_2$ is used for dehydration-drying (Brown, 2010; Brown et al., 2008, 2010; Khalloufi et al., 2010; Benali and Boumghar, 2014; Hofland, 2014; Wikipedia entry: Supercritical drying). This is a new technology in specific application to foods drying. It is being industrialized by the Dutch company CO2DRY (www.co2dry.com), created by Feyecon (www.feyecon.com; Feyecon, undated; Agterof et al. U.S. Pat. No. 8,187,655 B2, "Dehydration method."). Supercritical $CO_2$ can dehydrate foods at temperatures not higher than 35 degrees centigrade. Water absorbed into supercritical $CO_2$ can be removed by membrane separation methods (Koziara, undated; Lohaus et al., 2015).

Supercritical $CO_2$ is used as a replacement diluent-solvent for paint and adhesives spraying with ~80% reduction of environmentally harmful volatile organic compounds (VOCs). This process was industrialized by Union Carbide in ~1990 using the process trademark, "UNICARB" (Busby et al., 1990; Nielsen et al., 1993; Copeland, 1994; Lewis et al., 1997; Donahue, undated; Lee et al., U.S. Pat. No. 5,027,742, "Supercritical fluids as diluents in liquid spray applications of coatings." Hoy et al., U.S. Pat. No. 5,203,843, "Liquid spray applications of coatings with supercritical fluids as diluents and spraying from an orifice.")

High pressure $CO_2$ is used for a variety of broadly related methods for spraying applications to generate fine powders, aggregates and micro-encapsulations. The simplest method is depressurization-precipitation from pressurized $CO_2$ solvent solutions. It is known as the Rapid Expansion from Saturated Solutions, (RESS) process. Examples include the formation of fine particulate sprays of chocolate-rich and cocoa butter-rich particles onto fine confectionary foods (Letourneau et al., 2005, 2007). Other related methods identified by acronyms and utilizing high-pressure $CO_2$ include: the Supercritical Anti-solvent (SAS) process, the Particles from Gas Saturated Solutions (PGSS) process, the Concentrated Powder Form (CPF) process, the Continuous Powder Coating Spraying (CPCSP) process, the Carbon dioxide Assisted Nebulization with a Bubble Dryer (CAN-BD) process, the Supercritical Enhanced Atomization (SEA) process, the Supercritical Fluid Assisted Atomization (SAA) process, the Depressurization of an Expanded Liquid Organic Solution (DELOS) process, the Gaseous Anti-Solvent (GAS) process, the Aerosol Solvent Extraction (ASES) process, and the Solution Enhanced Dispersion by Supercritical Fluids (SEDS) process (Lack et al., 2005; Nunes and Duarte, 2011). These $CO_2$-utilizing technologies have many applications across a range of business areas such as foods, nutraceuticals, cosmetics and pharmacological/medical products manufacture. These methods noted above have been widely reviewed (Lack et al., 2005; Martin and Cocero, 2008; Cocero et al., 2009; Maryin et al., 2010; Augustin and Hemar, 2011; Kalani and Yunus, 2011; Khosravi-Darani and Mozafari, 2011; Montes et al., 2011; Munin and Edwards-Levy, 2011; Nunes and Duarte, 2011; Onwulata, 2012; Priamo et al., 2013; Santo et al., 2013; Fahim et al., 2014; Natu and Every, 2014; Silva and Meireles, 2014; Mishra, 2015).

Tea (Camellia sinensis) is a significant global crop with relevance for $CO_2$-based value-add processing into nutraceuticals and pharmacological treatments using supercritical $CO_2$. This is for differential caffeine and polyphenols extractions as well as via the particle trapping and encapsulation methods noted above (PGSS method) for powdered products. These methods are important for efficient capture of polyphenols in tea into nutraceutical products (Sajilata et al., 2008), particularly its abundant oxygen-sensitive medically beneficial catechins (Liu et al., 2015). For efficient processing, tea polyphenols need to be protected against oxidative destruction in both production and storage (Meterc et al., 2007, 2008; Sosa et al., 2011; Gadkari and Balaraman, 2014). Dietary intake of tea polyphenol flavanoids is known from numerous human studies, including numerous double-blind placebo-controlled clinical trials, to increase in human health by a variety of effects including blood pressure reduction, favorable blood lipids modulation, and glucose/insulin control (Liu et al., 2013; Onakpoya et al., 2014; Peng et al., 2014; Sonoda et al., 2015). An example of a former tea estate transformed into a nutraceutical production site is the Senteeko Estate of Mpumalanga, South Africa (SAASTA, 2014).

Mango peel waste and mango leaves have been recognized as another source of catechins-rich polyphenols suitable for nutraceuticals production (Maslbo and He, 2008; Jahurul et al., 2015). Supercritical $CO_2$ extraction has been demonstrated to be an effective extraction method (Pereira and Meireles, 2007; Garcia-Mendoza et al., 2015).

Eucalyptol (1,8-cineole) is the main compound present in *eucalyptus* oil. Along with various phytonutrients, it can be extracted efficiently using supercritical $CO_2$. Extracts are obtained from leaves of several different *Eucalyptus* tree species (Milner et al., 1997; Francisco et al., 2001; Zhao and Zhang, 2014). *Eucalyptus* leaves are an ancient traditional medicinal remedy of the Aboriginal peoples of Australia. The first medicinal *eucalyptus* oil was produced for sale in Australia in 1852: "Bosisto's Parrot Brand *Eucalyptus* Oil." This product may have been Australia's first novel indigenous export product. It is still produced and sold today (Abbott, undated; Kruszeinicki, 2015). Use of *eucalyptus* oil as an inhalant for relief of nasal and throat congestion spread rapidly in Europe and the United States (Fox, 1927). *Eucalyptus* oil continues in this use to the present, along with menthol and camphor. More recently, nutraceutical substances have been obtained from *eucalyptus* leaves by supercritical $CO_2$ extraction and Supercritical Anti-Solvent (SAS) particle formation methods (Chinnarasu et al., 2015).

The sweet potato tuber is the most productive food crop grown in the tropics when considered in terms of edible energy yield per hectare (Woolfe, 1992). Sweet potato is in the seventh largest food crop worldwide. It is grown predominantly in developing countries and very extensively in Sub-Saharan Africa. The leaves of the sweet potato plants are protein-rich (25 to 30%, An et al., 2013), widely eaten cooked in Asia, and contain high-levels of medicinally beneficial phytonutrients, typically exceeding those of kale and spinach (Islam et al., 2002; Islam, 2006; Menelaou et al., 2006; Truong et al., 2006; Lako et al., 2007; Johnson and Pace 2010; Karna et al., 2011; Nagai et al., 2011; Ghasemzadeh et al., 2012; Hue et al., 2012; Gundala et al., 2013; Luo et al., 2013; Mohanraj and Sivasnakar, 2014; Sani et al., 2014; Sun et al., 2014; Praderio, 2015; Dorman, 2015; Xi et al., 2015). Hence sweet potato can be cultivated on a "two-for-one" basis, harvesting both leaves and tubers. Leaves may be harvested by pruning during the period of tuber growth and also by co-harvesting leaves and stems at the time of tuber harvest. Sweet potato leaf phytonutrients are efficiently extractable by supercritical $CO_2$ (Chen et al., 2011). The residue of $CO_2$ extraction processing of sweet potato leaves is a low-fat, high-fiber, protein-rich, marketable powder. Separated sweet potato phytonutrients were commercialized in 2007 under the brand name "Toyo-KanSho" by the company Toyo Bio-Pharma (Nutraceuticals World, 2007; Yoshimoto et al., 2005; Shimada et al., 2010).

High-pressure $CO_2$ can be used for efficient "green" processing of harvested *stevia* (*Stevia rebaudiani*) leaves to obtain non-caloric *stevia* glycoside food sweeteners. These sweeteners are much-favored by diabetics and dieters worldwide. They are sold directly and in many food preparations as sugar-substitutes under a variety of trade names. The sought after molecules principally are two: (i) stevioside (typically ~6% by weight in the dried leaf), and (ii) a more valuable but less abundant (~1.5%) molecule: rebaudioside A. Rebaudioside A is the most sought-after substance. It has a taste most similar to sucrose with the least aftertaste. $CO_2$-based extraction methods for *stevia* initially were developed in Japan. German and US patents followed, for example: U.S. Pat. No. 5,112,610, U. Kienle, 1990, "Method of making a natural sweetener based on *Stevia rebaudiana*, and use thereof." In a first stage of processing with carbon dioxide, according to Kienle's method, supercritical $CO_2$ can be used as an initial washing step in order to remove several Sc—$CO_2$ extractable bitter phytonutrient substances from *stevia* dry leaves or dry leaf powder, leaving the ($CO_2$-insoluble) *stevia* glycosides behind with the leaf material. In a second stage of processing, supercritical $CO_2$ together with polar co-solvent water and/or ethanol or methanol admixed can be used to extract *stevia* glycosides from the pre-cleaned powder. Extraction by supercritical $CO_2$ in the presence of polar co-solvents can yield equivalent or superior yields relative to conventional water extraction (Nishiyama et al., 1992; Pasquel et al., 2000; Yoda et al., 2003; Erkucuk et al., 2009; Abou-Arab et al., 2010; Lemus-Mondaca et al., 2012; Abadalbasit et al., 2014; Jentzer et al., 2015). Third, decrease of the pressure and temperature conditions of the supercritical mixed solvent from step 2 can obtain a sub-critical liquid-liquid phase separation. *Stevia* glycosides then are present in the non-$CO_2$ phase dissolved in water and/or ethanol or methanol. *Stevia* processing with $CO_2$ thereby also can allow separation and collection of valuable components of *stevia* leaf phytonutrients and related substances from the first and/or third stages of processing noted above (Pasquel et al., 2000; Yoda et al., 2003; Yildaz-Ozturk at al., 2015).

High-pressure $CO_2$ has been demonstrated to provide an environmentally benign replacement for water in several steps in the industrial processing of animal skins into tanned leather (Perre et al., 2003; Hu and Deng, 2015). Water-based tanning is a high pollution intensity process. High-pressure $CO_2$ functions as a green solvent in the processes of deliming (Yang et al., 2009), enzymatic unhairing (Li et al., 2007), degreasing (Marsal et al., 2000), and tanning (Renner et al., 2009, 2012; Onem et al., 2015).

Small pressurized $CO_2$ reservoirs are used for propellant release firing in paintball guns. These guns are used for military training and recreational sport (Kingman Group, undated).

Gaseous $CO_2$ has a range of medical uses. Inhaled, it can modulate respiration and consciousness. Breathing $CO_2$ has potent anesthetic effects under certain conditions relative to oxygen levels. $CO_2$ is said to have been the first gaseous anesthetic used surgically almost 200 years ago (Duncum, 1947). It was used in human anesthesia in combination with other anesthetic agents into the mid-20$^{th}$ century. Today $CO_2$ is used as an anesthetic in the humane slaughter of animals. This is by anesthetic "stunning" followed by "controlled atmosphere killing." This combination of methods is commended by the organization PETA (People for the Ethical Treatment of Animals, PETA, undated). $CO_2$-based anesthetic slaughtering is widely used, especially with pigs (Holst, 2001; MPS, undated; Butina, undated; SFK Leblanc, undated). Chicken processors increasingly are using $CO_2$ stunning systems (Praxair, undated; Neuman, 2010; Meyn, undated), winning PETA commendation. Reviews are provided by Lombolt (undated), Grandin (2013), and Grandin and Smith (undated). A home-built system for small farm use is described by Rice et al., (2014).

Large scale industrialization of methods utilizing $CO_2$ to produce sodium carbonate ($Na_2CO_3$) and bicarbonate ($NaHCO_3$) has been in existence since the 1860s. The ammonia-soda process was industrialized by the Belgian chemist Ernest Solvay (https://en.wikipedia.org/wiki/Solvay_process; https://en.wikipedia.org/wiki/Ernest_Solvay), founder of the Belgian chemicals giant Solvay S.A (www.solvay.com). Similar methods were developed by the chemist Ludwig Mond (https://en.wikipedia.org/wiki/Ludwig Mond), co-founder of the British chemicals giant Imperial Chemicals Industries (ICI), now owned by Tata. The Chinese chemical engineer Hou Debang (https://en.wikipedia.org/wiki/Hou_Debang) later developed a more efficient variant known as the modified Solvay process. Debang's process avoids limestone input and gains ammonium chloride (a fertilizer) output with ammonia input. Recently, a new greentech variation on the ammonia-soda process was described by the Swiss chemist Martin Forster: the "$MgCl_2$/MgO modified ammonia soda process" (Forster, 2012, 2014). Forster's method utilizes solar thermal energy or low-grade heat (~525 C). It has the overall process formula: $2NaCl+H_2O+CO_2 \rightarrow Na_2CO_3+2HCl$. It therefore co-produces hydrochloric acid and does not require limestone input. Provided low-cost NaCl salt input is available, processes of this type can utilize $CO_2$ industrially to produce sodium bicarbonate and/or sodium carbonate along with hydrochloric acid.

Sodium bicarbonate ($NaHCO_3$) has been manufactured industrially by $CO_2$ carbonation of sodium carbonate since the mid-19th century. The method utilizes natural deposits of sodium carbonate ($Na_2CO_3$, "soda ash"), natron ($Na_2CO_3.10H_2O$), trona ($Na_2CO_3.2H_2O.NaHCO_3$), and also natural alkali brines (Wikipedia: "Sodium Bicarbonate"; Church & Dwight, website; Howe, 1928; Mineral Information Service, 1959; Garrett, 1995; Kostick, 1992, 1998; Cho et al., 2008). Deposits of soda ash, natron, trona, and associated alkali brines, are found on a very large scale in the state of Wyoming in the USA, and also in Turkey, China, Egypt, Sudan, Ethiopia, Botswana, Kenya, and Tanzania. Carbonation with $CO_2$ and water to produce sodium bicarbonate follows the exothermic low-temperature chemical reaction: $Na_2CO_3+H_2O+CO_2\rightarrow 2NaHCO_3$, (with precipitate composition control dependent upon temperature and $CO_2$ concentration. Eugster, 1966; Lowenstain and Demicco, 2006). Industrializations of this process utilizing the minerals noted above, and alkali brines, are extensive. Industrial processes have been widely patented beginning at least by 1911 (Wrinkle and Paddock, 1911: U.S. Pat. No. 1,000,138, "Method of obtaining bicarbonate of soda"). Substantial recent focus has been on the use of the Na-carbonate system in the capture of $CO_2$ in flue gases. Technology developments for $CO_2$ capture include sodium bicarbonate production (Huttenhuis et al., 2015) as well as cyclical processes of $CO_2$ capture and purification from powerplant flue gases via carbonation-hydration of sodium carbonate to produce sodium bicarbonate as a $CO_2$ capture process. This is followed by a regeneration step of decarbonation-dehydration back to sodium carbonate, yielding purified $CO_2$ (Liang, 2003; Liang et al., 2004; Nelson et al., 2009; Ficicilar and Dogu, 2006; Knuutila et al., 2009, 2010a,b; Spigarelli and Kawatra, 2013; Zhao et al., 2013; Stolaroff and Bourcier, 2014).

High pH alkaline brines (rich in sodium carbonate) are strong $CO_2$ absorbers from the atmosphere. They exhibit very high productivity for algal biomass growth of the "soda lake" type. $CO_2$ absorption lowers the pH of the brine, whereas photosynthesis raises it. This is the consequence of a pH-dependent transformation of the ion balance. There are two $Na^+$ cations per $CO_3^{2-}$ anion at higher pH, whereas $Na^+$ cations are balanced by one $HCO_3^-$ anion each at lower pH. Photosynthetic growth of algal biomass transforms carbon from bicarbonate anions into organic matter, causing an increase in pH. This is because algal cells capturing $HCO_3^-$ anions as a $CO_2$ source regulate pH by importing $H^+$. They do so in response to the $H^+$-consuming (and thereby $OH^-$-producing) equilibrium governing photosynthetic utilization of the bicarbonate ion as a carbon source: $H^++HCO_3^- \leftrightharpoons CO_2+H_2O$. As photosynthesis consumes $CO_2$ and boosts the pH in the medium cells inhabit, lake surface $CO_2$ absorption increases transporting more $CO_2$ into solution. Alkaline brines therefore function as $CO_2$ pumps in two different modes. These are: (i) first, as noted above, by inorganic "mineralization" pumping $CO_2$ into sodium bicarbonate precipitates (requiring continued input of both $CO_2$ and sodium carbonate), and (ii) second by photosynthetic pumping of the carbon in $CO_2$ into biomass.

Shulin Chen's research group at Washington State University (Chi et al., 2011, 2013, 2014) has shown how $CO_2$ utilization can employ these aspects of carbonate chemistry. The process is a "pH swing" cycle. $CO_2$ is absorbed into high pH sodium carbonate-rich solutions at night. This decreases pH to create bicarbonate ion dominance. Algal photosynthesis during the day absorbs this $CO_2$ (via bicarbonate), increasing pH. Photosynthetic production of biomass thereby transforms the remaining $Na^+$-balanced bicarbonate anions ($HCO_3^-$) in solution into a population of carbonate anions ($CO_3^{2-}$), each of which is charge-balanced by two sodium cations. Hence, combining carbonate chemistry for $CO_2$ absorption at night with aqueous photobiology for its uptake during the day, allows carbonate-rich bioculture solutions, inorganically to absorb, and photobiologically to fix $CO_2$ in a diurnal day-night cycle. Additional utility from $CO_2$ capture into a carbonate system follows from the ability of a high-pH sodium carbonate solution to be used to absorb and transport algal-bioavailable $CO_2$ in the form of bicarbonate anion in solution. This capacity can avoid gas compression by transportation of bicarbonate in situations where sources and sinks are separated only by a few kilometers (Chi et al., 2011). (See also: Guangmin et al., 2014).

Carbon dioxide is a thermodynamic end state for energy release in processes of hydrocarbon combustion. Lower energy states exist, however, when considered relative to mineralized states of carbon as carbonates. This is why most of the carbon in the Earth's crust-hydrosphere-atmosphere system is present in the crust in the form of carbonate rocks and minerals rather than as $CO_2$ elsewhere. Therefore, carbon dioxide can be utilized as a heat-releasing fuel via mineral weathering. $CO_2$, however, is not a fuel that allows trivially practical access to the energy it carries. Yet, very substantial energy is released in endothermic chemical transformations of $CO_2$ reacting with minerals such as olivine to produce hydrated and non-hydrated carbonate minerals (Schuiling, 2013). Olivine weathering also can produce hydrogen gas and reduce $CO_2$ into methane ethane and propane by a process of serpentinization (Akinfiev et al., 2005; Neubeck et al., 2011; Schrenk et al., 2013). $CO_2$ energy release technologies based on the weathering of olivine and related minerals and rocks have not yet been commercialized. The Dutch company Innovation Concepts, BV (www.innovationconcepts.eu) is focused on this task. Energy release from olivine carbonation may be important in the future in contexts relating to the industrial utilization of olivine combined with agendas for very large scale carbon sequestration.

Carbon dioxide can be utilized in large quantities via new forms of ore processing. Supercritical $CO_2$ can be used for low-energy extraction of lithium (Li) from lithium-bearing pegmatite minerals such as spudomene, petalite, zinnwaldite, amblygonite, lepidolite and triphylite. Lithium is in high and rapidly growing demand globally due to its use in Li-ion batteries. Typically lithium is sold from the mining sector in the chemical form of lithium carbonate: $Li_2CO_3$. A new method for lithium ore processing by $CO_2$ to extract lithium is described in a patent granted to Pedro Mauel Brito da Silva Correia (2015, U.S. Pat. No. 9,028,789 B2: "Process to produce lithium carbonate directly from aluminosilicate mineral"). This method requires inputs of $CO_2$, water and sodium bicarbonate. It uses high pressure and modest heating in the range 200 to 600 C. It operates without requiring acids. It therefore does not generate acidic processing waste. Related methods utilizing $CO_2$ are described in a patent application by the Finnish company Outec: US 2015/0044124 A1: Marika Tilhonen and Liisa Haavanlammi, "Method for recovering lithium carbonate," and in presentations by Nogueira (2011) and Margarido et al., (2014), described as "carbonate pressure leaching."

A second ore processing method utilizing $CO_2$ is focused on dissolving the mineral olivine [$(Mg,Fe, +minor Ni)_2SiO_4$]. It uses a chemical process of "carbon mineralization" (Power et al., 2013). This mimics natural weathering. [Forsterite weathering: $MgSiO_4+4CO_2+4H_2O\rightarrow 2Mg^{2+}+4HCO_3^-+H_4SiO_4^0$]. The method hugely accelerates the reaction rate without use of acids or high-temperature processing. The main element of the process is high-pressure processing of finely ground olivine in supercritical $CO_2$ and water with $NaHCO_3$ additive. It has been shown to dissolve finely ground olivine by more than 70% within two hours (Eikland et al., 2015; Gadikota et al., 2014; Gerdemann et al., 2007; Chen et al., 2006; O'Connor et al., 2005; for an overview see: Sanna et al., 2014, and Kelemen et al., 2011). Additional insights on optimizing olivine dissolution utilizing $CO_2$ and various additives have been published by the ETH-Swiss group of Marco Mazzotti and colleagues (Prigiobbe et al. 2009a,b, 2013a,b; Mazzotti, 2011; Prigiobbe and Mazotti, 2011). Olivine $CO_2$-dissolution processes yield mostly magnesium carbonates along with extractable forms of nickel, silicic acid ($H_4SiO_4$) and/or nano-silica ($SiO_2$), and oxidized forms of iron. Methods have been developed for the purpose of fixation of waste $CO_2$ by mineral carbonation. However, such methods likely can allow extractive industrialization of byproducts, for example metals production for iron, nickel, and possibly also magnesium. An example is the byproducts monetization agenda being developed by the mining company Orica in Australia. This is for very large scale carbonation of serpentinite for $CO_2$ sequestration (Brent et al., 2011; Brent, 2013, 2014; see also Ramao et al., 2015). Nickel production is a possibility. Large-scale production of nickel via olivine carbonation with $CO_2$ has been proposed by Santos et al., (2015). It also was considered by Thorliefson (2011) for the Duluth Complex in the state of Minnesota in the USA. Huge untapped dunite reserves exist in many world locations. Development of an olivine carbonation method of nickel (and iron and nano-silicon) production offers huge potential for very large scale $CO_2$ utilization. World nickel demand is ~2 million tonnes per annum (MTA). It is growing at about 10% per year (Pinizzotto, 2015). Nickel contents in olivine obtained from the olivine-dominated rock type dunite often are ~0.3% Ni by weight. For comparison, a good quality of viable lateritic nickel ore is ~2% Ni. Some world class nickel ore deposits are well below 1% Ni (see: page 11 diagram in Emery et al., undated). For example, Australia's largest nickel-producing mine, Mount Keith, has an ore grade of 0.5% nickel (Wilson et al., 2014). If half of the present scale of world nickel demand (at ~2 MTA Ni) were to be satisfied via olivine carbonation processing, with Ni at ~0.3 weight percent and a $CO_2$/olivine mass ratio corresponding to $4CO_2/MgSiO_4$, then the scale of associated $CO_2$ utilization-sequestration into Mg carbonates would be ~500 MTA of $CO_2$ capture-mineralization. ($CO_2$ utilization-sequestration in this process is ~500×Ni production, by weight, for a 0.3% Ni ore grade.) This is roughly 1.5% of total present day world anthropogenic $CO_2$ emissions. For nickel at US$10,000/tonne, a $CO_2$ utilization subsidy of US$20/tonne $CO_2$ for carbon sequestration would add $10,000/tonne to Ni sales (or neutralize a $20/tonne cost for obtaining usable $CO_2$). Iron often exceeds 10% by weight in olivine. Therefore, associated iron production could exceed 30× nickel at 30 MTA. Carbonation of ground olivine obtained from dunite bodies has been widely discussed as a potentially realistic means of very large scale carbon sequestration (Voormeij and Simandi, 2004; Schuiling and Krijgsman, 2006; Teir et al., 2010; Kohler et al., 2010, 2013; Schuiling et al., 2011; Schuiling and de Boer, 2011, 2013; Hartmann et al., 2013; Schuiling, 2014; Smartstones, 2014). The Mount Keith nickel mine in SW Australia is one of the world's largest reserves of Ni ore. It has a minerology of predominantly methamorphosed dunite (olivine). It has been strategized as having the capability to become the world's largest $CO_2$ sequestration operation at 4 MTA $CO_2$ by carbonation of mine tailings (Wilson et al., 2014: Power et al., 2014). Developing nickel mining via carboration processing of olivine would integrate Ni-production directly with $CO_2$ fixation, with co-production of iron, silicon and Mg-carbonates products. Realism for large-scale operations likely would require a profit-based situation where the value of a primary target product, such as nickel, exceeds production cost (Priestnall, 2014; Santos, 2014). The use of $CO_2$ in nickel ore processing is known. A $CO_2$ processing step is presented in the 1973 patent disclosure of Y. Sato et al., of the Nippon Yakin Kogyo Company: U.S. Pat. No. 3,765,873, "Method of producing ferro-nickel or metallic nickel." And a new process for laterite nickel ore processing with inclusion of $CO_2$-carbonation for magnesium separation has been described by Zhai et al., (2010). A positive factor for olivine carbonation on a large-scale, as noted above, is that the reaction is exothermic (Schuiling, 2013). Breakdown products of olivine carbonation can be useful as plant fertilizer (Berge et al., 2012; www.greensand.nl), especially in conditions of silicon, iron and magnesium demand, with nickel removed. Silicic acid fertilization can be of particular importance for the productivity of rice and banana (Guntzer et al., 2012; Fortunato et al., 2012; Kablan et al., 2012; Meena et al., 2014). $CO_2$-dissolution of olivine also can be an effective way to create nutrient Si- and Fe-rich nutrient water for the production of algal products from biocultures of algal diatoms (Schuiling, 2012, 2014).

Olivine carbonation utilizing $CO_2$ can be arranged to produce nano-silica. Nano-silica is useful as a pozzolanic cement strengthening additive in Portland cement (Lazaro et al., 2012, 2013; Gupta, 2013, 2014; Maheswaran et al., 2013; Singh et al., 2013; Yu et al., 2014; Quercia Bianci and Brouwers, 2015). Adding nano-silica additive into cement in modest amounts can add 40% to compressive strength to concrete made with it. It also accelerates hydration-setting, decreases porosity and Ca-leaching, and increases durability (Sing et al., 2013). Nano-silica transforms ordinary concrete into a high-performance concrete, allowing a higher aggregate-to-cement volume ratio and associated cost savings.

An additional use for $CO_2$ is via processes for alumina production from aluminosilicate ores as alternatives to the traditional alumina sources of bauxite. Aluminosilicate ores include nepheline ($Na_3KAl_4Si_4O_{16}$)-rich nephelinite, typically in the form of igneous nephelene syenite rock, and also separated aluminum feldspars ($KAlSi_3O_8$—$NaAlSi_3O_8$—$CaAl_2Si_2O_8$) such as the very common granitic mineral orthoclase ($KAlSi_3O_8$). Orthoclase can be processed to produce a potassium fertilizer co-product. Anorthite ($CaAl_2Si_2O_8$) can be processed to produce calcium carbonate as a co-product to alumina. Anorthite often is present in high purity in massive igneous cumulate complexes known as "anorthosite" massifs. Archibald filed a patent in 1942 for the Canadian company Nephiline Products Limited. His method utilizes the mineral nephiline to produce alumina. It involves limestone addition and carbonization steps with $CO_2$: U.S. Pat. No. 2,420,852, "Recovery of alumina from ores." A similar method has long been used in alumina production from nephelinite ores in the Soviet Union/Russia (Smirnov, 1996; Volsky, 21012). A recent publication describing a similar technique is Qui et al., (2015). A more recent process focused on anorthosite ore has been developed by the Norwegian company Nordic Mining (Nordic Mining, undated, 2011; Fossum, 2014; Aranda and Mastin: Norwegian patent granted in 2015: number 20140317, "En ny fremgangsmate for fremstilling av alumina og karbonat fra aluminiumrike materialer med integerert $CO_2$ utnyttelse"; also: WO 2015137823 A1, "Alumina and carbonate production method from al-rich materials with integrated $CO_2$ utilization."). The method obtains separated alumina, precipitated calcium carbonate and precipitated silica from HCl-leached aluminum-rich silicate minerals, particularly from anorthite from anorthosite ore. Carbon dioxide is used to separate calcium from aluminum chloride by precipitation of $CaCO_3$ from HCl acid solution of the mineral concentrate. A method for liberating potassium from potassium feldspar (orthoclase) with $CO_2$ carbonation has been described by Xie et al., (2013, 2015). The method dissolves orthoclase hydrothermally in the presence of $CO_2$ with added calcium chloride and triethanolamine. Variant methods have been described by Ye et al., (2014) and Wang et al., (2014). Future developments in this arena perhaps may be able to obtain separated alumina, silica, calcium carbonate, and potassium salts. The most interesting strategic possibility will be in the potential use of supercritical solutions of $CO_2$ plus water and reaction-accelerating substances to dissolve anorthite and/or K-feldspar efficiently at modest temperatures.

The "weathering" reaction of $CO_2$ with silicate minerals mostly is exothermic. Therefore mineral carbonation is a thermodynamically favored modality for $CO_2$ utilization and sequestration. However reaction kinetics often are very slow. Therefore accelerating mineral dissolution with low-energy, low-cost and low-waste methods is an important technology development challenge. Kakizawa et al., (2001), Tier at al., (2007), Ghoorah (2014), Ghoorah et al., (2014a, b), and Dlugogorski et al., in a patent application (US 2014/0065039, "Extraction of alkali metals and/or alkaline earth metals for use in carbon sequestration") have shown that weak solutions of acetic or formic acid can very strongly accelerate silicate mineral weathering under various conditions.

Titanium separation is an additional potential use for $CO_2$ in ore processing. The mineral ilmenite ($FeTiO_3$) is often used as a titanium ore. Carbochlorination treatment with chlorine gas and carbon monoxide produces separable Ti in the form of titanium tetrachloride ($TiCl_4$). Titanium is separated from iron by a wide variety of additional thermochemical methods in ilmenite processing. All are multi-stage and energy intensive (Zhang et al., 2011) with the exception of recent developments of low-temperature chlorination methods using carbon tetrachloride, $CCl_4$, sometimes in combination with $Cl_2$ (Fu et al., 2009; Norazharuddin et al., 2015), thereby combining chlorination with reduction. Tolley and Tester (1989), Tolley et al., (1992), and Tolly and Whitehead in U.S. Pat. No. 4,853,205, "Supercritical fluid halide separation process," all have shown that $TiCl_4$ is soluble at low temperature in supercritical $CO_2$. This insight combined with the new $CCl_4$-based chlorination process likely can allow an efficient separation of titanium from ilmenite in a "green chemistry" treatment process utilizing $CO_2$.

Tantalum- and niobium-rich "coltan" ores can be processed using carbon tetrachloride or silicon tetrachloride liquids reacting with ores to chlorinate niobium and tantalum at relatively low temperatures (Shainyan et al., 2008). Green chemistry advocate James Clark of the University of York has called for the development of a broadly similar green process for tantalum separation from coltan ores (York, 2014). An industrial niobium (Nb) and tantalum (Ta) separation processing method for coltan ores possibly could be developed utilizing tetrachlorides followed either by evaporation or by supercritical $CO_2$ liquid-liquid extraction to obtain separated Nb- and Ta-pentaclorides. A patent application for the use of carbon tetrachloride is: Terakhov et al., WO2015039219 A1, "Process for recovering tantalum and niobium with carbon tetrachloride."

Rare Earth Elements (REE) are an important strategic resource with rapidly increasing demand globally (McLellan et al., 2013). A fascinating proposal put forward by Arab et al., (2104, 2015) is to mine REEs by an extraction method of percolative leaching. Percolative leaching uses $CO_2$ injected into a REE-carrying ore zone at depth sufficient for $CO_2$ to be in a supercritical state. If realized, this mode of mining would involve either multiple drill holes, some for injection and some for collection, or alternately a single-hole flow reversing system with injection followed by collection. Use of horizontal drilling and fracture-generating injection technologies ("fracking") can be imagined. If developed, this proposed technology could provide a revolutionary mode for REE mining. Other elements potentially leachable by this $CO_2$-based method include gold (Glennon et al., 1999, 2003; Glennon, 2003; van Zyl, 2007) and uranium (Wang et al., 2013). Carbonatites and solidified magma bodies and plutons associated with highly alkaline volcanic provinces are an obvious target geology for testing this technology as a consequence of their typical REE enrichment (Verplanck and Van Gosen, 2011).

Magnesite ($MgCO_3$) ores can be purified by leaching and re-precipitation using pressurized $CO_2$, as demonstrated by Amer, (2010). Magnesite obtained from olivine dissolution-carbonation can be used as an additive in concrete production. It also can be decarbonated (with $CO_2$ recycling, if desired) to create magnesium oxide for use in cement production and also for producing "MgO board." MgO board (e.g., http://magobp.com) is a superior form of interior wall-building "wallboard" material. Its use is directly analogous to the (gypsum-based) "drywall" wallboard used very widely in construction. MgO board, however, possesses superior surface hardness, fire-resistance, mold-resistance, and installation workability relative to conventional drywall (Thomas, 2007; http://magobp.com/benefits/; https://en.wikipedia.org/wiki/Magnesium_oxide_wallboard). It is widely manufactured and used in China. The main cementitious process in its manufacture is based on the hydration of reactive MgO to micro-brucite, $Mg(OH)_2$. $CO_2$ utilization via carbonation-hydration in producing MgO board in a $CO_2$-rich atmosphere is possible, but not yet commercialized. Also, wallboard can be made with direct incorporation of magnesium carbonates, as disclosed in a 1933 patent: U.S. Pat. No. 1,896,689, Spenser, "Building Material and Method of Making the Same."

$CO_2$ utilization on a very large scale is possible by mass production of new types of cement and concrete, which structurally incorporate $CO_2$. This innovation has substantial environmental significance because Portland cement manufacture is responsible for ~9% of world total anthropogenic $CO_2$ emissions. The new mode of cement production is a consequence of the possibility to use magnesium (Mg) as a full or partial replacement for calcium (Ca), (Harrison, 2003, 2004, 2006, 2013, 2014, 2015a,b; Al-Tabbaa, 2013; Imbabi et al., 2012; Glasser et al., 2016; Evans, 2008, 2009, 2010; Evans and Vlasopoulos, 2010). The technology for the production of $CO_2$-utilizing Mg-based "eco-cements" and "eco-concretes" has been described and demonstrated by several institutions worldwide. These include, most notably: TecEco (www.tececo.com), a business created by the Australian inventor-entrepreneur John W. Harrison (Harrison, 2003, 2004, 2006, 2013, 2014, 2015a,b and U.S. Pat. No. 7,347,896 B2: "Reactive Magnesium Oxide Cements"), and the Cambridge University research group of Professor Abir Al-Tabbaa, in connection with the Cambridge-based David Ball Group plc (http://www.davidballgroup.co.uk; WO2013178967 A1: Martin et al., "Cementitious binders, activators and methods for making concrete.") via a former PhD student Martin Liska (Vandeperre and Al-Tabbaa, 2007; Liska et al., 2008, 2012a,b; Liska and Al-Tabbaa, 2008, 2009, 2012; Unluer and Al-Tabbaa, 2013, 2014, 2015a,b; Unluer, 2015). $CO_2$-incorporating Mg-based cements can be produced by at least three different modes to generate a cementitious matrix. One is to produce the dry cement mix containing reactive MgO (periclase) and/or magnesium hydroxide, $Mg(OH)_2$ (brucite), then hydrate and carbonate the cement during setting to form a range of cementitious magnesium carbonate hydrates. At the present level of technology, this requires setting within a thermally-controlled pressure chamber providing $CO_2$ and steam (Unluer, 2015). Cementitious hydrated Mg-carbonates include: nesquahonite [$MgCO_3.3H_2O$], landsfordite [$MgCO_3.5H_2O$], hydromagnesite [$4MgCO_3.Mg(OH)_2.4H_2O$], and dypingite [$4MgCO_3.Mg(OH)_2.5H_2O$]. Another mode is to produce the dry cement mix with Mg present in the already carbonated form of the anhydrous Mg-carbonate magnesite ($MgCO_3$), then to hydrate-transform-recrystallize it into hydrated carbonate phases during setting (Glasser et al., 2015). This method requires setting with thermal control, therefore within temperature-controlled premises. For optimality, it may require pressurized gas environment control also. This mode sequesters $CO_2$ if the input magnesite been produced by carbonation of brucite. The third type of $CO_2$-utilizing Mg-based cement and concrete can be produced beginning directly with hydrated Mg-carbonates in the dry cement formulation prior to use. In such cases, cementitious transformations are obtainable by cycling changes in temperature with or without hydration, and/or $CO_2$, and/or steam injection, in order to control transformation and recrystallization conditions, for example from nesquahonite to recrystallized nesquahonite via a thermal cycle exceeding nesquahonite's stability range. This mode may be possible for conventional pouring without need for a pressure chamber, requiring only the ability to heat-up the mixed concrete prior to pouring (Glasser et al., 2016). Such a mode sequesters $CO_2$ if the input phases have been produced by carbonation-hydration of brucite. Overall, a great many types of situations are possible via variable input chemistries, mixtures with conventional Portland cement, pozzolanic matrix additions, pozzolanic aggregate additions, $CO_2$ and/or steam input carbonation, and preparation, pouring and curing techniques. Production methods may range from casting and setting blocks and reinforced section within confined vessels under pressurized $CO_2$ with or without steam, to pouring and setting in the field like ordinary concretes made with Portland cement. The field of creating and industrializing Mg-based $CO_2$-utilizing cement and concrete technologies has a big future. However, it has only begun to be demonstrated in research labs and in a few pioneering industrial applications. Some of the demonstrated building materials exhibit superior properties of strength in comparison to conventional Portland cement. However, $CO_2$-utilizing Mg-based cements involving hydrated Mg-carbonates require careful formulation and preparation as well as use limitations to low temperatures (<~50 degrees C., Morgan et al., 2015). The latter is especially important due to thermal instabilities in the hydrated Mg-carbonates comprising the cementitious matrix, particularly nesquahonite. Nesquahonite has an excellent property in that it in cements it forms in strongly cementitious crystal whisker networks. However, it has a poor thermal stability range limiting for practical purposes to less than ~50 degrees centigrade (Walling and Provis, 2015; Unluer and Al-Tabbaa, 2015b; Highfield et al., 2013).

Carbonated Mg-based cements are different from Mg-based phosphatic cements such as Sorel cement (Shand, 2016). They also differ from non-carbonated MgO-based cements produced from magnesite or Mg-rich dolomite or dolomitic limestone inputs which are kiln-fired to drive-off $CO_2$ to produce reactive MgO. (That is: prepared from $MgCO_3$ in direct analogy to Portland cement using CaO obtained by decarbonation of $CaCO_3$ limestone, then cured by various hydration reactions.) Such reactive MgO-based cements are well-known for high performance. In New York State, the high performance of historic "Rosendale" cements and concretes is due to high magnesium in the limestone used to make it (TecEco, undated). Kiln-firing "calcination" of high Mg limestone generates MgO and Mg-carbonates in addition to the usual CaO content which is the main input into the formula of Portland cement. MgO-based concretes have been used extensively in China in dam construction. Their volume stability during curing is especially prized. See: Zheng et al., 1991; Du, 2005; Premier, undated; Mo et al., 2014).

By contrast, $CO_2$-utilizing Mg-based cements do not begin with a $CO_2$ releasing decarbonation step to prepare reactive MgO. The basic difference with respect to the calcium system is two-fold. First, both MgO and $Mg(OH)_2$ can be obtained without using natural $MgCO_3$ (magnesite) as a natural starting material, whereas CaO (burnt lime) and $Ca(OH)_2$ (calcium hydroxide Portlandite) are very rare in the Earth's crust. They typically are obtained by high-temperature kiln-firing of limestone: $CaCO_3 \rightarrow CaO+CO_2$. By contrast, magnesium hydroxide (brucite) can be obtained from natural deposits or by precipitation from either seawater or alkaline freshwaters and brines obtained from lakes or wells. Brucite then can be heated above 500 C to dehydrate it into reactive MgO (Shand, 2006; Alvarado et al., 2000). Second, $CO_2$-utilizing cements are based on a cementitious carbonate-hydrate mineralogy, whereas the setting of Portland cement predominantly is based on hydration mineralogy.

In U.S. Patent Application Publication No. 20160257577 A1, the present inventor disclosed a method and system that included a process of obtaining precipitate comprised predominantly of magnesium hydroxide in large quantities from Lake Kivu. The obtaining of this flux of precipitate was from a process of water treatment of return flow water following extractive degassing of an upflow of deepwater.

$CO_2$ also is utilized for carbonation of ordinary Portland cement in the solidification of pre-cast building materials. Two companies, Solidia Technologies (Riman, 2012; Sadu and Cristofaro, 2013; DeCristofaro and Sahu, 2014, 2015a, b; DeCristofaro et al., 2014; DeCristofaro, 2015; Jain et al., 2013, 2014, 2015), in partnership with LaFarge (Lafarge, 2015), and CarbonCure Technologies (www.carboncure.com; Monkman and Shao, 2010; Monkman, 2012; Monkman and Niven, 2010; Divon, 2015), have industrialized such processes for manufacturing pressed masonry blocks (known in the USA as "cinder blocks"). These companies variously carbonate and hydrate mold-injected masonry blocks in the processes of injection and curing.

Pressure carbonation with supercritical $CO_2$ has been well-demonstrated to enhance the strength and durability of a variety of composite objects molded with Portland cements and concretes (Rubin et al., 2003; Garcia-Gonzalez et al., 2007, 2008; Knopf et al., 1999; Fernandez Bertos et al., 2004; Farahi et al., 2007, 2013; Farahi, 2009). This technique was developed at Los Alamos National Lab in the 1990s (Rubin et al., 1997; Taylor et al., 1997). It led to a patent and a company producing products such as roofing tiles under the trade name "supramics" (Jones, 2001; Jones, 1996: U.S. Pat. No. 5,518,540: "Cement treated with high-pressure $CO_2$."). High-strength carbonated cement-bonded particleboard incorporating woody biomass is, for example, produced by rapid exposure to supercritical $CO_2$ (Suh et al., 2000; Hermawan et al., 2000, 2001; Maail et al., 2011). This method includes cement-bonded particleboard made with oil palm frond waste material (Hermawan et al., 2002). The method, however, has never taken off industrially. The obvious reason is that facilities for high-pressure carbonation treatment of molded building materials with supercritical $CO_2$ are rare and expensive, and also because $CO_2$ typically obtained for such uses is costly. However, such reasons are not fundamental impediments that apply to all circumstances.

High-value medical products for human implantation can be made with technologies developed for making molded composite materials incorporating carbonates formed by interactions with supercritical $CO_2$ (e.g., Garcia-Gonzalez et al., 2015).

Pressurized $CO_2$ is used in the production of the remarkable, newly discovered, magnesium carbonate material "Upsalite®" (Wikipedia: Upsalite; Forsgren et al., 2013; Frykstrand et al., 2014; TCE News, 2013; Yousefi, undated). Upsalite is an anhydrous micro- and macroporous form of magnesium carbonate, $MgCO_3$. It possesses an astonishingly large surface area of ~800 square meters per gram. Upsalite is a powerfully hygroscopic desiccant, functioning effectively at low humidity. It also has been shown to be effective as a biologically harmless, space-efficient, absorbant binding material for time-extended diffusional drug release in pharmaceutical tablets. (Zhang et al., 2016; Frykstrand et al., 2015). The Swedish company Disruptive Materials (www.disruptivematerials.com) has been created to pursue market development for Upsalite®.

The input and degassing of $CO_2$ into and out of aqueous solutions can be utilized for pH control and precipitation control. Decrease in pH is achieved by acidifying addition of $CO_2$ into solution, such as by sparging. The pH of an aqueous solution containing $CO_2$ and/or bicarbonate and/or carbonate anions can increased by removal of $CO_2$ from solution by equilibration with gas and by bubbling aeration, stirring, sparging with $CO_2$-free gases (e.g., $N_2$) and by vacuum degassing. For an example of $CO_2$ acidification, Ferreira et al, (2012) used $CO_2$ input to decrease and thereby stabilize the pH of an aqueous bioculture of *spirulina* algae housed in a recirculating photobioreactor. The increase of pH driven by photosynthetic activity of the algae was thereby balanced by $CO_2$ input acidification which also feeds the algae as a carbon source via bicarbonate ion. For an example of the opposite process, degassing $CO_2$ to increase pH, Cohen and Kirchmann, (2004) reported degassing of wastewater samples wherein use of atmospheric air as the stripping gas increased pH from a start at pH 8.3 to an equilibrium pH of 8.5, whereas using pure $N_2$ instead of air increased the endpoint pH to 10.3. This method was developed to allow precipitation of wastewater phosphorus as struvite to realize P-recycling (Cohen, 2001; see also: Fatteh et al., 2008a,b, 2010; Radev et al., 2015). Oliver et al., (2014) reported similar findings of pH increase to precipitate nesquahonite by $CO_2$ removal from a solution of magnesium carbonate by gas stripping with $N_2$. These authors reported additional results for $CO_2$ removal by algal biological $CO_2$ uptake, and by accelerated conversion of bicarbonate to aqueous $CO_2$ by addition of carbonic anhydrase. Nitrogen sparging to remove fermentation-$CO_2$ from (acidic) pickle brining operations is reviewed by Fleming (1979). Lisitsin at al., (2008) have shown that $CO_2$ stripping can precipitate calcium and magnesium from desalination feed waters as a method of water softening pretreatment replacing the use of chemical alkali addition. Israeli Technion scientists have further demonstrated methods based on $CO_2$ stripping to precipitate calcium from brackish waters prior to reverse osmosis membrane desalination (Hasson et al., 2011; Segev et al., 2011, 2013). Geroni et al., (2012) have demonstrated an analogous $CO_2$-stripping method for removing dissolved iron and associated metals from mine water. $CO_2$ degassing to increase the pH of river water samples containing calcium and magnesium in solution is used as a method to determine potential precipitative scaling of these elements in industrial water-cooling applications (Gauthier et al., 2012; Chao et al., 2014; Hamdi and Tlili, 2016). Circulating geothermal fluids rich in Mg, Ca and $CO_2$ will precipitate Mg and Ca out of solution under surface conditions with $CO_2$ degassing and consequent pH increase, as in the case of natural travertine deposition (Pentacost, 2005; Rodrigo-Naharro et al., 2013) and scale deposit clogging of pipes in geothermal energy operations (Wasch, 2014). Also, Spilling et al., (2010) demonstrated micro-precipitation of calcium carbonate and magnesium hydroxide onto diatoms in a photosynthetic algal bioculture by the simple process of discontinuing the $CO_2$ supply such that pH was increased by photosynthetic $CO_2$ removal from solution. This process is known as algal autoflocculation (Sukenik and Shelef, 1984). The Controlled Hydrodynamic Cavitation (CHC) method of Ecowater Systems provides an additional example (Ecowater Systems, undated). The German company Budenheim (www.budenheim.com) developed an industrial method for phosphorus recovery from waste streams that uses $CO_2$ for pH control in both directions via a "pH swing" method: the Budenheim Carbonic Acid Process (Stossel, 2013; Ewart et al., 2014; Wollman and Moller, 2015). This method removes phosphorus from sewage sludge first by injection of $CO_2$ at high pressure to solubilize organic P into dissolved inorganic phosphorus (DIP) in an acidic liquid phase for a liquid/solid separation step. A $CO_2$ vacuum degassing step follows. This precipitates P from the separated solution under high-pH conditions. To decrease pH, $CO_2$ pressure can be applied by sparging into and/or by providing $CO_2$ gas pressure over a solution. This can be done to keep magnesium and/or calcium in solution in conditions where pH is low enough to prevent precipitative saturation conditions from being reached. Such procedures are common in "recarbonation" steps following the lime-soda ash process for water softening (Butler, 1982; Wang et al., 2004; Messer, 2013). Thus $CO_2$-based pH modification can provide control over mineral precipitation, particularly magnesium hydroxide, and various magnesium and calcium carbonates. The systematics of aqueous carbonate chemistry are presented in Butler (1982, 1989), Emerson, (1975), Stumm and Morgan, (3 editions: 1970, 1981, 1996), Langmuir, (1997), Zeebe and Wolf-Gladrow, (2001), Bustos-Serrano, (2010), Talling, (2010), Millero, (2013), Munhoven (2013a,b), and Orr et al., (2015). Various computational models exist. These include PHREEQC (http://wwwbrr.cr.usgs.gov/projects/GWC_coupled/phreeqc/; www.hydrochemistry.eu; de Moel et al., 2015) and The Geochemists Workbench (www.gwb.com; Bethke, 2008). A detailed understanding of $CO_2$ degassing and consequent pH increase and precipitation has been obtained from the study of cave waters and speleothems (e.g., Holland et al., 1964; Dreybrodt, 1980, 2013; Hansen et al., 2013). A 1-page summary overview is provided by Railsback, (2006). Detailed systematics for $CO_2$ degassing from large scale water flows and in relation to carbonate water chemistry have been developed for application in aquaculture operations, particularly recirculating aquaculture systems (RAS), (Grace and Piedrahita, 1993, 1994; Summerfelt et al., 2000, 2003, 2015; Moran 2010a,b; Timmons et al., 2001, 2002; Timmons and Ebeling, 2007, 2010, 2013). The degassibility of $CO_2$ from alkaline solutions differs greatly as a function of pH (Hardy et al., 2007; Willauer et al., 2008, 2009a,b, 2010a,b, 2011, 2012a,b, 2014; DiMascio et al., 2010; Eisaman et al., 2012). High pH carbonate waters do not contain appreciable dissolved $CO_2$ in solution. They absorb $CO_2$ from air (e.g., Clark et al., 1992). Once dissolved into water, this $CO_2$ is rapidly transformed into bicarbonate and carbonate anions. Under conditions of exposure to $CO_2$-free air, or $N_2$, or vacuum, high-pH alkaline solutions degas $CO_2$ only very slowly. This is a consequence of the (pH-increasing) slow kinetics of the process of the combined dehydroxylation ($HCO_3^- \rightarrow CO_2 +$ $OH^-$) and dehydration ($H^+ + HCO_3^- \rightarrow CO_2 + H_2O$) of bicarbonate anion in aqueous solution into dissolved $CO_2$ (Grace and Piedrahita, 1993, 1994; Stumm and Morgan, 1996; Schulz et al., 2006; Guo et al., 2009; Cohen and Kirschmann, 2004; Moran, 2010).

Chemically, Lake Kivu deepwater is a $CO_2$-rich Mg(Na)-carbonate water type of geothermal derivation (Tassi et al., 2009). Its condition at depth is a natural example of $CO_2$-based pH control over Mg and Ca precipitation. Deepwater from 375 meters depth has 15.6 millimolar (mM) magnesium at pH=6.15 (Tassi et al., 2016). This is approximately 100× saturation for a solution fully degassed under surface conditions at 1 atmosphere without atmospheric $CO_2$ equilibration. This follows from the solubility product for magnesium hydroxide Ksp=$[Mg^{2+}][OH^-]^2=1.5 \times 10^{11}$. This relation determines a molar solubility of 0.16 mM/l solubility for $Mg(OH)_2$ and a pH=10.5 for a saturated equilibrium solution at 25° C. with no $CO_2$ gas equilibrium present. This condition is modulated to sub-saturation in $Mg(OH)_2$ and in Mg- and Ca-carbonates by $CO_2$ in situ in Lake Kivu at 375 meters, as a consequence of the acidifying effect of dissolved $CO_2$ generating a pH of 6.15. There is extremely high dissolved $CO_2$ at 375 m depth in Lake Kivu: 62 mM/l, (2.7 g/l), (Tassi et al., 2009). Magnesium hydroxide precipitates from aqueous solution at this Mg concentration at pH~10 once $CO_2$ in gas in equilibrium with the solution reaches a partial pressure ~$10^{-6}$, well below its present atmospheric partial pressure: ~$4 \times 10^{-4}$ atm (Stumm and Morgan, 1996 edition 2, FIG. 5.2; Hanchen et al., 2008; Zolotov, 2014). Such circumstances are observed in hyperalkaline springs in Oman, but are rare in terrestrial surface waters (Neal and Stanger, 1984; Cipolli et al., 2004; Paukert et al., 2012; Chavagnac et al., 2013a,b; Monnin et al., 2014; Olsson et al., 2014).

Recent years have observed massive effort to develop industrialize CCU via organic synthesis. A review is provided by Liu et al., (2015). Major advances have been obtained in scientific insight such as overcoming endothermic constraints in the catalytic copolymerization of $CO_2$ as a C1 feedstock combining with olefins (e.g., Nakano et al., 2014) and polycarbonates. $CO_2$-copolymerized polypropylene carbonate (PPC) is 44% $CO_2$ by weight (Darensbourg and Wilson, 2012). This can provide a major savings with respect to petrochemicals-sourced carbon mass. Hence, some methods have been industrialized. A prominent example was developed by Asahi Kasei Chemicals Corporation of Japan. Asahi's process produces polycarbonate plastics using inputs of $CO_2$ and ethylene oxide (Fukuoka, 2012; Fukuoka et al., 2003, 2007, 2010). Polycarbonates have been manufactured industrially in China since 2004 utilizing $CO_2$ and propylene oxide (Wang et al., 2011).

Carbon dioxide can be utilized as a low-cost feedstock for producing $CO_2$ polyols in polyurethane production. $CO_2$ comprises roughly 50% of the mass of the $CO_2$ polyols produced with $CO_2$ incorporation as polycarbonate via alternating copolymerization of carbon dioxide and epoxides. Industrialization of this process verifies the practicality of $CO_2$ utilization in plastics manufacturing (Taherimehr and Pescarmona, 2014). A substantial economic logic supports the production of plastics using $CO_2$ polyols because, as noted above, carbon from low-cost $CO_2$ replaces carbon from high-cost petroleum-based products. For example, the cost of carbon from $CO_2$ at ~US$50/tonne can be compared to the cost of carbon from petroleum-derived propylene oxide at ~US$2,000/tonne. Polyurethane is used, for example, to produce mattress foam (Langanke et al., 2013; von der Assen and Bardow, 2014; PU Magazine, 2013).

The German chemical giant Bayer has pioneered a $CO_2$-utilization "Dream" technology (Prokofyeva and Gurtler, 2015) with German Government support (FMER, 2014). Bayer will commence production of ~5,000 metric tons per year of $CO_2$ polyols in Dormagen, Germany beginning in early 2016 under the name of its spin-off company "Covestro" (www.covestro.com; Smock, 2015). The US company Novomer (www.novomer.com) developed and commercialized a similar $CO_2$-polyols production technology in 2014 (Anderson et al., 2012, 2013; Sawant, 2013; Novomer, 2013, 2014, 2015, and undated; Bioplastics, 2014). Novomer's technology originated in research at Cornell University (Allen et al., 2006). The British start-up company Econic Technologies (www.econic-technologies.com) is developing a similar industrialization of $CO_2$ polyols production (Kember, 2013; Sorlien, 2014; Broadwith, 2015). Econic's technology is based on research at Imperial College, London (Kember and Williams, 2012; Buchard et al., 2012; Chapman et al., 2015; Romain and Williams, 2015; Williams et al., 2015).

In the conventional process, polyurethane is produced by reacting polyols with isocyanate, typically with both polyols and isocyanate being petrochemical derivatives. It now is possible for almost all of the component inputs for polyurethane foam to be obtained from $CO_2$-polyols plus plant-sourced materials (Bonnaillie, 2007; Bonnaillie and Wool, 2007; Wool: U.S. Pat. No. 8,633,257 B2). A wide range of non-petrochemicals-based "green" production chemistries for polyurethane manufacture using bio-oils (and sometimes $CO_2$ in additional modalities) have been developed and industrialized by companies such as Dow, BASF, Bayer, Cargill, Bio-Based, and Urethane Soy Systems (Llgadas et al., 2010; Bahr and Mulhaupt, 2012; He et al., 2013; Blattman et al., 2014; Ji et al., 2015; Lee and Deng, 2015; Wikipedia: Natural oil polyols; Dow, undated). Algal oil as well as palm oils have been demonstrated as feedstocks (Petrovic et al., 2013; Jennewein, 2015; Arniza et al., 2015). The Malaysian company "Polygreen" has fully industrialized manufacture of polyols from palm oil (Polygreen, website). $CO_2$ also is utilized as a foaming agent in polyurethane production (Kim and Youn, 2000; Bonnaillie, 2007; Bonnaillie and Wool, 2007; Wool: U.S. Pat. No. 8,633,257 B2; Jacobs et al., 2008; Hicks et al., undated).

The Nottinghman University research group of Professor Steve Howdle coordinating with the European Union's REFINE project (www.fp7-refine.eu; REnewable FunctIoNal MatErial) is seeking to develop methods for low-temperature, low-cost, industrial polymerization-plasticization reactions of bio-derived monomers dissolved within supercritical $CO_2$ as a reaction medium (Howdle, 2001; Curia et al., 2015; Leitner, 2002; Kemmere and Meyer, 2005).

A possibility for $CO_2$ utilization is hydrogen peroxide ($H_2O_2$) production. Hydrogen peroxide is a basic input into many low-waste "green chemistry" processes, for example in the globally very high volume production of polypropylene plastics via propylene oxide ($C_3H_6O$) produced from propylene ($C_3H_6$). Propylene (propene) typically is produced in industry petrochemically or via coal-based syngas processes, or via dehydrogenation of propane. Hydrogen peroxide utilization allows a low waste synthesis of propylene oxide from propylene via the reaction: $C_3H_6 +$ $H_2O_2 \rightarrow C_3H_6O+H_2O$. Considerable effort has been invested attempting to develop an industrial method using supercritical $CO_2$ as the reaction medium for hydrogen peroxide production via cleantech "direct methods" (that is, by: $H_2+O_2 \rightarrow H_2O_2$), (Hancu et al., 2002a,b; Chen and Beckman, 2007; Chen, 2007; Garcia-Serna et al., 2014; Pashkova and Dittmeyer, 2015; Edwards et al., 2015). Direct production of $H_2O_2$ was industrialized by EVONIK and industrial partners using a nano-Pd—Pt "NXCAT" catalyst process developed by Bing Zhou at Headwaters Technology Innovation, Inc. This process used methanol as the reaction medium rather than $scCO_2$. It typically couples into propylene oxide production in its industrial applications, hence named the "HPPO" technology (Zhou, 2007, 2008; ThyssenKrupp, undated). The combined process now operates globally on a huge scale. The hydrogen peroxide synthesis component of the process, however, can operate in $scCO_2$ as well as in methanol. This was demonstrated initially by Chen and Beckman, (2007).

Propylene production also can utilize $CO_2$. As noted above, propylene (propene) is a basic input into industrial plastics manufacture on a huge scale globally. Propylene has been demonstrated by Dow to be bio-manufacturable by fermentation utilizing commodity sugar input, though not in an economically competitive manner (Rodriguez et al., 2014; Nextant, 2009). Sugars derived from future lignocellulosic biorefining may change the economics. At present, forms of "bio-polypropylene" can be produced industrially from commodity polypropylene that is dilution-mixed together with up to more than 50% treated algal biomass input, grown on $CO_2$ (Zeller et al., 2013; Cereplast, 2013; Algix, 2014). Moreover, $O_2$ inputs into hydrogen peroxide can be obtained as a byproduct of electrolytic $CO_2$ reduction processes, whereas $H_2$ can be obtained from biorefinery processing of algal and other types of biomass grown on $CO_2$. Therefore $CO_2$ utilization inputs can be substantial in propylene-based bioplastics production. Propylene and ethelyne are manufactured industrially (together with gasoline and propane outputs) on a large scale worldwide from natural gas inputs via methanol in Lurgi's Gas-to-Chemicals (GTC) and Methanol-to-Propylene (MTP) technologies (Koempel et al., 2005; Jasper and El-Halwagi, 2015) as well as in broadly similar UOP-Honeywell Methanol-to-Olefins (MTO) catalytic gas-phase synthesis processes (UOP, 2007, 2013, 2014). Methanol synthesis from natural gas via syngas processing can use substantial $CO_2$ input for process optimization (Luu et al., 2015; Milani et al., 2015).

Research developments indicate that economically industrializable catalysts may allow electrocatalytic production of ethylene ($C_2H_4$, also known as "ethene") by reduction of $CO_2$ according to the overall reaction: $2CO_2+2H_2O \rightarrow C_2H_4+3O_2$ (Kuhl et al., 2012; Ogura, 2013; Chen et al., 2015; Roberts et al., 2015). Worldwide production of ethylene exceeds that of any other organic molecule produced by reaction. Ethylene typically is produced by steam cracking of petroleum. Its major use is in plastics manufacture by polymerization into polyethylene. Polyethylene is the largest volume of any type of plastic produced worldwide. Catalytic carbonylation of ethylene with carbon monoxide allows a range of chemical synthesis reactions alternate to Fischer-Tropsch synthesis (Makaryan et al., 2015). Ethylene is oligomerizable into diesel and other liquid transport fuels (Heveling et al., 1998; OCMOL, undated). The EU "OCMOL" (Oxidative Coupling of Methane followed by Oligimerization to Liquids) consortium initiative (www.ocmol.eu) brought together a large group of chemicals and energy companies to develop this capacity. Thus far, "ethylene-to-liquids" processes have been industrialized on a pilot scale by the company Siluria Technologies. Siluria's processes allow attractive small-scale synthesis alternatives to large-scale indiustrial Fischer-Tropsch synthesis of fuels, plastics and other industrial chemicals (www.siluria.com). They were developed for stranded natural gas utilization by a methane-to-ethylene process of oxidative coupling of methane, followed by ethylene-to-liquids processing. Ethylene may become a basic output in the development of so-called "solar fuels" using electricity from solar and/or other renewable sources to power water hydrolysis and $CO_2$ reduction to ethylene followed by transformation into liquid transport fuels. A reasonable basis in both science and economics has been demonstrated by Singh et al., (2015).

Methanol is produced utilizing $CO_2$ via direct catalytic conversion/reduction/hydrogenation via the reaction: $CO_2+3H_2$ $CH_3OH+H_2O$. This can be an environmentally attractive form of $CO_2$ utilization. Methanol production from $CO_2$ and $H_2$ inputs depends for economic viability and environmental value upon the availability of either bio-hydrogen (as by enymatic processing of lignocellulosic sugars, for example) or low-cost electricity to obtain hydrogen by water electrolysis (Olah et al., 2009, 2011). A piloting scale industrial example (4,000 tonnes per year production) has been created in Iceland by the company Carbon Recycling International (CRI: www.carbonrecycling.is). CRU uses geothermally-generated $CO_2$ and electricity for electrolysis. The project demonstrates the base level of the $CO_2$-cycling "methanol economy" advocated by George Olah. In Olah's vision, methanol can be used directly, or as a hydrogen-carrier, or as an input in various ways for industrial production. One large-scale example of the latter, the "methanol pathway" in industrial production, is plastics manufacturing. The methanol pathway already operates on a huge scale globally. It is growing rapidly due to the economic incentives of switchover to natural gas feedstocks from petroleum feedstocks. Methanol is a conveniently transportable product of natural gas reforming via well-known long-industrialized synthesis gas ("syngas") processeing (Methanex, 2015). China is especially active making this switch, replacing petroleum with methanol in the manufacture of plastics and industrial chemicals. China imports methanol from the USA where it is manufactured from very low cost natural gas. World methanol production circa 2015 exceeds 60 million tonnes per year. Therefore industrialization conditions are excellent for connecting $CO_2$-utilizing direct synthesis of methanol (from $CO_2$ and $H_2$), wherever feasable economically, with industrial chemicals, fuels and plastics production. (Further details are provided below.)

$CO_2$ provides a basis for "green chemistry" chemical processing with wide flexibility for many different kinds of food, chemicals, fuels and biorefining processes, used in various combinations and states of pressure, temperature and gas-expansion with water, methanol, ethanol, ionic liquids and various other solvents (Aitkin and Poliakoff, 2009; Srinivas and King, 2010; King, 2014; Soh, 2014; Keskin et al., 2007; Medina-Gonzalez et al., 2014; Jutz et al., 2011; Hintermair et al., 2010: Francio et al., 2015; Wei et al., 2002; Fadhel et al., 2010; Jutz, 2009; Jessop and Subramanian, 2009; Jessop, undated; Jessop et al., 2005, 2011, 2012). For example, $CO_2$ utilization in the form new "smart solvents" processing allows a technologies suite for developing greentech production across a wide range of tasks in industrial chemicals manufacture and biorefining. Algal biomass biorefining is another example where extraction processes utilizing supercritical and dense $CO_2$ alone as well as in mixtures with water, methanol and other solvents have been demonstrated (Soh and Zimmerman, 2011, 2012; Bjornsson et al., 2012; Soh et al., 2014; Goto et al., 2015; Du et al., 2013, 2015; Boyd et al., 2012; Reyes et al., 2014; Paudel et al., 2015). The capability to extract lipids from wet algal biomass is a particularly significant breakthrough involving $CO_2$ utilization, as well as DME (Goto et al., 2015) which can be produced utilizing $CO_2$ input (as noted elsewhere herein).

In 2005, Professor Philip Jessop of Queens University in Canada developed a powerful "green chemistry" method of "switchable solvents." Switchable solvents utilize $CO_2$ and $N_2$ to switch the polarities and/or miscibility properties of ionic liquid solvents (Jessop, undated; Jessop and Subramanian, 2009; Jessop et al., 2005, 2011, 2012; http://www.switchablesolutions.com; Phan, 2008; Phan et al., 2008, 2009; Kerton, 2009; Mercer, 2012; Durelle, 2014; Vanderveen et al., 2014; Durelle et al., 2015; Boniface et al., 2016). The nature of the process can include "switchable hydrophilicity" triggered by $CO_2$ absorption into, and exsolution out of, a switchable solvent. This capacity can switch a miscible water-solvent mixture into an immiscible situation of water separated from a (switched) hydrophobic solvent. Phan et al., 2009 demonstrated use of this method for the extractive separation of soybean oil from flaked dried soybeans. Extraction of soybean oil into a switchable solvent was followed by addition of water, causing an immiscibility separation between the desired extracted oil product and a water phase into which the solvent was separeated and dissolved. By addition of bubbled $CO_2$ to this solvent-in-water phase, a "switching" of solvent polarity resulted. This created a 2-phase miscibility situation of water separated from a solvent-+-$CO_2$ phase. The latter phase allowed recovery of the solvent upon removal of dissolved $CO_2$ by removing the $CO_2$ atmosphere with nitrogen bubbling. Boyd et al., (2012) and Du et al., (2013, 2015) have applied this type of method to lipid extraction from wet algal biomass. Solvent swithing with $CO_2$ allows solvent processing of wet algal biomass without an energy intensive biomass drying step. It also allows lipid extraction with solvent recycling. Such methods avoid the energy intensive step of distillation-separation for solvent recovery. $CO_2$ provides the "switch" that allows water separation and solvent recycling via miscibility rather than distillation.

Additional methods pioneered by the Jessop group have created $CO_2$-switchable dehydration agents for the removal of water from organic liquids without distillation. A significant example of the capability of this method is removal of water from ethanol (Boniface et al., 2016).

Carbon dioxide can be utilized for carbon monoxide (CO) production. One example is via the endothermic reverse Boudouard reaction: $CO_2+C \leftrightarrows 2CO$ (Lahijani et al., 2014a; Wikipedia: Boudouard reaction). This reaction has been shown to be modifiable usefully to lower temperatures with microwave stimulation (Hunt, 2013; Lahijani et al., 2014b). Carbon monoxide is useful as a primary reducing agent in mineral smelting for value addition to mineral concentrates. The classic reaction is coal gasification to CO in an atmosphere of $CO_2$. However, the Boudouard reaction also is useful without coal input in syngas production from biomass and/or municipal waste using inputs of $CO_2$ such as pure $CO_2$, or $CO_2$—O2, or $CO_2$-steam.

$CO_2$ addition into biomass gasification is useful in two modes. The first is that it acts as a "gasifying agent." $CO_2$ addition into biomass gasification tends to increase both gasification extent and thermal efficiency, as described in a subsequent section. The second mode is via $CO_2$ utilization in conversion of (undesirable) char output within biomass gasification: increasing CO production from reduced carbon via the Boudouard reaction, thereby increasing the overall CO yield in syngas production (Kwon et al., 2009; Rafidah et al., 2011; Lahijani et al., 2014; Prabowo et al., 2014, 2015a,b; Yi et al., 2015). In some situations where CO directed into chemicals manufacture, $CO_2$ overall is net absorbed. $CO_2$-enhanced biomass gasification can be utilized as a form of advanced greentech for combined power and hydrocarbon chemicals manufacture. Many options are helpfully categorized and reviewed by Yi at al., (2015).

Another mode of production of carbon monoxide from $CO_2$ is by electrolysis, also known as "$CO_2$ splitting." Intense research has yielded a variety of potential modes of electrolytic $CO_2$ splitting to produce CO and $O_2$ in catalyzed aqueous reaction systems (Whipple and Kentis, 2010; Rosen et al., 2011, 2012; Chen et al., 2012; Tornow et al., 2012; Lu et al., 2013, 2015; DiMeglio and Rosenthal, 2013; Jhong et al., 2013; Kumar et al., 2012; Kumar et al., 2013; Saheli-Khojin et al., 2013; Asadi et al., 2014; Medina-Ramos et al., 2014, 2015; Costentin et al., 2014; Jones et al., 2014; Ma et al., 2014; Masel et al., 2014; Rosen et al., 2015; Mao and Hatton, 2015; Shen et al., 2015). A breakthrough in efficiency is the use of $Au_{25}$ nanoclusters as an electrocatalyst, allowing a production efficiency of ~3.8 MWh per tonne of $CO_2$ split into separated CO and $O_2$ streams (Kauffman et al., 2015). "Dioxide Materials" is a start-up company created as a result of research cited above created at the University of Illinois. Dioxide Materials seeks to develop commercially scaled systems using a combination of electrolytic $CO_2$ and $H_2O$-splitting, producing CO, $H_2$ and $O_2$. The purpose is to utilize $CO_2$ and renewable electricity as an alternate mode of production of fuels and industrial chemicals, replacing petroleum-based fuels and chemicals (www.dioxidematerials.com; ARPA-E, 2013; Masel et al., 2014; Dioxide Materials, 2014). In addition to carbon monoxide, direct production of formic acid by combined water and $CO_2$ electrolysis is included within the company's agenda (Whipple and Kenis, 2010; Whipple et al., 2010; Jhong et al., 2013; Masel et al., 2014).

A non-aqueous modality of CO production from $CO_2$ of particular interest is electrolysis in molten lithium carbonate, $Li_2CO_3$, developed by Valery Kaplan and colleagues in Igor Lubomirsky's research group at the Weizmann Institute in Israel (Valery et al., 2010; U.S. Pat. No. 8,906,219 B2). The net electrochemical reaction is: $CO_2 \rightarrow CO + \frac{1}{2}O_2$. It proceeds via $Li_2CO_{3\ (molten)} \rightarrow Li_2O_{(dissolved)} + CO_{(gas)} + \frac{1}{2}O_{2(gas)}$, balanced by continuous $CO_2$ influx: $Li_2O_{(dissolved)} + CO_{2\ (gas)} \rightarrow Li_2CO_{3\ (molten)}$. The process operates at ~900 degrees centigrade. It exhibits close-to-100% Faradaic and thermodynamic efficiency. It provides separated gas flows of CO and $O_2$ at the cathode and anode respectively.

A promising closely related mode of $CO_2$ utilization is the method of electrolytic $CO_2$ splitting in molten lithium carbonate developed by the research group of Stuart Licht at George Washington University (Ren et al., 2015; Li et al., 2015; Armitage, 2015; Licht et al., 2016). This method splits $CO_2$ into carbon nanofibers ($C_{CNF}$) and $O_2$ gas. It operates with near 100% Coulombic efficiency. (One mole of reduced carbon product is produced by ~4 moles of applied electric charge.) Between 8 MWh and 16 MWh of energy input are expected to be required for practical production of 1 tonne of carbon nanofiber/nanotubes product, according to Ren et al., 2015, and Licht et al., 2016. The lower end of this energy input range reaches and exceeds carbon neutrality for utilization of $CO_2$ when compared to the amount of $CO_2$ waste generated by generating process input power efficiently combusting natural gas. Using solar power input of course can make this process strongly $CO_2$ absorbing. The method offers a possibility for mass production of $C_{CNF}$ at a low cost with minimized expenditure of energy and with essentially zero associated waste. A key question for the future is whether this method can be refined to produce carbon nanofibers efficiently in the high value forms of either Multiple Walled Carbon Nanotubes (MWCNs), which have substantial value at ~US$100,000/kg, or Single Walled Carbon Nanotubes (SWCNs), which have extreme value in the range of ~US$1,000,000/kg (Wilkinson, 2015). SWCNs are distinctive for being low density (~1.4 g/cubic cm), while exhibiting the highest tensile strength (up to ~100 GPa) of any known material along their tube direction, also with the highest stiffness (elastic modulus) of any known material along their tube direction. Industrial use of MWCNs and SWCNs has been developing since the key publication heralding their discovery in 1991 (Ijima, 1991). A high cost of production has been a substantial impediment against rapid uptake involving a very wide variety of high tech uses involving strength as well as electronic properties. In principal, wires manufactures from carbon nanotubes could replace copper windings in electric motors. Carbon nanotubes could create the world's strongest, lightest-weight ropes and bullet-proof armor. They also can add substantial strength into aluminum Al-alloy and other metals as nanocomposites. These materials also may have many future electronic uses: in batteries, capacitors, computational integrated circuits, photovoltaics and light-emitting materials. Substantial early-stage industrialization using large quantities has been relatively simple thus far. It has followed the technology of fiberglass, using carbon nanotubes as a strengthening agent in materials created with epoxy matrix similar to other "carbon fiber" composites, only stronger and lighter. An example of a manufacturer is the company Zyvex Technologies (http://www.zyvextech.com). Zyvex has manufactured a range of epoxy resin based products using advanced carbon tube fibers in composites. These have been used in aerospace materials, superlight military drone-boat hull fabrication, and various uses for lightweight strong materials in high-end sports equipment ranging from bicycle wheels to baseball bats to lacrosse sticks to sailboat masts. The world market for carbon nanofibers, however, is small at present: perhaps less than 10,000 tonnes per year (Sherman, 2007; Johnson, 2014; Davenport, 2015; McKenna, 2015). Energy efficient production of these very high strength nanomaterials can be environmentally favorable in the context of life cycle analysis (Khanna et al., 2008). If produced at low cost using an efficient industriaization of the Licht method or developed analogs, $CO_2$ utilization to produce carbon nanofibers has substantial potential for both export and local manufacturing industrialization. The range of applications is immense for a low-cost production process (De Volder et al., 2013; Wikipedia: Potential applications of carbon nanotubes; NNI, 2014; Agarwal et al., 2010). The Licht method electrolyzes $CO_2$ absorbed into solution in a molten salt of lithium carbonate, $Li_2CO_3$, in the range ~725 to 800 degrees centigrade. Production of C-nanofibers proceeds according to the net reaction: $CO_2 \rightarrow C_{CNF} + O_2$. This is via: $Li_2CO_{3\ (molten)} \rightarrow Li_2O_{(dissolved)} + C_{CNF(solid)} + O_{2(gas)}$ with fiber nucleation initiated and catalyzed by trace zinc and nickel. A continuous process cycle is created by continuous absorbtion-infusion of $CO_2$: $Li_2O_{(dissolved)} + CO_{2\ (gas)} \rightarrow Li_2CO_{3\ (molten)}$ with removal of the products $C_{CNF}$ and pure $O_2$, with the latter being an additionally useful co-product. Other similar electrochemical $CO_2$ splitting technologies producing $O_2$ and carbon filamentrary material in molten alkali salt and chlor-alkali salt systems have been demonstrated by Yin at al., (2013) and Ge et al., (2015). The latter reports production of a form of amorphous carbon useful as negative electrode material for Li-ion batteries. The general opportunity of molten carbonates for $CO_2$ utilization is reviewed by Chery et al., (2015).

Other methods have been developed for $CO_2$ utilization by reduction to produce high-value pure carbon products. These include: C60 (Chen and Lou), Y-junction carbon nanotubes (Lou et al., 2006), diamond (Lou et al., 2003a,b, 2004) and dense nanoporous graphene useful as the energy storage material in high-power supercapacitors (Xing et al., 2015; Science News, 2014). Graphene and other C-based supercapacitor technologies have created many start-up companies.

$CO_2$ can be utilized as an input to produce formic acid ($HCO_2H$) via a number of catalyzed hydrogenation methods following the overall formulae: $CO_2 + H_2 \rightarrow HCO_2H$ and $CO_2 + H_2O \rightarrow HCO_2H + \frac{1}{2}O_2$. The Norwegian Company Det Noeske Veritas, DNV-GL (https://www.dnvgl.com/) developed an innovation agenda in the area of renewable energy management addressing environmental risk. DNV decided to develop a CCU expertise to produce formic acid (DNV, 2011; Sridhar et al., 2012; Agarwal et al., 2011). DNV's techno-economic analysis (DNV, 2011) indicates formic acid offers a potentially economically attractive mode for industrializinging a power-to-liquids (PTL) technology: the transformation of electric power, $CO_2$ and water into industrial hydrocarbon liquids, including but not limited to fuels. The attractiveness of electrochemical formic acid production according to DNV's analysis follows four factors: (i) the possibility to store electrical energy with carbon recycling; (ii) technological potential based on efficiency performance for the hydrogenation and de-hydrogenation of formate; (iii) formic acid industrial utility apart from its specific use for energy storage; and (iv) a market price situation for formic acid favoring the electricity inputs required for electrolytic hydrogenation. In respect of the fourth factor, DNV estimated that the electric power input cost for $CO_2$-recycling electrolytic production was less than half of the commodity price of formic acid. (This price is based on the dominant production method of methyl formate hydrolysis employed by the formic acid producers BASF and Kemira-Taminco. Methyl formate is produced from methanol and carbon monoxide inputs. Robledo-Diez, 2012.) An electricity input cost estimate is based on ~4 MW-h per tonne of formic acid produced (DNV, private communication). This corresponds to an electricity input price of ~$400/tonne of 100% formic acid at a power cost of ~US$0.10/kW-h. There has been special interest in Europe in both PTL and Power-To-Gas ($CH_4$) $CO_2$-recycling power-storage technologies. This interest is for stabilizing the intrinsically irregular streams of electric power generated by wind and solar energy. Stabilizing strategies that direct excess electric power flows into synfuels and industrial chemicals production are attractive if there are prospects for combining economic profitability with environmental sustainability. Formic acid ($H_2CO_2$) possibly can operate with superior performance in this function as a $CO_2$-based hydrogen carrier, allowing a carbon neutral process if renewable power sources are utilized. Formic acid therefore provides a basis for a "hydrogen battery."

The US start-up company "Liquid Light" (www.llchemical.com) developed out of electrocatalyst innovations at Princeton University in the PhD thesis of Emily Cole, advised by Professor Andrew Bocarsly (Cole, 2009; Cole and Bocarsly, 2010; Cole et al., 2010). The company has developed, patented and demonstrated several electrochemical methods of reduction of $CO_2$ into formate and formic acid (U.S. Pat. No. 8,562,811 B2). These methods require inputs of $CO_2$ and electricity. External hydrogen gas inputs are not required because hydrogen is provided by the electrochemical process which includes water-splitting. Liquid Light also has developed methods for $CO_2$ electrochemical reduction to produce other industrial biochemicals. The company is focused especially on monoethelyne glycol (MEG) used in many industrial processes including production of plastic beverage bottles made from polyethelene terephthalate, PET (Law, 2015a,b). Estimates provided in Parajuli et al., (2014) indicated electric power input costs in excess of the market price of formic acid. However, these authors noted this was based substantially on a low process selectivity, $CO_2$-to-formate of only 40%, with expectations of future enhancement. (A process improvement increase to 60% was documented in White et al., 2014.) Success in this agenda could offer useful opportunities for electrochemical production of formic acid utilizing $CO_2$ input. More broadly, Liquid Light represents an exciting agenda for industrializing $CO_2$ recycling into industrial chemicals via electrochemical technologies. As indicated by the company's name, a distinctive aspect of its vision is eventually to use photoelectric power and/or direct photocatalytic reduction of $CO_2$ (White et al., 2014; Bocarsly, 2014). At present, Liquid Light's main focus is on developing its $CO_2$-utilization core platform for formate electrosynthesis linking to oxalic acid then MEG production for use in PET beverage bottles manufacture (Zhu et al., 2013; Law, 2015a,b; SRI Equity Research, 2015).

An imidazolium-modified gold catalyst developed by Toshiba has been demonstrated to allow production of ethylene glycol by electrochemical reduction of carbon dioxide with high Faradaic efficiency (Tamura et al., 2015).

Hydrothermal conversion of $CO_2$ and water into formic acid is a biomimetic mode of $CO_2$ utilization developed by Fangmin Jin and collaborators. This method couples $CO_2$ reduction with water-splitting catalyzed by the oxidation of zero-valent metals (Al, Mn, Fe, Zn, Mn), especially zinc in the presence of copper, in a metal/metal-oxide redox cycle (Wu et al., 2009; Jin et al., 2011, 2012, 2014; Zhang et al., 2011; Lyu et al., 2014; Chen et al., 2015; Demirel et al., 2015; Yao et al., 2015; Zeng, 2014; Wang et al., 2015a,b; Zhong et al., 2015). Similar $CO_2$-utilizing methods have been demonstrated for hydrothermal conversion of $CO_2$ into methanol (Guan et al., 2003; Huo et al., 2012; Lyu et al., 2015; Ren et al., 2015.)

Formic acid is an industrial chemical with growing use globally. It has traditional utility as a pickling agent in the tanning of hides, as a preservative in silage animal feeds, and as a coagulant in the production of rubber. Ecologically beneficial uses replacing polluting industrial processes are of particular interest in the area of papermaking. Formic acid has been known as an economically attractive wood pulping agent since 1983 (Bucholtz and Jordan, 1983). It has been a pulping component in the environmentally beneficial "Organosolv" suite of technologies widely used in the pulp and paper industry, with special application to in the delignification of *eucalyptus* wood (Baeza et al., 1991). Rousu et al., (2002) first demonstrated the utility of formic acid as the basis for an ecologically attractive closed-cycle greentech pulping process for fibrous agricultural waste integrated with biorefining: the "Chempolis" process. The Rousu family industrialized this process in Finland via their company Chempolis (www.chempolis.com). Formic acid can be used in the hydrolysis of bamboo cellulose to liberate sugars with high efficiency (Sun et al., 2008; Zhuang and Li, 2012; Kupainem, 2012; Hagesawa et al., 2013; Li et al., 2014). Similarly, formic acid can be used to depolymerize bamboo lignin, and other sources of lignin, into valuable aromatic products such as, for example, vanillin (Rahimi et al., 2014). Additionally, formic acid can be used as an effective delignifying pulping agent for banana stem waste in papermaking (Mire et al., 2005; Jahan et al., 2007; Sridach, 2010; Sannigrahi and Ragauskas, 2013). Formic acid biomass treatment technology utilizing bamboo and banana tree waste and other non-food forms of biomass has many potential future bio-production applications additional to the direct one of papermaking. These range from sugars separation and production (from bamboo: principally glucose ~41% and xylose ~22% by weight: Li et al., 2012) to high-efficiency catalysis-based and also enzymatic bio-hydrogen production from sugars (Li et al., 2015; del Campo et al., 2013; Rollin et al., 2015), to fine bio-chemicals production in many and various modalities (Philbrook et al., 2013), to ethanol production by fermentation (Littlewood et al., 2013). Xylose can be processed into the valuable "tooth-friendly" food sweetener sugar-alcohol "birch sugar" xylitol (Dupont-Danisco trade name: "Xivia") which inhibits dental decay and is medically indicated for sucrose substitution for diabetics. Dupont is a major manufacturer of xylitol in the alternative sweeteners industry (Dupont, 2012).

Chempolis (www.chempolis.com) has successfully industrialized formic acid pulping via its formic acid-based biorefining process and plant design. Chempolis' plants are able to intake both tree wood and other non-wood biomass such as bamboo, banana stem waste, papyrus reeds, and corn/maize, and sorghum stover. The company's industrialized technologies include: (i) environmentally benign pulping ("formicofib") with co-production of potassium fertilizer and biochemicals including acetic acid, furfural, glucose and pentose sugars; and (ii) non-food cellulosic ethanol production ("formicobio"), (www.chempolis.com, various). Chempolis is developing biorefineries utilizing formic acid technologies in China, India and Indonesia. The chemistry of organic acid solvent effects in woody biomass breakdown and conversion reactions, including that of formic acid, is reviewed by Shuai and Luterbacher (2016).

$CO_2$ can provide related industrial value in the area of biomass preparation as a lignin solvent, as a sugars-releasing cellulose hydrolyzing agent, and as a mechanically explosive microshredding biomass agent for pulp production for paper and for pretreatment of both woody and non-woody for biorefining into chemicals and biofuels. The uses of $CO_2$ in this area include: (i) carbonic acid pretreatment (Walsum and Shi, 2004; Walsum et al. 2007; Jian et al., 2009), (ii) supercritical $CO_2$ pretreatment sometimes including micro-disaggregating pressure-release "$CO_2$ explosion" (Puri and Mamers, 1983; Zheng, 1995, 1998; Srinivasan and Ju, 2010; Narayanaswamy et al., 2011; Santos et al., 2011; Gu, 2013; Gu et al., 2013; Gurgel et al., 2014; Maurya et al., 2015; Relvas et al., 2015), and (iii) pressurized bi-phasic $CO_2$—$H_2O$ thermal pretreatment (Li and Kiran, 1988; Luterbacher et al., 2010, 2012a,b). These techniques allow $CO_2$ to be used as an effective agent for biomass pretreatment in a number of specific contexts, such as, for example, xylose separation for xylitol production from bamboo and/or banana stem waste as an extractive value-capturing process integrated into pulping processes for papermaking. The $CO_2$-specialized company, the Linde Group (www.linde-worldwide.com) has developed several additional uses for $CO_2$ in papermaking (Linde, 2012). These include soap acidulation, pulp washing, and process pH control and stabilization (Haring, 2008).

Supercritical $CO_2$ can be used for intake biomass treatment for the production of viscose textiles made from wood, bamboo and banana stem waste based on regenerated cellulose, (Zhang et al., 2013; Saxena, 2013; Lenzing, 2012; Medina-Gonzalez et al., 2012).

$CO_2$ provides an effective recovery mechanism for the lignocellulosic biomass solvent γ-valeractone (GVA). $CO_2$ generates a biphasic immiscibility separation. A GVA plus $CO_2$ phase autoseparates from a sugars-rich aqueous phase. This phenomenon creates the possibility of recovery-recycling of GVL in GVL-based biorefining scenarios utilizing $CO_2$ (Lueterbacher et al., 2014, 2015a,b; Luterbacher and Luterbacher, 2015; Fang and Sixta, 2015; Han et al., 2015; Shuai et al., 2016; Shuai and Luterbacher, 2016).

Formic acid is used as a fuel in Direct Formic Acid Fuel Cells (DFAFCs). This technology is well demonstrated as a form of high-efficiency, high energy density battery, recharagable by reloading formic acid. The technology was developed in the University of Illinois (Yeom et al., 2003; Ha et al., 2004). It was thereafter (abortively) industrialized by a group of large companies linked with the company Tekion (Wikipedia entry: "Formic Acid Fuel Cell"). Applied research continues, as reviewed by Wang et al., 2014). The University of Eindhoven's "Team FAST" is building a formic acid-powered car (www.teamfast.nl). There also is active start-up industrialization. The Mantra Venture Group (www.mantraenergy.com) has demonstrated a multi-fuel fuel cell called a Mixed-Reactant Fuel Cell (MRFC) which can function as a DFAFC (Mantra Energy Alternatives, undated). Formic acid also may be used in formic acid reformers providing hydrogen into fuel cells. This technology has been industrialized by Neah Power (www.neahpower.com). It is used in drones made by Silent Falcon UAS Technologies (www.silentfalconuas.com). Larger-scale industrialization of formic acid-based energy and hydrogen storage technologies is possible. A thermodynamic and economic analysis by Singh et al. (2015) shows that formic acid is in general a highly attractive business target for electrochemical $CO_2$ reduction to produce a commodity chemical with energy-carrying capacity. Research efforts developing improved efficiencies in catalysis and production modes for $CO_2$ hydrogenation to formic acid and formate have been proceeding with rapidity and many successes (Leitner, 1999; Li and Oloman, 2005, 2006, 2007; Oloman and Li, 2008; Whipple and Kenis, 2010; Whipple et al., 2010; Enthaler et al., 2010; Agarwal et al., 2011; Boddien et al., 2011; Hull et al., 2012; Martindale and Compton, 2012; Wesselbaum et al., 2012; Fujita et al., 2013; Jhong et al., 2013; Junge and Beller, 2013; Czaun et al., 2013; Beller and Bornscheuer, 2014; Zhang et al., 2014a,b; Jin et al., 2014; Filonenko et al., 2014; Schmidt, 2014; Moret et al., 2014; Takeda et al., 2014; Lu et al., 2014; Watkins and Bocarsly, 2014; Blas Molinos, 2015; Cheng et al., 2015; Wang et al., 2015; Zhang et al., 2015; Su et al., 2015a,b; Lee et al., 2015; Kortlever at al., 2015; Kothandaraman et al., 2015; Min and Kanan, 2015; Zhang et al., 2015; Del Castillo et al., 2015; Yoo et al., 2015; Gao et al., 2016).

$CO_2$ can be hydrogeneted to formate in non-photosynthetic bioengineered systems (Jajesniak et al., 2014; Alissandratos and Easton, 2015). Future $CO_2$ utilization may produce formic acid biocatalytically by enzymatic biotechnologies, either whole cell or cell-free, following initial work by Thauer, (1972), Ruschig et al., (1976), Klibanov et al., (1982), Obert and Dave, (1999), Miyatani and Amao, (2002), Lu et al., (2006) and Reda et al., (2008). Reviews have been provided by Lanjekar et al., (2011), Beller and Bornscheuer, (2014), Jajesniak et al., (2014), and Shi et al., (2015). A major breakthrough was made by Schuchmann and Muller (2013; see also Pereira, 2013). These researchers demonstrated that a single enzyme, "hydrogen-dependent carbon dioxide reductase" (HDCR), was able to hydrogenate $CO_2$ into formate efficiently and with a very high turnover rate without additional cofactors. They further demonstrated a whole-cell formate production technique that intakes $CO_2$ plus $H_2$, or CO plus $H_2$ (syngas), and outputs formate.

$CO_2$ utilization to produce formic acid can be combined with biotechnologies for biofuels production by microbial electrosynthesis. A formic-acid based "electromicrobial" system for electrolytic $CO_2$ utilization coupled with biosynthesis of biofuels such as butanol was developed by the UCLA group of James C. Liao (Liao, 2013; Li et al., 2012). This work provided a basis for the start-up company Easel Biotechnologies, LLC (www.easelbio.com). Easel Biotechnologies is focused on bioproduction of electrofuels.

The start-up biotechnology company Gingko Bioworks (www.gingkobioworks.com) bioengineered chemoautotrophic microbes capable of transforming formate input into a variety of biochemicals and biofuels (Lane, 2015).

Carbon dioxide can be utilized by the co-electrolysis (or "co-splitting") of $CO_2$ and $H_2O$ together in high-temperature solid oxide electrolyzer cells (SOECs). With intake of $CO_2$, $H_2O$ and electric power, SOECs yield an anode output of pure $O_2$ gas and a cathode output of syngas ($H_2$ and CO), according to the net reaction: $H_2O+CO_2 \rightarrow O_2+(H_2+CO)$, (Ebbesen et al., 2009; Ebesen and Mogensen, 2009; Graves, 2010; Graves et al., 2011; Mogensen, 2013; Chen et al., 2013; Stempien et al., 2013; Badwal et al., 2014). This technlogy allows storage of electrical energy (typically intermittant renewable energy when in excess) into methanol, DME and other synthetic liquid fuel outputs of syngas production (GTL). SOEC co-electrolyzer systems also can provide oxygen output. The technology is integrable with various modes of biomass gasification and upgrading ($CO_2$ methanification) and power generation, and with syngas production as noted above. Overall, $CO_2$ utilization-recycling via co-electrolysis with water in SOECs is a substantially promising and flexible "green" technology likely to be implemented in Europe future low-$CO_2$ energy and fuels economy. SOEC co-electrolysis and related technologies have been developed in a serious manner in Denmark with initial industrialization by the company Haldor Topsoe collaborating with a large research group at the Technical University of Denmark (Minh and Mogensen, 2013; Ridjan et al., 2013; Ryde, 2014; Hansen, 2015; Jensen, 2015). The German company "Sunfire GmbH" (www.sunfire.de) has commercialized a SOEC-based Power-to-Liquids system. Sunfire's method uses $H_2$ produced in a SOEC from steam (with $O_2$ byproduct). This $H_2$ is reacted with $CO_2$ input into syngas flowing into Fischer-Tropsch reactors. The combined process produces diesel and other synfuels with 70% capture of energy input into caloric value output in the synfuels (Sunfire, 2014). Development activity for SOEC co-electrolysis in the US is reviewed by Stoots (2011). Research describing a technologically different modality to co-electrolyze $CO_2$ and $H_2O$ with variability control in the $H_2$/CO ratio of syngas output has been described by Kang et al., (2014). Also, Walsh et al., (2014) demonstrated a potentially low-cost modality of co-electrolysis of $CO_2$ and $H_2O$ catalyzed in an aqueous flow using a molybdenum catalyst with multi-walled cabon nanotubes. The process yields an $H_2$/CO molar ratio of 2, ideal for methanol production.

Professor Jacob Karni of the Weizmann Institute developed a thermal process for the co-dissociation "splitting" of $CO_2$ plus water vapor (Karni, 2011) into syngas and oxygen.

Research of his group led to the formation of the start-up company NCF/NewC $O_2$-Fuels (http://www.newco2fuels.co.il/about/). This company is now a subsidiary of Australia-based GreenEarth Energy, Ltd (http://www.greenearthenergy.com.au).

Carbon dioxide can be utilized combined with methane for syngas production by catalyzed gas phase reactions for Gas-to-Liquids (GTL) production of methanol and higher molecular weight hydrocarbon fuels. For example, carbon dioxide can be utilized via the endothermic "dry reforming" reaction $CO_2+CH_4 \leftrightharpoons 2CO+2H_2$ to produce syngas with $H_2/CO=1$, though the net ratio is lower due to heat production required by the reaction. (See: Noureldin et al., 2015). One well-established example of commercialized industrial CO production by dry reforming natural gas or LPG with $CO_2$ is the "Calcor" process. This process was created by the German company Caloric Anlagenbau GmbH (Tuener et al., 2001).

Several modes exist for $CO_2$ input into syngas production in combination with natural gas for the purpose of producing methanol and/or other synthetic fuels and chemicals (Luu et al., 2015). "Methane oxyforming" (sometime called "Oxy-$CO_2$ reforming") utilizes inputs of methane, $CO_2$, water and $O_2$. It involves combinations of steam reforming of methane ($CH_4+H_2O \rightarrow CO+3H_2$), dry reforming of methane ($CH_4+CO_2 \rightarrow 2CO+2H_2$), and partial oxidation reforming of methane ($CH_4+\frac{1}{2}O_2 \rightarrow CO+2H_2$). With inclusion of dry reforming, this combination utilizes $CO_2$, yielding the net reactions: $3CH_4+O_2+CO_2 \rightarrow 4CO+6H_2$, and $5CH_4+2O_2+CO_2 \rightarrow 6CO+10H_2$ (York et al., 2007; Jiang et al., 2010). A variation known as "tri-reforming" adds-in the catalytic combustion of methane, releasing heat: $CH_4+2O_2 \rightarrow CO_2+2H_2O$. Tri-reforming has been developed as a possible widespead industrial modality of utilizing impure $CO_2$ from flue gases to create synthetic fuels ("synfuels") and chemicals by Fisher-Tropsch and related processes (Song, 2001, 2006; Song and Pan, 2004; Jiang et al., 2010). Fisher-Tropsch GTL historically has been limited to very large scale industrial complexes (Lewis, 2013). However, the situation has changed drastically with the development of a new market for small-scale GTL plants. The plants are being created for the utilization of "stranded gas" all over the world (Jacobs, 2013). Most of the existing companies involved are reviewed in a 2014 Word Bank report and slide deck by Fleisch, (2012, 2014). Companies include: Oberon Fuels (www.oberonfuels.com, Oberon Fuels, undated), Velosys (www.Velocys.com, Velosys, undated), Compact-GTL (www.compactGTL.com, CompactGTL, undated), GasTechno (www.GasTechno.com, GasTechno, undated; Breidenstein, 2015), Greyrock Energy (www.greyrock.com, Grey Rock Energy, undated) and Maverick Synfuels/(www.mavericksynfuels.com; www.mavericknorthstar.com). Small-scale GTL plants allow the conversion of "stranded" natural gas obtained from pipeline-isolated wells, into valuable products in combination with inputs of $CO_2$, water and sometimes separated oxygen, combined in various mixtures. Maverick has a line of small "Oasis" GTL plants focused on methanol production (Maverick Synfuels, 2014, undated).

Another process utilizing $CO_2$ is the production of acetic acid ($CH_3COOH$, or $CH_4CO_2$). Acetic acid is the active substance in vinegar obtained by fermentation of ethanol. It is a basic input into many industrial synthesis processes. World demand is ~12 million tonnes per year circa 2015 (Tweddle, 2014). Acetic acid produced for industrial use typically has been made by a non-biological syngas production process via methanol. To produce acetic acid, methanol is carbonylated with input of carbon monoxide, initially via the "Monsanto process" and later in the "Cativa process." In 2014, BP announced it had developed an improved large-scale industrial synthesis via the "SaaBre process," based on coal-to-syngas and/or natural gas reforming (Pavlechenko, 2014). BP announced it would apply the new synthesis method in a large facility planned for Oman (2b1st Consulting, 2014). The Gas Technology Institute is developing a direct catalytic gas synthesis GTL production process for acetic acid based on $CO_2$ and methane inputs (CCEMC, 2014). Acetate also can be produced using $CO_2$ directly by electrochemical reduction of $CO_2$. For example, impressive lab results were described by Yanming Liu et al. (2015) for an aqueous system using a non-metallic catalyst: nitrogen-doped nanodiamond deposited on the surface of an array of silicon micropillars.

Industrial bioproduction of acetic acid has been practiced for many centuries via the fermentive oxidation of ethanol by aerobic acetic acid bacteria (Ebner and Sellmer-Wilsberg, 2002; Raspor and Goranovic, 2008; Mamlouk and Gullo, 2013). An historic step towards $CO_2$ utilization in acetic acid bioproduction relates to the discovery of an acetone-butanol fermentation process used in the production of explosive munitions (smokeless powder cordite). A major breakthrough was developed by Chaim Weizmann, later first President of Israel, who patented a high-productivity process based upon the fermenting capacities of the aneorobic acetogenic (Hartmanis and Gatenbeck, 1984; Millat et al., 2011, 2013; Jeon et al., 2012) acetone-producing bacterium *Clostridium acetobutylicum*. This was in the UK in 1915 in the urgent wartime emergency of WWI (Jones and Woods, 1986; Krabben, 2014; Weizmann Magazine, 2015). Weizmann's method fed biocultures with various feed sources such as corn and potato mash starch and molasses glucose. However, more recently, broadly related industrial acetate bioproduction methods have been developed using gas inputs of $CO_2$ and/or CO, with and without $H_2$ addition, as carbon sources (Barker et al., 1945; Levy et al., 1981a,b; Worden et al., 1991: Daniell et al., 2012). Such processes follow what is believed possibly to be the oldest carbon-fixing process on Earth, utilizing $CO_2$ and $CO_2+H_2$ inputs (Poehlein et al., 2012) in a process known as gas fermentation. Acetic acid is produced by microbial gas fermentation with input of both syngas and $CO_2+H_2$ mixtures (Daniell et al., 2012; Liew et al., 2013; Khan et al., 2014; Latif et al., 2014; Kantzow et al., 2015; Devarapalli and Atiyeh, 2015; Durre and Eikmanns, 2015; Nybo et al., 2015). Acetate production from $CO_2+H_2$ gas fermentation is by cell excretion into the surrounding water medium. Therefore producing cells do not have to be harvested. Productivity can be extremely high in specialized bioreactors. Yields up to 148 $g^{-1}$ $d^{-1}$ acetate have been observed via a continuous dilution process of extraction from cell cultures of gas fermenting Acetobacterium woodii (Kantzow et al., 2015).

LanzaTech (www.lanzatech.com) is a dynamic global company focused on carbon recycling via gas fermentation biotechnology (Kopke et al., 2010, 2011; Daniell et al., 2012; Liew et al., 2013; Harmon, 2015, Holmgren, 2015). LanzaTech and two other companies, INEOS Bio and Coskata, have industrialized gas fermentation for commodity ethanol production from syngas (Kopke et al., 2011; Durre and Eikmanns, 2015). LanzaTech and its several industrial partner companies utilize process gas (for example from steel mill operations) and/or syngas (for example from biomass gasification) to feed microbes in large bubbled tanks yielding ethanol and other output commodity chemicals. LanzaTech also can utilize $CO_2$-rich input gas compositions. For example, the company's website describes a partnership with the Indonesian oil and gas and petrochemicals company Petronas to industrialize a process to utilize $CO_2$ by gas fermentation with $CO_2+H_2$ inputs using LanzaTech's genetically engineered platform organism (De Guzman, 2012). The process described uses gas fermentation to produce acetic acid. This then feeds a second fermentation process producing lipids. These lipids can be separated into two components: high-value nutraceuticals and a residue used for biofuels production (Daniell et al., 2012; LanzaTech, website; Goyal, 2014; Holmgren, 2014). LanzaTech's biological synthesis utilizing $CO_2$ employs what is thought to be the one of the Earth's oldest metabolic pathways. This is the Wood-Ljungdahl pathway of microbial $CO_2$ reduction/fixation utilizing hydrogen to produce acetic acid. The Wood-Ljungdahl pathway proceeds according to the overall stochiometry: $4H_2+2CO_2 \rightarrow CH_3COO^-+H^++2H_2O$, (Wood, 1991; Wood and Ljungdahl, 1991; Drake, 1994; Ragsdale and Pierce, 2008; Fuchs, 2011; Schuchmann and Muller, 2014). It is one of the modes whereby methane is produced in Lake Kivu via an acetogeneisis pathway in its sediments (Tietze at al., 1980; Leigh et al., 1981; Schoell et al., 1988; Lliros Dupre, 2009; Bhattarai et al., 2012; Pasche et al., 2011; Wuest et al., 2012).

An example of the Wood-Ljungdahl pathway operating is another industrial CCU mode: adding $CO_2$ to increase methane production in the anerobic digestion of sewage (Bajon Fernandez, 2014; Bajon Fernandez et al., 2014, 2015; Yasiin et al., 2015; Koch et al., 2016).

A modified mode of $CO_2$ utilization to produce acetate via the Wood-Ljungdahl pathway without hydrogen addition is "microbial electrosynthesis." Microbial electrosynthesis requires inputs of $CO_2$ and electricity. The biology involved is a recent discovery. It is fascinatingly interesting as well as open to innovations from synthetic biology to create new product output modes (Cheng et al., 2009; Lovely, 2010, 2011, 2012, 2015; Nevin et al., 2010, 2011; Rabaey and Rozendal, 2010; Rabaey et al., 2011; Lovley and Nevin, 2011, 2013; Jeon et al., 2012; Li et al., 2012; Logan and Rabaey, 2012; Hawkins et al., 2013; Lovely et al., 2013; Wang and Ren, 2013; Zaybak et al., 2013; Lovely and Malvankar, 2015; Bengelsdorf et al., 2013; Ueki et al., 2014; Xu et al., 2014; Bertsch and Muller, 2015; Durre and Eikmnns, 2015; Jourdin et al., 2015; Patil et al., 2015; Tremblay and Zhang, 2015; Gildemyn et al., 2015; Choi and Sang, 2016; www.electrofuels.org; www.geobacter.org). LanzaTech has developed a pilot-scale commercial biology platform to produce acetate and other commodity chemicals with this type of biotechnology (Mihalcea, 2015; Holmgren, 2015; Lai, 2015; Griffin, 2015) via both methods: (i) $CO+H_2$ and/or $CO_2+H_2$ gas fermentation, and (ii) "electrotrophic" microbial electrosynthesis utilizing $CO_2$+electrons as inputs. The company also has developed a platform using heterotrophic algae to transform acetate into the high-value omega-3 nutraceutical fatty acid DHA (Asian Scientist, 2014; Holmgren, 2014). OakBio is an additional start-up biotech company active in similar areas: utilizing $CO_2$-rich flue gases from cement production as inputs into gas fermentation to produce bioplastics (OakBio, 2014; Theulen, 2015a,b).

CCU to convert $CO_2$ to methane can be by means of a biological phenomenon called "electromethanogenesis" (Cheng et al., 2009) Electromethanogenesis can convert $CO_2$ into $CH_4$ using the input of electrons directly consumed by electrotrophic microbes (Van Eerten-Jansen et al., 2012, 2013 2015; Van Eerten-Jansen, 2014; Hara et al., 2013; Lohner et al., 2014). $H^+$ in water serves as the hydrogen source (Batlle-Vilanova et al., 2015; Fu et al., 2015; Beese-Vasbender et al., 2015; Tremblay and Zhang, 2015). Or electromethanogenesis can use other biological utilizations of electron inputs. Some very interesting laboratory results have been obtained using methanogenic microbes indigenous to depleted oil fields with interest to discover methods to produce methane underground via $CO_2$ flooding with electrical input (Kobayashi et al., 2012; Kuramochi et al., 2013; Sato et al., 2013; Fu et al., 2015; Maeda et al., 2015; Mu et al., 2014; Mu and Moreau, 2015; Vilcaez, 2015; Koide and Yamazaki, 2001; Beecy et al., 2001). This effort offers a new horizon in the field of Microbial Enhanced Oil Recovery, MEOR (Youssef et al., 2009). Very high conversion CUU efficiencies to produce methane and various biochemicals have been observed for hyperthermotrophic systems involving both $H_2$ pathways and direct electrotrophs (Keller et al., 2013, 2015; Sato et al., 2013; Hawkins et al., 2011, 2013; Hawkins, 2014; Maeda et al., 2015; Zeldes et al., 2015). These findings follow basic quantitative insights into biological thermodynamic as well as engineering process efficiencies. They suggest that CCU optimalities for "biosolar fuels" and "biosolar chemicals" are likely to be found in this direction (Hawkins et al., 2011, 2013; Bar-Even et al., 2012a,b; Ducat and Silver, 2012; Frock and Kelly, 2012; Fast and Papoutsakis, 2012). It is too early to know if such biological power-to-gas methods utilizing $CO_2$ will have sufficient efficiency to have commercial potential. The observations and insights are quite new and important, especially as the barriers to economic viability for biofuels other than ethanol are very substantial (Papoutsakis, 2015; Dimitrou et al., 2015; Han et al., 2015; Roken and Greenblatt, 2015) and require large efficiency improvements. No technoeconomic models have been published. The US company Cambrian Innovation (www.cambrianinnovation.com), however, already is using electromethanogenesis commercially in industrial water cleaning applications (Cambrian Innovation, 2013, 2015)

C-4 succinic acid ($C_4H_6O_4$) has many uses as a precursor chemical to polymers, resins, and solvents and as a food additive. It is a widely produced worldwide by biological fermentation (Cok et al., 2013). Lanzatech has developed a way to produce succinic acid via its gas fermentation platform utilizing $CO_2+H_2$ input. Gunnarsson et al., (2014) have demonstrated a labaratory method for fermenting succinic acid with input of glucose and biogas (60% $CH_4$, 40% $CO_2$, molar ratio). This provides a combined method for CCU and biogas upgrading to remove $CO_2$.

Overall, the new microbial gas fermentation industry has a highly promising future. It rapidly is developing wide-ranging flexibility through combinations of the diversity of natural capacities combined with the massive capabilities of synthetic biology to which recently has been added a new horizon of "electrotrophic" biotechnology connecting with renewable sources of electric power. The field offers many exciting possibilities for future $CO_2$ utilization (Durre and Eikmanns, 2015).

C-5 isoprene ($C_5H_8$, also known as 2-methyl-1,3-butadiene) is a core component in the production of synthetic rubber used in the manufacture of tires. The development of "bioisoprene" is an example of substituting a bio-based synthesis process for a petrochemicals-based process. Three company partnerships have developed bioisoprene production for ecological bio-tire manufacture: (i) Genencore/Dupont and Goodyear; (ii) Amyris and Michelin, and (iii) Ajinomoto and Bridgestone (Scandola, 2015). All of the bioproduction methods involved utilize non-gas carbon sources. Isoprene has been targeted for production via gas fermentation by LanzaTech as well as the US chemical giant DuPont. DuPont is seeking patent protection for a syngas-based gas fermentation method: Beck et al., 2014 US 2014/0234926 A1, "Recombinant anaerobic acetogenic bacteria for production of isoprene and/or industrial bio-products using synthesis gas." The new method compliments methods created by the start-up company Genencor (now merged with Dupont), collaborating with Goodyear, to create "bioisoprene" with glucose feeding of biocultures (Genencor, 2010; Whited et al., 2010; Straathof, 2013; Benko, 2012; ETC Group, 2014). Isoprene separates from biocultures as a gas, thereby conveniently avoiding distillation separation methods. It may become possible to bioproduce isoprene efficiently by gas fermentation. This could be a strategic modality for CCU, perhaps also including sourcing hydrogen via new "bio-GTL" natural gas fermentation technologies being developed (Harmon, 2015).

Dimethyl ether (DME: $CH_3OCH_3$) production is a "mini-GTL" modality for $CO_2$ and methane co-utilization. DME is an alternative fuel that can replace both propane and diesel (Semelsberger et al., 2006; Fleisch et al., 2012; GGFR-Fleisch, 2014). DME is useful as a propane/LPG replacement by blending or total substitution. It can be used within the propane/LPG infrastructure. It has substantially lower heating value compared to LPG. However, it fills more mass into standard LPG bottles. In competition between these two factors, the energy per bottle fill is 82% relative to LPG (IDA, 2010). Therefore DME can provide bottled home and business cooking gas based on a methane source, alternate to propane. DME replaces diesel fuel with minor engine modifications plus fuel storage in LPG-type tanks. It has the highest well-to-tank efficiency ratio of any transport fuel made from natural gas (Semelsberger et al., 2006). DME also is environmentally attractive because it is clean-burning. It has attractive performance relative to diesel. Oberon Fuels (www.oberonfuels.com) is specialized in a two-stage syngas-process production of methanol followed by DME utilizing inputs of methane and $CO_2$ (see: Lautzenberg, undated). Oberon's optimal target input mixture is 72% $CH_4$ and 28% $CO_2$, volume percent (corporate website and Corradini et al., 2014: U.S. Pat. No. 8,809,603 B2). A different tri-reforming technology exists for single-step synthesis of DME. It is via a syngas process using inputs of methane, steam and $CO_2$. The process was industrialized by the Korea Gas Coporation, KOGAS in the mid-2000s (Cho et al., 2009, 2011; Chung et al., 2012; Zhang et al., 2015). DME can be a useful non-toxic chemical for processing biomaterials.

DME is an attractive substance for highly efficient low temperature extraction of lipids from wet algal biomass. This is via a method allowing efficient recycling of DME in the vapor phase (Kanda, 2011; Kanda et al., 2012, 2015; Boonnoun et al., 2014; Goto et al., 2015).

Methanol ($CH_3OH$) production is one industrial mode of using $CO_2$ on a potentially very large scale, offering an attractive liquid fuel modality for hydrogen storage (Behrens, 2015; Wang et al., 2015; Perez-Fortes et al., 2016; Al-Kalbani et al., 2016). Methanol and its derivative DME have been advocated with a biomass source as the basis of a green fuels economy by the Nobel prize winning chemist George Olah and colleagues at USC (Olah et al., 2009; Goeppert et al., 2014). Methanol is a well-demonstrated and well-established substitution-blending additive in gasoline/petrol. Methanol's long industrialized dehydration derivative, DME, is produced traditionally via the catalyzed dehydration reaction: $2\ CH_3OH \rightarrow (CH_3)_2O + H_2O$. Or, as noted above, it may be produced by single-step syngas tri-reforming of natural gas with additional $CO_2$ and steam inputs.

Methanol is produced industrially in China from coal and in the US from natural gas. Methanol is used in China mainly as an alternative basis for petrochemicals production. It was widely promoted as a transport fuel in China in the interval 1998 to 2008. It remains widely blended into transport fuel there (CleanTechnica, 2013; Yang and Jackson, 2012; Prakash and Olah, 2014). Methanol is well demonstrated as an efficient clean-burning fuel in retrofitted diesel engines. The diesel engine manufacturer Wartsilla is involved in extensive conversion, converting ships active in the North Sea from bunker diesel fuel to methanol (Haraldson, 2015). Methanol also can be used as a battery-like hydrogen storage fluid. It has ~31% electricity-to-electricity efficiency (Behrens, undated). Matthias Beller and his research group in Rostock, Germany, have developed several efficient calaytic modes for methanol dehydrogenation (Boddien et al., 2011; Nielsen et al., 2013; Alberico et al., 2013; Sponholz et al. 2014; Monney et al., 2014; Alberica and Nielsen, 2015), contributing further towards the potential realization of a possible "methanol economy." This agenda would generate electricity via $H_2$ inputs from methanol dehydrogenation. The resulting $H_2$ flows would power fuel cell electricity generators.

In principle, the thermodynamically most efficient modality of methanol production from methane avoids a syngas step utilizing $CO_2$. Optimal production from natural gas, in principle, proceeds with input of pure $O_2$ by a single-step reaction of partial oxidation via $CH_4 + \frac{1}{2}O_2 \rightarrow CH_3OH$ (Jiang et al., 2010). However, catalysis for efficient production via this reaction has not yet been developed (Zhang et al., 2003: Khirsariya an Mewada, 2013). The company GasTechno appears to have developed a commercially workable modality by reaction flow recycling (Breidenstein, 2015; Fleisch, undated). Many methanol plants operate by inputs of natural gas plus $CO_2$ in order to produce syngas with a target composition optimal for methanol production: $H_2/CO \sim 2.0$. This ratio supports the efficient, long-industrialized, one-step, gas-phase catalyzed reaction: $2H_2 + CO \leftrightarrows CH_3OH$ (Lewis, 2013; Behrens, 2015). This highly selective syngas reaction was first industrialized by ICI in 1966 (Chen, undated).

The Danish technology company Haldor Topsoe is a leading specialist in catalytic syngas and fuel-cell processes, operating worldwide (Hansen and Clausen, 2015). The company's capabilities portfolio includes Gas-to-Liquids (GTL) methanol production from natural gas, with over forty plants constructed worldwide (Aasberg-Petersen et al., 2011; Haldor Topsoe, undated; Hansen, 2012a,b, 2014a,b,c, 2015a,b,c,d,e,f,g). Haldor Topsoe's capabilities portfolio also includes advanced greentech designs and plant constructions for syngas production from biomass inputs, for Power-to-Gas (PTG) producing Synthetic Natural Gas (SNG), and for $CO_2$-utilizing Power-to-Fuels (PTF) technologies. In EU strategies, Haldor Topsoe's technologies are expected to expand to be used for grid-balancing as required for expanding renewable electricity inputs. The agenda is to produce transportation fuels, including methanol, as well as using methanol for electricity-to-electricity energy storage.

Haldor Topsoe has developed processes for converting inputs of $CO_2$, steam and electric power into outputs of methanol and oxygen gas (Hansen, 2014ab, 2015a,c,f,g; Hansen et al., 2011). This technology innovatively combines the operation of a Solid Oxide Electrolysis Cell with a methanol reactor transforming syngas into methanol over a solid catalyst.

A recent method for efficient methanol production from syngas with the target composition by partial oxidation of methane has been developed by Olah and his research group. It is called "oxidative bi-reforming" (Olah et al., 2013a,b, 2015; Santos et al., 2015; Kumar et al., 2015; Olah and Prakash patents: U.S. Pat. Nos. 7,906,559 B2; 8,697,759 B1 and patent application: 2012/0115965 A1). Oxidative bi-reforming operates via a first stage of oxy-fueled methane combustion to produce a hot pressurized mixture of $CO_2$ and steam: $CH_4+2O_2\rightarrow CO_2+2\ H_2O$. Additional methane in 3× the combusted amount is then added for the second step. This produces a syngas-steam mixture with the right composition for methanol production ("metgas"): $3CH_4+CO_2+2H_2O\rightarrow 4CO+8H_2$. The full net reaction then is $4CH_4+2O_2\rightarrow 4CH_3OH$. It is exothermic. This reaction utilizes the $CO_2$ created internally by the combustion component of the synthesis. If, however, a mixture of hot steam and $CO_2$ already is available in the right molar ratio as an industrial by-product, then bi-reforming can simplify to its second stage process with a $CO_2$-utilizing net reaction: $3CH_4+CO_2+2H_2O\rightarrow 4CH_3OH$. It becomes a $CO_2$ utilization process for methanol production by addition of methane utilizing inputs of $CO_2$ and steam. Additional insights into the utilization of $CO_2$ in syngas production routes to methanol are provided by Baltrusaitis and Luyben (2015).

A goal of recent research is to develop improved methods of low-cost industrial catalytic hydrogenation of $CO_2$ to methanol using $H_2$ inputs. Hydrogen inputs may be obtained indirectly, such as $H_2$ obtained from water splitting using renewable electricity (Olah, 2013; Goeppert et al., 2014; Behrens, 2014, 2015; Demirel et al., 2015; Wang et al., 2015; Studt et al., 2014, 2015), or from the chlor-alkali process for chlorine ($Cl_2$) manufacture by electrolysis of NaCl (Kiss et al., 2016). Or hydrogen may be obtained via integrated chemical processes that include water-splitting, for example hydrothermal methods with coupled metal/metal-oxide redox cycling (Jin et al., 2012; Huo et al., 2012; Demirel et al., 2015; Lyu et al., 2015; Ren et al., 2015). Hydrothermal processing also can reduce formic acid into methanol with coupled metal/metal-oxide redox cycling (Zeng et al., 2011, 2014; Liu et al., 2012; Yao et al., 2012). Industrialization of $CO_2$ hydrogenation to methanol using hydrogen from water-splitting with renewable power has been achieved in Grindavik Iceland at the George Olah Plant (www.carbonrecycling.is; Wikipedia entry: Carbon Recycling International; Tran, 2010, 2011; Harp et al., 2015).

Professor Atsushi Urakawa at the ICIQ in Tarragona, Spain, created a one-pass catalyst method for converting high-pressure $H_2$ and $CO_2$ inputs into methanol or DME with high selectivity (Bansode and Urakawa, 2014; Bansode, 2014; Urakawa and Bansode, U.S. Pat. No. 9,133,084, "Process for the preparation of methanol and methanol-derived products from carbon oxides.") This method also allows production of alkane or alkene products with a coupled second reactor.

$CO_2$ can be utilized in combination with methanol to produce dimethyl carbonate (DMC) according to the $CO_2$-utilizing reaction: $2CH_3OH+CO_2\rightarrow (CH_3O)_2CO+H_2O$. DMC has potential for large-scale industrial use. It is an eco-friendly solvent used in the manufacture of paints. It also has very large scale potential, well-demonstrated, as a pollution-decreasing oxygenating additive to gasoline and diesel fuels (Honda et al., 2013). It moreover is used as an electrolyte in Li-ion batteries, as well as as a base material for polycarbonates production. Four synthesis routes, three reacting supercritical $CO_2$ with methanol, and the standard industrial process combining $O_2$ and CO with methanol are reviewed by Saavalianen et al., (2015), Wen et al., (2015), Santos et al., (2014) and Rivetti et al., (1996). Several electrolytic methods also are known. And at least two industrialization agendas are ongoing for a $CO_2$-utilizing direct reaction method (Austrian Institute of Tecnology, 2015; CCEMC-E3Tec Services, L L C, 2014).

$CO_2$ also can be utilized in combination with ethanol to produce diethyl carbonate (DEC) according to the reaction: $CH_3CH_2OH+CO_2\rightarrow (CH_3CH_2O)_2CO+H_2O$ (Gasc et al., 2009; Leino, 2015; Prymack et al., 2015). DEC is a widely used feedstock in various synthesis routes in petrochemical productions. And, like DMS, it has potential for large-scale future utilization as an oxygenating cleanfuel additive for both gasoline and diesel. It also is used as an electrolyte in Li-ion batteries.

Syngas for methanol production is obtainable by other means such as from biomass gasification. A full demonstration exists on an industrial scale in Sweden (Gillberg, 2012, 2013; Ridjan et al., 2013; Kolmogoren, 2014; Danish Methanol Association, 2011; Pedersen and Schultz, 2012; BioMCN, 2013; Landalv, 2014). Syngas with the desired composition, $H_2/CO \sim 2.0$, can be produced from biomass by two modes involving input of $CO_2$ as a biomass gasifying agent/reactant. These are: (i) by input of $CO_2$ reacting with dried biomass with or without steam, or (ii) by input of $CO_2$ with wet slurry biomass promoting gasification reactions in highly pressurized supercritical water. The latter situation is especially advantageous for use of harvested algal biomass that has not been dried or centrifuged to remove intra-cell water (thus saving a large component of energy expenditure). Biomass gasification with input of $CO_2$ reacting with dried biomass with or without steam has been researched extensively. Results indicate that $CO_2$ input can be modulated to obtain a target output of syngas with the ratio $H_2/CO \sim 2.0$. Reaction chemistries are observed with high gasification yields and thermal efficiency in conditions with or without steam (Butterman and Castaldi, 2007, 2008, 2009a, b, 2010, 2011; Prabowo et al., 2014, 2015a,b,c; Kwon et al., 2015; Yi et al., 2015).

Biomass gasification in supercritical water with $CO_2$ input has been modeled by Frietas and Guirardello (2012, 2013, 2015). Model results suggest $CO_2$ input modulation to obtain $H_2/CO \sim 2.0$ (optimal for methanol production) is possible. However, the high pressure and temperature process conditions are non-trivial for industrialization. Also the output syngas contains $CO_2$. Overall, $CO_2$-enhanced biomass gasification does not absorb $CO_2$ in the net of the reactions. However, it has the effect of suppressing the formation of excess $CO_2$ over input $CO_2$ in the output in comparison with syngas production without $CO_2$ input. $CO_2$ input increases gasification efficiency. Importantly, it also reduces the problematic formation of tars and chars. Biomass gasification of algal biomass in supercritical water also has the special advantage of allowing nutrient recycling by salts separation immiscibility between an aqueous phase and other oil-rich and/or gas phases (Yakaboylu et al., 2015).

A potentially large-scale future mode of CCU may follow from a cell-free electrosynthesis method of "artificial photosynthesis." The method utilizes enzymes in an electrical water splitting system to transform $CO_2$ and water into $O_2$ and carbohydrates such as sugars or starch. Energy stored in sugars is expected to become an efficient power storage method via enzymatic hydrogen release and also eventually, via carbohydrate fuel cells. This vision is being pursued by Percival Zhang and his research group at Virginia Tech (Zhang, 2010, 2011, 2013; Zhang and Huang, 2012; Zhang et al., 2012). Zhang's group has developed a cell-free method of enzymatic production of hydrogen from biomass (e.g., Rollin et al., 2015). Shi et al., (2015) provide a review of the field of enzymatic conversion of $CO_2$. Future developments in "artificial photosynthesis" technology development may benefit from from the fact that carbon dioxide reduction to methane and C2 hydrocarbons can be catalyzed by a single biomimetic enzyme, a remodeled nitrogenase (Yang et al., 2012; Rebelein et al., 2014, 2015).

More generally, solar power linked with electrolytic water-splitting and $CO_2$-utilizing "artificial photosynthesis" (Ciamician, 1912; Inoue et al., 1979; RSC, 2012; Purchase and de Groot, 2015) produces "solar fuels" (Harriman, 2013; https://rtsfi.rti.org/RTSFI what.html) and "solar chemicals" (Gates, 2015). This is an active and rapidly expanding field of research, device invention and entrepreneurial company formation (Olah, 2005; Olah et al., 2006; Barton et al., 2008; Walter et al., 2010; Lewis, 2011; Meyer et al., 2011; Lewis and Nocera, 2012; RSC, 2012; Barber and Tran, 2013; Handoko et al., 2013; Lewis, 2013, 2016; Berardi et al., 2014; Cox et al., 2014; Grahn et al., 2014; Ronge et al., 2014; Schlumberger, 2014; Wang et al., 2014; Ashford et al., 2015; Bonke et al., 2015; Alissandratos and Easton, 2015; Fenwick et al., 2015; Izumi, 2015; Kim et al., 2015; Su et al., 2015; Highfield, 2015; May et al., 2015; Modestino and Haussener, 2015; Peter, 2015; Schreier et al., 2015; Shin et al., 2015; Torella et al., 2015; Wang et al., 2015; White et al., 2015; Wikipedia: "Artificial photosynthesis"; Martin, 2016; Purchase and de Groot, 2016). The field includes many different technology modalities. It is being funded by the support of several governments in strategic programs (Faunce, 2012; Marshall, 2014). It is experiencing a high rate of innovation towards the possibility of industrial take-off (Herron et al., 2015). Three basic agendas are involved: (i) direct photochemical $CO_2$ reduction; (ii) $CO_2$ electrochemical reduction via electrochemistry or electro-biochemistry powered by solar-sourced electricity; and (iii) electrolysis of water to produce $H_2$ followed by use of this $H_2$ for independent $CO_2$ hydrogenation or electrochemical reduction or thermochemical reaction with $CO_2$ into product chemicals (such as formic acid, methane, methanol, etc.). Efforts to commercially industrialize artificial photosynthesis include large companies such as Panasonic, Toshiba and Lockheed-Martin (Nagata, 2015), as well as start-ups such as Liquid Light (www.llchemical.com), HyperSolar (www.hypersolar.com), Dioxide Materials (www.dioxidematerials.com), Sun Catalytix (purchased by www.lockheed martin.com), Sunfire (www.sunfire.de), and NewCO$_2$Fuels (www.newco2fuels.co.il).

This vision for artificial photosynthesis connects with business initiatives creating large-scale photovoltaic (PV) and concentrated solar power (CSP) electricity production units in high radiation intensity desert areas, for example Nur Energie in the desert of North Africa (www.nurenergie.com). Large solar power facilities in deserts eventually will produce fuels and industrial chemicals once doing so becomes economically competitive with long distance electricity sales and/or with the market cost of liquid fossil fuels used for transportation. The commercial future for the "solar economy" of artificial photosynthesis and CSP chemicals production (e.g., www.newco2fuels.co.il; www.solar-jet.aero; Romero and Steinfeld, 2012; Marxer et al., 2015) using $CO_2$ as a carbon source is presently (circa 2015) overshadowed by low-cost fossil fuels. However, both PV and CSP technologies are following well-demonstrated innovation trends of increasing efficiencies with decreasing costs in their industrial applications. Also, the science of catalyst design for industry is progressing rapidly. Moreover, most technologies for $CO_2$ electrochemical reduction can utilize power from a variety of additional renewable sources including hydropower, wind power and biomass- and biogas-based power. Therefore, industrialization of $CO_2$ reduction electrochemistries is generally to be expected for the future. The agenda for artificial photosynthesis with $CO_2$ recycling (the "solar chemical" agenda) is gaining traction in an environment of widespread and growing international commitment to develop efficient $CO_2$ recycling as a key part of a green technology transformation of the world energy economy on a very large scale (e.g., Gates, 2015; www-.breakthroughenergycoalition.com; King et al., 2015; King, 2016; Carrington, 2015; www.globalapolloprogramme.org; www.nurenergie.com; Moller, 2012; Wikipedia entry: Desretec; www.desertec.org; www.desertenergy.org; Trieb, 2013; Schlumberger, 2014). Favorable situations include locations where large quantities of purified $CO_2$ are available for free or at very low cost, where "green" venture-subsidies and low-cost investment capital are available, where low-cost electricity is available (for example from hydropower and/or future advanced low-cost solar mega-arrays), where co-produced $O_2$ can be utilized efficiently for oxyfuel combustion, and where prices are high for products due to suituations such as, for example, remoteness from ports. A "solar fuels roadmap" for South Africa is reviewed by van Ravenswaay et al., (2015).

The East African region contains very high solar radiation intensity regions, especially in typically cloudless regions of northwestern Uganda, NW Tanzania, and in northern and western Kenya. These areas are observable in GeoModel Solar's time-averaged horizontal irradiation map of Africa (Solargis, 2011). Some areas are favorable for the development of large solar arrays. An example is the 40 MW solar PV array being developed for installation in northern Kenya by the company Greenmillenia Energy, Ltd (www.greenmillenia.com; Breakbulk, 2015. A plan to create a much larger 320 MW PV solar park in central Kenya has been announced (Kumar, 2015). Also, a 50 MV PV solar park being developed by the Chinese firm CJIC in east-central Kenya (Nduire, 2015). Power from such arrays can be transported efficiently over long distances by high voltage direct current (HVDC). Technologies for grid development using HVDC technology are developing rapidly. Effective use of large inputs of solar power feeding directly into industrialized artificial photosynthesis will be favored by the development of efficient energy storage methods for load balancing to provide a continuous and level power output.

Despite these many, scientific and engineering insights, designs, teachings, products, methods, systems, business activities, safety threats, development-industrialization needs, and ecologically significant opportunities having to do with Lake Kivu, its deepwater resources, and $CO_2$ utilization, no efforts have been made to design inventive methods and/or systems to co-extract and co-utilize the lake's abundant $CO_2$ resource in the context of extracting and utilizing its methane resource. Accordingly, there is a need, a problem, and a spectacular opportunity to solve the problem by invention of a new method and system.

All references cited herein are incorporated herein by reference in their entireties.

BRIEF SUMMARY OF THE INVENTION

Accordingly, the invention comprises a method for obtaining and utilizing carbon dioxide gas from a body of water containing dissolved carbon dioxide gas and methane gas, said method comprising the steps of: (a) extracting water from at least one extraction depth of the body of water to obtain extracted water; (b) degassing the extracted water in at least one stage of degassing so as to provide degassed water and extracted gases comprising carbon dioxide gas and methane gas in at least one flow; (c) optionally combusting the extracted gases with oxygen to provide an exhaust gas comprising carbon dioxide and water; and (d) feeding to a utilization hub the carbon dioxide gas from at least one of step (b) and step (c), wherein the utilization hub is configured to collect the carbon dioxide gas for storage, distribution, processing and/or utilization.

In certain embodiments, the method further comprises utilizing the carbon dioxide collected by the utilization hub to perform at least one process selected from the group consisting of fertilizing growth of plants, fertilizing a biozone of Lake Kivu, lowering a pH of water returned into Lake Kivu, adjusting a pH of water exiting from a vacuum degassing system, adjusting a pH of water fed to an algal growth sector, cultivating algae, supplying a cryogenic energy storage reservoir, heating or cooling a supercritical $CO_2$ power cycle heat engine power generator, delivering pressurized carbon dioxide by pipeline, delivering pressurized carbon dioxide by tanks including by pressurized tank trucks, producing dry ice, storing, producing and distributing refrigerated liquefied and/or solidified carbon dioxide, producing a magnesium-based cement or concrete, producing urea, producing formic acid, producing oxalic acid, producing acetic acid, producing a solvent, producing carbon monoxide, producing a pyrethrum pesticide, producing an asphyxiant, producing a food packaging gas, pasteurizing milk, beer or an agricultural juice, processing an agricultural, food, forest, textile, waste or biofuel product, cleaning a textile, treating leather, extracting geothermal energy, producing a fuel, producing a syngas, producing a chemical via a formate and/or by an oxalic acid platform, producing a chemical by gas fermentation based on a microbial Wood Ljundahl pathway, producing a chemical by a synthetic pathway including carbon dioxide as a reactant, producing a plastic including carbon dioxide as an ingredient, producing carbonic acid, producing a carbonated and/or $CO_2$ pressurized beverage, producing sodium bicarbonate, producing a fracking fluid, producing silicic acid, producing microsilica, producing iron, producing nickel, processing an ore to produce a plant and/or aquatic fertilizer, processing an ore by solution extraction of one or more metals using supercritical carbon dioxide optionally injected into an ore zone, producing an elemental carbon product, producing oxygen gas, and injecting carbon dioxide via drillholes into subterranean strata for geostorage.

In certain embodiments of the method, step (c) is conducted and the carbon dioxide collected in step (d) is solely from the exhaust gas provided in step (c).

In certain embodiments, the method further comprises generation of electrical power.

In certain embodiments of the method, deep gas trapping layers of the body of water possess in their volume average a $CO_2/CH_4$ ratio greater than 4, and more than 98 wt. % of the $CH_4$ dissolved in the water is extracted by the extracting step.

In certain embodiments of the method, the body of water is Lake Kivu and the method reduces a risk of a limnic eruption.

In certain embodiments, the method further comprises extracting from the extracted water at least one product selected from the group consisting of ammonium, ammonia, phosphorous, magnesium and calcium.

In certain embodiments, the method further comprises: supplying the electrical power to a compression and refrigeration system; cooling with the compression and refrigeration system at least one gas to form at least one liquefied gas, wherein the at least one gas is at least one of oxygen, nitrogen, carbon dioxide that has been extracted from the extracted water, carbon dioxide that has been formed in a combustion of associated methane and methane that has been degassed from the extracted water; storing the at least one liquefied gas in at least one insulated storage tank; releasing from the at least one insulated storage tank a liquid flow of the at least one liquefied gas; optionally increasing a pressure of the liquid flow of the at least one liquefied gas; heating the liquid flow to form a subcritical gas flow or a supercritical fluid flow, wherein at least a portion of the heating is optionally conducted by heat exchange with a closed system heat engine; driving a turbine with a subcritical gas flow or with a supercritical fluid flow to generate electricity; and optionally driving a turbine within a closed system heat engine to generate electricity.

In certain embodiments of the method, the degassed water provided in step (b) is transported for water treatment, and the method further comprises the steps of: (i) photosynthetic treatment of the degassed water by growth of an algal biomass to convert bicarbonate anions to carbon fixed by photosynthesis into biomass and hydroxyl anions in the degassed water, such that the pH of the degassed water is increased and bicarbonate anions are converted into carbonate anions and magnesium and calcium precipitate out of the degassed water onto algal cells to provide de-densified water and flocculated biomass precipitate; (ii) separating the de-densified water from the flocculated biomass precipitate; (iii) optionally additionally treating the degassed water by electrochemical methods such that the pH of the degassed water is further increased and additional magnesium and calcium precipitate out of the degassed water to provide further de-densified water and magnesium and calcium precipitate; (iv) optionally separating the further de-densified water from magnesium and calcium precipitate; (v) optionally adjusting the pH of the de-densified water or further de-densified water by adding thereto a volume of the carbon dioxide gas collected by the utilization hub from at least one of step (b) and step (c); and (iv) reinjecting into Lake Kivu a return flow of the de-densified water or further de-densified water separated from the biomass and precipitate, wherein the return flow is reinjected into Lake Kivu at a reinjection depth which is shallower than the extraction depth and which is density matched with the de-densified water or further de-densified water.

In certain embodiments of the method, the utilization hub supplies a stream of carbon dioxide into the biozone of Lake Kivu as a carbon fertilizing source supporting photoautotrophic bioproductivity.

In certain embodiments of the method, the utilization hub supplies a stream of carbon dioxide which is injected into: (i) post-degassing return flow water containing nutrients that are being diffused into a biozone of Lake Kivu; (ii) de-densified high-pH post-degassing return flow water that is being injected into Lake Kivu underneath the biozone; and/or (iii) post-degassing return flow water for pH control.

In certain embodiments of the method, the utilization hub supplies a stream of carbon dioxide to a horticultural greenhouse.

In certain embodiments of the method, the utilization hub supplies a stream of carbon dioxide which is injected into algal growth biocultures.

In certain embodiments of the method, the utilization hub supplies a stream of carbon dioxide to a compressor to provide compressed carbon dioxide, the compressed carbon dioxide is optionally stored in a storage tank, and the compressed carbon dioxide is distributed through pipelines.

In certain embodiments of the method, the utilization hub supplies a stream of carbon dioxide gas to a compression and refrigeration system to provide compressed refrigerated liquid carbon dioxide and/or solid carbon dioxide, and the method optionally comprises at least one of the additional steps of: (i) storing the compressed refrigerated liquid and/or solid carbon dioxide; (ii) further cooling the compressed refrigerated liquid carbon dioxide to provide dry ice; (iii) storing the dry ice; (iv) using the stored dry ice as cryogenic energy with recovery to generate power; and (v) distributing the dry ice.

The invention further comprises a system configured to perform the method of the invention.

In certain embodiments, the system comprises: a water degassing system; and a carbon dioxide utilization hub in fluid communication with the water degassing system.

In certain embodiments of the system, the water degassing system comprises: an intake pipe system; at least one bubble capture unit positioned upwards along a system of degassing pipes; at least one degassing catalyst unit positioned further upwards along the system of degassing pipes; a bubbly flow turbine configured to capture and recycle power from jetting foam flow at a top of the system of degassing pipes, wherein the bubbly flow turbine is also configured to function as a foam separator; at least one vacuum degassing unit positioned at the top of the system of degassing pipes; and a water flow turbine capturing and recycling power in a downward outflow of degassed water from the vacuum degassing unit.

In certain embodiments, the system comprises: a water degassing system; an oxyfuel power generation system in fluid communication with the water degassing system; and a carbon dioxide utilization hub in fluid communication with the oxyfuel power generation system.

In certain embodiments of the system, the oxyfuel power generation system comprises a power generator and an air separation unit configured to provide oxygen for combustion.

In certain embodiments of the system, the water degassing system comprises: an intake pipe system; at least one bubble capture unit positioned upwards along a system of degassing pipes; at least one degassing catalyst unit positioned further upwards along the system of degassing pipes; a bubbly flow turbine configured to capture and recycle power from jetting foam flow at a top of the system of degassing pipes, wherein the bubbly flow turbine is also configured to function as a foam separator; at least one vacuum degassing unit positioned at the top of the system of degassing pipes; and a water flow turbine capturing and recycling power in a downward outflow of degassed water from the vacuum degassing unit.

In certain embodiments, the system further comprises a return flow system which comprises: an outflow pipe from the water degassing system; pipe systems connecting flow to at least one water treatment system; a return flow pipe system and horizontal diffuser to reinject degassed water into the body of water at a specified depth; and flow control valve systems with emergency shut-off capabilities.

In certain embodiments, the system further comprises: flow connection by pipes and channels to and from at least one surface water treatment system that decreases water density in the degassed water flow; and an inlet system configured to allow admixture of relatively low density near-surface water from the body of water into the return flow for reinjection at a specified depth.

In certain embodiments, the system further comprises a system configured for combustion preparation processing and transfer of degassed gas into the oxyfuel power generation system.

In certain embodiments, the system further comprises a control system configured for physical monitoring, system-wide functional integration and emergency response safety assurance.

In certain embodiments, the system is configured to extract more than 98 wt. % of $CH_4$ dissolved in a body of water having a $CO_2/CH_4$ ratio greater than 4.

The invention further provides a carbon dioxide utilization hub comprising: (a) pipes and control valves configured for transferring exhaust gases; (b) pumps configured for compressing and transferring the exhaust gases into at least one of a storage tank, a gas processing tank and a heat exchange system; (c) at least two of a storage tank for pressurized gas, a gas dehydration system and a heat exchange system; (d) at least one compressor for compressing dehydrated carbon dioxide; (e) at least one storage tank for storing compressed dehydrated carbon dioxide; (f) at least one dispensing valve for dispensing compressed dehydrated carbon dioxide from at least one storage tank storing compressed dehydrated carbon dioxide; (g) at least one refrigeration system for compressing and refrigerating dehydrated carbon dioxide gas into liquefied refrigerated carbon dioxide; (h) at least one of: (i) at least one insulated tank for storing dehydrated liquefied refrigerated carbon dioxide, (ii) at least one insulated tank for storing liquefied refrigerated nitrogen, (iii) at least one insulated tank for storing liquefied refrigerated oxygen, and (iv) at least one dispensing valve for dispensing at least one cryogenic refrigerated liquids selected from the group consisting of carbon dioxide, nitrogen and oxygen; (i) power generation cryoenergy recovery systems utilizing at least one of the following cryoenergy storing inputs: (i) liquefied refrigerated carbon dioxide, (ii) liquefied refrigerated nitrogen and (iii) liquefied refrigerated oxygen; (j) gas dispensing valves and pipes for transferring and dispensing at least one warmed gas emerging from cryoenergy recovery systems; and (k) at least one pressurizable reaction chamber configured to provide a mixture of carbon dioxide and water vapor under controlled and time-varying conditions of pressure, mixing ratio, temperature and time and admitting product producing forms containing at least one of the following carbon dioxide and water vapor absorbing substances: magnesium hydroxide, calcium carbonate, hydrated magnesium carbonates, concrete-forming aggregate, pozzolans, steel rebar, microsilica and plant materials.

In certain embodiments of the method, the utilization hub supplies at least one of liquefied natural gas, compressed natural gas and adsorbed natural gas.

In certain embodiments, the method further comprises supplying the electrical power to a compression and refrigeration system; cooling with the compression and refrigeration system at least one gas to form at least one liquefied gas, wherein the at least one gas is at least one of oxygen, nitrogen, carbon dioxide that has been extracted from the extracted water, carbon dioxide that has been formed in a combustion of associated methane and methane that has been degassed from the extracted water; and cooling a server with the at least one liquefied gas.

The invention further comprises a process for generating data, said process comprising: providing a server; cooling the server with at least one liquefied gas; and generating the data from the server, wherein the at least one liquefied gas comprises at least one of oxygen, nitrogen, carbon dioxide and methane from Lake Kivu water.

BRIEF DESCRIPTION OF SEVERAL VIEWS OF THE DRAWINGS

The invention will be described in conjunction with the following drawings in which reference numbers and their corresponding component names are identified in a listing herein (this listing also indicating like items according to like names across the set of figures), and referenced in descriptive discussions in the text according to a convention "X.Y", where "X" is the figure number, and "Y" represents numerical component item labels appearing within figure X, and wherein:

FIG. 2 represents the invention in the context of some aspects present in other related disclosures by the inventor involving the utilization of Lake Kivu deepwater resources and relating especially to the return flow of degassed water into the lake (34, 35, 36a,b,c). The figure is shown partly in vertical plane perspective: for Lake Kivu represented with three water layers, 23a,b,c. Otherwise, the figure is shown in non-spatially oriented representation of process flows. Box 1 is an inset showing the invention overall in its combinative aspect as a combination of submethods and subsystems (for the TDS modality only), where numerical labels correspond to identical labels elsewhere in FIG. 2. Box 2 illustrates aspects of the operations of the $CO_2$ Utilization Hub ($CO_2$-UH) and its twenty "main modes" of $CO_2$ utilization. Box 3 is another inset. It illustrates adjunct utilization of excess liquid nitrogen and/or oxygen (via flow vectors 39 and/or 40 and/or 42) to cool one or more large refrigeration utilization facilities, such as, for example, a digital data center (43).

LISTING AND BRIEF DISCUSSION OF REFERENCE NUMBERS APPEARING IN THE FIGURES

Figure 1:
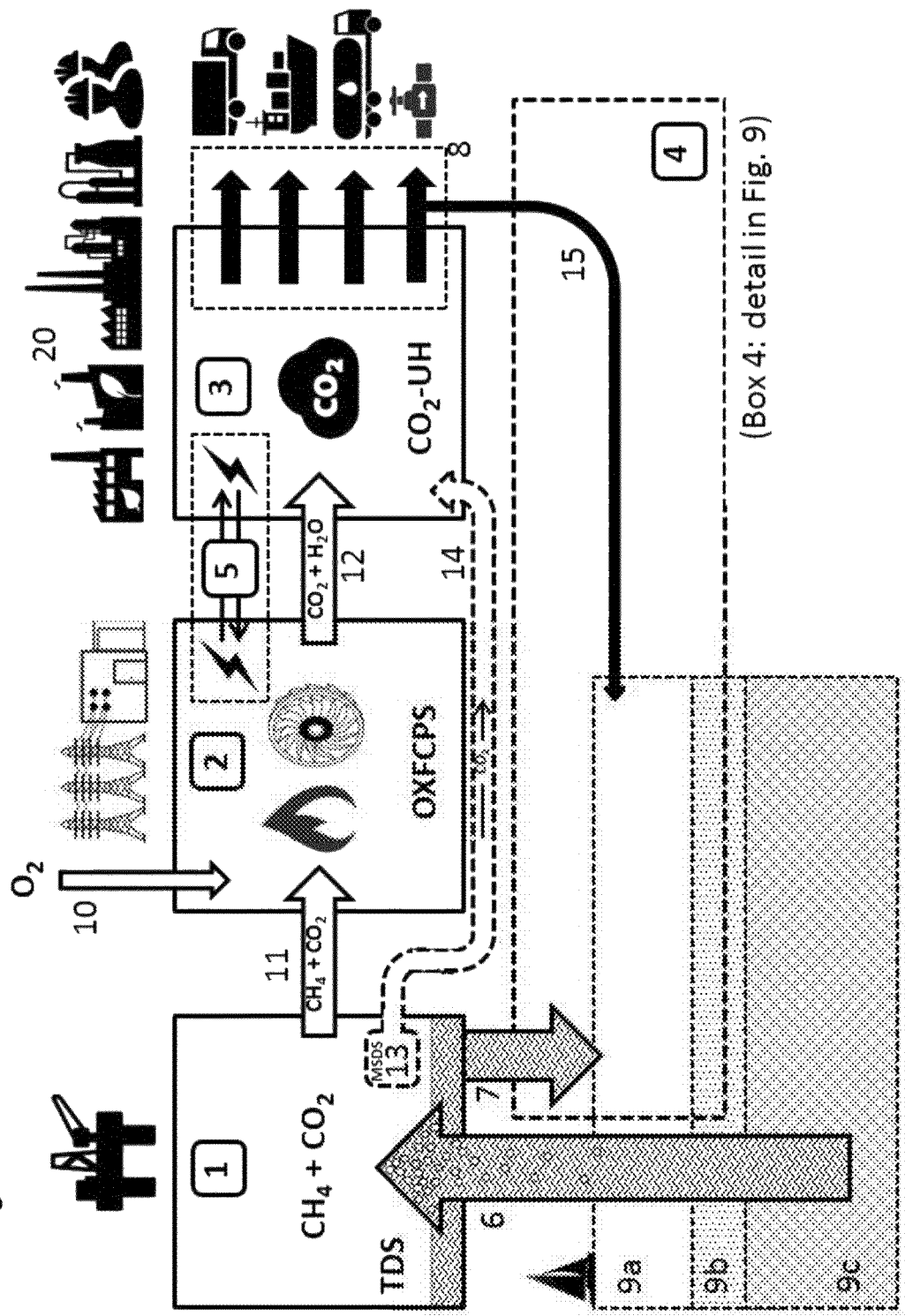
FIG. 1 is a simplified schematic and conceptual representation of the method and system of the invention shown as a process flow divided into five boxes representing different functional groupings of different components of the whole such as may be present in various embodiments. A representation of the Modified Staged Degassing System (MSDS) submethod and subsystem is shown by items 13 and 14. (See FIG. 8 for an overview of the MSDS.)
Figure 2:
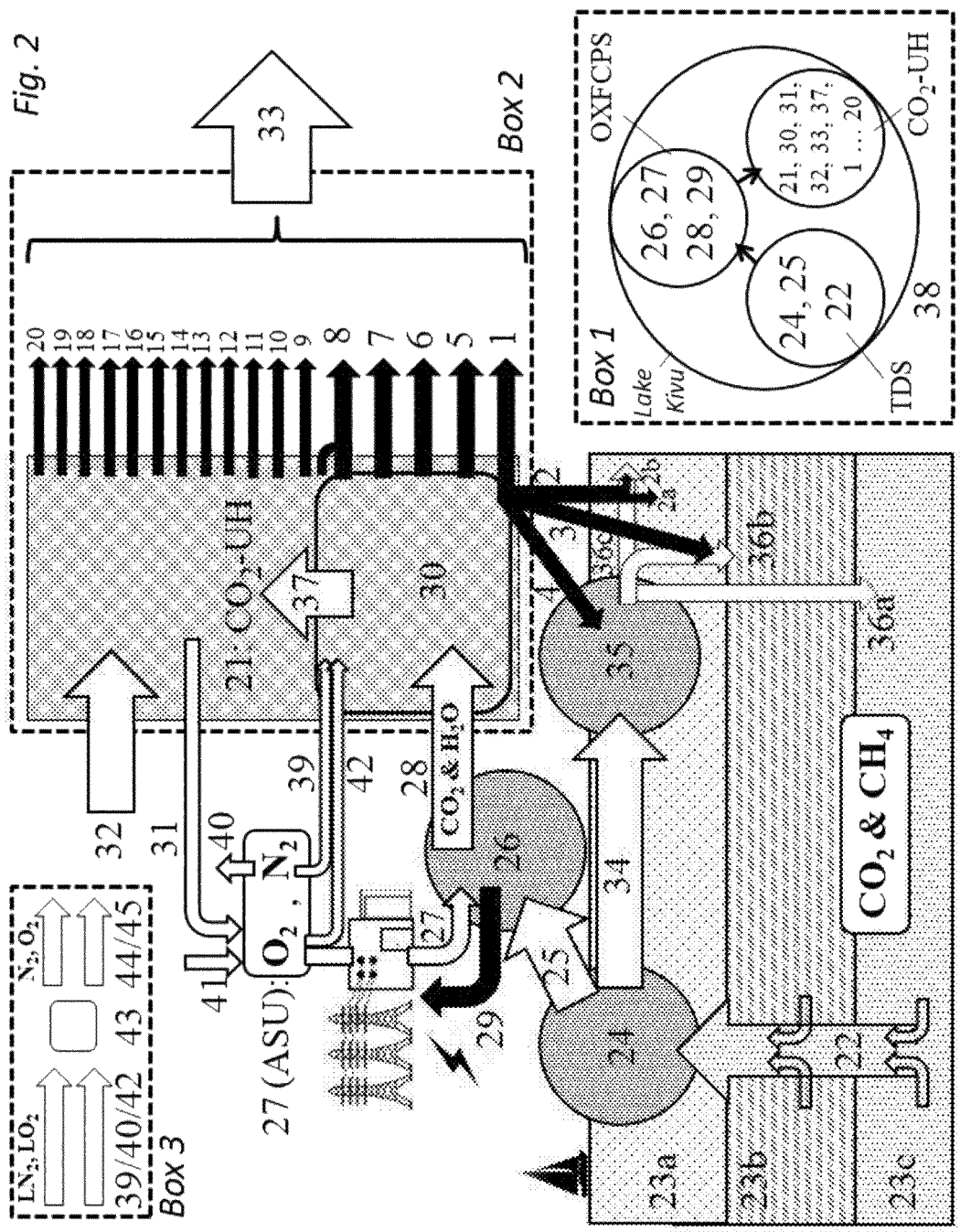
FIG. 2 is a schematic representation of an embodiment of the invention shown with additional detail relative to FIG. 1. Only the modality utilizing a Total Degassing System (TDS) is shown. The variant modality utilizing a Modified Staged Degassing System (MSDS) is not shown.
Figure 8:
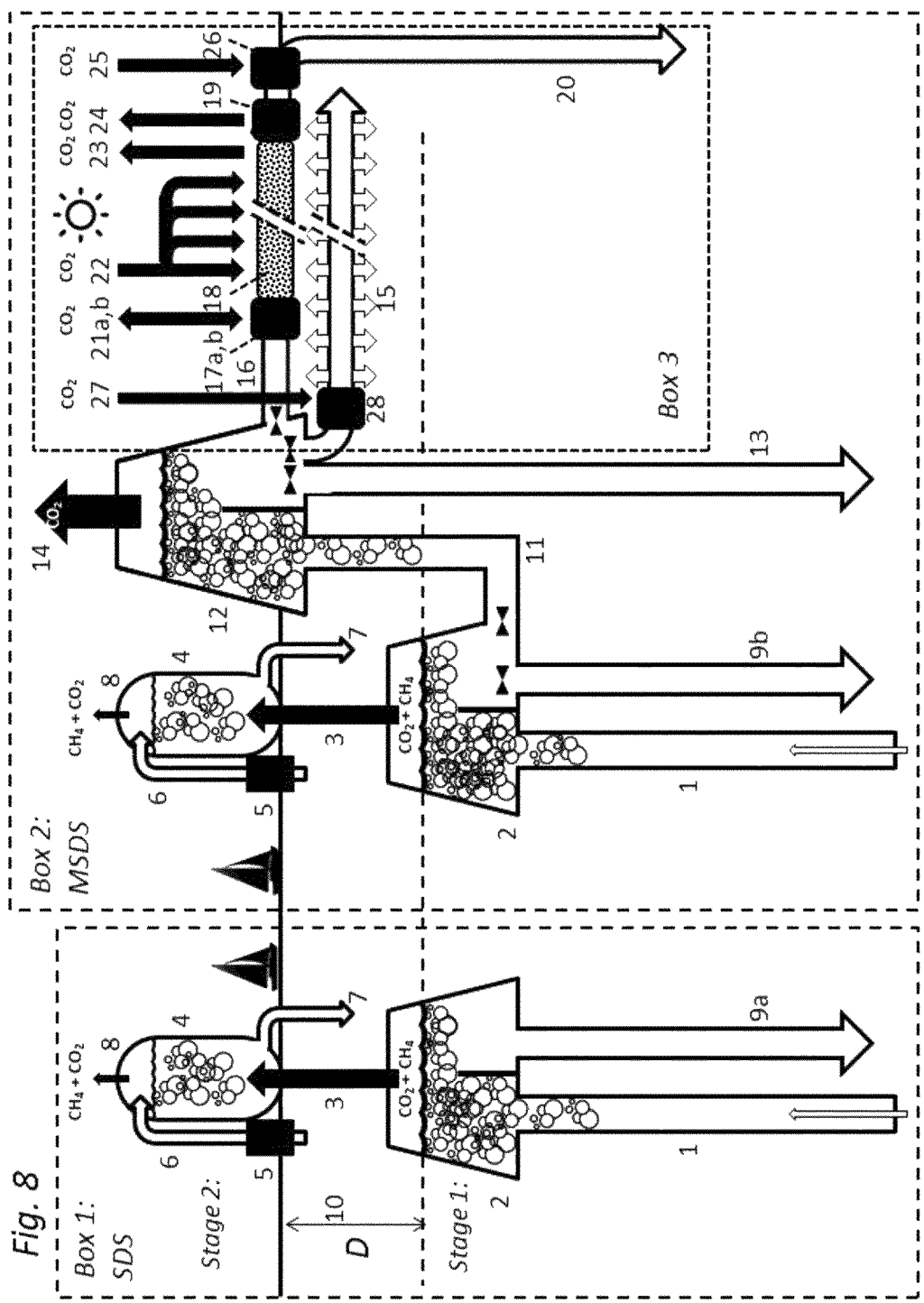
FIG. 8 is a schematic representation in vertical plane of: (i) in Box 1: a 2-stage representation of the Staged Degassing System (SDS) method invented by Belgian engineers in the 1950's and later practiced on Lake Kivu; and (ii) in Box 2: a modification of this staged method (MSDS, shown for 2-stages). The MSDS provides a means for separated degassing of $CO_2$, thereby allowing $CO_2$ utilization by adaptation of conventional operations. Box 3 illustrates a schematic representation of several pH control options utilizing $CO_2$ inputs (21a,b, 22, 25, 27) and removals: 21a,b, 23, 24) in two different modalities of return flow: (15) and (16-through-20). These modalities of return flow (15, 20) into shallow layers of Lake Kivu are different from (deep) return flow according to the standard modality of the SDS method (9a, 9b, 13). Both represent modes of $CO_2$ utilization by injection into Lake Kivu (for a range of various reasons).
Figure 9:
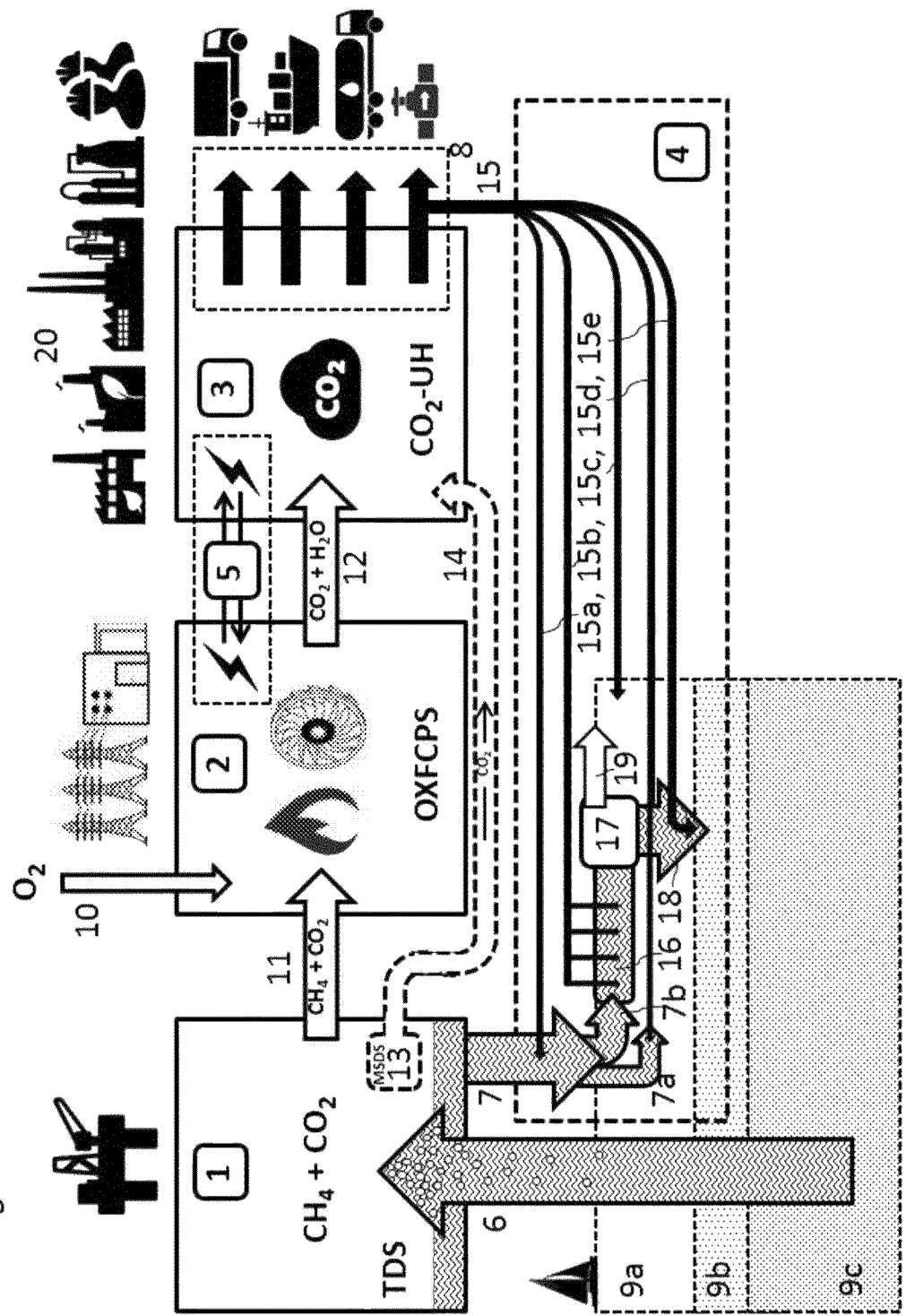
FIG. 9 republishes FIG. 1 except with addition of detail within Box 4. This extra detail shows several ways by which embodiments of the invention utilize $CO_2$ via a range of (optional) modes of injection-dissolution into return flow, as well as by (optional) direct diffusion into the lake. (Such injection of dissolution-absorbed $CO_2$ into higher-level layers does not enhance threat risks of limnic eruption).

A listing of reference numbers and their corresponding component names follows. These are provided according to the convention "X.Y" noted above. X represents the figure number. Y represents the component or item number label within figure X. References to numbered boxes in the figures sometimes differ from numbered items, but always in a simple and clear manner. In FIGS. 2 and 8 only, box numbers are differentiated from item label numbers. For example, FIG. 2 contains three boxes labeled "Box 1," "Box 2," and "Box 3," but also contains separate items numbered 1, 2 and 3. These clearly are illustrated as distinct entities. In such cases (also in FIG. 8), "X.BoxY" in the text is used to reference "Box Y" in the figure, these being different from items in the same figure labeled "Y" (referenced "X.Y" in the text). Boxes sometimes are labeled simply by numerals as ordinary items, (though as boxes indicating associated operationally integrated collections of items). Boxes also sometimes are identified with numerical labels surrounded by a small solid line box possessing rounded corners. Use of such small boxes with rounded corners surrounding number labels is a form of highlighting for purposes of clarity. Such highlighted labels always identify larger boxes. This highlighting can be seen in an obvious way in FIG. 1 for boxes labeled one through five. A listing follows upon this basis. The listing lists all labeling reference numbers in the figures. These are ordered via the "X.Y" convention. Label numbers are provided by item-component names and/or brief descriptions:

1. Aspects of FIG. 1 that are not shown within Box 4 are illustrated in FIG. 9. These are left out of FIG. 1 to avoid excessive complication. FIG. 1 mainly illustrates the process flow of degassing into oxy-fuel combustion into utilization of $CO_2$ representing an invention that, overall, creates an integrated method and/or system for Lake Kivu Carbon Capture Utilization (CCU) in combination with the "traditional" agenda of electric power production, while also increasing lake safety over time.

1.Box1. Box 1 represents a Total Degassing System (TDS, as labeled), generating efficient degassing of both methane and carbon dioxide together.

1.Box2. Box 2 represents an Oxy-Fueled Combustion Power System, (OXFCPS, as labeled). The Box contains icons representing methane combustion driving turbine blades.

1.Box3. Box 3 represents a $CO_2$ Utilization Hub, ($CO_2$-UH), as labeled. This generates product flows indicated by the black rightwards arrows jointly within Box 3 and Box 8.

1.Box4. Box 4 contains and thereby groups together a variety of useful outflows of pipe-delivered $CO_2$ (shown by arrows) from the $CO_2$-UH. These outflows are into injection-dissolution Lake Kivu in a range of modes, including integration of injection into a Return Flow System (7), and serving a variety of purposes. Details are provided in FIG. 9.

1.Box5. The dashed box labeled (5) connects together boxes 2 and 3. This connection represents a capacity for systems-integrative cryogenic energy storage utilizing refrigerated-liquified gases. Details are provided in FIG. 6.

1.6. Deepwater extraction method and/or system.

1.7. Return Flow System (sometimes labeled with the acronym RFS) as a main vector (7), also showing different plumbing options (7a, 7b) as well as integration into methods and/or systems for density reduction by removal of dissolved substances and also by removal of $CO_2$ by degassing.

1.Box8. Box 8 represents the set of product flows out of the $CO_2$-UH. Icons indicate different product transport modes applicable at Lake Kivu (which lacks a railway link at present). Air transport is not shown, but is available.

1.9. Labels 9a,b,c represent Lake Kivu according to three different layers. (The actual density structure of the lake is more complicated than shown by three layers.) 9a represents the biozone. 9c represent the resources-rich deepwater zone. 9b represents (a combination of) intermediate layers.

1.10. Arrow 10 most directly represents an oxygen input for oxy-fueled combustion of methane in the OXFCPS (Box 2). Arrow 10 also may be construed to include an Air Separation Unit (ASU, not shown. See FIG. 2) for the production of $O_2$ as well as co-production of $N_2$ both in liquid ($LN_2$) and gaseous ($N_2$) forms.

1.11. Arrow 11 indicates a method and/or system of mass transfer of degassed gas (containing both methane and carbon dioxide) from the TDS (Box 1) into the OXFCPS (Box 2).

1.12. Arrow 12 indicates a method and/or system of mass transfer of postcombustion gas (containing both carbon dioxide and water vapor) from the OXFCPS (Box 2) into the $CO_2$-UH (Box 3).

1.13. A small dashed box 13 (within Box 1 and labeled MSDS) represents an optional embodiment of the invention described as the Modified Staged Degassing System (and/or method). It is further illustrated in detail in FIG. 8. The MSDS method and/or system lacks an OXFCPS. Hence the $CO_2$ flux obtained from it is shown being provided directly (14) into the $CO_2$-UH (Box 3).

1.14. Item 14 is a $CO_2$ transfer line specific to the MSDS, as noted above.

1.15. Item 15 represents one or more $CO_2$ transfer lines (typically pipes) exporting $CO_2$ from the $CO_2$-UH (Box 3), as product flows (8), into Lake Kivu via a range of possible and optional sub-methods and/or sub-systems. (See FIG. 9 for detail for items not shown in FIG. 1: 15a, 15b, 15c, 15d, 15e, 16, 17, 18, and 19.)

1.20. Label 20 indicates a set of icons on top of Box 3 as well as to its right. These indicate various exemplary aspects of greentech industrialization in the $CO_2$-UH (top), including product export (side).

2.Box1. Box 1 is a symbolic inset indicating the invention as a combination of submethods and subsystems (specifically for the TDS-to-OXFCPS modality embodiment) with numbers corresponding to labeled items elsewhere in the diagram.

2.Box2. Box 2 contains a core aspect of the invention, Carbon Capture Utilization (CCU) via greentech industrial processing and manufacturing using $CO_2$ and consequent productive outputs/outflows. Specifically, Box 2 encloses an illustration of the $CO_2$-UH (21) incorporating twenty different modes of $CO_2$ distribution and Carbon-Capturing product production and export. Productive flows exiting the $CO_2$-UH are shown as black arrows.

2.Box3. Box 3 is a symbolic inset illustrating optional adjunct utilization of liquefied nitrogen and oxygen ($LN_2$, $LO_2$) for provision of cooling in a Digital Data Center (43: DDC), where items 39, 40 and 42 reference storage-directed flow vectors illustrated in the main part of the figure. (Note: A cryogenic ASU {item 27} produces $LN_2$, $LO_2$.) Such provision of cryogenic $LN_2$ and $LO_2$ is a capacity of some embodiments of the invention via adjunct capacities of the $CO_2$-UH.

NB: Items 2.1 through 2.20 are all $CO_2$ utilization modes described in Table 2.

2.1. One (1) represents ($CO_2$ provided to) local greenhouse horticulture.

2.2. Two (2) represents ($CO_2$ provided to) Lake Kivu Biozone fertilization (with two different injection-dissolution options noted as 2a and 2b).

2.3. Three (3) represents ($CO_2$ provided to) Return Flow System (RFS) for purposes of pH lowering.

2.4. Four (4) represents ($CO_2$ provided to) return flow water treatment of a variety of types involving $CO_2$ injection for pH control.

2.5. Five (5) represents ($CO_2$ provided to) algal production (including bicarbonate).

2.6. Six (6) represents ($CO_2$ provided by) high-pressure pipeline delivery.

2.7. Seven (7) represents ($CO_2$ provided by) refrigerated delivery (as liquid and/or solid).

2.8. Eight (8) represents $CO_2$ incorporated into production of eco-cements and concretes and related materials.

2.9. Nine (9) represents ($CO_2$ utilized in) urea production from ammonia.

2.10. Ten (10) represents ($CO_2$ input into) production of formic acid.

2.11. Eleven (11) represents ($CO_2$ input into) production of carbon monoxide.

2.12. Twelve (12) represents ($CO_2$ input into) production of pyrethrum biopesticide. (Compressed $CO_2$ is a diluent carrier fluid in canisters for spraying.)

2.13. Thirteen (13) represents ($CO_2$ use in various processes of) forest products processing and production.

2.14. Fourteen (14) represents $CO_2$ use in geothermal energy extraction (typically by pipeline delivery).

2.15. Fifteen (15) represents various $CO_2$ uses in fuels and chemicals production.

2.16. Sixteen (16) represents $CO_2$ uses as an input into syngas production.

2.17. Seventeen (17) represents $CO_2$ use as an input into syngas manufacturing of fuels and chemicals.

2.18. Eighteen (18) represents $CO_2$ use in gas fermentation production of various products (typically with hydrogen gas inputs).

2.19. Nineteen (19) represents plastics production incorporating $CO_2$ in various modalities.

2.20. Twenty (20) represents production of a variety of high-value carbon products by reduction of $CO_2$. (For example C-nanotubes.)

2.21. Label 21 identifies a stippled box containing a combination of elements that together an example of a (large-scale multi-product example embodiment of a $CO_2$-Utilization Hub: $CO_2$-UH). Note that a $CO_2$-UH in some embodiments includes large areas of algal/phytoplanktonic production which additionally may include zooplanktonic as well as fish production in various embodiments, and where injection can function as a $CO_2$-fertilizing carbon source for photosynthesis.

2.22. Item 22 is a method and/or system of upward extractive flux of gas-rich deepwater into a Total Degassing System (24: TDS) 2.23. Labels 23a, 23b, and 23c together identify Lake Kivu in upper, middle, and lower layers, respectively, as shown.

2.24. Item 24 is a Total Degassing System (TDS) receiving deepwater flux (22) and splitting its output into fluxes of degassed gas (25) and degassed water (34).

2.25. Item 25 is a method and/or system and/or apparatus of gas transfer (with hydrogen sulfide scrubbing if/as needed and gas compression and/or gas dehydration if/as needed). The transfer couples the flow of gas exiting from degassing and coordinates it to be fed into the Oxy-Fueled Combustion Power System (OXFCPS) and/or method.

2.26. Item 26 is an Oxy-Fueled Combustion Power System (OXFCPS) and/or method. The OXFCPS receives transferred gas from item 25. It exhausts a mixture of nominally pure carbon dioxide and water vapor into a gas transfer exhaust system and/or method (28) transferring gas into an exhaust receiving and gas processing unit (30) within the $CO_2$-UH (21).

2.27. Item 27 is a method and/or system of oxygen transfer into the Oxy-Fueled Combustion Power System (26: OXFCPS) and/or method. In FIG. 2, as shown, the source is an Air Separation Unit (27: ASU); however other types of sources may provide input oxygen into combustion.

2.28. Item 28 is a method and/or system and/or apparatus of gas ($CO_2+H_2O$) transfer for directing post-combustion hot exhaust gases from the Oxy-Fueled Combustion Power System (26: OXFCPS) into a gas-receiving processing, storage and purveying unit (30) within the OXFCPS (21).

2.29. Item 29 is the transfer of power provided by the OXFCPS (26). This may be mechanical power or electrical power. An associated icon indicates production of electric power into a distribution grid.

2.30. Item 30 is a gas-receiving processing, storage and purveying/distribution unit (30) within the OXFCPS (21).

2.31. Item 31 indicates an optional transfer flux of oxygen from the $CO_2$-UH into the oxygen supply for combustion in the OXFCPS. Such a flow, for example, might be sourced as waste from electrolytic hydrogen production from water operating within the $CO_2$-UH, and/or from $CO_2$ splitting or other processes of $CO_2$ deoxygenation.

2.32. Item 32 identified a generic flux of inputs (including power) into the $CO_2$-UH (21) other than the gas inputs specified by specific labels (28, 39, 42).

2.33. Item 33 is an arrow representing the accumulation of all of the flux of product outputs out of the $CO_2$-UH.

2.34. Item 34 is a connecting method and/or system for transferring degassed deepwater from a Total Degassing System (24: TDS) into a Return Flow System (RFS: 35, 36a,b,c). Typically this involves pipes, pumps and valves.

2.35. Item 35 represents the reception, storage, coordinating delivery and water-treatment parts of the overall Return Flow System (RFS: 35, 36a,b,c). In some embodiments, item 35 will include extensive operations for water treatment. As shown (2, 3, 4), these may involve connections with $CO_2$ export from the $CO_2$-UH (21).

2.36. As shown, item 36 has three distinct modalities: 36a, 36b, and 36c. The differences are for different return flow water densities corresponding to different depth of reinjection into Lake Kivu. Differences correspond mostly to whether or not de-densification water treatment occurs, and if so, to what degree. Reinjection flux vector 36c represents diffusive fertilizing injection of post-degassing deepwater, (which may be without de-densification water treatment).

2.37. Item 37 represents flows of $CO_2$ proceeding from treatment and storage (in unit 30) into forms of production that transform $CO_2$ into carbon-containing products. Types of processed $CO_2$ are obtained from treatment of OXFCPS exhaust (in unit 30) with storage and disposition of it (in unit 30) into utilizing production activities within the wider parts of the overall $CO_2$-UH (21).

2.38. Item 38 is labeled within the Box 1 inset. It is the large circle that also is labeled as "Lake Kivu." It represents both the domain of operations specific to Lake Kivu as well as the combinative domain of the invention as an integration of component sub-methods and/or sub-systems.

2.39. Item 39 is a flux vector representing transfer of nitrogen gas, typically in liquefied form, into storage within unit 30. Typically, embodiments will include cryogenic methods and/or systems for transfer of liquefied nitrogen.

2.40. Item 40 is a flux vector representing general production and use of liquefied nitrogen ($LN_2$), for example, for use in Digital Data Center (43) cooling, or more generally for sale.

2.41. Item 41 represents input of air or air-like gas into the Air Separation Unit (ASU: 27). "Air-like gas" here refers to gas obtained from canopies over areas of photosynthetic activity such as, for example, covered algal growth operations producing oxygen.

2.42. Item 42 is a flux vector representing transfer of oxygen gas, typically in liquefied form, into storage within unit 30. Typically, embodiments will include cryogenic methods and/or systems for transfer of liquefied oxygen.

2.43. Item 43 is a small box labeled within the inset Box 3. It represents a Digital Data Center (DDC) receiving cooling flows labeled 39, 40 and 42, these numbers referring to items shown elsewhere in the figure (all three associated with the ASU, 27).

2.44. Item 44 is a flux vector representing the potential of utilization of flows of gaseous nitrogen after use in cooling a Digital Data Center (DDC: 43), for various purposes, for example in algal production operations and/or in horticultural uses.

2.45. Item 45 is a flux vector representing the potential of utilization of flows of gaseous oxygen after use in cooling a Digital Data Center (DDC: 43), for example for oxyfuel combustion operations.

3.1. Item 1 is identical to item 12 in FIG. 1 and item 28 in FIG. 2. It is a transfer flux of exhaust from the OXFCPS into the $CO_2$-UH (which is detailed in FIG. 3). The flux is comprised of a hot and nominally pure mixture of carbon dioxide and water vapor.

3.2. Item 2 is an optional component present in some high efficiency embodiments: a Heat Exchanger Power Production Unit (HEPPU) obtaining post-combustion power from heat present in the OXFCPS exhaust. Such units also can function as water separators by condensation of water vapor upon cooling (3, illustrated by an icon).

3.3. Item 3 represents a water separation capacity by condensation. This water separation capacity also is shown as first stages within a process trains labeled 22 and 24. It also is shown as a stage within process train 23.

3.4. Item 4 is a 3-way valve allowing input of $CO_2$ into a treatment chamber (5) possessing pressurization (10) capacity for pressurized "carbonization" ($CO_2$ absorption) into the production of eco-cements and concretes and other building materials.

3.5. Item 5 is a treatment chamber described immediately above.

3.6. Item 6 represents post-production product storage for carbonated building materials, as indicated by icons.

3.7. Item 7 represents building materials product export/delivery by truck.

3.8. Item 8 represents building materials product export/delivery by ship.

3.9. Item 9 represents a storage capacity within process train 23. It is for storage, along with cooling and dehydration (3), of moderately compressed (10) carbon dioxide prior to further compression (10) prior to pipeline export (11a, 11b).

3.10. The label 10 and an associated icon represents a $CO_2$ compressor. This label and icon appears in several locations in the figure.

3.11a,b. Pipe-&-valve icons labeled 11a and 11b indicate a range of pipeline delivery systems at various pressures and pipeline diameters for local distribution/delivery of relatively low-pressure (non-supercritical) $CO_2$.

3.12. Tank icons labeled 12 represent a tank farm storage depot for pre-delivery storage of relatively high-pressure (typically supercritical) non-refrigerated $CO_2$.

3.13. Pipe-&-valve icon labeled 13 represents pipeline(s) delivery of relatively high-pressure (typically supercritical) non-refrigerated $CO_2$.

3.14. Pipe-&-valve icon labeled 14 represents by-truck delivery of relatively high-pressure (typically supercritical) non-refrigerated $CO_2$.

3.15 a,b. Items 15a and 15b represent pipeline connections within the $CO_2$-UH that supply high pressure $CO_2$ into refrigeration stages for liquification (15a) and dry ice production (15b).

3.16. The icon set labeled 16 indicates a cryogenic capacity for liquification of $CO_2$ with associated insulated tank storage (17). This capacity may be identical with or supplementary to an Air Separation Unit (ASU, illustrated in other figures). In relation to the dashed box labeled 36, this cryogenic capacity may include refrigeration of other gases: oxygen and nitrogen, along with insulated tank storage (30, 31).

3.17. Insulated tank storage for refrigerated liquid $CO_2$.

3.18. Insulated by-truck transport of refrigerated liquid $CO_2$.

3.19. The icon set labeled 19 indicates a cryogenic capacity for solidification of $CO_2$ into dry ice, with associated cool storage (20).

3.20. Icon 20 represents dry ice storage.

3.21. Icon 21 represents by-truck transport/delivery of dry ice. Transport/delivery additionally may be by any other means as well, including boat and motorcycle.

3.22. Label 22 (inside a highlighting circle) indicates a process train for $CO_2$ utilization for the production of eco-cement and concrete products produced with absorption of $CO_2$ (and also water vapor for hydration).

3.23. Label 23 (inside a highlighting circle) indicates a process train for $CO_2$ utilization as relatively unprocessed gas delivered at relatively low pressures.

3.24. Label 24 (inside a highlighting circle) indicates a process train for $CO_2$ production/delivery as relatively high pressure gas.

3.25. Label 25 (inside a highlighting circle) indicates a process train for $CO_2$ production/delivery as refrigerated liquified gas.

3.26. Label 26 (inside a highlighting circle) indicates a process train for $CO_2$ production/delivery as dry ice.

3.27. Label 27 represents crossover transfer if/as needed from high-pressure $CO_2$ storage to low-pressure delivery.

3.28. Label 28 represents control over the temperature and water vapor content of $CO_2$ input into carbonation and hydration facilities for eco-cement and concrete and related products production (=process train 22).

3.29. Label 29 identifies a cryogenic energy storage method, system, capability or unit utilizing liquefied liquefied nitrogen and/or liquefied oxygen (and/or $CO_2$ linkage, not shown except as two-sided vector 34).

3.30. Label 30 indicates an icon representing tank (or tank farm) storage of refrigerated liquefied oxygen.

3.31. Label 31 indicates an icon representing tank (or tank farm) storage of refrigerated liquefied nitrogen.

3.32. Label 32 indicates connectivity of the cryogenic energy storage capacity (29) with tank(s) for insulated storage of liquid oxygen.

3.33. Label 33 indicates connectivity of the cryogenic energy storage capacity (29) with tank(s) for insulated storage of liquid nitrogen.

3.34. Label 34 indicates that in some embodiments, there can be connectivity of cryogenic energy storage methods and/or systems (29) with production and storage of solid $CO_2$.

3.35. Label 35 of a two-sided arrow represents a gas transfer linkage between cryogenic energy storage capacities (29) connecting (32) to liquid oxygen storage (30). The transfer linkage connects (outside of the figure) into the intake oxygen supply into oxyfuel combustion (OXFCPS) and to the Air Separation Unit (ASU, not shown) oxygen supply that produces liquid oxygen in cases where oxygen separation from air is via cryogenic methods.

3.36. Label 36 represents the overall capacity of the linkage with the cryogenic capabilities of the ASU to provide refrigeration into process trains 25 and 26. In some embodiments this capacity includes and integrates cryogenic energy storage (29).

3.37. Icon 37 indicates a general capacity for provision/sales of refrigerated liquid oxygen.

3.38. Icon 38 indicates a general capacity for provision/sales of refrigerated liquid nitrogen.

3.39. Label 39 indicates a transfer capacity for connecting stored refrigerated liquefied $CO_2$ into specialized cryogenic energy storage for $CO_2$ (40).

3.40. Item 40 indicates options for inclusion in some embodiments of specialized cryogenic energy storage utilizing liquid $CO_2$.

3.41. Item 41 indicates embodiments that include integration of cryogenic $CO_2$ energy storage into cryogenic energy storage methods and/or systems utilizing $LN_2$ and/or $LO_2$ (29). (NB: As indicated by item 40, cryogenic energy storage methods and/or systems utilizing $CO_2$ may be separate from cryogenic energy storage utilizing $LN_2$ and/or $LO_2$ (29).)

4.1. Item 4.1 is a schematic flux vector representing methods and/or system of extraction and separation of Lake Kivu deepwater (12). Deepwater is directed into several components (2) for utilization operations, shown involving, for $CO_2$, a $CO_2$-Utilization Hub ($CO_2$-UH) utilizing combined $CO_2$ (10, 11) from deepwater degassing (3) as well as combustion (9) of co-extracted deepwater methane (6).

4.2. Dashed box 2 represents the cumulate of utilizable resource components of Lake Kivu deepwater (12).

4.3. Box 3 represents one component: degassed deepwater $CO_2$.

4.4. Box 4 represents another component: deepwater bicarbonate ion.

4.5. Box 5 represents additional chemically dissolved resource components such as dissolved Mg and Ca cations as well as NPK fertilizers and additional important fertilizing trace elements.

4.6. Box 6 represents degassed deepwater biomethane.

4.7. Box 7 represents a $CO_2$-Utilization Hub ($CO_2$-UH), with icons indicating its aspect as a basis for jobs-creating greentech industrialization.

4.8. Box 8 represents the outcomes of greentech industrialization exemplified by jobs, economic growth and increased per capita GDP.

4.9. Box 9 represents power production via combustion with efficient carbon capture.

4.10. Arrow 10 represents efficient carbon ($CO_2$) capture with transfer into a $CO_2$-Utilization Hub ($CO_2$-UH).

4.11. Arrow 11 represents capture and transfer of deepwater $CO_2$ into a $CO_2$-Utilization Hub ($CO_2$-UH). NB: This capture and transfer can be routed through combustion (9) in the case of a Total Degassing System (TDS) combined with oxyfueled combustion.

4.12. Label 12 indicates resource-rich Lake Kivu deepwater.

5.1. Box 1 encloses a representation of the standard, practiced "Staged Degassing System" (SDS) of methane extraction and power production on Lake Kivu showing both the return of $CO_2$ into the deepwater layer, and loss of postcombustion $CO_2$ to the atmosphere.

5.2. Box 2 encloses a representation of one mode of Lake Kivu deepwater resource extraction and utilization disclosed herein: the method and/or system of total degassing (TDS) combined with $CO_2$ utilization.

5.3. Label three (3) marks the a-depth inlet of Lake Kivu deepwater for methane extraction in the Staged Degassing System (SDS) method and/or system.

5.4. A stippled box labeled four (4) indicates a two-staged degassing system.

5.5. The numerical label five (5) represents the reinjection of dissolved $CO_2$ (from Stage-1) into Lake Kivu's deepwater reservoir after degassing by the SDS method.

5.6. The numerical label six (6) represents the reinjection of dissolved $CO_2$ (from Stage-2, dissolved in "washing water") into Lake Kivu's biozone after degassing by the SDS method.

5.7. Label seven (7) marks a gas (methane-rich gas) transfer line from an offshore floating platform (12a) to an onshore power-generating facility (8).

5.8. Label eight (8) marks an icon representing an onshore power-generating facility. (Placed onshore due to the very large sizes and weights of piston engine power generators utilized in the SDS method.)

5.9. Label nine (9) indicates that $CO_2$ formed from combustion in the SDS method is not captured. This $CO_2$ is released into the atmosphere.

5.10. Label ten (10) marks a depth inlet of Lake Kivu deepwater for methane extraction in the Total Degassing System (TDS) method and/or system.

5.11. Label eleven (11) indicates a floating platform (also icon 12b) in the TDS-OXFCPS method and/or system (Box 2). As shown, the figure in Box 2 shows the possibility that the platform could include power plant operations (13). OXFCPS turbines utilizing a $CO_2$ power cycle are much smaller than power generation operations utilizing large and heavy piston-type gas burning engines (8).

5.12. Labels 12a and 12b both indicate icons representing floating offshore platforms.

5.13. Label 13 indicates an icon representing power generation, in this case situated on a floating platform (11, 12b).

5.14. Label 14 indicates that degassed $CO_2$ is captured and enters a $CO_2$-UH in the TDS-OXFCPS method (Box 2).

5.15. Label 15 indicates that combustion-formed $CO_2$ is captured and enters a $CO_2$-UH in the TDS-OXFCPS method (Box 2).

5.16. Label sixteen (16) indicates a $CO_2$-UH, shown with icons representing greentech industrialization.

5.17. Label seventeen (17) indicates a transition depth in Lake Kivu separating a resource-rich deepwater reservoir below an upper reservoir without concentrated resources. (This is a simplified representation. The actual situation is multi-layered.) For comparison, Box 2 indicates that this transition depth can move downwards (from 17 to 18) over time in some embodiments of the TDS method and other advanced methods of utilizing Lake Kivu deepwater resources (when return flow water can be de-densified so that it can be returned in higher-level layers and "push down" the depth of the transition later over time, as shown by arrows: 17 to 18).

5.18. Label eighteen (18) indicates the time trend of deepening of a transition layer boundary in some embodiments of the TDS method and other advanced methods of utilizing Lake Kivu deepwater resources.

5.19. Label nineteen (19, located in Box 1) indicates one aspect of methane loss or "slip" occurring in the SDS method. This loss is due to non-total degassing at the stage-1 transition wherein gas is degassed at a depth typically of ~20 meters.

5.20. Label twenty (20, located in Box 1) indicates another aspect of methane loss or "slip" in the SDS method. This loss is due to re-dissolution of methane degassed in Stage-1 into "washing water" degassed gas is bubbled through in Stage-2 operations for the purpose of $CO_2$ separation.

5.21. Label twenty-one (21) indicates a set of icons representing products output and transport from the $CO_2$-UH (16).

5.22. Label twenty-two (22) is a dashed circle within Box 1. It circles Stage-1 degassing operations whereby an upflow of deepwater (3) is separated into two fractions. These are: (i) a gas fraction which proceeds upward (23), and (ii) a water fraction containing most of the $CO_2$ in solution (5) and some of the methane remaining in solution (19).

5.23. Label twenty-three (23) indicates the upflow of degassed gas proceeding upwards into Stage-2 separation by means of bubbling up through an intensely showered downflow of near surface "washing water" (24).

5.24. Label twenty-four (24) represents a "washing water" flow of near-surface water (which absorbs $CO_2$ into solution) through Stage-2 "water washing" within Stage-2 (25). This water flows out of Stage 2 (25) and is reinjected into Lake Kivu's upper (above 17) Biozone (vector 6 carrying a load of re-dissolved $CO_2$).

5.25. Label twenty-five (25) indicated a sector secured to a floating platform (4, 12a) within which Stage-2 "water washing" occurs. Typically this is in an above-water tower supported on top of a floating platform.

5.26. Label twenty-six (26) labels an upflow vector indicating an upward flow of Lake Kivu deepwater containing water (unfilled outer arrow), dissolved $CO_2$ (black inner vector) and methane (thin stippled core vector).

5.27. Label twenty-seven (27) indicates a total degassing separator wherein water is shown being separated into a return flow (28, 29, 30), while degassed gas flows upwards into oxyfueled combustion (13) for power generation (as indicated by icons).

5.28. Label twenty-eight (28) indicates an early pretreatment part of a Return Flow System (RFS).

5.29. Label twenty-nine (29) indicates a water treatment phase in flow through a Return Flow System (RFS)

5.30. Label thirty (30) indicates relatively shallow injection of return flow into the water column (causing "push down" 17 to 18) of the transition layer.

5.31. Label 31 indicates reinjection of $CO_2$-carrying (5) return flow water into the deepwater reservoir from which the methane-bearing deepwater (3) was obtained. Methane loss or "slip" (5) also is shown.

6.1. Box 1 identifies/contains the OXFCPS and its intersections with various cryogenic energy storage components (Boxes 2, 3, 4, 22, and 23).

6.2. Box 2 identifies/contains an Air Separation Unit (ASU) integrated with part of a CRyogenic Processing Unit (Box 22: CRPU) and liquefied gases storage units (Box 4, Box 28).

6.3. CRyo-Energy Recovery Unit (Box 3: CRERU) showing its various interconnections with other components.

6.4. $CO_2$-UH (Box 4) with $LN_2$, $LO_2$, $LCO_2$ and LNG storage capacities (Box 28).

6.5. Item 5 represents a Digital Data Center (DDC) with capacities for being cooled by inputs of either or both cold gaseous $N_2$ (12) and $LN_2$ (11).

6.6. Item 6 represents a flow transfer of liquified oxygen ($LO_2$) from a cryogenic condenser source (29) in an Air Separation Unit-Cryo-Production Unit (Box 2: ASU-CRPU) into one or more storage tanks (23) within a cryo-storage domain for liquefied gases (28) obtained from air (or air-like) inputs (14).

6.7. Item 7 represents a flow transfer of liquified nitrogen ($LN_2$) from a cryogenic condenser source (29) in an Air Separation Unit-Cryo-Production Unit (Box 2: ASU-CRPU) into one or more storage tanks (24) within a cryo-storage domain for liquefied gases (28) obtained from air (or air-like) inputs (14).

6.8. Item 8 represents a flow transfer of gaseous $CO_2$ and/or liquified carbon dioxide ($LCO_2$) from a cryogenic condenser source (30) intersecting (via Box 22: CESSI) with $CO_2$-carrying post-combustion exhaust created in the OXFCPS (Box 1) and stored into one or more storage tanks (25) within a cryo-storage domain for liquefied gases (28) possessing general cryogenic capacities or integration into other cryogenic capacities within the overall system (27b, as indicated by the icon), and existing as a part of the $CO_2$-UH (Box 4 and detailed in FIG. 3).

6.9. Item 9 represents a flow transfer of liquified carbon dioxide ($LCO_2$) from storage (25) into a $CO_2$-specific heat exchanger turbine system (within Box 22: CESSI, as indicated by icons) that converts the cryogenic energy stored in liquefied $CO_2$ into mechanical, then electric power (18a).

6.10. Item 10 represents a flow transfer of liquified oxygen ($LO_2$) from storage (23) into an $O_2$-specific heat exchanger turbine system (within Box 22: CESSI, as indicated by icons) that converts the cryogenic energy stored in liquefied $O_2$ into mechanical, then electric power (18b).

6.11. Item 11 represents a flow transfer of liquified nitrogen ($LN_2$) from storage (24) into an $N_2$-specific heat exchanger turbine system (within Box 22: CESSI, as indicated by icons) that converts the cryogenic energy stored in liquefied $N_2$ into mechanical, then electric power (18c).

6.12. Item 12 is a captured flow of cold gaseous nitrogen from the outflow of the part of the Cryo-Energy Recovery Unit (Box 3: CRERU) that recovers cryo-energy stored in $LN_2$. This cold gas is directed as a coolant flow into a Digital Data Center (5: DDC).

6.13. Item 13 represents a flow transfer of (utilizable) warmed-up nitrogen gas out of the Digital Data Center (5) after absorbing heat.

6.14. Input of air (or air-like gas) into the Air Separation Unit—Cryogenic Processing Unit (Box 2: ASU-CRPU).

6.15. Black arrow 15 indicates inflow of electric power from the grid (33) into an electricity handling nexus (Box 41) integrated into the OXFCPS (Box 1).

6.16. The black arrow labeled 16 indicates outflow of electric power into the grid (33) from an electricity handling nexus (Box 41) that is integrated into the OXFCPS (Box 1).

6.17. Black arrow 17 indicates deployment of electric power from the electricity handling nexus (Box 41) into the ASU-CRPU (Box 2) to power cryogenic condensation of gases.

6.18. Black arrows 18, 18a, 18b, and 18c indicate power inputs into the electricity handling nexus (Box 41) from in the Cryo-Energy Recovery Unit (Box 3: CRERU).

6.19. Black arrow 19 indicates power provision from the electricity handling nexus (41) in the OXFCPS (Box 1) into the $CO_2$-UH (Box 4) with its cryogenic capacities (27b) integrated with those (27a) in the Air Separation Unit—Cryogenic Processing Unit (Box 2: ASU-CRPU).

6.20. Item 20 represents electrical power input from solar and/or wind power arrays. Typically these will be situated at remote locations with respect to Lake Kivu.

6.21. Item 21 represents the connection of electric power inputs from solar and/or wind power arrays into the electricity handling nexus (Box 41) integrated with the OXFCPS (Box 1). The invention's optional inclusion of cryo-energy storage capacities allows energy storage of irregular inputs of renewable energy and consequently an important potential function in grid-balancing.

6.22. Box 22 ("CESSI") represents systems/methods of integration described as, "Cryogenic Energy Storage Systems Integration" (CESSI) coupling together an Oxy-Fuel Combustion Power System (Box 1: OXFCPS), an integrated Air Separation Unit—Cryo-Production Unit (Box 2: ASU-CRPU), a Cryo-Energy Recovery Unit (Box 3: CRERU), as well as a cryo-storage domain for liquefied gases (Box 28) functioning as a cryo-energy power-storage battery (26, as indicated by the battery icons).

6.23. Liquefied oxygen ($LO_2$) storage in a tank or tank farm.

6.24. Liquefied nitrogen ($LN_2$) storage in a tank or tank farm.

6.25. Liquefied carbon dioxide ($LCO_2$) storage in a tank or tank farm.

6.26. Iconic representation of liquefied gases storage as a power battery.

6.27. Items/icons 27a and 27b represent integrated cryogenic systems serving the ASU-CRPU (Box 2) and the cryo-storage domain (Box 28) within the $CO_2$-UH (Box 4)

6.28. Box 28 (dashed box) contains the cryo-storage domain within the $CO_2$-UH (Box 4)

6.29. Item 29 is a refrigerating heat exchanging air condensing unit within the ASU-CRPU (Box 2).

6.30. Item 30 represents refrigerating heat exchanging condensing unit for refrigeration of $CO_2$ to liquid within the CESSI (Box 22), exporting liquefied $CO_2$ (8) into tank storage (25). This capacity may be considered to be identical to capacities labeled 27a and 27b for the specific case of the refrigeration-liquification of $CO_2$.

6.31. Item 31 is a captured flow of cold gaseous oxygen from the outflow of the part of the Cryo-Energy Recovery Unit (Box 3: CRERU) that recovers cryo-energy stored in $LO_2$. This cold gas is directed as a coolant flow into input into oxy-fueled combustion in the OXFCPS (Box 1).

6.32. Flux arrow 32 is a flow of post-combustion exhaust from the OXFCPS (Box 1) into the $CO_2$-UH (Box 4). A note below the label clarifies an important matter that is not otherwise shown in the figure: that the exhaust flow is connected to heat exchange capacities within the CRERU-CESSI.

6.33. An icon labeled thirty-three (33) represents connectivity with the grid. [Arrows fifteen (15) and sixteen (16) represent power flows into and out of the electricity handling nexus (Box 41) from and to the grid (33), respectively, indicating (cryogenic) power storage capacities as well as the conventional powerplant power production capacities.]

6.34. The tank icon is labeled representing both LNG storage as well as a capacity for use of LNG in cryo-processing $CH_4$—$CO_2$ mixtures to obtain additional LNG and extracted dry ice (e.g., Baxter: WO2013062922A1, "System and Methods For Integrated Energy And Cryogenic Carbon Capture.") Interconnection details are not shown in FIG. 6 (or in other figures).

6.35. Cryogenic production capacity for LNG as well as for separation of $CO_2$ as noted immediately above 6.36. Box thirty-six (36) represents specialized cryogenic operations for LNG production as well as for separation of $CO_2$ as noted for item 6.34.

6.37. Flux vector representing inflow of biomethane with $CO_2$ into LNG-specialized operations noted above.

6.38. Source of biomethane with $CO_2$ (=Lake Kivu deepwater via degassing operations).

6.39. Flux vector representing the flow of separated biomethane with $CO_2$ from LNG-specialized operations.

6.40. Flux vector representing a general capacity for Natural Gas (NG) production (LNG, CNG, and ANG). This production follows cryogenic $CO_2$ separation within LNG (item 35, by means of the elegant methods pioneered by Larry Baxter and colleagues). Output flux vector 40 also can indicate an output into energy storage via both LNG cryoenergy and LNG fuel energy (though icon/item 34 itself indicates this capacity).

6.41. Label forty-one, (Box) 41, represents an electricity handling nexus whereby grid (33) power inputs (15) and outputs (16), as well as special inputs (21) of renewable power sources (20), are integrated into the OXFCPS (Box 1) NB: Label thirty-three (33) indicates the grid in connection to the electric power producing powerplant component of the OXFCPS.

Figure 7:
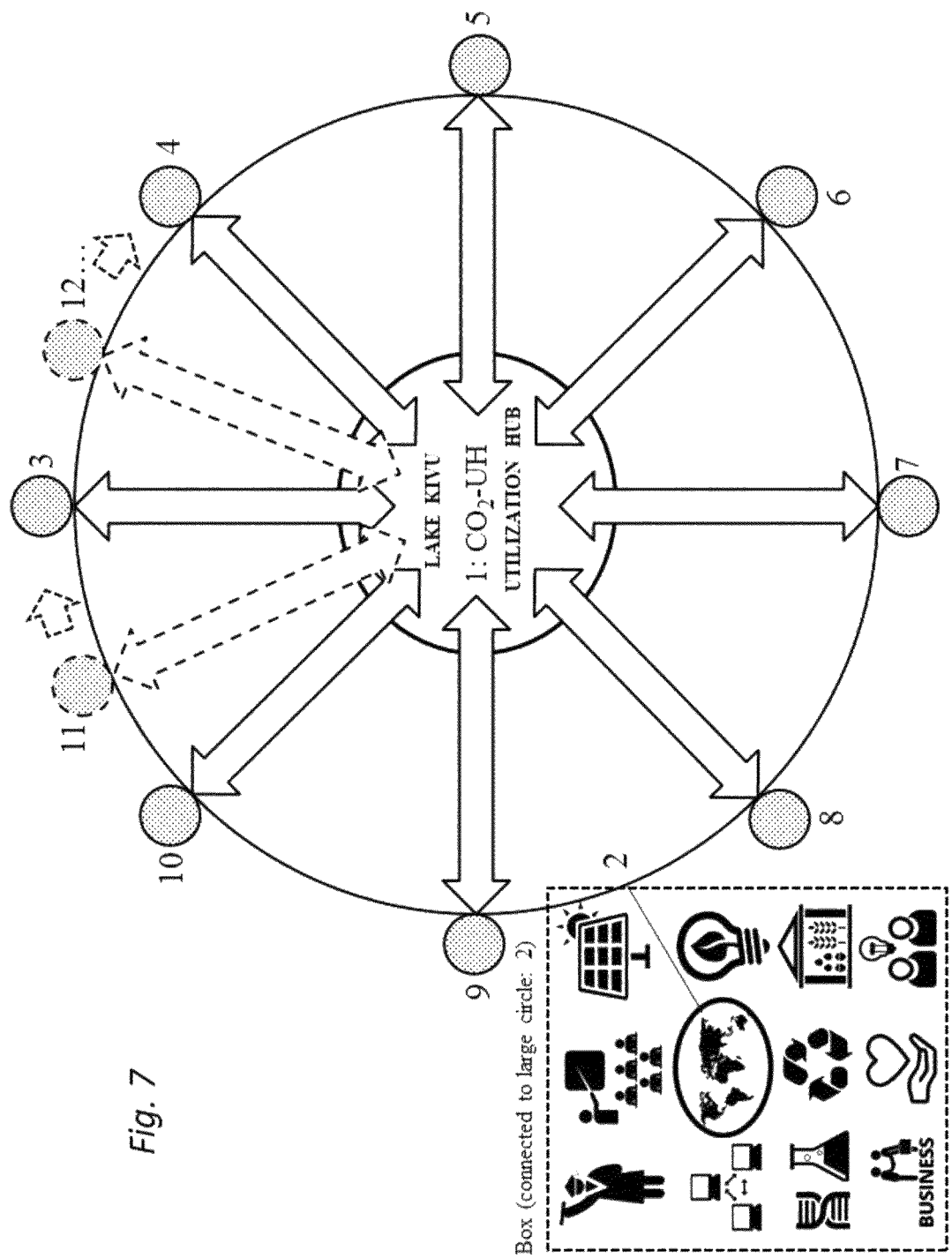
FIG. 7 is a purely symbolic "hub-&-spokes" representation of embodiments of the $CO_2$-UH (and, more broadly, of the invention overall) located at Lake Kivu functioning as a hub (1) center for a global network (2: large circle plus associated box containing icons). The network can connect together many and various worldwide collaborations (3, 4, 5, 6, 7, 8, 9, 10, 11, 12 . . . ) with companies, research institutions and philanthropic agendas attracting talent into the overall venture. Entities work together in concert with respect to addressing the challenge to create business-scalable innovations in $CO_2$ utilization recycling. Icons inside the dashed box represent multiple types of aspects of such a hub-and-spokes global network.

7. FIG. 7 is purely conceptual representing the invention in terms of its potential for global network creation by offering an attractive opportunity for the coordinated realization of many $CO_2$-utilizing technologies.

7.1. Item one (1) is the $CO_2$-Utilization Hub (1: $CO_2$-UH) represented as the hub of a wheel-like hub-&-spokes network in which each spoke (3, 4, 5, 6, 7. 8, 9, 10, 11, 12 . . . ) is a specific collaboration for a type of $CO_2$ utilization.

7.2. Item two (2) is the larger circle representing the outer wheel hosting spokes at a (global) distance from the hub but connecting into it. A box connecting to this large circle on the lower left represents by icons various aspects or types of collaborations. Also represented is its worldwide global aspect, attracting talent into the project as well as possessing an openness to host new inventive modes of $CO_2$ utilization.

7.3 through 7.12 are described in section 7.1 above.

8. FIG. 8 provides a systems comparison. The comparison is focused on the modification of a conventional Staged Degassing System (SDS, Box 1). An SDS is shown with two stages as practiced on Lake Kivu. It is compared with a Modified Staged Degassing System (Box 2) allowing carbon ($CO_2$) capture as well as utilization of non-degassed resources in the degassed return flow water. FIG. 8 contains Box 1 enclosing a Staged Degassing System (SDS), Box 2 enclosing a Modified Staged Degassing System (MSDS), and Box 3, (which is within Box 2), enclosing two modes of Return Flow Systems. These two RFS modes are different from deep reinjection modes indicated (depth not to scale) in items 9a, 9b, and 13. Note that in FIG. 8, the three box numbers noted above are distinct from item numbers 1, 2 and 3.

8.Box1. Box 1 encloses a representation of a Staged Degassing System (SDS).

8.1. Item 1 (shown in both boxes 1 and 2) represents a deepwater extraction pipe or riser.

8.Box2. Box 2 encloses a representation of a Modified Staged Degassing System (MSDS).

8.2. Item 2 (shown in both boxes 1 and 2) represents a stage-1 degassing and separation chamber, with a degassing surface positioned at depth D (10), showing how water flows up into the chamber, over a barrier, and then down reinjection pipes or risers (9a and 9b)

8.Box3. Box 3, (which is within Box 2), encloses two modes of Return Flow Systems. One (15) is for diffusive admixing of degassed deepwater into the biozone as a mode of (carefully monitored and controlled) lake fertilization with controlled $CO_2$ injection (27, 28). The other (proceeding along the surface, 16) is a water treatment water de-densification bioproduction and Mg, Ca-precipitation system, also with controllable $CO_2$ input (e.g., 22, 25) and removal (e.g., 25) capacities.

8.3. Item three (3), (shown in both boxes 1 and 2) represents a gas transfer line transferring degassed gas upwards from Stage-1 degassing into Stage-2 gas cleaning operations (4, 5, 6, 7, 8).

8.4. Item four (4) represents an enclosed chamber, typically a tower, wherein gas flow from Stage-1 rises upwards through either via a bubbling upflow or upwards through a showered and/or packing-mediated trickling (6) downflow of water obtained from a near-surface location (5). The "washing water" is then expelled (7) into the biozone carrying absorbed $CO_2$ that has been "cleaned" during the upwards gas flow. Cleaned methane gas consequently containing a reduced amount of $CO_2$ is extracted at the top of the tower (8) for use in combustion. Bubble flow is indicated in the diagram. However, as noted herein, such a gas-cleaning tower may not use bubbling gas flow. It may contain packing materials promoting large area trickle flow interaction between the percolating down-flowing water and the up-flowing gas that is in close contact with the down-flowing water within the tower.

8.5. Item five (5) represents near-surface extraction of water to supply gas "washing water" with pumped flow (6) to the top of the gas-washing tower (4).

8.6. Item six (6) represents a pumped near-surface extraction of water to supply "washing water" with pumped flow (6) to the top of the gas-washing tower (4).

8.7. Item seven (7) represents return flow (typically via one or more pipes) of the flow of gas-washing water into the biozone.

8.8. Item eight (8) represents the gas extractor area (including gas extraction line) at the top of the gas-cleaning tower. In a bubbled flow, this is a gas zone above the surface of the mixed flow. In a tower operating by trickling flow, it is simply the area where the upward-flowing gas is extracted (in combination with the extraction line, and typically but not necessarily involving pumped control of gas flow).

8.9a,b. Items nine (9a and 9b) represent return flow reinjection pipes. Depths are not shown to scale. Reinjection in the modes illustrated by necessity must be in the deep-water layer due to the density of the water (changed only to a modest degree by degassing).

8.10. Double-sided arrow ten (10, shown within Box 1) represents a depth, D, for a degassing surface within the Stage-1 degassing chambers shown in Boxes 1 and 2.

8.11. Item eleven (11) shown within Box 2 represents a key modification of the SDS method and/or system. This modification ports water after Stage-1 degassing upwards into a second stage of degassing, thereby allowing degassing and capture of $CO_2$ as well as utilization of additional resources present in return flow water, by modification (such as of existing systems or designs).

8.12. Item twelve (12) represents a second degassing chamber for separation of $CO_2$ from the return flow. As illustrated, valves (indicated by bow tie icons) allow directing of return flow into different types of systems.

8.13. Item thirteen (13) represents one such return flow system: conventional reinjection at depth similar to 9a and 9b.

8.14. Item fourteen (14) represents extraction of $CO_2$ out of the top of the second degassing chamber for separation of $CO_2$ from the return flow (12).

8.15. Item fifteen (15) represents (an array of) pipe diffusers for diffusive admixing of degassed return flow deepwater into Lake Kivu's biozone (as a mode of controlled lake fertilization).

8.16. Item sixteen (16) represents a mode of water treatment of return flow.

8.17a,b. Item seventeen (17a,b) represents a capacity for $CO_2$ content control corresponding to vectors 21a,b. Capacity 17a represents control for $CO_2$ input into the return flow. Capacity 17b represents control for $CO_2$ removal such as by sparging and/or vacuum extraction of dissolved gas the return flow. Such capacities also are pH control capacities.

8.18. Item eighteen (18) indicates a water biotreatment zone (typically involving algal growth in some embodiments). In some embodiments, as shown, $CO_2$ inputs (22) are staged along the flow.

8.19. Item nineteen (19) represents a capacity for two functions. The first is for $CO_2$ extraction (as indicated by vector 24), such as by sparging and/or by vacuum extraction of dissolved gas the return flow. The second is for precipitation of Mg and Ca from solution according to a variety of possible methods and/or systems.

8.20. Item twenty (20) represents return flow reinjection at a lesser depth than in the cases of return flow without de-densifying water treatment (that is: 9a, 9b, 13).

8.21a,b. Item twenty-one (21a,b) is a double-sided arrow representing a capacity for either $CO_2$ input (21a), or $CO_2$ extraction (21b), with directionality specified as needed.

8.22. Item twenty-two (22) indicates a capacity for input of $CO_2$ into water treatment operations (18), typically involving algal growth.

8.23. Item twenty-three (23) represents modes of $CO_2$ removal from solution prior to entry into unit/process/method/system 19.

8.24. Item twenty-four (24) indicates a capacity for $CO_2$ removal from unit 19.

8.25. Item twenty-five (25) indicates a capacity for $CO_2$ injection into unit 26.

8.26. Item twenty-six (26) represents a capacity for $CO_2$ dissolution into the return flow (20).

8.27. Item twenty-seven (27) indicates a capacity for pumping $CO_2$ into the return flow modality shown as item 15, via a $CO_2$ injection-dissolution unit labeled 28.

8.28. Item twenty-eight (28) represents a $CO_2$ injection-dissolution unit for return flow being diffused in a carefully controlled manner into the biozone via (typically an array of) pipe diffusers (15).

9. FIG. 9 adds detail to FIG. 1. It does so within Box 4 (that is left empty in FIG. 1). Boxes 1 through three, and items 1 through 14, excepting items 7a and 7b, are identical to those displayed in FIG. 1. Therefore, below, names of items and brief associated contextual descriptions are provided only for the following labeled items: 7a and 7b, and items 15a,b,c,d,e, 16, 17, 18 and 19. (The set of icons labeled as item 20 is identical in FIG. 9 as in FIG. 1.)

9.7 a,b. Items labeled seven (7a and 7b) indicate different modalities of return flow. Flow vector 7a corresponds to a method and/or system similar to item 15 in the previous figure (8.15). Flow vector 7b corresponds to return flow input entering into a water treatment method and/or system (as is shown, for example, in FIG. 8, items 17a.b, 18, 19, and 26).

9.15 a,b,c,d,e. Items fifteen (15 a through e) indicate $CO_2$ input flows from a $CO_2$ Utilization Hub (1: $CO_2$-UH) into a range of components of return flow operations (15a,b,d, e) as well as by direct diffusion-dissolution (15c) into the lake's biozone via an array of gas diffusers. Item 15a indicates pH-controlling $CO_2$ injection-dissolution into return flow after "total degassing" via a TDS method and/or system (Box 1: TDS). Item 15b indicates $CO_2$ injection-dissolution into return flow water treatment operations similar to those shown in FIG. 8, box 3 in a flow series beginning with item 16 (8.16). Item 15c indicates $CO_2$ injection-dissolution directly into Lake Kivu's biozone by gas diffuser pipes as noted above. Item 15d indicates $CO_2$ injection-dissolution into return flow directed into a water diffusion system diffusing return flow water into Lake Kivu's biozone. Item 15e indicates injection of $CO_2$ into reinjection pipe systems

(18) carrying water out from water treatment (16). This form of $CO_2$ injection-dissolution is a mode of pH control (de-alkalization).

9.16. Item sixteen (16) represents a water treatment sector utilizing biological processes such as algal photosynthesis. Such operations are known as Biological Production Units (BPUs).

9.17. Item seventeen (17) represents a water treatment unit for precipitation of Mg and Ca. In some embodiments, this involves algal flocculation and harvesting.

9.18. Item eighteen (18) represents return flow reinjection pipe systems carrying water out from water treatment (16) and in some embodiments utilizing $CO_2$ injection-dissolution (15e) as a mode of pH control (de-alkalization).

9.19. Item/vector nineteen (19) represents materials extractions supporting products production (8) modes based upon de-densifying water treatment of the return flow of degassed deepwater. Flow vector 19 should be considered as delivering materials into the $CO_2$ Utilization Hub ($CO_2$-UH: Box 1), for example Mg and Ca precipitates and algal biomass.

DETAILED DESCRIPTION OF PREFERRED EMBODIMENTS OF THE INVENTION

The disclosure of the invention presented herein is a teaching. It reveals to the Republic of Rwanda, and more broadly to the Kivu region of the DRC, an unprecedented possibility and opportunity for global leadership in advanced greentech industrialization, specifically in productive utilization of $CO_2$ in amounts equal to the world's largest industrial flows of $CO_2$. The location of Lake Kivu close to the geographical center of the African continent offers an economically favored opportunity for $CO_2$-utilizing industrial production of products that are expensive to import from the coast. $CO_2$ utilization also offers ways to produce a large number of high-value export products. The scale of the opportunity is very large within its context. A doubling of Rwanda's rate of per capita economic growth is possible.

Carbon dioxide has never been extracted from a lake for industrial use. No prior art exists in this specific category of activity. Carbon dioxide has been vented from lakes in Cameroon and in Spain (Halbwachs et al., 2004; Kling et al., 2005; Sanchez-Espana et al., 2014) for safety purposes using auto-siphoning pipe-jet fountains. There has been no capture and utilization of the gas.

Lake Kivu's dissolved gases trapped at depth are a mixture of methane and $CO_2$. This situation presents a difficulty: too much $CO_2$ is present for efficient combustion such that gas-cleaning stages are required, causing substantial efficiency losses. This problem has been solved by the inventor in a previous disclosure documented herein presenting a method and system of "total gas" extraction into an oxyfuel combustion heat engine that exhausts nominally pure $CO_2$ (excepting water vapor which can be removed easily if desired). The situation also presents a difficulty for the use of the $CO_2$ present, as noted, in a vast store in Lake Kivu of approximately 600 million tonnes. The invention disclosed herein discloses a method and system that allows hyper-efficient utilization and effective separation of both methane and $CO_2$. This is via two variant processes: one involving modification of existing methane degassing methods, systems, designs and apparatus, and the other in conjunction with the oxyfuel method of power generation which utilizes unseparated "total gas" degassed by deepwater extraction degassing without a separation method separating $CO_2$ from methane. It is surprising that it can be possible to unlock Lake Kivu's resources in such efficient ways without wasting either $CO_2$ or methane. In the present disclosure, the primary focus is on unlocking Lake Kivu's $CO_2$ resource in coordination with efficient capture and use of Lake Kivu's biomethane reserve. Degassing $CO_2$ additionally can secure lake safety against a limnic eruption mega-catastrophe. This is a vital associated goal.

As noted herein, industrial sources of $CO_2$, when obtained from natural occurrences, typically are nominally pure. A particularly pertinent example is the Kereita Forest spring source (actually a drilled fountaining jet of water and $CO_2$) used by the Kenyan company Carbacid ($CO_2$) Limited (www.carbacid.co.ke). Carbacid ($CO_2$) Limited provides and sells $CO_2$ from this source for use in beverage carbonation all over East Africa. It is ironic that businesses operating on the shores of Lake Kivu buy Carbacid $CO_2$ obtained from the distant Kereita Forest while 600 million tonnes is trapped nearby, and when nearby volcanoes and mazuku vents bordering the lake naturally emit perhaps as much as 30 million tonnes $CO_2$ per year into the local atmosphere. Another ironic aspect is the way the standard technology practiced on Lake Kivu returns $CO_2$ into the depths of the lake (and thereby extends the mortal danger from a possible limnic eruption). As the MSDS method and system disclosed herein shows, $CO_2$ can de degassed by a relatively simple design modification. However, when the standard design was created, it was not obvious how such large amounts of degassed $CO_2$ could be used, whereas it generally is well understood that venting $CO_2$ to the atmosphere is environmentally problematic. The present disclosure provides the surprising insight that many useful uses exist. These sum together to a very large scale of potential $CO_2$ utilization. Unlocking Lake Kivu's trapped mega-source of $CO_2$ offers a transformation by the creation of a massive flux of purified, naturally-sourced $CO_2$ herein estimated roughly as ~9 million tonnes per year. That is a surprise.

Separating $CO_2$ by means of modifying the traditional staged degassing system design (SDS to MSDS as shown in FIG. 8) yields $CO_2$ with residual methane present. It does not yield a purified $CO_2$. (Avoiding methane wastage is one of the efficiency gains of the variant process based on total degassing followed by oxyfuel combustion.) This type of methane-laced $CO_2$ has a special utility as an aquatic carbon source. When carbon dioxide in injected into the biozone, any accompanying methane can be utilized by oxidizing bacteria present in the biozone. Such bacteria can utilize methane as an energy source and also as a carbon source. Their growth can increase overall bioproductivity.

A particular challenge the invention addresses is $CO_2$ utilization on a scale sufficient to match the scale of $CO_2$ degassed in power plant operations obtaining Lake Kivu's methane and degassing its deepwater $CO_2$. For the Rwandan side of the lake this scale is roughly 10 million tonnes of $CO_2$ per year. That approximately equals the largest single source $CO_2$ extraction flux in the world (from a $CO_2$ well used to supply $CO_2$ for EOR in west Texas, USA). Herein it is shown that at least $\frac{1}{3}^{rd}$ of powerplant (OXFCPS) $CO_2$ flux can be utilized valuably in direct connection with treatment of powerplant return flow reinjection into the lake. It is shown that this fraction increases to over ½ with inclusion of related $CO_2$ utilization processes set by levels of different resources present in the deepwater. Several other $CO_2$ utilization processes can boost the overall level of $CO_2$ utilization to match the total level of flux. The invention demonstrates that it is possible to utilize the full scale of $CO_2$ flux in an industrially productive manner. This is shown in Table 2.

The Lake Kivu region is magnificently attractive. The area has strong eco-tourism potential. It could be spectacular for real estate development. Accelerated development of the area will require concrete and other building materials for roads, culverts, bridges, runways, dams, buildings, tunnels, piers, docks and walkways. Magnesium-mineralized $CO_2$ can provide a source of mineral carbonate mass for advanced construction materials sourced from $CO_2$ combining with precipitated magnesium hydroxide, and also via carbonation of additional pozzolanic materials from abundant local volcanic ash sources. The region possesses densely populated hyper-fertile lands with a strong farming tradition. It is a situation likely to be enthusiastic for the development of $CO_2$-boosted very-high-yield greenhouse horticulture. Farmers can utilize urea made with deepwater $CO_2$ and bio-ammonium to intensify crop yields in the region, and to expand agro-production for exporting flowers, high-value specialty foods, plant extracts and other exports. These can include a wide variety of potential nutraceutical and pharmaceutical products linked with CCU. Pyrethrum production offers a substantial opportunity for organic biopesticide production linked with $CO_2$ because it is a longstanding crop in the region. The wider region also has huge potential for minerals/metals extraction with value-add ore processing. A low-cost $CO_2$ supply can assist several modes of metals extraction and value-add processing, as noted herein. These range from use of carbon monoxide in smelting tin to new technologies of coltan value-add refining, to dunite-olivine carbonation for production of silicon-, magnesium-, and iron-rich plant fertilizers, as well as eco-nickel from Mg-carbonate mineralization of $CO_2$. The wider Lake Kivu region has huge potential for dry ice distribution. Dry ice can provide efficient off-grid refrigeration linked with beverage and food distribution. To the west, the great Congo forests have substantial potential for sustainable forestry products development. Production possibilities exist in many areas of $CO_2$-utilizing industrial technology, ranging from bioplastics to biochemicals to biosynthetic textiles, to paper, xylitol, wallboard production and biofuels. All of these types of forest biomass-related products utilize $CO_2$, and some use formic acid that can be produced from $CO_2$. To the east are huge reserves of alkaline brines and soda ash already being used for sodium bicarbonate production. Sodium bicarbonate can be used in high-value algal products production. It also is useful in biomass and mineral ores processing. To the north, multi-billion barrel opportunities exist for extraction of oils supported by $CO_2$-EOR technologies. Oil fields exist in the range 150 to 400 km distant from Lake Kivu. To the east, radiation-optimal locations for solar power arrays in NW Tanzania, NW Kenya and NE Uganda. These areas are attractive for solar power generation for the purpose of powering production of $CO_2$-utilizing "solar fuels"/"electrofuels" production. High voltage wires can transport solar power from these regions to the $CO_2$ supply at Lake Kivu. Lake Kivu biomethane can be used with $CO_2$ input to produce Gas-to-Liquids (GTL) biomethanol for transport fuel admixing. Large-scale algae production utilizing $CO_2$ as a carbon source offers opportunities for high-value nutraceuticals and pharmaceuticals production as well as biofuels, bio-asphalt, bio-nitrogen and bio-char fertilizers, $CO_2$-utilizing bioplastics, and other green chemicals. In the future, many attractive commercialized technologies will emerge for large-scale $CO_2$ utilization, for example, high-value carbon nanofiber and nanotubes production from $CO_2$.

Numbers describing resource abundances in Lake Kivu deepwater and deepwater inflows are provided in Table 1 scaled to 100 MW for electric power output. Estimates of potential practical scales for the examples provided of 20 "main mode" possibilities for $CO_2$ utilization shown in Table 2. These are scaled to roughly a 400 MW power output. The comparison shows that $CO_2$ output at this scale (~9 MTA $CO_2$) can be utilized practically.

TABLE 1

LAKE KIVU DEEPWATER RESOURCES & ANNUAL FLUXES

| Resource | Kivu Total (Resource zone, tonnes) | MRZ conc. (per 1000 litres) | 100 MW scale* (T: tonnes/yr) |
|---|---|---|---|
| Methane | ~47 Million T*** | ~250 grams | ~132,000 T/yr |
| $CO_2$ (from CH4 combustion): | | | ~363,000 T/yr |
| $CO_2$ (gas) | ~400 Million T** | ~3.5 kg | ~1.9 Million T/yr |
| $CO_2$ (total degassed + combustion): | | | ~2.3 Million T/yr |
| $HCO_3^-$ | ~500 Million T** | ~4.2 kg | ~2.2 Million T/yr |
| Ammonium | ~12 MT (UE)** | ~60 g ($NH_4^+$) | ~53,000 T (UE)/yr |
| Phosphorus | ~0.6 MT (P)** | ~5 g (P) | ~2,600 T (P)/yr |
| Magnesium | ~35 MT (Mg)** | ~300 g (Mg) | ~156,000 T (Mg)/yr |

MRZ = Main Resource Zone. MRZ volume: ~118 km3 deepwater.
*Deepwater extraction/use scaled to 100 MW power output for the method and system disclosed herein: 0.53 cubic km deepwater/yr
**Main Resource Zone (MRZ) only.
***Methane total estimate for Lake Kivu for all zones reported by Wuest et al., (2012). Other concentrations from Tassi et al., (2009).
UE = Urea Equivalent mass.

TABLE 2

$CO_2$ UTILIZATION MODES & ESTIMATES

| Mode of $CO_2$ Utilization | Scale Potential (MTA) (Million Tonnes CO2 per Annum) | Notes |
|---|---|---|
| 1. Local greenhouse horticulture | ~2 | area: ~5,000 hectares |
| 2. Lake Kivu biozone $CO_2$-fertilization | ~2 | scaled to ~400 MW |
| 3. Lake Kivu return flow pH-lowering | ~1 | scaled to ~400 MW |

TABLE 2-continued

CO$_2$ UTILIZATION MODES & ESTIMATES

| Mode of CO$_2$ Utilization | Scale Potential (MTA) (Million Tonnes CO2 per Annum) | Notes |
|---|---|---|
| 4. pH control, return flow water treatment | n.e. | Precip. control & algal C-source |
| 5. Algal production (incl. bicarbonate): | ~0.5 to 5 | >35 tonnes dryweight/ha/yr |
| 6. High-pressure CO$_2$ pipeline delivery | ~1 to 4 | mostly for CO$_2$-EOR |
| 7. Refrigerated CO$_2$ delivery: | ~0.1 | liquid CO$_2$ & dry ice |
| 8. Eco-concrete & related materials: | ~0.7 | scaled to Mg-hydroxide flux |
| 9. Urea production from NH$_3$: | ~0.3 | scaled to NH$_4^+$ flux |
| 10. CO$_2$ to formic acid: | ~0.01 | many & various uses |
| 11. CO$_2$ to carbon monoxide (CO): | ~0.01 | for example tin smelting |
| 12. CO$_2$-pyrethrum biopesticide: | ~0.02 | e.g., BRA: Botan. Res. Austr. |
| 13. Forest products CO$_2$ processing: | n.e. | e.g., Chempolis (formic acid) |
| 14. CO$_2$-geothermal energy extraction: | n.e. | emerging technology |
| 15. Fuels & chemicals production: | n.e. | many companies |
| 16. CO$_2$ + H$_2$O to syngas: MeOH, DME: | n.e. | e.g., Haldor Topsoe |
| 17. CO$_2$ to oxalic acid platform: | n.e. | e.g., LiquidLight |
| 18. CO$_2$ + H$_2$ into gas fermentation: | n.e. | e.g., LanzaTech |
| 19. CO$_2$ into plastics: | n.e. | e.g., Covestro, Novomer |
| 20. CO$_2$ into high-value C-products | n.e. | e.g., C-nanotubes |
| TOTAL, ESTIMATED SOURCES: | ~>9 MTA | |
| CO$_2$ output, 400 MW power plant: | ~9 MTA | | n.e. = not estimated

A reasonable scale for application of the invention disclosed herein is ~400 MW of total electrical power generation. This scale is based on combustion efficiency optimization suggested by a business partnership that manufactures advanced oxyfuel turbine systems. A reference scale target for CO$_2$ utilization therefore is set by the sum of degassed CO$_2$ and combustion-created CO$_2$ for 400 MW on power output. This result is: 9 MT CO$_2$/yr. Input data for this calculation are provided in Table 1. A rough maximum scale for CO$_2$ utilization corresponds to degassing of the entire budget of CO$_2$ in Lake Kivu (~600 million tonnes) in ~30 years plus 50 MT biomethane converted to CO$_2$ mass (=138 MT CO$_2$). This amounts to a production of roughly 700 to 750 MT CO$_2$ in 30 years, hence up to: ~25 MTA CO$_2$. This maximum CO$_2$ utilization opportunity scale is close to the world's largest scale of CO$_2$ utilization in the context of a CO$_2$ pipelines hub: ~30 MTA CO$_2$ through the West Texas Denver City hub for CO$_2$-EOR. Note that removal of Lake Kivu's deepwater CO$_2$ is essential for long-term human safety in the Lake Kivu basin involving millions of human lives as well as the ecological survival of Lake Kivu's fauna (which periodically has been destroyed by past limnic eruptions).

The system of the invention comprises subsystems including a carbon dioxide utilization hub (CO$_2$-UH). In certain embodiments, the system comprises two or three coupled subsystems shown in FIG. 1: (i) TDS or MSDS variant; (ii) OXFCPS (not present in the MSDS variant); and (iii) CO$_2$-UH. Other embodiments additionally comprise other subsystems such as at least one CO$_2$ utilization subsystem expressed as a specific modality or associated set of modalities of production and output operating via the CO$_2$-UH. Certain embodiments of the invention differ from one another only in the nature and quantity of these CO$_2$ utilization subsystems supplied with CO$_2$ by the CO$_2$-UH.

CO$_2$ utilization subsystems suitable for use in the invention are not particularly limited in scope or quantity. The hundreds of possibilities for CO$_2$ utilization described herein are exemplary rather than exclusive. The twenty different subsystems or main modes of CO$_2$ utilization described below and in Table 2 above exemplify a wide spectrum of embodiments of the invention. Potential CO$_2$ utilization scales are cited where it has seemed reasonable to do so, but such scales are not intended to have a limiting effect on the scope of the invention. Certain preferred embodiments presented under the categories of the twenty main modes of CO$_2$ utilization included in the following sections are not exclusive of one another. They may be performed independently or in any of a large number of combinations. The listing and illustration of twenty main modes is not meant to be delimiting. The general concept of a CO$_2$ Utilization Hub is that it is open to the incorporation of new modality types (as is illustrated in FIG. 7). This aspect of openness is a preferred embodiment of the invention.

The invention disclosed herein solves a major unsolved technological problem of practical CO$_2$ utilization on a large scale in the context of a developing economy remote from railway connections and oceanic ports. Specifically, the major challenge is CO$_2$ utilization: to degas and then productively utilize Lake Kivu's huge (~600 million tonnes) supply of deepwater dissolved CO$_2$. Simultaneously, certain embodiments of the invention solve five additional big problems and challenges: (i) efficient power production utilizing Lake Kivu's deepwater methane with avoidance of wastage of a limited resource; (ii) insuring lake safety (as well as resource loss) against the possibility of mega-catastrophe from CO$_2$ asphyxiation via a runaway "limnic eruption" degassing event; (iii) building-up regional development on a large scale via industrialization; (iv) power load balancing in various contexts including load balancing for the local and national power grid and for intake and industrial utilization of solar power; and (v) creating a globally strategic demonstration of large scale CO$_2$ industrial utilization as a major contribution towards solving problems of rapid and accelerating CO$_2$ accumulation in the atmosphere.

FIG. 1, shows a novel method and system based upon linking specific opportunities of Lake Kivu power production to a large and diverse body of technological insight and innovation on CO$_2$ utilization such as is documented very extensively herein as a teaching. This teaching clarifies the background and nature of the invention, especially in the context of generic conventional beliefs that CO$_2$ is useless in the context of Lake Kivu and, if degassed, would be vented and hence an environmental nuisance.

Figure 6:
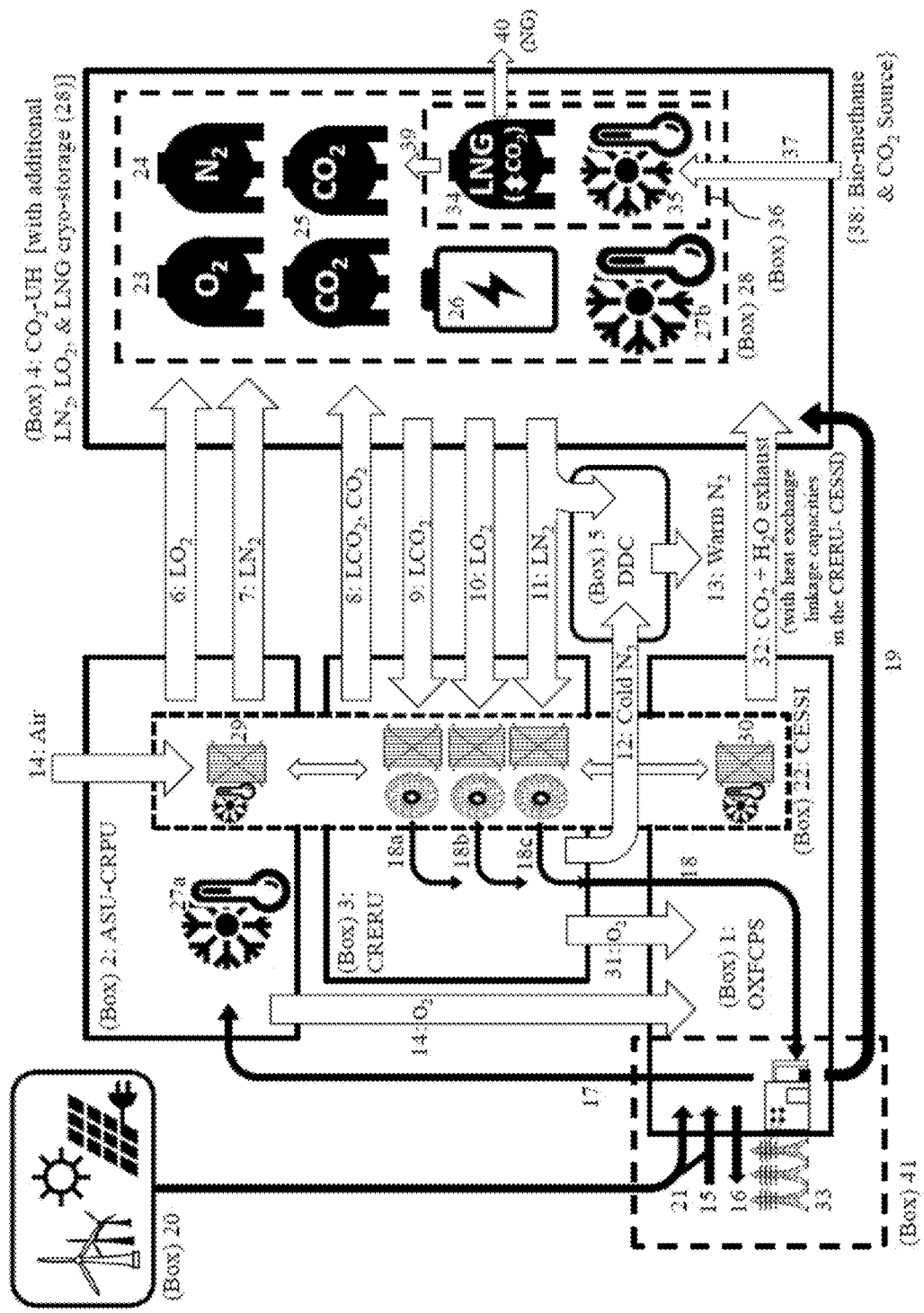
FIG. 6 is a schematic representation of cryogenic aspects of the invention including energy storage.

The inventive embodiment shown in FIG. 1 integrates insight on $CO_2$ utilization into an overall method and system for Lake Kivu deepwater gas extraction and use via a core combination of three submethods and subsystems. These are shown within boxes 1, 2 and 3 as represented in the figure: (i) degassing in a total degassing system (TDS: 1) that includes extracting (6) gas-rich deepwater (9c) from Lake Kivu (9a,b,c); (ii) power production and $CO_2$-dominated exhaust creation by means of an oxyfuel combustion power system (OXFPCS: 2) which intakes (and includes production of) pure oxygen for oxy-combustion (10); and (iii) receiving, processing and utilizing $CO_2$ in a $CO_2$ utilization hub ($CO_2$-UH: 3), with the overall activity generating electrical power as well as various types of product streams from various modalities of $CO_2$ utilization (8). Flow vectors, (11, 12) are shown connecting these boxes with flow compositions as identified. In addition to the three core submethods and subsystems (1, 2, 3), two additional boxes are shown in dashed outline (4, 5). These represent non-core aspects of the process flow of the invention. Box 4 includes a set of five modalities of $CO_2$ utilization, but these are shown in detail only in FIG. 9 (FIG. 9: 15a,b,c,d,e). These are abbreviated as a single flow-designating arrow (15) in FIG. 1. Box 5 represents cryo-energy storage capacities linking the OXFCPS (2) to the $CO_2$-UH (3) where cryogenically liquefied gases are stored. Embodiments with this capacity are included and preferred. They allow the powerplant to provide electric power load-balancing services for its own output as well as for solar power inputs into the operations of the $CO_2$-UH. Further expansion of cryo-energy storage capacities, included as a preferred embodiment, also may allow load-balancing services to be provided to the grid. This is done via the powerplant's (included) Air Separation Unit (ASU), which is shown in FIG. 1 only as item 10 providing oxygen gas for oxyfueled combustion. Thus, in the full modality of incorporation of the capacity indicated by box 5 within the invention, the ASU operates in an expanded modality embodiment as a Cryo-Production Unit (ASU-CRPU. FIG. 6 and associated text provide further detail). Note, however, that the ASU providing oxygen into oxyfueled combustion is not limited to a cryogenic method. Non-cryogenic modalities of provision of oxygen herein are included as embodiments such as, for example, ion transport membranes (ITMs) and other oxygen-selective membrane separation methods.

The modalities of $CO_2$ utilization shown in FIG. 1, box 4 are aspects of the extended function (8) of the $CO_2$-UH (box 3). They are shown as a separate box because they all recycle $CO_2$ from one part of Lake Kivu (9c) to a variety of uses within, and floating on, the lake's biozone (9a). These uses provide a means to utilize $CO_2$ in a substantial fraction of the total flow FIG. 1 represents the core aspect of the invention as a combinative integration of three submethods and subsystems represented by the three boxes labeled 1, 2 and 3, with their interconnections 11 and 12. A variant of this core is represented wherein a modification of the standard degassing method (SDS: Staged Degassing System: see FIG. 8) is shown identified by the acronym MSDS (10, 14). This variant represents a modification of the Belgian method (of methane purification by staged separation/removal of $CO_2$ using gas-water partitionings differentiating between methane and $CO_2$) that has been designed and deployed on Lake Kivu ever since it was created in the 1950s. The MSDS method is illustrated in FIG. 8 and described in associated text.

In FIG. 1, the MSDS is indicated by item 13 (representing a $CO_2$ degasser within a MSDS) connecting (14) into the $CO_2$-Utilization Hub (3). Item 13 transfers $CO_2$ flux into a $CO_2$-UH from a MSDS-type degassing system and method that degasses deepwater $CH_4$ and $CO_2$ separately. (For details see FIG. 8.)

The invention does not subsist in its constituent submethods and subsystems. FIG. 1 describes the invention in its aspect of being an integrative combination of submethods and subsystems. Shown for the TDS variation is an integration of three submethods and subsystems. These are labeled 1, 2 and 3 described by the acronyms, TDS (for: Total Degassing System), OXFCPS (for: Oxy-Fuel Combustion Power System) and $CO_2$-UH ($CO_2$ Utilization Hub), respectively. Vertical plane perspective is employed only for Lake Kivu (9) with gas-rich water extraction (6) from deep in the lake (9c), and degassed water flow return (7) connecting via the TDS (1) located partly above the surface of the lake.

Embodiments of the TDS and the OXFCPS suitable for use in the present invention are disclosed by the inventor in U.S. Patent Application No. 62/007,912, filed Jun. 4, 2014. The present invention is not limited to such embodiments, however.

The OXFCPS is a submethod and/or subsystem which combusts methane present within the degassed gas transferred from the TDS. It transforms released energy into mechanical power extracted via a heat engine. Typically, but not always, this power is transformed into electricity. The central aspect of oxyfuel combustion is that the method and system inputs nominally pure oxygen into combustion rather than air (with its associated large component of nitrogen gas accompanying oxygen gas). The OXFCPS here defined incorporates sourcing of separated oxygen in some form of Air Separation Unit (ASU), but is open with respect to the specific technologies employed for oxygen separation. Methods and systems used may be traditional cryogenic air separation or newer ion transport membrane (ITM) processes, or any effective method. All are herein included in embodiments: any separation process or processes such as may provide nominally pure oxygen into oxyfuel combustion. It is not necessary for atmospheric air to be input. Other input gas sources are possible.

The OXFCPS defined herein may or may not include one or more supercritical $CO_2$ power cycles. The OXFCPS facilitates efficient use of a total gas input from the TDS, containing methane efficiently extracted, modified only as needed for $H_2S$ removal and/or removal of water vapor, and efficiently combusted under oxyfuel conditions forming an exhaust stream of easily separable $CO_2+H_2O$. A strong efficiency advantage may optionally be supplied by intake compression of the "total gas" inflow into a supercritical $CO_2$ power cycle.

The $CO_2$-UH is a submethod and/or subsystem of the invention described and defined in its basic attributes as follows. Detailed physical specifications for components may be many and varied such as correspond to matters of design at a level of detail unrelated to the inventive art disclosed herein. Such matters are known to those skilled in the art. The $CO_2$-UH: (i) receives exhaust either from the OXFCPS comprised of a nominally two-component mixture of $CO_2$ and steam, or in the variant MSDS-based method and system as $CO_2$ and water vapor; (iii) processes this gas flow initially, if and as needed, for example in some embodiments via heat exchange energy capture, and in some other embodiments by gas dehydration, or with combination of both; (iv) partitions and directs the resulting gas flow into one or more process trains; (v) prepares and produces such flows through one or more of these process trains for utilization in one or more ways, for example as a mode of raw gas (in some process trains), or in various grades and forms of $CO_2$ (in other process trains), and/or uses the resulting gas flows from one or more of these process trains to produce products requiring $CO_2$ inputs (in other process trains) and/or requiring the use of $CO_2$ in their production (in other process trains). In certain preferred embodiments, one or more process trains may share cryogenic functions with the ASU component of the OXFCPS. In certain preferred embodiments, process trains purposed for $CO_2$ refrigeration are co-utilized for cryogenic gas processing, storage and dispersing of liquid nitrogen and liquid oxygen and/or liquefied natural gas (LNG). In summary, the $CO_2$-UH in its operation transforms the flow of $CO_2$-containing exhaust from the OXFCPS into flows of various $CO_2$ products, and/or $CO_2$-containing products, and/or products manufactured with the use of $CO_2$. In some preferred embodiments, these features are supplemented by add-on capabilities for receiving, storing and dispensing pressurized and/or liquefied nitrogen and pressurized and/or liquefied oxygen and pressurized and/or liquefied natural gas. Sometimes these supplemented capacities support the storage and recovery of cryo-energy such as can be useful for varying power output to the grid and/or for grid balancing, sometimes involving cryogenically storing inputs of time-varying power inputs from the grid such as renewable power sources (see FIG. 6). Production of purified NG and LNG also opens up possibilities, herein included as preferred embodiments, for conventional energy storage as well as providing the capacity for sales of LNG, Compressed Natural Gas (CNG), and Absorbed Natural Gas (ANG) if/as desired. Production of LNG also offers a mode of dry ice production as a byproduct of $CO_2$ separation from biogas (Fazlollahi and Baxter, 2017). Such dry ice also can be used for cryo-energy storage via the methods developed by Larry Baxter and colleagues (explanations and publications posted on https://sesinnovation.com)

FIG. 2 provides further detail to illuminate the representation made in FIG. 1 but does not include illustration of the MSDS-based variant shown in FIGS. 1 and 8. FIG. 2 shows in schematic representation the invention as an industrial process arising out of Lake Kivu's layered structure represented by arrows, circles and boxes. Deepwater resources of dissolved gases are extracted (22), and then utilized (26, 21, 1, 2, 3, 4, 5, 6, 7, 8, 9, 10, 11, 12, 13, 14, 15, 16, 17, 18, 19, 20). These deepwater resources are present principally, (but not exclusively), in Lake Kivu's so-called Main Resource Zone (23c). FIG. 2, box 2 encloses schematically the method and system of a $CO_2$-UH (21) organizing the transformation of inputs (28; 32; 39), especially $CO_2$ plus water vapor (28), into outputs (item 33), comprising twenty or more main modes (represented in FIG. 2 by vectors 1 through 20). The industrial process creates products that include electric power (29) produced by an oxyfuel combustion power production method and/or system (26; 27; 28; 29) including an air separation unit (27). In the TDS-based variant of the invention, the power production method and system is the OXFCPS. It is shown as a circle (26) linking together a nexus of inflows (25; 27) of fuel gases (25; 27) and outflows of power (29) and post-combustion exhaust (28). The main carbon source input into the $CO_2$-UH is the post-combustion exhaust (28) expelled by the OXFCPS. The $CO_2$-UH receives, stores, dispenses and utilizes this exhaust, which is comprised mostly of carbon dioxide and water, either in the form of vapor or condensed liquid water. It uses electric power, either internally produced by the powerplant (as represented by output vector 29), or from any other source. Inputs of any type needed for production are represented by vector 32. These inputs enter into the $CO_2$-UH. The industrial process (and method and/or system) also produces a suite of carbon-containing (and hence carbon-capturing) industrial products [1 through 20 as outputs (33) of $CO_2$-UH (21)]. Outputs are created by means of submethods and/or subsystems organized within an integrated $CO_2$-UH submethod and/or subsystem (21) shown with outputs (1 to 20) within box 2. The $CO_2$-UH is defined herein to include within its domain any modality and combination of modalities of $CO_2$ utilization and associated product outflow based upon $CO_2$ inflows obtained from Lake Kivu in the course of deepwater methane-based power production, including both deepwater $CO_2$ and $CO_2$ formed from combustion of deepwater methane (or, in the case of the MSDS method and/or system, deepwater $CO_2$ only).

FIG. 2 shows Lake Kivu on the bottom left in vertical slice perspective in three layers (23 a, b, c). These are: the bottom "Main Resource Zone" (23c: MRZ: ~250 to ~485 meters depth), the near-surface "BioZone" (23a: BZ, 0 to ~80 meters depth) and a middle zone (23b: ~250 to ~80 meters depth). The middle zone as shown is a combination of two zones: the "Potential Resource Zone" (PRZ) and the "Intermediate Zone" (IZ), represented in scientific and engineering reports describing the gas resources and limnological structure of the lake (Descy et al., 2012; Wuest et al., 2012a,b). The industrial process begins with the extraction of deepwater in a system of flow organized by one or more riser pipe submethods and subsystems (22). See, e.g., US 2015/0354451 A1. These submethods and/or subsystems transport deepwater rich in dissolved methane and $CO_2$ into a degassing submethod and/or subsystem (24). This should be considered to include the riser or risers (22) themselves. The degassing submethod and/or subsystem (22, 24) separates the inflow of gas-rich water (22) into outflows of separated degassed water (34) and separated gases (25). Separated degassed water is transferred by a submethod and/or subsystem of return flow pipes, pumps and containing reservoirs (34, 35) that variously control the reinjection of return flow waters into Lake Kivu via various options (36a, 36b, 36c). These reinjection options are not exclusive of one another. Preferred embodiments thereof are described, as noted herein, in other disclosures focused on Lake Kivu made by the inventor. The variant MSDS-based form of the invention is shown in FIG. 1.

As shown in FIG. 2, separated gas from the TDS (22, 24, 25, as shown in box 1) comprised mostly of $CO_2$ plus methane plus water vapor is transported and processed, if and as needed, for input into an oxyfuel combustion system (26, 27) into which oxygen is added via an air separation unit (27) which is a component of the powerplant (26, 27). Combustion of methane with pure oxygen transforms the input gases (25, 27, 31) into mechanical power used to generate electric power (29) and an output exhaust stream (28) comprised of mostly $CO_2$ plus condensable water vapor. FIG. 2 shows a post-combustion exhaust stream (28). It provides oxyfuel powerplant combustion exhaust of carbon dioxide and steam as input into a $CO_2$ utilization hub ($CO_2$-UH, item: 21). In the variant MSDS-based form of the invention, the connection between the degassing system and the $CO_2$-UH is simpler, as represented by item 14 in FIG. 1.

$CO_2$ is provided in post-combustion exhaust expelled by the OXFPCS (which may or may not be a combined cycle). It also is provided by degassed $CO_2$ from a MSDS. These sources of $CO_2$ initially enter a processing, storage and purveying/distribution unit (30), shown in FIG. 3. This unit

(30) processes, handles and stores input exhaust (28) and disperses the flow into different streams. (It is the subject of FIG. 3, which in part displays its components, methods, systems and activities.) These streams are comprised of $CO_2$ products in different forms symbolized by eight specific arrows corresponding to modalities of use (1, 2, 3, 4, 5, 6, 7, 8). A flux vector labeled as item 37 represents the use of any of these $CO_2$ product streams internally within the $CO_2$ utilization hub for additional modes of product manufacture utilizing $CO_2$ (8 through 20). (Note that arrow number 8 is intermediate. It is both a mode of $CO_2$ product and a mode of creating products utilizing $CO_2$.) Overall, in the sum of any to all of its preferred embodiments, the $CO_2$-UH can produce an overall output of products shown as vector 33. This output is comprised of one or more of a suite of carbon-containing and purified and non-purified $CO_2$ products, plus products produced using $CO_2$ in some way but not incorporating its carbon. One non-purified $CO_2$ product is a stream of "raw" (unprocessed or relatively unprocessed) $CO_2$ and steam or condensed water (vectors 1, 2, 3 and 4). It may be disseminated and diffused into the biozone (23a: BZ) of Lake Kivu in order to provide a carbon source for photoautotrophic bioproductivity, as shown for vectors 2a and 2b. Or this form of $CO_2$ may be provided to local greenhouses, as shown by vector 1.

As shown in FIG. 2 by flux vector 31, oxygen gas output may be obtained as a byproduct of chemical production and/or bio- or artificial-photosynthetic processes and/or water electrolysis in the $CO_2$-UH (21). Such oxygen may be used for increased power production efficiency by supplying a component of oxygen otherwise provided by the Air Separation Unit (27, utilizing atmospheric air input shown as vector 41).

As shown in FIG. 2, the ASU (27) also produces liquefied nitrogen gas, ($LN_2$) separated from oxygen gas (39, 40). Some of this $LN_2$ is used internally within the ASU for cryogenic energy recovery by means of cooling incoming air via a heat exchange process. In certain preferred embodiments, excess $LN_2$ from the ASU is provided (42) into the gas processing, storage and handling unit (30) of the $CO_2$-UH, as shown by vector 39. Or it may be provided otherwise for other purposes, as shown by vector 40.

Figure 3:
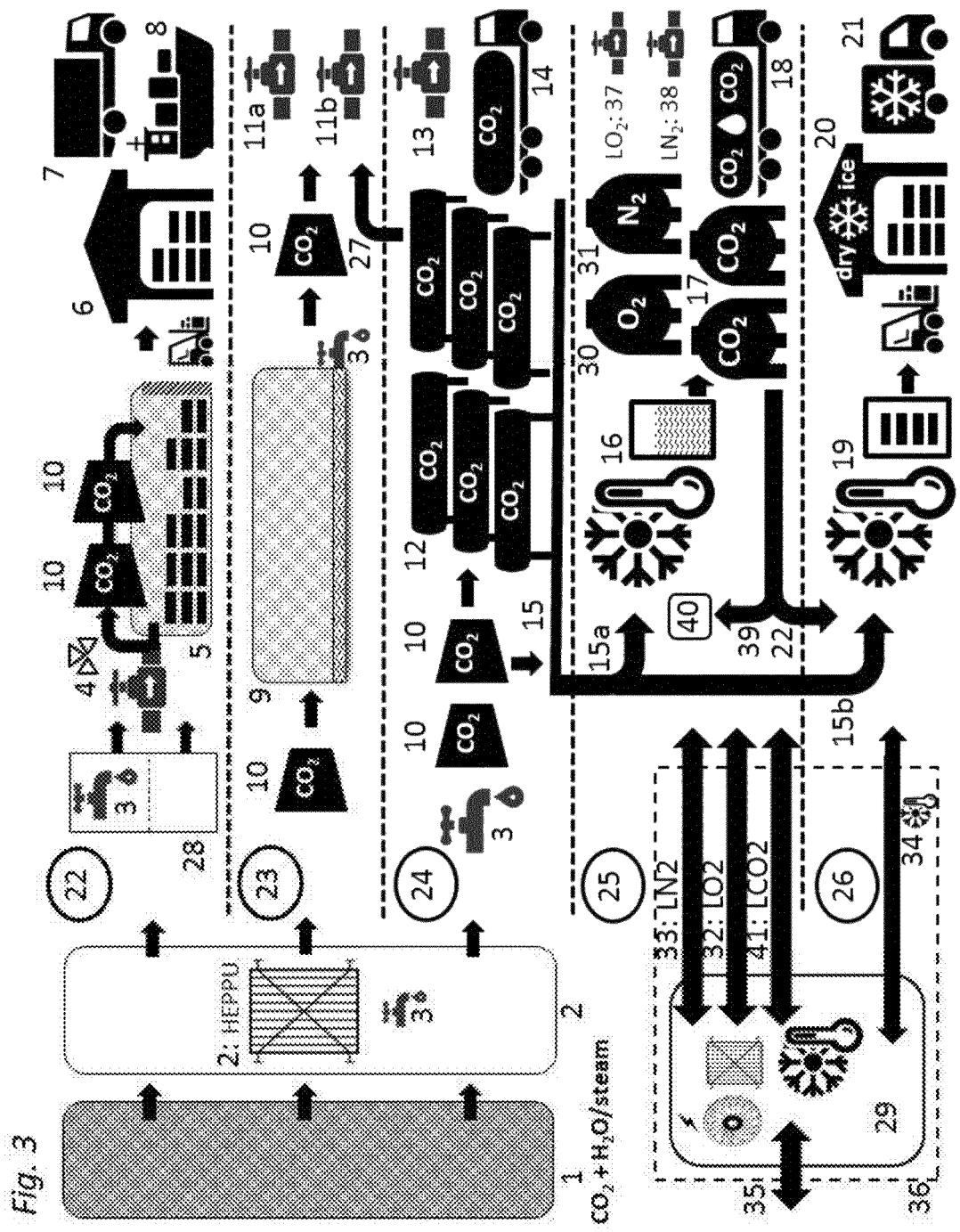
FIG. 3 is a schematic representation of an embodiment of the receiving (1, 2), processing, storage, and purveying aspects of the $CO_2$ Utilization Hub ($CO_2$-UH), with additional inclusion of the storage and utilization of liquefied nitrogen and oxygen in certain preferred embodiments. Most production flows ("process trains") proceed from left to right. Five types of production flows are illustrated as horizontal sequences, left-to-right, stacked vertically (22, 23, 24, 25, 26). An additional dashed box (36) represents optional cryo-energy storage capacities utilizing liquefied gases.

FIG. 2, Box 3, illustrates adjunct utilization of excess liquid nitrogen and/or oxygen (via flow vectors 39 and/or 40 and/or 42) to cool one or more large refrigeration utilization facilities (43), such as, for example, a digital data center. Flow vectors 39 and 42 flow into the liquefied gas storage units within the gas-processing (30) sector of the $CO_2$-UH (21), (see process train 25, units 30 and 31 in FIG. 3). In FIG. 2, box 3, the vectors labeled 39 and 42 indicate either direct flow from the ASU (27) or flow from $LN_2$ and $LO_2$ storage facilities as shown in FIG. 3. (In FIG. 3, $LO_2$ and $LN_2$ storage units 30 and 31 connect via insulated pipe transfer systems labeled 37 and 38, respectively.) Post-cooling flows of gasified $N_2$ (44) are available for various uses such as, for example, can be engaged to pH control and related algae culturing operations as illustrated partially in FIG. 8, Box 3, return flow water treatment (flow direction 16). Post-cooling flows of gasified $LO_2$ (45) are provided into oxyfuel combustion (item 27). Aspects of such gas plumbing associated with utilization of cryo-energy for cooling as well as for cryo-storage of energy are represented in FIG. 6 and explained in accompanying text describing the utilization of $LO_2$ and/or $LN_2$ and/or refrigerated liquefied $O_2$ ($LCO_2$ or $LCO_2$) for this purpose. For reasons of already considerable complexity, FIG. 2 avoids representing these aspects of the invention. They are reserved for FIG. 6 and its explanations.

In certain preferred embodiments, $LN_2$ is utilized for cryoenergy storage for load balancing purposes, facilitating the operation of the OXFCPS (shown in FIGS. 1 and 2). This stored energy is released by heat exchange with atmospheric air and/or powerplant exhaust, whereby the phase-changed expanding gas drives a power-producing turbine heat engine. See FIG. 6.

In certain preferred embodiments, storage of liquefied oxygen ($LO_2$) similarly provides stored cryo-energy. Similarly, this cryo-energy is released by heat exchange with the atmosphere, and/or powerplant exhaust, whereby the phase-changed expanding gas drives a power-producing turbine heat engine wherewith and whereby the warmed-up $O_2$ emerging is fed into oxy-combustion in the OXFCPS. See FIG. 6.

In certain preferred embodiments, refrigerated liquid $CO_2$ is utilized for cryoenergy storage for load balancing purposes, thereby facilitating the operation of the OXFCPS powerplant (shown in FIGS. 1 and 2). Stored cryo-energy present in the $CO_2$-UH as stored refrigerated liquid $CO_2$ is releasable by conversion into electricity by heat exchange with atmospheric air and/or by heat exchange with the exhaust of the powerplant. The phase-changing expanding gas drives a power-producing turbine. In this way, refrigeration-liquefaction of $CO_2$ is used as a $CO_2$ storage mechanism for energy storage. (Of course refrigerated-liquefied $CO_2$ also is sold into the market as a product of the $CO_2$-UH.) The refrigeration-liquefaction process requires input of power from the powerplant, typically at night when power demand from the grid is low. In a day-night cycle, a substantial fraction of this cryogenically stored energy is recovered, typically during the day, when power demand from the grid is high. Phase-changing expanding $CO_2$ gas is warmed by heat exchange. For best system efficiency, this heat exchange is via cooling the intake of air fed into the ASU and/or by utilizing exhaust heat from the powerplant as a higher temperature heat source. After the phase-changing expansion of $CO_2$ drives a power-producing turbine engine, the warmed-up gas then is fed into various modes of utilization via the $CO_2$-UH. Further representation and discussion of this capacity for $CO_2$ utilization is provided in FIG. 6 and its accompanying discussion.

In certain preferred embodiments, the $CO_2$-UH, and/or the ASU cryosystem, and/or both working in concert, receives inputs of solar power transmitted by one or more long-distance transmission wires, transmitted to support various modes of production utilizing $CO_2$ inputs, or transmitted in the context of a need for load balancing. Cryogenic energy storage using practically liquefiable gases, $N_2$, and/or $O_2$, and/or $CO_2$ allows balancing of the irregularity of flows of solar power into the grid such that a continuous regularized flow of power input may be sustained into $CO_2$-utilizing modes of production. Additionally, the cryogenic energy manipulation and storage capabilities of the overall method and system of the invention provides capacities suitable to serve load-balancing needs that are generic for solar power provision into the grid. Turn-around power storage efficiencies by such methods are expected to be >60% (power out/power in), and possibly as high as 95%, as described in references cited herein (cf, Park et al., 2017). Certain preferred embodiments include this capability to receive solar power and provide energy storage for load balancing to regularize the input of solar power to the grid.

In certain preferred embodiments, the $CO_2$-UH, and/or the ASU cryosystem, and/or both working in concert, provide(s) cryogenic energy storage load-balancing services for the management of one or more electrical power grids connecting into the invention as implemented (in the same manner as described for the input of solar power in the section immediately above).

FIG. 2, box 1 is a schematic representation showing the delimitation of the invention in relation to Lake Kivu and in respect to various elements diagrammed within the figure and the names of the submethods and subsystems indicated by their acronyms. (An equivalent diagram is not shown for the simpler case of the MSDS-based variation of the invention. FIG. 1, box 13 and $CO_2$ flow line 14 are sufficient for this purpose in combination with detail provided in FIG. 8.) The invention has specific applicability to problems and challenges of Lake Kivu (represented by the circle labeled number 38 which also represents the combinative domain of the invention), specifically to safe, efficient, optimally productive deepwater resources utilization. The invention solves problems and challenges of Lake Kivu such as efficient power production, securing long-term lake safety, environmental responsibility, and economic innovativeness and productivity by utilizing $CO_2$. It does so by combining submethods and/or subsystems within three subdomains operating in inter-coordination. These are shown as circles within the larger circle marked "Lake Kivu" (38) in Box 1: (i) deepwater extraction (22), degassing (22, 24), and gas transfer and processing for dehydration and/or $H_2S$ removal (25), if and as needed, preparatory to oxyfuel combustion; (ii) oxyfuel combustion (26, 27) with inputs of separated deepwater gases (25) and oxygen (27, 31), and outputs of electric power (29) and exhaust comprising nearly pure $CO_2$ with condensable $H_2O$ (28); and (iii) a $CO_2$-UH submethod and/or subsystem (21) which produces, in the limited set of examples provided for purposes of description, a suite of twenty main modes of carbon-containing product production (1 through 20, and in sum: 33) including $CO_2$ for biozone input (vectors 2a, 2b and 3), utilizing the input of exhaust (28) expelled from the oxyfuel power plant (26, 27). Note that 20 modes are provided only for reasons of limiting the discussion to a reasonable package of examples, whereas the invention is generically open to any modes of $CO_2$ utilization such as might support realistic business activities or at least developmental research and development in order to create business activities via developmental investment.

FIG. 2, box 2 shows aspects of the operation of the $CO_2$ utilization hub (21: $CO_2$-UH). The $CO_2$-UH (21) transforms the exhaust (28) from the OXFCPS (26, 27) plus additional inputs (32), into horticultural, aquacultural, and industrial output main modes (1, 2, 3, 4, 5, 6, 7, 8, 9, 10, 11, 12, 13, 14, 15, 16, 17, 18, 19, 20, 33). Table 2 lists them and provides additional information.

FIG. 3 provides detail on five types of gas processing trains present within the $CO_2$-UH (as shown in FIG. 2 as item 30 without any detail). Note that the process shown in process train 22 is different from processing trains that produce $CO_2$ products. Train 22, however, demonstrates production utilizing relatively "raw" $CO_2$ with respect to the exhaust output of the OXFCPS. These trains and their various combinations are all preferred embodiments. In FIG. 3, the five processing trains are labeled 22, 23, 24, 25 and 26. Horizontal dashed lines separate these five processing trains. FIG. 3 exhibits four cases of the production of $CO_2$ products (rows marked by circles numbered 23, 24, 25, 26), and one case of manufacturing a product incorporating $CO_2$ (22). The five different submethods and subsystems of receiving, processing, storing and purveying $CO_2$ (rows 23, 24, 25, 26), and $CO_2$-incorporating products (row 22) are referred to herein as "process trains." A dashed box (dashed box 36) encloses a representation of subsystems and submethods present in certain preferred embodiments. These connect and integrate cryogenic capacities of the OXFCPS involving liquefied nitrogen (31) and oxygen (30), with cryogenic capacities of process trains 25 and 26.

FIG. 3 shows the initial reception of raw exhaust (1) from the OXFCPS or MSDS (as shown in FIGS. 1 and 2). Initial processing of OXFCPS raw exhaust gas, in certain preferred embodiments, includes capture of heat energy by a heat exchanger connected to a power production unit. Such a submethod and/or subsystem, a Heat Exchanger Power Production Unit (2: HEPPU) is represented by (and/or identical to) a fence-like symbol within box 2. A drain, shown as an icon labeled 3 (present in four locations within the figure), drains condensed water from the HEPPU (2). In some embodiments, this heat exchanger power unit is a part of the OXFCPS. In other embodiments, the HEPPU (2) is included within the $CO_2$-UH. FIG. 3 shows it as the latter. The distinction is simply a definitional choice. FIG. 3 shows five different modalities of $CO_2$ handling, processing and disposition for use (22, 23, 24, 25, 26). In one case (22), $CO_2$ is directly utilized. This utilization is in a sense referring to the transformation of $CO_2$ into a product that is not itself $CO_2$, or otherwise more broadly refers to any industrial process that utilizes $CO_2$ but that is not overlapping with $CO_2$ processing into other forms of $CO_2$. In the others cases (23, 24, 25, 26), $CO_2$ in various forms is modified and made available for delivery as a $CO_2$ product. Thus four of the five modalities are for $CO_2$ products as shown for process trains 23, 24, 25, and 26.

In FIG. 3, the process train modality, labeled 23, is production of relatively unprocessed gas into short-term process storage (9). This storage (9) is shown as a pressurizable chamber allowing condensation and removal of water (icon: 3) prior to pumping (10) of stored $CO_2$ for use. The next flow stage in this process train is low-pressure pipeline delivery (11a, b). The double representation (11a and 11b) indicates a multiplicity of uses, but does not indicate either a necessity of multiple uses or an absence of multiplicity for outputs of the other process trains shown. $CO_2$ in this relatively low-pressure form delivered by pipelines is for local and/or semi-local horticultural and/or aquacultural and/or return-flow-modifying uses, as shown in FIG. 2.

In FIG. 3, the process train modality labeled 24 is production of dehydrated pressurized gas. Dehydration steps (icon 3: shown in four locations) may in some embodiments precede compression (10), as shown. (High pressure is indicated by two compressor symbols.) $CO_2$ processed in this modality typically is stored in one or more tanks, or in a farm or farms of such tanks (12) prior to export by one or more high-pressure pipelines (13) or by pressurized tank truck (14). Distribution of high pressure $CO_2$ internally within the $CO_2$-UH is shown by item 15 showing two uses: 15a and 15b. Flow vector 15a represent transfer from pressure storage of $CO_2$ into refrigeration processing into refrigerated liquefied $CO_2$, whereas the extension (15b) represents a transfer directly into refrigeration for dry ice production, if desired. Flow vector 27 indicates that compressed $CO_2$ may be supplied into outputs of process train 23.

In FIG. 3, the process train labeled 25 is refrigerated liquefied $CO_2$ production, storage and disposition (18, 22, 39). Storage is in one or more thermally insulated liquid $CO_2$ tanks (17), or in a farm or farms of such tanks (17), prior to export by refrigerated tank trucks (18), or transfer by insulated pipeline (22) into dry ice production (process train 26), storage (20) and delivery (21).

In FIG. 3, flow vector 39 represents transfer of stored refrigerated liquid $CO_2$ by insulated pipeline for recovery of cryo-energy. One of the functions of the $CO_2$-UH facility is storage of refrigerated liquid $CO_2$ (17: "$LCO_2$") by means of refrigeration energy input. This energy can be recovered such that storage of $LCO_2$ acts as a battery. For recovery of energy stored in this way, the cold liquid is transferred through an insulated pipeline (39) to a heat exchanger and turbine energy extraction system (represented by item 40). Heat exchange with the atmosphere (preferably via the air intake of the ASU), or with powerplant exhaust, causes a phase-changing expansion of $CO_2$. This flow of expanding gas drives a turbine generating electrical power for export into the grid, typically for load balancing purposes. (An overview of this cryo-system for energy storage is provided in FIG. 6.) In some embodiments, this capacity for cryogenic energy storage in the $CO_2$-UH facility includes additional storage of liquefied $N_2$ (31, "LN2") or liquefied $O_2$ (30, "LO2"), or both, as shown. These additional capacities for $LN_2$, $LO_2$ and $LCO_2$ handling for cryo-energy storage are described in subsequent sections. They have the capacity to provide load-balancing services for three uses. These uses are: (i) for energy storage internally to allow variable power output into the grid for the powerplant (OXFCPS); (ii) to provide energy storage capacity for the grid, if desired; and (iii) to provide energy storage capacity to handle irregular renewable power inputs for $CO_2$-UH production modes (such as "solar fuels" and/or "wind fuels" and/or "hydro fuels" production using $CO_2$ as a carbon source), if desired.

The process train modality labeled 26 in FIG. 3 is dry ice production by refrigeration (19) of $CO_2$ supplied by other process trains (15*b*, 22). Dry ice is stored in an insulated storage warehouse (20) prior to delivery by truck (21), typically with thermal insulation storage and/or packaging. In some embodiments, dry ice is used for cryogenic energy storage. (Note that specific system linkages are not illustrated for this use).

In FIG. 3, the process train labeled 22 shows $CO_2$ utilized for transformation of $CO_2$ into $CO_2$-containing products and/or more broadly for production utilizing $CO_2$ in conditions that may require time-varying steps of $CO_2$ input in different conditions of temperature, pressure and steam and/or water vapor content according to production recipes. This may occur within the $CO_2$-UH defined within a local or semi-local geographical domain. Process train 22 provides an example of a type of $CO_2$ utilization via a pressure chamber for carbonation. Gas proceeds by a choice (28, typically determined and directed by means of a valve) for processing with or without, a dehydration step (3). The gas flow proceeds though a valve disposition subsystem (4). This valve disposes flow to proceed without or with degrees of compression (10) into a processing chamber unit (5). The unit shown (5) is meant to be representative of many different modalities of $CO_2$ utilization involving many different types of industrial $CO_2$ use. Simply for example, in FIG. 3 unit (5) is shown by icons representing a carbonation-reaction chamber appropriate for the carbonation of cementitious building materials. After a suitable period of carbonation, materials created in a processing unit (5) are stored and/or possibly cured under gas composition, temperature and humidity controls in a warehouse (6), before being purveyed by means of any appropriate mode of transportation, as represented in the figure symbolically by truck (7) and ship (8) icons. Again, many other modalities of industrial processing for utilizing $CO_2$ could be represented for this modality of $CO_2$ utilization involving a process recipe of scheduled inputs with variability of composition and state. The carbonation pressure chamber mode, as shown (5), is one example only. It includes the main processing steps of gas preparation by purification and/or compression followed by one or more processes of product manufacture utilizing $CO_2$, a large number of which are referenced herein.

In FIG. 3, box 36 represents an integrative linkage of cryogenic capacities between the OXFCPS (not shown) and the two cryogenic process trains labeled 25 and 26. This linkage exists in certain preferred embodiments. A double-sided arrow (35) represents a capacity for flow in both directions between the ASU-OXFCPS complex (as shown in FIG. 2) and process train 25 for liquefied nitrogen and/or oxygen and/or carbon dioxide. This linkage adds handling, storage and disposition of liquid oxygen (30, 32) and liquid nitrogen (31, 33) to process train 25, which otherwise is a process train with cryogenic capacities specialized only in the freezing, handling, storage and dispersal of liquefied $CO_2$ (17, 18). As shown by icons within box 29, the linkage also included the capacity to generate electric power by releasing cryo-energy by venting $LN_2$ to the atmosphere or to various uses via a heat engine (33) and similarly via a heat engine by gasifying $LO_2$ into the OXFCPS (32 via 35). An icon representing refrigeration within box 29 represents the capacity of the linkage (represented by box 36) to provide refrigeration into process trains 25 and 26, drawing from the cryogenic capabilities of the ASU (if the ASU is of the cryogenic modality). In certain preferred embodiments, the linkage (36, 29, 32) also gasifies stored liquefied oxygen (30) via a heat engine power generator (represented by icons within 29) connecting to the $O_2$ intake supply for oxyfuel combustion (via 35). The linkage labeled as number 34 offers the possibility to contribute cryogenic cooling into the cryogenic capacity of the process train dedicated to produce dry ice (26). Overall, in certain preferred embodiments, this integration (symbolized by box 29 and box 36) connects (35) the $CO_2$-UH to the Air Separation Unit (ASU) within the OXFCPS. The linkage makes cryogenic cooling available to be used in the cryogenic process trains 25 and 26, specifically to the cooling units labeled 16 and 19. Further detail is provided in FIG. 6.

The linkage represented within box 36 plus items 39 and 40 establish a cryo-energy storage capability for the invention overall, connecting with the ASU-OXFCPS complex. A capacity to store cryogenic energy is a method of storage for electric power. Cryogenic energy storage allows the capacity to vary the level of electricity export into the receiving grid while from the oxyfuel powerplant operates at a constant optimal rate of internal power production. It can also provide additional energy storage grid services as noted above. For natural gas oxyfuel turbines, a connected oxygen-supplying (14) ASU typically draws ~10% of the powerplant's internal power production when operated continuously at a constant level of production of oxygen. The use of cryogenic energy storage is valuable to powerplant operations. It allows diurnal modulation of power export output to be by up to a scale of a roughly 20% spread between high and low output to the grid with constant continuous internal power production by the central turbine(s) system burning degassed Lake Kivu methane. That is to say, a 20% spread would be the difference in power export to the grid for a daily cycle with 12 hours of ASU oxygen production on, followed by 12 hours with ASU oxygen production off. The operation of such a modality of energy storage is dependent upon the operational capacity of the ASU. Operating by cryogenic energy storage in this 12-hours-on, 12-hours-off mode requires capacity to operate the ASU at a level of production ~2× the rating for round-the-clock continuous oxygen production. As noted above, additional cryo-energy storage may be obtained by operating separate power-generating heat engine turbines utilizing cryo-energy stored in insulated reservoirs of liquefied nitrogen and oxygen (as shown in FIG. 3, items 30 and 31). $LCO_2$ also may be used in cryogenic energy storage (17, 39, 40). The method and system of these cryo-energy-tapping heat engine turbines and their heat exchangers are represented by two icons placed in the upper sector of Box 29 shown in FIG. 3. (The system of item 40 recovering cryo-energy stored in $LCO_2$ is not shown extensively in FIG. 3. It is shown in FIG. 6.) This box represents a part of the interconnections between the ASU (as shown in FIG. 2: item 27) and the component of the $CO_2$-UH identified by item 30 in FIG. 2. (In FIG. 2, these connections are labeled 33 for $LN_2$, 32 for $LO_2$ and 41 and 40 for $LCO_2$). Generalized sales/delivery of $LO_2$ and $LN_2$ is shown by pipeline icons (37 and 38). Flow vector 34 shows interconnection of cryogenic systems storing $LCO_2$ with dry ice storage and manufacture (the process train labeled 26).

Figure 4:
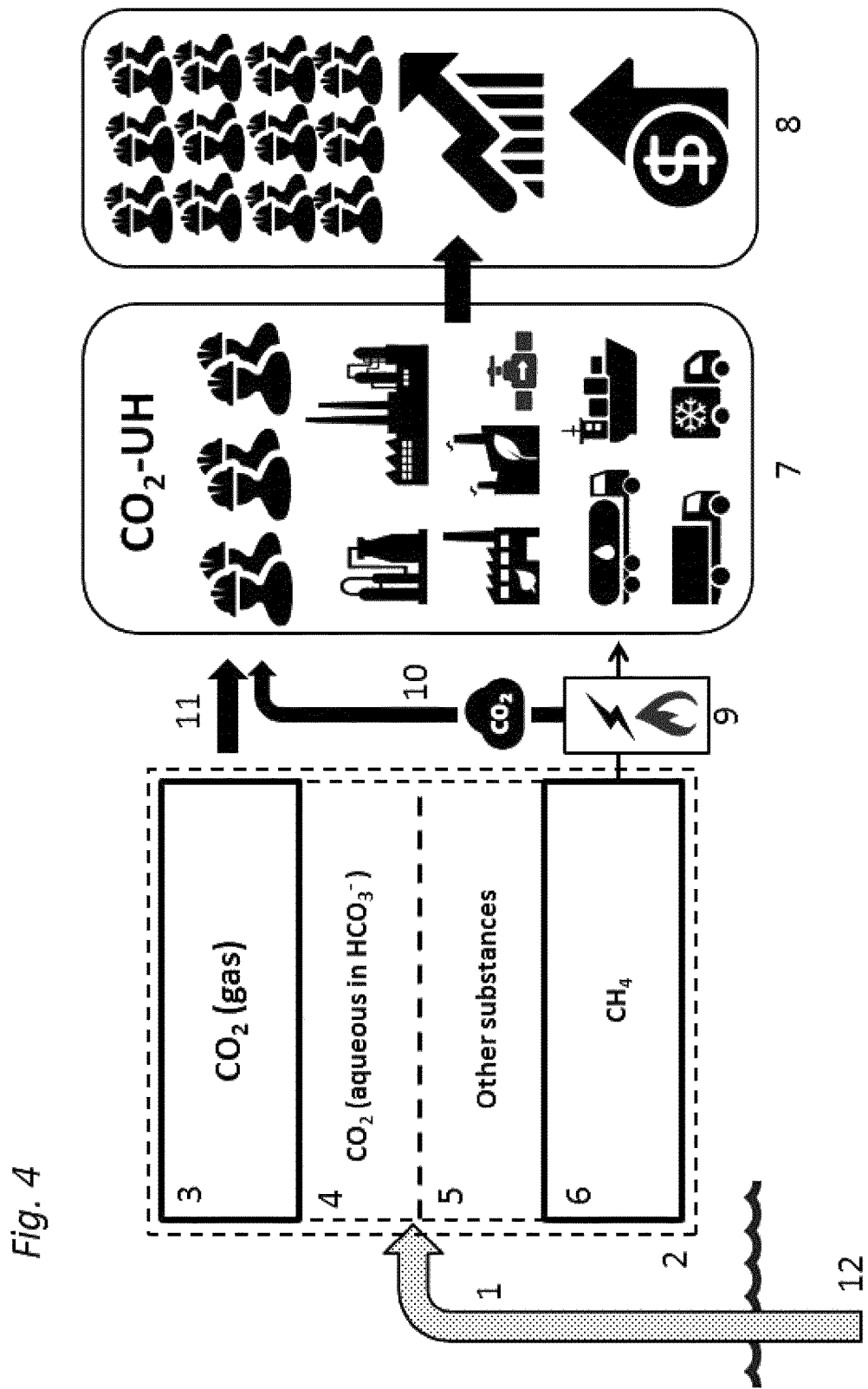
FIG. 4 is a symbolic representation of an embodiment of the invention disclosed herein construed as a method and system of jobs-creation via greentech industrialization (7) in the Lake Kivu region measured by performance metrics reporting upon these factors symbolized by icons within item 8.

FIG. 4 represents the invention disclosed herein as a method and system for industrializing economic development. According to the invention, Lake Kivu deepwater processing creates a multiplicity of outputs that can be described by economic metrics. Such economic metrics are causally linked to the product flows shown in FIGS. 1, 2 and 3 as measures of economic output. Shown on the left side of the diagram are extracted (1) Lake Kivu deepwater (12) resource flows (labeled: 3, 4, 5, 6, and altogether: 2). These, variously in the middle of the diagram (9, 10, 11), are shown inputting $CO_2$ (that would otherwise be waste) into a productive, jobs-creating, $CO_2$ utilization Hub (7, illustrated with exemplary, non-limiting icons), while simultaneously efficiently combusting methane (6) to produce power (9) in an optimal manner with efficient carbon capture (10). Lake Kivu deepwater (12) contains (Box 2) several types of useful resources (sub-boxes: 3, 4, 5, 6). Lake Kivu's deepwater is extracted (1) with its dissolved resources flowing into separation operations (Box 2, which encloses Boxes 3, 4, 5 and 6). Each sub-box represents different types of utilizable substances, as noted. All can be directed into useful industrial production. The invention disclosed herein pertains primarily to the utilization of methane (Box 6) and $CO_2$ (Box 3), both degassed from Lake Kivu deepwater via transformation into a stream of $CO_2$ and steam exhaust entering a $CO_2$-UH (item 7), whereby the submethods and subsystems of oxyfuel combustion, or MSDS in the variant form of the invention (both as described herein but not shown in FIG. 4) provides means for transformation. The flux of $CO_2$ from degassing (11) joins together with a flow of $CO_2$ produced (10) by methane combustion (9) in the TDS modality. This provides (as represented by transfer vector 10) a material basis for $CO_2$ utilization in a $CO_2$ utilization hub ($CO_2$-UH, item 7). As indicated by representative icons, the $CO_2$-UH (7) creates jobs, industrial production, and consequent economic growth (item 8). Note that dissolved magnesium (Mg) may be co-utilized with $CO_2$ in the production of materials containing Mg-carbonates. Also, ammonium ion ($NH_4^+$) may be co-utilized with $CO_2$ both in the production of urea as well as in the nutrient fertilization of algal biocultures which may co-fertilized with $CO_2$. These resources are identified together in Box 5 labeled "other substances." Utilizations of dissolved magnesium and/or $NH_4^+$ are, however, optional features of the invention disclosed herein. The utilization of dissolved magnesium is described in an independent disclosure by the inventor in U.S. Patent Application Publication No. 20160257577 A1.

Figure 5:
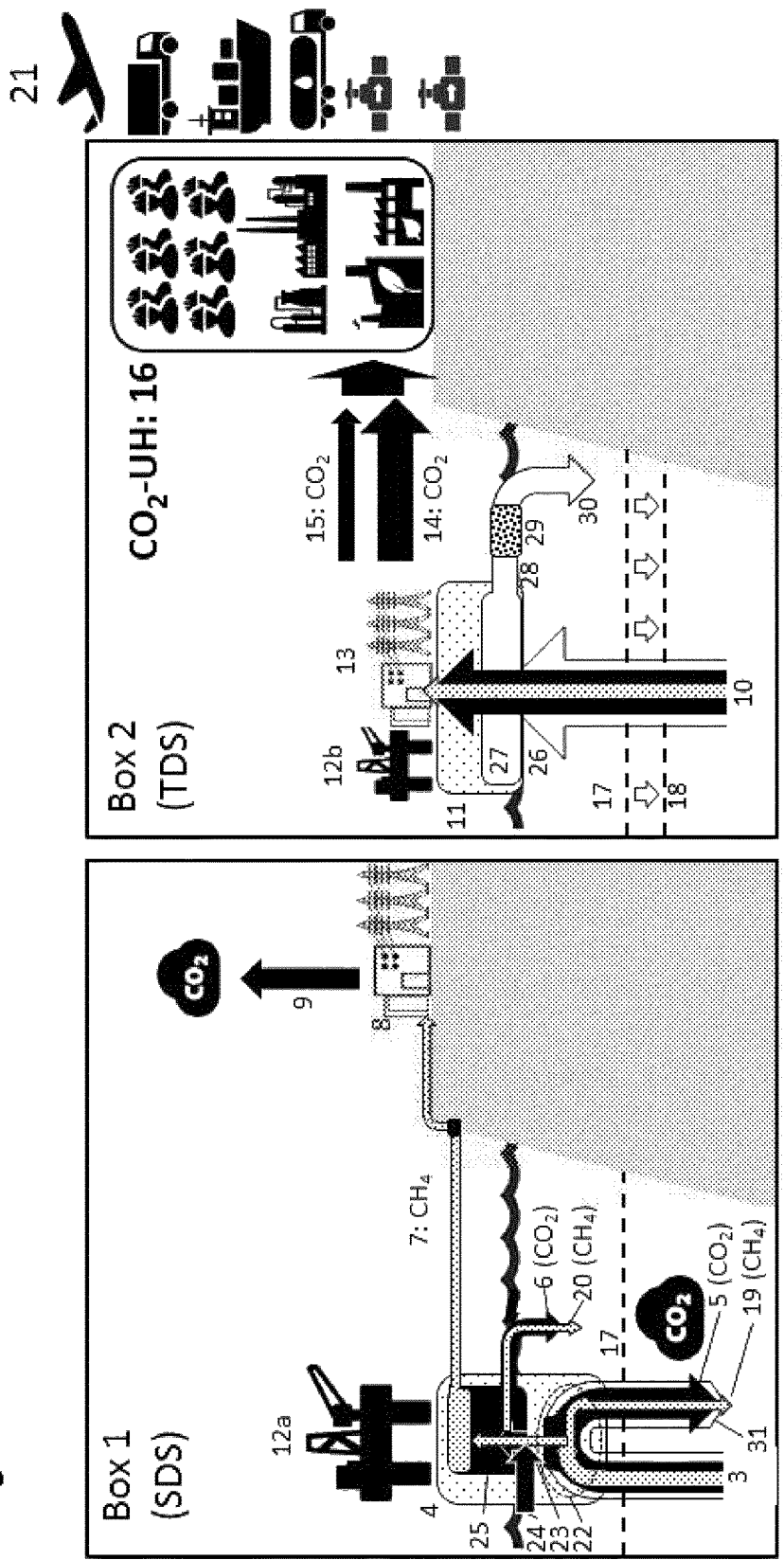
FIG. 5 is a comparative representation shown mostly in vertical plane schematic representation. The figure compares basic aspects of an embodiment of the invention (shown in Box 2) in with existing practiced technology, (as shown in Box 1), for extracting methane and generating power from Lake Kivu deepwater (circa 2015: SDS). Only the modality of the invention utilizing a TDS (rather than a MSDS) is shown in Box 2.

FIG. 5 illustrates and summarizes several benefits of the invention disclosed herein, shown in Box 2, in comparison with existing (circa 2016) technology shown in box 1. The figure highlights aspects whereby the invention offers substantial contributions to power production efficiency, lake safety, environmental stewardship and economic development. The invention is indicated in Box 2 only its TDS-based modality. TDS refers to the method of a Total Degassing System. The MSDS (Modified Staged Degassing System) variant is not shown in FIG. 5. (FIG. 8 provides details.) Black vectors illustrate $CO_2$ flux through systems. (Except for vector 24 which represents flow of near-surface water.) These, in comparison, highlight the $CO_2$-utilizing aspect of the invention via a $CO_2$ Utilization Hub (16). The existing technology practiced on Lake Kivu utilizes the method of staged degassing" (SDS) for gas extraction and cleaning prior to combustion. As illustrated (Box 1), the SDS method proceeds in (minimally) two stages. A first stage of separation is enclosed by a dashed oval (22). Item 22 is a gas-water separator. It is located at a specified depth corresponding to a useful pressure for fractionation to optimize the $CH_4/CO_2$ ratio and minimize $CH_4$ retention losses in solution through the degassing process. Typically the preferred depth is ~20 meters. A substantial fraction (~>20%) of methane remains in solution and is returned to the deep lake (19) in the return flow of water (31) which also contains ~80% of the initial concentration of $CO_2$ (5). A second stage (25) utilizes scrubbing with water to absorb $CO_2$. The process uses near-surface water that is not saturated in $CO_2$. The scrubbing process acts by gas-water equilibrium between gas bubbles and/or gas flow of stage-1 interacting/equilibrating with $CO_2$-undersaturated near-surface water. Gas bubbles and/or flows upwards through a platform-supported (4, icon 12a) scrubbing device (25). This process preferentially resorbs $CO_2$ (with respect to $CH_4$) back into solution. Some methane is absorbed into solution in stage-2 and plumbed back into the lake (20). Hence methane is lost in both stages so that the flux of methane piped (7) into conventional piston engines (8) is substantially reduced. This "slip" wastage is shown for both stages: 19 and 20. One aspect of the comparison shows that utilization of $CO_2$ in a $CO_2$-UH (16) creates a basis for large-scale industrial development (16, 21), represented by icons. Another aspect is securing lake safety against limnic eruption such as may be triggered by sub lacustrine volcanism or other types of triggering phenomena. Lake Kivu's main density discontinuity is presently located at ~260 meters depth. It is represented by a dashed horizontal line (17). $CO_2$ flux is represented with black vectors in both boxes in the figure (3, 5, 6, 9, 10, 14, 15, 25). $CH_4$ flux is represented with stippled vectors in both boxes in the figure (3, 7, 10, 19, 20, 23). Water flux is shown as flow vector 3-to-31 in box 1. In Box 2, water flux is shown as flow via a deepwater inlet (10) to intake (26) into a gas-water separator (27). Water flow proceeds out of the separator via directed flow (28) into de-densifying water treatment (29). Flow then continues back into the lake (30) where it is released well above the main density discontinuity (17). The de-densifying water treatment method and system (29) have been disclosed by the inventor in U.S. Patent Application Publication No. 20160257577 A1.

In Box 2 (which represents the invention) of FIG. 5, utilization of $CO_2$ is facilitated by an initial process of total degassing. This is via a total degassing system, TDS (27), hosted in a floating structure (11), linked with an icon representing a water-borne platform (12b). Return flow in the TDS-based method, as noted above, does not return $CO_2$ and $CH_4$ into the lake. By contrast, in the SDC-method (Box 1), most of the $CO_2$ flowing upwards into the intake (3) is returned into Lake Kivu (5, 6). Most is being returned (5) into to the gas-rich deepwater reservoir existing below the main density discontinuity (17). Such a situation preserves and extends a dangerous condition due to limnic eruption catastrophe hazard. In Box 2 (representing the invention), return flow can be de-densified (in item 29) such that it can be reinjected into the lake above the main density discontinuity (30). This increases lake safety. It does so by drawing down the volume of the gas-rich deep layer. This drawing down "deflation" is illustrated in Box 2 as a time transition. It is shown by small downward arrows illustrating movement of line 17 to a later situation identified by line 18.

FIG. 5 illustrates a key factor of inefficiency in the standard (SDS-based) method. This is the loss or "slip" of methane shown as vectors 19 and 20. Methane returned via stage-2 into Lake Kivu's bio-zone upper layer (20) is irrevocably lost by biological capture and metabolism, typically by bacteria. Methane "slip" lost into the lake's deeper resource zone (19) remains extractable in principle. However, in practice, this methane is not extractable. This is for two reasons. First, return of this "slip" methane into the deep layer is associated with dilution of the methane concentration in the deepwater reservoir over time. Dilution increases extraction inefficiency. Late in the extraction, inefficiency increases drastically. Effectively this means that the returned methane is lost. Second, some actual operations are not returning the flow (indicated as 31, 5, 19) into the deep lake below the main density discontinuity (17). Water is being mixed with near surface water and reinjected at a higher level in a depth range where it is not extractable by the SDS method. Mixing-in near-surface water also oxygenates the flow such that methane is lost by bacterial uptake. Direct methane losses in the SDS-based method are roughly one third. Indirect methane losses via the effect of dilution of the deep layer add additional degrees of inefficiency.

Overall, the invention disclosed herein and in the related disclosures of U.S. Patent Application Publications Nos. 20150354451 A1 and 20160257577 A1 creates an efficiency gain of approximately ×2.4 in terms of total power produced by an OXFCPS (13) from the lake in comparison to the SDS-based method. The use of supercritical $CO_2$ power cycle technology can increase this factor to ~×3.0.

FIG. 6 illustrates special cryogenic aspects of the invention. These aspects are diverse and powerfully versatile. They include cryo-energy storage (23, 24, 25, 28) and recovery (3, 18, 29, 30), as well as provision of coolant flows of liquid (11) and/or cold (12) nitrogen to a Digital Data Center (5, DDC). Cryogenic aspects also include capacities for powerplant (1, 33) temporal load-balancing (18), provision of grid balancing services (15, 16), utilization of remote solar and/or wind power (20) inputs (21), and production and utilization of LNG (36, see below) and other forms of NG (40), such as CNG and ANG. Irregular solar and wind power inputs may be stored and used in power-absorbing modes of production within the $CO_2$-UH (Box 4), for example production of $H_2$, $O_2$ and "solar chemicals," including carbon-recycling, hydrogen-binding "solar fuels" such as methanol and/or DME. FIG. 6 illustrates detail that is not provided in Box 5 shown in FIG. 1. Cryogenic aspects of the invention are illustrated in all modalities based upon the three different available gases: $N_2$, $O_2$ and $CO_2$. These are all present in preferred embodiments of the invention, as is any subset using only one or only two of these gases. A particular utilization of nitrogen gas also is shown. It is for cooling of a Digital Data Center (DDC, 5). Cryogenic equipment for air separation and other gas cooling tasks exists within an Air Separation Unit (2). This unit is shown functioning with expanded capacities as a CRyogenic Processing Unit (2, ASU-CRPU). This expanded capacity may be shared with the $CO_2$-UH (box 4), as shown (via same number labeling of the cryo-production icons: 27a and 27b, however not represented spatially in connection in the figure). Or separate cryogenic facilities may exist within the $CO_2$-UH (Box 4) supplied with power (17, 19) from the powerplant (icon in Box 1) and/or from the grid (15, 33), if desired. Open arrows with single ends (such as, for example, 6 through 13) represent matter flows. Solid black arrows represent flows of electric power. (Power may be mechanically transmitted and/or more typically transmitted by wires as electric power. Of course power is supplied into (16) the grid (33).) Two double-ended arrows appear within Box 22 (CESSI). These connect to heat exchanger icons labeled 29 and 30. They represent options of connectivity shared by a CRyo-Energy Recovery Unit (Box 3: CRERU), which is adjunct to both the Air Separation Unit (ASU, Box 2) and the OXyFuel Combustion Power System (Box 1, OXFCPS). These options of connectivity of the CRERU (Box 3) connect cryogenic heat engine power generator systems (shown within Box 22) with the heat sources of the air intake (14) of the Air Separation Unit's CRyo-Production Unit (Box 2: ASU-CRPU), and/or with the $CO_2$ and water vapor exhaust (32) of the OXyFuel Combustion Power System (Box 1: OXFCPS). Again, these connections are symbolized by heat exchanger icons 29 and 30, respectively, linked to the center of Box 22 (CESSI) by the double-ended arrows. The power generator systems are symbolized by icons shown in the inner part of Box 22 (CESSI) within the CRERU (Box 3). These icons are shown as three pairs. They illustrate power sources connecting to power transmission wires (18a, 18b and 18c). These power sources tapping stored cryo-energy provide recovered stored power (18) into a nexus of electrical power regulation and disposition (dashed Box 41) connecting the powerplant (Box 1) to the grid (33, 15, 16). These systems (18a, 18b, 18c) extract stored cryo-energy, respectively, from flows of stored (25) refrigerated liquid $CO_2$ (9, $LCO_2$), stored (23) liquid oxygen (6, 10, $LO_2$), and stored (24) liquid $N_2$ (7, 11, $LN_2$). Liquified Natural Gas (LNG) also optionally is stored (34) within the $CO_2$-UH (Box 4). LNG provides very high efficiency cryo-energy storage with efficiencies above 90% for round trip energy storage. LNG also of course provides efficient storage of chemical energy that can be transported as well as sold in various forms, LNG, CNG and ANG (40). Inclusion of cryogenic capacities for LNG production additionally provides the basis for a method and/or system for LNG production via cryo-separation of methane from carbon dioxide, (with $CO_2$ separating in the form of dry ice according to elegant methods patented and demonstrated by Larry Baxter and colleagues). Dashed Box 36 indicates a specialized domain for such LNG-based operations, possessing LNG-specialized cryo-capacities (35) with $CO_2$ separation capacity. This domain (35) intakes a mixed gas inflow (37), degassed from a Lake Kivu deepwater source (38). It produces outflows of separated solidified and/or liquified $CO_2$ (39) and LNG (40). LNG cryo-energy production and storage therefore also serves as a mode of $CO_2$ processing appropriate as a valuable capacity of a $CO_2$-UH for the production of dry ice and/or $LCO_2$ as well as for cryo-energy storage. Storage of cryogenic liquids is provided within a cryo-storage domain (28) within the $CO_2$-UH (Box 4). This domain (within dashed Box 28) functions both for liquefied gases storage generally as well as in the capacity of a power-storage battery as indicated by an icon (26). Cryogenic energy storage systems can possess attractively high round trip efficiency and flexibility, as has been well demonstrated. As shown by the icons, heat engine power generator systems (within Box 22, CESSI) are comprised of heat exchange equipment combined with gas flow turbine generators. The Air Separation Unit (2, ASU-CRPU) produces liquid oxygen (6: $LO_2$) and liquid nitrogen (7: $LN_2$) for energy storage as well as $O_2$ gas for direct intake into combustion in the OXFCPS (1). After passing through heat exchangers linked to power generating turbines, gas flows are distributed as follows. Cold nitrogen gas (12) is distributed as a cooling flow (to 5: a Digital Data Center, DDC, or other facility requiring large cooling flows), and may be otherwise directed (13) for additional uses after serving its function. Warmed-up nitrogen (13) exiting the DDC (5) may be utilized for various purposes. Oxygen gas (31) is fed into oxyfuel combustion (1). Carbon dioxide gas (8) is returned to the $CO_2$-UH for disposition for utilization (4).

Such cryo-processing and cryo-energy storage capabilities are expanded and used, if desired, for load balancing of solar power (20) and/or wind power and/or hydropower inputs (21) flowing into the electricity handling nexus (Box 41) of the powerplant (Box 1), or some adjunct electrical facility if/as needed. Cryogenic energy storage capabilities present in some preferred embodiments thereby allow power storage as well as utilization of inputs (21) of solar and/or other sources of renewable power (20) plus $CO_2$ within the $CO_2$-UH (4) for production of "solar chemicals," including "solar fuels." Efficiency factors are reported within research reports incorporated into this disclosure. The development of such capabilities for solar power utilization in support of $CO_2$ utilization is very highly desirable. This is from the perspective of the global need for economically useful innovations in the development of solar and/or other renewable sources of power, for example, demonstrating economically viable large-scale cases of "artificial photosynthesis" based upon solar power inputs. The invention offers this possibility utilizing carbon dioxide both as a cryo-energy storage liquid and as a carbon source.

FIG. 7 introduces a perspective of the invention as a collaboration and talent attractor. This perspective is based upon the international strategic significance of large scale $CO_2$ utilization combined with national economic development in a region that has suffered massive catastrophes and that also is extraordinarily beautiful as well as subject to a pleasantly attractive climate year round. FIG. 7 shows a preferred embodiment of the invention in its aspect being an open hub attracting the development of a global network. The focus of the invention is the internationally strategic goal to create commercially viable new examples of very large scale $CO_2$ utilization. The NRG Cosia carbon X-Prize competition (http://carbon.xprize.org) exemplifies this situation. The invention creates an opportunity to attract talent, capital, interest, publicity, and innovative new ideas and technologies. The $CO_2$-UH (Box 1), representing the invention overall, provides a global focus hub for the growth of an international network represented by the large peripheral circle (2) and its connected box ("Box") containing a group of icons representing several different modalities of collaboration. This network structures collaborations with companies, research institutions, financing institutions, non-profit funders and philanthropic agendas. Each collaboration is represented by a spoke (double-ended arrow) connecting to a numbered ball situated on the network circle. There is no closed number of collaborations. (Each collaboration is represented by a ball and spoke combination: 3, 4 5, 6, 7, 8, 9, 10, 11, 12.) This openness is shown by the " . . . " following the number identifying the twelfth ball-and-spoke. Components of the hub work in concert on the challenge of creating business-scalable innovations in carbon utilization recycling. The icons inside the dashed box represent the multiple aspects of the network: research, training, e-platformed networking and knowledge dissemination, for-profit business and non-profit charitable involvements, new ventures formation, technology pilot projects, networked brainstorming, etc. The hub-structured open aspect of the $CO_2$-UH (1) creates an intrinsic attractiveness with an open modularity for adding and developing specific modalities of $CO_2$ utilization within a common framework.

FIG. 8 shows a system, method and apparatus concept that modifies the standard "staged" gas extraction technology presently utilized on Lake Kivu (Box 1: SDS), as shown by items 13 and 14 in FIG. 1. The modification is into a system, method and apparatus concept (Box 2) possessing the capability to degas $CO_2$ in a flow sequence following after stages 1 and 2. This method and system of modification makes it possible to create a $CO_2$-UH connected to an existing conventional staged gas extracting and powerplant operation/apparatus. This type of modification, and/or method, and/or system is an embodiment of the invention. This method and system of modification also makes it possible to design and develop a staged extraction powerplant system that degasses $CO_2$ and therefore that can be constructed with addition of a $CO_2$-UH. The present disclosure is a method and system that links a $CO_2$-UH to a Lake Kivu deepwater degassing system. The latter may be either of both known types: (i) a modification (MSDS) of the conventional "staged" degassing technology; or (ii) a "total degassing technology" (TDS). Both types of degassing system (MSDS & TDS) are variant sub-components of the invention. Both can connect to a $CO_2$-UH, as shown in FIG. 1. Both can connect to return flow systems as shown in Box 3 of FIG. 8.

FIG. 8, Box 1 illustrates the conventional staged method (SDS) as follows. Deepwater enters a riser system (1) via auto-siphoning flow, and/or with pumping assistance. Flowing upwards, it enters a degassing system (1, 2). Degassed gas is collected at a depth (10) below the surface of Lake Kivu indicated as "D." This depth typically is selected to optimize both $CH_4$ yield and the $CH_4/CO_2$ ratio in a situation of a divergence of two factors: (i) maximizing the degree of methane extraction by degassing (which increases with decreasing D); and (ii) minimizing the degree of $CO_2$ extraction by degassing (which also increases with decreasing D). Gas obtained by stage-1 degassing is separated from the deepwater flow (2, 9*a*) and directed to flow upward (3) in a contained gas transfer riser system. In some designs, this gas enters into a $2^{nd}$ stage gas-cleaning process positioned near to the lake's surface. (Some designs clean gas in a $2^{nd}$ stage below the surface. Others clean gas above the surface in bubble or trickle towers.) As shown, the gas-cleaning process utilizes near surface water (5, 6, 7). This water is pumped (5) upwards (6) and released downwards to flow downwards inside a bubble or trickle tower (4), then out of it (7) and back into the lake. This method and system absorbs and removes $CO_2$ preferentially from the gas flow (3). Cleaned gas is collected and extracted at the top of the chamber by exit flow (8, which may be pumped in some embodiments) at the completion of the gas-cleaning process. It is then provided by pipeline into combustion (not shown). The $2^{nd}$-stage "water washing" method is designed to minimize methane "slip" loss and maximize the $CH_4/CO_2$ ratio of the gas exiting the overall multi-stage system (8). However, methane slip from both stages may be as high or higher than 30%, whereas power output utilization for the water pumping process (5) may be as high higher than 12% of total power output. For this and other reasons, the standard staged method and system shown in FIG. 8, Box 1 is only ½ to ⅓rd as efficient in power production efficiency relative to the "total degassing oxyfuel combustion" method and system disclosed in US 2015/0354451. Despite these limitations, it may be modified as shown in Box 2 to degas $CO_2$ for utilization and in order to degas the deep lake to increase lake safety. Bow tie symbols represent flow valves. If flow is directed away from conventional return flow (9b) and into a diversion line (11), then the redirected flow auto siphons into a degassing chamber (12). This process degasses a substantial fraction of degassable $CO_2$ into the gas phase as an extraction flow (14). (The remainder remains in solution.) Thus, a conventional Staged Degassing System (SDS, Box 1) is modifiable, as shown, into a modified system that degasses a substantial faction of $CO_2$ (MSDS, Box 2, with or without the additional modifications shown in Box 3). The $CO_2$ degasser separates a flow of $CO_2$ gas (14) out of solution in the return flow (11). The resulting doubly degassed return flow may be injected into the deep lake in the conventional manner (13). Otherwise it may be diverted into additional modifications as shown in Box 3.

Box 3 within Box 2 shows how a MSDS can connect by additional modification into submethods and subsystems for organizing deepwater return flow as have been disclosed by the inventor in U.S. Patent Application Publication No. 20160257577 A1. The method and system and apparatus design concept illustrated within Box 2 is applicable to both types of deepwater degassing method and system: staged degassing as shown in FIG. 8, and the total degassing," as disclosed by the inventor in U.S. Patent Application Publication No. 20150354451 A1. As specified in FIG. 1 and in FIG. 2, Box 1, the invention does not include a return flow system in its most basic form of definition. However, certain preferred embodiments connect "main modes" of $CO_2$ utilization in the $CO_2$-UH connect into types of return flow system. Therefore these modalities and the return flow systems they connect into are described in the following sections.

Three non-exclusive options are shown within Boxes 2 and 3 of FIG. 8 for the fully degassed return flow of deepwater. These are: (i) conventional deep reinjection (13), identical to that shown as 9a and 9b; (ii) admixing into the biozone of Lake Kivu (15) as a means of fertilization to boost ecosystem output; and (iii) return flow with inclusion of de-densifying water treatment by algal growth (18) and mineral precipitation (19), thereby allowing reinjection of the de-densified return flow into the Intermediate Zone (IZ) of Lake Kivu, (as disclosed by the inventor in U.S. Patent Application Publication No. 20160257577 A1).

FIG. 8, Box 3 shows various different modalities for $CO_2$ utilization in the context of the return flow options shown. Two of these involve $CO_2$ injection diffusers into the return flow. These diffusers are indicated as 28 and 26. Item 28 represents a diffuser for $CO_2$ input (27 into 28) into a component of return flow directed into Lake Kivu's biozone (0 to ~80 meters depth) for biozone fertilization (as shown in item 15, a diffuser). This flux of $CO_2$ corresponds to $CO_2$ injection vector 2b in FIG. 2. (Vector 2a in FIG. 2 represents a $CO_2$ diffusion system separate from that for nutrient-rich return flow water.) $CO_2$ diffusion into Lake Kivu's biozone via flux (27) released into diffuser(s) (28) corresponds to mode 2 in Table 1. Item 26 represents a pH-balancing diffuser. It diffuses $CO_2$ input (25) into the flows of de-densified return flow reinjected into Lake Kivu. This is for (optional) "recarbonation" to conversion of carbonate anions to bicarbonate anions associated with sodium and potassium. This flux of $CO_2$ (25 via 26) corresponds to $CO_2$ injection vector 3 in FIG. 2. It also corresponds to mode 3 in Table 1.

FIG. 8, Box 3 includes a 3rd additional modality for $CO_2$ utilization by diffusion into return flow. This is in a surface flow (16) method and system for return flow water treatment (18, 19) prior to reinjection into Lake Kivu (26, 20). This method and system of de-densifying water treatment is disclosed by the inventor in U.S. Patent Application Publication No. 20160257577 A1. $CO_2$ utilizing inputs are shown in FIG. 8 for pH control (21a, 22). Related $CO_2$ inputs also provide carbon feeding for algal biomass growth in a biological water treatment system method (21a into 17a, and 22 into 18). Items 17a and 17b represent different possible modalities. These correspond, respectively, to $CO_2$ flux into (17a) and $CO_2$ flux out of (17b) the flow, as shown by the double arrow (21a,b). These different modalities are: (i) first, $CO_2$ injection into the flow (21a, 17a) representing a pH-controlling submethod and subsystem for avoiding mineral precipitation; and (ii) second, $CO_2$ removal out of the flow (17b, 21b). The latter modality is not described herein. It only is illustrated as an option included in some embodiments.

In FIG. 8, item 18 in Box 3 represents a photosynthetic method and/or system for growing algae within the return flow over an extended period of time. Arrows 21b, 23 and 24 represent $CO_2$ removal as a means of pH-raising associated with processes for precipitation of Mg and Ca. Arrows 21a and 22 represent $CO_2$ input into a photosynthetic method and system for growing algae in the return flow over an extended period of time. $CO_2$ input provides carbon for photosynthesis. Its photosynthetic utilization raises pH. Arrows (21 a and 22) represent a method and system of pH control by provision of $CO_2$ for algal carbon source supply and in order to suppress high-pH conditions such as would precipitate magnesium and calcium. Flux of $CO_2$ into the bioculture method and system (21a and 22 into 17b and 18) corresponds to $CO_2$ injection vector 4 in FIG. 2. It also corresponds to mode 4 in Table 1.

FIG. 9 is quasi-identical to FIG. 1. The labeling in FIG. 9 is identical to that in FIG. 1 excepting that additional detail has been provided within dashed Box 4. Therefore the labeling is not repeated in this section, except for items within box 4. For other items, refer to the items list and to sections discussing FIG. 1. The focus of FIG. 9 Box 4 is upon illuminating distinct modes in the utilization of $CO_2$ "going back" to be used within Lake Kivu (9 *a,b,c*) for several different purposes. Some modes of $CO_2$ utilization into Lake Kivu (15c, 15d, place $CO_2$ into the biozone (9a) for use in C-fertilizing aquatic photosynthesis. Mode 15d does this by injection of $CO_2$ into return flow diffused into the biozone (7a) as a C-fertilizing flux (as shown in FIG. 8, item 15). Mode 15c does this by direct diffusion into the biozone without connection with admixture of return flow water. Mode 15e places $CO_2$ into the Intermediate Zone (9b) in a context of pH-balancing of de-densified return flow (18) that has become high in pH via bioproduction (16) followed by harvesting and mineral precipitation processes (17). Injecting $CO_2$ into this return flow (18) after completion of de-densifying processes (16, 17) transforms its alkaline chemistry rich in (Na- and K-complexed) carbonate anions at high-pH into bicarbonate anions at a lesser pH. The flux of CO$_2$ labeled 15a injected into return flow (7) flowing out of the Total Degassing System (Box 1) is for purposes of acidification, if and as needed, to avoid and/or control precipitation of Mg and Ca in this flow. The flux of CO$_2$ labeled 15b is provided as a carbon source into photosynthesis in (typically floating) algal growth operations (16) positioned on the surface of Lake Kivu but not communicating with it. The open arrow labeled 19 represents extractive flows from algal harvesting and from the capture of Ma and Ca precipitates.

Twenty "main mode" selected examples of CO$_2$ utilization are described in following. These correspond to CO$_2$ flux vectors labeled 1 through 20 shown in FIG. 2. These represent product flows (FIG. 2, Box 8) exiting the CO$_2$-UH (FIG. 2, Box 21). Use of CO$_2$ for cryo-energy storage is not included in this list of "main modes" because it mainly is not a mode whereby CO$_2$ flows out of the CO$_2$-UH (21) as a product stream. The first seven of the twenty "main modes" all are CO$_2$ flows. The eighth mode is a transitional type. It represents a modality of CO$_2$ flow connecting into a building materials production flow based upon absorption of CO$_2$ flow and hydration into cementitious carbonating mineralization. The eighth mode (FIG. 2, arrow or vector 8) represents a time-varying and properties-varying flow of CO$_2$ input corresponding to a production recipe. CO$_2$ products of the CO$_2$-UH are represented in FIG. 2 by arrows or vectors 1 through 7, and transitionally by arrow or vector 8. All provide flows of CO$_2$, with or without associated steam, with or without a high degree of compression, and with or without cryo-preparation to states of liquid CO$_2$ and dry ice. Such product flows of CO$_2$ can be categorized into five types. (NB: "Types" of CO$_2$ flows are different from "main modes" of CO$_2$ utilization.) Each type corresponds to a different process train shown in FIG. 3 (22, 23, 24, 25, 26). They are as follows. The first type of flow corresponds to process train 23 in FIG. 3. It is relatively "raw" CO$_2$ exhaust gas. The flow is not dehydrated or compressed to high pressure for long-distance pipeline transport. It is compressed only, if and as needed, to pressures sufficient for local pipeline transport. In FIG. 2, vectors 1, 2a, 2b, 3, 4 and 5, (the last having to do with local algal biomass feeding), are CO$_2$ flows of this type. The second type of CO$_2$ flow is CO$_2$ exhaust gas that has been dehydrated and compressed to pressures that are sufficient for long-distance pipeline transport. This flow is directed into pipeline transport as needed. It corresponds to process train 24 in FIG. 3. In FIG. 2, arrow or vector 6, and sometimes arrow or vector 5 (having to do with algal biomass carbon source feeding, when the CO$_2$ transport distance is large), are CO$_2$ flows of this second type. The third type of CO$_2$ flow is refrigerated CO$_2$ in the form of liquefied CO$_2$. This type corresponds to process train 25 in FIG. 3. In FIG. 2, vector 7 includes liquefied CO$_2$. The fourth type of CO$_2$ flow is of frozen CO$_2$ "dry ice." This type of flow corresponds to process train 26 in FIG. 3. In FIG. 2, arrow or vector 7 includes solidified CO$_2$. The fifth type of CO$_2$ flow is a flow with properties that vary in time according to a product production recipe. It corresponds to process train labeled 22 in FIG. 3. Process train 22 is drawn to display the specific case of cement-based eco-concretes and building materials involving cementitious carbonation and hydration. This is as an example appropriate to display in time-varying production flow with changing properties. In FIG. 2, arrow or vector 8 corresponds to this specific option. In the case of eco-concrete and related building materials, it represents a transitional situation from a CO$_2$ product (delivery of a CO$_2$ and steam flow according to a time-varying recipe) to a product created by utilizing CO$_2$. However, this type of CO$_2$ flow is not limited only to production of eco-concretes and related building materials. Other products may require time-varying recipes for the input of CO$_2$ with or without associated steam, and at various pressures and temperatures, for example involving pressure-temperature-gas-composition variation schedules. The remaining arrows or vectors, 9 through 20, represent additional "main modes" of CO$_2$ utilization. In these, CO$_2$ is used as an input ingredient or otherwise as a processing substance utilized for production of products within the domain of the CO$_2$-UH (FIG. 2, 21), shown in FIG. 2.

The first "main mode" of CO$_2$ utilization (FIG. 2, arrow 1) is CO$_2$ fertilization in greenhouse horticulture for plant growth acceleration and yield boosting. This mode of CO$_2$ utilization is a preferred embodiment. In FIG. 2, arrow 1 is shown for this use locally. Unprocessed gas may be used for this purpose. Modest compression only is needed for distribution via a local network of pipes. If an areal extent of 5,000 hectares (a square area, 5 km×10 km) is chosen, then the approximate CO$_2$ utilization will be ~2 MTA CO$_2$ (based on calculations given herein). The amount of CO$_2$ utilization scales roughly as the area of greenhouse horticulture using CO$_2$. The provision of large amounts of CO$_2$ for use in distant greenhouse horticulture on a large scale requires dehydration and pressurization of CO$_2$ for long-distance pipeline transportation.

The second "main mode" of CO$_2$ utilization is Lake Kivu biozone fertilization. This mode of CO$_2$ utilization is a preferred embodiment. It is represented as flow arrow 2 in FIG. 2. This vector split into two sub-vectors, 2a and 2b. This mode of CO$_2$ utilization requires only unprocessed gas (as shown in the process train labeled 23 in FIG. 3). It is approximately pure CO$_2$, except with no need for it to be dehydrated or highly pressurized. The CO$_2$ is injected into Lake Kivu in two ways. First, it can be disseminated by a system of diffusers directly into the biozone of the Lake. This is shown in FIG. 2 as vector 2a. Second, it can be disseminated into a return flow of degassed deepwater diffused into the biozone of Lake Kivu as a nutrient source. This is shown in FIG. 2 as vector 2b, (with CO$_2$ dissolving into the return flow water disseminated into the biozone shown as vector 2b connecting into the return water flow vector labeled number 36c). Doing so under ecosystem feedback monitoring and control boosts the lake's biological productivity and fish yield. Inventive details will be disclosed elsewhere. An estimate for an appropriate scale of CO$_2$ utilization for diffusion into Lake Kivu's biozone is as follows. The natural scale of deepwater upflux from Lake Kivu's Main Resource Zone (MRZ) has been roughly estimated to be ~0.15 km$^3$/yr across an areal extent of ~1000 km$^2$ by Schmid and Wuest, (2012). This flux corresponds to an influx volume from deep springs emitting CO$_2$-rich high-density water into the MRZ. It provides a minimum determination of natural CO$_2$ flux into the base of the biozone. Using the CO$_2$ concentration reported in Table 1 (from Wuest et al., 2012), this determines a CO$_2$ upflux of ~0.5 MTA (million tonnes per year). A more precise estimate has been obtained from NH$_4^+$ data in the analysis of Pasche et al., (2011, 2012). Pasche's analysis determines an upflux of ~0.7 MTA CO$_2$. This natural upward flux of CO$_2$ nutrient from below into Lake Kivu's biozone is shut-off or diluted by some return flow injection schemes. In such circumstances, the upward flux of CO$_2$ into the biozone can be replaced by artificial diffusion into the return flow flux being reinjected into the lake. In general, increasing the CO$_2$ flux from below boosts the ecological productivity of the lake. It acts as a carbon source for algal photosynthesis. Pending input-response testing in test areas in the lake, a scientifically informed rough estimate for a reasonable boost is at least a factor-of-three increase. This indicates a target delivery at least ~2 MTA of $CO_2$ into the biozone.

The third "main mode" of $CO_2$ utilization (FIG. 2, arrow 3) is diffusion-dissolution of $CO_2$ into high-pH (pH >10) return flow water following water treatment processing by pH-raising methods. This mode of utilization of $CO_2$ relates the return flow water treatment process disclosed in U.S. Patent Application Publication No. 20160257577 A1. This disclosure presents a method for treating nutrient-rich dense deepwater from Lake Kivu in such a way that the outflow of the process yields a de-densified water at a high pH. Addition of $CO_2$ by injective dissolution may be used to treat this water for purposes of pH reduction prior to reinjection into Lake Kivu at a depth level below the biozone, most desirably within the so-called Intermediate Zone (IZ). This mode of $CO_2$ utilization for pH reduction of high-pH return flow treated water is a preferred embodiment. It is shown in FIG. 2 as $CO_2$ flow vector 3 connecting into return water flow vector 36b. Sourcing for this $CO_2$ in the $CO_2$-UH is shown in FIG. 3 as process train 23. This offers an opportunity to sequester $CO_2$ in Lake Kivu in a non-dangerous situation more than 100 meters above the ~260 meter deep main density discontinuity. Utilizing $CO_2$ for pH-balancing may be ecologically prudent even though the injection level is under the biozone rather than within it. Lowering of pH involves dissolving $CO_2$ into alkaline solution causing transformation of doubly charged carbonate anions, each associated with two sodium cations, into singly charged bicarbonate anions, each associated with one sodium cation. The scale of $CO_2$ utilization via this modality depends on the sodium concentration and the total flow of return flow water processed according to the bio-treatment and Mg+Ca-precipitation method. A simple rough estimate is to assume that $CO_2$ absorption into the high pH solution will convert all sodium-associated ions ($2Na^+::1CO_3^{2-}$) into sodium-associated bicarbonate ions ($2Na^+::2HCO_3^-$). This will be by addition into solution of $CO_2$ in the molar ratio: $CO_2/Na=0.5$, with respect to the sodium concentration of the water. For clarity, this assumption is coupled with the additional simplifying assumptions that all initial sodium associated anions at pH~10.5 are carbonate ($CO_3^{2-}$), and all final sodium-associated anions are bicarbonate ($HCO_3^-$) at lower pH, and that sodium (Na) is the predominant cation active in the carbonate-bicarbonate equilibrium. (The last assumption follows from the prior precipitative removal of both calcium and magnesium by pH ~10.5.) Using input data for sodium at 300 meters depth in Lake Kivu's main basin from Tassi et al., (2009), Na ~0.0175 moles/l, a rough estimate for $CO_2$ absorption into the high-pH solution is: ~0.0088 moles/l (=~0.39 grams per liter). This may be compared to the initial $CO_2$ concentration in the deepwater at 300 meters depth prior to degassing: $CO_2$~0.055 moles/l, ~2.42 g/l. Therefore if all of the return flow is bio-processed and de-densified, then ~16%, roughly one sixth of the $CO_2$ degassing flux, is absorbable for pH-balancing prior to reinjection into Lake Kivu (at an appropriate density-matched depth in the interval ~90 meters to ~150 meters). Adjustments for the addition of combustion-derived $CO_2$ and other corrections suggests that a reasonable expectation for $CO_2$ utilization in pH-balancing is ~12% of the total flux out of the OXFCPS. For an output of ~400 MW, this is roughly 1 MTA (Million Tonnes per Annum) of $CO_2$. Together therefore, biozone fertilization and return flow pH-balancing represent the second and third "major modes" of $CO_2$ utilization, shown in FIG. 2 as vectors 2a, 2b and 3, respectively. The simple estimates provided herein indicate it is possible to utilize quite a large fractional component of $CO_2$ exhaust locally by shallow injection in Lake Kivu for biozone fertilization and return flow pH-balancing: altogether roughly one third of the total degassing flux of $CO_2$. (Note there is no increased limnic eruption risk by these methods because the chemical state of the absorbed $CO_2$ would be in the form of bicarbonate anion in a chemical state close to that of water in the biozone.)

The fourth "main mode" of $CO_2$ utilization (FIG. 2, arrow 4) is a pH-controlling modality preparatory to return flow into an algal growth sector. This mode of $CO_2$ utilization is a preferred embodiment. $CO_2$ input in this modality is shown in FIG. 8 as flow vector 12a providing $CO_2$ in item 17a. Item 17a is a diffuser. It adds $CO_2$ into solution prior to flow into an algal growth sector identified as item 18. No estimate for this modality is provided in table 2. The scale of $CO_2$ input is dependent on a range of factors having to do with the specific conditions of degassing and specifications for control over Mg and Ca precipitation.

The fifth "main mode" of $CO_2$ utilization (FIG. 2, arrow 5) is local algal production. This mode of $CO_2$ utilization is a preferred embodiment. $CO_2$ is disseminated into algal biocultures both by direct $CO_2$ dissolution into biocultures and indirectly by addition of sodium bicarbonate (which may be formed by water absorbing carbonation of alkaline brine or sodium carbonate molecules, $Na_2CO_3$, into two bicarbonate molecules $NaHCO_3$). Degassed Lake Kivu deepwater carries dissolved inorganic carbon accessible for algal carbon fixation in the form of bicarbonate anion. It also carries NPK bionutrients. A substantial crop of algae therefore can be grown to certain concentration levels without adding any additional carbon source. However, with addition of extra nutrients (as may be accessed by various methods of nutrient recycling in algal production and processing), further algal biomass can be grown if a new source of carbon is provided. $CO_2$ can be used as a carbon source for this purpose. It may be utilized via a pH-lowering input chemistry, as noted herein, converting doubly-charged carbonate anions to singly-charged bicarbonate anions. Algal production can follow a two-step focus: (i) first, initial separation of very high value nutraceutical compounds, followed by (ii) high-pressure hydrothermal processing of residues with nutrient recycling for production of biofuels, bio-asphalt and bio-fertilizers. The production of high-value nutraceutical products depends on the species mix of algae grown. It therefore depends on the biotechnological set-up, controls and inputs. Many options are possible. For example, $CO_2$ may be used to grow diazotrophic cyanobacteria algae via P-only nutrient feeding into biocultures. Such biocultures also may be grown under various low-oxygen $N_2:CO_2$ canopy conditions to optimize cyanobacterial growth and dominance conditions (Smith and Evans, 1971; Fay, 1992; Thomas et al., 2005; Berman-Frank et al., 2005; Molot et al., 2014). This produces cyanobacteria biomass harvestable as NP-rich biofertilizers where nitrogen has been fixed by the diazotrophic activity of the cyanobacteria, and where carbon has been fixed by photosynthesis from the $CO_2$. $CO_2$ additionally may be utilized as a coagulation-flocculation agent in harvesting, as noted herein. $CO_2$ may be used for post-harvest processing to separate algal oil, including high-value nutraceutical/pharmaceutical components. Algal biomass production can utilize $CO_2$ in many and different ways.

Two estimates for $CO_2$ utilization follow relating to algal production. If 0.5 MTA $CO_2$ is utilized for carbonation of (1.2 MTA of) sodium carbonate, ($Na_2CO_3$), to sodium bicarbonate, (NaHCO$_3$), then the amount of sodium bicarbonate produced at 100% efficiency is: ~1.9 MTA. Some fraction of this sodium bicarbonate production may be used for large-scale algal production, for example growing *spirulina* as a high-value protein and nutrients source for mother and child nutritional supplement feeding addressing widespread regional dietary protein deficiency. Second, if 1.0 MTA CO$_2$ is directly diffused into algal bioculture, then if ~½ of that carbon is harvestable in algal biomass, and if ~½ of that carbon is convertible into (for example) transportation biofuel carbon (therefore a carbon mass of: 1MTA×12/44×0.25~80,000 tonnes/yr), then the amount of refined biofuel (assuming an average molecular formula: C$_{12}$H$_{23}$) produced is ~93,000 tonnes per year, or ~110 million liters at a density of ~0.83 tonnes per 1,000 liters. For comparison, Rwanda's total annual consumption of transportation fuel is roughly 400 million liters. Overall, ambitious target scales for algal bioproduction utilization for Lake Kivu CO$_2$ ranges roughly from 0.5 to 5 MTA. The scale of direction of CO$_2$ utilization is dependent on the techno-economics of developing appropriate engineering biosystems for algal growth and harvesting integrated with biomaterials processing (such as for high-value nutraceutical/pharmaceutical oil production followed by high-pressure hydrothermal residue processing into fertilizers, biofuels, syngas and other products).

The sixth "main mode" of CO$_2$ utilization is pressurized CO$_2$ delivery by pipeline. This mode of CO$_2$ utilization is a preferred embodiment. Typically, pressurized CO$_2$ delivery by pipeline is in high volumes over substantial distances. As this "main mode" specifies a gas specification and associated delivery technology, several specific "main modes" of CO$_2$ utilization are referenced together under this mode. All are included as preferred embodiments. Five specific types of CO$_2$ utilization by means of this method of CO$_2$ delivery are included. The first example of a potential large-scale use of high-pressure CO$_2$ delivered by a long pipeline is CO$_2$ delivered for Enhanced Oil Recovery (EOR) to the Albertine Rift of the Uganda-DRC border region, or to any future area in the region found to be oil-rich, including locations within the Lake Kivu basin itself. This mode of CO$_2$ utilization is a preferred embodiment. Oil-bearing formations are known to exist roughly from south of Lake Edward north along the border rift through to the northern boundary of Lake Albert. At present, the entire extractable oil resource is estimated to be ~2 billion barrels. Initial oil extraction operations have been developed on Lake Albert. This location is roughly 400 km northeast of the northern boundary of Lake Kivu.

The second example of a potentially large-scale use of high-pressure dehydrated CO$_2$ delivered at a distance by CO$_2$ pipeline is large-scale olivine carbonation. This use of CO$_2$ for this purpose typically would be associated with mining activity, typically involving dunite-containing nickel-rich ore bodies. Such bodies exist in the NE of Rwanda as well as in Tanzania and Burundi close to their borders with Rwanda. Olivine carbonation can be a greentech method of nickel mining when dunite deposits are available with high nickel contents and/or that contain nickel-concentrating sulfides. Olivine carbonation also can be used as a way to produce silicic acid together with iron and magnesium carbonates. This mix is useful for plant feeding as a mineral fertilizer. Uses include algal biomass fertilization focused on diatom species (many of which require silicon feeding). Utilization of CO$_2$ for the production of mineral fertilizers for diatom algal production within a Lake Kivu CO$_2$-UH is an attractive prospect in view of associated high-value nutraceuticals and pharmaceuticals export potential. This mode of CO$_2$ utilization is a preferred embodiment.

The third example is delivery of CO$_2$ for distant greenhouse horticultural utilization, (for example in Kenya). This mode of CO$_2$ utilization is a preferred embodiment.

The fourth example is delivery of CO$_2$ for use in "solar fuels" and/or "solar chemicals" (or, more generally, "renewables-based" fuels and chemicals) manufacture in connection with renewable electric power provided by solar arrays and/or by wind farms, and/or from hydropower. Pipeline export of CO$_2$ may be combined with CO$_2$-EOR, for example, in eastern components of the East African rift in both Kenya and Tanzania where there are rift oil sectors as well as zones of very high average solar radiation intensity suitable for large solar power generation arrays (see: Solargis, 2011). This mode of CO$_2$ utilization is a preferred embodiment.

The fifth example is delivery of high-pressure pipeline CO$_2$ to areas in Kenya and Tanzania where sodium carbonate and sodium carbonate-rich brines are mined and processed, and where CO$_2$ carbonation can produce a sodium bicarbonate product, and where solar radiation conditions are excellent for high-value algal biomass production in alkaline biocultures, for example *spirulina* farming. This mode of CO$_2$ utilization is a preferred embodiment.

The seventh "main mode" of CO$_2$ utilization involves cryogenic treatment to create CO$_2$ products by refrigeration, both liquid and solid CO$_2$. This mode of CO$_2$ utilization is a preferred embodiment. It is a mode of CO$_2$ preparation and delivery rather than a specified mode of CO$_2$ utilization. Therefore several specified sub-modes are included within this section as preferred embodiments. Again, refrigerated CO$_2$ may be in the form of liquefied CO$_2$ and/or as dry ice. Both of these modes are shown in FIG. 3 as process trains labeled 25 and 26, respectively. Liquefied CO$_2$ is transported across long distances in large amounts typically in thermally insulated tanker trucks and large ships similar to those used for LNG transportation. In central Africa, liquid CO$_2$ may be transported by insulated tanker truck. It may be delivered for many uses. These uses do not depend on the CO$_2$ being in a liquid form in so far as liquefaction simply can be an efficient mode for transporting CO$_2$ utilized in other forms. Uses include, for example, beverage carbonation, insect protection and fumigation (for example in grain storage), horticultural use (including algal production), wastewater pH-lowering, tank re-filling for example for local dry ice manufacturing, food product packaging, use in supercritical extraction processing, supercritical CO$_2$ dry cleaning, medical gas mixing, waterless textiles dyeing, charging of fire extinguishing systems and refrigeration systems using CO$_2$ as a thermal transfer fluid, cold pasteurization of milk, beer and juices, humane animal slaughtering, CO$_2$ fracking or frack fluid mixing, and lithium processing. Liquid CO$_2$ also may be transported by means of short-distance insulated pipelines, for example within a geographically disseminated CO$_2$-UH. An estimate for potential CO$_2$ utilization of liquid CO$_2$ in the region is ~50,000 tonnes per year.

Dry ice typically is transported in insulated and/or refrigerated delivery trucks. It also can be sub-delivered in insulated packages via motorbikes to remote off-grid locations. It is generally used as a coolant. In the area of Lake Kivu, dry ice can be utilized to supply needs for off-grid refrigeration. An example is delivery as a refrigerant with beverages served chilled and/or with spoilable meats, including fish. If beverages are supplied in kegs or other tanks, then off-grid dry ice refrigeration makes it possible to avoid the high cost of bottles and bottling. Dry ice also can be used as a non-wetting refrigerant to be used within coolers and other insulated packaging for truck transport of perishables (such as fish, milk, flowers and fruits) in trucks otherwise not equipped for cargo refrigeration. An estimate for potential $CO_2$ utilization as dry ice in the region may be as high as 50,000 tonnes per year for such uses. Altogether, therefore, a rough estimate under this sixth "main mode" of $CO_2$ utilization is ~100,000 tonnes per year in total. Dry ice production is a preferred embodiment of the invention.

The eighth "main mode" of $CO_2$ utilization is provision of unprocessed or mildly processed hot and wet (steam-rich) exhaust from oxyfuel combustion into cementing mineral carbonation in the production of concrete products and other building materials that include mineral cements. This mode of $CO_2$ utilization is a preferred embodiment. It is shown in FIG. 2 as vector 8. It also is shown in FIG. 3 as the example displayed for the representation of the process train labeled as 22. This process can use magnesium hydroxide (brucite) as the main reactant with $CO_2$ for mineralization into various Mg-carbonates. Or it can remineralize pre-carbonated nesquahonite to generate various output carbonated and hydrated mineralogies. Or it can involve $CO_2$ carbonation of conventional Portland cements in various ways. The use of magnesium is of special interest for Lake Kivu. This is because it can be obtained as a precipitated product of de-densifying return flow water treatment according to the method disclosed by the inventor in U.S. Patent Application Publication No. 20160257577 A1. The scale of $CO_2$ use by this method can be estimated at a minimum scale via the flux of precipitated magnesium associated with treatment or degassed return flow deepwater according to the above-noted method. Magnesium hydroxide stoichiometry is used as the example. Scaled to a 400 MW power output, the dissolved Mg flux through the degassing system is close to 0.6 MTA of magnesium. Given assumptions of (for example) ~90% Mg capture and ~70% partitioning of return flow into an Mg-precipitating water treatment mode, the captured Mg flux estimate is: ~0.4 MTA Mg. Using a nesquahonite composition, ($MgCO_3.3H_2O$), for a carbonation target composition, the mass flow of the associated Mg-based component of carbonated and hydrated cement is ~2.3 MTA for the hydrated Mg-based cement component. (For comparison, Rwanda's dominant cement producer, CIMERWA, produces ~0.6 MTA of dryweight Portland cement. Bateta, 2015). The rate of $CO_2$ consumption for cementitious mineralization in this process is ~0.7 MTA $CO_2$. For concrete with a mass ratio of >5 for aggregate-to-cement, this corresponds to in excess of 12 million tonnes of concrete production per year. Moreover, in concretes cementing with Mg-hydroxide ("brucite") carbonation reactions, $CO_2$ additionally can be mineralized by carbonation reactions within pozzolanic aggregates. And, as an alternative, $CO_2$ can be mineralized into ordinary cementing reactions with Portland-type cement chemistries using pressure chambers for setting and curing. Overall, there are many opportunities across a range of cementitious chemistries and pozzolan addition situations. A rough estimate of utilizable $CO_2$ from cementitious mineralization-incorporation is: ~1 MTA $CO_2$. This scale of $CO_2$ utilization represents a gigantic capacity for $CO_2$-mineralizing eco-concrete production. It represents more than a doubling of Rwanda's circa 2015 cement production capacity. $CO_2$-mineralizing eco-concrete and related building materials may be factory-made as pre-cast molded stock. Advanced $CO_2$-mineralizing eco-concretes may be developed that can be poured and set (and process remineralized) in the field. $CO_2$-mineralizing eco-concrete production are included as embodiments of the invention, capturing degassed (and post methane combustion) Lake Kivu $CO_2$ into building materials.

The ninth "main mode" of $CO_2$ utilization is urea manufacture. This mode of $CO_2$ utilization is a preferred embodiment. The potential for urea production in the context of the invention disclosed herein follows from the availability of $CO_2$ and also from the fact that a large flux of ammonium ion is present in Lake Kivu deepwater passing through the TDS. Additionally, the Air Separation Unit (ASU) component of the OXFCPS generates a large flux of purified nitrogen gas. This can be used for ammonia ($NH_3$) production, combining with $H_2$. Algal biomass processing also can use methods that allow nutrient recycling that allows capture of ammonia. At a power production level of 400 MW, the mass of urea equivalent for 100% capture and conversion of $NH_4^+$ flux present in the extracted deepwater stream is 212,000 tonnes per year. This is equivalent to ~200,000 tonnes per year of ammonia ($NH_3$). This number provides a useful reference point. For urea synthesis, $CO_2$ is used on a molar ratio basis of $CO_2/NH_3=1.0$. Therefore a flux of ~200,000 tonnes of ammonia determines an intake of ~518,000 tonnes of $CO_2$. Assuming, for example, a situation of capture and conversion of ~60% of the ammonium flux through deepwater processing, then $CO_2$ utilization is ~300,000 tonnes per year and urea production is ~400,000 tonnes per year. No disclosure of a method or system for removal of this ammonium from Lake Kivu deepwater is included herein.

The tenth "main mode" of $CO_2$ utilization is formic acid production. This mode of $CO_2$ utilization is a preferred embodiment. As referenced herein, there are many possibilities for modes of production utilizing $CO_2$ to produce formic acid. These include production with electrolytic hydrogen as a "solar chemical" or "solar fuel," and hydrothermal production using water as the hydrogen source linked with zero-valent metals redox cycling. Both $CO_2$ and formic acid also can be used for animal hide processing and as tanning agents in developing a leather products industry. A reasonable target for $CO_2$ utilization to produce formic acid is 10,000 tonnes per year. A much larger scale of production would be possible if formic acid fuel cell technologies were to become widespread.

The eleventh "main mode" of $CO_2$ utilization is production of carbon monoxide (CO). This mode of $CO_2$ utilization is a preferred embodiment. Carbon monoxide has use in metals smelting, especially tin (Sn), zinc (Zn) and iron (Fe). Several modes for CO production from $CO_2$ have been described herein, such as, for example, that of Igor Lubomirsky and his Weitzmann Institute colleagues. Lubomirsky's method creates both CO and a separated stream of $O_2$ gas useful for input into oxyfuel combustion as shown in FIG. 2, flow vector 31. Rwanda has long been a tin-producing country utilizing cassiterite-rich ores. Rwandan cassiterite ($SnO_2$) production circa 2015 is approximately 5,000 tonnes per year. Potential production capacity is much higher. A rough estimate of the amount of $CO_2$ needed to smelt cassiterite from CO is a molar ratio of ~$2CO_2/SnO_2$, corresponding to a mass ratio of ~0.58. Consequently, a rough estimate of $CO_2$ potential for CO production for cassiterite smelting is ~3,000 tonnes per year scaled to Rwandan production. Much larger amounts of carbon monoxide could be utilized for scaled-up tin production as well as for smelting of other metal oxide ores and for metals processing.

The twelfth "main mode" of $CO_2$ utilization is input of $CO_2$ into the manufacture of pyrethrum biopesticide. This mode of $CO_2$ utilization is a preferred embodiment. Pyrethrum biopesticide is sold in returnable pressurized tank bottles of $CO_2$. $CO_2$ functions in a dual mode as a greentech solvent and non-toxic propellant. Pyrethrum-in-$CO_2$ "organic" biopesticide can be used in greenhouses as a form of insecticide that additionally provides $CO_2$ plant fertilization. Organic biopesticides have a potentially very large market. In the region of Lake Kivu, this market can scale with the growth of high-intensity greenhouse cultivation with $CO_2$ yield boosting. A rough estimate for $CO_2$ utilization in this eleventh category is included as 20,000 tonnes per year.

The thirteenth "main mode" of $CO_2$ utilization is for $CO_2$ use in forest products production. This mode of $CO_2$ utilization is a preferred embodiment. This is a wide category. Many types of inputs are possible. An example is using supercritical $CO_2$, formic acid and sodium carbonate chemicals for pulping of bamboo to produce bamboo-based chemicals (such a xylitol), paper, viscose-type bamboo textiles and lignocellulosic biofuels. No estimate for a scale of utilization is presented. Bioprocessing of forest products using $CO_2$ and derivative chemicals represents a huge opportunity in the Lake Kivu region. This is in view of the great forests of the DRC existing to the west of the Lake.

The fourteenth "main mode" of $CO_2$ utilization is $CO_2$ Plume Geothermal (CPG) (and/or mixed $CO_2$—$H_2O$ plume) extraction of geothermal energy, possibly connected with $CO_2$ geosequestration. This mode of $CO_2$ utilization is a preferred embodiment. Lake Kivu is situated in a region with huge geothermal resources. No estimate for a scale of utilization is presented.

The fifteenth "main mode" of $CO_2$ utilization is fuels production by reaction of $CO_2$ with hydrogen, and/or water, and/or methane in various production processes, with or without electric power inputs, yielding methanol, dimethyl ether (DME) and other fuels and chemicals, including those produced by mini-GTL processes. This mode of $CO_2$ utilization is a preferred embodiment. Many such methods are referenced and briefly reviewed herein. Many additional methods will be developed in the future as relatively small scale GTL technologies develop and grow, and as new economically viable turnkey plant options are developed to use stranded and/or otherwise flared natural gas, and also as $CO_2$-utilizing transport fuels production options become commercially viable based on the need for energy storage from intermittent supplies of renewable electric power (that is: "solar-" or "electro-" fuels and chemicals). Methanol and DME are of particular interest in the location of Lake Kivu. They both can be utilized as a transport fuel fuels and fuel additives. DME also could be used as a cost-lowering substitute for imported bottled propane gas used in home cooking and by businesses. DME additionally can be useful for algal products processing utilizing wet algal biomass, as noted herein. Both methanol and DME also are of special global environmental interest. They represent the $CO_2$-recycling "methanol economy" vision of George Olah and colleagues. No estimate for a scale of utilization is presented.

The sixteenth "main mode" of $CO_2$ utilization is a special case of the previous main mode. It is input of hot $CO_2$ plus steam exhaust from the OXFCPS into syngas production of methanol and DME. This mode of $CO_2$ utilization is a preferred embodiment. It aims to capture heat energy from combustion for $CO_2$ utilization purposes using the outflow of the OXFCPS exhaust directly. It includes, for example, application of methods and systems of technologies of the type being developed by the Danish company Haldor Topsoe for the transformation of inputs of $CO_2$, steam and mechanical and/or electric power into outputs of methanol and oxygen gas (Hansen, 2014ab, 2015a,c,f). These methods involve designs that incorporate Solid Oxide Electrolysis Cell (SOEC) technologies into production of syngas from $CO_2$ and steam mixtures. The OXFCPS submethod and subsystem described as a part of the invention disclosed herein generates exhaust outputs of $CO_2$, steam and electric power. OXFCPS exhaust and power production therefore matches inputs to the new technology being developed by Haldor Topsoe, though not necessarily with the correct range of $H_2O/CO_2$ input ratios. However, heat capture within the system can modulate steam addition to reach targets for the input ratio of $H_2O$ to $CO_2$ into the reactor system. Extra power for $CO_2$ plus steam electrolysis via SOEC can be obtained additionally from renewable energy inputs transmitted by high-voltage wires. An extra bonus is that in an integrated system, co-produced $O_2$ can be fed into the input into oxyfuel combustion. No estimate for a scale of utilization is presented.

The seventeenth "main mode" of $CO_2$ utilization is another special case of a previous main mode. It is inputs of $CO_2$ and water into electrosynthesis of various chemicals via formate and oxalic acid ($H_2C_2O_4$) platforms such are being developed by the company Liquid Light, for example for the production on mono-ethylene glycol (MEG) for use in production of PET plastic bottles. This mode of $CO_2$ utilization is a preferred embodiment. Use of these methods with solar power inputs generates "solar chemicals" (including "solar fuels"). This displaces the use of petroleum by utilizing waste $CO_2$ as an alternate carbon source. No estimate for a scale of utilization is presented.

The eighteenth "main mode" of $CO_2$ utilization is deployment of gas fermentation biotechnologies based on the microbial Wood-Ljundahl pathway to produce acetate and other chemicals. This mode of $CO_2$ utilization is a preferred embodiment. It is done via inputs of either mixtures of $CO_2$ and $H_2$ mixtures, or $CO_2$ alone with electrons provided to the microbes ("electrobiosynthesis"). As noted herein, the company LanzaTech is developing these methods commercially. No estimate for a scale of utilization is presented.

The nineteenth "main mode" of $CO_2$ utilization is plastics manufacture with chemical incorporation of $CO_2$. This mode of $CO_2$ utilization is a preferred embodiment. Examples of technologies include the processes of $CO_2$ incorporation into $CO_2$-polyols developed by companies such as Novomer, Bayer/Covestro and Econic Technologies. $CO_2$-utilizing plastics can be produced in synergy with the production of $CO_2$-utilizing bioplastics, for example using algal biomass and/or separated algal oils. No estimate for a scale of utilization is presented.

The twentieth "main mode" of $CO_2$ utilization is high-value carbon products production. What is referred to by "carbon products" is products composed mostly (though not strictly only) of forms of elemental carbon. This mode of $CO_2$ utilization is a preferred embodiment. Examples of attractive possibilities are dense nanoporous graphene used in supercapacitors, carbon nanotubes used in new battery technologies, and carbon nanofibers used in high-strength composites. Byproduct oxygen gas can feed $O_2$ into the ASU oxygen supply for oxyfuel (as shown by flow vector 31 in FIG. 2). Using an oxygen stream that otherwise might be vented as a waste can provide an efficiency boost in cases where large quantities of $CO_2$ are utilized to produce carbon products by splitting $CO_2$ into C and $O_2$.

An additional preferred embodiment of the invention disclosed herein pertains to a co-product adjunct to $CO_2$. This is purified nitrogen in both gaseous ($N_2$) and liquefied forms ($LN_2$). Purified nitrogen is co-produced with pure oxygen gas in the submethod and subsystem of an Air Separation Unit (ASU). As shown in FIG. 2, box 1, the OXFCPS overall is defined to be an integrative combination of items 26, 27, 28 and 29, with item 27 being an ASU. An ASU is herein defined to be any technology that can obtain a supply of separated $O_2$ for infeed into oxyfuel combustion. A cryogenic air separation unit is the conventional (but by no means the only) technology component of the overall OXFCPS. If implemented in a specific design as an option within the overall scope of the invention disclosed herein, a cryogenic ASU produces an adjunct supply of liquefied nitrogen gas ($N_2$). This is shown in FIG. 2 as a part of item 27, yielding flows of liquid (or gaseous) nitrogen. These flows are shown as flow vectors 39 and 40. Flow vector 39 enters the $CO_2$-UH (via item 30 where cryo-capacities are present).

Production of cryo-liquefied nitrogen ($LN_2$ or LN2) by the ASU also is shown in FIG. 6. FIG. 6 shows a preferred embodiment utilizing this $LN_2$ both for cryo-energy storage and for cooling of a Digital Data Center (DDC). Cryogenic energy provided by the ASU in the form of $LN_2$ (or $LO_2$) can be used in the production of liquefied and/or solidified $CO_2$ within the $CO_2$-UH (FIG. 2, item 21). Also it can be utilized independently of the $CO_2$-UH, as shown by flow vector 40 in FIG. 2. The capacity of the overall system to produce and store liquefied $N_2$ in excess of that used within the ASU (for energy recycling efficiency) can be considered as an adjunct capacity assisting powerplant efficiency as well as $CO_2$ utilization. Utilization of cold nitrogen gas also can supply Digital Data Center (DDC) cooling. This is illustrated herein in FIG. 6 and its accompanying text. Both cold $N_2$ and $LN_2$ also may be used for DDC cooling. Use of cold nitrogen produced by OXFCPS operations as a utilization of otherwise wasted material and associated cryo-energy can assist realization of DDC industrialization by lessening the (often very substantial) electric power draw of such a facility. Nitrogen gas also has numerous other productive uses, for example in algal production where it provides a $N_2$ source for diazotrophic (nitrogen-fixing) cyanobacteria. It also is useful for algal culture sparging and related uses for removal of growth-inhibiting $O_2$. Nitrogen gas also may provide basic chemical inputs for various purposes into a large number of types of chemical synthesis reactions. FIG. 6 shows a preferred embodiment (as item 13) providing a source of "warm" nitrogen gas as an outflow of cold nitrogen into DDC cooling. This cooling is fed either directly from stored $LN_2$ (FIG. 6, item 11) or from cold nitrogen gas after being used in recovery of stored cryo-energy (cf, FIG. 6, item 18c feeding an outflow as item 12). More generally, the overall method and system provides nitrogen gas as outflow (FIG. 6, item 12) that is available for utilization for any purposes.

An additional adjunct capacity of the invention is production of Liquefied Natural Gas (LNG) and associated forms of Natural Gas (NG) that can be produced and sold as a consequence of the capability to separate natural gas (see FIG. 6, item 40) from an inflow of mixed NG and $CO_2$ from Lake Kivu (FIG. 6, item 38). (NB: NG deriving from Lake Kivu is biogas.) These associated forms of NG are highly useful for various purposes. These can be produced and sold as adjunct capacities of the invention in preferred embodiments. They are: (i) Compressed Natural Gas (CNG, see Wikipedia entry: https://en.wikipedia.org/wiki/Compressed_natural_gas), and Adsorbed Natural Gas (ANG, see Wikipedia entry: https://en.wikipedia.org/wiki/Adsorbed_natural_gas). The capacity to produce NG in any of these forms (LNG, CNG, ANG) derives from a $CO_2$ separation processing function within the $CO_2$-UH (FIG. 6, Box 4). This $CO_2$ separation processing function produces dry ice and/or $LCO_2$. It is indicated in FIG. 6 circumscribed within Box 36 (and including items 35, 37, 39 and 40). This adjunct capacity for NG production is a part of the cryogenic capacities, including the cryogenic fluids and cryo-energy storage capacities, of the invention (FIG. 6, Box 28), and is a preferred embodiment. Such an adjunct capacity has potent potential in the locus of Lake Kivu for purposes such as: (i) providing bottled NG (CNG and/or ANG) for home and business cooking and other similar uses of heat energy from NG combustion; (ii) providing bottled NG (CNG and/or ANG) as a source of fuel for internal combustion engines such as, for example, those in motorcycles, cars and trucks modified to run on NG. Of course, the capacity to produce LNG for $CO_2$ separation processing and cryo-energy storage also allows LNG to be sold as well as used as a stored energy "backup" reservoir of both cryo-energy and chemical energy for powerplant operations backup purposes such as may be necessary, for example, in situations of maintenance and improvements of extractive degassing equipment.

While the invention has been described in detail and with reference to specific examples thereof, it will be apparent to one skilled in the art that various changes and modifications can be made therein without departing from the spirit and scope thereof.

REFERENCES CITED 1. 2b1sr Consulting, (2014). BP considers to invest $1 billion in Duqm acetic acid. Online: http://www.2b1stconsulting.com/bp-mulls-over-world-scale-petrochemical-complex-in-oman/
2. 8 Rivers, (2015). Coal syngas combustor development for high-pressure, oxy-fuel supercritical $CO_2$ cycle applications (DE-FE0023985). 8 Rivers slide deck presentation, 2015 University Turbine Systems Research Workshop, November 3, online: http://netl.doe.gov/File%20Library/Events/2015/utsr/Tuesday/Fetvedt.pdf
3. Aasberg-Petersen, Nielsen, C. S., Dybkjaer, I., and Perregaard, J., (2011). Large scale methanol production from natural gas. Haldor Topsoe Corporate brochure, online: http://www.topsoe.com/sites/default/files/topsoe_large_scale_methanolprodpaper.ashx_.pdf
4. Abbot, P. S., (undated). History of *eucalyptus* oil. Online on www.eucalyptusoil.com, http://www.eucalyptusoil.com/schools-info/39-book
5. ABC, (2014). Doubling of Australian pyrethrum production tipped. Australian Broadcasting Corporation (with audio interview), online: http://www.abc.net.au/news/2014-02-03/pyrethrum-insecticide-crops-botanical-resources-australia/5234186
6. Abcarian, L., (2015). Utah facility reinforces Houweling's position as a greenhouse industry leader. The Produce News, Mar. 4, 2015, online: http://www.houwelings.com/blog/utah-greenhouse-project-update
7. Abdalbasit, M., Gasmalla, A., Yang, R., and Hua, X., (2014). *Stevia rebaudiana* Bertoni: an alternative sugar replacer and its application in food industry. Food Eng. Rev., 6(4): 150-162
8. Abdo, R. F., Pedro, H. T. C., Koury, R. N. N., Machado, L., Cpimbra, C. F. M., and Porto, M. P., (2015). Performance evaluation of various cryogenic energy storage systems. Energy, 90: 1024-1032
9. Abeinomugisha, D., and Kasande, R., (2012). Tectonic control on hydrocarbon accumulation in the intracontinental Albertine Graben of the East Africa rift system, chapter 9, pp. 209-228 in: D. Gao, (ed.), *Tectonics and Sedimentation: Implications for Petroleum Systems*. AAPG Memoir 100.
10. Abou-Arab, A. E., Abou-Arab, A. A., Abu-Salem, M. F., (2010). Physico-chemical assessment of natural sweeteners steviosides produced from *Stevia rebaudiana bertoni* plant. Ar. J. Food Sci., 4(5): 269-281.
11. Ackiewicz, M., Foster, C., Bonjoly, D., Ramsak, P., Al-Eidan, A., Surridge, T., and Sharman, P., (2013). Final phase II report by the CSLF task force on $CO_2$ utilization options. Carbon Sequestration Task Force, online: http://www.cslforum.org/publications/documents/CO2UtilizationOptions_Phase2FinalReport.pdf
12. Adams, B. M., (2015). On the power performance and integration of Carbon dioxide Plume Geothermal (CPG) electrical energy production. PhD Thesis, University of Minnesota, USA, online: https://conservancy.umn.edu/bitstream/handle/11299/175183/Adams_umn_0130E_15893.pdf?sequence=1&isAllowed=y
13. Adams, B. M., Kuehn, T. H., Bielicki, J. M., Randolph, J. B., and Saar, M. O., (2015). A comparison of electric power output of $CO_2$ Plume Geothermal (CPG) and brine geothermal systems for varying reservoir conditions. Applied Energy, 140: 365-377.
14. Adams, B. M., Kuehn, T. H., Bielicki, J. M., Randolph, J. B., and Saar, M. O., (2014). On the importance of the thermosiphon effect in CPG ($CO_2$ plume geothermal) power systems. Energy, 69: 409-418.
15. ADEME, (2014). Valorisation chimique du $CO_2$. Agence De l'Environment et de la Maitrise de l'Energie (France: French Environment and Energy Management Agency), report, 148pp, online: http://www.ademe.fr/sites/default/files/assets/documents/valorisation-chimique-co2-etat-lieux-2014-rapport-final.pdf
16. Advanced Research International, (2006). Basin oriented strategies for $CO_2$ Enhanced Oil Recovery. Report to the US Department of Energy, online: http://www.adv-res.com/pdf/Basin%20Oriented%20 Strategies%20-%20Mid-Continent.pdf
17. Advantage Environment, (2013). Industrial symbiosis grows tomatoes. Advantage Environment, Online: http://advantage-environment.com/livsmedel/industrial-symbiosis-grows-tomatoes/
18. Afreen, F., Zobayed, S. M. A., and Kozai, T., (2002). Photoautotrophic culture of *Coffea arabusta* somatic embryos: development of a bioreactor for large-scale plantlet conversion from cotyledonary embryos. Ann. Botany, 90: 21-29.
19. African Transformation Report, (2014). Growth with DEPTH. African Center for Economic Transformation. Online: http://africantransformation.org/wp-content/uploads/2014/02/2014-african-transformation-report.pdf Summary side deck: http://fonctionpublique.gouv.cd/wp-content/uploads/2014/10/2_Edward-K.-Brown.pdf
20. Agarwal, A., Bakshi, S. R., and Lahiri, D., (eds.), (2010). *Carbon Nanotubes: Reinforced Metal Matrix Composites*. CRC Press, pp. 325.
21. Agarwal, A. S., Zhai, Y., Hill, D., and Sridhar, N., (2011). The electrochemical reduction of carbon dioxide to formate/formic acid: engineering and economic feasibility. ChemSusChem, 4: 1301-1310.
22. Agrium, (2015). Borger nitrogen operations. Corporate information online: http://www.agrium.com/sites/default/files/borger broch_2015.pdf
23. Ahn, Y., Bae, S. J., Kim, M., Cho, S. K., Baik, S., Lee, J. I., and Cha, J. E., (2015). Review of supercritical $CO_2$ power cycle technology and current status of research and development. Nucl. Eng. Technol., 47: 647-661.
24. Air Liquide, (undated). $CO_2$ use in cheese production. Air Liquide product advisory note, online: http://www.air-liquide.gr/en/air-liquide-is-a-world-leader-in-industrial-and-medical-gases/food-beverage/co2-use-in-cheese-production.html
25. Aitkin, G. R., and Poliakoff, M., (2009). A critical look at reactions in class-I and class-II gas-expanded liquids using $CO_2$ and other gases. Green Chem., 11: 1083-1100
26. Akanda, M. J. H., Sarker, M. Z., Ferdosh, S., Manap, M. Y. A., Rahman, N. N. N. A., Kadir, M. O. A., (2012). Applications of supercritical fluid extraction (SFE) of palm oil and oil from natural sources. Molecules, 17: 1764-1794.
27. Akgun, N. A., Gece, G., and Tekneci, E., (2013). Strategies to obtain tocopherols, phytosterols and squalene from deodorizer distillates and acid oils using supercritical fluids. Recent Res. Devel. Lipids, 9: 67-84
28. Akinfiev, N., McGovern, J., and Yantovski, E., (2005). Zero emissions power generation with $CO_2$ reduction by fayalite. Int. J. Thermodynamics, 8(3): 155-157, online: http://ijoticat.com/article/view/1034000156
29. Alberico, E. and Nielsen, M., (2015). Towards a methanol economy based on homogeneous catalysis: methanol to $H_2$ and $CO_2$ to methanol. Chem. Comms., 51(31), DOI: 10.1039/C4CC09471A
30. Alberico, E., Sponholz, P., Cordes, C., Nielsen, M., Drexler, H.-J., Baumann, W., Junge, H., and Beller, M., (2013). Selective hydrogen production from methanol with a defined pincer catalyst under mild conditions. Angew. Chem. Int. Ed., 52(52): 14162-14166.
31. Alboudwarej, H., et al., (2006). Highlighting heavy oil. (Schlumberger) Oilfield Review, 18(2)/Summer 2006, pp. 34-53, online: https://www.slb.com/resources/publications/industry_articles/oilfield_review/2006/or2006sum03highlighting_heavyoil.aspx
32. Alford, B., (2014). Perspectives on $CO_2$ EOR. Maersk Oil slide deck presentation, online: http://www.slideshare.net/globalccs/day-2-panel-4-3-alford-map-removed
33. Algal Biomass Organization, (2015). Algae industry project book 2015. Online: http://algaebiomass.org/wp-content/gallery/2012-algae-biomass-summit/2015/07/ABO_project_book_July2015.pdf
34. ALGIX, (2014). ALGIX—formulating the potential of algae. Algix corporate slide deck presentation, online: http://www.adem.state.al.us/misc/npsconf2014/7-EricGobert.pdf
35. Ali, M. B., Hahn, E.-J., and Paek, K.-Y., (2005). $CO_2$-induced total phenolics in suspension cultures of *Panax ginseng* C. A. Meyer roots: role of antioxidants and enzymes. Plant Physiol. And Biochem., 43: 449-547.
36. Ali, M. B., Hahn, E.-J., and Paek, K.-Y., (2007). Methyl jasmonate and salycilic acid induced oxidative stress and accumulation of phenolics in *Panax ginseng* bioreactor root suspension cultures. Molecules, 12: 607-621.
37. Ali-Nehari, A., Kim, S.-B., Lee, Y.-B., Lee, H.-Y., and Chun, B.-S., (2012). Characterization of oil including astaxanthin extract from krill (*Euphausia superba*) using supercritical carbon dioxide and organic solvent as comparative method. Korean J. Chem. Eng., 29(3): 329-336, DOI: 10.1007/s11814-011-0186-2.
38. Alissandratos, A., and Easton, C. J., (2015). Biocatalysis for the application of $CO_2$ as a chemical feedstock. Beilstein J. Inorg. Chem., 11 2370-2387.
39. Al-Jarba, M., and Al-Anazi, B. D., (2009). A Comparison Study of the of the $CO_2$—Oil Physical Properties Literature Correlations Accuracy Using Visual Basic Modelling Technique. Nafta Scientific J., 60(5): 288-291 Online: http://hrcak.srce.hr/index.php?show=clanak&id_clanak_jezik=61657&lang=en
40. Allam, R. J., (2013). NET Power's $CO_2$ cycle: the breakthrough that CCS needs. Modern Power Systems, 10 Jul. 2013, online: http://www.modernpowersystems.com/features/featurenet-powers-co2-cycle-the-breakthrough-that-ccs-needs
41. Allam, R. J., Fetvedt, J. E., Forrest, B. A., and Freed, D. A., (2014). The oxy-fuel, supercritical $CO_2$ Allam cycle: new cycle developments to produce even lower-cost electricity from fossil fuels without atmospheric emissions. GT2014-26952, pp. V03BT36A016, ASME Turbo Expo 2014: Turbine Technical Conference and Exhibition, Dusseldorf, Germany, Jun. 16-20, 2014.
42. Allam, R. J., Palmer, M. R., Brown, G. W. Jr., Fetvedt, J., Freed, D., Nomoto, H., Itoh, M., Okita, N., and Jones, C. Jr., (2013). High efficiency and low cost of electricity generation from fossil fuels while eliminating atmospheric emissions, including carbon dioxide. Energy Procedia, 37: 1135-1149.
43. Allhart, T., (2016). This scientist's got the power(plant) in his hands. GE Reports, Mar. 15, 2016, online: http://www.gereports.com/this-scientists-got-the-power-plant-in-his-hands/
44. Allis, R., Chidsey, T., Gwynn, W., Morgan, C., White, S., Adams, M., and Moore, J., (undated). Natural CO2 reservoirs on the Colorado Plateau and the Southern Rocky Mountains: candidates for CO2 sequestration. Online: http://www.netl.doe.gov/publications/proceedings/01/carbon_seq/6a2.pdf
45. Al-Kalbani, H., Xuan, J., Garcia, S., and Wang, H., (2016). Comparative energetic assessment of methanol production from $CO_2$: chemical versus electrochemical process. Applied energy, 165: 1-13.
46. Al-Mashhadani, M. K. H., Hemeka Bandulasena, H. C. and Zimmerman, W. B., (2012). $CO_2$ mass transfer induced through an airlift loop by a microbubble cloud generated by fluidic oscillation. Ind. Eng. Chem. Res., 51: 1864-1877
47. Al-Mjeni, R., et al., (2010/2011). Has the time come for EOR? Oilfield Review, Winter 2010/2011: volume 22, no. 4, pp. 16-35. Online: https://www.slb.com/~/media/Files/resources/oilfield_review/ors10/win10/eor.pdf
48. Al-Tabba, A. (2013). Reactive magnesia cement. Chapter 19, pp. 523-543 in: Pacheco-Torgal et al., (eds), *Eco-Efficient Concrete*. Elsevier
49. Allen, L. H. Jr., Baker, J. T., and Boote, K. J., (1996). The $CO_2$ fertilization effect: higher carbohydrate production and retention as biomass and seed yield. Pp. 65-100 in: F. A. Bazzaz and W. G. Sombroek (eds.). *Global Climate Change and Agricultural Production*. FAO, pp. 345.
50. Allen, S. D.; Byrne, C. M.; Coates, G. W. Carbon Dioxide as a Renewable C1 Feedstock: Synthesis and Characterization of Polycarbonates from the Alternating Copolymerization of Epoxides and $CO_2$. ACS Symp. Ser., 921: 116-129.
51. Almqvist, E., (2003). *History of Industrial Gases*. Springer, pp. 472
52. Alvarado, E., Torres-Martinez, L. M., Fuentes, A. F., and Quintana, P., (2000). Preparation and characterization of MgO powders obtained from different magnesium salts and the mineral dolomite. Polyhedron, 19: 2345-2351.
53. Alverez-Guerra, M., Albo, J., Alvarez-Guerra, E., and Irabien, A., (2015). Ionic liquids in the electrochemical valorization of $CO_2$. Energy & Environmental Rev., 8: 2574-2599.
54. Amer, A. M., (2010). Hydrometallurgical processing of low grade Egyptian magnesite. Physicochem. Probl. Miner. Process., 44: 5-12.
55. Ampelli, C., Perathoner, S., and Centi, G., (2015). $CO_2$ utilization: an enabling element to move to a resource- and energy-efficient chemical and fuel production. Phil. Trans. R. Soc. A 373(2037), DOI: 10.1098/rsta.2014.0177
56. An, L. V., Frankow-Lindberg, B. E., and Lindberg, J. E., (2003). Effect of harvesting interval and defoliation on yield and chemical composition of leaves, stems and tubers of sweet potato (*Ipomoea batatas* L. (Lam.)) plant parts. Field Crop Res., 82: 49-58.
57. Anastas, P. T., Leitner, W., and Jessop, P. G., (2014). *Green Solvents. Handbook of Green Chemistry, Volume 4: Supercritical Solvents*. Wiley, pp. 400.
58. Anderson, J. M., Allen, S., Camargo, R., and Rosenvasser, D., (2012). Renewable footwear systems based on polyols derived from waste carbon dioxide. Poster presentation, American Chemistry Council, online: http://www.huntsman.com/polyurethanes/Media%20Library/a_MC1CD1F5AB7B B1738E040EBCD2B6B01F1/Products_MC1CD1F5AB8081738E040EBCD2B6B01F1/files/CPI2012%20Huntsman-Novomer%20Revised%2008142012.pdf http://www.americanchemistry.com/Media/PressReleasesTranscripts/RelatedPDF/CPI-Congratulates-Paper-and-Poster-Winners-from-2012-Polyurethanes-Technical-Conference.pdf
59. Anderson J. M., Shepherd, P., and Valente, R., (2013). Catalytic transformation of waste $CO_2$ into valuable producrs. US DOE Final scientific/Technical Report DE-FE0002474, online: http://www.osti.gov/scitech/servlets/purl/1127075
60. Anderson, L. L., Armstrong, P. A., Repasky, J. M., and Stein, V. E., (2011). Enabling clean coal power generation: ITM oxygen technology. Air Products conference paper, International Pittsburgh Coal Conference 2011, Pittsburgh, Pa., USA, Sep. 12-15, 2011, online: http://www.airproducts.hu/~/media/Files/PDF/industries/enabling-clean-coal-power-generation-280-11-005-GLB.pdf?la=hu-HU
61. Anderson, L. L., Armstrong, P. A., Broekhuis, R. R., Carolan, M. F., Chen, J., Hutcheon, M. D., Lewinsohn, C. A., Miller, C. F., Repasky, J. M., Taylor, D. M., and Woods, C. M., (2011). Advances in ion transport membrane technology for oxygen ad syngas production. Solid State Ionics, DOI: 10.1016/j.ssi.2015.11.010
62. Anderson, R. A., (2005, editor). *Algal Culturing Techniques*. Elsevier, 589 pp.
63. Anderson, R., (2001). Development of a unique gas generator for a non-polluting power plant. EISG report on project EISG 99-20, California Energy Commission Grant #99-20, online: http://cdm16254.contnttdm.oclc.org/cdm/ref/collection/p178601ccp2/id/2541
64. Anderson, R., and Bischoff, R., (2003). Mobile propulsion and fixed power production with near-zero atmospheric emissions. Conference paper, Tri-Service Power Expo 2003, Norfolk, Va., USA, Jul. 15-17, 2003, online: http://www.dtic.mil/ndia/2003triservice/bisl.pdf
65. Anderson, R. E., Doyle, S. E., and Pronske, K. L., (2004). Demonstration and commercialization of zero-emmision power plants. Conference paper, 29th International Technical Conference on Coal Utilization & Fuel Systems, Apr. 18-22, 2004, Clearwater, Fla., USA. Online: https://www.researchgate.net/publication/228974521_Demonstration_and_commercialization_of_zero-emission_power plants
66. Anderson, R., Hustad, C., and Hollis, R., (2014). Oxy-fuel turbo machinery development for energy intensive industrial applications. Energy Procedia, 63: 511-523
67. Anderson, R. E., MacAdam, S., Viteri, F., Davies, D. O., Downs, J. P., and Paliszewski, A., (2008). Adapting gas turbines to zero-emission oxy-fuel power plants. GT2008-51377, Proceedings of the ASME Turbo Expo 2008 for Land, Sea and Air, June 9-13, Berlin, Germany, online: http://diogenesinstitute.org/images/2/29/Adapting_Gas_Turbines_to_Zero_Emission_Oxy_Final.pdf
68. Anderson, R. E., Viteri, F., Hollis, R., Hebbar, M., Downs, J. P., Davies, D. O., and Harris, M., (2009). Adapting gas turbines to zero-emission oxy-fuel power plants. GT2009-59995 pp. 469-479, Proceedings of the ASME Turbo Expo 2009 for Land, Sea and Air, June 8-12, Orlando, Fla., USA, online: http://proceedings.asmedigitalcollection.asme.org/proceeding.aspx?articleid=1608542
69. Anderson, R. E., Viteri, F., Hollis, R., Keating, A., Shipper, J., Merrill, G., Schillig, C., Shinde, S., Downs, J. P., Davies, D. O., and Harris, M., (2010). Adapting gas turbines to zero-emission oxy-fuel power plants. GT2010-23001, pp. 733-743, Proceedings of the ASME Turbo Expo 2010 for Land, Sea and Air, June 14-18, Glasgow, UK, online: http://proceedings.asmedigitalcollection.asme.org/proceeding.aspx?articleid=1608542
70. Aneke, M., and Wang, M., (2015). Process analysis of pressurized oxy-coal power cycle for carbon capture application integrated with liquid air power generation and binary cycle engines. Applied Energy, 154: 556-566.
71. Angelino, G., (1968). Carbon dioxide condensation cycles for power production. ASME Paper No. 68-GT-23
72. Ansarizadeh, M., Dodds, K., Gurpinar, O., Kalfa, U., Ramakrishnan, T. S., Sacuta, N., and Whittaker, S., (2015). Carbon dioxide—challenges and opportunities. Oilfield Rev., 27(2): 36-50.
73. Antares Offshore LLC, website: http://www.antaresoffshore.com/projects.php (showing an engineering diagram: http://www.antaresoffshore.com/images/kivuwatlarge.jpg; http://www.antaresoffshore.com/images/floaterimage6.jpg)
74. Anton, D., (2015). Advancing commercialization of algal biofuels through increased biomass productivity and technical integration. DOE Bioenergy Technologies Office (BETO) 2015 Project Peer Review (of Cellana), online: http://www.energy.gov/sites/prod/files/2015/04/f21/algae_anton_135250.pdf
75. Apache, (undated). $CO_2$ EOR. Apache Corporation public information brochure, online: http://www.apachecorp.com/Operations/Canada/CO2_EOR/index.aspx
76. Appel, A. M., Bercaw, J. E., Bocarsly, A. B., et al., (2013). Frontiers, opportunities, and challenges in biochemical and chemical catalysis of $CO_2$ fixation. Chem. Rev., 113(8): 6621-6658.
77. Arab, A., Bertau, M., Mischo, H., and Merkel, B., (2014). Enhanced in situ leaching (EISLEACH) mining by means of supercritical carbon dioxide—TOUGHREACT modeling. Pp. 190-194, in: Sui et al., (eds.), *An Interdisciplinary Response to Mine Water Challenges*. China Univ. of Sci. Technol., ISBN 978-7-5646-2437-8, online: https://www.imwa.info/docs/imwa_2014/IMWA2014_Arab_190.pdf
78. Arab, A., Bertau, M., Mischo, H., and Merkel, B., (2015). Enhanced in-situ leaching mining—modeling with TOUGHREACT. Online: http://www.researchgate.net/publication/272163827_EISLEACH
79. Arakawa, H., Aresta, M., et al., (2001). Catalysis research of relevance to carbon management: progress, challenges and opportunities. Chem. Rev., 101: 953-996.
80. Araujo, O. de Q., de Medeiros, J. L., and Alves, R. M. B., (2014). $CO_2$ utilization: a process systems engineering vision. Chapter 2, pp. 35-88, in: C. d. R. V. Morgado and V. P. P. Esteves (eds.), *$CO_2$ Sequestration and Valorization*. Intech, online: http://www.intechopen.com/books/co2-sequestration-and-valorization
81. Aresta, M., (2016). ICCDU and JCOU: two different entities, one common goal. J. $CO_2$ Util., January 2016 online preprint.
82. Aresta, M., (2006). Carbon dioxide reduction and uses as a chemical feedstock. Chapter 1, pp. 1-41, n: W. B. Tolman (ed.), *Activation of Small Molecules*. Wiley-VCH
83. Aresta, M., (2010, editor). *Carbon Dioxide as Chemical Feedstock*. Wiley-VCH, pp 414.
84. Aresta, M., (2003, editor). *Carbon Dioxide Recovery and Utilization*. Springer, pp. 408.
85. Aresta, M., and Dibenedetto, A., (2007). Utilization of $CO_2$ as a chemical feedstock: opportunities and challenges. Dalton Trans., 28: 2975-2992.
86. Aresta, M., and Dibenedetto, A., (2015). *Reaction Mechanisms in Carbon Dioxide Conversion*. Springer, pp. 413.
87. Aresta, M., and Forti, G., (1987/2011). *Carbon Dioxide as a Source of Carbon: Biochemical and Chemical Uses*. NATO Sci. Ser. (book 206), pp. 441.
88. Aresta, M. and van Eldik, R., (2014, editors). *$CO_2$ Chemistry*. Volume 66 of the series: *Advances in Inorganic Chemistry*. Academic Press/Elsevier, pp. 416
89. Aresta, M., Dibenedetto, A., and Angelini, A., (2013). The changing paradigm in $CO_2$ utilization. J. $CO_2$ Util., 3-4: 65-73.
90. Aresta, M., Dibenedetto, A., and Angelini, A., (2014). Catalysis for the valorization of exhaust carbon: from $CO_2$ to chemicals, materials and fuels: technological use of $CO_2$Chem. Revs., 114(3): 1709-1742.
91. Aresta, M., Dibenedetto, A., and Angelini, A., (2015). The use of solar energy can enhance the conversion of carbon dioxide into energy-rich products: stepping toward artificicial photosynthesis. Phl. Trans. R. Soc. A 371: 20120111. http://dx.doi.org/10.1098/rsta.2012.0111
92. Aresta, M., Dibenedetto, A., Corone, M., Colonna, T., and Fragale, C., (2005). Production of biodiesel from microalgae by supercritical $CO_2$ extraction and thermochemical liquefaction. Environ. Chem. Letts, 3(3): 136-139.
93. Aresta, M., Dibenedetto, A., and Quaranta, E., (2015). *Reaction Mechanisms in Carbon Dioxide*. Springer.
94. Arevalo-Galarza, L., Neumann, G., and Follett, P. A., (2010). Potential for metabolic stress disinfection and disinfestation (MSSD) treatment to disinfect commodities of white peach scale and other surface pests. Proc. Hawaiian Entomological Soc., 42: 49-52.
95. Arkhangelskaya, A., and Taylor, I., (2014). What Africa needs. Valdai Papers #05. Online: http://valdaiclub.com/publication/74160.html
96. Armannsson, H., (2003). $CO_2$ emission from geothermal plants. International Geothermal Conference, Reykjavik, Iceland, September, 2003, online: https://www.researchgate.net/profile/Halldor_Armannsson/publication/

228405084_CO2_emission_from_geothermal_plants/links/0c96053bd2a3b789c9000000.pdf 97. Armannsson, H., Fridriksson, T., Kristjansson, B. R., (2005). $CO_2$ emissions from geothermal power plants and natural geothermal activity in Iceland. Geothermics, 34: 286-296.

98. Armitage, H., (2015). A carbon capture strategy that pays. Science, August 19th DOI: 10.1126/science.aad1644 online: http://www.sciencemag.org/news/2015/08/carbon-capture-strategy-pays 99. Armstrong, T., (2013). An overview of global cement sector trends. International Cement Review slide deck presentation, online: http://www.ficem.org/boletines/ct-2013/presentaciones2013/1-EXPERTOS/2_THOMAS-ARMSTRONG/ICR-FICEM-Presentation-Handout-30Aug13.pdf 100. Arniza, M. Z., Hoong, S. S., Idris, Z., Yeong, S. K., Hassan, H. A., Din, A. K., and Choo, Y. M., (2015). Synthesis of transesterified palm olein-based polyol and rigid polyurethanes from this polyol. J. Am. Oil Chem. Soc., 92: 234-255.

101. ARPA-E. Dioxide Materials (December 2013 overview), online: http://www.arpae-summit.com/paperclip/exhibitor_docs/14AE/Dioxide_Materials_199.pdf http://www.arpae-summit.com/paperclip/exhibitor_docs/15AE/Dioxide_Materials_347.pdf 102. Asadi, M., Kumar, B., Behranginia, A., Rosen, B. A., Baskin, A., Repnin, N., Pisasale, D., Phillips, P., Zhu, W., Haasch, R., Klie, R. F., Kral, P., Abiade, J., and Salehi-Khojin, A., (2014). Robust carbon dioxide reduction on molybdenum disulphide edges. Nature Comms., 5, article #4470. DOI: 10.1038/ncomms5470.

103. Ashford, D. L., Gish, M. K., Vannucci, A. K., Brennaman, M. K., Templeton, J. L., Papanikolas, J. M., and Meyer, T. J., (2015). Molecular chromophore-catalyst assemblies for solar fuel applications. Chem. Revs., DOI: 10.1021/acs.chemrev.5b00229

104. Asian Scientist, (2014). Recycling $CO_2$ into Omega-3. Asian Scientist, Nov. 14, 2014, online: http://www.asianscientist.com/2014/11/tech/recycling-co2-omega-3/

105. Atrens, A., D., (2011). Carbon-dioxide-based engineered geothermal systems. PhD Thesis, University of Queensland, Australia, 120pp.

106. Atrens, A. D., and Gurgenci, H., (2013). Design of $CO_2$-based geothermal power plant for transient reservoir dry-out- or enhanced water recovery. In: Proceedings of the 38th Workshop on Geothermal Reservoir Engineering. Stanford University, California, USA, online: http://www.geothermal-energy.org/pdf/IGAstandard/SGW/2013/Atrens.pdf 107. Atrens, A., D., Gurgenci, H., and Rudolph, V., (2014). Water condensation in carbon-dioxide-based engineered geothermal power generation. Geothermics, 51: 397-405.

108. Atrens, A., D., Gurgenci, H., and Rudolph, V., (2011a). Economic optimization of a $CO_2$-based EGS power plant. Energy and Fuels, 25(8): 3765-3775

109. Atrens, A., D., Gurgenci, H., and Rudolph, V., (2011b). Removal of water for carbon-dioxide-based EGS operation. Proceedings of the 36th Workshop on Geothermal Reservoir Engineering. Stanford University, California, USA, online: https://pangea.stanford.edu/ERE/pdf/IGA-standard/SGW/2011/atrens.pdf 110. Atrens, A., D., Gurgenci, H., and Rudolph, V., (2010a). Electricity generation using a carbon-dioxide thermosiphon. Geothermics, 39(2): 161-169

111. Atrens, A., D., Gurgenci, H., and Rudolph, V., (2010b). Economic analysis of a $CO_2$ thermosiphon. Proceedings of the World Geothermal Congress, Apr. 25-29, 2010, Bali, Indonesia, online: http://www.geothermal-energy.org/pdf/IGAstandard/WGC/2010/3136.pdf 112. Atrens, A., D., Gurgenci, H., and Rudolph, V., (2009a). $CO_2$ thermosiphon for competitive geothermal power generation. Energy and Fuels, 23(1): 553-557

113. Atrens, A., D., Gurgenci, H., and Rudolph, V., (2009b). Exergetic performance and power conversion of a $CO_2$ thermosiphon. Australian Geothermal Energy Conference 2009, online: http://www.geothermal-energy.org/pdf/IGAstandard/AGEC/2009/Atrens_et_al_2009.pdf 114. Atrens, A., D., Gurgenci, H., and Rudolph, V., (2009c). Exergy analysis of a $CO_2$ thermosiphon. Proceedings of the 34th Workshop on Geothermal Reservoir Engineering. Stanford University, California, USA, online: https://pangea.stanford.edu/ERE/db/IGAstandard/record_detail.php?id=5562

115. Atti-Santos, A. C., Rossato, M., Serafini, L. A., Cassel, E., and Moyna, P., (2005). Extraction of essential oils from lime (Citrus latifolia Tanaka) by hydrodistillation and supercritical carbon dioxide. Braz. Arch. Biol. Technol., 48(1): 155-160.

116. Atwell, B., J., Kriedemann, P. E., Turnbull, C. G. N., and Farquhar, G., (1999 eds.) *Plants in Action: Adaptation in Nature, Performance in Cultivation*. Chapter 13.4: Horticultural applications of $CO_2$ enrichment. Online: http://plantsinaction.science.uq.edu.au/edition1/?q=content/title-page Chapter 13, section 4: http://plantsinaction.science.uq.edu.au/edition1/?q=content/13-4-horticultural-applications-co2-enrichment 117. Audo, M., Paraschiv, M., Queffelac, C., Louvet, I., Hemez, J., Fayon, F., Lepine, J., Legrand, J., Tazerout, M., Chailleux, E., Bujoli, B., (2015). Subcritical hydrothermal liquefaction of microalgae residues as a green route to alternative road binders. ACS Sustainable Chem. & Eng., 3: 583-590.

118. Augustin, M. A., and Hemar, Y., (2009). Nano- and micro-structured assemblies for encapsulation of food ingredients. Chem. Soc. Revs., 38(4): 902-912.

119. Austin, B. T., and Sumathy, K., (2011). Transcritical carbon dioxide heat pump systems: a review. Renewable and Sustainable energy Systems, 15: 4013-4029.

120. Austrian Institute of Technology (2015). Industrialization agenda slide deck presentation, online: https://f69aa27b9b6c6702e27b-ffbfdeddb5f7166a1729dfea28599a63.ssl.cf3.rackcdn.com/raw_60736_fa7bde81590d698ce742bc2ae0456329_DMC%20Synthesis_Info%20v12.pdf 121. Ausubel, J. H., (2004). Big green energy machines. The Industrial Physicist, October/November 2004, pp. 20-24, online: http://phe.rockefeller.edu/docs/BigGreen.pdf 122. Ausubel, J. H., (1999). Five worthy ways to spend large amounts of money for research on environment and resources. The Bridge (National Academy of Engineering), Fall 1999, pp. 4-16, online: https://www.nae.edu/Publications/Bridge/EngineeringChallenges/FiveWorthyWaystoSpendLargeAmountsofMoneyforResearchonEnvironmentandResources.aspx Also, modified: http://phe.rockefeller.edu/five_worthy_ways/

123. Azam, A., Khan, I., Mahmood, A., and Hameed, A., (2013). Yield, chemical composition and nutritional quality responses of carrot, radish and turnip to elevated carbon dioxide. J. Sci. Food Agric., 93(13): 3237-3244.

124. Aznar-Sanchez, J. A., Galdeano-Gomez, E., and Perez-Mesa, J. C., (2011). Intensive horticulture in Almeria (Spain): a counterpoint to current European rural policy strategies. J. Agrarian Change, 11(2): 241-261.

125. Azzolina, N. A., Nakles, D. V., Gorecki, C. D., Peck, W. D., Ayash, S. C., and Melzer, L. S., (2015). $CO_2$ storage associated with $CO_2$ enhanced oil recovery: a statistical analysis of historical operations. Int. J. Greehouse Gas Control, 37: 374-397

126. Bach, E., Cleve, E., and Schollmeyer, E., (2002). Past, present and future of supercritical fluid dyeing technology—an overview. Rev. Prog. Coloration Related Topics, 32(1): 88-102.

127. Badwal, S. P. S., Giddey, S. S., Munnings, C., Bhatt, A. I., and Hollenkamp, A. F., (2014). Emerging electrochemical energy conversion and storage technologies. Frontiers in Chem., 2, #79; DOI: 10.3389/fchem.2014.00079.

128. Bahamonde Noriega, J. S., (2012). Design method for s-$CO_2$ gas turbine power plants. MSc Thesis, TU Delft, online: http://repository.tudelft.nl/view/ir/uuid%3Ae157e264-f384-4641-8293-8362fb0dc7f9/

129. Bahr, M., and Mulhaupt, R., (2012). Linseed and soybean oil-based polyurethanes prepared via the non-isocyanate route and catalytic carbon dioxide conversion. Green Chem., 14: 438-489.

130. Bahr, M., Bitto, A., and Malhaupt, R., (2012). Cyclic limonene dicarbonate as a new monomer for non-isocyanate oligo- and polyurethanes (NIPU) based upon terpenes. Green Chem., 14: 1447-1454.

131. Bajon Fernandez, Y. B., (2014). Carbon dioxide utilization in anaerobic digesters as an on-site carbon revalorization strategy. PhD Thesis, Cranfield University (UK), online: https://dspace.lib.cranfield.ac.uk/bitstream/1826/9287/1/Bajon-Fernandez_Yadira_Thesis_2014.pdf 132. Bajon Fernandez, Y., Green, K., Schuler, K., Soares, A., Vale, P., and Alibardi, L., (2015). Biological carbon dioxide utilization in food waste anaerobic digesters. Water Research, 87: 467-475

133. Bajon Fernandez, Soares, A., Villa, R., Vale, P., and Cartmell, E., (2014). Carbon capture and biogas enhancement by carbon dioxide enrichment of anaerobic digesters treating sewage sludge or food waste. Bioresource Technol., 159: 1-7

134. Baker, J., (2013). The use of olivine nano-silica in the construction industry. ProMine slide deck presentation, April, 2013, online: http://promine.gtk.fi/documents_news/promine_final_conference/14_05_Baker.pdf 135. Baker, J. T., (2004). Yield responses of southern US rice cultivars to $CO_2$ and temperature. Agricultural and Forest Meteorology, 122: 129-137.

136. Baker, J. T., Allen Jr., L. H., and Boote, K. J., (1990). Growth and yield responses of rice to carbon dioxide concentration. J. Agricultural Sci., 115(3): 313-320.

137. Baltrusaitis, J., and Luyben, W. L., (2015). Methane conversion to syngas for Gas-to-Liquids (GTL): is sustainable $CO_2$ reuse via Dry Methane Reforming (DMR) cost competitive with SMR and ATR processes? ACS Sustainable Chem. Eng., 3: 2100-2111.

138. Bansode, A., (2014). Expoiting high pressure advantages in catalytic hydrogenation of carbon dioxide to methanol. PhD Thesis, ICIQ & Univ. Rovira I Virgili, online: https://oatd.org/oatd/record?record=handle%5C%3A10803%5C%2F135008

139. Bansode, A., and Urakawa, A., (2014). Towards full one-pass conversion of carbon dioxide to methanol and methanol-derived products. J. Catal., 309: 66-70.

140. Barber, J., and Tran, P. D., (2013). From natural to artificial photosynthesis. J. R. Soc. Interface, 10: 20120984 http://dx.doi.org/10.1098/rsif.2012.0984

141. Bar-Even, A., Flamholz, A., Noor, E., and Milo, R., (2012). Thermodynamic constraints shape the structure of carbon fixation pathways. Biochimica et Biophysica Acta, 1817: 1646-1659

142. Bar-Even, A., Noor, E., and Milo, R., (2012b). A survey of carbon fixation pathways through a quantitative lens. J. Experimental Botany, 63(6): 2325-2342

143. Barton, E. E., Rampulla, D. M., and Bocarsley, A. B., (2008). Selective solar-driven reduction of $CO_2$ to methanol using a catalyzed p-GaP based photoelectrochemical cell. JACS Comms., 130: 6342-6344.

144. Balaban, M. O., and Ferrintino, G., (2012). *Dense Phase Carbon Dioxide: Food and Pharmaceutical Applications*. John Wiley & sons, pp. 352.

145. Banks, H. J., and Annis, P. C., (1990). Comparative advantages of High $CO_2$ and Low $O_2$ types of controlled atmospheres for grain storage. Chapter 7, pp. 93-122 in: M. Calderon and R. Baraki-Golan (eds.), *Food Preservation By Modified Atmospheres*. CRC Press.

146. Barker, H. A., and Kamen, M. D., (1945). Carbon dioxide utilization in the synthesis of acetic acid by *Clostridium thermoaceticum*. PNAS, 31: 219-225.

147. Bateta, A. (2015). Cement plant opens in Rwanda. East Africa Business Week, online: http://www.busiweek.com/index1.php?Ctp=2&pI=4005&pLv=3&srI=51&spI=26

148. Battle-Vilanova, P., Puig, S., Gonzalez-Olmos, R., Vilajeliu-Pons, A., Balaguer, M. D., and Colprim, J., (2015). Deciphering the electron transfer mechanisms for biogas upgrading to biomethane within a mixrd culture biocathode. RSC Adv., 5: 52243-52251

149. Batubara, M., Purwanto, W. W., and Fauzi, A., (2014). Development of East Natuna Gas Field for fulfilling long-term national gas demand. Proceedings of the $3^{rd}$ Applied Science for Technology Innovation ASTECHNOVA International Energy Conference, Yogyakarta, Indonesia, 13-14 Aug. 2014, online: http://tf.ugm.ac.id/astechnova/proceeding/Vol3No2/Astechnova_2014_2_02.pdf 150. Baxter, L., (2015). Cryogenic Carbon Capture™ as a holistic approach to a low-emissions energy system. Online article in Cornerstone: The Official Journal of the Coal Industry. http://cornerstonemag.net/cryogenic-carbon-capture-as-a-holistic-approach-to-a-low-emissions-energy-system/

151. Baxter, L. (2015 video). Capturing $CO_2$ with Cryogenic Carbon Capture. Online: https://www.youtube.com/watch?v=6kZ6EyI_iBc 152. Baxter, L., (2016a). Energy storing Cryogenic Carbon Capture. Wyoming Clean Coal Technologies meeting, June, 2016. Online Final Executive Summary, https://www.uwyo.edu/ser/research/_files/final-executive-summary-reports/wes-report.pdf 153. Baxter, L., (2016b). Cryogenic Carbon Capture development. Slide deck presentation, NETL, Pittsburgh meeting, Dec. 9, 2016, https://www.netl.doe.gov/File%20Library/Research/Coal/carbon%20capture/post-combustion/SES-FE0028697-kick-off.pdf 154. Baxter, L., Bence, A., Frankman, D., and Hoeger, C., (2016). Cryogenic Carbon Capture. CO2 Summit II: Technologies and Opportunities, Nov. 4, 2016. Online slide deck, http://dc.engconfintl.org/cgi/viewcontent.cgi?article=1010&context=co2_summit2

155. Baxter, P. J., Kapila, M., and Mfonfu, D. (1989). Lake Nyos disaster, Cameroon, 1986: medical effects of large-scale emission of carbon dioxide. British Medical Journal, v. 298, pp 1437-1441.

156. Bayat, A. E., Junin, R., Kharrat, R., Hejri, Sh., (2015a). Evaluation of vapor extraction process and its prospect as enhanced recovery method. Intl. J. Oil Gas Coal Technol., 9(4): 394-421.

157. Bayat, A. E., Junin, R., Kharrat, R., Shamshirband, Sh., Akib, S., and Buang, Z., (2015b). Optimization of solvent composition and injection rate in vapor extraction process. J. Petroleum Sci. Eng., 128: 33-43.

158. Bayat, A. E., Junin, R., Hejri, S., Fazeli, A., and Afsari, K., (2015c). Application of $CO_2$-based vapor extraction process for high pressure and temperature heavy oil reserves. J. Petroleum Sci. Eng., 135: 280-290.

159. BBC, (2013). Could power plants of the future produce zero emissions? Sep. 27, 2013 by Pia Gadkari, online: http://www.bbc.com/news/business-24225901

160. Beach, C., (2014). US grants patent for Ultra-Clima greenhouse system. The Packer, Feb. 26, 2014, online (with video): http://www.thepacker.com/fruit-vegetable-news/US-grants-patent-for-Ultra-Clima-greenhouse-system-247275501.html 161. Beckman, E. J., (2004). Supercritical and near-critical $CO_2$ in green chemical synthesis and processing. J. Supercrit. Fluids, 28: 121-191.

162. Beckman, E. J., (2003). Supercritical and near-supercritical $CO_2$ processing. Chapter 10, pp. 239-271 in: J. I. Boye and Y. Arcand (eds.), *Green Technologies in Food Production and Processing*. Springer 163. Beecy, D. J., Ferrell, F. M., and Carey, J. K., (2001). Biogenic methane: a long-term $CO_2$ recycle concept. US DOE conference proceedings publication, online: https://www.netl.doe.gov/publications/proceedings/01/carbon_seq/5a1.pdf 164. Beese-Vasbender, P. F., Grote, J. P., Garrelfs, J., Stratmann, M., and Mayrhofer, K. J., (2015). Selective microbial electrosynthesis of methane by a pure culture of a marine lithoautotrophic archaeon. Bioelectrochemistry, 102: 50-55

165. Beeson, R. C., Jr., and Graham, M. E. D., (1991). $CO_2$ enrichment of greenhouse roses affects neither rubisco nor carbonic anhydrase activities. J. Amer. Hort. Sci., 116(6): 1040-1045.

166. Beeza, J., Urizar, S., Erismann, N. de M., Freer, J., Schmidt, E., and Duran, N., (1991). Organosolv pulping—V: formic acid delignification of *Eucalyptus globulus* and *Eucalyptus grandis*. Bioresource Technol., 37(1): 1-6.

167. Behr, A., (1987). Use of carbon dioxide in industrial organic syntheses. Chem. Eng. Tech., 10(1): 16-27.

168. Behr, A., (1988). Carbon dioxide as an alternate C1 synthetic unit: activation by transition-metal complexes. Angew. Chem. Int. Ed., 27(5): 661-678.

169. Behrens, M., (2015). Chemical hydrogen storage by methanol: challenges for the catalytic methanol synthesis from $CO_2$. Recycl. Catal., 2: 78-86.

170. Behrens, M., (2014). Heterogeneous catalysis of $CO_2$ conversion to methanol on copper surfaces. Angew. Chem. Intl Ed., 53(45): 12022-12024.

171. Behrens, M., (2013). Utilization of $CO_2$. Lecture series slide deck presentation, online: http://www.fhi-berlin.mpg.de/acnew/department/pages/teaching/pages/teaching_wintersemester_2012_2013/malte_behrens_utilization_of_carbon_dioxide_130125.pdf 172. Beller, M., and Bornscheuer, U. T., (2014). $CO_2$ fixation through hydrogenation by chemical or enzymatic methods. Angew. Chem. Int. Ed., 53: 4527-4528.

173. Belman-Flores, J. M., Perez-Garcia, V., Ituna-Yudonago, J. F., Rodriguez-Munoz, J. L., and de Ramirez-Minguela, J., (2014). Use of hybrid solar-wind energy generation for remote area electrification in South-Eastern Nigeria. J. Energy in South Africa, 25(2): 96-106.

174. Ben-Amotz, A., (2011). Algae applications for power generation and $CO_2$ recycling. Seambiotic slide deck presentation, Tel-Aviv, Oct. 5, 2011, online: http://www.ises.org.il/assets/files/Conference%202011/Ben-Amotz%20ISES2011.pdf 175. Benali, M., and Boumghar, Y., (2014). Supercritical fluid-assisted drying. Entry 63, pp. 1261-1270, in: A. S. Mujumdar (ed.), *Handbook of Industrial Drying, Fourth Edition*. CRC Press, pp. 1348.

176. Benemann, J., (2013). Microalgae for biofuels and animal feeds. Energies, 6: 5869-5886.

177. Benemann, J., (2003). Biofixation of $CO_2$ and greenhouse gas abatement with microalgae—technology roadmap. Report submitted to the DOE/NETL, online: http://moritz.botany.ut.ee/~olli/b/RepBenemann03.pdf 178. Benemann, J., (1997). $CO_2$ mitigation with microalgae systems. Energy Conservation and Management, 38 Suppl., S475-S479

179. Benemann, J. R., (1979). Production of nitrogen fertilizer with nitrogen-fixing blue-green algae. Enzyme Microbial Technol., 1(2): 83-90

180. Benemann, J., and Oswald, W. J., (1996). Systems and economic analysis of macroalgae ponds for conversion of $CO_2$ to biomass. Final Report, DOE, Grant No. DE-FG22-93PC93204, online: http://digital.library.unt.edu/ark:/67531/metadc680796/m1/1/

181. Benemann, J., Tillet, D. M., and Weismann, J. C. (1987). Microalgae biotechnology. Trends Biotechnol., 5(2): 47-53

182. Bengelsdorf, F. R., Straub, M., and Durre, P., (2013). Bacterial synthesis gas (syngas) fermentation. Environmental Technol., 34(13-14): 1639-1651

183. Benko, D., Feher, F., Wong, T., Bohlmann, G., Whited, G., Cervin, M., McAuliff, J., LaDuca, R., Sanford, K., (2012). Development of a bio-based process for isoprene. DuPont slide deck presentation, October, 2012, online: http://www.assobioplastiche.org/wp-content/uploads/2012/10/Benko-David 1.pdf 184. Benson, S., (2015). Status and opportunities in $CO_2$ capture, storage and utilization. Presentation slidedeck: http://www.aps.org/meetings/march/events/upload/BensonAPSCCUS-2015.pdf 185. Benson, E. E., Kubiak, C. P., Sathrum, A. J., and Smeija, J. M., (2009). Electrocatalytic and homogeneous approaches to conversion of $CO_2$ to liquid fuels. Chem. Soc. Revs., 38: 89-99.

186. Berardi, S., Drouet, S., Francas, L., Gimbert-Surinach, C., Guttentag, M., Richmond, C., Stoll, T., and Llobet, A., (2014). Molecular artificial photosynthesis. Chem. Soc. Rev., DOI: 10.1039/c3cs60405e 187. Berman-Frank, I., Chen, Y.-B., Gerchman, Y., Dismukes, G. C., and Falkowski, P. G., (2005). Inhibition of nitrogenase by oxygen in marine cyanobacteria controls the global nitrogen and oxygen cycles. Biogeosciences Discussions, 2: 261-273

188. Bermejo, D. V., Ibanez, E., Reglero, G., Turner, C., Fornari, T., and Rodriguez-Meizoso, I., (2015). High catechins/low caffeine powder from green tea leaves by pressurized liquid extraction and supercritical antisolvent precipitation. Sep. Sci. Purif. Technol., 148: 49-58.

189. Bertsch, J., and Muller, V., (2015). Bioenergetic constraints for conversion of syngas to biofuels in acetogenic bacteria. Biotechnol. Biofuels, 8: 210, online: http://download.springer.com/static/pdf/176/ art%253A10.1186%252Fs13068-015-0393-x.pdf?originUrl=http%3A%2F%2Fbiotechnologyforbiofuels.biomedcentral.com%2Farticle%2F10.1186%2Fs13068-015-0393-x&token2=exp=1454337057~acl=%2Fstatic%2Fpdf%2F176%2Fart%25253A10.1186%2525 2Fs13068-015-0393-x.pdf*~hmac=ee40bb7b007c3cd6437861bda2f37d330a7222adf6211931b2f7babc70aaba46

190. Bethke, C. M., (2008). *Geochemical and Biogeochemical Reaction Modeling*. Cambridge University Press, pp. 543

191. Bhanage, B. M., and Arai, M., (2014). *Transformation and Utilization of Carbon Dioxide*. Springer, pp. 338.

192. Bhattarai, S., Ross, K. A., Schmid, M., Anselmetti, F. S., and Burgmann, H., (2012). Local conditions structure unique archaeal communities in the anoxic sediments of meromictic Lake Kivu. Microb. Ecol., 64: 291-310.

193. BioMCN, (2013). BioMCN: driven by nature. BioMCN (Holland) Slide deck presentations (2), online: http://www.wermutham.com/pdf/presentations-april2013/06_Rob%20Voncken_CEO_BioMCN_Industrial%20Scale%20Biomethanol%20from%20Biomass.pdf; http://decarbonizingfires.com/Bio-MCN%20-%20Methanol%20-%20Slide%20Show.pdf 194. Bioplastics Magazine, (2014). First commercial adoption of Novomer's $CO_2$-based polyols for polyurethane adhesive. Nov. 4, 2014, online: http://www.bioplasticsmagazine.com/en/news/meldungen/Novomer-s-CO2-based-polyols.php 195. Bishop, K. A., Leakey, A. D. B., Ainswort, E. A., (2014). How seasonal temperature or water inputs affect the relative response of C3 crops to elevated [$CO_2$]: a global analysis of open top chamber and free air $CO_2$ enrichment studies. Food and Energy security 2014: 3(1): 33-45.

196. Bjornsson, W. J., MacDougall, K. M., Melanson, J. E., O'Leary, S. J. B., and McGinn, P. J., (2012). Pilot-scale supercritical carbon dioxide extractions for the recovery of triacylglycerols from microalgae: a practical tool for algal biofuels research. J. Appl. Phycol., 24: 547-555.

197. Blas-Molinos, B., (2015). Carbon dioxide as a C-1 building block in combination with amines: carbonylation and hydrogenation reactions. PhD Thesis, RTWH Aachen University, Germany, online: https://publications.rwth-aachen.de/record/466203/files/466203.pdf 198. Blattman, H., Fleischer, M., Bahr, M., and Malhaupt, R., (2014). Isocyanate- and phosgene-free troutes to polyfunctional cyclic carbonates and green polyurethanes by fixation of carbon dioxide. Macromolecular Rapid Comms., 35: 1238-1254.

199. Block, C., et al., (2011). Toward a carbon dioxide neutral industrial park. A case study. J. Industrial Ecology, 15(4): 584-596. Online: http://www.pomwvl.be/sites/default/files/uploads/duurzaam_ondernemen/doc/energie/Wetenschappelijke%20publicatie%20CO2-neutraliteit%20Herdersbrug%20aug2011.pdf 200. Blom, T. J., Straver, W. A., Ingratta, F. J., Khosla, S., and Brown, W., (2015). Fact Sheet: Carbon dioxide in greenhouses. ISSN 1198-712X, Ontario (Canada) Ministry of Agriculture, Food and Rural Affairs. Online: http://www.omafra.gov.on.ca/english/crops/facts/00-077.htm 201. BlueBio, (2013). Microalgae: A market analysis carried out as a part of the Interreg KASK IVA project Blue Biotechnology for Sustainable Innovations, "Blue Bio" Report Online: https://connect.innovateuk.org/c/document_library/get_file?groupd=3285671&folderId=8339168&title=BlueBio+Microalgae+report+Feb13.pdf 202. Boaxing, (2008). About grain storage pest's and control technology. UNIDO conference on Sharing Innovative Agribusiness Solutions, Beijing Liangmao Technology Development Co., Ltd., corporate slide deck presentation, Cairo, Egypt, 26-27 Nov. 2008, online: https://unido.org/fileadmin/user_media/Services/Industrial_Competitiveness/Trade_Capacity Building/CairoConference2008/2st-Day-_3.1_-B._Zhao-Grain_Storage_Technology-China.pdf 203. BOC, (undated). Friendly agricultural solutions derived from nature's components. Online brochure: http://www.boc-gas.com.au/internet.lg.lg.aus/en/images/MP12-0008-2_GAS%20A%20Agricultural%20Solutions%20Brochure_Update%20310513_FA351_68076.pdf 204. Bocarsly, A., (2014). $CO_2$ conversion to fuels: a progress report on Liquid Light, Inc. Slide deck presentation, April, 2014, online: http://energy.columbia.edu/files/2014/02/2-Bocarsly-Presentation.pdf 205. Bocin-Dumitru, A., del Mar Perez Fortes, M., and Sveen, T., (2013). Carbon Capture and Utilization Workshop: Background and Proceedings. European Commission, Joint Research Center, Institute for Energy and Transport. Online: http://publications.jrc.ec.europa.eu/repository/bitstream/JRC86324/co2%20re-use%20workshop%20report_isbn_online_eur_pages.pdf.

206. Boddien, A., Gartner, F., Federsel, C., Sponholz, P., Mellmann, D., Jackstell, R., Junge, H., and Beller, M., (2011). $CO_2$-"Neutral" hydrogen storage based on bicarbonates and formates. Angw, Chim. Int. Ed., 50(28): 6411-6414.

207. Boddien, A. M., Mellmann, D., Gartner, F., Jackstell, R., Junge, H., Dyson, P. J., Laurenczy, G., Ludwig, R., and Beller, M., (2011). Efficient dehydrogenation of formic acid using an iron catalyst. Science, 333: 1733-1736

208. Bodinus, W. S., (1999). The rise and fall of carbon dioxide systems: the first century of air conditioning. ASHRAE J., April 1999, pp. 37-42.

209. Bonailllie, L., (2008). Bio-based polymeric foam from soybean oil and carbon dioxide. PhD Thesis, University of Delaware, online: http://www.researchgate.net/publication/259147765_Bio-based_Polymeric_Foam_from_Soybean_Oil_and_Carbon_Dioxide 210. Boniface, K. J., Dykeman, R. R., Cormier, A., Wang, H.-B., Mercer, S. M., Liu, G., Cunningham, M. F., and Jessop, P. G., (2016). $CO_2$-switchable drying agents. Green Chem., 18: 208-213.

211. Bonke, S. A., Wiechen, M., MacFarlane, D. R., and Spicca, L., (2015). Renewable fuels from concentrated solar power: towards practical artificial photosynthesis. Energy Environ. Sci., 8: 2791-2796.

212. Bonnaillie, L., and Tomasula, P. M., (2012). Sequential fractionation of milk and whey proteins with supercritical carbon dioxide for new health-promoting food ingredients. Conference paper, Conference: International Symposium on Supercritical Fluids, ISSF 2012, At San Francisco, Calif., online: http://www.researchgate.net/publication/259092404_Sequential_fractionation_of_milk_and_whey_proteins_with_supercritical_carbon_dioxide_for_new_health-promoting_food_ingredients; http://issf2012.com/handouts/documents/227_004.pdf 213. Bonnaillie, L., and Tomasula, P. M., (2015). Carbon dioxide: an alternative processing method for milk. Chapter 8., pp, 205-250 in: N. *Datta* and P. M. Tomasula (eds.), Emerhing Dairy Processing Technologies: Opportunities for the Dairy Industry. John Wiley & Sons, pp. 360.

214. Bonnaille, L., and Wool, R. P., (2008). Thermosetting foam with a high bio-based content from acrylated epoxidized soybean oil and carbon dioxide. Applied Polymer Sci., 105(3): 1042-1052, 215. Boonnoun, P., Kurita, Y., Wahyudiono, Machmudah, S., Okita, Y., Ohashi, E., Kanda, H., and Goto, M., (2014). Wet extraction of lipids and astaxanthin from by liquefied dimethyl ether. Nutrition and Food Sci., 4(5): #1000305. DOI: 10.4172/2155-9600

216. Borem, F. M., Riberiro, F. C., Figueiredo, L. P., Giomo, G. S., Fortunato, V. A., and Isquierdo, E. P., (2013). Evaluation of the sensory and color quality of coffee beans stored in hermetic packaging. J. Stored Products Res., 52: 1-6.

217. Borgniez, G. (1960). Donnees pour la mise en valeur du gisement de methane du lac Kivu. Acad. Royale des Sciencesv d'Outre-Mer, classe de sciences techniques. Memoires 8, Nouvelle serie. Tome XIII, fasc. 1., 113pp.

218. Borowitzka, M. A., and Borowitzka, L. J., (1988). *Micro-Algal Biotechnology*. Cambridge University Press, pp. 488

219. Borowitzka, M. A., and Moheimani, N. R., (2013, editors). *Algae for Biofuels and Energy*. Springer, pp. 284.

220. Boschee, P., (2012). Processing of sour natural gas reaches new highs. Oil and Gas Facilities, December 2012, pp. 8-12, online: http://www.spe.org/ogf/print/subscribers/2012/12/07_Feature_SourGas_12_12_OGF.pdf 221. Botanical Resources Australia Pty. Ltd., (undated). Website sections: "Company profile," and "a brief history," online: www.botanicalra.com.au/company_profile.html www.botanicalra.com.au/company_history.html 222. Boussiba, S., (2015). Astaxanthin from Haematococcus "The long way to glory." Newsletter, International Society for Applied Phycology (ISAP), January 2015, pp. 5-8, online: http://www.appliedphycologysoc.org/newsletter/ISAP_Newsletter_January_2015.pdf 223. Bower, J., (2013). Appendix C: Combined heat and power greenhouses, a carbon, energy, and water opportunity. WaterEnergy Innovations (Pasadena, Calif., USA). In: The role of natural gas in california's water-energy nexus. Report online: http://www.waterenergyinnovations.com/publication/the-role-of-natural-gas-in-californias-water-energy-nexus/

224. Boyd, A. R., Champagne, P., McGinn, P. J., MacDougall, K. M., Melanson, J. E., and Jessop, P. G., (2012). Switchable hydrophilicity solvents for lipid extraction from microalgae for biofuel production. Bioresource Technol., 118: 628-632.

225. BP, (2015). BP statistical review of world energy, June 2015. British Petroleum online report: https://www.bp.com/content/dam/bp/pdf/energy-economics/statistical-review-2015/bp-statistical-review-of-world-energy-2015-full-report.pdf 226. Braunstein, P., Matt, D., and Nobel, D., (1988). Reactions of carbon dioxide with C—C bond formation catalyzed by transition metal complexes. Chem. Rev., 88: 747-764.

227. Breakbulk, (2015). Greenmillenia to build large-scale solar plant in Kenya. Online news article: http://www.breakbulk.com/greenmillenia-to-build-large-scale-solar-plant-in-kenya/

228. Breidenstein, W., (2015). North Dakota leads the mini-GTL revolution. GasTechno slide deck presentation, Jan. 5, 2015, online: https://cms.oilresearch.nd.gov/image/cache/GasTechno_-_North_Dakota_Presentation_Final.pdf 229. Brent, G. F., (2014). Opportunities for CCSU via mineral carbonation: the MCi project. MCi-Orica slide deck presentation, Sep. 1-3, 2014, online: http://www.nationalccsweek.com.au/wp-content/uploads/2014/09/05_Geoff-Brent_MCi-project.pdf 230. Brent, G. F., (2013). Mineral carbonation for large scale $CO_2$ storage & utilization. MCi-Orica slide deck presentation, 17 Oct. 2013, online: http://sydney.edu.au/engineering/chemical/s2c2/2013/documents/Geoff-Brent-Mineral-Carbonation-for-Large-Scale-$CO_2$-Storage-and-Utilisation.pdf 231. Brent, G. F., Allen, D. J., Eichler, B. R., Petrie, J. G., Mann, J. P., and Haynes, B. S., (2011). Mineral carbonation as the core of an industrial symbiosis for energy-intensive minerals conversion. J. Industr. Ecol., 16(1): 94-104.

232. Brett, G., and Barnett, M., (2014). The application of liquid air energy storage for large scale long duration energy solutions to grid balancing. EPJ Web of Conferences, 79: 03002, DOI: 10.1051/epjconf/20147903002, online: http://www.epj-conferences.org/articles/epjconf/pdf/2014/16/epjconf_e2c2013_03002.pdf 233. Broadhead, R. F., Mansell, M., and Jones, G., (2009). Carbon dioxide in New Mexico: geological distribution of natural occurrences. New Mexico Bureau of Geology and Natural Resources, Open File Report No. 515, online: https://geoinfo.nmt.edu/publications/openfile/downloads/500-599/514/NMBGMR%20Open%20file%20report%20514%20CO2%20in%20New%20Mexico.pdf 234. Broadwith, P., (2015). Catalytic carbon dioxide convertors. ChemistryWorld (Royal Society of Chemistry), 24 Feb. 2015, online: http://www.rsc.org/chemistryworld/2015/02/catalytic-co2-convertors-econic-profile-0

235. Brown, D. W., (2000). A hot dry rock geothermal energy concept utilizing supercritical $CO_2$ instead of water. Proceedings $25^{th}$ Workshop on Geothermal Reservoir Engineering, Stanford University, California, online: https://pangea.stanford.edu/ERE/pdf/IGAstandard/SGW/2000/Brown.pdf 236. Brown, Z. K., (2010). The drying of foods using supercritical carbon dioxide. PhD thesis, Birmingham University, online: http://core.ac.uk/download/pdf/76653.pdf 237. Brown, Z. K., Fryer, P. J., Norton, I. T., and Bridson, R. H., (2010). Drying of agar gels using supercritical carbon dioxide. J. Supercrit. Fluids, 54(1): 89-95.

238. Brown, Z. K., Fryer, P. J., Norton, I. T., Bakalis, S., and Bridson, R. H., (2008). Drying of foods using supercritical carbon dioxide—investigations with carrot. Innovative Food Sci. & Emerging Technol., 9(3): 280-289.

239. Brownsort, P., Scott, V., and Sim, G., (2015). Carbon dioxide transport plans for Carbon Capture and Storage in the North Sea Region: A summary of existing studies and proposals applicable to the development of projects of common interest. Project SCCC0123. Online: http://www.sccs.org.uk/images/expertise/reports/working-papers/wp-2015-02.pdf (In: http://www.sccs.org.uk/expertise/reports/working-papers)

240. Buchard, A., Bakewell, C. M., Weiner, J., and Williams, C. K., (2012). Recent developments in catalytic activation of renewable resources for polymer synthesis. Topics in Organometallic Synthesis, v. 39, pp. 175-224.

241. Bucholtz, M., and Jordan, R. K., (1983). Formic acid woodpulping could yield valuable chemical products. Pulp and Paper, 57(9): 102-104.

242. Buckhorn Springs, (2015). Dry ice from carbon dioxide, 1930's. Online: http://buckhornsprings.org/history/buckhorn-history/dry-ice-from-carbon-dioxide-1930s/

243. Bunce, J. A., (2014a). Corn growth response to elevated $CO_2$ varies with the amount of nitrogen applied. Am. J. Plant Sci., 5: 306-312.

244. Bunce, J., A., (2014b). $CO_2$ enrichment at night affects the growth and yield of common beans. Crop Sci., 54: 1744-1747

245. Bundock, T., (2010). Commercial protected cropping production methodologies and systems applicable to vegetable growers in Southern Victoria. ISS Institute (Australia), online report: http://c.ymcdn.com/sites/www.agrifoodskills.net.au/resource/resmgr/fellowship_reports/iss_fel_report_t_bundock_low.pdf 246. Burlew, J. S., (1953, editor). *Algal Culture: From Laboratory to Pilot Plant*. Carnegie Institution of Washington Publication 600, online: http://publicationsonline.carnegiescience.edu/publications_online/algal_culture/

247. Burney, J. A., Davis, S. J., and Lobell, D. B., (2010). Greenhouse gas mitigation by agricultural intensification. PNAS, 107(26): 12052-12057.

248. Burton, M., Sawyer, G., and Granieri, D., (2013). Deep carbon emissions from volcanoes. Revs. Mineral. & Geochem., 75: 323-354.

249. Busby, D. C., Glancy, C. W., Hoy, K. L., Kuo, A. C., Lee, C., and Nielsen, K. A., (1990). Supercritical fluid spray application technology: a pollution prevention technology for the future. Conference presentation paper, Water-Borne & Higher-Solids Coatings Symposium, University of Southern Mississippi and Southern Society for Coatings Technology. Online: http://infohouse.p2ric.org/ref/25/24795.pdf 250. Busch, A., and Gensterblum, Y., (2011). CBM and $CO_2$-ECBM related sorption processes in coal: a review. Int. J. Coal Geology, 87: 49-71

251. Bustos-Serrano, H., (2010). The Carbonate System in Natural Waters. Ph.D. Thesis, University of Miami, pp. 260, online: http://scholarlyrepository.miami.edu/oa_dissertations/493/

252. Butina, (undated). Website: http://www.butina.eu

253. Butler, J. N., (1998). *Ionic Equilibrium: Solubility and pH Calculations*. Wiley, pp. 576

254. Butler, J. N., (1982). *Carbon Dioxide Equilibria and Their Applications*. Addison-Wesley.

255. Butler, R. M., and Mokrys, I. J., (1991). A new process (VAPEX) for recovering heavy oils using hot water and hydrocarbon vapour. J. Can. Petrol. Technol., 30(1): 97-106.

256. Butterman, H. C., and Castaldi, M. J., (2011). Experimental and kinetic investigation of $CO_2$ and $H_2O/N_2$ gasification of biomass fuels. Chapter 2, pp. 27-73 in: *Synthetic Liquids Production and Refining*. ACS Symposium Series, v. 1084. Amer. Chem. Soc.

257. Butterman, H. C., and Castaldi, M. J., (2010). Biomass to fuels: Impact of reaction medium and heating rate. Environmental Engineering Sci., 27(7): 539-555.

258. Butterman, H. C., and Castaldi, M. J., (2009a). Syngas production via $CO_2$ enhanced gasification of biomass fuels. Environmental Engineering Sci., 26(4): 703-713.

259. Butterman, H. C., and Castaldi, M. J., (2009b). $CO_2$ as a carbon neutral fuel source via enhanced biomass gasification. Environ. Sci. Technol., 43: 9030-9037.

260. Butterman, H. C., and Castaldi, M. J., (2008). $CO_2$ enhanced steam gasification of biomass fuels. NAWTEC16-1949. Proc. NAWTEC16 16th North American Waste-to-Energy Conference, May 19-21, 2008, Philadelphia, Pa., USA, 16pp.

261. Butterman, H. C., and Castaldi, M. J., (2007). Influence of $CO_2$ injection on biomass gasification. Ind. Eng. Chem. Res., 46(26): 8875-8886.

262. Buurma, J. S., and Ruijs, M. N. A., (2011). Sustainable greenhouse horticulture and energy provision: two regional transition processes compared. Pp. 91-111 in: S. Vellema (ed). *Transformation and Sustainability in Agriculture*. Wageningen Academic Publishers.

263. Byrne, C. M., Allen, S. D., Lobkovsky, E. B., and Coates, G. W., (2004). Alternating copolymerization of limonene oxide and carbon dioxide. J. Am. Chem. Soc., 126: 11404-11405.

264. Cai, C., Li, G., Huang, Z., and Chi, H., (2015). A waterless fracturing treatment: liquid nitrogen fracturing and its application prospect. ELMI Proceedings, no. 3: 35-40, online: http://proceedings.socar.az/uploads/pdf/25/cai-35-40.pdf 265. Callebaut, K., (2015). Towards a low carbon emission industry in the Port of Antwerp: The role of Carbon Capture, Utilization and Storage. Presentation slide decks. Online: http://www.vndelta.eu/index.php/download_file/view/732/207/http://37bb9d709b12f82108f5-9c2e4ff85887ecb 8517b4a9289519d49.r69.cf1.rackcdn.com/Karen%20antwerp.pdf 266. Calvin, W. M., and Pace, E. L., (2016). Utilizing HyspIRI prototype data for geological exploration applications: a Southern California case study. Geosciences, 6: 11: DOI: 10.3390/geosciences6010011

267. Cambrian Innovation, (2013). Cambrian's Ecovolt bio-electric wastewater treatment system now commercially available. Corporate press release, online: http://cambrianinnovation.com/ecovolt-now-commercially-available/

268. Cambrian Innovation, (2015). Taking the waste out of wastewater. Corporate website information, online: http://cambrianinnovation.com/wp-content/uploads/2015/03/Taking-the-Waste-Out-of-Wastewater-FINAL.pdf 269. Campernolle, T., Witters, N., Van Passel, S., Thewys, T., (2011). Analyzing a self-managed CHP system for greenhouse cultivation as a profitable way to reduce $CO_2$-emissions. Energy, 36(4): 1940-1947.

270. Capart, A., (1954). La mission Belge d'Exploration aux Lacs Kivu, Edouard et Albert Congo Belge 1952-1954. Pp. 59-61 in: Comptes rendus et rapports de la commission des eaux de surface. Pub. No. 38, Tome III. (Louvain).

271. Capart, A., (1960). Le Lac Kivu. Les Naturalistes Belge, v. 41: 397-417.

272. Capart A, and Kufferath J (1956). Recherches hydrobiologiques au Congo belge et leurs resultats pratiques. Bull. Agric. Congo Belg., v. 47:1-2

273. Capart, A., and Kufferath, J., (1962). Oceanographie. Pp. 645-655, Extrait du Tome II du Livere Blanc de l'Academie royale de Sciences d'Outre-Mer. Bruxelles.

274. Capart, A., Godfrine, A., and Kufferath, J. (1957-1958). Le Gaz Methane du Lac Kivu. Ministere du Congo Belge et du Ruanda-Urundi, Zaire et Rwanda. Silent film. Titles in French.

275. Cardoso, L., Bartosik, R., Campabadal, C.,and De La Torre, D., (2012). Air-tightness level in hermetic plastic bags (silo-bags) for different storage conditions. Pp. 583-589 in S. Navarro et al., (eds.), Proc. 9th Intl. Conf. on Controlled Atmospheres and Fumigation in Stored Products, Atalya, Turkey, 15019 October, 2012. Online: http:// inta.gob.ar/documentos/air-tightness-level-in-hermetic-plastic-bags-silo-bags-for-different-storage-conditions/at_multi_download/file/INTA%20-%20Cardoso-_et_al_2012_AIR-TIGHTNESSLEVEL_IN_HERMET-IC_PLASTIC_BAGS_-SILO-BAGS-FOR_DIFFER-ENT_STORAGE_CONDITIONS.pdf
276. Carr, M., (2015). The little algae that could. Biomass Magazine, Sep. 21, 2015, online: http://biomassmagazine.com/articles/12397/the-little-algae-that-could
277. Carrington, D., (2015). Global Apollo programme seeks to make clean energy cheaper than coal. The Guardian, Jun. 2, 2015, online: http://www.theguardian.com/environment/2015/jun/02/apollo-programme-for-clean-energy-needed-to-tackle-climate-change
278. Carbon Capture Journal, (2014). CCS in the Netherlands and the future of ROAD. Jul. 1, 2014. Online: http://www.carboncapturejournal.com/ViewNews.aspx?NewsID=3482
279. Cardox, (undated), Corporate website: www.Cardox.net See also: http://pneumat.com/products/cardox-co2-blaster/; http://www.enviro-cor.com/pdf/cardox.pdf
280. Carroll, S., and Stillman, G., (2014). Assessment of key physical and chemical research findings for the use of $CO_2$ as a heat exchanging fluid for geothermal energy development. Proceedings $39^{th}$ Workshop on Geothermal Reservoir Engineering, Stanford University, California, USA, online: https://pangea.stanford.edu/ERE/pdf/IGA-standard/SGW/2014/Carroll.pdf
281. Carter, L. D., (2012). An early deployment strategy for carbon capture, utilization and storage (CCUS) technologies. United States Carbon Sequestration Council, report, online: http://www.uscsc.org/Files/Admin/Educational_Papers/20120604_Early%20Deployment%20Strategy%20for%20CCUS%20Technologies_FINAL.pdf
282. Carvalho, M. O., Pires, I., Barbosa, A., Barros, G., Riudavets, J., Garcia, A. C., Brites, C., and Navarro, S., (2012). The use of modified atmospheres to control *Sitophilus zeamais* and *Sitophilus oryzae* on stored rice in Portugal. J. Stored Products Res., 50: 49-56.
283. Caselato-Sousa, V. M., and Amaya-Farfan, J., (2012). State of knowledge on Amaranth grain: a comprehensive review. J. Food Sci., 77(4): R93-R104
284. Castillo-Ruz, M. C., Guillermo-Alcocer, C. G., Bojorquez-Gamboa, R. R., and Rocha-Uribe, G. J. A., (2011). Extraction of vanilla oleoresin (*Vanilla planifolia* Andrews) with supercritical $CO_2$. Tecnol. Ciencia Ed. (IMIQ), 26(2): 80-84
285. Castro-Osma, J. A., North, M., and Wu, X., (2014). Development of a halide-free aluminium-based catalyst for the synthesis of cyclic carbonates from epoxides and carbon dioxide. Chemistry—A European Journal, 20(46): 15005-15008.
286. Cavallini, A., (2004). Properties of $CO_2$ as a refrigerant. Online seminar paper: http://www.centrogalileo.it/nuovaPA/Articoli%20tecnici/INGLESE%20CONVEGNO/CO$_2$/Cavallini%20-%20Milano04CO$_2$.pdf
287. CCUS-China, (2011). Carbon capture, utilization and storage: technology development in China. Online report: http://www.acca21.org.cn/gest/etc/CCUS_en.pdf
288. CCEMC, (2014). Direct catalytic synthesis of acetic acid from $CO_2$ and $CH_4$. Online: http://ccemc.ca/project/direct-catalytic-synthesis-acetic-acid-co2-ch4/
289. CCEMC-E3Tec Services, Ltd., (2014). CCEMC $35 million Grand Challenge Innovative carbon uses. Carbon Capture Journal, May-June, 2014, pp. 2-4.
290. Ceni, G., Silva, M. F., Valerio, C. Jr., Cansian, R. L., Oliveira, J. V., Dalla Rosa, C., and Mazutti, M. A., (2016). Continuous inactivation of alkaline phosphatase and *Escherichia coli* in milk using compressed carbon dioxide as inactivating agent. J. $CO_2$ Util., 13: 24-28
291. Cenovus Energy, (undated). Increasing oil production and reducing greenhouse gas emissions: Weyburn project overview. Cenovus Energy corporate public information brochure, online: https://www.cenovus.com/operations/docs/Weyburn-Facility-Profile.pdf
292. Centi, G., and Perathoner, S., (2014, editors). *Green Carbon Dioxide: Advances in $CO_2$ Utilization*. Wiley, pp. 326.
293. Centi, G., and Perathoner, S., (2014). Perspectives and state of the art in producing solar fuels and chemicals from $CO_2$. Chapter 1, pp. 1-24, in: G. Centi and S. Perathoner (eds.), *Green Carbon Dioxide: Advances in $CO_2$ Utilization*. Wiley, pp. 326.
294. Centi, G., Iaquaniello, G., and Perathoner, S., (2011). Can we afford to waste carbon dioxide as a valuable source of carbon for the production of light olefins. ChemSusChem, 4(9): 1265-1273.
295. Centi, G., Quadrelli, E. A., and Perathoner, S., (2013). Catalysis for $CO_2$ conversion: a key technology for rapid introduction of renewable energy in the value chain of chemical industries. Energy Environ. Sci., 6: 1711-1731.
296. Centre for Low Carbon Futures, (2013). Liquid air in the energy and transport systems: opportunities for industry and innovation in the UK. Summary and full reports, online: http://www.liquidair.org.uk/files/summary-report.pdf; http://www.liquidair.org.uk/files/summary-report.pdf
297. Century Plant, (2014). Fact sheet: Century Plant. Department of Mines and Petroleum, Government of Western Australia, online: http://www.dmp.wa.gov.au/documents/Century_Plant.pdf
298. Cereplast, (2013). Cereplast announces new bioplastic resin grade with 51% algae biomass. Press release online: http://globenewswire.com/news-release/2013/04/30/542923/10030480/en/Cereplast-Announces-New-Bioplastic-Resin-Grade-With-51-Algae-Biomass.html; http://files.shareholder.com/downloads/CERP/0x0x658357/39945152-a346-458a-a6fc-7333bc9f3c8d/CERP_News_2013_4_30_General_Releases.pdf
299. Cernansky, R., (2015). Super vegetables: long overlooked in parts of Africa, indigenous greens are now capturing attention for their nutritional and environmental benefits. Nature, 522: 146-148.
300. Cha, M., Yin, X., Kneafsey, T., Johanson, B., Alqahatani, N., Miskimins, J., Patterson, T., and Wu, Y.-S., (2014). Cryogenic fracturing for reservoir stimulation—laboratory studies. J. Petroleum Sci. Eng., 124: 436-540.
301. Chan, P., Tomlinson, B., Lee, C.-B., and Lee, Y.-S., (1996). Effectiveness and safety of low-dose Pravastatin and squalene, alone and in combination, in elderly patients with hypercholesterolemia. J. Clin. Pharmacol., 36(5): 422-427.
302. Chao, Y., Homer, O., Vallee, P., Meneau, F., Alos-Ramos, O., Hui, F., Turmine, M., Perrot, H., and Ledion, J., (2014). In situ probing calcium carbonate formation by combining fast controlled precipitation method and small-angle X-ray scattering. Langmuir, 30(12): 3303-3309
303. Chapman, A. M., Keyworth, C., Kember, M. R., Lennox, A. J. J., and Williams, C. K., (2015). Adding value to power station captured $CO_2$: Tolerant Zn and Mg homogeneous catalysts for polycarbonate polyol production. ACS Catal., 5(3): 1581-1588.
304. Chavagnac, V., Ceuleneer, G., Monnin, C., Lansac, B., Hoareau, G., and Boulart, C., (2013a). Mineralogical assemblages forming at hyperalkaline warm springs hosted on ultramafic rocks: a case study of Oman and Ligurian ophiolites. Geochem. Geophys. Geosystems, 14(7): 2474-2495

305. Chavagnac, V., Monnin, C., Ceuleneer, G., Boulart, C., and Hoareau, G., (2013b). Characterization of hyperalkaline fluids produced by low-temperature sepentinization of mantle peridotites in the Oman and Ligurian ophiolites. Geochem. Geophys. Geosystems, 14(7): 2496-2522

306. Chaves, R. B., (1996). Geothermal gases as a source of commercial CO2, in Miravailles, Costa Rica and Haedarendi, Iceland. United Nations University, Geothermal Training Programme, Reports 1996, No. 3, online: www.os.is/gogn/unu-gtp-report/UNU-GTP-1996-03.pdf 307. Chempolis website: www.chempolis.com Brochures and slide deck presentations: http://www.chempolis.com/wp-content/uploads/formicofib_ENG.pdf; http://www-.chempolis.com/wp-content/uploads/yleisesite_ENG.pdf; http://www.chempolis.com/wp-content/uploads/formico-bio_ENG.pdf; Also: http://biomass-sp.net/wp-content/uploads/2012/05/CHEMPOLIS.pdf; https://www.finpro.fi/c/document_library/get_file?uuid=1e956eaf-44f3-44a0-ad0d-ba420d1a2a0b&groupId=10304; http://www.kcpk.nl/algemeen/bijeenkomsten/presentaties/20120214ConferenceChempolisFinal.pdf 308. Chen, C. S., Handoka, A. D., Wan, J. H., Ma, L., Ren, D., and Siang, B., (2015). Stable and selective electrochemical reduction of carbon dioxide to ethylene on copper mesocrystals. Catalysis Sci. Tech., 5: 161-168.

309. Chen, C., and Lou, Z., (2009). Formation of C60 by reduction of $CO_2$. J. Supercrit. Fluids, 50: 42-45.

310. Chen, F., Yao, G., Huo, Z., and Jin, F., (2015). A novel method of $NaHO_3$ reduction into formic acid with $N_2H_4H_2O$ over Ni catalyst. RSC Advances, 8: 11257-11260.

311. Chen, H., Cong, T. N., Yang, W., Tan, C., Li, Y., and Ding, Y., (2009). Progress in electrical energy storage: a critical review. Progress in Natural Science, 19: 291-312

312. Chen, M., Hogh, J. V. T., Nielsen, J. U., Bentzen, J. J., Ebbesen, S. D., and Hendriksen, P. V., (2013). High temperature co-electrolysis of steam and $CO_2$ in an SOC stack: performance and durability. Fuel Cell, 13(4): 638-645

313. Chen, Q., (2007). Direct synthesis of hydrogen peroxide from oxygen and hydrogen using carbon dioxide as an environmentally benign solvent and its application in green oxidation. PhD Thesis, University of Pittsburgh. Online: http://d-scholarship.pitt.edu/9387/

314. Chen, Q., and Beckman, E. J., (2007). Direct synthesis of $H_2O_2$ from $O_2$ and $H_2$ over precious metal loaded TS-1 in $CO_2$. Green Chem., 9: 802-808.

315. Chen, S., (undated). Energy storage: an electrochemical perspective. UC Santa Cruz course lectude slide deck, online: http://chen.chemistry.ucsc.edu/Lectures-2.pdf 316. Chen, Y., Sun, X.-l., and Wang, W.-y., (2011). Study on extraction of flavones from sweet potato leaves by supercritical $CO_2$ fluid. Guanzhou Chemical Industry 2011, Issue 6, pp. 82-84, online: http://www.oriprobe.com/journals/gzhg/2011_6.html http://caod.oriprobe.com/articles/26691351/Study_on_Extraction_of Flavones_from_Sweet_Potato_Leaves_by_Supercriti.htm 317. Chen, Z., Conception, J. J., Brennaman, M. K., Kang, P., Norris, M. R., Hoertz, P. G., and Meyer, T. J., (2012). Splitting $CO_2$ into CO and $O_2$ by a single catalyst. PNAS, 109(39): 15606-15611.

318. Chen, Z.-Y., O'Connor, W. K., and Gerdemann, S. J., (2006). Chemistry of aqueous mineral carbonation for carbon sequestration and explanation of experimental methods. Environmental Progr., 25: 161-166.

319. Cheng, M.-J., Kwon, Y., Head-Gordon, M., and Bell, A. T., (2015). Tailoring metal porphyrin-like active sites on grapheme to improve the efficiency and selectivity of electrochemical $CO_2$ reduction. J. Phys. Chem. C, DOI: 10.1021/ace.jpcc.5b05518

320. Cheng, S., Xing, D., Call, D. F., and Logan, B. E., (2009). Direct biological conversion of electrical current into methane by electromethanogenesis. Environ. Sci. Technol., 43: 3953-3958

321. Chery, D., Lair, V., and Cassir, M., (2015). Overview on $CO_2$ valorization: challenges of molten carbonates. Frontiers in Energy Res., 3:43. DOI: 10.3389/fenrg.2015.00043

322. Chi, Z., Elloy, F., Xie, F., Hu, Y., and Chen, S., (2014). Selection of microalgae and cyanobacteria strains for bicarbonate-based integrated carbon capture algae production system. Appl. Biochem. Biotechnol., 172: 447-457.

323. Chi, Z., O'Fallon, J. V., and Chen, S., (2011). Bicarbonate produced from carbon capture for algae culture. Trends. Biotechnol., 29(11): 537-541.

324. Chi, Z., Xie, Y., Elloy, F., Zheng, Y., Hu, Y., and Chen, S., (2013). Bicarbonate-based integrated carbon capture and algae production system with alkalihalophilic cyanobacterium. Bioresour. Techn., 133: 513-521.

325. Chinnarasu, C., Montes, A., Fernandez-Ponce, M. T., Casas, L., Mantell, C., Pereyra, C., de la Ossa, E. J. M., and Pattabhi, S., (2015). Natural antioxidant fine particles recovery from *Eucalyptus globulus* leaves using supercritical carbon dioxide assisted processes. J. Supercrit. Fluids, 101: 161-169.

326. Cho, C., Song, T., Mitsos, A., McKinnon, J. T., Ko, G. H., Tolsma, J. E., Denholm, D., and Park, T., (2009). Optimal design and operation of a natural gas tri-reforming reactor for DME synthesis. Catalysis Today, 139: 261-267.

327. Cho, K. J., Keener, T. C., and Khang, S.-J., (2008). A study on the conversion of trona to sodium bicarbonate. Powder Techn., 184: 58-63.

328. Cho, W., Song, T., Lee, H., Baek, Y., Denholm, D., Ko, G., and Choi, C., (2011). Production of DME from CBM by KOGAS DME process. Translation of the Korean Hydrogen and New Energy Society, (2011, 12), v. 22(6): 925-933.

329. Choi, O., and Sang, B.-I., (2016). Extracellular electron transfer from cathode to microbes: application for biofuel production. Biotechnol. Biofuels, 9: 11, DIO 10.1186/s13068-016-0426-0

330. Chopra, S., Lines, L., Schmitt, D. R., and Batzle, M., (2010). Heavy-oil reservoirs: their characterization and production. Chapter 1, pp. 1-69 in: S. Chopra et al., (eds.), *Heavy Oils: Reservoir Characterization and Production Monitoring*. Soc. Exploration Geophysicists, pp. 339.

331. Chordia, L., (2015). Thar Energy: manufacturer of heat exchangers for $sCO_2$ power cycles. Thar Energy slide deck presentation, 2015 University Turbine Systems Research Workshop, Atlanta, Ga., Nov. 3, 2015, online: https://www.netl.doe.gov/File%20Library/Events/2015/utsr/Tuesday/Chordia.pdf 332. Christensen, C. M., (2014). What causes development? Online video lecture: https://www.youtube.com/watch?v=Mb6D3h4n0xo 333. Chung, J., Cho, W., Baek, Y., and Lee, C., (2012). Optimization of KOGAS DME process from demonstra- 333. (continued) tion long-term test. Trans. Of the Korean Hydrogen and New Energy Society (2012, 10), v. 23(5): 559-571.

334. Church & Dwight, (undated). Corporate website: "Company history." Online: http://www.churchdwight.com/company/who-we-are/history.aspx 335. Ciamician, G., (1912). The photochemistry of the future. Science, 36: 385-394.

336. CINTRA, (2011). Factsheet May 2011. Online: http://www.rotterdamclimateinitiative.com/documents/Factsheets/CINTRA.pdf 337. Cipolli, F., Gambardella, B., Marini, L., Ottonello, G., Zuccolini, M. V., (2004). Geochemistry of high-pH waters from serpentinites of the Gruppo di Voltri (Genova, Italy) and reaction path modeling of $CO_2$ sequestration in serpentine aquifers. Appl. Geochem., 19: 787-802

338. Ciriminna, R., Lomeli-Rodriguez, M., Cara, P. D., Lopez-Sanchez, J. A., and Pagliaro, M., (2014). Limonene: a versatile chemical of the bioeconomy. Chem. Commun., 50: 15288-15296.

339. Clark, D. A., (2014). Kinder Morgan: Vast opportunity looms. Seeking Alpha, Jun. 18, 2015, online: http://seekingalpha.com/article/2273843-kinder-morgan-vast-untapped-opportunity-looms 340. Clark, I. D., Fontes, J.-C., and Fritz, P., (1992). Stable isotope disequilibria in travertine from high-pH waters: laboratory investigations and field observations from Oman. Geochim. Cosmochim. Acta, 56(5): 2041-2050.

341. Clarke Energy, (undated). Greenhouse power and $CO_2$ fertilization. Online brochure: https://www.clarke-energy.com/wp-content/uploads/Greenhouse-Power.pdf 342. Clean Energy Systems, (2012). Youtube video: "CES OFT900." Online: https://www.youtube.com/watch?v=-53170uf7 nM. A smaller system with a different modified turbine is shown in a similar video: https://www.youtube.com/watch?v=x1D6vuIkkm0

343. Cleanenergyauthority, (2012). Southwest Research Institute grabs $12.5M for CSP projects. Online news, Jul. 30, 2012, online: http://www.solarfeeds.com/southwest-research-institute-grabs-12-5m-for-csp-projects/

344. CleanTechnica, (2013). China's growing methanol economy. Apr. 15, 2013, online: http://cleantechnica.com/2013/04/15/chinas-growing-methanol-economy/

345. CNW Group, (2015). Groundbreaking tire recycling facility opens. Design Product News, Sep. 21, 2015, online: http://www.dpncanada.com/industry-news/groundbreaking-tire-recycling-facility-in-waterloo-opens-6814

346. $CO_2BIO$, (2012). $CO_2$ to Bio: Microalgae as an omega-3 rich feedstock integration $CO_2$-sequestration and aquafeed production. Project Final Report. Online: http://www.hordaland.no/PageFiles/47013/FUV%2021.11.12/FUV%2021.11.12.%20Vedlegg%20sak%20291.%20CO₂%20til%20bio%20og%20fiskefor.pdf 347. Cockerill, R., (2016). The industrial gas world in 2016. Gasworld 4 part series, online: http://www.gasworld.com/the-industrial-gas-world-in-2016-part-1/2009726.article; http://www.gasworld.com/the-industrial-gas-world-in-2016-part-2/2009727.article; http://www.gasworld.com/the-industrial-gas-world-in-2016-part-3/2009728.article; http://www.gasworld.com/the-industrial-gas-world-in-2016-part-4/2009729. article 348. Cohen, Y., (2001). Nutrient recovery from wastewater. Swedish University of Agricultural Sciences, Thesis, online: http://www.vaxteko.nu/html/sll/slu/ex_arb_vaxtnaringslara/EVN119/EVN119.HTM 349. Cohen, Y., and Kirchmann, H., (2004). Increasing the pH of wastewater to high levels with different gases—$CO_2$ stripping. Water, Air, and Soil Pollution, 159: 265-275

350. Connelly, R., (2014). How algal biofertilizers can accelerate sustainable agriculture. University of Texas Sustainability Symposium, online: http://www.utexas.edu/sustainability/pssc/symposium/2011/16/

351. Cocero, M. J., Martin, A., and Varona, S., (2009). Encapsulation and co-precipitation processes with supercritical fluids: fundamentals and applications. J. Supercrit. Fluids, 47(3): 546-555.

352. Cockerill, R., (2015). Linde Gas Turkey brings $CO_2$ plant on-stream. Gasworld.com, 20 Nov. 2015, online: http://www.gasworld.com/linde-gaz-turkey-brings-co2-plant-on-stream/2009603.article 353. Cok, B., Teiropoulos, I., Roes, A. L., and Patel, M. K., (2014). Succinic acid production derived from carbohydrates: an energy and greenhouse gas assessment of a platform chemical towards a bio-based economy. Biofuels, Bioprod. Bioref., 8: 16-29

354. Cokoja, M., Bruckmeier, C., Rieger, B., Herrmann, W. A., and Kuhn, F. E., (2011). Transformation of carbon dioxide with homogeneous transition-metal catalysts: a molecular solution to a global challenge? Angew. Chem. Int. Ed., 50(37): 8510-8537.

355. Cokoja, M., Wilhelm, M. E., Anthofer, M. H., Herrmann, W. A., and Kuhn, F. E., (2015). Synthesis of cyclic carbonates from epoxides and carbon dioxide by using organocatalysts. ChemSusChem, 8(15): 2436-2454.

356. Cole, E. B., (2009). Pyridinium-catalyzed electrochemical and photoelectrochemical conversion of carbon dioxide to fuels. PhD Thesis, Princeton University.

357. Cole, E. B., and Bocarsly, A. B., (2010). Photochemical, electrochemical, and photoelectrochemical reduction of carbon dioxide. Chapter 11, pp. 291-334, in: M. aresta (ed.), *Carbon Dioxide as Chemical Feedstock*. Wiley-VCH.

358. Cole, E. B., Lakkaraju, P. S., Rampulla, D. M., Morris, A. J., Abelev, E., and Bocarsly, A. B., (2010). Using a one-electron shuttle for the multielectron reduction of $CO_2$ to methanol: kinetic, mechanistic, and structural insights. J. Am. Chem. Soc., 132: 11539-11551.

359. Coles, T., (2014). Benefits of Amaranth: 14 reasons to get into this grain. Huffington Post Canada, online: http://www.huffingtonpost.ca/2014/03/26/benefits-of-amaranth_n_5036060.html 360. Colonna, P., (2016). Feasibility of a $CO_2$ power cycle for aircraft propulsion systems. Technical University of Delft news note, online: http://www.lr.tudelft.nl/organisatie/afdelingen/aerodynamics-wind-energy-flight-performance-and-propulsion/flight-performance-and-propulsion/propulsion-and-power/research/projects/feasibility-of-a-co2-power-cycle-for-aircraft-propulsion-systems/

361. Commercial Greenhouse Grower, (November 2012). Engine exhaust grows tomatoes. The Commercial Greenhouse Grower, November, 2012, p. 9, online: http://greenhousegrower.co.uk/wp-content/uploads/magazines/magazine-november-2012/files/assets/common/downloads/GH%20Nov%202012.pdf 362. Compact GTL Website and slideck presentations: www.CompactGTL.com; e.g., http://www.compactgtl.com/wp-content/uploads/2015/04/CompactGTL-presentation-for-IGTC-2015-English-version.pdf 363. CompanyWeek, (2015, May 1st). Tersus Solutions. Online: http://companyweek.com/company-profile/tersus-solutions
364. Condon, C., and Kelman, S., (2012). Shute Creek facility and Controlled Freeze Zone™ updates. ExxonMobil slide deck presentation, Wyoming EORI 6$^{th}$ Annual CO2 Conference, Jul. 11, 2012, online: https://www.uwyo.edu/eori/_files/co2conference12/clay_exxonmobil%202012%20eori%20wyoming%20co2%20conference_070312.pdf
365. Connery, K. A., Shah, P., Coleman, L., and Hunek, B., (2005). Commercialization of Better Than Fresh™ dense phase carbon dioxide processing. ISSF 2006, Orlando, Fla.
366. Conroy, J. P., Milham, P. J., and Barlow, E. W. R., (1992). Effect of nitrogen and phosphorus availability on the growth response of *Eucalyptus grandis* to high $CO_2$. Plant, Cell and Environment, 15: 843-847.
367. Cooney, G., Littlefield, J., Marriott, J., Skone, T. J., (2015). Evaluating the climate benefits of $CO_2$-Enhanced Oil Recovcery using Life Cycle Analysis. Environ. Sci. Tech., 49(12): 7491-7500
368. Copeland, E. R., (1994). UNICARB Adhesion promoters for plastic applications. Conference paper, Society for Manufacturing Engineers, online: http://infohouse.p2ric.org/ref/25/24247.pdf
369. Corazza, M. L., Cardozo-Filho, L., Antunes, O. A. C., and Dariva, C., (2003). Phase behavior of the reaction medium of limonene oxidation in supercritical carbon dioxide. Ind. Eng. Chem. Res., 42(13): 3150-3155.
370. Costa, A. and Chiodini, G., (2015). Modelling Air Dispersion of $CO_2$ from Limnic Eruptions. In: D. Rouwet et al. (eds.), *Volcanic Lakes*, pp. 451-465.
371. Costentin, C., Passard, G., Robert, M., and Saveant, J.-M., (2014). Ultraefficient homogeneous catalysts for the $CO_2$-to-CO electrochemical conversion. PNAS, 111 (42): 14990-14994.
372. Costentin, C., Robert, M., and Saveant, J.-M., (2013). Catalysis of the electrochemical reduction of carbon dioxide. Chem. Soc. Rev., 42: 2423-2436.
373. Cox, C. R., Lee, J. Z., Nocera, D. G., and Buonassisi, T., (2014). Ten-percent solar-to-fuel conversion with non-precious materials. PNAS, 111(39): 14057-14061
374. Craggs, R., Sutherland, D., and Campbell, H., (2012). Hectare-scale demonstration of high-rate algal ponds for enhanced wastewater treatment and biofuel production. J. Appl. Phycology, 24(3): 329-337.
375. Crawford, M., (2015). Taking the hydro out of hydraulic fracturing. Mechanical Eng. Mag., 137(3): 30-35, online: http://expansion-energy.com/yahoo_site_admin/assets/docs/Mechanical_Engineering_Magazine_ASME_-_Waterless_Fracturing_-_VRGE_-March_2015_-ASMEcopyright.55132122.pdf
376. Creutz, C., and Fujita, E., (2001). Carbon dioxide as a feedstock. Pp. 83-92 in: *Carbon Management: Implications for R&D in the Chemical Sciences and Technology*. National Academies of Sciences.
377. Cuellar-Bermudez, S. P., Aguilar-Hernandez, I., Cardenas-Chavez, D. L., Ornelas-Soto, N., Romero-Ogawa, M. A., and Parra-Saldivar, R., (2014). Extraction and purification of high-value metabolites from microalgae: essential lipids, astaxanthin and phycobiliproteins. Microbial Biology, 8(2): 190-209
378. Cuellar-Franca, R. M., and Azapagic, A., (2015). Carbon capture, storage and utilization technologies: a critical analysis and comparison of their life cycle environmental impacts. J. $CO_2$ Util., 9: 82-102.
379. Curia, S., Barclay, A., and Howdle, S. M., (2015). Low-temperature lipase-catalyzed synthesis of reneable functional telechelicpolyesters in supercritical $CO_2$. J. Material Sci. Eng., 4:4, online: http://www.omicsgroup.org/journals/2169-0022/2169-0022.S1.022_010.pdf
380. Cyanotech, (2015). Cyanotech adds astaxanthin productivity enhancement. Cyanotech press release, online: http://www.cyanotech.com/news/news_061215.html
381. CyclicCO$_2$R, (undated). Website: http://www.cyclicco2r.eu
382. Cytec, (undated). ECO$_2$FUME fumigant gas. https://www.cytec.com/sites/default/files/files/ECO_SPEC_SHEET_2-16-11_FINAL.pdf; ECO$_2$FUME Product safety summary, online: https://www.cytec.com/sites/default/files/files/ECO$_2$FUME%20phosphine%20fumigant_PSS.pdf
383. Czaplicki, S., Ogrodowska, D., Zadernowski, R., and Derewiaka, D., (2012). Characteristics of biologically-active substances of Amaranth oil obtained by various techniques. Pol. J. Food Nutr. Sci., 62(4): 235-239.
384. Czech, B. C., (2014). Our food in a changing climate: growth, yield, and nutrient changes of sweet potato across the spectrum of $CO_2$ concentrations projected in the next 150 years. Masters Thesis, University of Hawaii at Manoa, 88 pp, online: https://www.soest.hawaii.edu/GG/resources/theses/Czeck_Masters_Thesis.pdf
385. Czuan, M., Goeppert, A., Kothandaraman, J., May, R. B., Haiges, R., Surya Prakash, G. K., and Olah, G. A., (2013). Formic acid as a hydrogen storage medium: ruthenium-catalyzed generation of hydrogen from formic acid in emulsions. ACS Catal., 4: 311-320.
386. Dagan, G. E., and Balaban, M. O., (2006). Pasteurization of beer by a continuous dense-phase $CO_2$ system. J. Food Sci., 71(3): E164-E169.
387. Dai, W., Luo, S., Yin, S., and Au, S.-T., (2010). A mini review on chemical fixation of $CO_2$: absorption and catalytic conversion into cyclic carbonates. Frontiers of Chem. Eng. In China, 4(2): 163-171.
388. Damar, S., and Balaban, M. O., (2006). Review of dense phase $CO_2$ technology: microbial and enzyme inactivation, and effects of food quality. J. Food Sci., 71(1), R1-R10.
389. Damar, S., Balaban, M. O., and Sims, C. A., (2009). Continuous dense-phase $CO_2$ processing of coconut water. Intl. J. Food Sci. Tech., 44(4): 666-673.
390. Damas, H., (1937a). Recherches hydrobiologiques dans les Lacs Kivu, Edouard et Ndalaga. Imprint Hayez.
391. Damas, H., (1937b). La Stratification Thermique et Chimique des Lacs Kivu, Edouard et Ndaleger. Verh. Int. Ver. Theor. Angew Limnol. V 8. Pp. 51-68.
392. Daniell, J., Kopke, M., and Simpson, S. D., (2012). Commercial biomass syngas fermentation. Energies, 5: 5372-5417.
393. Daniels, J., (2015). Carbon Capture and Stirage (CCS): a US DOE perspective. US Department of Energy slide deck presentation, USEA 8$^{th}$ Annual Energy Supply Forum & WEC North America Regional Energy Forum, 14 September, 2015, online: https://www.usea.org/sites/default/files/event-/Jarad%20Daniels%20-%202015%20WEC%20NA%20Regional%20Energy%20Forum.pdf
394. Danish Methanol Association, (2011). Bio-Methanol. Report TM01-2e. Online: http://www.starch.dk/methanol/energy/img/TM01-02e.pdf 395. Dannehl, D., Schuch, I., and Schmidt, U., (2013). Plant production in solar collector greenhouses—influences on yield, energy use and reduction in $CO_2$ emissions. J. Agric. Sci., 5(10): 34-45.

396. Daolin, G., et al., (2007). Evaluation of large, modern warehouse storages designed and constructed for application of carbon dioxide. Pp. 579-589, in: E. J. Donahaye et al. (eds.), Proc. Int. Conf. Controlled Atmosphere and Fumigation in Stored Products, Gold-Coast Australia, 8-13 Aug. 2004. FTIC Publishing, Israel. Online: http://ftic.co.il/2004gold-coastPDF/P4.pdf; http://ftic.co.il/2008ChengduPDF/SESSION.pdf 397. Daraei, H. N., Khodapanah, E., and Sahraei, E., (2015). Experimental investigation of steam-$CO_2$-foam flooding: combination of $CO_2$-foam flooding and steam injection as an effective enhanced oil recovery (EOR) method in heavy oil reservoirs. Asia-Pacific J. Chem. Eng., 10(3): 377-386

398. Darensbourg, D. J., (2007). Making plastics from carbon dioxide: salen metal complexes as catalysts for the production of polycarbonates from epoxides and $CO_2$. Chem. Rev., 107: 2388-2410.

399. Darensbourg, D. J., (2010). Chemistry of carbon dioxide relevant to its utilization: a personal view. Inorg. Chem., 49(23); 10765-10780.

400. Darensbourg, D. J., (2014). Chapter one—Personal adventures in the synthesis of copolymers from carbon dioxide and cyclic ethers. Chapter 1, pp. 1-23 in: M. Aresta and R. van Eldik, (eds.), *$CO_2$ Chemistry* (Advanced in Inorganic Chemistry, v. 66).

401. Darensbourg, D. J., Andreatta, J. R., and Moncada, A. I., (2010). Polymers from carbon dioxide: polycarbonates, polythiocarbonates and polyurethanes. Chapter 8, pp. 213-248, in: M. Aresta, (ed.), *Carbon Dioxide as Chemical Feedstock*. Wiley 402. Darensbourg, D. J., and Holtcamp, M. W., (1966). Catalysts for the reactions of epoxides and carbon dioxide. Coord. Chem. Rev., 153: 155-174.

403. Darensbourg, D. J., and Wilson, S. J., (2012). What's new with $CO_2$?Recent advances in its copolymerization with oxiranes. Green Chem., 14: 2665-2671.

404. Davenport, M., (2015). Twists and shouts: a nanotube story. C&EN, Jun. 8, 2015, v. 93(23): 10-15, online: http://cen.acs.org/articles/93/i23/Twists-Shouts-Nanotube-Story.html 405. Davison, J., Mancuso, L., Ferrari, N., Chiesa, P., Martelli, E., and Romano, M., (2015). Techno-economic assessment of oxy-combustion turbine power plants with $CO_2$ capture. Slide deck presentation, 5$^{th}$ Oxy-combustion Network Meeting, Wuhan, China, 27-30 Oct. 2015, online: http://www.ieaghg.org/docs/General_Docs/IEAGHG_Presentations/6B-04_-_S._Santos_IEAGHG_SEC.pdf 406. Daymondi, A. J., Wheeler, T. R., Hadley, P., Morison, L., (1997). The growth, development and yield of onion (*Allium cepa* L.) in response to temperature and $CO_2$. J. Hort. Sci., 72(1): 135-145.

407. De Falco, M., Iaquaniello, G., and Centi, G., (2013, editors). *$CO_2$: A Valuable Source of Carbon*. Springer, pp. 194.

408. De Gelder, A., Dieleman, J. A., Bot, G. P. A., and Marcelis, L. F. M., (2012). An overview of climate and crop yield in closed greenhouses. J. Horticultural Sci. & Biotechnol., 78(3): 193-202.

409. De Gelder, A., Warmenhoven, M., Dieleman, A., Klapwijk, P., and van Baar, P. H., (2014). Light dependent $CO_2$ supply in a tomato crop. Wageningen University online report: http://edepot.wur.nl/294206

410. De Guzman, (2012). LanzaTech in $CO_2$-to-acetic acid. Green Chemicals Blog, Dec. 16, 2012. Online: http://greenchemicalsblog.com/2012/10/16/lanzatech-in-co2-to-acetic-acid/

411. De la Victoire, A., (2014). Rwanda eyes 35% of urbanization rate. http://en.igihe.com/news/rwanda-eyes-35-of-urbanization-rate.html 412. De los Reyes-Gavilan, Ruas-Madiedo, P., Gueimonde, M., and Noriega, L., (2005). Application of low-pressure dissolved carbon dioxide to the manufacture and preservation of milk and dairy products. Pp. 133-151 in: A. O. Riley, (ed.), *Food Research, Safety and Policies*. Nova Science Publishers.

413. de Moel, P. J., van Dijk, J. C., and van der Meer, W. G. J., (2015). *Aquatic Chemistry for Engineers, v. 1, Starting with PHREEQC for Water Treatment*. TU Delft, online: http://ac4e.omnisys.nl/wp-content/uploads/2015/09/AC4E_Vol_.pdf 414. De Visser, P., ad Dijkxhoorn, Y., (2011). Business opportunities for protected horticulture in South Africa. Wageningen University online report: http://www.wageningenur.nl/en/show/Report-Business-opportunities-for-protected-horticulture-in-SouthAfrica-1.htm 415. De Wit, S., (2014). Gas-fuelded CHP delivers heat, $CO_2$ for greenhouses. Consulting Specifying Engineer, Jul. 25, 2014, online: http://www.csemag.com/single-article/gas-fueled-chp-delivers-heat-co2-for-greenhouses/9ba0c4e00a8339e4deb1222860685745.html 416. de Wolff, J., Mikunda, T., Catau, R., Blank, F., Khawaja, S. Z., (2013). Technical and legal aspects of $CO_2$ transport by ship and implementation of the $CO_2$ flow monitoring. CATO-2 report, online: http://www.co2-cato.org/publications/library 1/technical-and-legal-aspects-of-co2-transport-by-ship-and-implementation-of-the-co2-flow-monitoring 417. DeCristofaro, N., (2015). Reducing the clinker factor. World Cement, September, 2015, online: http://solidiatech.com/wp-content/uploads/2015/09/Reducing-the-Clinker-Factor-World-Cement.pdf 418. DeCristofaro, N., and Sahu, S., (2014). $CO_2$-reducing cement. World Cement, January 2014, online: http://solidiatech.com/wp-content/uploads/2014/02/World-Cement-Article.pdf 419. DeCristofaro, N., and Sahu, S., (2015a). Exploring the chemical properties and performance results of sustainable Solidia Cement and Solidia Concrete. The Masterbuilder, February 2015, pp. 82-88.

420. DeCristofaro, N., and Sahu, S., (2015b). Exploring the chemical properties and performance results of sustainable Solidia Cement and Solidia Concrete Part II. The Masterbuilder, March 2015, pp. 116-124.

421. DeCrisofaro, N., Atakan, V., and Sahu, S., (2014). Curing concrete with carbon. Concrete Engineering Int'l., July/August, 2014, pp. 32-34, online: http://solidiatech.com/wp-content/uploads/2014/07/Concrete-UK-Engineering-Intl-with-cover-V48I06P32.pdf 422. Deep Earth, (2015). Technological deficiencies to limit sale of Uganda's test oil. Deep Earth International, online article, 17 Feb. 2015, online: http://deepearthint.com/index.php?Item=5051

423. Del Campo, J. S. M., Rollin, J., Myung, S., Chun, Y., Chandrayan, S., Patino, R., Adams, M. W. W., and Zhang, Y.-H. P., (2013). High-yield production of dihydrogen from xylose by using a synthetic enzyme cascade in a cell-free system. Angew. Chem. Int. Ed., 52(17): 4587-4590.
424. Del Castillo, A., Alvarez-Guerra, M., Solla-Gullon, J., Saez, A., Montiel, V., ans Irabien, A., (2015). Electrolytic reduction of $CO_2$ to formate using particulate Sn electrodes: effect of metal loading and particle size. Applied Energy, 157: 165-173.
425. Demirel, Y., Matzen, M., Winters, C., Gao, X., (2015). Capturing and using $CO_2$ as feedstock with chemical looping and hydrothermal technologies. Int. J. Energy Res., 39(8): 1011-1047.
426. Denbury, (2011). Denbury Resources, Inc., 2011 Corporate Responsibility Report. Online: http://www.denbury.com/files/doc_downloads/denburycrr_final_050313.pdf
427. Denbury, (2009a). $CO_2$ pipelines: Infrastructure for $CO_2$-EOR and CCS. Slide deck presentation, online: http://www.purdue.edu/discoverypark/energy/assets/pdfs/cctr/cctr-meetings/march2009/CCTR-Tucker-03-05-09.pdf
428. Denbury, (2009b). Anthropogenic $CO_2$ sources. Slide deck presentation March 2009. Online: http://docs.nrdc.org/globalWarming/files/glo_09031101 f.pdf
429. Dennis, R., (2014). Summary of U.S. Department of Energy supercritical $CO_2$ projects. NETL slide deck presentation, Sep. 11, 2014 Online: http://www.netl.doe.gov/File%20Library/Events/2014/sco2workshop/1-3---US-DOE-SCO$_2$-Project-summaries.pdf
430. Denton, R. D., Maher, D. W., Mart, C. J., and Valencia, J. A., (2015). ExxonMobil: commercializing SE Asia sour gas resources. GasTech News, 27 Aug. 2015, online: http://www.gastechnews.com/uncategorized/exxonmobil-commercializing-se-asia-sour-gas-resources/
431. Department of Energy (USA), (2015). A review of the $CO_2$ pipeline infrastructure in the U.S. Report DOE/NETL-2014/1681. 44pp. Online: http://energy.gov/sites/prod/files/2015/04/f22/QER%20Analysis%20-%20A%20Review%20of%20the%20CO$_2$%20Pipeline%20Infrastructure%20in%20the%20U.S_0.pdf
432. Der, V., (2014). Status and development of CCS/CCUS in US. Global CCS Institute slide deck presentation, Oct. 7-8, 2014, online: http://wyia.org/wp-content/uploads/2014/10/vic-der.pdf
433. Descy, J.-P., Darchambeau, F., and Schmid, M., (2012). *Lake Kivu: Limnology and Biochemistry of a Tropical Great Lake*. Aquatic Ecology Series, v. 5. Springer
434. Descy, J.-P., Darchambeau, F., and Schmid, M., (2012), Lake Kivu: Past and Present. Chapter 1, pp. 1-11, in: Descy, J.-P., Darchambeau, F., and Schmid, F., (eds). *Lake Kivu: Limnology and Biochemistry of a Tropical Great Lake*. Springer.
435. Descy, J-P., Darchambeau, F., Schmid, M., (2012). (Chapter 11) Lake Kivu Research: Conclusions and Perspectives. Pp. 181-190, in: Descy, J-P., Darchambeau, F., Schmid, M., 2012 (editors). *Lake Kivu: Limnology and Biochemistry of a Tropical Great Lake*. Springer.
436. DeSimone, J. M., (2002). Practical approaches to green solvents. Science, 297(5582): 799-803
437. DeSimone, J. M., and Tumas, W., (editors, 2003). *Green Chemistry Using Liquid and Supercritical Carbon Dioxide*. Oxford Univ. Press, pp. 288
438. Devanna, L., (2007). Coal-based oxy-fuel system evaluation and comustor development. International Oxy-Combustion Research Network, $2^{nd}$ workshop, 25-26 January, 2007, Windsor, Conn., USA, online: http://ww-w.ieaghg.org/docs/oxyfuel/MTG2Presentations/Session%2007/26%20-%20L.%20Devanna%20(CES).pdf
439. Devanna, L., (2011). Advanced turbine development for pressurized oxy-combustion commercial scale-up. Clean Energy Systems slide deck presentation, Oct. 25, 2011, online: http://www.westcarb.org/pdfs_Lodi/Devanna.pdf
440. Devanna, L., (2012). Advanced turbine developments for oxycombustion Trigen plants. Clean Energy Systems corporate presentation slide deck, Oct. 16, 2012, online: http://www.westcarb.org/pdfs_bakersfield12/Devanna.pdf
441. Devanna, L., (2013). Clean Energy Systems, Inc., update on oxyfuel combustion. January 2013 slide deck presentation, online: http://www.mcilvainecompany.com/Universal_Power/Subscriber/PowerDescriptionLinks/Leonard%20Devanna%20-%20Clean%20Energy%20Systems%20-%201-10-13.pdf
442. Devearapalli, M., and Atiyeh, H. K., (2015). A review of conversion processes for bioethanol production with a focus on syngas fermentation. Biofuel Research J., 7: 268-280
443. Di Giacomo, G., Taglieri, L., and Carozza, P., (2009). Pasteurization and sterilization of milk by supercritical carbon dioxide treatment. Proc. $9^{th}$ Int'l. Symp. Supercritical Fluids, 18-20 May, Archachon, France, online: http://www.isasf.net/fileadmin/files/Docs/Arcachon/oraux/c87-C075%20Di%20Giacomo%20ISSF%202009%20BORDEAUX.pdf
444. DiMascio, F., Willauer, H. D., Hardy, D. R., Lewis, M. K., and Williams, F. W., (2010). Extraction of carbon dioxide from seawater by an electrochemical acidification cell Part I—initial feasibility studies. Naval Research Laboratory, NRL/MR/8180-10-9274
445. diMeglio, J. L., and Rosenthal, J., (2013). Selective conversion of $CO_2$ to CO with high efficiency using an inexpensive bismuth based electrocatalyst. J. Am. Chem. Soc., 135(24): 8798-8801.
446. Dimitriou, I., Garcia-Gutierrez, P., Elder, R. H., Cuellar-Franca, R. M., Azapagic, A., and Allen, R. W. K., (2015). Carbon dioxide utilization for production of transport fuels: process and economic analysis. Energy Environ. Sci., 8: 1775-1789
447. Dioxide Materials (2014). NETL presentation poster overview, online: http://www.netl.doe.gov/File%20Library/Events/2014/2014%20NETL%20CO$_2$%2 OCapture/Poster-R-Masel-Dioxide-Materials-Economically-Viable-CCR.pdf
448. DiPietro, P., Balsh, P., and Wallace, M., (2012). A note on sources of CO2 supply for Enhanced-Oil-Recovery Operations. April 2012 SPE Economics and Management, paper EM-111-0002, online: http://www.netl.doe.gov/energy-analyses/temp/FY12_ANoteonSourcesofCO2SupplyforEnhancedOilRecoveryOperations_040112.pdf
449. District Energy, (2015). Leading European greenhouse tomato grower to pilot GE's new asset performance management solution for cogeneration. Online (with video): http://www.districtenergy.org/blog/2015/06/12/leading-european-greenhouse-tomato-grower-to-pilot-ges-new-asset-performance-management-solution-for-cogeneration-plants/
450. Divon, J., (2015). Halifax startup recycles carbon dioxide to make greener concrete products. Globe & Mail, Apr. 6, 2009, online: http://www.theglobeandmail.com/report-on-business/small-business/sb-growth/sustainability/halifax-startup-recycles-carb on-dioxide-to-make-greener-concrete-products/article23744134/
451. DNV, (2011). Carbon dioxide utilization: Electrochemical conversion of $CO_2$—Opprtunities and challenges. Research and Innovation Position Paper 07—2011, online: http://www.dnv.com/binaries/DNV-positionpaper_CO₂_Utilization_tcm4-445820.pdf Associated video: https://www.youtube.com/watch?v=yS_0SopyRs 452. Doctor, R., Palmer, A., and others, (2005). Transport of $CO_2$. Cambridge University Press. *IPCC special report on Carbon Dioxide Capture and Storage*, online: https://www.ipcc.ch/pdf/special-reports/srccs/srccs_chapter4.pdf (In: https://www.ipcc.ch/pdf/special-reports/srccs/srccs_wholereport.pdf)

453. Dodge, E., (2014). CCS breakthrough: $sCO_2$ power cycles offer improved efficiency and integrated carbon capture. Breaking Energy, Nov. 14, 2014, online: http://breakingenergy.com/2014/11/14/ccs-breakthrough-sco2-power-cycles-offer-improved-efficiency-and-integrated-carbon-capture/

454. DOE, (2015a). Quadrennial Technology Review: An Assessment of Energy Technologies and Research Opportunities. Online: http://www.energy.gov/sites/prod/files/2015/09/f26/Quadrennial-Technology-Review-2015_0.pdf 455. DOE, (2015b). SEP: Fiscal Year 2016 Science and Energy Plan. US Department of Energy Report, online: http://energy.gov/sites/prod/files/2015/10/f27/SEP-book-10-7-2015.pdf 456. DOE, (1993). A research needs assessment for the capture, utilization and disposal of carbon dioxide from fossil fuel-fired power plants. Volume II Technical Reports. DOE/ER-30194. US Department of Energy report, online: http://www.osti.gov/scitech/servlets/purl/10192734

457. DOE/NETL, (2015). 2104 Technology readiness assessment. US Department of Energy/National Energy Technology Laboratory/Clean Coal Research Program, DOE/NETL-2015/1710, online: http://www.netl.doe.gov/File%20Library/Research/Coal/Reference%20Shelf/DOE-NETL-20151710-2014-Technology-Readiness-Assessment-Comprehensive.pdf; http://www.netl.doe.gov/File%20Library/Research/Coal/Reference%20Shelf/DOE-NETL-20151711-2014-Technology-Readiness-Assessment-Overview.pdf 458. DOE/NETL, (2015b). A review of the CO2 pipeline infrastructure in the U. S. DOE/NETL-2014/1681, online http://energy.gov/sites/prod/files/2015/04/f22/QER%20Analysis%20-%20A%20Review%20of%20the%20CO2%20Pipeline%20Infrastructure%20in%20the%20U.S_0.pdf 459. DOE/NETL, (2012). Supercritical $CO_2$ power cycles literature survey. Slide deck presentation, Dec. 12, 2012, online: http://www.netl.doe.gov/energy-analyses/temp/SupercriticalCO2PowerCycles-LiteratureSurvey_121212.pdf 460. Donahue, M., (undated). Supercritical carbon dioxide and paints: the UNICARB process. Online: http://www.nigelworks.com/mdd/PDFs/UNICARB.pdf 461. Dorman, K., (2015). How to prepare sweet potato leaves for optimum nutrition. Oct. 6, 2015, Livestrong online: http://www.livestrong.com/article/521136-how-to-prepare-sweet-potato-leaves-for-optimum-nutrition/

462. Dostal, V., Driscoll, M. G., and Hejzlar, P., (2004). A supercritical carbon dioxide cycle for next generation nuclear reactors. Advanced Nuclear Power Technology Program, Report: MIT-ANP-TR-100, pp. 307.

463. Dow, (undated). Natural oil-based polyols. Dow magazine, RE:INVENT online: http://msdssearch.dow.com/PublishedLiteratureDOWCOM/dh_009d/0901b8038009d9af.pdf?filepath=renuva/pdfs/noreg/109-01729.pdf&fromPage=GetDoc 464. Drake, H. L., (1994, editor). *Acetogenesis*. Chapman & Hall.

465. Drennan, P. M., and Nobel, P. S., (2000). Responses of CAM species to increasing atmospheric $CO_2$ concentrations. Plant, Cell, Environ., 23: 767-781.

466. Dreybrodt, W., (1980). Deposition of calcite from thin films of natural calcareous solutions and the growth of speleothems. Geology, 29(1-4): 89-105

467. Dreybrodt, W., Hansen, M., and Scholz, D., (2013). Processes inside the cave imprinting isotope changes into calcite precipitated to speleothems. University of Bremen slide deck presentation: http://www.speleothem2013.uni-hd.de/materials/S4_Dreybrodt.pdf 468. Du, C., (2005). A review of magnesium oxide in concrete: a serendipitous discovery leads to new concrete for dam construction. Concrete Intl., December 2005, 45-50, online: http://www.premiermagnesia.com/userdata/userfiles/file/CPG/About%20section/A%20Review%20of%20Magesium%20Oxide%20in%20Concrete.pdf 469. Du, Y., Schuur, B., Kersten, S. R. A., and Brilman, D. W. F., (2015). Opportunities for switchable solvents for lipid extraction from wet algal biomass: an energy evaluation. Algal Res., 11: 271-283.

470. Du, Y., Schuur, B., Samori, C., Tagliavini, E., Brilman, D. W. F., (2013). Secondary amines as switchable solvents for lipid extraction from non-broken algae. Bioresource Technol., 149: 253-260.

471. Ducat, D. C., and Silver, P. A., (2012). Improving carbon fixation pathways. Curr. Opinion Chem. Biol., 16: 1-8

472. Ducos, J.-P., Lambot, C., amd Petiard, V., (2007). Bioreactors for coffee mass production by somatic embryogenesis. Int. J. Plant Developmental Biol., 1: 1-12, Online: http://www.researchgate.net/publication/228680212_Bioreactors_for_coffee_mass_propagation_by_somatic_embryogenesis 473. Duncum, (1947). *The Development of Inhalation Anaesthesia*. Oxford Univ. Press.

474. Dupont, (2012). Xyvia xylitol white paper Online: http://www.danisco.com/fileadmin/user_upload/danisco/documents/products/2e_XIVIAWhite_Paper.pdf 475. Durelle, J., (2014). Designing switchable-hydrophilicity solvents and modeling their behavior. PhD Thesis, Queen's University, Kingston, Ontario, Canada. Online: https://qspace.library.queensu.ca/bitstream/1974/12528/1/Durelle_Jeremy_201409_MSc.pdf 476. Durelle, J., Vanderveen, J. R., Quan, Y., Chalifoux, C. B., Kostin, J. E., and Jessop, P. G., (2015). Extending the range of switchable-hydrophilicity solvents. Phys. Chem. Chem. Phys., 17: 5308-5313.

477. Durre, P., and Eikmanns, B. J., (2015). C1-carbon sources for chemical and fuel production by microbial gas fermentation. Curr. Opin. Biotechnol., 35: 63-72

478. DyeCoo, (2010). DyeCoo: waterless dying. Online: http://www.dyecoo.com/pdfs/colourist.pdf 479. E4tech, (2014). Relevance and commercial prospects of algal energy for the Swiss energy strategy 2050. Online report: http://www.sccer-biosweet.ch/export/sites/SC-CER-BIOSWEET/outreach/.content/downl_outreach/Relevance-and-commercial-prospects-of-algal-energy-for-the-Swiss-energy-strategy-2050_2015.pdf 480. Eastman, A. D., (2014). GreenFire Energy, Phase I Final Report, DOE Award DE-EE0004432. Online: http://www.osti.gov/geothermal/servlets/purl/1164240/

481. Eastman, A. D., and Muir, M. P., (2012). $CO_2$-based geothermal energy at St. John's Dome—a status report. GRC Transactions, 36: 407-414

482. Eastman, A. D., and Muir, M. P., (2013). $CO_2$ EGS and the utilization of highly pressured $CO_2$ for purposes other than power generation. Proc. 38$^{th}$ Workshop on Geothermal reservoir Engineering, Stanford University, online: https://pangea.stanford.edu/ERE/pdf/IGAstandard/SGW/2013/Eastman.pdf 483. Ebbesen, S. D., and Mogenen, M., (2009). Electrolysis of carbon dioxide in solid oxide electrolysis cells. J. Power Sources, 193: 349-358.

484. Ebbesen, S. D., Graves, C., and Mogensen, M., (2009). Production of synthetic fuels by co-electrolysis of steam and carbon dioxide. Int. J. Green Energy, 6: 646-660.

485. Ebner, H., and Sellmer-Wilsber, S., (2002). Vinegar, acetic acid production. *Encyclopedia of Bioprocess Technology*. Joh Wiley & Sons.

486. Ebrahimzadeh, E., (2016). Mitigating transients and azeotropes during natural gas processing. PhD Thesis, Brigham Young University, BHU Scholasrs Archive, http://scholarsarchive.byu.edu/etd/5880/

487. Ebrahimzadeh, E., Wilding, P., Frankman, D., Fazlollahi, F., and Baxter, L. L., (2016a). Theoretical and experimental analysis of dynamic plate heat exchanger: Non-retrofit configuration. Applied Thermal Engineering, 93: 1006-1019

488. Ebrahimzadeh, E., Wilding, P., Frankman, D., Fazlollahi, F., and Baxter, L. L., (2016b). Theoretical and experimental analysis of dynamic plate heat exchanger: Retrofit configuration.

489. Eby, G. N. and Evans, W. C., (2006). Taming the killer lakes of Cameroon. Geology Today, v. 22 (1): 18-22

490. Echogen Power Systems, (2014). Press release: Echogen's power systems' waste heat recovery system available as turnkey solution. Online: http://www.echogen.com/news-resources/news-events/echogen-power-systems-waste-heat-recovery-system-available-as-turnkey-solution 491. Echogen Power Systems, (2012). Heat to power systems. EnergyTech 2012 slide deck presentation, online: http://energytech2012.org/wp-content/uploads/2012/05/W-S2-D-ECHOGEN-PRESENTATION_30MAY12_.pdf 492. Economic Commission for Africa, (2015a). Industrializing Through Trade. Economic Report on Africa. United Nations ECA, Addis Ababa. Online: http://www.uneca.org/publications/economic-report-africa-2015

493. Economic Commission for Africa, (2015b). ERA 2015—An argument for trade-induced industrialization. United Nations ECA, Addis Ababa, press release, online: http://www.uneca.org/stories/era-2015-argument-trade-induced-industrialization 494. Economic Commission for Africa, (2014). Dynamic Industrial Policy in Africa. United Nations ECA, Addis Ababa. Online: http://www.uneca.org/sites/default/files/PublicationFiles/final_era2014_march25_en.pdf 495. Ecowater Systems, (undated). Controlled Hydrodynamic Cavitation: chemical-free cooling tower water treatment system. Ecowater Systems slide deck presentation, online: http://www.slideshare.net/RonColetta1/ecowater-chc-chemical-free-cooling-tower-water-treatment-system 496. Edwards, D. R., (2008). Towards a plant-based method of guiding $CO_2$ enrichment in greenhouse tomato. Ph.D. Thesis, University of British Columbia (Candada), online: https://circle.ubc.ca/bitstream/id/9872/ubc_2009_spring_edwards_diane.pdf 497. Edwards, J. K., Freakley, S. J., Lewis, R. J., Prichard, J. C., and Hutchings, G. J., (2015). Advances in direct synthesis of hydrogen peroxide from hydrogen and oxygen. Catalysis Today, 248: 3-9.

498. Eikeland, E., Blichfeld, A. B., Tyrsted, C., and Jensen, A., (2015). Optimized carbonation of magnesium silicate mineral for $CO_2$. ACS Appl. Mater. Interfaces, 7: 5258-5264.

499. Eisaman, M. D., Parajuly, K., Tuganov, A., Eldershaw, C., Chang, N., and Littau, K. A., (2012). $CO_2$ extraction from seawater using bipolar membrane electrodialysis. Energy Environ. Sci., DOI: 10.1039/c2ee03393c 500. Emadi, A., Sohrabi, M., Jamiolahmady, M., Ireland, S., and Robertson, G., (2011). Reducing heavy oil carbon footprint and enhancing production through $CO_2$ injection. Chem. Eng. Res. Design, 89(9): 1783-1793

501. Emerson, S., (1975). Chemically enhanced $CO_2$ gas exchange in a eutrophic lake: a general model. Limnology and Oceanography, 20(5): 743-753

502. Emery, J., Salier, B., and Michniewicz, A., (undated). The nickel sector: metal and equity review. FD Capital.

503. Enik, R. E., and Olsen, D. K., (2011). Mobility and conformance control for carbon dioxide enhanced oil recovery ($CO_2$-EOR) via thickeners, foams, and gels: a detailed literature review of 40 years of research. DOE Report DOE/NETL-2012/1540, online: http://www.netl.doe.gov/file%20library/research/oil-gas/$CO_2$-mobility-control-report-2011.pdf 504. Enoch, H. Z., and Kimball, B. A., (1986). *Carbon Dioxide Enrichment of Greenhouse Crops, V.1: Status and $CO_2$ Sources, V.2: Physiology, Yield and Economics*. CRC Press, Boca Raton, Fla., USA 505. Enthaler, S., von Langermann, J., and Schmidt, T., (2010). Carbon dioxide and formic acid—the couple for environmental-friendly hydrogen storage? Energy & Environmental Sci., 3: 1207-1217.

506. ETC Group, (2014). Rubber and synthetic biology: a case study. Online: http://www.etcgroup.org/sites/www.etcgroup.org/files/ETC-rubber-synbio-casestudy2014.pdf 507. ETOGAS, (2015). $CO_2$ reutilization in industrial projects—state of art and realization of concrete projects for the production of renewable methane and solid products based on $CO_2$. Presentation slidedeck by S. Rieke online: http://www.ceops-project.eu/sites/default/files/documents/ceops_ws_5._rieke.pdf 508. Eugster, H. P., (1966). Sodium carbonate-bicarbonate minerals as indicators P $CO_2$. J. Geophys. Res., 71(14): 3369-3377

509. Evans, C. L., (2010). $CO_2$ unit coolers for supermarket refrigeration systems. Online: http://www.heatcraftrpd.com/newsletters/rnews/2010/february/lib/files/BN-CUCWP-0909.pdf 510. Evans, S. M., (2008). Novacem: carbon negative cement to transform the construction industry. Novacem slide deck presentation, London, Oct. 15, 2008, online: http://www3.imperial.ac.uk/pls/portallive/docs/1/50161701.PDF 511. Evans, S. M., (2009) Novacem: carbon negative cement to transform the construction industry. Novacem slide deck presentation, Cambridge, Dec. 4, 2010, online: http://www.cir-strategy.com/uploads/17 StuartEvansNovacemHeat09.pdf 512. Evans, S. M., and Vlasopoulos, N., (2010). Novacem: carbon negative cement and the green cement bond. Navacen slide deck presentation, Warsaw, Poland, 14 Sep. 2010, online: http://www.wbcsdcement.org/pdf/CSIForum2010/05%20Novacem%20at%20CSI%20Forum. 14%20Sept%202010.for%20distribution.pdf; http://docsfiles.com/pdf_csi_forum_2010_cement.html 513. Evonic (online information, undated). Online: http://extraction.evonik.com/product/extraction/en/Pages/default.aspx http://extraction.evonik.com/product/extraction/Documents/product-story---a-natural-pleasure.pdf http://extraction.evonik.com/product/extraction/en/application-areas/Pages/default.aspx; http://extraction.evonik.com/product/extraction/Documents/application-areas.pdf 514. Ewart, W., Hermanussen, O., Kabbe, C., Mele, C., Niewersch, C., Paillard, H., Stossel, E., Wagenbach, A., and Stenmann, J., (2014). P-Rex: sustainable sewage sludge management fostering phosphorus recovery and energy efficiency. Online: http://cordis.europa.eu/project/rcn/105528_en.html 515. Expert Working Group on Lake Kivu Extraction, (2009, 2010). Management Prescriptions for the Development of Lake Kivu Resources. Prepared for the Ministry of Infrastructure, Republic of Rwanda, and Ministry of Hydrocarbons, Democratic Republic of the Congo. Online: https://www.eawag.ch/fileadmin/Domain1/Abteilungen/surf/projekte/kivu/kivu_management_prescriptions.pdf 516. Fabroni, S., Amenta, M., Timparano, N., and Raisarda, P., (2010). Supercritical carbon dioxide-treated blood orange juice as a new product in the fresh juice market. Innovative Food Sci. and Emerging Technologies, 11: 477-484.

517. Fadhel, A. Z., Pollet, P., Liotta, C. L., and Eckert, C. A., (2010). Combining the benefits of homogeneous and heterogeneous catalysis with tunable solvents and near-critical water. Molecules, 15: 8400-8424

518. Fahim, T. K., Zaidul, I. S. M., Bakar, A., Salim, U. M., Awang, M. B., Sahena, F., Jalal, K. C. A., Sharif, K. M., and Sohrab, M. H., (2014). Particle formation and micronization using non-conventional techniques—review. Chem. Eng. and Processing: Process Intensification, 86: 47-52.

519. Fang, W., and Sixta, H., (2015). Advanced biorefinary based on the fractionation of biomass in γ-valeractone and water. ChemSusChem, 8: 73-76.

520. FAO, (2014). 2013 global forest products facts and figures. UN Food & Agriculture Organization online report: http://www.fao.org/forestry/35445-0e287e9c252335f2936d3cdc5b6bbd5ff.pdf 521. FAO, (2013). Good Agricultural Practices for Greenhouse Vegetable Crops: Principles for Mediterranean Climate Areas. FAO Plant Production and Protection Paper 217, pp. 620, online: http://www.fao.org/docrep/018/i3284e/i3284e.pdf 522. Farahi, E., (2009). Advanced calcareous ceramics via novel green processing and supercritical carbonation. PhD Thesis, University of Warwick, UK.

523. Farahi, E., Purnell, P., and Short, N. R., (2007). Advanced calcareous ceramics via novel green processing and supercritical carbonation. In: Proceedings of the International Conference on Sustainable Construction Materials and Technologies. Coventry, UK, Jun. 11-13, 2007, pp. 359-366.

524. Farahi, E., Purnell, P., and Short, N. R., (2013). Supercritical carbonation of calcareous composites: influence of curing. Cement and Concrete Composites, 43: 48-53.

525. Farzaneh, S. A., and Sohrabi, M., (2015). Experimental investigation of $CO_2$-foam stability improvement by alkaline in the presence of crude oil. Chem. Eng. Res. Design, 94: 375-389/

526. Fast, A. G., and Papoutsakis, E. T., (2012). Stochiometric and energetic analyses of non-photosynthetic $CO_2$-fixation pathways to support synthetic biology strategies for production of fuels and chemicals. Curr. Opin. Chem. Eng., 1: 380-395

527. Fatteh, K. P., Mavinic, D. S., and Koch, F. A., (2010). Use of carbon dioxide stripping for struvite crystallization to save caustic dosage: performance at pilotscale operation. Can. J. Civil Eng., 37(9): 1271-1275

528. Fatteh, K. P., Sabrina, N., Mavinic, D. S., and Koch, F. A., (2008a). Reducing operating costs for struvite formation with a carbon dioxide stripper. Water Sci. Technol., 58: 957-962

529. Fatteh, K. P., Zhang, Y., Mavinic, D. S., and Koch, F. A., (2008b). Application of carbon dioxide stripping for struvite crystallization. I. Development of a carbon dioxide stripper model to predict $CO_2$ removal and pH changes. J. Environmental Eng. Sci., 7: 345-346

530. Fay, P., (1992). Oxygen relations of nitrogen fixation in cyanobacteria. Microbiological Revs., 56(2): 340-373

531. Fazlollahi, F., Brown, A., Ebrahimzadeh, E., and Baxter, L. L., (2015). Design and analysis of the natural gas liquefaction optimization process—CCC-ES (energy storage of cryogenic carbon capture). Energy, 90(1): 244-257.

532. Fazlollahi, F., (2016). Dynamic liquefied Natural Gas (LNG) processing with energy storage applications. PhD Thesis, Brigham Young University, BYU scholars Archive, http://scholarsarchive.byu.edu/etd/5956/

533. Fazlollahi, F., and Baxter, L., (2017). Modeling and analysis of natural gas liquefaction process: Energy Storage of Cryogenic Carbon Capture (CCC-ES). Online article, EM: Air and Waste Management Association for Environmental Managers, 65: 28-35, online: http://pubs.awma.org/gsearch/em/2015/8/fazlollahi.pdf 534. Fazlollahi, F., and Baxter, L., (2017). Effect of operating conditions on cryogenic CO2 removal. Energy Technology, (in press).

535. Fazlollahi, F., Bown, A., Saeidi, S., Ebrahimzadeh, E., and Baxter, L. L., (2016a). Transient natural gas liquefaction and its application to CCC-ES (energy storage with cryogenic carbon Capture™). Energy, 103: 369-384

536. Fazlollahi, F., Bown, A., Saeidi, S., Ebrahimzadeh, E., and Baxter, L. L., (2016b). Transient natural gas liquefaction process comparison-dynamic heat exchanger under transient changes in flow. Applied Thermal Engineering, 109: 775-788

537. Feher, E. G., (1968). The supercritical themodynamic power cycle. Conference paper: Douglas Paper No. 4348, IECEC, Miami, Fla., USA, online: http://users.ugent.be/~mvbelleg/literatuur%20 SCHX%20-%20Stijn%20Daelman/ORCNext/Supercritical/Literature%20Study/Literature/Papers%200RC/ORC%20Transcritical/1968%20-%20Feher%20-The%20supercritical%20thermodynamic%20power%20cycle.pdf 538. Fei, L., and Weathers, P. J., (2014). From cells to embryos to rooted plantlets in a mist bioreactor. Plant Cell Tiss. Organ Cult., 116: 37-46.

539. Fenwick, A. Q., Gregoire, J. M., and Luca, O. R., (2015). Electrocatalytic reduction of nitrogen and carbon dioxide to chemical fuels: challenges and opportunities for a solar fuel device. J. Photochem. Photobiol. B: Biol. V. 152, Part A, pp. 45-57.

540. Ferhat, M. A., Meklati, B. Y., and Chemat, F., (2007). Comparison of different isolation methods of essential oil from *Citrus* fruits: cold pressing, hydrodistillation and microwave 'dry' distillation. Flavor and Fragrance J., 22(6): 494-504.

541. Fernandes Bertos, M., Simons, S. J. R., Hills, C. D., and Carey, P. J., (2004). A review of accelerated technology in the treatment of cement-based materials and sequestration of $CO_2$. J. Hazardous Materials, B112: 193-205

542. Ferreira, L. S., Rodrigues, M. S., Converti, A., Sato, S., Carvalho, J. C. M., (2012). Arthrospira (*Spirulina*) *platensis* cultivation in tubular photobioreactor: Use of no-cost $CO_2$ from ethanol fermentation. Applied Energy, 92: 379-385

543. Ferrentino, G., Bruno, M., Ferrari, G., Poletto, M., and Balaban, M. O., (2009). Microbial inactivation and shelf life of apple juice treated with high pressure carbon dioxide. J. Biol. Engineering, 3:3 doi: 10.1186/1754-1611-3-3

544. Ferus, (2015). Statoil, Ferus plan $CO_2$ Bakken completion project. Online: http://www.ferus.com/statoil-ferus-plan-c02-bakken-completion-project/

545. Feyecon, (undated). Dried and still tasty? We know how. Feyecon slide deck presentation, online: http://www.easyfairs.com/uploads/tx_ef/FeyeCon-DRYING.pdf 546. FFTC, (2004). Carbon dioxide fumigation technique to control insect pests in stored products. PT2004-15, online: www.agnet.org/htmlarea_file/library/20110716183913/pt2004015.pdf 547. Fichtali, J., and Senanayake, S. P. J. N., (2010). Development and commercialization of microalgae-based functional lipids. Chapter 10, pp. 206-225, in: J. Smith and E. Charter, (eds.), Functional Food Product Development. Wiley-Blackwell.

548. Ficicilar, B., and Dogu, T., (2006). Breakthrough analysis for $CO_2$ removal by activated hydrotalcite and soda ash. Catalysis Today, 115(1): 274-278.

549. Filonenko, G. A., van Putten, R., Schulpen, E. K., Hensen, E. J. M., and Pidko, E. A., (2014). Highly efficient reversible hydrogenation of carbon dioxide to formats using a ruthenium PNP-pincer catalyst. ChemCatChem. 6(6): 1526-1530.

550. Finn, A. J., O'Brian, J. V., (2014). Processing of carbon dioxide rich gas. Costain Group PLC, conference paper, GPA Annual Conference, Madrid, 17-19 Sep. 2014, online: http://www.spe.org/ogf/print/subscribers/2012/12/07_Feature_SourGas_12_12_OGF.pdf 551. Fishell, D., (2015). Maine firm thinks it has solution to New England's energy woes. Bangor Daily News, Sep. 4, 2015, online: http://bangordailynews.com/2015/09/04/business/maine-firm-thinks-it-has-solution-to-new-englands-energy-woes/

552. Fleisch, T. H., (2012). Small scale gas monetization via miniGTL options. Slide deck presentation online: http://www.epa.gov/gasstar/documents/workshops/2012-annual-conf/fleisch.pdf 553. Fleisch, T., (2014). Associated gas monetization via miniGTL: Conversion of flared gas into liquid fuels and chemicals. World Bank and Global Gas Flaring Reduction (GGFR) Partnership, 37pp. online: http://siteresources.worldbank.org/EXTGGFR/Resources/Associated_gas_utilization_via_MiniGTL_Jan_2014_update.pdf?resourceurlname=Associated_gas_utilization_via_MiniGTL_Jan_2014_update.pdf 554. Fleisch, T., Basu, A., and Sills, R. A., (2012). Introduction and advancement of a new clean global fuel: The status of DME developments in China and beyond. Int. J. Natural Gas Sci. and Eng., 9(November): 94-107.

555. Fleming, H. P., (1979). Purging carbon dioxide from cucumber brines to prevent bloater damage—a review. Pickle Pak Science, VI (1, December): 8-22

556. FMER (Federal Ministry of Education and Research, Germany. 2014). Technologies for sustainability and climate protection—chemical processes and use of $CO_2$. Research Funding Programme Information Brochure., online: http://www.bmbf.de/pub/technologies_for_sustainability_climateprotection.pdf 557. Folkes, G., (2004). Pasteurization of beer by a continuous dense-phase $CO_2$ system. Ph.D Thesis, University of Florida, online: http://etd.fcla.edu/UF/UFE0006549/folkes_g.pdf 558. Forsgren, J., Frykstrand, S., Grandfield, K., Mihranyan, A., and Stromme, M., (2013). A template-free, ultra-adsorbing, high surface area carbonate nanostructure. PLOS One, 8(7), e68486, online: http://journals.plos.org/plosone/article?id=10.1371/journal.pone.0068486

559. Forster, M., (2012). Investigations for the environmentally friendly production of $Na_2CO_3$ and HCl from exhaust $CO_2$, NaCl and $H_2O$. J. Cleaner Prod., 23: 195-208.

560. Forster, M., (2014). Investigations to convert $CO_2$, NaCl and $H_2O$ into $H_2O$ and HCl by thermal solar energy with high solar efficiency. J. $CO_2$ Utilization, 7: 11-18.

561. Fortunato, A. A., Rodriguez, F. A., Baroni, J. C. P., Soares, G. C. B., Rodriguez, M. A. D., and Pereira, O. L., (2012). Silicon suppresses *fusarium* wilt development in banana plants. J. Phytopathol., 160(11-12): 674-679.

562. Fossum, I. S., (2014). New technology for production of alumina from alternative feedstock. Nordic Mining slide deck presentation, Feb. 26, 2014, online: http://www.nordicmining.com/getfile.php/Bilder/Innovation/Alumina/Mona%20Schanche.pdf 563. Fox, N., (1927). Effect of camphor, eucalyptol and menthol on the vascular state of the mucous membrane. Arch. Otolaryngol., 6(2): 112-122.

564. Foy, K., and Yantovski, E., (2006). History and state-of-the-art of fuel fired zero emission power cycles. Int. J. Thermodynamics, 9(2): 37-63, online: https://www.researchgate.net/publication/42539891_History_and_State-of-the-Art_of_Fuel_Fired_Zero_Emission_Power_Cycles 565. FPA, (2006). Dry ice invention. Food Processing Africa (digital magazine), online: http://www.foodprocessingafrica.com/dry-ice-invention 566. Francio, G., Hintermair, U., and Leitner, W., (2016). Unlocking the potential of supported liquid phase catalysts with supercritical fluids: low temperature continuous flow catalysis with integrated product separation. Phil. Trans. Roy. Soc. A 373: 2015005; http://dx.doi.org/10.1098/rsta.2015.0005

567. Francisco, J. d C., Jarvenpaa, E. P., Houpalahti, R., and Sivik, B., (2001). Comparison of *Eucalyptus camaldulensis* Dehn. Oils from Mozambique as obtained by hydrodistillation and supercritical carbon dioxide extraction. J. Agric. Food Chem., 49(5): 2339-2342.

568. Freifield, B., Pan, L., Doughty, C., Hart, K., Hostler, S., Zakem, S., Cutright, B., and Terrall, T., (undated). Cranfield $CO_2$ geothermal field demonstration. Slide deck presentation, online: http://ieaghg.org/docs/General_Docs/8_Mon/6-_Freifeld_CO2GeothermalSEC.pdf 569. Freifield, B., Zakim, S., Pan, L., Cutright, B., Sheu, M., Doughty, C., and Held, T., (2013). Geothermal energy production coupled with CCS: a field demonstration at the SECARB Cranfield Site, Cranfield, Miss., USA. Energy Procedia, 37: 6595-6603

570. Freitas, A. C. D., and Guirardello, R., (2015). Use of $CO_2$ as a co-reactant to promote syngas production in supercritical water gasification of sugarcane bagasse. J. $CO_2$ Utilization, 9: 66-73.

571. Freitas, A. C. D., and Guirardello, R., (2014). Hydrogen production from supercritical water gasification of different biomass materials: thermodynamic behavior. Chem. Eng. Trans., 37: 223-228.

572. Freitas, A. C. D., and Guirardello, R., (2013). Thermodynamic analysis of supercritical water gasification of microalgae biomass for hydrogen and syngas production. Chem. Eng. Trans., 32: 553-558.

573. Freitas, A. C. D., and Guirardello, R., (2012). Supercritical water gasification of glucose and cellulose for hydrogen and syngas production. Chem. Eng. Trans., 27: 361-366.

574. Frock, A. D., and Kelly, R. M., (2012). Extreme thermophiles: moving beyond single-enzyme biocatalysis. Curr. Opin. Chem. Eng., 1: 1-10

575. Frykstrand, S., Forsgren, J., Mihranyan, A., Stromme, M., (2014). On the pore forming mechanism of Upsalite, a micro- and mesoporous magnesium carbonate. Micropor. Mesopor. Mat., 190: 99-104

576. Frykstrand, S., Forsgren, J., Zhang, P., Stromme, M., and Ferraz, N., (2015). Cytotoxicity, in vivo skin irritation and acute systemic toxicity of the mesoporous magnesium carbonate Upsalite®. J. Biomaterials Nanobiotechnol., 6: 257-266

577. Fu, Q., Kuramochi, Y., Fukushima, N., Maeda, H., Sato, K., and Kobayashi, H., (2015). Bioelectrochemical analyses of the development of a thermophilic biocathode catalyzing electromethanogenesis. Environ. Dci. Technol., 49: 1225-1232

578. Fu, X., Wang, Y., Xiong, L., and Wei, F., (2009). Enhancement of the low temperature chlorination of ilmenite with CC14 by adding C12. J. Alloys Compounds, 486(1-2): 365-370.

579. Fuance, T., (2012). Towards a global solar fuels project—artificial photosynthesis and the transition from anthropocene to sustainocene. Procedia Eng., 49: 348-356

580. Fuchs, G., (2011). Alternate pathways of carbon dioxide fixation: insights into the early evolution of life. Ann. Rev. Microbiol., 65: 631-658.

581. Fukuoka, S., (2012). *Non-Phosgene Polycarbonate From $CO_2$ Industrialization of Green Chemical Process*. Nova Science Publishers, pp. 315.

582. Fukuokua, S., Fukawa, I., Tojo, M., Oonishi, K., Hachiya, H., Aminaka, M., Hasegawa, K., and Komiya, K., (2010). A novel non-phosgene process for polycarbonate production from $CO_2$: green and sustainable chemistry in practice. Catal. Surv. Asia, 14: 146-163.

583. Fukuoka, S., Kawamura, M., et al., (2003). A novel non-phosgene polycarbonate production process using by-product $CO_2$ as starting material. Green Chem., 5: 497-507.

584. Fukokua, S., Toijo, M., Hachiya, H., Aminaka, M., and Hasegawa, K., (2007). Green and sustainable chemistry in practice: development and industrialization of a novel process for polycarbonate production from $CO_2$ without using phosgene. Polymer J., 39(2): 91-114.

585. Fujita, E., Muckerman, J. T., and Himeda, Y., (2013). Interconversion of $CO_2$ and formic acid by bio-inspired Ir complexes with pendent bases. Biochim. Biophys. Acta, 1827: 1031-1038.

586. Gadikota, G., Matter, J., Kelemen, P., nd Park, A.-h. A., (2014). Chemical and morphological changes during olivine carbonation for $CO_2$ storage in the presence of NaCl and $NaHCO_3$. Phys. Chem. Chem. Phys., 16: 4679-4693.

587. Gadkari, P. V., and Balaraman, M., (2015). Catechins: sources, extraction and encapsulation. Food and Bioproducts Processing, 93: 122-138.

588. Galvez-Nogales, (2010). Agro-based clusters in developing countries: staying competitive in a globalized economy. FAO, Agricultural Management, Marketing and Finance Occassional Paper #25. FAO, Rome, pp. 107.

589. Galvis, J. A., Arjona, H., Fischer, G., and Martinez, R., (2005). Using modified atmospheric packaging for storing 'Van Dyke' mango (*Mangifera indica* L.) fruit. Agronomia Columbiana, 23(2): 269-275.

590. Gao, C., Li, X., Guo, L., and Zhao, F., (2013). Heavy oil production by carbon dioxide injection. Greenhouse Gases: Science and Technology, 3(3): 185-195.

591. Gao, D., (2012). Dynamic interplay among tectonics, sedimentation, and petroleum systems: an introduction and overview. Chapter 1, pp. 1-14 in: D. Gao, (ed.), *Tectonics and Sedimentation: Implications for Petroleum Systems*. AAPG Memoir 100.

592. Gao, S., Lin, Y., Jiao, X., Sun, Y., Luo, Q., Zhang, W., Li, D., Yang, J., and Xie, Y., (2016). Partially oxidized atomic cobalt layers for carbon dioxide electroreduction to liquid fuel. Nature, 529: 68-71. Doi: 10.1038/nature16455

593. Garapati, N., Randolph, J. B., Valencia, J. L., and Saar, M. O., (2014). $CO_2$—plume geothermal (CGP) heat exchange in multi-layered geologic reservoirs. Energy Procedia, 63: 7631-7643.

594. Garcia-Gonzalez, C. A., Concheiro, A., and Alvarez-Lorenzo, C., (2015). Processing of materials for regenerative medicine using supercritical fluid technology. Bioconjugate Chem., 26(7): 1159-1171

595. Garcia-Gonzalez, C. A., el Grough, N., Hidalgo, A., Fraile, J., Lopez-Perlago, A. M., and Andrade, C., (2007). Porosity and water permeability study of supercritically carbonated cement pastes involving mineral additions. J. Supercrit. Fluids, 43(3): 500-509.

596. Garcia-Gonzalez, C. A., el Grough, N., Hidalgo, A., Fraile, J., Lopez-Perlago, A. M., Andrade, C., and Domingo, C., (2008). New insights on the use of supercritical carbon dioxide for the accelerated carbonation of cement pastes. Ind. Eng. Chem. Res., 46(8): 2488-2496

597. Garcia-Gonzalez, L., Geeraerd, A. H., Spilimbergo, S., Elst, K., Van Ginneken, L., Debevere, J., Van Impe, J. F., and Devlieghere, F., (2007). High pressure carbon dioxide inactivation of microoganisms in foods: the past, the present and the future. Int. J. Food Microbial., 117: 1-28.

598. Garcia-Mendoza, M. P., Paula, J. T., Paviani, L. C., Cabral, F. A., Martinez-Correa, H. A., (2015). Extracts from mango peel by-product obtained by supercritical $CO_2$ and pressurized solvent processes. LWT—Food Sci. and Technol., 62(1): 131-137

599. Garcia-Serna, J., Moreno, T., Biasi, P., Cocero, M. J., Mikkola, J.-P., and Salmi, T. O., (2014). Engineering in direct synthesis of hydrogen peroxide: targets, reactors and guidelines for operational conditions. Green Chem., 16: 2320-2343.

600. Garmo, O., and Escudero, C., (2014). Using $CO_2$-gas to lower the pH of tunneling waste water. NPRA (Norwegian Public Roads Administration) Reports, Mr. 298, online: https://www.researchgate.net/file.PostFileLoader.html?id=566144b7614325b6f48b4596&assetKey=AS%3A302844484227076%401449215159811

601. Garner, A., and Keoleian, G. A., (1995) Industrial ecology: An introduction. National Pollution Prevention Center for Higher Education, University of Michigan.

Online: http://www.umich.edu/~nppcpub/resources/compendia/INDEpdfs/INDEintro.pdf 602. Garrett, D. E., (1997). Soda ash from trona and other natural sources. Encylopedia entry, pp. 115-126, in: J. J. McKetta, Jr (ed), *Encyclopedia of Chemical Processing and Design: v. 51—Slurry Systems: Instrumentation to Solid-Liquid Separation*. CRC Press.

603. Gas Turbine World, (2015). Gearing up for a new supercritical $CO_2$ power cycle system. November-December 2015 print edition, p. 14 & following. Available online: http://www.gasturbineworld.com/gearing-up.html 604. Gasc, F., Thiebaud-Roux, S., and Mouloungui, Z., (2009). Methods for synthesizing diethyl carbonate from ethanol and supercritical carbon dioxide by one-pot or two-step reactions in the presence of potassium carbonate. J. Supercrit. Fluids, 50(1): 46-53.

605. Gastechno, (undated). Website (www.GasTechno.com) and product sheet online: http://www.gastechno.com/pdf/GasTechno-Mini-GTL-Data-Sheeet.pdf 606. Gates, B., (2015). Energy Innovation: why we need it and how to get it. Breakthrough Energy Coalition, online: http://www.breakthroughenergycoalition.com/assets/resources/Energy-Innovation-by-Bill-Gates-Nov-30-2015.pdf 607. Gauthier, G., Chao, Y., Homer, O., Alos-Ramos, O., Hui, F., Ledion, J., and Perrot, H., (2012). Application of the fast controlled precipitation method to assess the scale-forming ability of raw river waters. Desalination, 299: 89-95

608. GE, (undated brochure). Growing your greenhouse business faster with gas engines. Online: https://www.ge-distributedpower.com/component/cck/?task=download&file=seb_media_document&id=4081

609. Ge, J., Hu, L., Wang, W., Jiao, H., and Jiao, S., (2015). Electrochemical conversion of $CO_2$ into negative electrode materials for Li-ion batteries. ChemElectroChem, 2: 224-230.

610. Geerlings, H., and Zevenhoven, R., (2013). $CO_2$ mineralization—bridge between storage and utilization. Ann. Rev. Chem. Biomol. Eng., 4: 103-117.

611. Geiver, L., (2015). Straight from the Bakken source. The Bakken Magazine, Mar. 3, 2015, online: http://thebakken.com/articles/1030/straight-from-the-bakken-source 612. Gelder, A. de., Heuvelink, E., and Opdam, J. J. G., (2005). Tomato yield in a closed greenhouse and comparison with simulated yields in closed and conventional greenhouses. Acta Hort., 691: 549-552.

613. Genencor, (2010). BioIsoprene monomer. Coporate communications bbackgrounder, online: http://www.genencor.com/uploads/tx_tcdaniscofiles/GENC-10053_BioIsoprene_Backgrounder_prt.pdf 614. Gerdemann, S. J., O'Connor, W. K., Dahlin, D. C., Penner, L. R., and Rush, H., (2007). Ex situ aqueous mineral carbonation. Environ. Sci. Technol., 41(7): 2587-2593.

615. Gerolsteiner, (2015). Die Gerolsteiner Brunnengeschichte. 50 pages, online: https://issuu.com/gerolsteiner/docs/150331122010-54aea4bb728d4fb88919417c4435c45e/1?e=7450575/12110491

616. Gerolsteiner, (2013). 125 *Jahre: Das Wasser Mit Stern*. Online book: https://issuu.com/gerolsteiner/docs/125-jahre-gerolsteiner 617. Geroni, J. N., Cravotta, C. A., III., and Sapsford, D. J., (2012). Evolution of the chemistry of Fe bearing waters during $CO_2$ degassing. Appl. Geochem., 27: 2335-2347.

618. Gershwin, M. E., and Belay, A., (2008, editors). *Spirulina* in Human Nutrition and Health. CRC Press, pp. 312

619. GGFR-Fleisch, T., (2014). Associated gas monetization via miniGTL: conversion of flared gas into liquid fuels & chemicals. Global Gas Flaring Reduction Partnership, online report: http://siteresources.worldbank.org/EXTGGFR/Resources/Associated_gas_utilization_via_MiniGTL_Jan_2014_update.pdf?resourceurlname=Associated_gas_utilization_via_MiniGTL_Jan_2014_update.pdf 620. Ghasemzadeh, A., and Jaafar, H. Z. E., (2011). Effect of $CO_2$ enrichment on synthesis of some primary and secondary metabolites of ginger (*Zingiber officianale* Roscoe). Int. J. Mol. Sci., 12: 1101-1114.

621. Ghasemzadeh, A., Omidvar, V., and Jaafar, H. Z. E., (2012). Polyphenolic content and their antioxidant activity in leaf extract of sweet potato (*Ipomoea batatas*). J. Medicinal Plants, 6(15): 2971-2976.

622. Ghoorah, M., (2014). Investigating the suitability of the weak acid process for carbon dioxide mineralization. PhD Thesis, University of Newcastle (Australia), online: http://nova.newcastle.edu.au/vital/access/manager/Repository/uon:15251

623. Ghoorah, M., Dlugogorski, B. Z., Balucan, R. D., and Kennedy, E. M., (2014a). Selection of acid for weak acid processing of wollastonite for mineralization of $CO_2$. Fuel, 122: 277-286.

624. Ghoorah, M., Dlugogorski, B. Z., Oskierski, H. C., and Kennedy, E. M., (2014b). Study of thermally conditioned and weak acid-treated serpentinites for mineralization of carbon dioxide. Min. Eng., 59: 17-30.

625. Gildemyn, S., Verbeeck, K., Slabbinck, R., Andersen, S. J., Prevoteau, A., and Rabaey, K., (2015). Integrated production, extraction and concentration of acetic acid from $CO_2$ through microbial electrosynthesis. Environ. Sci. & Tech. Letts., in press. DOI: 10.1021/acs.estlett.5b00212

626. Gillberg, B., (2012). World's first commercial scale biomethanol plant in Hagfors Sweden. Varmlandsmetanol report, online: http://www.varmlandsmetanol.se/dokument/History%20March%2012.pdf 627. Gillberg, B., (2013). From wood to wheel: Varmland-Metanol—a pioneer project. Slide deck presentation online: http://sgc-konf.camero.se/ckfinder/userfiles/files/5_3_B%20Gillberg,%20Värmlandsmetanol.pdf 628. Glasser, F. P., Jauffret, G., Morrison, J., Galvez-Martos, J.-L., Patterson, N., and Imbabi, M. S.-E., (2016). Sequestering $CO_2$ by mineralization into useful nesquahonite-based products. Frontiers in Energy Research, 4, article 3, DOI: 10.3389/fenrg.2016.00003

629. Gleadow, R. M., Foley, W. J., and Woodrow, I. E., (1998). Enhanced $CO_2$ alters the relationship between photosynthesis and defense in *Eucalyptus cladocalyx* F. Muell. Plant, Cell and Environment, 21: 12-22

630. Glennon, J. A., and Pfaff, R. M., (2004). The operation and geography of carbon-dioxide-driven, cold-water "geysers." GOSA Transactions, IX: 184-192, online: http://alanglennon.com/ColdWaterGeysersGlennonPfaff.pdf 631. Glennon, J. D., (2003). An eco-friendly chemistry for gold extraction using supercritical carbon dioxide. CIM (Canadian Institute of Mining), Metsco Proceeding, "Gold 2003."

632. Glennon, J. D., Harris, S. J., Walker, A., McSweeney, C. C., and O'Connell, M., (1999), Carrying gold in supercritical $CO_2$. Gold Bulletin, 32(2): 52-58.

633. Glennon, J. D., Treacy, J., O'Keefe, A. M., O'Connell, M., McSweeney, C. C., Walker, A., and Harris, S. J., (2003). Extracting gold in supercritical $CO_2$: fluorinated molecular baskets and thiourea ligands for Au. Chapter 6, pp. 67-79, in: A. S. Gopalan et al., (eds), *Supercritical Carbon Dioxide*, ACS Symp. Ser., 860.

634. Global CCS Insitute, (2011). Appendix C: $CO_2$ as a working fluid for enhanced geothermal systems (EGS). In, report: *Accelerating the Uptake of CCS: Industrial Use of Captured Carbon Dioxide*. Online: http://decarboni.se/publications/accelerating-uptake-ccs-industrial-use-captured-carbon-dioxide/appendix-c-co2-working 635. Global CCS Insitute, (2011). Appendix E: $CO_2$ for use in algae cultivation. In, report: *Accelerating the Uptake of CCS: Industrial Use of Captured Carbon Dioxide*. Online: https://hub.globalccsinstitute.com/publications/accelerating-uptake-ccs-industrial-use-captured-carbon-dioxide/appendix-e-co2-use-algae 636. Global CCS Institute/Parsons Brinckerhoff, (2011). Accelerating the uptake of CCS: industrial use of captured carbon dioxide. Report, online: http://www.globalccsinstitute.com/publications/accelerating-uptake-ccs-industrial-use-captured-carbon-dioxide 637. Global Energy Prize, (2013). Lecture by Professor Rodney J. Allam: The energy systems of the future. The place for fossil fuels. http://www.globalenergyprize.org/en/media-room/news/2013/04/lecture-by-professor-rodney-j.-allam-the-energy-systems-of-the-future.-the 638. Global Energy Prize, (2012). Rodney John Allam (UK). (Bio), online: http://energyprize.clients.morris-chapman.net/en/laureates/2012/laureate-31

639. GlobalEconomy.com, (undated). Manufacturing value added. Country rankings using data from official sources. World Bank data. http://www.theglobaleconomy.com/rankings/manufacturing_value_added/

640. Glueck, S. M., Gumus, S., Fabien, W. M. F., and Faber, K., (2010). Biocatalytic carboxylation. Chem. Soc. Revs., 39: 313-328.

641. Godec, M., Koperna, G., and Gale, J., (2014). $CO_2$-ECBM: a review of its status and global potential. Energy Procedia, 63: 5858-5869

642. Godec, M. L., Kuuskraa, V. A., and Dipietro, P., (2013). Opportunities for using anthropogenic $CO_2$ for enhanced oil recovery and $CO_2$ storage. Energy & Fuels, 27(8): 4183-4189.

643. Goepel, A., Lonschinski, M., Viereck, L., Buchel, G., and Kukowski, N., (2014). Volcano-tectonic structures and CO2-degassing patterns in the Laacher See basin, Germany. Int. J. Earth Sci., DOI 10.1007/s00531-014-1133-3

644. Goerke, K., Kunstner, H., and Unger, C., (2005). Response of aphids and greenhouse plants to insecticidal concentrations of carbon dioxide. J. Plant Diseases and Protection, 112(5): 508-518.

645. Goeppert, A., Czuan, M., Jones, J.-P., Prakash, J.-P., and Olah, G. A., (2014). Recycling of carbon dioxide to methanol and derived products—closing the loop. Chem. Soc. Rev., 43: 7995-8048.

646. Gomes, H. I., Mayes, W. M., Rogerson, M., Stewart, D. I., (2016). Alkaline residues and the environment: a review of impacts, management practices and opportunities. J. Cleaner Production, 112: 3571-3582

647. Gong, Y., and Gu, Y., (2015). Miscible $CO_2$ simultaneous Water-and-Gas ($CO_2$—SWAG) injection in the Bakken Formation. Energy Fuels, 29(9): 5655-5665.

648. Goodson III, T., (2015). *Solar Fuels: Materials, Physics, and Applications*. CRC Press, pp. 376.

649. Goosman, J. C., (1906). *The Carbonic Acid Industry: A Comprehensive Review of the Manufacture and Uses of $CO_2$*. Nickerson and Collins Co., Pp. 384

650. Goto, M., Kanda, H., Wahyudiono, and Mchmuda, S., (2015). Extraction of carotenoids and lipids from algae by supercritical $CO_2$ and subcritical dimethyl ether. J. Supercrit. Fluids, 96: 245-251.

651. Gou, Y., Hou, Z., Liu, H., Zhou, L., and Were, P., (2014). Numerical simulation of carbon dioxide injection for enhanced gas recovery ($CO_2$-EGR) in Altmark natural gas field. Acta Geochimica, 9: 49-58

652. Gouk, S. S., He, J., and Hew, C. S., (1997). Effects of super-elevated $CO_2$ on the growth and carboxylating enzymes in an epiphytic CAM orchid plantlet. J. Plant Physiol., 151: 129-136.

653. Gouk, S. S., He, J., and Hew, C. S., (1999). Changes in photosynthetic capability and carbohydrate production in an epiphytic CAM orchid plantlet exposed to super-elevated $CO_2$. Environ. Exper. Botany, 41: 219-230.

654. Gourmelon, G., (2015). Global plastic production rises, recycling lags. Worldwatch Institute Vital Signs report, online: http://vitalsigns.worldwatch.org/vs-trend/global-plastic-production-rises-recycling-lags 655. Government of Rwanda (website documents): (i) Rwanda Vision 2020: http://www.minecofin.gov.rw/fileadmin/templates/documents/NDPR/Vision_2020_.pdf (ii) EDPRS2 (Economic Development and Poverty Reduction Strategy 2013-2018): http://www.minecofin.gov.rw/index.php?id=149

656. Goyal, J., (2014). Gas fermentation to produce fuels & chemicals. LanzaTech slide deck presentation, World PetroCoal Congress, New Delhi, India, Feb. 15-17, 2014, online: http://worldpetrocoal.com/brochure/wpc-cPPT2014/Day2/MrJonnyGoyal.pdf 657. GPIC (Gulf Petroleum Industries Corporation), (undated). Website, carbon dioxide recovery. http://www.g-pic.com/responcibility/CDRmoved/

658. Grace, G. R., and Piedrahita, R. H., (1993). Carbon dioxide control with a packed column aerator. Pp. 496-505, in: J. K. Wang, (ed.), *Techniques in Modern Aquaculture*. Am Soc. Ag. Engineers.

659. Grace, G. R., and Piedrahita, R. H., (1993). Carbon dioxide control. Pp. 209-234, in: M. B. Timmons and T. M. Lorsado, (eds.), *Aquaculture Water Reuse Systems: Engineering Design and Management*. Elsevier 660. Grahan, M., Taljegard, M., Ehnberg, J., and Karlsson, S., (2014). Utilizing excess power: the case for electrofuels for transport. Chapter 12, pp. 128-137, in: Systems Perspectives on Renewable Power 2014. ISBN 978-91-980974-0-5. http://publications.lib.chalmers.se/records/fulltext/210531/local_210531.pdf; https://www.chalmers.se/en/areas-of-advance/energy/cei/Pages/Systems-Perspectives-on-Renewable-Power.aspx 661. GrainSaver (undated). Safe storage of dry grain in silo bags with GRAIN SAVER SYSTEM. Corporate paper online: www.grainsaver.com/images/stories/pdf/GRAIN%20 SAVER_2015.pdf 662. Grandin, T., (2003). The welfare of pigs during transport and slaughter. Pig News and Information 24, 83N-90N Online: http://dspace.library.colostate.edu/webclient/DeliveryManager/digitoolitems/csu01_storage/2008/09/09/file_1/16341

663. Grandin, T., (2013). Making slaughterhouses more humane for cattle, pigs, and sheep. Ann, Rev. Animal Biosci., 1: 491-512, DOI: 10.1146/annurev-animal-031412-103713

664. Grandin, T., and Smith, G. C., (undated). Animal welfare and humane slaughter. EOLS S, online: www.eolss.net/sample-chapters/c10/e5-11-06-01a.pdf 665. Graves, C. R., (2010) Recycling $CO_2$ into sustainable hydrocarbon fuels: electrolysis of $CO_2$ and $H_2$). PhD Thesis, Columbia University. Online: http://orbit.dtu.dk/fedora/objects/orbit:83036/datastreams/file_5193307/content 666. Graves, C., Ebbesen, S. D., and Mogensen, M., (2011). Co-electrolysis of $CO_2$ and water in solid oxide cells: Performance and durability. Solid State Ionics, 192(1): 398-403.

667. Green Farming, (2012). Partners for perfect solutions: Connecting horticultural networks of the Netherlands, Kenya and Ethiopia. Green Farming (Netherlands) online report: http://www.greenfarming.nl/nl/system/files/private/Green%20Farming%20program%20book_1.pdf 668. GreenEnergyFutures, (2014). Industrial symbiosis: growing tomatoes with an ethanol plants waste. Online: http://www.greenenergyfutures.ca/episode/71-industrial-symbiosis-turning-waste-valuable-resource 669. GreenPort, (2009). Industrial symbiosis in Moerjijk. Online: http://www.greenport.com/news101/europe/industrial-symbiosis-in-moerdijk 670. Grey Rock Energy, (undated). Company website (www.GreyRock.com) and news, online: http://bakken.com/news/id/237144/greyrock-makes-the-most-of-natural-gas-prices/; http://www.greyrock.com/newsroom/press-releases/greyrock-energy-recognized-as-most-advanced-new-technology-provider-in-world-bank-report-on-mini-gas-to-liquid-conversion-solutions 671. Griffin, D., (2015). LanzaTech: creating a carbon smart future! LanzaTech corporate presentation slide deck, IBBC 2015 Atlanta, online: www.tappi.org/Hide/Conference-Proceedings/15 BBC/15ibbc01/

672. Groensmit, E., (2010). $CO_2$ logistics: Developing a business case for Vopak. VOPAK slide deck presentation, Jun. 25, 2010, online: http://www.co2-cato.org/cato-download/1371/20100628_151002_CATO_2_Presentation_Utrecht_250610.pdf 673. Grombone-Guarantini, M. T., Gaspar, M., Olivera, V. F., Torres, M. A. M. G., de Nascimento, A., and Aidar, M. P. M., (2013). Atmospheric $CO_2$ enrichment markedly increases photosynthesis and growth in a woody tropical bamboo from the Brazilian Atlantic Forest. New Zealand J. Botany, http://dx.doi.org/10.1080/0028825X.2013.829502

674. Gu, T., (2013). Pretreatment of lignocellulosic biomass using supercritical carbon dioxide as a green solvent. Chapter 5, pp. 107-125, in: T. Gu (ed.), Green Biomass Pretreatment for Biofuels Production. Springer.

675. Gu, T., Held, M. A., and Faik, A., (2013). Supercritical $CO_2$ and ionic liquids for the pretreatment of lignocellulosic biomass in bioethanol production. Environ. Technol., 34(13-14): 1735-1749.

676. Guan, G., Kida, T., Ma, T., Kimura, K., Abe, E., and Yoshida, A., (2003). Reduction of aqueous $CO_2$ and ambient temperature using zero-valent iron-based composites. Green Chem., 5: 630-634.

677. Guangmin, L., Lina, Q., Hong, Z., Shumei, X., and Dan, Z., (2014). The capacity of bicarbonate capture of a continuous microalgae photo-bioreactor system. Energy Procedia, 61: 361-364.

678. Gubbuk, H., and Pekmezci, M., (2004). Comparison of open-field and protected cultivation of banana (Musa spp. AAA) in coastal area of Turkey. New Zealand J. Crop and Hort. Sci., 32: 375-378.

679. Gundala, S. R., Yang, C., Lakshminarayana, N., Asif, G., Gupta, M. V., Shamsi, S., and Aneja, R., (2013). Polar biophenolics in sweet potato greens extract synergize to inhibit prostate cancer cell proliferation and in vivo tumor growth. Carcinogenesis, 34(9): 2039-2049.

680. Gunnarsson, I. B., Alvarado-Morales, M., and Angelidaki, I., (2014). Utilization of $CO_2$ fixating bacterium *Actinobacillus succinogenes* 130Z for simultaneous biogas upgrading and biosuccinic acid production. Environmental Sci. Technol., 48(20): 12464-12468

681. Guntzer, F., Keller, C., and Meunier, J.-D., (2012). Benefits of plant silicon for crops: a review. Agron. Sustain. Devel., 32: 201-213.

682. Gupta, S., (2013). Application of silica fume and nanosilica in cement and concrete—a review. J. Today's Ideas Tomorrow's Technologies, 1(2): 85-98, online: http://dspace.chitkara.edu.in/jspui/bitstream/1/39/4/12006_JOTITT_Sakshi_Gupta.pdf 683. Gupta, S., (2014). A review on the use of nano-silica in cementitious compositions. Intl. J. Concr. Technol., 1(1): 1-15

684. Guo, W., Daeron, M., Niles, P., Goddard, W. A., and Eiler, J. M., (2009). Isotopic fractionsations associated with degassing of $CO_2$ from aqueous solutions and implications for carbonate clumped isotope thermometry. Chapter 4, CalTech Ph.D thesis of Wangzhu Guo, online: http://thesis.library.caltech.edu/5058/7/07Chapter4.pdf 685. Gurgel, L. V. A., Pimenta, M. T. B., da Silva Curvelo, A. A., (2014). Enhancing liquid hot water (LHW) pretreatment of sugarcane bagasse by high pressure carbon dioxide (HP-$CO_2$). Ind. Crops. Prod., 57: 141-149.

686. Gutierrez, C., (2014). Valorization of polystyrene wastes using natural terpenes and high-pressure $CO_2$. PhD Thesis, Universidad de Castilla-La Mancha, online: https://ruidera.uclm.es/xmlui/handle/10578/4152

687. Gutierrez, C., Garcia, M. T., Gracia, I., de Lucas, A., and Rodriguez, J. F., (2012). Recycling of extruded polystyrene wastes by dissolution and supercritical $CO_2$ technology. J. Material Cycles and Waste Management, 14(4): 308-316.

688. Gutierrez, C., Rodriguez, J. F., Gracia, I., de Lucas, A., and Garcia, M. T., (2013a). Development of a strategy for the foaming of polystyrene dissolutions in sc$CO_2$. J. Supercrit. Fluids, 76: 126-134.

689. Gutierrez, C., Rodriguez, J. F., Gracia, I., de Lucas, A., and Garcia, M. T., (2013b). High-pressure phase equilibria of polystyrene dissolutions in limonene in presence of $CO_2$. J. Supercrit. Fluids, 84: 211-220.

690. Gutierrez, C., Garcia, M. T., Gracia, I., de Lucas, A., and Rodriguez, J. F., (2013c). The selective dissolution technique as initial step for polystyrene recycling. Waste and Biomass Valorization, 4: 29-36.

691. Gutierrez, C., Garcia, M. T., Curia, S., Howdle, S. M., and Rodriguez, J. F., (2014a). The effect of $CO_2$ on the viscosity of polystyrene/limonene solutions. J. Supercrit. Fluids, 88: 26-37.

692. Gutierrez, C., Rodriguez, J. F., Gracia, I., de Lucas, A., and Garcia, M. T., (2014b). Preparation and characterization of polystyrene foams from limonene solutions. J. Supercrit. Fluids, 88: 92-104.

693. Gutierrez, C., Rodriguez, J. F., Gracia, I., de Lucas, A., and Garcia, M. T., (2014b). Determination of the high-pressure phase equilibria of polystyrene/p-cymene in presence of $CO_2$. J. Supercrit. Fluids, 92: 288-298.

694. Gutierrez, C., Garcia, M. T., de Lucas, A., Gracia, I., Rodriguez, J. F., (2010). Recycling of polystyrene wastes by supercritical $CO_2$ technology. Proceedings Book of 12th European Meeting on Supercritical Fluids. Graz, Austria. ISBN: 978-2905267-72-6 Online: www.isasf.net/fileadmin/files/Docs/Graz/HtmlDir/Papers/CO56.pdf 695. Gutierrez, C., de Haro, J. C., Garcia, M. T., Gracia, I., de Lucas, A., and Rodriguez, J. F., (2015). Polystyrene wastes: threat or opportunity? Pp. 261-268, in: W. Jimenez et al., (eds.), *Environment, Energy and Climate Change I: Environmental Chemistry of Pollutants and Wastes*. Hdb. Env. Chem, 32: 261-286. DOI 10.1007/698_2014_279, Springer.

696. Ha, S., Adams, B. and Masel, R. I., (2004). A miniature air breathing direct formic acid fuel cell. J. Power Sources, 128: 119-124.

697. Haberyan, K. A., and Hecky, R. E., (1987). The late Pleistocene and Holocene stratigraphy and paleolimnology of Lakes Kivu and Tanganyika. Palaeogeography, Paleoclimatology, Palaeoecology, 61: 169-197

698. Hage, K., (2007). Overview of European Technology Platform zero emission power planys ZEP—aims and vision. ZEP slide deck presentation, Mar. 6, 2007, Leipzig, Germany, online: http://www.bine.info/fileadmin/content/Publikationen/Projekt-Infos/Zusatzinfos/2007-12_praesentation_zero_emission_powerplants.pdf 699. Halbwachs, Michel. Website: http://mhalb.pagesperso-orange.fr/kivu/eg/index.htm 700. Halbwachs, M. (2012). Risque d'explosion gazeuse dans le golfe de Kabuno: projet industriel de degazage. Unpublished report. Provided by the author.

701. Halbwachs, M. (2014). Limnological Engineering. (Slide deck presentation.) (On line: http://moletta-methanisation.fr/diaporama/S54Halbwachs.pdf)

702. Halbwachs, M., Sabroux, J.-C., Grangeon, J., Kayser, G., Tochon-Danguy, J.-C., Felix, A., Beard, J.-C., Villevieille, A., Vitter, G., Richon, P., Wuest, A., & Hell, J., (2004). Degassing the 'killer lakes' Nyos and Monoun, Cameroon. EOS, Transactions AGU, v. 85, pp. 281-285.

703. Haldor Topsoe (undated). Topsoe methanol technology. Haldor Topsoe corporate capabilities document, online: http://www.topsoefuelcell.com/business_areas/methanol/~/media/PDF%20files/Methanol/topsoe_methanol_technology_nov2011.ashx 704. Halman, M. M., (1993). *Chemical Fixation of Carbon Dioxide: Methods for Recycling CO, into Useful Products*. CRC Press, pp. 192.

705. Hamadate, N., et al., (2015). Vascular effects and safety of supplementation with shark liver oil in middle-aged and elderly males. Experimental and Terapeutic Medicine, 10: 641-646.

706. Hamadi, R., and Tlili, M. M., (2016). Conductometric study of calcium carbonate prenucleation stage: underlining the role of $CaCO_3^0$ ion pairs. Cryst. Res. Technol., 51(1): 99-109

707. Han, J., Luterbacher, J. S., Alonso, D. M., Dumesic, J. A., and Maravelias, C. T., (2015). A lignocellulosic ethanol strategy via nonenzymatic sugar production: process synthesis and analysis. Bioresour. Technol., 182: 258-266.

708. Han, J., Murat Sen, S., Luterbacher, J. S., Alonso, D. M., Dumesic, J. A., and Maravelias, C. T., (2015). Process systems engineering studies for synthesis of catalytic biomass-to-fuels strategies. Computers Chem. Eng., 81: 57-69

709. Hanchen, M., Prigiobbe, V., Baciocchi, R., and Mazzotti, M., (2008). Precipitation in the Mg-carbonate system—effects of temperature and $CO_2$ pressure. Chem. Eng. Sci., 63: 1012-1028

710. Hancu, D., Green, J., and Beckman, E. J., (2002a). $H_2O_2$ in $CO_2/H_2O$ biphasic systems: green synthesis and epoxidation reactions. Ind. Eng. Chem. Res., 41: 4466-4474.

711. Hancu, D., Green, J., and Beckman, E. J., (2002b). $H_2O_2$ in $CO_2$: sustainable production and green reactions. Acc. Chem. Res., 35(9): 757-764.

712. Handler, R. M., Shonnard, D. R., Griffing, E. M., Lai, A., and Palou-Rivera, I., (2015). Life cycle assessments of ethanol production via gas fermentation: anticipated greenhouse gas emissions for cellulosic and waste gas feedstocks. I&C Res., DOI: 10.1021/acs.iecr.5b03215

713. Handoko, A. D., Li, K., and Tang, J., (2013). Recent progress in artificial photosynthesis: $CO_2$ photoreduction to valuable chemicals in a heterogeneous system. Curr. Opin. Chem. Eng., 2: 200-206.

714. Hansen, J. B., (2015a). Methanol production technology: todays and future renewable solutions. Haldor Topsoe corporate presentation slide deck, March 17th, online: http://www.lth.se/fileadmin/mot2030/filer/9._Bogild_Hansen_-_Methanol_Production_Technology_Todays_and_Future.pdf 715. Hansen, J. B., (2015b). Methanation and SOEC. Haldor Topsoe corporate presentation slide deck, October 5th, online: http://www.inbiom.dk/Files//Files/Præsentationer-2015/HT_Foulum.pdf 716. Hansen, J. B., (2015c). $CO_2$ utilization for fuel and chemical production. Haldor Topsoe corporate presentation slide deck, October 13th, online: https://eu-ems.com/event_images/presentations/John%20Bøgild%20Hansen.pdf 717. Hansen, J. B., (2015d). Catalytic and electrochemical conversion of biomass resources. Haldor Topsoe corporate presentation slide deck, October 27th, online: https://ieabioenergy2015.org/fileadmin/veranstaltungen/2015/IEA_Bioenergy_Conference/S01-4Bogild.pdf 718. Hansen, J. B., (2015e). Biogas upgrading to pipeline quality by means of Solid Oxide Electrolysis. Haldor Topsoe corporate presentation slide deck, November 8th, online: https://www.energinet.dk/SiteCollectionDocuments/Danske%20dokumenter/Forskning/IPB%2015.08.11_10.%20ForskNG%20følgegruppemøde_Projekt%2010677%20Haldor%20Topsøe.pdf 719. Hansen, J. B., (2015f). Fuel processing for fuel cells and power to fuels as seen from an industrial perspective. J. Catal., 328: 280-296.

720. Hansen, J. B., (2015g). Solid oxide electrolysis—a key enabling technology for sustainable energy scenarios. Faraday Discussions, 182: 9-48.

721. Hansen, J. B., (2014a). Methanol synthesis from $CO_2$. Haldor Topsoe corporate presentation slide deck, April 14th, online: http://energy.columbia.edu/files/2014/02/3-Hansen-Methanol-Synthesis-from-CO₂.pdf 722. Hansen, J. B., (2014b). Fuels from renewable resources. Haldor Topsoe corporate presentation slide deck, May 22nd, online: http://www.ieatask33.org/app/webroot/files/file/2014/WS2/Hansen.pdf 723. Hansen, J. B., (2014c). Syngas routes to alternative fuels from renewable resources. Haldor Topsoe corporate presentation slide deck, November 4th, online: http://iea-amf.org/app/webroot/files/file/ExCo%20Meetings/ExCo%2047/Site%20Visit%20Haldor%20Topsoe.pdf 724. Hansen, J. B., (2012a). Creating renewable natural gas: what could Power-to-Gas provide to the EU energy future? Haldor Topsoe corporate presentation slide deck, May 24th, online: http://www.gie.eu/conference/presented/2012/S2/3.John%20Bogild%20Hansen_2012.pdf 725. Hansen, J. B., (2012b). Upgrading $CO_2$ in biogas to methane. Haldor Topsoe corporate presentation slide deck, September 28th, Lyon, France, online: http://lavande.cpe.fr/co2forum/c02$f0rum$/CO2Forum_2012_11.Hansen.pdf 726. Hansen, J. B., and Clausen, B., S., (2015). Haldor Aksel Topsoe: the man, the scientist and the company. J. Catalysis, 328: 2-4.

727. Hansen, J. B., Christiansen, N., and Nielsen, J. U., (2011). Production of sustainable fuels by means of solid oxide electrolysis. ECS Trans., 35(1): 2941-2948

728. Hansen, M., Dreybrodt, W., and Scholz, D., (2013). Chemical evolution of dissolved inorganic carbon species flowing in thin water films and its implications for (rapid) degassing of $CO_2$ during speleotherm growth. Geochimica et Cosmochimica Acta, 107: 242-251

729. Hansen, T., (2014). Video: Exelon, CB&I, 8 Rivers proceed with carbon capture power plant. Electric Light & Power, Oct. 15, 2014, online: http://www.elp.com/articles/2014/10/exelon-cb-i-8-rivers-proceed-with-carbon-capture-power-plant.html 730. Hanushek, E. A., and Woessmann, L., (2015). *The Knowledge Capital of Nations: Education and the Economics of Growth*. MIT Press, pp. 262

731. Hanushek, E. A., and Woessmann, L., (2016). Knowledge capital, growth, and the East Asian miracle. Science, 351(6271): 344-345.

732. Hara, M., Onaka, Y., Kobayashi, H., Fu, Q., Kawaguchi, H., Vilcaez, J., and Sato, K., (2013). Mechanism of electromethanogenic reduction of $CO_2$ by a thermophilic methanogen. Energy Procedia, 37: 7021-7028

733. Haraldson, L., (2015). Methanol as fuel. Wartsilla slide deck presentation, Mar. 17, 2015, online: http://www.lth.se/fileadmin/mot2030/filer/12._Haraldsson_-_Methanol_asfuel.pdf Part of: http://www.marinemethanol.com/publications/category/4-methanol-as-a-marine-fuel 734. Hardy, D., Zagrobelny, M., Willauer, H. D., and Williams, F. W., (2007). Extraction of carbon dioxide from seawater by ion exchange resin Part I: Using a strong cation exchange resin. Naval Research Laboratory, NRL/MR/6180-07-9044

735. Haring, H.-W., (2008). Carbon Dioxide. Chapter 6, pp. 185-216 in H.-W. Haring (ed.), *Industrial Gases Processing*. Wiley-VCH 736. Harmon, L., (2015). Gas fermentation & modular manufacturing. LanzaTech slide deck presentation, Dec. 4, 2015, online: https://www.ameslab.gov/sites/default/files/Laurel%20Harmon%20Gas%20Fermentation%20and%20Modular%20Manufacturing%20-%20LanzaTech.pdf 737. Harp, G., Tran, K. C., Sigurbjornsson, O., Bergins, C., Buddenberg, T., Drach, I., and Koytsoumpa, E. I., (2015). Application of power to methanol technology to integrated steelworks for profitability, conversion efficiency, and $CO_2$ reduction. Conference paper, METEC & 2md ESTAD 2015, online: http://www.metec-estad2015.com/papers2015final/P643.pdf 738. Harriman, A., (2013). Prospects for conversion of solar energy into chemical fuels: the concept of a solar fuels industry. Phil. Trans. R. Soc. A 371: 20110415. http://dx.doi.org/10.1098/rsta.2011.0415

739. Harris, P. M., (2014). Theoretical and experimental analysis of supercritical carbon dioxide cooling. Master's Thesis, North-West University, South Africa, online: http://dspace.nwu.ac.za/bitstream/handle/10394/11722/Harris_PM.pdf?sequence=1

740. Harrison, J. W., (2015a). The N—Mg Nesquahonite—TecEco cement route to a man made carbonate built environment solution to global warming. Slide Deck presentation, Sapienza Universita Di Roma, online PPT presentation: file http://www.tececo.com/files/conference%20presentations/JHarrisonNesquehonite14Feb10.ppt 741. Harrison, J. W., (2015b). An overview of future cements. TecEco slide deck presentation, online: http://www.tececo.com/files/conference%20presentations/JHarrisonNewCementsOverview8Feb10_4Feb11.ppt 742. Harrison, J. W., (2013). Low carbon cements and concretes in modern construction. The Masterbuilder, July 2013, online: http://www.masterbuilder.co.in/data/edata/Articles/July2013/148.pdf And TecEco associated slide deck presentation: http://www.tececo.com/files/conference%20presentations/JHarrisonLowCarbonCement&Concrete.pdf 743. Harrison, J. W., (2006). Sustainable materials for the built environment. Chapter 7, pp. 271-348 in: H. C. Wu, (editor), *Advanced Civil Infrastructure Materials*. Woodhead Publishing Co., Cambridge, UK.

744. Harrison, J. W., (2004). Magnesian cementa—fundamental for sustainability in the built environment. In J. Weiss et al., (eds.), *Proceedings of the First International RILEM Symposium on Advanced in Concrete Through Science and Engineering*. Online: http://www.tececo.com/files/conference%20papers/MagnesianCementsFundamentalToSustainabilityAdvancesinConcreteThroughScienceandEngineeringEvanstonIllinois240904.pdf 745. Harrison, J. W., (2003). The case for and ramifications of blending reactive magnesia with Portland cement. Conference paper for the 28$^{th}$ Conference on Our world in Concrete & Structures: 28-29 Aug. 2003, Singapore, pp. 319-332, Online: http://www.cipremier.com/e107_files/downloads/Papers/100/28/100028036.pdf 746. Hartmanis, M. G. N., and Gatenbeck, S., (1984). Intermediary metabolism in *Clostridium acetobutylicium*: levels of enzymes involved in the formation of acetate and butyrate. Appl. Envoronmental Biol., 47(6): 1277-1283

747. Hartmann, J., West, A. J., Renforth, P., Kohler, P., De La Rocha, C. L., Wolf-Gladrow, D. A., Durr, H. H., and Scheffran, J., (2013). Enhanced chemical weathering as a geoengineering strategy to reduce atmospheric carbon dioxide, supply nutrients, and mitigate ocean acidification. Revs. Geophys., 51, DOI: 10.1002/rog.20004

748. Hasan, M. M. F., Boukouvaia, F., First, E. L., and Floudas, C. A., (2014). Nationwide, Regional, and Statewide $CO_2$ Capture, Utilization, and Sequestration Supply Chain Network Optimization. Ind. Eng. Chem. Res., 53(18): 7489-7506.

749. Hasegawa, T., Sakai, H., Tokida, T., et al., (2013). Rice cultivar responses to elevated $CO_2$ at two free-air $CO_2$ enrichment (FACE) sites in Japan. Functional Plant Biol., 40: 148-159.

750. Hasson, D., Segev, R., Lisitsin, D., Liberman, B., and Semiat, R., (2011). High recovery brackish water desalination process devoid of precipitation chemicals. Desalination, 283: 80-88

751. Haszeldine, S., (2015). CSS past present and future. RSC slide deck presentation, Edinburgh 22 Jul. 2015. Online: http://www.maggichurchouseevents.co.uk/cec/Downloads/Programme%20and%20poster%20abstracts/8%20Haszeldine%20 Stuart%20-%20ppt.pdf 752. Hauenstein, O., Reiter, M., Agarwal, S., Rieger, B., and Greiner, A., (2015). Bio-based polycarbonate from limonene oxide and $CO_2$ with high molecular weight, excellent thermal resistance, harness and transparency. Green Chem., DOI: 10.1039/c5gc01694k 753. Haverkvort, A. J., Franke, A. C., and Engelbrecht, F. A., (2013). Climate change and potato production in contrasting South African agro-ecosystems 1. Effects on land and water use efficiencies. Potato Research, 56: 31-50.

754. Hawkins, A. W., (2014). Elucidation and implementation of a thermophilic carbon fixation cycle for electrofuels metabolic engineering. PhD Thesis, University of North Carolina, online: http://repository.lib.ncsu.edu/ir/handle/1840.16/10203

755. Hawkins, A. S., Han, Y., Lian, H., Loder, A. J., Menon, A. L., Iwuchukwu, I. J., Keller, M., Leuko, T. T., Adams, M. W. W., and Kelly, R. M., (2011). Extremely thermophilic routes to microbial electrofuels. ACS Catal., 1: 1043-1050.

756. Hawkins, A. S., McTernan, P. M., Lian, H., Kelly, R. M., and Adams, M. W. W., (2013). Biological conversion of carbon dioxide and hydrogen into liquid fuels and industrial chemicals. Curr. Opinion Biotechnol., 24(3): 376-384

757. Hayashi, M., Lee, H.-C., and Kozai, T., (1993). Photoautotrophic micropropagation of rose plantlets under $CO_2$ enriched conditions. SHITA J., 4(2): 107-110.

758. HDC Energy News, (May 2014). Evesham Vale Growers and R&L Holt partner for AD project. Online: http://www.growsave.co.uk/userFiles/1011_newsletter_for_energynews_may_14_4_singlepages.pdf 759. He, H.-P., Cai, Y., and Corke, H., (2002). Extraction and purification of squalene from *Amaranthus* grain. J. Agric. Food Chem., 50(2): 368-372.

760. He, H.-P., and Corke, H., (2003). Oil and squalene in *Amaranthus* grain and leaf. J. Agric. Food Chem., 51(27): 7913-7920.

761. He, H.-P., Corke, H., and Cai, J.-G., (2003). Supercritical carbon dioxide extraction of oil and squalene from *Amaranthus* grain. J. Agric. Food Chem., 51(27): 7921-7925.

762. He, L.-N., Wang, J.-Q., and Wang, J.-L., (2009). Carbon dioxide chemistry: examples and challenges in chemical utilization of carbon dioxide. Pure Appl. Chem., 81(11): 2069-2080

763. He, L.-N., Yang, Z.-Z., Liu, A.-H., and Gao, J., (2010). $CO_2$ chemistry at Nankai group: catalytic conversion of $CO_2$ into value-added chemicals. Chapter 6, pp. 77-101 in: Y. H. Hu, (ed.), *Advances in $CO_2$ Conversion and Utilization*. ACS Symposium Series, v. 1056. American Chemical Society.

764. He, W., Fang, Z., Ji, D., Chen, K., Wan, Z., Li, X., Gan, H., Tang, S., Zhang, K., and Guo, K., (2013). Epoxidation of soybean oil by continuous micro-flow system with continuous separation. Organic Process Research & Development, 17: 1137-1141.

765. Hecky, R., Reinthal, P. 2010. The late Pleistocene-Holocene History of the Lake Kivu Ecosystem. Slides given at: Tropical Rift Lake Systems: Integrated Volcanologic, Tectonic, and Biogeochemical, and Geohazard Assessment of Lake Kivu Gisenyi, Rwanda Jan. 13-15, 2010 (http://dirs.cis.rit.edu/taxonomy/term/26) www.cis.rit.edu/~axvpci/docs/Kivu/Hecky_Kivu%20presentation%20Gisenyi%20version%201.pdf 766. Held, T. J., (2014). Initial test results of a megawatt-class supercritical $CO_2$ heat engine. Echogen Power Systems, conference paper, 4$^{th}$ International Symposium Supercritical $CO_2$ Power Cycles, September 9-10, Pittsburgh, Pa., USA, online: http://www.swri.org/4org/d18/sco2/papers2014/testing/28-Held.pdf 767. Hellivan, P.-J. (2012). The expanding supercritical fluid $CO_2$ extract universe. Perfumer & flavorisr, November 2012, v. 37: 26-34. Online: http://extraction.evonik.com/product/extraction/Documents/perfumer--flavorist-magazine.pdf 768. Hember, M., and Williams, C. K., (2012). Efficient magnesium catalysts for the copolymerization of epoxides and $CO_2$; using water to synthesize polycarbonate polyols. J. Am. Chem. Soc., 134(38): 15676-15679.

769. Hende, L., and Bek-Pedersen, E., (2012). CCS with EOR in the Danish North Sea/Trigen as an $CO_2$ EOR enabler. Maersk Oil slide deck presentation, London, 18 Apr. 2012, online: http://c335584.r84.cf1.rackcdn.com/maerskEOR.pdf 770. Hendriks, C., Noothaut, P., Zakkour, P., and Cook, G., (2013). Implications on the reuse of captured $CO_2$ for European climate action policies. Carbon Counts/ECOFYS report, online: http://www.scotproject.org/sites/default/files/Carbon%20Count,%20Ecofys%20(2013)%20Implications%20of%20the%20reuse%20of%20captured%20CO$_2$%20-%20report.pdf 771. Henneberger, R., Cooksley, D., and Hallberg, J., (2000). Geothermal resources of Armenia. Proc. World Geothermal Congress 2000, Kyushu Tohoku-Japan, May 28-Jun. 10, 2000, online: http://www.geothermal-energy.org/pdf/IGAstandard/WGC/2000/R0822.PDF 772. Henni, A., (2014). Technology could cut $CO_2$ cost sharply for enhanced oil recovery. JPT: Journal of Petroleum Technology, Article 6427, online: http://www.spe.org/jpt/article/6427-technology-update-21/

773. Herron, J. A., Kim, J., Upadhye, A. A., Huber, G. W., and Maravelias, C. T., (2015). A general framework for the assessment of solar fuel technologies. Energy Environ. Sci., 8: 126-157.

774. Hertwig, T. A., Xu, A., Indala, S., Pike, R. W., Knopf, F. C., Hopper, J. R., and Yaws, C. L., (2002). Integrated chemical complex and cogeneration analysis system: energy conservation and greenhouse gas management solutions. AICHE Presentation, 2002 Annual Mtg. Online:http://www.mpri.lsu.edu/Integrated%20Chemical%20Complex%20and%20Cogen%20Analysis%20.pdf 775. Herbertson, J. A., Parker, M. E., Duncan, W. T., Fogelsong, R. E., Northrop, S., and Valencia, J., (2011). $CO_2$ management at ExxonMobil's LaBarge Field, Wyo., USA. ExxonMobil slide deck presentation, London, Nov. 23, 2011, online: https://www.geolsoc.org.uk/~/media/shared/documents/Events/2012%2013%20events/presentations/Herbertson%20presentation.pdf?la=en 776. Hermawan, D., Hata, T., Kawai, S., Nagadomi, W., and Kuroki, Y., (2002). Manufacturing oil palm fronds cement-bonded board cured by gaseous or supercritical carbon dioxide. J. Wood Sci., 48: 2-24

777. Hermawan, D., Hata, T., Umemura, K., Kawai, S., Nagadomi, W., and Kuroki, Y., (2001). Rapid production of high-strength cement-bonded particleboard using gaseous or supercritical carbon dioxide. J. Wood Sci., 47: 294-300

778. Hermawan, D., Hata, T., Kawai, S., Nagadomi, W., and Kuroki, Y., (2000). New technology for manufacturing high-strength cement-bonded particleboard using supercritical carbon dioxide. J. Wood Sci., 46: 85-88

779. Hettinga, K., (2013). Liquid transport fuel production from renewable energy, $CO_2$ and water. Carbon Recycling International, side deck presentation, Jun. 7, 2013, Brussels, in A. Bocin-Dumitru, M. del Mar Perez Fortes, and T. Sveen, (2013), Carbon Capture and Utilization Workshop: Background and Proceedings. European Commission, Joint Research Center, Institute for Energy and Transport. Online: http://publications.jrc.ec.europa.eu/repository/bitstream/JRC86324/co2%20reuse%20workshop%20report_isbn_online_eurpages.pdf.

780. Heveling, J., van der Beek, A., and Pender, M., (1988). Oligomerization of ethane over nickel-exchanged zeolite y into a diesel-range product. Appl. Catal., 42(2): 325-336.

781. Hew, C. S., and Yong, J. W. H., (2004, 2nd edition). *Physiology of Tropical Orchids in Relation to the Industry*. World Scientific, pp. 350.

782. Hicks, D., Davies, G., Spertini, S., and Chaffanjon, P., (undated). An expanded range of all-MDI flexible foam slabstock for HR and CMHR applications. Huntsman Polyurethanes technical document online: http://www.huntsman.com/polyurethanes/Media%20Library/a_MC1CD1F5AB7BB1738E040EBCD2B6B01F1/Products_MC1CD1F5AB8081738E040EBCD2B6B01F1/Bedding%20%20%20furniture_MC1CD1F5AFE351738E040EBCD2B6B01F1/Technical%20presentati_MC1CD1F5B05731738E040EBCD2B6B01F1/files/utech_2000_paper_d_hicks.pdf 783. Higgins, E. W., (2015). *Liquid Nitrogen: Characteristics, Uses and Safety Concerns*. Nova Science Publishers.

784. Highfield, J., (2015). Advances and recent trends in heterogeneous photo(electro)-catalysts for solar fueld and chemicals. Molecules, 20: 6739-6703.

785. Highfield, J., Chen, J., Bu, J., Abacka, J., Fagerlund, J., and Zevenhoven, R., (2013). Steam-produced gas-solid carbonation of magnesia and brucite below 200 C. Pp. 161-172 in: R. Nasser et al., (eds.), *Proceeedings of the 4th International Conference on Accelerated Carbonation for Environmental and Materials Engineering*, ACEME 2013, Leuven, Belgium, KE Leuven.

786. Highview Power Storage, (2014). Liquid air energy storage (LAES): from pilot plant to multi MW demonstration plant. Highview Power Storage, slide deck presentation, online: http://www.all-energy.co.uk/_nova-documents/54268?v=635376493882370000

787. Highview Power Storage, (2017). Liquid Air Energy Storage. Online company brochure slide deck: http://www.highview-power.com/wp-content/uploads/Highview-Brochure-2017-A4.pdf 788. Hill, B., Hovorka, S., and Melzer, S., (2013). Geological carbon storage through enhanced oil recovery. Energy Procedia, 37: 6808-6830

789. Hintermair, U., Leitner, W., and Jessop, P., (2010). Expanded liquid phases in catalysis: gas-expanded liquids and liquid-supercritical fluid biphasic systems. In: Handbook of Green Chemistry, 4:4: 101-187

790. Hochstein, D. P., (1940). Carbon dioxide power cycle. Soviet Boiler and Turbine Construction, No. 10, pp. 420-423. (in Russian)

791. Hofer, D., (2016). Phased approach to development of a high temperature sCO2 power cycle pilot test facility. The 5th International Symposium—Supercritical CO2 Power Cycles, March 28-31, San Antonio, Tex. Online: http://www.swri.org/4org/d18/sco2/papers2015/069.pdf 792. Hofland, G., (2014). PRESERF: Preserving raw materials into excellent and sustainable end products while remaining fresh. Feyecon European Union, FP7 support program, final report, online: http://cordis.europa.eu/docs/results/245/245280/final1-preserf-final-report-v7-21-july-2014.pdf 793. Holland, H. D., Kirsipu, T. V., Huebner, S., and Oxburgh, U. M., (1964). On some aspects of the chemical evolution of cave waters. J. Geol., 72(1): 36-67

794. Hollingsworth, R. G., Armstrong, J. W., and Campbell, E., (2002). Caffeine as a repellant for slugs and snails. Nature, 417: 915-916.

795. Hollingsworth, R. G., Armstrong, J. W., and Campbell, E., (2003). Caffeine as a novel toxicant for slugs and snails. Ann. Appl. Biol., 142: 91-97.

796. Hollis, R., Skutley, P., Ortiz, C., Varkey, V., LePage, D., Brown, B., Davies, D., and Harris, M., (2012). Oxy-fuel turbomachinery development for energy intensive industrial applications. GT2012-69988, pp. 431-439, conference paper, ASME Turbo Expo 2012: Turbine Technical Conference and Exhibition, Copenhagen, Jun. 11-15, 2012, online: http://proceedings.asmedigitalcollection.asme.org/proceeding.aspx?articleid=1694303

797. Holm, L. W., (1959). Carbon dioxide solvent flooding for increased oil recovery. Petrol. Trans AIME, 216: 225-231.

798. Holm, M., (2015). Klare til a bygge testsenter for alger pa Mongstad. SYSLA, online (in Norwegian): http://sysla.no/2015/06/02/fornybar/klare-til-a-bygge-testsenter-for-alger-pa-mongstad_50818/

799. Holmgren, J., (2015). The road to awesome. LanzaTech slide deck presentation, University of Illinois, May, 2015, online: http://bioenergy.illinois.edu/education/050415%20Jennifer%20Holmgren%20-%20LanzaTech.pdf 800. Holmgren, J., (2015). Going commercial: the road to awesome. LanzaTech slide deck presentation, Argonne National Laboratory, Mar. 13, 2014, online: http://energy.gov/sites/prod/files/2014/04/f14/d_and_d_workshop_holmgren.pdf 801. Holscher, M., Gurtler, C., Keim, W., Muller, T. E., Peters, M., and Leitner, W., (2012). Carbon dioxide as a carbon resource—recent trends and perspectves. Zeitschr. fur Naturforsch. B, 67(10): 961-975.

802. Holst, S., (2001). $CO_2$ stunning of pigs for practical guidelines for good animal welfare. 47th Int. Congr. Meat Sci, & Tech., conference paper, online: http://www.butina.eu/fileadmin/user_upload/images/articles/co2_stunning.pdf 803. Honari, A., Bijeljic, B., Johns, M. L., and May, E. F., (2015). Enhanced gas recovery with $CO_2$ sequestration: the effect of medium heterogeneity on the dispersion of supercritical $CO_2$—$CH_4$. Int. J. Greenhouse Gas Control, 39: 39-50

804. Honari, A., Hughes, T. J., Fridjonsson, E. O., Johns, M. L., and May, E. F., (2013). Dispersion of supercritical $CO_2$ and $CH_4$ in consolidated porous media for enhanced gas recovery simulations. Int. J. Greenhouse Gas Control, 19: 234-242

805. Honda, M., Tamura, M., Nakagawa, Y., Sonehara, S., Suzuki, K., Fujimoto, K.-I., and Tomishige, K., (2013). Ceria-catalyzed conversion of carbon dioxide into dimethyl carbonate with 2-cyanopyridine. ChemSusChem., 6: 1341-1344.

806. Hongmei, L., Zhong, K., Liao, X., and Hu, X., (2014). Inactivation of microorganisms naturally present in raw bovine milk by high-pressure carbon dioxide. Int. J. Food Sci. Technol., 49(3): 696-702.

807. Hortidaily, (2014). Spain: Greenhouses generate 70,000 Euro per hectare per year. Online: http://www.hortidaily.com/article/12371/Spain-Greenhouse s-generate-70,000-Euro-per-hectare-per-year 808. Hotchkiss, J. H., Chen, J. H., and Lawless, H. T., (1999). Combined effects of carbon dioxide addition and barrier films on microbial and sensory changes in pasteurized milk. J. Dairy Sci., 82(4): 690-695.

809. Hotchkiss, J. H., Werner, B. G., and Lee, E. Y. C., (2006). Addition of carbon dioxide to dairy products to 810. Houwelings, (2014). Utah greenhouse project update. Company website, Apr. 11, 2014 Online: http://www.houwelings.com/blog/utah-greenhouse-project-update
811. Houwelings, (undated). Overview brochure. http://www.houwelings.com/files/Houwelings.FOSA.pdf
812. Houwelings, (undated). Energy project: Delta, BC. Company website, online (with visit): http://www.houwelings.com/files-2/energy-project.php
813. Howdle, S. M., (2001). Supercritical fluids: a clean route to polymer synthesis and polymer processing. Jerwood Salter's Environment Award paper, online: http://www.greenchemistrynetwork.org/pdf/Howdle.pdf
814. Howe, H. E., (1928). Manufacture of carbon dioxide. Ind. Eng. Chem., 20(10): 1091-1094
815. Hu, J., and Deng, W., (2015). Application of supercritical carbon dioxide for leather processing. J. Cleaner Prod., 113: 931-946
816. Hu, Y., and Yan, J., (2015). Oxyfuel combustion for $CO_2$ capture. *Handbook of Clean Energy Systems*, pp. 1-29. Wiley.
817. Hu, Y. H., (2011, editor). *Advances in $CO_2$ Conversion and Utilization*. ACS Syposium Series (Book 1056), American Chemical Soc., pp. 296.
818. Huang, C.-H., and Tan, C.-S., (2014). A review: $CO_2$ utilization. Aerosol and Air Qual. Res., 14: 480-499.
819. Huang, K., Sun, C.-L., Shi, Z.-J., (2011). Transition-metal-catalyzed C—C bond formation through fixation of carbon dioxide. Chem. Soc. Revs., 40(5): 2435-2452.
820. Hue, S.-M., Boyce, A. N., and Somasundram, C., (2012). Antioxidant activity, phenolic and flavonoid contents in the leaves of different varieties of sweet potato (*Ipomoea batatas*). Australian J. Crop Sci., 6(3): 375-380/
821. Hug and von der Weid, D., (2011). *Spirulina* in the fight against malnutrition. Foundation Antenna Technologies, Geneva, Switzerland report, online: http://www.antennaindia.org/Spirulina_spirulina%20assesment%20and%20procespects.PDF
822. Hughes, T. J., Honari, A., Graham, B. F., Chauhan, A. S., Johns, M. L., and May, E. F., (2012). $CO_2$ sequestration for enhanced gas recovery: new measurements of supercritical $CO_2$—$CH_4$ dispersion in porous media and a review of recent research. Int. J. Greenhouse Gas Control, 9: 457-468
823. Hull, J. F., Himeda, Y., Wang, W.-H., Hashigushi, B., Periana, R., Szalda, D. J., Muckerman, J. T., and Fujita, E., (2012). Reversible hydrogen storage using $CO_2$ and a proton-switchable iridium catalyst in aqueous media under mild temperatures and pressures. Nature Chem., 4: 383-388.
824. Hunt, J., Ferrari, A., Lita, A., Crosswhite, M., Ashley, B., and Steigman, A. E., (2013). Microwave-specific enhancement of the carbon-carbon dioxide (Boudard) reaction. J. Phys. Chem C, 117: 26871-26880.
825. Huntsman, (2013). Huntsman textile effects: recent efforts in sustainable dyes and processes. Huntsman Corporation slide deck presentation, Jul. 9, 2013, online: http://www.wewear.org/assets/1/7/cheek_-_advances_in_dyeing_and_sustainability_-_7-9-13.pdf
826. Huo, Z., Hu, M., Zeng, X., Yun, J. and Jin, F., (2012). Catalytic reduction of carbon dioxide into methanol over copper under hydrothermal conditions. Catalysis Today, 194(1): 25-29.
827. Hussain, I., and Tarar, O. M., (2014). Pulp and paper making by using waste banana stem. J. Modern Sci. Tech., 2(2): 36-40.
828. Hussen, C., Amin, R., Madden, G., and Evans, B., (2012). Reservoir stimulation for enhanced gas recovery: an economic evaluation. J. Natural Gas Science Engineering, 5: 42-50
829. Husted, C.-W., (2009). $CO_2$ compression for advanced oxyfuel cycles. Mar. 30-31, 2009, Workshop on large $CO_2$ compression systems, DOE/EPRI/NIST, Gaithersburg, Md., USA, online: http://www.nist.gov/pml/high_megawatt/upload/6_2-Hustad-Approved.pdf
830. Huttenhuis, P. J. G., Roeloffzen, A., and Versteeg, G. F., (2015). $CO_2$ capture and re-use at a waste incinerator. The $8^{th}$ Trondheim CCS Conference, presentation abstract, online: http://tccs-8.exordo.com/files/papers/139/final_draft/abstract_TCCS-8_rev2.pdf
831. Hydrogenics website: http://www.hydrogenics.com/hydrogen-products-solutions/energy-storage-fueling-solutions/power-to-gas
832. Ibrahim, M. H. and Jaafar, H. Z. E. 2012. Impact of elevated carbon dioxide on primary, secondary metabolites and antioxidant responses of *Eleais guineensis* Jacq. (oil palm) seedlings. Molecules 17: 5195-5211.
833. Ibrahim, M. H., Jaafar, H. Z. E., Harun, M. H., and Yusop, M. R., (2010). Changes in growth and photosynthetic patterns of palm oil (*Eleais guineensis* Jacq.) seedlings exposed to short-term $CO_2$ enrichment in an open top chamber. Acta Physiol. Plant., 32: 305-313.
834. IDA, (2010). IDA fact sheet" DME/LPG blends, Online: https://www.aboutdme.org/aboutdme/files/ccLibraryFiles/Filename/000000001519/IDA_Fact_Sheet_1_LPG_DME_Blends.pdf
835. Idso, S. B., and Kimball, B. A., (1989). Growth response of carrot and radish to atmospheric $CO_2$ enrichment. Environmental and Experimental Botany, 29(2): 135-139.
836. IEA, (2015). Storing $CO_2$ through enhanced oil recovery. International Energy Agency, Insight Series 2015, OECD/IEA, online: https://www.iea.org/publications/insights/insightpublications/CO2EOR_3Nov2015.pdf
837. IEA, (2016). Webinar slide deck: "Storing $CO_2$ through enhanced oil recovery." International Energy Agency, Insight Series 2015, OECD/IEA, online: http://www.slideshare.net/internationalenergyagency/storing-co2-through-enhanced-oil-recovery
838. IEAGHG, (2015). Carbon capture and storage projects: review and future opportunities. International Energy Agency, report, online: http://www.ieaghg.org/docs/General_Docs/Reports/2015-03.pdf
839. Ijima, A., (1991). Helical microtubules of graphitic carbon. Nature, 354: 56-58
840. Imbabi, M. S., Carrigan, C., and McKenna, S., (2012). Trends and developments in green cement and concrete technology. Int. J. Sustainable Built Environ., 1: 194-216.
841. Indala, S., (2004). Development and integration of new processes consuming carbon dioxide in multi-plant chemical production complexes. Masters Thesis, Louisiana State University, online: http://etd.lsu.edu/docs/available/etd-01212004-125820/unrestricted/Indala_thesis.pdf
842. Inoue, T., Fujishima, A., Konishi, S., and Honda, K., (1979). Photoelectrocatalytic reduction of carbon dioxide in aqueous suspensions of semiconductor powders. Nature, 277: 637-638.
843. Inui, T., Anpo, M., Izui, K., and Yamaguchi, T., (1998, editors). *Advances in Chemical Conversions for Mitigating Carbon Dioxide*. Elsevier, pp. 698.
844. IPCC (2015). Climate Change 2014: Synthesis report. Online: http://www.ipcc.ch/report/ar5/syr/

845. IPCC, (2005). IPCC Special Report on Carbon Dioxide Capture and Storage. Prepared by Working Group III of the Intergovernmental Panel on Climate Change [Metz, B., O. Davidson, H. C. de Coninck, M. Loos, and L. A. Meyer (eds.)]. Cambridge University Press, Cambridge, United Kingdom and New York, N.Y., USA, 442 pp. Online: https://www.ipcc.ch/pdf/special-reports/srccs/srccs_chapter4.pdf https://www.ipcc.ch/pdf/special-reports/srccs/srccs_wholereport.pdf 846. Irfan, U., (2015). Can carbon dioxide replace steam to generate power? Scientific American (via ClimateWire), Mar. 3, 2015, online: http://www.scientificamerican.com/article/can-carbon-dioxide-replace-steam-to-generate-power/

847. Islam, S., (2014). Nutritional and medicinal qualities of sweetpotato tops and leaves. FSA6135, Cooperative Extension Program, University of Arkansas at Pine Bluff. Online: https://www.uaex.edu/publications/PDF/FSA-6135.pdf 848. Islam, S., (2006). Sweetpotato (*Ipomoea batatas* L. leaf: its potential effect on human health and nutrition. J. Food Sci., 71(2): R13-R21.

849. Islam, S., Yoshimoto, M., Yahara, S., Okuno, S., Ishiguro, K., and Yamakawa, O., (2002). Identification and characterization of foliar polyphonic composition in sweetpotato (*Ipomoea batatas* L.) genotypes. J. Agric. Food Chem., 50: 3718-3722.

850. Isles, J., (2014). Gearing up for a new supercritical $CO_2$ power cycle system. Gas Turbine World, November-December issue, pp. 14-18, Online: http://www.legis.nd.gov/files/committees/64-2014%20appendices/17_5039_03000appendixd.pdf?720160115111120

851. Ismail, B. I., (2013). ORC-based geothermal power generation and $CO_2$-based EGS for combined green power generation and $CO_2$ sequestration. Chapter 13, pp. 303-328, in: H. Arman and I. Yuksul, *New Developments in Renewable Energy*. Intech, online: http://www.intechopen.com/books/new-developments-in-renewable-energy 852. Iwai, Y., and Itoh, M., (2015). Gas turbine combustor for supercritical carbon dioxide cycle. Toshiba Review, 70(5): 16-19 (in Japanese), online: https://www.toshiba.co.j p/tech/review/2015/05/70_05pdf/a05.pdf 853. Iwai, Y., Itoh, M., Morisawa, Y., Suzuki, S., Cusano, D., and Harris, M., (2015). Development approach to the combustor of gas turbine for oxy-fuel, supercritical $CO_2$ cycle. Paper GT2015-43160, pp. V009T36A013, 7 pp, ASME Turbo Oxpo 2015, Turbine Technical Conference, Montreal, Quebec, Canada, June 15-19, online: http://proceedings.asmedigitalcollection.asme.org/proceeding.aspx?articleid=2428759

854. Izumi, Y., (2015). Recent advances (2012-2015) in the photocatalytic conversion of carbon dioxide to fuels using solar energy: feasibility for a new energy. Chapter 1, pp. 1-46, in: Fangmin Jin et al., ACS Symp. Ser. V. 1194, *Advances in $CO_2$ Capture, Sequestration, and Conversion*. American Chemical Society 855. Jaafar, H. Z. E., and Ibrahim, M. H., (2012). Photosynthesis and Quantum Yield of Oil Palm Seedlings to Elevated Carbon Dioxide, Advances in Photosynthesis—Fundamental Aspects, Dr Mohammad Najafpour (Ed.), ISBN: 978-953-307-928-8, InTech, Available from: http://www.intechopen.com/books/advances-in-photosynthesis-fundamental-aspects/photosynthesis-and-quantum-yield-responses-of-oil-palm-to-elevated-carbon-dioxide 856. Jablonski, L. M., Wang, X., and Curtis, P. S., (2002). Plant reproduction under elevated $CO_2$ conditions: a meta-analysis of eports on 79 crop and wild species. New Phytologist, 156: 9-26.

857. Jackson, D., (2015). 30,000 ha of Almeria covered by greenhouses. DavidJackson blog, Feb. 14, 2015, online: http://www.davidjackson.info/blog/2015/02/14/30000-ha-of-almeria-covered-by-greenhouses/

858. Jacobs, L. J. M., Kemmere, M. F., and Keurentjes, J. T. F., (2008). Sustainable polymer foaming using high pressure carbon dioxide: a review on fundamentals, processes and applications. Green Chem., 10: 731-738.

859. Jacobs, T., (2014). Shale revolution revisits the energized fracture. JPT, Jun. 1, 2014, online: http://www.spe.org/jpt/article/6439-shale-revolution-revisits-the-energized-fracture/

860. Jacobs, T., (2013). Gas-to-Liquids comes of age in a world full of gas. JPT, August, 2013, pp. 68-73.

861. Jahan, M. S., Chowdhury, D. A. N., and Islam, M. K., (2007). Atmospheric formic acid pulping and TCF bleaching of dhaincha (*Sesbania aculeate*), kash (*Saccharum spontaneum*) and banana stem (*Musa Cavendish*). Indust. Crops and Products, 26: 324-331.

862. Jahaveri, M., (2013). *Natural convection in porous media: $CO_2$ sequestration and $CO_2$-Vapex*. Lambert Academic Publishing, pp. 124.

863. Jahurul, M. H. A., Zaidul, I. S. M., Ghafoor, K., Al-Juhaimi, F. Y., Nyam, K.-L., Norulani, N. A. N., Sahena, F., and Omar, A. K. M., (2015). Mango (*Mangifera indica* L.) by-products and their valuable components: a review. Food chemistry, 183: 173-180.

864. Jahurul, M. H. A., Zaidul, I. S. M., Norulaini, N. N. A., Sahena, F., Jaffri, J. M., and Omar, A. K. M., (2014). Supercritical carbon dioxide extraction of mango seed kernel for cocoa butter analogy fats. CyTA—Journal of Food, 12(1): 97-103.

865. Jain, J., Atakan, V., Sahu, S., DeCristofaro, N., Jeong, H., and Olek, J., (2015). Performance of calcium silicate-based carbonated concretes vs. hydrated concretes under freeze-thaw conditions. The Master Builder, July 2015, pp. 66-68, online: http://solidiatech.com/wp-content/uploads/2015/07/Solidia-Purdue-Freeze-Thaw-White-Paper-7-1-15.pdf 866. Jain, J., Deo, O., Sahu, S., DeCristofaro, N., (2014). Solidia Concrete: Part two of a series exploring the chemical properties and performance results of sustainable solidia cement and Solidia concrete. Solidia Technologies website online: http://solidiatech.com/wp-content/uploads/2014/02/Solidia-Concrete-White-Paper-FINAL-2-19-14.pdf 867. Jajesniak, P., Ali, H. E. M. O., and Wong, T. S., (2014). Carbon dioxide capture and utilization using biological systems: opportunities and challenges. J. Bioprocessing & Biotechniques, 4(3). http://dx.doi.org/10.4172/2155-9821.1000155

868. Jaramillo, P., Griffin, W. M., and McCoy, S. T., (2009). Life cycle inventory of $CO_2$ in an Enhanced Oil Recovery system. Environ. Sci. Technol., 43: 8027-8032

869. Jarrett, D., (2014). Oil discoveries in the East African Rift. Gaffnet Cline & Associates slide deck presentation, online: http://www.gaffney-cline.com/downloads/east_africa_workshop/Oil%20Discoveries%20in%20the%20East%20African%20Rift.pdf 870. Jarvie, D. M., Maende, A., Echegu, S., and Irumba, C., (2007). Realization of the petroleum potential of the Albertine Graben" production and geochemical perspectives. Conference paper, East African Petroleum Conferene, EAPC '07, online: http://www.tpdc-tz.com/eapc07/pdfs/REALIZATION%20OF%20THE%20PETROLEUM%20POTENTIAL.pdf
871. Jasper, S., El-Halwagi, M. M., (2015). A techno-economic comparison between two methanol-to-propylene processes. Processes, 3: 684-698.
872. Jauffret, G., Morrison, J., Glasser, F. P., Galvez-Martos, J.-L., Yoon, S., and Imbababi, M. S., (2015). Low carbon cement based on hydrated magnesium carbonate. Poster presentation, 2015 Scottish Carbon Capture & Storage meeting, Oct. 28, 2015, online: http://www.sccs.org.uk/images/events/2015/SCCS_Conf_15/C05_J_Morrison_Poster.pdf
873. Jay, E. G., (1971). Suggested conditions and procedures for using carbon dioxide to control insects in grain storage facilities. U.S. Dept. agriculture. ARS51-46, 6pp.
874. Jay, E. G., and Pearman Jr., G. C., (1973). Carbon dioxide for control of an insect infestation in stored corn (maize). J. Stored Products Res., 9(1); 25-29.
875. Jennewein, J., (2015). Algae oil used to make surfboard blanks: UC San Diego scientists produce surfboard from algae. The Urethane Blog, Apr. 21, 2015, online: http://urethaneblog.typepad.com/my_weblog/2015/04/algae-oil-used-to-make-surfboard-blanks.html
876. Jensen, M. J., (2015). Energy processes enabled by Cryogenic Carbon Capture. PhD dissertaition, Brigham Young University, BYU Scholars Archive, online: http://scholarsarchive.byu.edu/cgi/viewcontent.cgi?article=6710&context=etd
877. Jensen, M. L., (2015). Prediction and validation of external cooling loop cryogenic carbon capture (CCC-EL) for full-scale coal-fired power plant retrofit. Int. J. Greenhouse Gas Control. 42: 200-212.
878. Jensen, S. H., (2015). Methanol production from biomass and intermittent power. DTU slide deck presentation, March 17$^{th}$, online: http://www.lth.se/fileadmin/mot2030/filer/5._Hojgard_-_Methanol_Production_from_ Biomass_and_Intermittent_Power.pdf
879. Jentzer, J.-B., Alignan, M., Vaca-Garcia, C., Rigal, L., and Vilarem, G., (2015). Response surface methodology to optimize accelerated solvent extraction of steviol glycosides from *Stevia rebaudiana* Bertoni leaves. Food Chem., 166: 561-567.
880. Jeon, B. Y., Jung, I. L., and Park, D. H., (2012). Conversion of carbon dioxide to metabolites by *Clostridium acetobutylicium* KCTC cultivated with electrochemical reducing power. Adv. Microbiol., 2: 332-339, online: http://dx.doi.org/10.4236/aim.2012.23040
881. Jessen, H., (2013). Greenhouse to utilize $CO_2$, waste heat from adjacent ethanl plant. Ethanol Producer Magazine, Jan. 4, 2015. Online: http://www.ethanolproducer.com/articles/9426/greenhouse-to-utilize-co2-waste-heat-from-adjacent-ethanol-plant
882. Jessop, P. G., (undated). Jessop Research group webpage, research overview & publications: http://faculty.chem.queensu.ca/people/faculty/Jessop/switchable.html
883. Jessop, P. G., Heldebrant, D. J., Li, X., Eckert, C. A., and Liotta, C. L., (2005). Reversable nonpolar-to-polar solvent. Nature, 368: 231-233
884. Jessop, P. G., Kozycz, L., Rahami, Z. G., Schoenmakers, d., Boyd, A. R., Wechsler, D., and Holland, A. M., (2011). Tertiary amine solvents having switchable hydrophilicity. Green Chem., 13: 619-623.
885. Jessop, P. G., Mercer, S. M., and Heldebrant, D. J., (2012). $CO_2$-triggered switchable solvents, surfactant, and other materials. Energy Environ. Sci., 5: 7240-7253.
886. Jessop, P. G., and Subramanian, B., (2007). Gas-expanded liquids. Chem. Rev., 107(6): 2666-2694
887. Jhong, H.-R., M., Ma, S., and Kenis, P. J. A., (2013). Electrochemical conversion of $CO_2$ to useful chemicals: current status, remaining challenges and future opportunities. Curr. Opinion in Chem. Eng., 2: 191-199.
888. Ji, D., Fang, Z., He, W., Zhang, K., Luo, Z., Wang, T., and Guo, K., (2015). Synthesis of soy-polyols using a continuous microflow system and preparation of soy-based polyurethane rigid foams. ACS Sustainable Chem. & Eng., 3(6): 1197-1204
889. Jiang, Z., Xiao, T., Kuznetsov, V. L., and Edwards, P. P., (2010). Turning carbon dioxide into fuel. Phil. Trans. R. Soc. A, 368: 3343-3364.
890. Jiao, J., Zhang, Y., Lou, D., Wu, X., and Zhang, Y., (2007). Antihyperlipidemic and antihypertensive effect of a triterpenoid-rich extract from bamboo shavinbgs and vasodilator effect of friedelin on phenylephrine-induced vasoconstriction in thoracic aortas of rats. Phytotherapy Res., 21: 1135-1141.
891. Jin, F., He, L.-N., and Hu, Y. H., (2015). *Advances in $CO_2$ Capture, Sequestration, and Conversion.* ACS Symposium Series, v. 1194. American Chemical Society
892. Jin, F., Zeng, X., Jing, Z., and Enomoto, H., (2012). A potentially useful technology by mimicking nature—rapid conversion of biomass and $CO_2$ into chemicals and fuels under hydrothermal conditions. I&EC Res., 51: 9921-9937
893. Jin, F., Gao, Y., Jin, Y., Zhang, Y., Cao, J., Wei, Z., and Smith, R. L. Jr., (2011). High-yield reduction of carbon dioxide into formic acid by zero-valent metal/metal-oxide redox cycles. Energy Environ. Sci., 4: 881-884.
894. Jin, F., Zeng, X., Liu, J., Jin, Y., Wang, L., Zhong, H., Yao, G., and Huo, Z., (2014). Highly efficient and auto-catalytic $H_2O$ dissociation for $CO_2$ reduction into formic acid with zinc. Nature Sci. Reports, 4, article No. 4503.
895. Jitaru, M., (2007). Electrochemical carbon dioxide reduction—fundamental and applied topics (review). J. Univ. Chemical Technol. Metall., 42(4): 333-344
896. Johnson, M., and Pace, R. D., (2010). Sweet potato leaves: properties and synergistic interactions that promote health and prevent disease. Nutrition Revs., 68(10): 604-615.
897. Johnson, R. C., (2014). China takes lead in carbon nanotubes & graphene. EE Times, Apr. 25, 2014, online: http://www.eetimes.com/document.asp?doc_id=1322105
898. Johnson, R. E., (2011). Bravo Dome carbon dioxide area, Northeast New Mexico. In: J. E. Fassett, (ed.), Oil ad Gas Fields of the Four Corners Area. Four Corners Geological Society, pp. 745-748, online: http://archives.datapages.com/data/fcgs/data/016/016001/745_four-corners160745.htm
899. Jones, D. T., and Woods, D. R., (1986). Acetone-Butanol fermentation revisited. Microbiological Revs., 50(4): 484-524
900. Jones, J.-P., Prakash, G. K. S., and Olah, G., A., (2015). Electrochemical $CO_2$ reduction: recent advances and current trends. Isr. J. Chem., 54: 1451-1466.
901. Jones, R., (2001). Supercritical $CO_2$ carbonation of cement and cement—fiber composites: the Supramics process. Pp. 124-135 in: P. Anastas et al., (eds.), *Green Engineering.* American Chemical Society, ACS Symp. Ser. 766.
902. Jourdin, L., Grieger, T., Monetti, J., Flexer, V., Fregula, V., Lu, Y., Chen, J., Romano, M., Wallace, G. G., and Keller, J., (2015). High acetic acid production rate obtained by microbial electrosynthesis from carbon dioxide. Environ. Sci. Technol., 49(22): 13566-13574

903. Journal of $CO_2$ Utilization (2013-2015). http://www.journals.elsevier.com/journal-of-co2-utilization/

904. Jung, H. B., Carroll, K. C., Kabilan, S., Heldebrant, D. J., Hoyt, D., Zhong, L., Varga, T., Stephens, S., Adams, L., Bonneville, A., Kuprat, A., and Fernandez, C. A., (2015). Stimuli-responsive/rheoreversible hydraulic fracturing fluids as a greener alternative to support geothermal and fossil energy production. Green Chem., 17: 2799-2812

905. Junge, H., and Beller, M., (2013). Carbon dioxide—a suitable material for hydrogen storage. Slide deck presentation, Nov. 19-20, 2013, online: http://www.iass-potsdam.de/sites/default/files/files/junge_-presentation.pdf 906. Jutz, F. D., (2009). Prospects in utilizing carbon dioxide in catalytic chemical synthesis. PhD Thesis, ETH No. 18768, Zurich, Switzerland, online: http://e-collection.library.ethz.ch/eserv/eth:1168/eth-1168-02.pdf 907. Jutz, F., Andanson, J.-M., and Baiker, A., (2011). Ionic liquids and dense carbon dioxide: a beneficial biphasic system for catalysis. Chem. Rev., 111: 322-353

908. Kaberuka, D., (2015). Africa's policy choices in an era of rapid growth. Pp. 39-44 in, E. Zedillo, O. Cattaneo and H. Wheeler (eds.), *Africa at a Fork in the Road: Taking Off or Disappointment Once Again?* Yale Center for the Study of Globalization.

909. Kablan, L., Lagauche, A., Delvaux, B., and Legreve, A., (2012). Silicon reduces black sigatoka development in banana. Plant Disease, 96(2): 273-278.

910. Kader, A. A., (1986). Biochemical and physiological basis for effects of controlled and modified atmospheres on fruits and vegetables. Food Technol., 40(5): 99-104.

911. Kakizawa, M., Yamasaki, A., and Yanagisawa, Y., (2001). A new $CO_2$ disposal process via artificial of calcium silicate accelerated by acetic acid. Energy, 26(4): 341-354

912. Kalani, M., and Yunus, R., (2014). Application of supercritical antisolvent method in drug encapsulation: a review. Intl. J. Nanomedicine, 2011(6): 1429-1442, 913. Kalra, C., Hofer, D., Servincer, E., Moore, J., and Brun, K., (2014). Development of high efficiency hot gas turboexpander for optimized CSP supercritical $CO_2$ power block operation. The 4$^{th}$ International Symposium—Supercritical $CO_2$ Power Cycles, September 9-10, Pittsburgh, Pa. Online: http://www.swri.org/4org/d18/sCO2/papers2014/turbomachinery/74-Kalra.pdf 914. Kanda, H., (2011). Simple extraction method of green crude from natural blue-green algae by dimethyl ether. Fuel, 90: 1264-1266

915. Kanda, H., Li, P., Goto, M., and Makino, H., (2015). Energy-saving lipid extraction from wet *Euglena gracilis* by the low-boiling-point solvent dimethyl ether. Energies, 15(8): 610-620.

916. Kanda, H., Li, P., Ikehara, T., Yasumoto-Hirose, M., (2012). Lipids extracted from several species of natural blue-green algae by dimethyl ether: extraction yield and properties. Fuel, 95: 88-92.

917. Kang, P., Chen, Z., Nayak, A., Zhang, S., and Meyer, T. J., (2014). Single catalyst electrocatalytic reduction of $CO_2$ in water to $H_2$—CO syngas mixtures with water oxidation to $O_2$. Energy Environ. Sci., 7: 4007-4012.

918. Kantzow, C., Mayer, A., and Weuster-Botz, D., (2015). Continuous gas fermentation by Acetobacterium woodii in a submerged membrane reactor with full cell retention. J. Biotechnol., 212: 11-18

919. Kaplan, V., Wachtel, E., Gartsman, K., Feldman, Y., and Lubomirsky, I., (2010). Conversion of $CO_2$ to CO by electrolysis of molten lithium carbonate. J. Electrochem. Soc., 157(4): B552-B556.

920. Kapteijn, P., Biebuyck, C., and Kutscha, E., (2011). TriGen, an innovative oxy-fuel technology to convery high $CO_2$ gas reserves into power. Maersk Oil slide deck presentation, Seoul Korea, Oct. 19, 2011, online: http://members.igu.org/old/IGU%20Events/igrc/igrc2011/igrc-2011-proceedings-and-presentations/oral-presentations/c/OP_C_2 PieterKapteijn.pdf 921. Kapteijn, P. K., Kutscha, E., Perron, J., (2012). Breakthrough oxy-fuel technology for cost-effective $CO_2$-enhanced oil recovery. SPE-162541-MS, Society of Petroleum Engineers, Abu Dhabi International Petroleum Conference and Exhibition, Nov. 10-14, 2012.

922. Karna, P., Gundala, S. R., Gupta, M. V., Shamsi, S. A., Pace, R. D., Yates, C., Narayan, S., and Aneja, R., (2011). Polyphenol-rich sweet potato greens extract inhibits proliferation and induces apoptosis in prostate cancer cells in vitro and in vivo. Carcinogenesis, 32(12): 1872-1880.

923. Karni, J., (2011). From concept to product: solar thermal development at the Weizmann Insitute. Slide deck presentation, Oct. 30, 2011, online: http://www.weizmann.ac.il/AERI/sites/AERI/files/karnioct2011.pdf 924. Karp, T., Scholz, C. A., and McGlue, M. M., (2012). Structure and stratigraphy of the Lake Albert Rift, East Africa: observations from seismic reflection and gravity data. Chapter 12, pp. 299-318, in: O. W. Bagnaz et al., (eds.), Lacustrine Sandstone Reservoirs and Hydrocarbon Systems. AAPG Memoir 95.

925. Kassim, A., Workneh, T. S., and Bezuidenhout, C. N., (2013). A review on postharvest handling of avocado fruit. Afr. J. Agric. Res., 8(21): 2385-2402.

926. Kauffman, D. R., Thakkar, J., Siva, R., Matranga, C., Ohodnicki, P. R., Zeng, C., and Jin, R., (2015). Efficient electrochemical $CO_2$ conversion powered by renewable energy. ACS Applied Materials & Interfaces, 7(28): 15626-15632.

927. Kaushik, (2015). 7 famous man-made geysers. Amusing Planet, online: http://www.amusingplanet.com/2015/04/7-famous-man-made-geysers.html See also: http://www.amusingplanet.com/2014/03/cold-water-geysers-of-analavory.html 928. Kelemen, P. B., Matter, J., Streit, E. E., Rudge, J. F., Curry, W. B., and Blausztajn, J., (2011). Rates and mechanisms of mineral carbonation in peridotite: natural processes and recipes for enhanced, in situ $CO_2$ capture and storage. Ann. Rev. Earth Planet. Sci., 39: 545-576.

929. Keller, M., Loder, A., Basen, M., Izquierdo, J., Kelly, R. M., and Adams, M. W. W., (2015). Production of lignofuels and electrofuels by extremely thermophilic microbes. Biofuels, 5(5): 499-515

930. Keller, M. W., Schut, G. J., Lipscomb, G. L., Menon, A. L., Iwuchukwu, I. J., Leuko, T. T., Thorgersen, M. P., Nixon, W. J., Hawkins, A. S., Kelly, R. M., and Adams, M. W. W., (2013). Exploiting microbial hyperthermophilicity to produce an industrial chemical, using hydrogen and carbon dioxide. PNAS, 110, No. 15, DOI: 10.1073/pnas.1222607110

931. Kelley, B. T., Valencia, J. A., Northrop, P. S., and Mart, C. J., (2011). Controlled Freeze Zone™ for developing sour gas reserves. Energy Procedia, 4: 824-829

932. Kember, M., (2013). $CO_2$ use in plastic materials. Econic Technologies slide deck presentation, 13$^{th}$ Annual APGTF Workshop, online: http://www.apgtf-uk.com/files/workshops/13thWorkshop2013/53MichaelKember.pdf 933. Kemper Project, (undated Wikipedia entry). https://en.wikipedia.org/wiki/KemperProject
934. Kendall, J. L., Canelas, D. A., Young, J. L., and DeSimone, J. M., (1999). Polymerizations in supercritical carbon dioxide. Chem. Rev., 99: 543-563.
935. Kenis, P. J. A., (2015). Conversion of $CO_2$ into value-added chemicals. Slide deck presentation, 9/2015, online: https://www.differ.nl/sites/default/files/multimedia/organization/sec/2015-04-09_NWO_Symposium/12%20Kenis%20-%20Conversion%20of%20CO2%20into%20value-added%20chemicals.pdf
936. Kerton, F. M., (2009). Tunable and switchable solvent systems. Chapter 9, pp. 188-203 in, F. M. Kerton, *Alternative Solvents for Green Chemistry*. Royal Soc. Chem.
937. Keskin, S., Kayrak-Talay, Akman, U., and Hortacsu, O., (2007). A review of ionic liquids towards supercritical fluid applications. J. Supercrit. Fluids, 43: 150-180.
938. Khalloufi, S., Almeida-Rivera, C., and Bongers, P., (2010). Supercritical-$CO_2$ drying of foodstuffs in packed beds: experimental validation of a mathematical model and sensitive analysis. J. Food Eng., 96(1): 141-150.
939. Khan, C., Amin, R., and Madden, G., (2013a). Effects of $CO_2$ and acid gas injection on enhanced gas recovery. J. Petrol. Explor. Prod. Technol., 3: 55-60
940. Khan, C., Amin, R., and Madden, G., (2013b). Carbon dioxide injection for enhanced gas recovery and storage (reservoir stimulation). Egyptian J. Petroleum, 22: 225-240
941. Khan, N. E., Myers, J. A., Tuerk, A. L., and Curtis, W. R., (2014). A process economic assessment of hydrocarbon biofuels production using chemoautotrophic organisms. Bioresource Technol., 172: 201-211
942. Khanna, V., Bakshi, B. R., and Lee, L. J., (2008). Carbon nanofiber production: life cycle energy consumption and environmental impact. J. Industrial Ecol., 12(3): 394-410.
943. Khemmere, M. F., and Meyer, T., (2005). *Supercritical Carbon Dioxide in Polymer Reaction Engineering*. Wiley-VCH.
944. Khirsariya, P., amd Mewada, R., K., (2012). Single step oxidation of methane to methanol—towards better understanding. Procedia Engin., 51: 409-415.
945. Khosravi-Darani, K., and Mozafari, M. R., (2011). Supercritical fluid application in food and bioprocess technology. Chaper 24, pp. 555-578 in, H, Nakajima (ed.), *Mass Transfer—Advanced Aspects*. InTech, pp. 824.
946. Kim, C., and Youn, J.-R., (2000). Environmentally friendly processing of polyurethane foam for thermal insulation. Polym.-Plast. Technol. Eng., 39(1): 163-185,
947. Kim, D., Sakimoto, K. K., Hong, D., and Yang, P., (2015). Artificial photosynthesis for sustainable fuel and chemical production. Angew. Chem. Int. Ed., 54: 2-10.
948. Kim, M.-H., Pettersen, J., and Bullard, C. W., (2004). Fundamental processes and system design issues in $CO_2$ vapor compression systems. Prog. Energy Comb. Sci., 30: 119-174
949. Kim, Y., Wyslouzil, B. E., and Weathers, P. J., (2002). Secondary metabolism of hairy root cultures in bioreactors. In Vitro Cell Devel. Biol.-Plant, 38: 1-10
950. Kim, Y. M., Kim, C. G., and Favrat, D., (2012). Transcritical or supercritical $CO_2$ cycles using both low- and high-temperature heat sources. Energy, 43: 402-415.
951. Kim, Y.-S., Choi, Y. E., and Sano, H., (2010). Plant vaccination: stimulation of defense system by caffeine production in planta. Plant Signaling & Behavior, 5:5: 489-493
952. Kimball, B. A., (2013). The seventeen year orange study: feasibility for increasing productivity of commercial orange orchards with $CO_2$ enrichment. Online: http://www.carbogation.com/the-seventeen-year-orange-study.html
953. Kincal, D., Hill, W. S., Balaban, M., Portier, K. M., Sims, C. A., Wei, C. I., and Marshall, M. R., (2005). A continuous high-pressure carbon dioxide system for cloud and quality retention in orange juice. J. Food Sci., 70: M249-M254.
954. King, D., (2016). Biggest opportunity of our age. Science, 351, Issue 6269, pp. 107
955. King, D., Browne, J., Layard, R., O'Donnell, Rees, M., Stern, N., and Turner, A., (2015). A global apollo programme to combat climate change. Global Apollo Programme Report, online: http://cep.lse.ac.uk/pubs/download/special/Global_Apollo_Programme_Report.pdf
956. King, J. W., (2013). Integration and optimization of supercritical fluid technology into the algae- and marine-products industry. Conference paper, Supergreen 2013, Kaohsiung, Taiwan. 6 pp.
957. King, J. W., (2014). Modern supercritical fluid technology for food applications. Ann. Rev. Food Sci. Technol., 5: 215-238.
958. King, J. W., and Srinivas, K., (2014). Development of multiple unit-fluid processes and bio-refineries using critical fluids. Chaper 13, pp. 455-478, in: T. Fornari and R. P. Stateva (eds), *High Pressure Fluid Technology for Green Food*. Springer.
959. Kingman Group, (undated). Military combat training with Spyder paintball markers. Corporate information (and video) online: http://www.kingman.com/military-combat-training-with-spyder-paintball-markers/
960. Kiriamiti, H. K., Camy, S., Goudon, C., and Condoret, J. S., (2003a). Pyrethrin exraction from pyrethrum flowers using carbon dioxide. J. Supercrit. Fluids, 26: 193-200. (Sic: "exraction")
961. Kiriamiti, H. K., Camy, S., Goudon, C., and Condoret, J. S., (2003b). Supercritical carbon dioxide processing of pyrethrum oleoresin and pale. J. Agric. Food Chem., 51(4): 880-884.
962. Kiriamiti, H., Sarmat, S., and Nzila, C., (2006). Fractionation of crude pyrethrum extract using supercritical carbon dioxide., Pp. 339-346 in: J. A. Mwakali and G. Taban-Wani, (eds.), *Advances in Engineering and Technology: Proceedings of the First International Conference in Engineering and Technology*, 16-19 Jul. 2006, Entebbe, Uganda. Elsevier.
963. Kiss, A. A., Pragt, J. J., Vos, H. J., Bargeman, G., and de Groot, M. T., (2016). Novel efficient process for methanol synthesis by $CO_2$ hydrogenation. Chem. Eng. J., 284: 260-269.
964. Kivu Belt, (2013). Rwanda Kivu Belt, Tourism Sub Master Plan. http://www.westernprovince.gov.rw/uploads/media/Rwanda_Kivu_Belt_Sub_Master_Plan_01.pdf
965. Kjarstad, J., Skagestad, R., Eldrup, N. H., and Johnsson, F., (2014). Transport of $CO_2$ in the Nordib region. Energy Procedia, 63: 2683-2690.
966. Kleivdal, H., (2015). Nasjional mikroAlgaepilot Mongstad. Conference: SIG Microalgae: Optimization and Production on Microalgae, Tromso, Norway, May 20, 2015, (http://www.indbiotech.no/sites/default/files/

Invitasjon_Program_SIG_Microalgae_20_mai%202015.pdf) conference slide deck presentation, online: http://www.indbiotech.no/sites/default/files/6-Kleivdal_UNIRESEARCH.pdf Other conference presentations: http://www.indbiotech.no/content/presentations-sig-microalgae-optimization-and-production-microalgae 967. Kleivdal, H., Chauton, M. S., Reitan, K. I., (2013). ProAlgae: Industrial production of marine microalgae as a source of EPA and DHA rich raw material in fish feed—Basis, knowledge and possibilities. Final Report. FHF project no. 900771, Online: http://www.indbiotech.no/sites/default/files/ProAlgae%20FINAL%20April%202013.pdf 968. Kleivdal, H., Mijo, U., Nordvik, S. M., Mork-Pedersen, T., (2012). $CO_2$ to Bio: Microalgae as an omega-3 rich feedsyock—integrating $CO_2$ sequestration and aquafeed production. Project Final Report, online: http://www.hordaland.no/PageFiles/47013/FUV%2021.11.12/FUV%2021.11.12.%20Vedlegg%20sak%20291.%20CO$_2$%2°til%20bio%20og%20fiskefor.pdf 969. Klibanov, A. M., Alberti, B. N., and Zale, S. E., (1982). Enzymatic synthesis of formic acid from $H_2$ and $CO_2$ and production of hydrogen from formic acid. Biotechnol. Bioeng., 24(1): 25-36.

970. Klimkowski, L., Nagy, S., Papeiernik, B., Orlic, B., amd Kempka, T., (2015). Numerical simulations of Enhanced Gas Recovery at the Zalecze gas field in Poland confirm high $CO_2$ storage capacity and mechanical integrity. Oil & Gas Science and Technology, 70(4): 655-680, online: https://doaj.org/article/9ec7324c7ac14055801852d28e025a2e 971. Kling, G. (undated online slide deck) "The Killer Lakes of Cameroon." http://globalchange.umich.edu/globalchange1/current/lectures/kling/killer_lakes/Killer_lakes_lecture.pdf 972. Kling, G. W.; Clark, M. A.; Wagner, G. N.; Compton, H. R.; Humphrey, A. M.; Devine, J. D.; Evans, W C.; Lockwood, J. P. et al. (1987). The 1986 Lake Nyos Gas Disaster in Cameroon, West Africa. Science 236 (4798): 169-75

973. Kling, G. W., Evans, W. C., Tanyileke, G., Kusakabe, M., Ohba, T., Yoshida, Y., and Hell, J. V., (2005). Degassing Lakes Nyos and Monoun: defusing cerain disaster. PNAS, 102(40): 14185-14190

974. Klins, M. A., (1982). Heavy oil production by carbon dioxide injection. J. Can. Petroleum Technol., 21(5): 64-72

975. Knittel, D., Saus, W., and Schollmeyer, E., (1993). Applications of supercritical carbon dioxide in finishing processes. J. Textile Institute, 84(4): 534-552.

976. Knopf, F. C., Roy, A., Samrow, H. A., and Dooley, K. M., (1999). High-pressure molding and carbonation of cementitious materials. Ind. Eng. Chem. Res., 38: 2641-2642.

977. Knuutila, H., Hessen, E. T., Kim, I., Haug-Warberg, T., and Svendsen, H. F., (2010a). Vapor-liquid equilibrium in the sodium carbonate-sodium bicarbonate-water-$CO_2$-system. Ind. Eng. Chem. Res., 65: 2218-2226.

978. Knuutila, H., Juliussen, O., Svendsen, H. F., (2010b). Kinetics of the reaction of carbon dioxie with aqueous sodium and potassium carbonate solutions. Chem. Eng. Sci., 65: 6077-6088.

979. Knuutila, H., Svendsen, H. F., and Anttila, M., (2009). $CO_2$ capture from coal-fired power plants based on sodium carbonate slurry; a systems feasibility and sensitivity study. Int. J. Greenhouse Gas Control, 3: 143-151.

980. Kobayashi, H., Kawaguchi, H., Endo, K., and Sato, K., (2012). Analysis of methane production by microorganisms indigenous to a depleted oil reservoir for application in Microbial Enhanced Oil Recovery. J. Bioscience and Bioengineering, 113(1): 84-87

981. Koch, K., Huber, B., Fernandez, Y. B., and Drewes, J. E., (2016). Methane from $CO_2$: influence of different $CO_2$ concentrations in the flush gas on the methane production in BMP tests. Waste Management, DOI: 10.1016/j.wasman.2016.01.021

982. Koempel, H., Liebner, W., and Wagner, M., (2005). Lurgi's gas to chemicals (GTC): advanced technologies for natural gas monetization. Gastech 2005 conference paper. Online: http://www.ivt.ntnu.no/ept/fag/tep4215/innhold/LNG%20Conferences/2005/SDS_TIF/050140.pdf 983. Koide, H., and Yamazaki, K., (2001). Subsurface $CO_2$ disposal with enhanced gas recovery and biogeochemical carbon recycling. Environmental Geosciences, 8(3): 218-224

984. Kok, M. V., and Ors, O., (2012). The evaluation of an immiscible-$CO_2$ Enhanced oil recovery technique for heavy crude oil reservoirs. Energy Sources, Part A: Recovery, Utilization and Environmental Effects, v. 34(8): 673-681.

985. Kohler, P., Abrams, J. F., Volker, C., Hauk, J., and Wolf-Gladrow, D. A., (2013). Geoengineering impact of open ocean dissolution of olivine on atmospheric $CO_2$, surface ocean pH and marine biology. Environ. Res. Lett., 8: 014009 (9pp), online: http://iopscience.iop.org/article/10.1088/1748-9326/8/1/014009/pdf 986. Kohler, P., Hartmann, J., and Wolf-Gladrow, D. A., (2010). Geoengineering potential of artificially enhanced silicate weathering of olivine. PNAS, 107(47): 20228-20233.

987. Kolmogoren, B., (2014). Uhde HTW™ and PRENFLO Gasification: Latest developments and global projects. ThyssenKrupp slide presentation online: http://www.icheme.org/events/conferences/past-conferences/2014/gasification-2014/~/media/782481B30DC24470AC5A2F9A10A5673D.pdf 988. Kondratenko, E. V., Mul, G., Baltrusaitis<Larrazabal, G. O., and Perez-Ramirez, J., (2013). Staus and perspectives of $CO_2$ conversion into fuels and chemicals by catalytic, photocatalytic and electrocatalytic processes. Energy Environ. Sci., 6: 3112-3135.

989. Kopke, M., Held, C., Hujer, S., Liesegang, H., Wiezer, A., Wollherr, A., Ehrenreich, A., Liebl, W., Gottschalk, G., and Durre, P., (2010). *Clostridium ljungdahlii* represents a microbial production platform based on syngas. PNAS, 107: 13087-13092

990. Kopke, M., Mihalcea, C., Bromley, J. C., and Simpson, S. D., (2011). Fermentive production of ethanol from carbon monoxide. Curr. Opinion Biotechnol., 22: 320-325

991. Kortilever, R., Peters, I., Koper, S., and Koper, M. T. M., (2015). Electrochemical $CO_2$ reduction to formic acid at low overpotential and high faradaic efficiency on carbon-supported bimetallic Pd—Pt nanoparticles. ACS Catal., 5(7): 3916-3923.

992. Kortilever, R., Shen, J., Schouten, K. J. P., Calle-Vallejo, F., and Koper, M. T. M., (2015). Catalysts and reaction pathways for the electrochemical reduction of carbon dioxide. J. Phys. Chem. Lett., 6: 4073-4082.

993. Kostick, D. S., (1998). The origin of the U.S. natural and synthetic soda ash industries. Wyoming State Geological Survey Public Information Circular 39, 1998, 33pp.

994. Kostick, D. S., (1992). Soda ash. Bureau of Mines Mineral Yearbook, v. 1, pp. 1237-1259 Online: http://images.library.wisc.edu/EcoNatRes/EFacs2/Minerals- YearBk/MinYB 1992v1/reference/econatres.minyb1992v1.dkostick2.pdf 995. Kothandaraman, J., Czaun, M., Goeppert, A., Haiges, R., Jones, J. P., May, R. B., Prakash, G. K., and Olah, G. A., (2015). Amine-free reversible hydrogen storage in formate salts caytalyzed by ruthenium pincer complex without pH control or solvent change. ChemSusChem, 8(8): 1442-1451.

996. Koziara, B., (undated). Membrane dehydration of supercritical $CO_2$. WETSUS poster presentation document, online: https://www.wetsus.nl/includes/downloadFile.asp?id=M2Q1TWpnME9RPTOyMjE%3D&date=3d5221

997. Krabben, P., (2015). Acetone production during the First World War. Microbiology Today, May 29, 2015, online: http://www.microbiologysociety.org/all-microsite-sections/microbiology-today/index.cfm/article/44A96CBA-C42F-40A7-8DA583E47DDA6986/external/1

998. Krotz, D., (2011). Store $CO_2$ underground and extract electricity? A Berkeley lab-led team is working on it. Lawrence Berkeley National Laboratory, news update, Aug. 8, 2011, online: http://newscenter.lbl.gov/2011/08/08/geothermal-co2/

999. Kruszeinicki, K., (2015). *Doctor Karl's Australia: Great Australian Facts & Figures*. Xou Pty Ltd., pp. 416.

1000. Kuhl, K. P., Cave, E. R., Abram, D. N., and Jaramillo, T. F., (2012). New insights into the electrochemical reduction of carbon dioxide on metallic copper surfaces. Energy Environ. Sci., 5: 7050-7059.

1001. Kuhn, M., (2015). *CLEAN: $CO_2$ Large-Scale Enhanced Gas Recovery in the Altmark Gas Field*. Geotechnologien Science Report No. 19. Springer, pp. 202

1002. Kuhn, M., Forster, A., Grossmann, J., Lillie, J., Pilz, P., Reinicke, K. M., Schafer, D., Tesmer, M., and CLEAN Partners. Energy Procedia, 37: 6777-6785

1003. Kulga, B., Dilmore, R., Wyatt, C., and Ertekin, T., (2014). Investigation of $CO_2$ storage and enhanced gas recovery in depleted shale gas formations using a dual-porosity/dual-permeability multiphase reservoir simulator. NETL-TRS-4-2014, NETL Technical Report Series, NETL=TRS-4-2014, pp. 72, online: https://www.netl.doe.gov/File%20Library/Research/onsite%20research/publications/NETL-TRS-4-2014_$CO_2$—Storage-and-Enhanced-Gas-Recovery_20140925.pdf 1004. Kumar, B., Asadi, M., Pisasale, D., Sinha-Ray, S., Rosen, B. A., Haasch, R., Abiade, J., Yarin, A. L., Salehi-Khojin, A., (2013). Renewable and metal-free carbon nanofibre catalysts for carbon dioxide reduction. Nature Comms., 4: 2819, DOI: 10.1038/ncomms3819.

1005. Kumar, B., llorente, M., Freohlich, J., Dang, T., Sathrum, A., and Kubiak, C. P., (2012). Photochemical and photoelectrochemical reduction of $CO_2$. Annu. Rev. Phys. Chem. 63: 541-569.

1006. Kumar, N., Shojaee, M., and Spivey, J. J., (2014). Catalytic bi-reforming of methane: from greenhouse gases to syngas. Curr. Opin. Chem. Eng., 9: 8-15.

1007. Kuramochi, Y., Fu, Q., Kobayashi, H., Ikarashi, M., Wayayama, T., Kawaguchi, H., Vilcaez, J., Maeda, H., and Sato, K., (2013). Electromethanogenic $CO_2$ conversion by subsurface-reservoir microorganisms. Energy Procedia, 37: 7014-7020

1008. Kurooka, H., Fukunaga, S., Yuda, E., Nakagawa, S., and Horiuchi, S., (1990). Effect of carbon dioxide on vine growth and berry quality of 'Kyoho' grapes. J. Japanese Soc. Horticultural Sci., 59(3): 463-470.

1009. Kuang, K., Seo, Y., Chang, D., Kang, S.-G., and Huh, C., (2015). Estimation of $CO_2$ transport costs in South Korea using a techno-economic model. Energies, 8: 2176-2196.

1010. Kumar, A., (2015). TARDA plans 320-MW solar park in Kenya. Greentech Lead news, Sep. 22, 2015, online: http://www.greentechlead.com/solar/tarda-plans-320-mw-solar-park-in-kenya-28222

1011. Kupiainen, L., (2012). Dilute acid catalyzed hydrolysis of cellulose—extension to formic acid. PhD thesis, Acta Universitatis Ouluensis, C438, University of Oulu, Finland.

1012. Kuuskraa, V. A., Godec, M. L., and Dipietro, P., (2013). $CO_2$ utilization from "next generation" $CO_2$ enhanced oil recovery technology. Energy Procedia, 37: 6854-6866.

1013. Kuuskraa, V. A., (2014). The $CO_2$-EOR oil recovery technology and $CO_2$ utilization "prize." Presentation slide deck, April $8^{th}$, Florence, Italy, online: http://www.gotia.org/pdf/florence2014/Vella_Kuuskraa_Subsurface_and_EOR.pdf 1014. Kuuskraa, V. A., and Wallace, M., (2014). $CO_2$-EOR set for growth as new $CO_2$ supplies emerge. Oil and Gas J., Apr. 7, 2014, pp. 66-67. Online: http://digital.ogj.com/ogjournal/20140407_USA?pg=68

1015. Kwon, E. E., Cho, S.-H., and Kim, S., (2015). Synergetic sustainability enhancements via utilization of carbon dioxide as carbon neutral chemical feedstock in the thermo-chemical processing of biomass. Environmental Sci. Eng., 49(8): 5028-5034.

1016. Kwon, E. E., Westby, K. J., and Castaldi, M. J., (2009). An investigation into syngas production from municipal solid waste (MSW) gasification under various pressures and $CO_2$ concentration atmospheres. NAWTEC17-2351. Proc. $17^{th}$ North American Waste-to-Energy Conference NAWTEC17, May 18-20, 2009, Chantilly, Va.

1017. Kyushu University, Novel Carbon Resource Sciences, (2011). Kyushu University G-COE Program: Novel Carbon Resource Sciences—Coal-Based Eco-Innovations. Online: http://ncrs.cm.kyushu-u.ac.jp/ncrs2/assets/files/pamphlet/en/NCRS-GCOE_PamphletE.pdf 1018. Lack, E., and Seidlitz, H., (2012). Commercial scale decafferination of coffee and tea by supercritical $CO_2$. Chaper 5, pp. 101-139 in: M. B. King and T. R. Bott (eds.), Extraction of Natural Products Using Near Critical Solvents. Springer.

1019. Lack, E., Weidner, A. E., Knez, B. Z., Gruner, C. S., Weinreich, D. B., and Seidlitz, A., (2005). Particle generation with supercritical $CO_2$. In: Proceedings of the 1st Vienna International Conference: Micro- and Nano-Technology. Ed. Osterr. Tribolog. Gesellschaft, Vienna, Austria, 2005. Online: http://www.natex.at/download/CPF-PGSS-article.pdf 1020. Lafarge, (2015). Lafarge and Solidia commercialize a new low-carbon solution for the construction sector. Press release online: http://www.lafarge.com/en/04282015-Lafarge-Solidia-commercialize-new-low-carbon-solution-for-construction-sector 1021. Lahijani, P., Zainal, Z. A., Mohamed, A. R., and Mohammedi, M., (2014b). Microwave-enhanced $CO_2$ gasification of oil palm shell char. Bioresource Technol., 158: 193-200.

1022. Lahijani, P., Zainal, Z. A., Mohammedi, M., and Mohamed, A. R., (2014a). Conversion of the greenhouse 1023. Lai, K. C., (2015). LanzaTech: creating a carbon smart future! LanzaTech corporate presentation slide deck, ICEF 2015 Tokyo, online: https://www.icef-forum.org/annual_2015/speakers/october8/cs3/alb/pdf/cs-3_20098_ken_c._lai.pdf 1024. Lako, J., Trenerry, V. C., Wahlqvist, M., Wattenapenpaibon, N., Sotheeswaran, S., and Premier, R., (2007). Phytochemical flavonols, carotenoids and the antioxidant properties of a wide selection of Fijian fruit, vegetables and other readily available foods. Food Chem., 101: 1727-1741.

1025. LaMoreaux, P. E., and Tanner, J. T., (2002). *Springs and Bottled Waters of the World: Ancient History, Source, Occurrence, Quality and Use*. Springer, pp. 315

1026. Landalv, I., (2014). Renewable fuels—opportunities to grasp and barriers to overcome. Slide deck presentation, Gothenburg, May 6-7, 2014, online: http://www.marinemethanol.com/publications/category/5-promsus-workshop?download=30:11-renewable-fuel s-opportunities-to-grasp-and-barriers-to-overcome-by-ingvar-landaelv 1027. Lane, J., (2015). Gingko Bioworks: the Digest's 2015 8-slide guide. Biofuels Digest, Jul. 26, 2015, online: http://www.biofuelsdigest.com/bdigest/2015/07/26/ginkgo-bioworks-the-digests-2015-8-slide-guide/

1028. Langanke, J., Wolf, A., Hofman, J., Bohm, K., Subhani, A. A., Muller, T. E., Leitner, W., and Gurtler, C., (2013). Carbon dioxide ($CO_2$) as sustainable feedstock for polyurethane production. Green Chem., 16:1865-1870

1029. Lange, S., Pellegrini, L. A., Vergani, P., and Savio, M. L., (2015). Energy and economic analysis of a new low-temperature distillation process for the upgrading of high-$CO_2$ content natural gas streams. Ind. Eng. Chem. Res., 54: 9770-9782

1030. Langmuir, D., (1997). *Aqueous Environmental Geochemistry*. Prentice-Hall, pp. 600

1031. Lanjekar, K., Gharat, N., and Thakare, D., (2011). Green conversion technology for carbon dioxide utilization—a short review. Int. Conf. on Curr. Trends in Technol., 'NUiCONE—2011,' Inst. Of Technol., Nirma Univ., Ahmedabad, India, 8-10 Dec. 2011, online: http://nuicone.org/site/common/proceedings/Chemical/oral/CH_05.pdf 1032. Lanzatech (website: www.lanzatech.com): http://www.lanzatech.com/innovation/markets/chemicals/; http://www.lanzatech.com/innovation/markets/fuels/

1033. Latif, H., Zeidan, A. A., Nielsen, A. T., and Zengler, K., (2014). Trash into treasure: production of biofuels and commodity chemicals via syngas fermenting microorganisms. Curr. Opinion Biotechnol., 27: 79-87

1034. Laumb, J. D., Cowan, R. M., Azenkeng, A., Hanson, S. K., Heebink, L. V., Letvin, P. A., Jensen, M. D., and Raymond, L. J., (2012). Beneficial use of $CO_2$ for North Dakota lignite-fired plants. University of North Dakota report 2012-EERC-01-28, online: http://www.canadiancleanpowercoalition.com/files/7914/3018/3625/CU13_-_Beneficial_Use_of_CO2 Final_report.pdf 1035. Lautzenberg, F. M., (undated). Launching dimethyl ether is diesel fuel in North America. Online: https://www.academia.edu/9641840/Launching_dimethyl_ether_as_diesel_fuel_in_North_America 1036. Law, D., (2015b). Harnessing bio-$CO_2$ as a low cost feedstock to make more sustainable chemicals. Liquid Light slide deck presentation, Jul. 20, 2015, online: http://llchemical.com/sites/all/themes/clean/pdfs/BIOWorldCongressJuly2015_LiquidLight.pdf 1037. Law, D., (2015a). Harnessing $CO_2$: A market-focused perspective. Liquid Light slide deck presentation, March, 2015, online: http://www.ascension-publishing.com/ABLC15/Law.pdf 1038. Lazaro, A., Brouwers, H. J. H., Quercia, G., and Geus, J. W., (2012). The properties of amorphous nano-silica synthesized by the dissolution of olivine. Chem. Eng. J., 211/212: 112-121

1039. Lazaro, A., Quercia, G., Brouwers, H. J. H., and Geus, J. W., (2013). Synthesis of a green nano-silica material using beneficiated waste dunites and its application in concrete. World J. Nano Sci. Eng., 3: 41-51.

1040. Lee, A., and Deng, Y., (2015). Green polyurethane from lignin and soybean oil through non-isocyanate reactions. Eur. Polymer J., 63: 67-73.

1041. Lee, H., Muirhead, J. D., Fischer, T. P., Ebinger, C. J., Kattenhorn, S. A., Sharp, Z. D., and Kianji, G., (2016). Massive and prolonged deep carbon emissions associated with continental rifting. Nature Geoscience, DOI: 10.1038/NGEO2622

1042. Lee, J., Lee, J. I., and Ahn, Y., (2012). Design methodology of supercritical $CO_2$ Brayton cycle turbomachineries. Paper No. GT2012-68933, pp. 975-983, ASME Turbo Expo 2012: turbine Technical Conference and Exposition, Copenhagen, Jun. 11-15, 2012.

1043. Lee, J. H., Lee, D. W., and Shim, J.-G., (2015). Development status of $CO_2$ utilization technology. Chemical Industry Outlook, No. 18(3): 28-40 (in Korean). Online: https://www.cheric.org/PDF/PIC/PC18/PC18-3-0028.pdf 1044. Lee, R., Jessop, P. G., and Champagne, P., (2015). Carbon dioxide pressure-induced coagulation of microalgae. *Phil. Trans. R. Soc. A* 373: 20150016. http://dx.doi.org/10.1098/rsta.2015.0016

1045. Lee, S., Ju, H., Machunda, R., Uhm, S., Lee, J. K., Lin, H. J., and Lee, J., (2015). Sustainable production of formic acid by electrolytic reduction of gaseous carbon dioxide. J. Mats. Cem. A, 3: 3029-3034.

1046. Leeuwenburgh, O., Neele, F., Hofstee, C., Weijermans, P.-J., de Boer, H., Oosthoek, P., Lefebvre, A., Godderij, R., and Gutierrez-Neri, M., (2014). Enhanced gas recovery—a potential 'U' for CUUS in The Netherlands. Energy Procedia, 63: 7809-7820

1047. Legere, E., (2015). Algenol: DOE Bioenergy Technologies Office—IBR Project Peer Review, Mar. 24, 2015, online: http://www.energy.gov/sites/prod/files/2015/05/f22/demonstration_market_transformationlegere_3323.pdf 1048. Leigh, J. A., Mayer, F., and Wolfe, R. S., (1981). Acetogenium kivui, a new thermophilic hydrogen-oxidizing, acetogenic bacterium. Arch. Microbiol., 129: 275-280

1049. Leino, E., (2015). Transformation of carbon dioxide to diethyl carbonate over ceria and creia-supported catalysts. PhD thesis, Abo Akademi University, Finland. Online: http://www.doria.fi/handle/10024/104312

1050. Leitner, W., (1995). Carbon dioxide as a raw material: the synthesis of formic acid and its derivatives from $CO_2$. Angew. Chem. Int. Ed., 34(20): 2207-2221.

1051. Leitner, W., (1996). The coordination chemistry of carbon dioxide and its relevance for catalysis: a critical survey. Coord. Chem. Revs., 153: 257-284.

1052. Leitner, W., (2001). Supercritical carbon dioxide as a green reaction medium for catalysis. Acc. Chem. Res., 35: 746-756.

1053. Lemus-Mondaca, R., Vega-Galvez, A., Zura-Bravo, L., and Ah-hen, K., (2012). *Stevia rebaudiana* Bertoni, source of a high potency natural sweetener: a comprehensive review on the biochemical, nutritional and functional aspects. Food Chem., 132: 1121-1132.

1054. Lenzing, (2012). Lenzing Modal® produced by edelweiss technology. Company (Lenzing) slide deck presentation, online: http://lenzinginnovation.lenzing.com/fileadmin/template/pdf/Texworld_USA_2012/16_01_2012_2_PM_Lenzing_Edelweiss.pdf 1055. Letourneau, J.-J., Englert, K., Rodier, E., and Fages, J., (2007). A supercritical process to produce cocoa butter and chocolate particles for the seeding of chocolate. ISASF 9$^{th}$ Meeting on Supercritical Fluids, Trieste Italy, conference paper, online: http://www.isasf.net/fileadmin/files/Docs/Trieste/Papers/Md07.pdf 1056. Letourneau, J.-J., Vigneau, S., and Fages, J., (2005). Micronized cocoa butter particles produced by a supercritical process. Chem. Eng. and Processing: Process Intensification, 44(2): 201-207.

1057. Levy, P. F., Barnard, G. W., Garcia-Martinez, D. V., Sanderson, J. E., and Wise, D. L., (1981). Organic acid production from $CO_2/H_2$ and $CO/H_2$ by mixed-culture anaerobes. Biotechnol. Bioeng., 23(10): 2293-2306

1058. Levy, P. F., Sanderson, J. E., Kispert, R. G., and Wise, D. L., (1981). Biorefining of biomass to liquid fuels and organic chemicals. Enzyme and Microbial Technol., 3(3): 207-215

1059. Lewis, J., Argyopoulos, J. N., and Nielson, K. A., (1997). Supercritical carbon dioxide spray systems. Metal Finishing, April 1997: 33-41.

1060. Lewis, N. S., (2011). Accelerating solar conversion science. Research Corporation for Science Advancement, online: http://rescorp.org/gdresources/publications/Lewis-Book.pdf 1061. Lewis, N. S., (2013). An integrated, systems approach to the development of solar fuel generators. Electrochemical Society Interface, Summer 2013, pp. 43-49

1062. Lewis, N. S., (2016). Research opportunities to advance solar energy utilization. Review summary (p. 353) and review, Science, v. 351, Issue 6271, DOI: 10.1126/science.aad1920

1063. Lewis, N. S., and Nocera, D. G., (2012). Powering the planet: chemical challenges in solar energy utilization. PNAS, 103(43): 15729-15735.

1064. Lewis, P. E., (2013). Gas to liquids: Beyond Fischer Tropsch. SPE 1657-MS, online: http://zeep.com/wp-content/uploads/2013/11/WhitePaper-Phil-E-Lewis-ZEEP.pdf 1065. Lewis, W. W., (2004). *The Power of Productivity: Wealth, Poverty, and the Threat to Global Stability*. University of Chicago Press.

1066. Li, F.-F., Liu, S., Cui, B., Lau, J., Stuart, J., Wang, B., and Licht, S., (2015). A one-pot synthesis of hydrogen and carbon fuels from water and carbon dioxide. Adv. Energy. Mats., 5: 1401791

1067. Li, H., Opgenorth, P. H., Wernick, D. G., Rogers, S., Wu, T.-Y., Higashide, W., Huo, Y.-H., Cho, K. W., and Liao, J. C., (2012). Integrated electromicrobial conversion of $CO_2$ to higher alcohols. Science, 335: 1596.

1068. Li, H., and Oloman, C., (2005). The electroreduction of carbon dioxide in a continuous reactor. J. Appl. Eletrochem., 35: 955-965, 1069. Li, H., and Oloman, C., (2006). Development of a continuous reactor for the electro-reduction of carbon dioxide to formate—Part 1: Process variables. J. Appl. Electrochem., 36: 1105-1115.

1070. Li, H., and Oloman, C., (2007). Development of a continuous reactor for the electro-reduction of carbon dioxide to formate—Part 2: scale-up. J. Appl. Electrochem., 37: 1107-1117.

1071. Li, L., and Kiran, E., (1988). Interaction of supercritical fluids with lignocellulosic materials. Ind. Eng. Chem. Res., 27(7): 1301-1312.

1072. Li, X., and Fang, Z.-m., (2014). Current status and technical challenges of $CO_2$ storage in coal seams and enhanced coalbed methane recovery. Int. J. Coal Sci. Technol., 1(1): 93-102

1073. Li, X., and Ellsworth, D., (2014). Geomechanics of $CO_2$ enhanced shale gas recovery. J. Nat. Gas Sci. Eng., 26" 1607-1619

1074. Li, Y., Sponholz, P., Nielsen, M., Junge, H., and Beller, M., (2015). Iridium-catalyzed hydrogen production from monosaccharides, disaccharide, cellulose, and lignocellulose. ChemSusChem, 8(5): 804-808

1075. Li, Z., Duan, W. W., Feng, Y. C., (2007). Study on the enzyme unhairing in carbon dioxide supercritical fluids. Leather Sci. Eng., 17: 45-51.

1076. Li, Z., Fei, B., and Jiang, Z., (2014). Bamboo organic acid pretreatment. BioResources, 9(3): 5652-5661.

1077. Liang, Y., (2003). Carbon dioxide capture from flue gas using regenerable sodium-based sorbents. MSc Theis, Louisians State Univ., online: http://etd.lsu.edu/docs/available/etd-0702103-151700/unrestricted/Liang_thesis.pdf 1078. Liang, Y., Harrison, D. P., Gupta, R. P., Green, D. A., and McMichael, W. J., (2004). Carbon dioxide capture using dry sodium-based sorbents. Energy & Fuels, 18(2): 569-575.

1079. Liao, J. C., (2013). Towards a biological replacement of petroleum. Chapter 1, pp. 1-17, in: A. Katardjieff et al., (ed.), *Developments in Biotechnology and Bioprocessing*. ACS Symp. Ser., v. 1125

1080. Liao, S.-K., and Chang, P.-S., (2012) Literatures on dyeing technique of supercritical fluid carbon dioxide. Am. J. Anal. Chem., 3: 923-930.

1081. Licht, S., Douglas, A., Ren, J., Carter, R., Lefler, M., and Pint, C. L., (2016). Carbon nanotubes produced from ambient carbon dioxide for environmentally sustainable lithium-ion and sodium-ion battery. ACS Central Science, DOI: 10.1021/acscentsci.5b00400

1082. Liebscher, A., Moller, F., Bannach, A., Kohler, S., Wiebach, J., Schmidt-Hattenberger, C., Weiner, M., Pretschner, C., Ebert, K., and Zemke, J., (2013). Injection operation and operational pressure-temperature monitoring at the $CO_2$ storage pilot site Ketzin, Germany—Design results recommendations. Intl. J. Greenhouse Gas Control, 15: 163-173.

1083. Liew, F. M., Kopke, M., and Simpson, S. D., (2013). Gas fermentation for commercial biofuels development. Chapter 5, pp. 125-173, in: Z. Fang, (ed.), *Liquid, Gaseous and Solid Biofuels—Conversion Techniques*. Inchopen, online: http://cdn.intechopen.com/pdfs-wm/43690.pdf 1084. Lignite Energy Council, (2015). North Dakota's energy innovation reneaissance: Allam Cycle for ND lignite. Slide deck presentation, online: http://www.energynd.com/wp-content/uploads/2012/04/ND-Energy-Innovation-Renaissance-Jones.pdf 1085. Lim, X., (2015). How to make the most of carbon dioxide. Nature 526: 628-630, online: http://www.nature.com/news/how-to-make-the-most-of-carbon-dioxide-1.18653

1086. Lima, L. F., Cardozo-Filho, L., Arroyo, P. A., Marquez-Alvarez, H., and Antunes, O. A. C., (2005). Metal (salen)-catalyzed oxidation of limonene in supercritical $CO_2$. React. Kinet. Catal. Lett., 84(1): 69-77.

1087. Linde, (2010). Miniature factories from the sea: $CO_2$ as a basis for the production of bioethanol using blue-green algae. Linde Technology #1/10, online: http://www.the-linde-group.com/internet.global.thelindegroup.global/en/images/Linde%20Technology_1_2010_engl4_10183.pdf 1088. Linde, (2012). Gas application for the pulp and paper industry. Linde online report: http://www.lindeus.com/internet.lg.lg.usa/en/images/gas_applications_pulp_paper_industry138_82243.pdf See also: http://www.linde-gas.com/en/industries/pulp_and_paper/index.html 1089. Linde, (2014). Vapormate™ introduction: Biosecurity treatments 2014. Methyl Bromide and alternatives conference. Online: http://www.biosecurity.govt.nz/files/regs/treat/dolman-vapormate-introduction-biosecurity-treatments-2014.pdf 1090. Linde, (2014b). Carbon dioxide management for enhanced plant growth: learning from terrestrial plants to full solutions for algae biofuels. Linde slide deck presentation, Sep. 30, 2014, San Diego, Calif., online: http://www.algaebiomass.org/wp-content/gallery/2012-algae-biomass-summit/2010/06/T2_Tue_1500_MMostertz1.pdf http://www.researchgate.net/publication/272439289_Carbon_Dioxide_Management_for_Enhanced_Plant_Growth_Learning_from_Terrestrial_Plants_to_Full_Solutions_for_Algae_Biofuels 1091. Linde, (2013a). Linde to build the world's largest $CO_2$ purification and liquefaction plant. Online press release: http://www.linde.pt/en/news_and_media/press_releases/news_20130822.html 1092. Linde, (2013b). Linde takes over joint venture OCAP in Netherlands as sole shareholder. Online press release: http://www.the-linde-group.com/en/news_and_media/press_releases/news_130311_2.html 1093. Linde, (undated). Neutralization of alkaline wastewater: a simple and environmentally friendly process using carbon dioxide. Online brochure: http://lindeplin.hr/dat/neutralisationwastewater_e.pdf 1094. Linde, (undated). VAPORMATE (ETF+$CO_2$) Fumigation for soft and sensitive materials. Online: http://www.linde-gas.com/en/products_and_supply/fumigants/vapormate.html Also: http://cropscience.linde-gas.com/internet.lg.cropprotection.global/en/images/Vapormate_Application_guide903_119147.pdf 1095. Linde, (undated). The ultimate combination for freshness. MAPAX modified atmosphere packaging. Online: http://www.linde-gas.com/internet.global.lindegas.global/en/images/MAPAX%20brochure17_4683.pdf 1096. Liquid Air Energy Network, (undated). The cold economy: a liquid air solution for the developing world. LAEN, report online: http://staticl.squarespace.com/static/54858edee4b0b0ce78c2e93c/t/5486c967e4b04af8a8c94e56/1418119527760/Cold-Economy-Liquid-Air.pdf 1097. Lirong, D., Cheng, D., Wang, J., Rubondo, E. N. T., Kasande, R., Byakagaba, A., and Mugisha, F., (2004). Geochemical significance of seepage oils and bituminous sandstones in the Albertine Graben, Uganda. J. Petrol. Geol., 27(3): 299-312.

1098. Lirong, D., Wang, J., Chen, D., Ran, X., Rubondo, E. N. T., Kasande, R., Byakagaba, A., and Mugisha, F., (2004). Geological conditions and petroleum exploration potential of the Albertine Graben of Uganda. Acta Geologica Sinica, 78(4): 1002-1010

1099. Lisitsin, D., Hasson, D., and Semiat, R., (2008). The potential of $CO_2$ stripping for pretreating brackish and wastewater desalination feeds. Desalination, 222: 50-58

1100. Liska, M., and Al-Tabbaa, A., (2012). Performance of magnesia cements in porous blocks in acid and magnesium environments. Adv. Cement Res., 24(4): 221-232.

1101. Liska, M., and Al-Tabbaa, A., (2009). Ultra-green construction: reactive magnesia masonry products. Proc. of ICE, Waste and Water Resource Management, 162: 185-196.

1102. Liska, M., and Al-Tabbaa, A., (2008). Performance of magnesia cements in pressed masonry units with natural aggregates: production parameters optimized. Contruction and Building materials, 22: 1789-1797.

1103. Liska, M., Al-Tabbaa, A., Carter, K., and Fifield, J., (2012). Scaled-up commercial production of reactive magnesia cement pressed masonry units. Part I: production. Proc. ICE, Construction Mats., 165(CM4): 211-223.

1104. Liska, M., Al-Tabbaa, A., Carter, K., and Fifield, J., (2012). Scaled-up commercial production of reactive magnesia cement pressed masonry units. Part II: performance. Proc. ICE, Construction Mats., 165(CM4): 225-243.

1105. Liska, M., Vandeperre, L. J., and Al-Tabba, A., (2008). Influence of carbonation on the properties of reactive magnesia cement-based pressed masonry units. Adv. Cement Res., 20: 53-64.

1106. Littlewood, J., Turnbull, C., and Murphy, R. J., (2013). Techno-economic potential of bioethanol from bamboo in China. BiJ., otech. For Biofuels, 6: 173-186.

1107. Litynski, J., Vikara, D., Tennyson, M., and Webster, M., (2014). Using $CO_2$ for advanced coalbed methane recovery and storage. CBM Review, June 2014, online: https://www.netl.doe.gov/File%20Library/Research/Carbon-Storage/Project-Portfolio/CBM-June-2014.pdf 1108. Liu, C.-J., and Mallinson, R. G., (2003). *Utlization of Greenhouse Gases*. ACS Symposiuym Series, Book 852, American Chemical Society, pp. 424.

1109. Liu, J., and Hu, Q., (2013). *Chlorella*: Industrial production of cell mass and chemicals. Chapter 16, pp. 329-337 in: A. Richmond and Q. Hu, *Handbook of Microalgal Culture*, Blackwell.

1110. Liu, J., Zeng, X., Cheng, M., Yun, J., Jing, Z., and Jin, F., (2012). Reduction of formic acid to methanol under hydrothermal conditions in the presence of Cu and Zn. Bioresource Technol., 114: 658-662.

1111. Liu, K., Zhou, R., Wang, B., Chen, K., Shi, L.-Y., Zhu, J.-D., and Mi, M.-T., (2013). Effect of green tea on glucose control and insulin sensitivity: a meta-analysis of 17 randomized controlled trials. Am. J. Clin. Nutr., 98(2): 340-348.

1112. Liu, M., Tian, H.-L., Wu, J.-H., Cang, R.-R., Wang, R.-X., Qi, X.-Q., Xu, Q., and Chen, X.-H., (2015). Relationship between gene expression and the accumulation of catechin during spring and autumn in tea plants (*Camellia sinensis* L.) Hort. Res., 2: 15011; doi:10.1038/hortres.2015.11

1113. Liu, Q., Wu, L., Jackstell, R., and Beller, M., (2015). Using carbon dioxide as a building block in organic synthesis. Nature Comms., 5:5933, DOI: 10.1038/ncomms6933

1114. Liu, Y., Chen, S., Quan, X., and Yu, H., (2015). Efficient electrochemical reduction of carbon dioxide to acetate on nitrogen-doped nanodiamond. J. Am. Chem. Soc., 137: 11631-11636.

1115. Llgadas, G., Ronda, J. C., Galia, M., and Cadiz, V., (2010). Plant oils as platform chemicals for polyurethane synthesis: current state of the art. Biomacromolecules, 11(11): 2825-2835.

1116. Lliros Dupre, M., (2009). Diversity, dynamics and activity of mesophilic Archea in stratified freshwater lagoons. Implications for biogeochemical cycles. PhD Thesis, University of Girona (Catalonia, Spain), online: http://dugi-doc.udg.edu/bitstream/handle/10256/4546/tmld.pdf?sequence=1

1117. Loeve, D., Neele, F., Hendriks, C., and Koorneel, J., (2013). D08: Transport and storage economics of CCS networks in the Netherlands: Analysis of the international CCS business cases around the Noth Sea (Phase 2). CATO-2 report, online: https://www.globalccsinstitute.com/publications/transport-and-storage-economics-ccs-networks-netherlands 1118. Logan, B. E., and Rabaet, K., (2012). Conversion of wastes into bioelectricity and chemicals by using microbial electrochemical technologies. Science, 337: 686-690

1119. Lohaus, T., Scholz, M., Koziara, B. T., Benes, N. E., and Wessling, M., (2015). Drying of supercritical carbon dioxide with membrane processes. J. Supercrit. Fluids, 98(3): 137-149

1120. Lohner, S. T., Deutzmann, J. S., Logan, B. E., Leigh, J., and Spormann, A. M., (2014). Hydrogenase-independent uptake and metabolism of electrons by the archaeon *Methanococcus maripaludis*. ISME J,m 8: 1673-1681

1121. Lombolt, N., (undated). The use of carbon dioxide anaesthesia before slaughter. Online: http://www.butina.eu/fileadmin/user_upload/images/articles/cabon_dioxide.pdf 1122. Lopes, C., (2015a). Industrialization: The good road ahead. Pp. 45-51 in, E. Zedillo, O. Cattaneo and H. Wheeler (eds.), *Africa at a Fork in the Road: taking Off or Disappointment Once Again*? Yale Center for the Study of Globalization.

1123. Lopes, C., (2015b). Three factors that make African industrialization different. Online video: https://www.youtube.com/watch?v=w7hNrTNYo 1124. Lopez, C., (2014). Powering Africa's industrialization and agricultural revolution with renewable energies. Our Planet/UNEP, June 2014, pp. 5-51.

1125. Lopez-Periago, A. M., Pacciani, R., Garcia-Gonzalez, C., Vega, L. F., and Domingo, C., (2010). A breakthrough technique for the preparation of high-yield precipitated calcium carbonate. J. Supercrit. Fluids., 52: 298-305.

1126. Lou, Z., Chen, C., Huang, H., and Zhao, D., (2006). Fabrication of Y-junction carbon nanotubes by reduction of carbon dioxide with sodium borohydride. Diamond and Related Materials, 15: 1540-1543.

1127. Lou, Z., Chen, C., Zhang, Y. F., Wang, W., and Qian, Y. T., (2003a). Diamond formation by reduction of carbon dioxide at low temperature. J. Am. Chem. Soc., 125: 9302-9303.

1128. Lou, Z., Chen, Q., Wang, W., Qian, Y., and Zhang, Y., (2003b). Growth of large diamond crystals by reduction of magnesium carbonate with metallic sodium. Angew. Chem. Intl. Ed., 42(37): 4501-4503.

1129. Lou, Z., Chen, C., Zhang, Y. F., Qian, Y. T., and Wang, W., (2004). Synthesis of large-size diamonds by reduction of dense carbon dioxide with alkali metals (K, Li). J. Phys. Chem. B 108: 4239-4241

1130. Lovley, D. R., (2015). Electrobiocommodities from carbon dioxide: enhancing microbial electrosynthesis with synthetic electromicrobiology and system design. Slide deck presentation, DOE Wastewater Workshop, Mar. 19, 2015, online: http://energy.gov/sites/prod/files/2015/04/f21/fcto_beto_2015_wastewaters_workshop_lovley.pdf 1131. Lovley, D. R., (2012). Electromicrobiology. Ann. Rev. Microbiol., 66: 391-409.

1132. Lovley, D. R., (2011). Reach out and touch someone: potential impact of DIET (direct interspecies energy transfer) on anaerobic biogeochemistry, bioremediation and bioenergy. Revs. Environ. Sci. Bio/Technol., 10: 101-105

1133. Lovley, D. R., (2010). Powering microbes with electricity: direct electron transfer from electrodes to microbes. Environmental Microbiology Reports, 3(1): 27-35.

1134. Lovley, D. R., and Malvankar, N. S., (2015). Seeing is believing: novel imaging techniques help clarify microbial nanowire structure and function. Environmental Microbiology, 17(7): 2209-2215, online: http://onlinelibrary.wiley.com/doi/10.1111/1462-2920.12708/epdf 1135. Lovley, D. R., and Nevin, K. P., (2013). Electrobiocommodities: powering microbial production of fuels and commodity chemicals from carbon dioxide with electricity. Curr. Opinion Biotechnol., 24(3): 385-390

1136. Lovley, D. R., and Nevin, K. P., (2011). A shift in the current: new applications and concepts for microbe-electrode electron exchange. Curr. Opin. Biotechnol., 22(3): 441-448

1137. Lowenstein, T. K., and Demicco, R. V., (2006). Elevated Eocene atmospheric $CO_2$ and its subsequent decline. Science, 313: 1928.

1138. Lu, B., Liu, L., Zhen, X., Wu, X., and Zhang, Y., (2010). Anti-tumor activity of triterpenoid-rich extract from bamboo shavings (*Caulis bamfusae* in *Taeniam*). African J. Biotech., 9(38): 6430-6436.

1139. Lu, Q., Rosen, J., and Jiao, F., (2015). Nanostructured metallic electrocatalysts for carbon dioxide reduction. ChemCatChem, 7: 38-47.

1140. Lu, Q., Rosen, J., Zhou, Y., Hutchings, G. S., Kimmel, Y., Chen, J. G., and Jiao, F., (2014). A selective and efficient electrocatalyst for carbon dioxide reduction. Nature Comms., 5:3242, DOI: 10.1038/ncomms4242

1141. Lu, X., (2014). Flexible integration of the $sCO_2$ Allam cycle with coal gasification for low-cost emission-free electricity generation. 8 Rivers Capital slide eeck presentation, GTC (Gasification Technologies Council) 2014, 28 Oct. 2014, online: http://www.gasification-syngas.org/uploads/eventLibrary/2014_11.2_8_Rivers_Xijia_Lu.pdf 1142. Lu, X., and Darensbourg, D. J., (2012). Cobalt catalysts for the coupling of $CO_2$ and epoxides to provide polycarbonates and cyclic carbonates. Chem. Soc. Rev., 41: 1462-1484.

1143. Lu, X., Leung, D. Y. C., Wang, H., Leung, M. K. H., and Xuan, J., (2014). Electrochemical reduction of carbon dioxide to formic acid. ChemElectroChem, 1(5): 836-849.

1144. Lu, Y., Jiang, Z.-y., Xu, S.-w., and Wu, H., (2006). Efficient conversion of $CO_2$ to formic acid by formate dehydtogenase immobilized in a novel alginate-silica hybrid gel. Catalysis Today, 115(1-4): 263-268. ChemElectroChem, 1(5): 836-849.

1145. Luca, O. R., and Fenwick, A. Q., (2015). Organic reactions for the electrochemical and photochemical production of chemical fuels from $CO_2$—the reduction chemistry of carboxylic acids and derivatives as bent $CO_2$ surrogates. J. Photochem. Photobiol. B, S1011-1344(15) 00138-4. doi: 10.1016/j.jphotobiol.2015.04.015

1146. Ludewig, F., Sonnewald, U., et al., (1998). The role of transient starch in acclimatization to elevated atmospheric $CO_2$. FEBS Letters, 429: 147-151.

1147. Lundquist, T. J., Woertz, I. C., Quinn, N. W. T., and Benemann, J. R., (2010). A realistic technology and engineering assessment of algae biofuel production. Energy Biosciences Institute, U. C. Berkeley, online report: http://www.energybiosciencesinstitute.org/media/AlgaeReportFINAL.pdf 1148. Luo, C., Wang, X., Gao, G., Wang, L., Li, Y., Sun, C., (2013). Identification and quantification of free, conjugate and total phenolic compounds in leaves of 20 sweetpotato cultivars by HPLC-DAD and HPLC-ESI-MS/MS. Food Chem., 141: 2697-2706.

1149. Luterbacher, C. E. S., and Luterbacher, J. S., (2015). Break it down! How scientists are making fuel out of plants. Frontiers for young minds, July 2015, v. 3, article 10, online: www.journal.frontiersin.org/article/10.3389/frym.2015.00010/pdf 1150. Luterbacher, J. S., Alonso, D. M., and Dumesic, J. A., (2015a). Targeted chemical upgrading of lignocellulosic biomass to platform molecules. Green Chem., 16: 4816-4838.

1151. Luterbacher, J. S., Alonso, M., Rand, J. M., Questell-Santiago, Y. M., Yeap, J. H., Pfleger, B. F., Dumesic, J. A., (2015b). Solvent-enabled nonenzymatic sugar production from biomass for chemical and biological upgrading. ChemSusChem, 8(8): 1317-1322.

1152. Luterbacher, J. S., Rand, J. M., Alonso, D. M., Han, J., Youngquist, J. T., and Maravelias, C. T., (2014). Nonenzymatic sugar production from biomass using biomass-derived γ-valeroactone. Science, 343: 277-280.

1153. Luterbacher, J. S., Tester, J. W., ad Walker, L. P., (2012a). High-solids biphasic $CO_2$—$H_2O$ pretreatment of lignocellulosic biomass. Biotech. Bioeng., 107(3): 451-460.

1154. Luterbacher, J. S., Tester, J. W., ad Walker, L. P., (2012b). Producing concentrated solutions of monosaccharides using biphasic $CO_2$—$H_2O$ mixtures. Energy & Environmental Sci., 5(5): 6990-7000, DOI: 10.1039/c2ee02913h 1155. Luterbacher, J. S., Tester, J. W., ad Walker, L. P., (2010). Tow-temperature stage biphasic $CO_2$—$H_2O$ pretreatment of lignocellulosic biomass at high solid loadings. Biotech. Bioeng., 109(6): 1499-1507.

1156. Luu, M. T., Milani, D., Bahadori, A., and Abbas, A., (2015). A comparative study of $CO_2$ utilization in methanol synthesis with various syngas production technologies. J. $CO_2$ Utilization, 12: 62-76.

1157. Lyu, L., Zeng, X., Yun, J., Wei, F., and Jin, F., (2014). No catalyst addition and highly efficient dissociation of $H_2O$ for the reduction of $CO_2$ to formic acid with Mn. Environ. Sci. Technol., 48: 6003-6009.

1158. Lyu, L., Jin, F., Zhong, H., Chen, H., and Yao, G., (2015). A novel approach to reduction of $CO_2$ into methanol by water splitting with aluminum over a copper catalyst. RSC Adv., 5: 31450-31453.

1159. Ma, S., Lan, Y., Perez, G. M. J., Moniri, S., amd Kenis, P. J. A., (2014). Silver supported on titania as an active catalyst for electrochemical carbon dioxide reduction. ChemSusChem, 7: 866-874.

1160. Maail, R. S., Umemura, K., Aizawa, H., and Kawai, S., (2011). Curing and degradation processes of cement-bonded particleboard by supercritical $CO_2$ treatment. J. Wood Sci., 57: 302-307

1161. MacAdam, S., and Anderson, R., (2007). Not just rocket science. TCE (The Chemical Engineer), October 2007, pp. 36-37, online: https://www.tcetoday.com/~/media/Documents/TCE/Articles/2007/796/796oxyfuel.pdf 1162. MacAdam, S., Biebuyck, C., Anderson, R., and Pronske, K., (2007). Coal-based oxy-fuel system evaluation and combustor development. Conference paper: $24^{th}$ Annual International Pittsburgh Coal Conference, Johannesburg, SA, Sep. 10-11, 2007, online: http://www.tu-freiberg.de/~wwwiec/conference/conf07/pdf/P14P.pdf 1163. Madan, K., Shukla, D. S., Tripathi, R., Tripathi, A., and Dwivedi, H. D., (2014). Effect of elevated $CO_2$ over sugarcane crop. Am. Int'l. J. Res. Formal, Applied and Natural Sciences, 14-219: 37-38

1164. Maddison, A., (2001). *The World Economy: A Millenial Prespective*. OECD, Paris.

1165. Maddison, A., (2005). *Growth and Interaction in the World Economy: The Rise of Modernity*. AEI, Washngton, D.C., pp. 95.

1166. Maddison, A., (2007). *Contours of the World Economy 1-2030 AD: Essays in Macro-Economic History*. Oxford University Press. Pp. 418

1167. Maddison, A., (2008). The West and the Rest in the World Economy: 1000-2030: Maddisonian and Malthusian interpretations. World Economics, 9(4): 75-99.

1168. Maeda, H., Ikarashi, M., Fukushima, N., Kobayashi, H., and Sato, K., (2015). Possibility of bioelectrochemical conversion of carbon dioxide into methane in depleted oil fields. Conference paper: SPE-176954-MS, Society of Petroleum Engineers Asia Pacific Unconventional Resources Conference and Exhibition, 9-11 November, Brisbane, Australia.

1169. Maersk Oil, (2013). Trigen: a CCUS game changer. Maersk Oil slide deck presentation, online: http://www.co2conference.net/wp-content/uploads/2014/01/8-Maersk-and-TriGenCCUS.pdf 1170. Maersk Oil, (2012). Maximize recovery: fast track $CO_2$ EOR technology implementation in the post easy-oil era (Bob Alford) & panel discussion. ADIPEC conference, "knowledge series highlights," corporate publication online: http://www.thegulfintelligence.com/uploads/Publications/Maersk%20Oil_FINAL.pdf 1171. Maersk Oil and CES, (undated). The oxyfuel combustion process. Information sheet, online: http://www.maerskoil.com/Lists/NewsAttachments/MaerskOilacquiresZeroEmissiontechnologyrights/CES%20Oxyfuel%20combustion%20process%20factsheet.pdf 1172. Maher, K., (2014). Demand for ginseng root boosts prices, tempts poachers. Wall Street Journal, Sep. 17, 2014, online: http://www.wsj.com/articles/demand-for-ginseng-boosts-prices-tempts-poachers-1410971637

1173. Maheswaran, S., Bhuvaneshwari, B., Palani, G. S., Iyer, N. R., and Kalaiselvam, S., (2013). An overview on the influence of nano silica in concrete and a research initiative. Res. J., Recent Sci., 2(ISC-2012): 17-24.

1174. Maisto, M., (2011). Rediscovering Amaranth, the Aztec superfood. Forbes, Dec. 5, 2011, online: http://www.forbes.com/sites/michellemaisto/2011/12/05/meet-amaranth-quinoas-ancient-superfood-cousin/

1175. Maj, G./YLec Consultants, (2009). Exploitation of Lake Kivu Gas Resource. Consequences of the re-injection of degassed water into the resource zone. GMW292. Online: www.dataenvironnement.com/kivu2011/rapylec.pdf 1176. Makaryan, I., Sedov, I., and Savchenko, V., (2015). Platinum group metal-catalysed carbonylation as the basis of alternative Gas-To-Liquids processes. Jahnson Matthey Yech. Rev., 59(1): 14-25.

1177. Making Lewes, (undated). Eco-Industrial parks & industrial ecology. Online: http://makinglewes.org/tag/eco-industrial-parks/
1178. Makowa, N./NAFED, (undated). Why carbon dioxide ($CO_2$) in fire suppression systems? Online: http://www.nafed.org/whyco2
1179. Mamlouk, D., and Gullo, M., (2013). Acetic acid bacteria: physiology and carbon sources oxidation. Indian J. Microbiol., 53(4): 377-384
1180. Manan, Z. A., Siang, L. C., Mustapa, A. N., (2009). Development of a new process for palm oil refining based on supercritical fluid extraction technology. Ind. &E=Eng. Chem. Res., 48(11): 5420-5426.
1181. Mangi, P., (2013). Direct utilization in Kenya: a case of a geothermal spa and demonstration center at Olkaria. Presentation paper, Short Course VIII on Exploration for Geothermal Resources, UNU-GTP, KenGen and GDC, at Lake Bogoriavand Lake Naivasha, Kenya, Oct. 31-Nov. 22, 2013, online: http://www.os.is/gogn/unu-gtp-sc/UNU-GTP-SC-17-0904.pdf
1182. Mantell, C., Casas, L., Rodriguez, M., de la Ossa, E. M., (2013). Supercritical fluid extraction. Chapter 4, pp. 79-100 in S. Raramaswamy et al. (eds.), *Separation and Purification Technologies in Biorefineries*. Wiley
1183. Mantra Energy Alternatives, (undated). ERC and MFRC technologies. Corporate brochure, online: http://mantraenergy.com/wp-content/uploads/brochure.pdf
1184. Marsai, A., Celma, P. J., Cot, J., Cequier, M., (2000). Supercritical $CO_2$ extraction as a clean degreasing process in the leather industry. J. Supercrit. Fluids, 16: 217-223.
1185. Marsal, A., Celma, P. J., Cot, J., and Cequier, M., (2000). Supercritical $CO_2$ extraction as a clean degreasing process in the leather industry. J. Supercrit. Fluids, 16: 217-233.
1186. Marshall, J., (2014). Springtime for the artificial leaf. Nature, news Jun. 4, 2015, online: http://www.nature.com/news/solar-energy-springtime-for-the-artificial-leaf-1.15341
1187. Martin, A., and Cocero, M. J., (2008). Micronization processes with supercritical fluids: fundamentals and mechanisms. Adv. Drug Delivery Revs., 60: 339-350.
1188. Martin, A., Varona, S., Navarrete, A., and Cocero, M. J., (2010). Encapsulation and co-precipitation processes with supercritical fluids: applications with essential oils. Open Chem. Eng. J., 4: 31-41
1189. Martin, M., (2016). Optimal year-round production of DME from $CO_2$ and water using renewable energy. J. $CO_2$ Util., 13: 105-113
1190. Martindale, B. C., and Compton, R. G., (2012). Formic acid electrosynthesis from carbon dioxide in a room temperature ionic liquid. Chem. Comms., 48(52): 6487-6489.
1191. Marxer, D., Furier, P., Scheffe, J., Geerlings, H., Falter, F., Batteiger, V., Sizmann, A., and Steinfeld, A., (2015). Demonstration of the entire production chain to renewable kerosene via solar thermochemical splitting of $H_2O$ and $CO_2$. Energy Fuels, 29(5): 3241-3250.
1192. Masdar/Al Reyadah (undated). CCUS project. Online fact sheet 268. http://www.masdar.ae/assets/downloads/content/268/factsheet-ccus.pdf
1193. Margarido, F., Vieceli, N., Durao, F., Guimaraes, C., and Nogueira, C. A., (2014). Minero-metallurgical process for lithium recovery from pegmatitic ores. Comunicacoes Gelogicas, 101(11): 795-798, online: www.l-neg.pt/download/9655/41_2904_ART_CG14_ESPECIAL_II.pdf
1194. Masel, R., Ni, R., Liu, Z., Chen, Q., Kutz, R., Nereng, L., Lutz, D., and Lewinski, K., (2014). Energy Procedia, 63: 7959-7962.
1195. Maslbo, M., and He, Q., (2008). Major mango polyphenols and their significance to human health. Comprehensive Revs. Food Sci. Food Safety, 7: 309-319.
1196. Maslin, E., (2014). A $CO_2$ EOR solution. OE Digital (Offshore Engineer), Feb. 7, 2014, online: http://www.oedigital.com/pipelines/item/4972-a-carbon-dioxide-eor-solution
1197. Mattessen, R., Fransaer, J., Binnemans, K., and De Viss, D. E., (2014). Electrocarboxylation: towards sustainable and efficient synthesis of valuable carboxylic acids. Beilstein J. Org. Chem., 10: 2484-2500.
1198. Mattos, L. M., Moretti, C. L., and Ferreira, M. D., (2012). Modified Atmosphere Packaging for Perishable Plant Products. Chapter 7, pp 95-110, in: Polypropylene, Dr. Fatih Dogan (Ed.), ISBN: 978-953-51-0636-4, InTech, Available from: http://www.intechopen.com/books/polypropylene/modified-atmosphere-for-perishable-plant-products
1199. Mauney, J. R., Kimball, B. A., Pinter, P. J. Jr., LaMorte, R. L., Lewin, K. F., Nagy, J., and Hendrey, G. R., (1994). Growth and yield of cotton in response to a free-air carbon dioxide enrichment (FACE) environment. Agric. Forest Meteorol., 70(1-4): 49-67.
1200. Maurya, D. P., Singla, A., and Negi, S., (2015). An overview of key pretreatment processes for biological conversion of lignocellulosic biomass to bioethanol. 3 Biotech, 5(5): 597-609.
1201. Maverick Synfuels, (undated). Brochure: Maverick Oasis small-scale methanol plants. Online: http://www.mavericksynfuels.com/wp-content/uploads/2013/07/Maverick-Oasis-Brochure.pdf
1202. Maverick Synfuels, (2014). Maverick synfuels introduces modular GTL methanol plants. Biodiesel magazine, Sep. 23, 2014, online: http://www.biodieselmagazine.com/articles/186199/maverick-synfuels-introduces-modular-gtl-methanol-plants
1203. May, C. Y., Lau, H., et al., (2009). Value addition from crude palm oil—integrated production of palm biodiesel, phytonutrients and other value-added products. MBOM Information Series, #469/MPOB TT No. 428, online: http://www.palmoilworld.org/PDFs/Biodiesel/11-TT-428_biodiesel.pdf
1204. May, M. M., Lewerenz, H. J., Lackner, D., Dimroth, F., and Hannappel, T., (2015). Efficient direct solar-to-hydrogen conversion bu in situ interface transformation of a tandem structure. Nature Communications, DOI:: 10.1038/ncomms9286
1205. Mazzotti, M., (2011). $CO_2$ capture and storage systems. ETHZ slide deck presentation online: http://www.up.ethz.ch/education/carbon_mitigation/c-mitigation_ccs_mazzotti_marl2.pdf
1206. Mazzotti, M., et al., (2005). Mineral carbonation and industrial uses of carbon dioxide. Chapter 7, pp. 319-336, in: *Carbon Capture and Storage: Special Report of the Intergovernmental Panel on Climate Change*. Cambridge University Press, pp. 431
1207. McClung, A., Brun, K., and Chordia, L. (2014). Technical and economic evaluation of supercritical oxy-combustion for utility scale power generation. SWRI slide deck presentation, online: http://www.swri.org/4org/d18/sCO$_2$/papers2014/systemConcepts/40PPT-McClung.pdf
1208. McCoy, M., (2015). The elusive dream of tire recycling. Chemical & Engineering News, ACS.org, online: http://cen.acs.org/articles/93/i16/Elusive-Dream-Tire- Recycling.html?type=paidArticleContent; http://doc-slide.net/environment/the-elusive-dream-of-tire-recycling.html 1209. McKenna, P., (2015). From greenhouse gas to the Dreamliner, nanofibers offer new life for $CO_2$. Inside Climate News, Aug. 19, 2015, online: http://insideclimatenews.org/news/19082015/greenhouse-gas-dreamliner-nanofibers-offer-new-life-co2-carbon-geoengineering 1210. McKenzie, L. C., Thompson, J. E., Sullivan, R., and Hutchison, J. E., (2004). Green chemical processing in the teaching laboratory: a convenient liquid $CO_2$ extraction of natural products. Green Chem., 6: 355-358.

1211. McLellan, B. C., Corder, G. D., and Ali, S. H., (2013). Sustainability of rare earths—an overview of the state of knowledge. Minerals, 3: 304-317.

1212. McQuaid, J., (2011). The secrets behind your flowers: chances are the bouquet you're about to buy came from Columbia. What's behind the blooms? Smithsonian Magazine, February, 2011, online: http://www.smithsonianmag.com/people-places/the-secrets-behind-your-flowers-53128/

1213. Medina-Gonzalez, Y., Camy, S., and Condoret, J.-S., (2012). Cellusosic materials as biopolymers and supercritical $CO_2$ as a green process: chemistry and applications. Int. J. Sustainable Engineering, 5(1): 47-65.

1214. Medina-Gonzalez, Y., Camy, S., and Condoret, J.-S., (2014). Sc$CO_2$/green solvents: biphasic promising systems for cleaner chemicals manufacturing. ACS Sustainable Chem. Eng., 2(12): 2523-2636

1215. Medina-Ramos, J., DiMeglio, J. L., and Rosenthal, J., (2014). Efficient reduction of $CO_2$ to CO with high current density using in situ prepared Bi-based materials. J. Am. Chem. Soc., 136(23): 8361-8376.

1216. Medina-Ramos, J., Pupillo, R. C., Keane, T. P., DiMeglio, J. L., and Rosenthal, J., (2015). Efficient conversion of $CO_2$ to CO using tin and other inexpensive and easily prepared post-transition metal catalysts. J. Am. Chem. Soc., 137(15): 5012-5027.

1217. Meena, V. D., Dotaniya, M. L., Coumar, V., Rajendiran, S., Kundu, A. S., and Rao, A. S., (2014). A case for silicon fertilization to improve crop yields in tropical soils. Proc. Natl. Acad. Sci., India, Sect. B Biol. Sci., 84(3): 505-518.

1218. Melzer, L. S., (2007).The history and development of $CO_2$ EOR in the Permian Basin with an emphasis on pipelines. Slide deck presentation online: https://www.u-wyo.edu/eori/_files/co2conference07/steve_melzer_%20historyofpbco2eor.pdf 1219. Menelaou, E., Kachatryan, A., Losso, J. N., Cavalier, M., and la Bonte, D., (2006). Lutein content in sweetpotato leaves. HortScience, 41(5): 1269-1271.

1220. Menhert, V., (2016). Heisser rip—Geysire, maare und krater in der Eifel. Die Welt, online: http://www.welt.de/reise/article4790288/Heisser-Tipp-Geysire-Maare-und-Krater-in-der-Eifel.html 1221. Mercer, S. M., (2012). The development of $CO_2$-switchable technologies for separation of organic compounds. PhD Thesis, Queen's University, Kingston, Ontario, Canada. Online: https://qspace.library.queensu.ca/handle/1974/7710

1222. Messer, (2013). $CO_2$ applications for drinking water production, process water treatment and waste water treatment. Corporate slide deck presentation, online: http://www.messer.be/nieuws/$CO_2$-Seminar/$CO_2$-applications-in-water-treatment.pdf 1223. Meterc, D., Petermann, M., and Weidner, E., (2007). Extraction of green tea and drying with a high pressure spray process. Hemijska Industrija, 61(5): 222-227.

1224. Meterc, D., Petermann, M., and Weidner, E., (2008). Drying of aqueous green tea extracts using a supercritical fluid spray process. J. Supercrit. Fluids, 45(2): 253-259.

1225. Methanex, (2015). Methanex investor presentation. August 2015, online: https://www.methanex.com/sites/default/files/investor/MEOH%20Presentation%20-%20August%202015.pdf 1226. Metropolitan Food Clusters, (2013). Metropolitan Food Clusters: sustainable food for $21^{st}$ century global urban society. Alterra/Wageningen University (www.metropolitanfoodclusters.nl) slide deck presentation, online: This is the html version of the file https://www.wageningenur.nl/web/file?uuid=8b1 ed9eb-c86b-4d9f-9d96-d59f2e4e7dbc&owner=0d9ebc4c-9f7f-4d28-a894-1c49961 ab829

1227. Meyer, J. P., (2007). Summary of carbon dioxide enhanced oil recovery ($CO_2$EOR) injection well technology. American Petroleum Institute. Online: http://www.api.org/~/media/files/ehs/climate-change/summary-carbon-dioxide-enhanced-oil-recovery-well-tech.pdf 1228. Meyer, T. J., Papanikolas, J. M., and Heyer, C. M., (2011). Solar fuels and next generation photosynthesis: the UNC-CH energy frontier research center. Catal. Lett., 141: 1-7

1229. Meylan, F. D., Moreau, V., and Erkman, S., (2015). $CO_2$ utilization in the perspective of industrial ecology: an overview. J. $CO_2$ Utilization, http://www.sciencedirect.com/science/article/pii/S2212982015300020

1230. Meyn (undated). Multistage $CO_2$ stunning system. Meyn company online information: https://www.meyn.com/en-GB/322/multistage-co2-stunning-system.html 1231. Meysami, M., and Tzoganakis, C., (2009). Thermomechanical devulcanization of tire rubber crumb with supercritical $CO_2$: devulcanizationized rubber properties. Waterloo University slide deck presentation online: https://uwaterloo.ca/institute-polymer-research/sites/ca.institute-polymer-research/files/uploads/files/ipr_mohammedmeysami.pdf 1232. Meysoumi, M., (2012). Tyromer Inc., a socially responsible, environmentally sustainable and financially viable solution to the global scrap tire problem. Slide deckresentation for the competition, "Recycling Idol," online (in): http://riccentre.ca/wp-content/uploads/2012/12/Dec6-Recycling-Idol.pdf 1233. Mezue, B. C., Christensen, C. M., and van Bever, D., (2015). The power of market creation: how innovation can spur development. Foreign Affairs, January/February 2015, pp. 69-76.

1234. Middleton, R. S., et al., (2015). Shale gas and non-aqueous fracturing fluids: opportunities and challenges for supercritical $CO_2$. Applied Energy, 147: 500-509.

1235. Miglietta, F., Bindi, M., Vaccari, F. P., Schapendonk, A. H. C. M., Wolf, J., and Butterfield, R. E., (2000). Crop ecosystem responses to climatic change: root and tuberous crops. Chapter 9, pp. 189-212, in K. R. Reddy and H. F. Hodges, (eds.): Climate Change and Global Crop Productivity.

1236. Mihalcea, C., (2015). Industrial waste gases and the circular economy. LanzaTech slide deck presentation, Advanced Bioeconomy Feedstocks Conference, New Orleans, La., USA, June 2015, online: http://www.ascension-publishing.com/ABFC15/Mihalcea-LanzaTech.pptx 1237. Mikkelsen, M., Jorgensen, M., and Krebs, F. C., (2010). The teraton challenge. A review of fixation and transformation of carbon dioxide. Energy Environ. Sci., 3: 43-81.

1238. Milanesio, D., (1998). (In Spanish) Injection of carbon dioxide to control insects in hermetic plastic bags. Batchelor Thesis, Balacare Agricultural Sciences Faculty, UNMdP, Balacare, pp. 52.

1239. Milani, D., Khalilpour, R., Zahedi, G., and Abbas, A., (2015). A model-based analysis of $CO_2$ utilization in methanol synthesis plant. J. $CO_2$ Util., June edition, pp. 12-22.

1240. Millat, T., Janssen, H., Bahl, H., Fischer, R.-J., and Wolkenhauer, O., (2011). The pH-induced metabolic shift from acidogenesis to solventogenesis in *Chlostridium acetobutylicium*—from experiments to models. Beilstein Institut conference paper, Experimental Standard Conditions of Enzyme Charaterization, Septemenber 12-16, 2011, Rudesheim/Rhein, online: http://www.beilstein-institut.de/escec2011/Proceedings/Millat/Millat.pdf 1241. Millat, T., Janssen, H., Bahl, H., Fischer, R.-J., and Wolkenhauer, O., (2013). Integrative modeling of pH-dependent enzyme activity and transcriptomic regulation of the acetone-butanol-ethanol fermentation of *Chlostridium acetobutylicium* in continuous culture. Microbial Biotechnol., 6: 526-539, online: http://www.ncbi.nlm.nih.gov/pmc/articles/PMC3918155/pdf/mbt0006-0526.pdf 1242. Millero, F. J., (2013). *Chemical Oceanography*, $4^{th}$ edition, CRC Press, pp. 591

1243. Millet, T., (2015). The springs of Sarasota Spa State Park. Online: https://saratogaspringsguide.com/the-springs-of-saratoga-spa-state-park-written-by-trent-millet-of-the Middleton, R. S., et al., (2015). Shale gas and non-aqueous fracturing fluids: opportunities and challenges for supercritical $CO_2$. Applied Energy, 147: 500-509.

1244. Milner, C. P., Trengove, R. D., Bignell, C. M., and Dunlop, P. J., (1997). Supercritical $CO_2$ extraction of the essential oils of Eucalypts: a comparison with other methods. Pp. 141-158, in: H. F. Linskens and J. F. Jackson, (eds.), *Plant Volatile Analysis*, Volume 19, of the series: *Modern Methods of Plant Analysis*, Springer.

1245. Min, X., and Kanan, M. W., (2015). Pd-catalyzed electrohydrogenation of carbon dioxide to formate: high mass activity at low overpotential and identification of the deactivation pathway. J. Am. Chem. Soc., 137(14): 4701-4708.

1246. Mineral Information Service, (1959). Soda ash industry of Owens Lake. State of California Mineral Information Service, v. 12, issue 10. 8pp. Online: http://cgsdigitalarchive.conservation.ca.gov/cdm/compoundobject/collection/p16780co112/id/14102/rec/17

1247. Minh, N. Q., and Mogensen, M. B., (2013). Reversible solid oxide fuel cell technology for green fuel and power technology. Electrochemical Society Interface, Winter 2013, pp. 55-62.

1248. Ministry of Trade and Industry, Rwanda (2011). National Industrial Policy. Ministry of Trade and Industry, Government of Rwanda. Online: http://www.minicom.gov.rw/fileadmin/minicom_publications/policies/Industrial_Policy-2.pdf 1249. Mira, B., Blasco, M., Berna, A., and Subirats, S., (1999). Supercritical $CO_2$ extraction of essential oil from orange peel. Effect of operation conditions on the extract composition. J. Supercrit. Fluids, 14(2): 95-104

1250. Mire, M.-A., Milayah, B. B., Delmas, M., and Bravo, R., (2005). Formic acid/acetic acid pulping of banana stem (*Musa Cavendish*). Appita Journal: Journal of the Australiand and New Zealand Pulp and Paper Industry, 58(5): 393-396.

1251. Mishra, M., (2015, editor). *Handbook of Encapsulation and Controlled Release*. CRC Press, pp. 1512

1252. MIT, (2015a). Val Verde fact sheet: Commercial EOR using anthropogenic carbon dioxide. Online: https://sequestration.mit.edu/tools/projects/val_verde.html 1253. MIT, (2015b). Statoil Mongstad Fact Sheet: Carbon dioxide capture and storage project. Online: https://sequestration.mit.edu/tools/projects/statoil_mongstad.html 1254. MIT, (2015a). Val Verde fact sheet: Commercial EOR using anthropogenic carbon dioxide. Online: https://sequestration.mit.edu/tools/projects/val_verde.html 1255. MIT, (2015b). Statoil Mongstad Fact Sheet: Carbon dioxide capture and storage project. Online: https://sequestration.mit.edu/tools/projects/statoil_mongstad.html 1256. Miyatani, R., and Amato, Y., (2002). Bio-$CO_2$ fixation with formate dehydrogenase from *Saccharomyces cerevisiae* and water-soluble zinc porphyrin by visible light. Biotechnol. Lett., 24: 1931-1934.

1257. Mo, L., Deng, M., Tang, M., and Al-Tabbaa, A., (2014). MgO expansive cement and concrete in China: past, present and future. Cement and Concrete Res., 57: 1-12.

1258. Modestino, M. A., and Haussener, S., (2015). An integrated device view on photo-electrochemical solar-hydrogen generation. Ann. Re. Chem. Biomol. Eng., 6: 13-34.

1259. Mogensen, M. B., (2013). Electrochemical reduction of $CO_2$ and $H_2O$ into fuels: cell types and kinetic barriers. Technical University of Denmark (DTU), slide deck presentation, Sep. 9, 2013, online: http://orbit.dtu.dk/en/publications/electrochemical-reduction-of-co2-and-h2o-into-fuels-cell-types-and-kinetic-barriers(e94a3c6c-0a6f-4c36-861b-4a4d8d00b881).html 1260. Mohamed, A., and Eastoe, J., (2011). How can we use carbon dioxide as a solvent? School Science Review, 93(343): 73-80.

1261. Mohammadpoor, M., and Torabi, F., (2014). Experimental investigation of $CO_2$ utilization as an injection solvent in vapour extraction (VAPEX) process. Energy Procedia, 63: 7867-7877

1262. Mohammadpoor, M., and Torabi, F., (2015a). Extensive experimental investigation of the effect of drainage height and solvent type on the stabilized rainage rate in vapour extraction (VAPEX) process. Petroleum, 1: 187-199.

1263. Mohammadpoor, M., and Torabi, F., (2015b). Comprehensive experimental study and numerical simulation of vapour extraction (VAPEX) process in heavy oil systems. Can, J. Chem. Eng., 93(11): 1929-1940.

1264. Moller, D., (2012). SONNE: solar-based man-made carbon cycle and the carbon dioxide economy. Ambio, 41: 413-419.

1265. Molot, L. A., Watson, S. B., Creed, I. F., Trick, C. G., McCabe, S. K., Verschoor, M. J., Sorichetti, R. J., Powe, C., Venkiteswaran, J. J., and Schiff, S. L., (2014). A novel model for cyanobacteria bloom formation: the critical role of anoxia and ferrous iron. Freshwater Biology, 59: 1323-1340

1266. Monetro, G. A., Smith, C. B., Hendrix, W. A., and Butcher, D. L., (2000). Supercritical fluid technology in textile processing: an overview. Ind. Eng. Chem. Res., 39(12): 4806-4812.

1267. Monge, B., (2014). Design of supercritical carbon dioxide centrifugal compressors. PhD Thesis, University of Seville, Spain, online: https://www.researchgate.net/publication/263714020_Design_of_supercritical_carbon_dioxide_centrifugal_compressors 1268. Monkman, S., (2012). CarbonCure Technologies: simply better concrete. Slide deck presentation, 6 Sep. 2012, online: https://www.concretesdc.org/meetings/past_meeting&sessions/session32/6.pdf 1269. Monkman, S., and Niven, R., (2010). Integration of carbon dioxide curing into precast concrete production. CarbonCure Conference Paper, online: http://conf.tac-atc.ca/english/resourcecentre/readingroom/conference/conf2010/docs/k3/niven.pdf 1270. Monkman, S., and Shao, Y., (2010). Integration of carbon sequestration into precast concrete. Can. J. Civ. Eng., 37: 302-310.

1271. Monney, A., Barsch, E., Sponholz, P., Junge, H., Ludwig, R., and Beller, M., (2014). Base-free hydrogen generation from methanol using a bi-catalytic system. Chem. Comms., 50: 707-709.

1272. Monnin, C., Chavagnac, V., Boulart, C., Menez, B., Gerard, M., Gerard, E., Pisapia, C., Quemeneur, M., Erauso, G., Postec, A., Guentas-Dombrowski, L., Payri, C., and Pelletier, B., (2014). Fluid chemistry of the low temperature hyperalkaline hydrothermal system of Prony Bay (New Caledonia). Biogeosciences, 11: 5687-5706

1273. Montes, A., Gordillo, M. D., Pereyra, C., de la Ossa, M., (2011). Chapter 20, pp. 461-480, in: H. Nakajima (ed.), *Mass Transfer—Advanced Aspects*. InTech, pp. 824.

1274. Moodley, M., Schorn, P. M., Walthew, D. C., and Masinga, P., (2002). Optimizing the carbonation process. Proc. S. Afr. Sugar Technol. Assn., 76: 469-476.

1275. Moore, M. E., (2005). A case for a $CO_2$-EOR market. $CO_2$ Global/Falcon ES slide deck presentation, Dec. 13, 2005, Houston Tex., online: www.beg.utexas.edu/pttc/ . . . /moore1205.pdf 1276. Mohan, A. R., Turaga, U., Subbaraman, V., Shembekar, V., Elsworth, D., and Pisupati, S. V., (2015). Modeling the $CO_2$-based enhanced geothermal system (EGS) paired with integrated gasification combined cycle (IGCC) for symbiotic integration of carbon dioxide sequestration with geothermal heat integration. Int. J. Greenhouse Gas Control, 32: 197-212

1277. Mohanraj, R., and Sivanskar, S., (2015). Sweet potato (*Ipomoea batatas* [L.] Lam)—a valuable medicinal food: a review. J. Medicinal Food, 17(7): 733-741.

1278. Moran, D., (2010a). Carbon dioxide degassing in fresh and saline water. I: Degassing performance of a cascade column. Aquaculture Engineering, 43: 29-36

1279. Moran, D., (2010b). Carbon dioxide degassing in fresh and saline water. II: Degassing performance of an air-lift. Aquaculture Engineering, 43: 120-127

1280. Morgan, B., Wilson, S. A., Madsen, I. C., and Gozukara, Y. M., (2015). Increased thermal stability of nesquahonite ($MgCO_3 \cdot 3H_2O$) in the presence of humidity and $CO_2$: implications for low-temperature $CO_2$ storage. Int. J. Greenhouse Gas Control, 39: 366-376

1281. Morreale, B., and Shi, F., (2015). *Novel Materials for Carbon Dioxide Mitigation Technology*. Elsevier.

1282. Moret, S., Dyson, P. J., and Laurenczy, G., (2014). Direct synthesis of formic acid from carbon dioxide by hydrogenation in acidic media. Nature Comms., 5, article 4017, DOI: 10.1038/ncomms5017

1283. Morgan, R., Nelmes, S., Gibson, E., and Brett, G., (2015). Liquid air energy storage—analysis and first results from a pilot scale demonstration plant. Applied Energy, 137: 845-853

1284. Mortensen, L. M., (1987). Review: $CO_2$ enrichment in greenhouses. Crop responses. Scientia Horticulturae, 33(1/2): 1-25.

1285. Mosavat, N., (2014). Utlization of carbonated water injection (CWI) as a means of improved oil recovery in light oil systems: pore-scale mechanisms and recovery evaluation. University of Regina PhD thesis, online: http://ourspace.uregina.ca/handle/10294/5816

1286. MPS (undated). Butina $CO_2$ gas stunning system. Meat Processing Systems corporate information online: http://www.mps-group.nl/en/mps-red-meat-slaughtering/pig-slaughter-lines/butina-co2-gas-stunning-system/

1287. Mu, A., Boreham, C., Leong, H. X., Haese, R. R., and Moreau, J. W., (2014). Changes in the deep subsurface microbial biosphere resulting from a field-scale $CO_2$ geosequestration experiment. Front. Microbiol., 5: 209, DOI: 10.3389/fmicb.2014.00209

1288. Mu, A., and Moreau, J. W., (2015). The geomicrobiology of $CO_2$ geosequestration: a focused review on prokaryotic community responses to field-scale $CO_2$ injection. Frontiers in Microbiology, 6, article 263, online: http://journal.frontiersin.org/article/10.3389/fmicb.2015.00263/abstract 1289. Muggeridge, A., Cockin, A., Webb, K., Frampton, H., Collins, I., Moulds, T., and Salino, P., (2015). Recovery rates, enhanced oil recovery and technological limits. Phil. Trans. R. Soc. A., 372: 20120320 http://dx.doi.org/10.1098/rsta.2012.0320

1290. Muller, G., (undated). Mineralquellen des Paderborner Landes—Spiegel der geologisch-hydrologischen Vielfalt und Basis fur unterschiedliche Entwicklungen und Nutzungen. Geographische Kommission fur Westfalen. Online: https://www.lwl.org/westfalen-regional-download/PDF/S034_Mineralquellen.pdf 1291. Munhoven, G., (2013a). Mathematics of the total alkalinity-pH equation-pathway to robust and universal solution algorithms: the SolveSAPHE package v1.0.1. Geosci. Model Dev., 6: 1367-1388

1292. Munhoven, G., (2013b). Supplementary material to: "Mathematics of the total alkalinity-pH equation-pathway to robust and universal solution algorithms." Online at: http://orbi.ulg.ac.be/handle/2268/155792

1293. Munin, A., and Edwards-Levy, F., (2011). Encapsulation of natural polyphonic compounds: a review. Pharmaceutics, 3: 793-829.

1294. Munshi, P., and Bhaduri, S., (2009). Supercritical $CO_2$: a twenty-first century solvent for the chemical industry. Curr. Sci., 97(1): 63-71.

1295. Murcillo, J. F., and Bolanos, G., (2013). Separation of vitamin-E isomers from palm oil FAME's by supercritical desorption. Iberoamerican Conference on Supercritical Fluids (Columbia), online conference paper: www.nupeg.ufrn.br/prosciba/prosciba2013/Papers/T2-88.pdf 1296. Murga, R., Ruiz, R., Beltran, S., and Cabezas, J. L., (2000). Extraction of natural phenols and tannins from grape seeds by using supercritical mixtures of carbon dioxide and alcohol. J. Agric. Food Chem., 48(8): 3408-3412.

1297. Nagai, M., Tani, M., Kishimoto, Y., Lizuka, M., Saita, E., Toyozaki, M., Kamiya, T., Ikeguchi, M., and Kondo, K., (2011). Sweet potato (*Ipomoea batatas* L.) leaves 1297. suppressed oxidation of low density lipoprotein (LDL) in vitro and in human subjects. J. Clin. Biochem. Nutr., 48(3): 203-208.

1298. Nagata, K., (2015). Lab photosynthesis begins to bloom. Japan Times, Apr. 12, 2015, online: http://www.japantimes.co.jp/news/2015/04/12/national/science-health/lab-photosynthesis-begins-to-bloom/#.VIyWG-Mad_rN 1299. Nakhle, C., (2015). Uganda oil sector: a mixed picture. Crystol Energy report, online: http://www.crystolenergy.com/uganda-oil-sector-mixed-picture/

1300. Narayanaswamy, N., Faik, A., Goetz, D. J., and Gu, T., (2011). Supercritical carbon dioxide pretreatment of corn stover and switchgrass for lignocellulosic ethanol production. Bioresource Technol., 102: 6995-7000.

1301. Natex, (undated). Website (www.natex.at) materials: (i) Company brochure: http://www.natex.at/download/Folder.pdf; (ii) Sc—$CO_2$ rice treatment product example: http://www.natex.at/download/Rice-Taiwan.pdf; (iii) Rice treatment plant in Taiwan: http://www.natex.at/indusextractionplants.html 1302. National Academy of Sciences (USA), (2001). *Carbon Management: Implications for R&D in the Chemical Sciences and Technology*. National Academies Press.

1303. Natu, M. V., and Every, H. A., (2014). Supercritical $CO_2$ encapsulation of cosmetic ingredients: novel methods for tailoring ingredients for the cosmetics industry. H&PC: Household and Personal Care Today, 9(3, May/June): 42-45.

1304. Ndimubanzi, E., (2014). Etat de lieux de la recherché petroliere et gaziere dans le Lac Kivu. Slide deck presentation for the Deuxieme Edition De La Conference Miniere Sur La Bonne Gouvernance Et La Transparance, Goma, 24-25 Mar. 2014, online: http://www.mines-rdc.cd/fr/documents/Expose_cd_ndimubanzi.pptx 1305. Nduire, J., (2015). Chinese firm CJIC to build Kenya's largest solar park. Construction Business Review, Jun. 14, 2015, online: http://www.constructionkenya.com/2747/china-garissa-kenya-solar-plant/

1306. Neal, C., and Stanger, G., (1984). Calcium and magnesium hydroxide precipitation from alkaline groundwaters in Oman, and their significance to the process of serpentinization. Min. Mag., 48: 237-241

1307. Nederhoff, E., (2004). Carbon dioxide enrichment: fuels & figures Practical Hydroponics & Greenhouses, May/June 2004, pp. 50-59, online: http://www.crophouse.co.nz/crophouse/pdf/CO2%20&%20Plant%20Growth%20-Nederhof-PH&G-may04-proofs.pdf 1308. Neele, F., Quinquis, H., Read, A., m Wright, M., Lorsong, J., Poulussen, D. F., (2014). $CO_2$ storage development: status of the large European CCS projects with EEPR funding. Energy Procedia, 63: 6053-6066.

1309. Nelson, T. O., Coleman, L. J. I., Green, D. A., and Gupta, R. P., (2009). The dry carbonate process: carbon dioxide recovery from power plant flue gas. Energy Procedia, 1: 1305-1311.

1310. NET Power, (2015). NET Power: truly clean, cheaper energy. California Energy Commission $CO_2$ Capture Technology Workshop, Apr. 16, 2015, online: http://www.energy.ca.gov/research/notices/2015-04-16_workshop/presentations/NET_Power_presentation_CEC_16Apr15_FINAL.pdf 1311. NET Power, (2013). The NET power process. NET Power, slide deck presentation, London, 21 Feb. 2013, online: http://www.apgtf-uk.com/files/workshops/13thWorkshop2013/36RobbKirchner.pdf 1312. NETL/DOE, (undated). $CO_2$ utilization focus area (with $CO_2$ utilization map diagram). NETL/DOE website, accessed Feb. 4, 2016: http://www.netl.doe.gov/research/coal/carbon-storage/research-and-development/co2-utilization 1313. NETL/DOE (USA), (2010). Carbon dioxide enhanced oil recovery: untapped domestic energy supply and long-term carbon storage solution. National Energy Technology Laboratory/Department of Energy Report, online: https://www.netl.doe.gov/file%20library/research/oil-gas/small_CO2_EOR_Primer.pdf 1314. NETL/DOE (USA), (2015). National Energy Technology Laboratory/Department of Energy (USA) project factsheet, online: https://www.netl.doe.gov/publications/factsheets/project/Proj282.pdf 1315. Neubeck, A., Duc, N. T., Bastviken, D., Crill, P., and Holm, N. G., (2011). Formation of $H_2$ and $CH_4$ by weathering of olivine at temperatures between 30 and 70° C. Geochem. Trans., 12(6), DOI: 10.1186/1467-4866-12-6, online: http://www.geochemicaltransactions.com/content/12/1/6

1316. Neuman, W., (2010). New way to help chickens cross to the other side. New York Times, Oct. 21, 2010, online: http://www.nytimes.com/2010/10/22/business/22chicken.html?_r=0

1317. Neven, L. G., (2003). Physiological effects of physical postharvest treatment on insects. HorTechnology, 13(2): 272-275.

1318. Neville, A., (2009). Top plants: Royal Pride Holland commercial greenhouse cogeneration plant, Middenmeer, North Holland Province, Netherlands. Power Magazine, Sep. 1, 2009, online: http://www.powermag.com/top-plantsroyal-pride-holland-commercial-greenhouse-cogeneration-plant-middenmeer-north-holland-province-netherlands/?printmode=0

1319. Nevin, K. P., Hensley, S. A., Franks, A. E., Summers, Z. M., Ou, J., Woodard, T. L., Snoeyenbos-West and Lovley, D. R., (2011). Electrosynthesis of organic compounds from carbon dioxide is catalyzed by a diversity of acetogenic microoganisms. Appl. Environmental Microbiol., 77(9): 2882-2886

1320. Nevin, K. P., Woodard, T. L., Franks, A. E., Summers, Z. M., and Lovley, D. R., (2010). Microbial electrosynthesis; feeding microbes electricity to convert carbon dioxide and water to multicarbon extracellular organic compounds. mBio, 1(2): e000103-10, online: http://mbio.asm.org/content/1/2/e00103-10.full.pdf+html 1321. Nextant, (2009). Green propylene: process technology, Nextant, Chemsystems PERP Program, report PERP07/08S11, online: http://thinking.nexant.com/sites/default/files/report/field_attachment_abstract/200901/0708S11_abs.pdf 1322. Nguyen, K., Barton, P., and Spencer, J. S., (1991). Supercritical carbon dioxide extraction of vanilla. J. Supercrit. Fluids, 4(1): 40-46.

1323. Nielsen, K. A., Argyropoulos, J. N., Clark, R. C., and Goad, J. D., (1993). Technical development of the supercritical fluid spray process for application of coatings. Conference paper, Third Annual Advanced Coatings Technology Conference, online: http://infohouse.p2ric.org/ref/29/28142.pdf 1324. Nielsen, M., Alberico, E., Baumann, W., Drexler, H.-J., Junge, H., Gladiali, S., and Beller, M., (2013). Low-temperature aqueous-phase methanol dehydrogenation to hydrogen and carbon dioxide. Nature, 495: 85-89.

1325. Nieses, T., and Turchi, C., (2014). A comparison of supercritical carbon dioxide power cycle configurations with a emphasis on CSP applications. Energy Procedia, 49: 1187-1196

1326. NIPCC, (2014). Biological effects of carbon dioxide enrichment. Chapter 7, pp. 361 and following in: Climate Change Reconsidered II Biological Impacts, online: http://www.nipccreport.org/reports/2009/pdf/Chapter%207.pdf.

1327. Nirmala, C., and Bisht, M. S., (2015). Bamboo: a prospective ingredient for functional food nutraceuticals. $10^{th}$ World Bamboo Conference, Korea, conference paper, online: http://www.worldbamboo.net/wbcx/Sessions/Theme%20Food%20Pharmaceuticals/Nirmala%20C.,%20M.%20S.%20Bisht.pdf 1328. Nishiyama, P., Alvarez, M., and Vieira, L. G. E., (1992). Quantitative analysis of stevioside in the leaves of *Stevia rebaudiana* by near infared reflectance spectroscopy. J. Food Sci. Ag., 59(3): 277-281

1329. NISR, (2014), Statistical Yearbook 2014. National Institute of Statistics of Rwanda. http://statistics.gov.rw/publications/statistical-yearbook-2014

1330. Nogueira, C., (2014). Recuperacao de litio de minerios Portugueses de lepidolite. Mini-Forum CYTED-UBEROEKA "Valorizatcao de Pegmatitos Litiniferos (Litio)", 26 May 2011, slide deck presentation online (in Portuguese): http://repositorio.lneg.pt/handle/10400.9/1408

1331. Noothout, P., Wiersma, F., Hurtado, O., Macdonald, D., Kemper, J., and van Alphen, K., (2014). $CO_2$ pipeline infrastructure—lessons learnt. Energy Procedia, 63: 2481-2492.

1332. Norazharuddin, S. A., Azizan, A., Kamarudin, H., (2015). Ilmenite chlorination: usage of gaseous carbon tetrachloride at relatively lower temperatures. Adv. Mats. Res., 1087: 389-393.

1333. Nordic Mining, (undated). We are developing a new innovative process for environmentally friendly extraction of alumina from anorthosite with low waste streams and substantial consumption of $CO_2$. Online: http://www.nordicmining.com/alumina-from-anorthosite/category8.html 1334. Nordic Mining, (2011). Nordic Mining: progress for production of alumina from anorthosite. Nordic Mining press release, Oct. 20, 2011, online: http://www.nordicmining.com/nyhetsarkiv-oaax-vis-nyhet/category293.html?itemId=425604

1335. Norhidayah, S., Baharin, B. S., Hamed, M., and Zaidul, I. S. M., (2012). Squalene recovery from palm fatty acid distillate using supercritical fluid extraction. Int. Food Res. J., 19(4): 1661-1667.

1336. Norikane, A., Takamura, T., Morokuma, M., and Tanaka, M., (2013). In vitro growth and single leaf photosynthetic response of Cymbidium plantlets to super-elevated $CO_2$ under cold cathone fluorescent lamps. Plant cell Reports 29: 273-282.

1337. Norstebo, S., Midthun, K. T., Bjorkvall, T. H., and Kolbeinsen, L., (2012). Use of natural gas with high $CO_2$ content in an integrated industrial park. ISIJ International, 52(8): 1439-1446. Online: https://www.jstage.jst.go.jp/article/isijinternational/52/8/52_1439/pdf 1338. North, M., (2012). Synthesis of cyclic carbonates from epoxides and carbon dioxide using bimetallic aluminium(salen) complexes. ARKIVOC 2012.

1339. North, M., Pasquale, R., and Young, C., (2010). Synthesis of cyclic carbonates from epoxides and $CO_2$. Green Chemistry, 12: 1514-1539.

1340. Northrop, P. S., and Valencia, J. A., (2009). The CFZ™ process: a cryogenic method for handling high-$CO_2$ and $H_2S$ gas reserves and facilitating geosequestration of $CO_2$ and acid gases. Energy Procedia, 1: 171-177

1341. Noureldin, M. M. B., Elbashir, N. O., Gabriel, K. J., and El-Halwagi, M. M., (2015). A process integration approach to the assessment of $CO_2$ fixation through dry reforming. ACS Sustainable Chem. Eng., 3: 625-636.

1342. Novomer, (2013). $CO_2$-based polycarbonate polyols as strength enhancers in flexible foams. Slide deck presentation online: http://www.novomer.com/sites/default/files/PPC%20in%20Flex%20Foams.pdf 1343. Novomer, (2014). CO chemicals platform. Slide deck "confidential" overview presentation, online: http://www.renewable-waste.com/biofuels/pdf/Novomer.pdf 1344. Novomer, (2015). Conversion of waste $CO_2$ and shale gas to high value chemicals. Slide deck presentation to US DOE Advanced Manufacturing Office, online: http://energy.gov/sites/prod/files/2015/06/f22/R16-AMO%20RD%20Program%20Review%20Presentation%20May_2015.pdf 1345. Novomer (undated). Our Technology. Online: http://www.novomer.com/our-technology Also: http://www.novomer.com/sites/default/files/PPC%20in%20Flex%20Foams.pdf 1346. Nuhoff-Isakhanyan, G., et al., (2015). Synergy Parks: collaborative strategies to valorize side streams between companies. Case study report. ARBOR, online: http://www.list.lu/fileadmin//files/projects/ARBOR/ARBOR_Synergypark_Case_Study_Report.pdf (and in: http://arbornwe.eu/downloads) And associated slide deck presentation: http://www.izes.de/cms/upload/pdf/ARBOR_15_Nohoff-Isakhanyan_Gohar-Wageningen_Loosvelt_POM_West_Flanders.pdf 1347. Nunes, A. V. M., and Duarte, C. M. M., (2011). Dense $CO_2$ as a solute, co-solute or co-solvent in particle formation processes: a review. Materials, 4: 2017-2041

1348. Nutraceuticals World, (2007). Sweet potato leaf. Oct. 1, 2007, online: http://www.nutraceuticalsworld.com/issues/2007-10/view suppliers-corner/sweet-potato-leaf/

1349. Nybo, S. E., Khan, N. E., Woolston, B. M., and Curtis, W. R., (2015). Metabolic engineering in chemolithoautotrophic hosts for the production of fuels and chemicals. Metabolic Eng., 30: 105-120

1350. OakBio, (2014). Carbon dioxide capture and conversion to chemical products. Prepared by OakBio, Inc., for the California Energy Commission, report CEC-500-2015-031, online: http://www.energy.ca.gov/2015publications/CEC-500-2015-031/CEC-500-2015-031.pdf 1351. Oberon Fuels website (www.OberonFuels.com) and slide deck presentations: http://www.ascension-publishing.com/ABLC-NEXT-2014/Oberon-Boudreaux.pdf, http://www.methanolfuels.org/wp-content/uploads/2013/05/Rebecca-Boudreaux-President-Oberon-Fuels.pdf 1352. Obert, R., and Dave, B. C., (1999). Enzymatic conversion of carbon dioxide to methanol: enhanced methanol production in silica sol-gel matrices. J. Am. Chem. Soc., 121: 12192-12193.

1353. OCAP, (2012) Factsheet. Online: www.ocap.nl/files/Ocap_Factsheet2012_UK.pdf 1354. Ochan, A., and Amusugut, C., (2012). Reservoir characterization for field development, Albertine Graben, East African rift system. Search and Discovery article #20130. Online: http://www.searchanddiscovery.com/documents/2012/20130ochan/ndx_ochan.pdf 1355. OCMOL (undated). Oxidative coupling of methane followed by oligomerization to liquids: towards sustainable production of high quality fuels and petrochemicals.

Ocmal website brochure online: http://www.ocmol.eu/uploads/media/OCMOL_brochure.pdf; Summary video: http://www.ocmol.eu/press-room/the-video.html 1356. O'Connor, W. K., Dahlin, D. C., Rush, G. E., Gerdemann, S. J., Penner, L. R., and Nilsen, D. N., (2005). Final Report: Aqueous Mineral Carbonation: Mineral Availability, Pretreatment, Reaction Parametrics, and Process Studies. DOE/ARC-TR-04-002, online: https://www.netl.doe.gov/File%20Library/Research/Coal/NETLAlbanyAqueousMineralCarbonation.pdf 1357. OECD/IEA, (2015). Storing $CO_2$ through Enhanced Oil Recovery. International Energy Agency report, online: https://www.iea.org/publications/insights/insightpublications/Storing_CO2_through_Enhanced_Oil_Recovery.pdf 1358. Ogura, K., (2013). Electrochemical reduction of carbon dioxide to ethylene: mechanistic approach. J. $CO_2$ Utilization, 1: 43-49.

1359. OIES, (2015). Oil in Uganda: hard bargaining and complex politics in East Africa. Oxford Institute for Energy Studies report, OIES Paper: WPM 60 by Like Patey, online: http://www.oxfordenergy.org/wpcms/wp-content/uploads/2015/10/WPM-601.pdf 1360. Oil in Uganda, (2014). Total to recover more oil with new technology. Online: http://www.oilinuganda.org/features/companies/total-to-recover-more-oil-with-new-technology.html 1361. Olah, G. A., (2013). Towards oil independence through renewable methanol chemistry. Angew. Chem. Intl. Ed., 52(1): 104-107

1362. Olah, G. A., (2005). Beyond oil and gas: the methanol economy. Angew. Chem., 44(18): 2636-2639

1363. Olah, G. A., Goeppert, A., and Surya Prakash, G. K., (2006) *Beyond Oil and Gas: The Methanol Economy*. Wiley-VCH, pp. 304.

1364. Olah, G. A., Goeppert, A., and Surya Prakash, G. K., (2009). Chemical recycling of carbon dioxide to methanol and dimethyl ether: from greenhouse gas to renewable environmentally carbon neutral fuels and synthetic hydrocarbons. J. Org. Chem., 74: 487-498.

1365. Olah, G. A., Goeppert, A., Czaun, M., Mathew, T., May, R. B., and Surya, G. K., (2015). Single step bi-reforming and oxidative bi-reforming of methane (natural gas) with steam and carbon dioxide ($CO-2H_2$) for methanol synthesis: self-sufficient effective and exclusive oxygenation of methane to methanol with oxygen. J. Am. Chem. Soc., 137(27): 8720-8729

1366. Olah, G. A., Surya Prakash, G. K., Goeppert, A., Czaun, M., and Mathew, T., (2013a). Self-sufficient and exclusive oxygenation of methane and its source materials with oxygen to methanol via metgas using oxidative bi-reforming. J. Am. Chem. Soc., 135(27): 10030-10031.

1367. Olah, G. A., Goeppert, A., Czaun, M., and Surya Prakash, G. K., (2013b). Bi-reforming of methane from any source with steam and carbon dioxide exclusively to metgas ($CO-2H_2$) for methanol and hydrocarbon synthesis. J. Am. Chem. Soc., 135(2): 648-650.

1368. Oldenburg, C. M., (2003a). Carbon dioxide as cushion gas for natural gas storage. Energy & Fuels, 17: 240-246

1369. Oldenburg, C. M., (2003b). Carbon sequestration in natural gas reservoirs: enhanced gas recovery and natural gas storage. Proceedings TOUGH Symposium, LBNL, Berkeley, Calif., USA, May 12-14, 2003, online: http://www.osti.gov/scitech/servlets/purl/813580

1370. Oldenburg, C. M., and Benson, S. M., (2001). $CO_2$ injection for enhanced gas production and carbon sequestration. SPE-74367, Conference paper, Society of Petroleum Engineers, Villahermosa, Mexico, 10-12 Feb. 2001, online: http://www.osti.gov/scitech/servlets/purl/790035

1371. Oldenburg, C. M., Pruess, K., and Benson, S. M., (2001). Process modeling of $CO_2$ injection and natural gas reservoirs for carbon sequestration and enhanced gas recovery. Energy & Fuels, 15(2): 293-298

1372. Oliver, T. K., Dlugogorski, B. Z., and Kennedy, E. M., (2014). Biologically enhanced degassing and precipitation of magnesium carbonates derived from bicarbonate solutions. Minerals Engineering, 61: 113-120

1373. Oloman, R., (2009). Carbon recycling: an alternative to carbon capture and storage. District Energy/Fourth Quarter 2009, pp. 25-27, online: http://www.districtenergy-digital.org/districtenergy/2009Q4?pg=67#pg67

1374. Oloman, C., and Li, H., (2008). Electrochemical processing of carbon dioxide. ChemSusChem, 1: 385-391.

1375. Olsson, J., Stipp, S. L. S., and Gislason, S. R., (2014). Element scavenging by recently formed travertine deposits in the alkaline springs from the Omn Semail Ophiolite. Min. Mag., 78(6): 1479-1490

1376. Omae, I., (2012). Recent developments in carbon dioxide utilization for the production of organic chemicals. Coord. Chem. Revs., 256(13-14): 1384-1405.

1377. Omae, I., (2006). Aspects of carbon dioxide utilization. Catalysis Today, 115(1-4): 33-52

1378. Oman, M., Skerget, M., and Knez, Z., (2013). Application of supercritical fluid extraction for the separation of nutraceuticals and other phytochemicals from plant material. Macedonian J. Chem. And Chem. Eng., 32(2): 183-226.

1379. Omenda, P., and Simiyu, S., (2015). Country update report for Kenya 2010-2014. Proc. World Geothermal Congress 2015, Melbourne, Australia, 19-25 Apr. 2015, online: https://pangea.stanford.edu/ERE/db/WGC/papers/WGC/2015/01019.pdf 1380. Onakpoya, I., Spencer, E., Heneghan, C., and Thompson, M., (2014). The effect of green tea on blood pressure and lipid profile: a systematic review and meta-analysis of randomized clinical trials. Nutrition, Metablism & Cardiovascular Disease, 24: 823-836.

1381. Onem, E., Gulumser, G., Renner, M., and Yesil-Celiktas, O., (2015). High pressure vegetable tanning of sheepskins using supercritical carbon dioxide. J. Supercrit. Fluids, 104: 259-264.

1382. Onwaluta, C. I., (2012). Encapsulation of new active ingredients. Ann. Rev. Food Sci and Technol., 3: 183-202.

1383. Opdam, J. J. G., Schoonderbeek, G. G., and Heller, E. M. B., (2005). Closed greenhouse: a starting point for sustainable entrepreneurship in horticulture. Acta Hort., 691: 517-524.

1384. Open Oil, (2012). Crude oil qualities in Uganda. Open Oil online: http://wiki.openoil.net/index.php?title=Crude_Oil_Qualities in Uganda 1385. Orr, J. C., Epitalon, J.-M., and Gattuso, J.-P., (2015). Comparison of ten packages that compute ocean carbonate chemistry. Biogeosciences, 12: 1483-1510

1386. Orr, L., (2015). Quadrennial Technology Review. US Department of Energy slide deck presentation overview, Princeton University, Nov. 20, 2015, online: http://acee.princeton.edu/e-ffiliates/files/2015/05/Orr-Lynn_5-QTR-Princeton-11-20-15.pdf 1387. Ortiz, D. S., Samaras, C., and Molina-Perez, E., (2013). The industrial base for carbon dioxide storange. RAND Technical Report ISBN: 978-O-8330-7867-4, Online: http://www.rand.org/content/dam/rand/pubs/technical_reports/TR1300/TR1300/RAND_TR1300.pdf 1388. Osterdijk, H. and Hoencamp, T. (2012). Lake Kivu: Turning threat into prosperity. TCE, The Chemical Engineer, issue 852, June 2012, pp: 32-35. (http://www.infrassure.com/images/uploads/user/TCE852kivuenergy.pdf)

1389. Oswald, W. J., (1962). The coming industry of controlled photosynthesis. Am. J. Public Health, 52(2): 235-242.

1390. Oswald, W. J., (1988). Micro-algae and waste-water treatment. Chapter 12, pp. 305-328, in: M. A. Borowitzka and L. J. Borowitzka (eds.), *Micro-Algal Biotechnology*. Cambridge University Press 1391. PTRC, (undated). The Weyburn-Midale $CO_2$ Monitoring and Storage Project. Petroleum Technology Research Centre, website section on the Weyburn-Midale Project, online: http://ptrc.ca/projects/weyburn-midale 1392. Padayatchi, S., (2004). Artemisinin content of sc-$CO_2$ derived extracts from *Artemisia annua*. M.Sc thesis, Northwest University, South Africa, online: http://dspace.nwu.ac.za/bitstream/handle/10394/72/padayatchi_s.pdf?sequence=1

1393. Pan, M., Sikorski, J., Kastner, C. A., Akroyd, J., Mosbach, S., Lau, R., and Kraft, K., (2015 preprint for publication in Energy Procedia). Applying industry 4.0 to the Jurong Island Eco-industrial Park. Online: http://como.cheng.cam.ac.uk/preprints/c4e-Preprint-150.pdf 1394. Pan, W., Chang, C. C., Su, T. T., Lee, F., and Fuh, M.-R. S., (1995). Preparative supercritical fluid extraction of pyrethrin I and II from pyrethrum flower. Talenta, 42(11): 1745-1749.

1395. Papoutsakis, E. T., (2015). Reassessing the progress in the production of advanced biofuels in the current competitive environment and beyond: what are the successes and where progress eludes us and why. Ind. Eng. Chem. Res., 54(42): 10170-10182

1396. Parajuli, R., Gerken, J. B., Keyshar, K., Sullivan, I., Sivasankar, N., Teamey, K., Stahl, S. S., and Cole, E. B., (2014). Integration of anodic and cathodic catalysts of earth-abundant materials for efficient, scalable $CO_2$ reduction. Topics Catal., 58(1): 67-66.

1397. Pardossi, A., Tognoni, F., and Incrocci, L., (2004). Mediterranean greenhouse technology. Chronica Horticulturae, 44(2): 28-34.

1398. Park, H. S., (2013). Eco-Industrial Park (EIP) initiative in Korea. Slide deck presentation, Green Industry Conference 2013, Guangzhou, China, 7-9 November. Online: file http://www.unido.org/fileadmin/user_media_upgrade/Media_center/2013/News/Green_Industry_Conference/Hung-Suck_Park_en_.pdf 1399. Park, J., Lee, I., and Moon, I., (2017). A novel design of Liquefied Natural Gas (LNG) regasification power plant integrated with cryogenic energy storage system. Ind. Eng. Chem. Res., 56 (5): 1288-1296

1400. Park, S.-J., Lee, J.-I., and Park, J., (2002). Effects of a combined process of high-pressure carbon dioxide and high hydrostatic pressure on the quality of carrot juice. J. Food Sci., 67(5): 1827-1834.

1401. Parker, M. E., Northrop, S., Valencia, J. A., Fogelsong, R. E., and Duncan, W. T., (2011). CO2 management at ExxonMobil's La Barge Field, Wyo., USA. Energy Procedia, 4: 5455-5470

1402. Parton, T., Bertucco, A., Elvassore, N., and Grimolizzi, L., (2007). A continuous plant for food preservation by high pressure $CO_2$. J. Food Engineering, 79: 1410-1417

1403. Pasche, N., Muvundja, F. A., Schmid, M., Wuest, A., and Muller, B., (2012). Nutrient cycling in Lake Kivu. Chapter 3, pp. 31-46, in: Descy, J-P., Darchambeau, F., Schmid, M., 2012 (editors). *Lake Kivu: Limnology and Biochemistry of a Tropical Great Lake*. Springer.

1404. Pasche, N., Schmid, M., Vazquez, F., Schubert, C. J., Wuest, A., and Kessler, J. D., (2011). Methane sources and sinks in Lake Kivu. J. Geophys. Res., 116: G03006. doi: 10.1029/2011JG001690.

1405. Pashkova, A., and Dittmeyer, R., (2015). Carbon dioxide as an alternative solvent for the direct synthesis of hydrogen peroxide: a review of recent activites. Cataalysis Today, 248: 128-137.

1406. Pasquel, A., Meireles, M. A. A., Marques, M. O. M., and Petenate, A. J., (2000). Extraction of *stevia* glycosides with $CO_2$+water, $CO_2$+ethanol, and $CO_2$+water+ethanol. Brazilian J. Chem. Eng., 17(3): 271-282.

1407. Patel, D., Kellici, S., and Saha, B., (2014). Green process engineering as the key to future process. Processes, 2: 311-332.

1408. Patil, S. A., Gildemyn, S., Pant, D., Zengler, K., Logan, B. E., and Rabaey, K., (2015). A logical data representation framework for electricity-driven bioproduction processes. Biotecnol. Advances, 33: 736-744.

1409. Paudel, A., Jessop, M. J., Stubbins, S. H., Champagne, P., and Jessop, P. G., (2015). Extraction of lipids from microalgae using $CO_2$-expanded methanol and liquid $CO_2$. Bioresource Technol., 184: 286-290.

1410. Paukert, A. N., Matter, J. M., Kelemen, P. B., Shock, E. L., and Havig, J. R., (2012). Reaction path modeling of enhanced in situ $CO_2$ mineralization for carbon sequestration in the peridotite of the Samail Ophiolite, Sultanate of Oman. Chem. Geol., 330/331: 86-100

1411. Pavlechenko, P. D., (2014). Acetic acid from syngas via the BP SaaBre process. HIS Chemical, November 2014 report, online: https://www.ihs.com/products/sricreport-pepreview2014-10-acetic-acid-syngas-saabre.html 1412. Peach, J., and Eastoe, J., (2014). Supercritical carbon dioxide: a solvent like no other. Beilstein J. Organic Chem., 10: 1878-1895.

1413. Pearson, A., (2005). Carbon dioxide—new uses for an old refrigerant. Int. J. Refrig., 28: 1140-1148.

1414. Pearson, R. J., Eisaman, M. D., Turner, J. W. G., Edwards, P. P., Jiang, Z., Kuznetsov, V. L., Littau, K. A., Di Marco, L., and Taylor, S. R. G., (2012). Energy storage via carbon-neutral fuels made from $CO_2$, water, and renewable energy. Proc. IEEE, 100(2): 440-460

1415. Pedersen, T. H., and Schultz, R. H., (2012). Technical and economic assessment of methanol production from biogas. MS Thesis, University of Aalborg, Denmark, online: http://projekter.aau.dk/projekter/files/63472425/Technical_and_Economic_Assessment_of_Methanol_Production_from_Biogas.pdf 1416. Peng, X., Zhou, R., Wang, B., Yu, X., Yang, X., and Mi, M., (2014). Effect of green tea consumption on blood pressure: a meta-analysis of 13 randomized controlled trials. (Nature) Scientific Rpts., DOI: 10.1038/srep06251

1417. Pentacost, A., (2005). *Travertine*. Springer, pp. 446

1418. Perathone, S., and Centi, G., (2014). $CO_2$ recycling: a key strategy to introduce green energy in the chemical production chain. ChemSusChem, 7(5): 1274-1282.

1419. Pereira, C. G., and Meireles, A. A., (2007). Evaluation of global yield, composition, antioxidant activity and cost of manufacturing of extracts from lemon verbena (*Aloysia Triphylla* [L'Herit.] Britton) and mango (*Mangifera indica* L.) leaves. J. Food Process Eng., 30(2): 150-173.

1420. Pereira, I. A. C., (2013). An enzymatic route to $H_2$ storage. Science, 342: 1329-1330.

1421. Perez, J. M., Poston, S. W., and Sharif, Q. J., (1992). Carbonated water imbibition flooding: an enhanced oil 1422. Perez-Fortes, M., Bocin-Dumitriu, A., and Tzimas, E., (2014). $CO_2$ utilization pathways" techno-economic assessment and market opportunities. Energy Procedia, 63: 7968-7975
1423. Perez-Fortes, M., Schoneberger, J. C., Boulamanti, A., and Tzimas, E., (2016). Methanol synthesis using captured $CO_2$ as raw material: techno-economic and environmental assessment. Applied Energy, 161: 718-732.
1424. Perez-Mesa, J. C., Galdeano-Gomez, E., Quiles, M. C. G., (2015). Technology diffusion in agro-cluster: the role of multinational companies in the case of Almeria (Spain). Online: www.eoq.hu/iama/conf/1028_case.pdf
1425. Perre, C., Hans, A. L., Dedieu, M., Gand, O., Saldinari, L., and Dutel, L., (2003). From skin to leather in dense pressurized $CO_2$. In: Proc. ISAF, Versailles, France, online: http://www.isasf.net/fileadmin/files/Docs/Versailles/Papers/PN65.pdf
1426. Persichilli, M., Kacludis, A., Zdankiewicz, E., and Held, T., (2012). Supercritical $CO_2$ power cycle developments and commercialization: why $sCO_2$ can displace steam. Echogen Power Systems LLC, conference paper, Power-Gen India & Central Asis 2012, 19021 April, 2012, New Delhi, India, online: http://www.echogen.com/documents/why-sco2-can-displace-steam.pdf
1427. PETA, (undated). The case for controlled atmosphere killing: a comparative analysis of poultry-slaughter systems. PETA report, online: http://www.mediapeta.com/peta/PDF/CAKreport.pdf
1428. PETA, (undated). The case for controlled-atmosphere-killing. Report overview, online: http://www.peta.org/features/case-controlled-atmosphere-killing/
1429. Peter, L. M., (2015). Photoelectrochemical water splitting. A status assessment. Electroanalysis, 27(4): 864-871
1430. Peters, C., (2012). The future of oxy-fuel systems for $CO_2$ sourcing. Clean Energy Systems slide deck presentation, Dec. 12, 2012, Midland, Tex., Online: http://www.co2conference.net/wp-content/uploads/2012/12/1330-C-Peters-CES-Oxy-Fuel-Systems-12-4-12.pdf
1431. Peters, M., Kohler, B., Kuckshinrichs, W., Leitner, W., Markewitz, P., and Muller, T. E., (2011). Chemical technologies for exploiting and recycling carbon dioxide into the value chain. ChemSusChem, 4: 1216-1240.
1432. Petrovic, Z. S., Wan, X., Bilic, O., Zlatanic, A., Hong, J., Javni, I., Ionescu, M., Milic, J., Degruson, D., (2013). Polyols and polyurethanes from crude algal oil. J. Am. Oil Chem. Soc., 90(7): 1073-1078.
1433. Phan, L. N., (2008). $CO_2$-triggered switchable solvent systems and their applications. PhD Thesis, Queen's University, Kingston, Ontario, Canada. Online: https://qspace.library.queensu.ca/handle/1974/1563
1434. Phan, L., Andreatta, J. R., Horvey, L. K., Edie, C. F., Luco, A.-L., Mirchandani, A., Darensbourg, D. J., and Jessop, P. G., (2008). Switchable-polarity solvents prepared with a single liquid component. J. org. chem., 73: 127-132
1435. Phan, L., Brown, H., White, J., Hodgson, A., and Jessop, P. G., (2009). Soybean oil extraction and separation using switchable or expanded solvents. Green Chem., 11: 53-59.
1436. Philbrook, A., Alissandratos, A., and Easton, C. J., (2013). Biochemical processes for generating fuels and commodity chemicals from lignocellulosic biomass. Chapter 3, pp. 39-64, in: M. Petre, (ed), Environmental Biotechnology—New Approaches and Prospective Applications. INTECH
1437. Pinizzotto, S., (2015). INSG: changes in nickel production capacity on the horizon. Stainless Steel World, March 2015, pp. 1-3, online: http://www.stainless-steel-world.net/pdf/INSG_Changes in Nickel_Production_Capacity_On_The_Horizon.pdf
1438. Plaksina, T., and White, C., (2016). Modeling coupled convection and carbon dioxide injection for improved heat harvesting in geopressured geothermal reservoirs. Geothermal Energy, 4(2): DOI 10.1186/s40517-016-0044-x
1439. Plantagon, (2015). Clever greenhouses for urban farming. Online: http://www.ima.kth.se/utb/MJ 1501/2015/PlantagonSweco.pdf
1440. Plantagon, (undated). Industrial symbiosis. Derscroption of the PlantaSymbioSystem® system. Online: http://plantagon.com/urban-agriculture/industrial-symbiosis
1441. Poehlein, A., et al., (2012). An ancient pathway combining carbon dioxide fixation with the generation and utilization of a sodium ion gradient for ATP synthesis. PLOSone, 7(3) e33439
1442. Pohl, M., Subhani, M. A., and Muller, T. E., (2014). $CO_2$-expanded liquids in the synthesis of high-functionality $CO_2$-based polyols. Book of Abstracts, $7^{th}$ Green Solvents Conference, Dresden, 19-22 Oct. 2014. Lectures: #4, online: http://e-collection.library.ethz.ch/eserv/eth: 1168/eth-1168-02.pdf
1443. Pons, M. J., Camara, A. G., Guri, S., and Riudavets, J., (2010). The use of carbon dioxide in big bags and containers for the control of pest in food products. Conference paper online: http://pub.jki.bund.de/index.php/JKA/article/download/523/1238
1444. Pontaweesap, J., Saradhuldhat, P., and Imsabai, W., (2011). $CO_2$ and $N_2$ fumigation for orchid snail control. J. Int. Soc. SE Asian Ag. Sci. (ISSAAS).
1445. Polygreen Natural Polyols (Malaysia, Palm Oil-based polyurethanes), website: http://www.polygreen.com.my
1446. Popa, O., Babeanu, N. E., Popa, I., Nita, S., and Dinu-Parvu, C. E., (2015). Methods for obtaining and determination of squalene from natural sources. BioMed Research Int., Article ID 367202. http://dx.doi.org/10.1155/2015/367202
1447. Popa, O., Babeanu, N. E., Popa, I., Nita, S., and Popa, O., (2014). Squalene—natural resources and applications. Farmacia, 62(5): 840-862.
1448. Power, I. M., Harrison, A. L., Dipple, G. M., Wilson, S. A., Kelemen, P. B., Hitch, M., and Southam, G., (2013). Carbon mineralization: from natural analogues to engineered systems. Revs. Mineral. And Geochem., 77: 305-360.
1449. Power, I. M., McCutcheon, J., Harrison, A. L., Wilson, S. A., Dipple, GF. M., Kelly, S., Southam, C., and Southam, G., (2014). Strategizing carbon-neutral mines: a case for pilot projects. Minerals, 4: 399-436.
1450. Power Engineering, (2014). Cummins power generation introduces CHP systems for commercial greenhouse growers in U.S., Canada. Power Engineering, Apr. 14, 2014, online: http://www.power-eng.com/articles/2014/04/cummins-power-generation-introduces-chp-systems-for-commercial-greenhouse-growers-in-u-s-canada.html
1451. Porosoff, M. D., Yan, B., and Chen, J. G., (2016). Catalytic reduction of $CO_2$ by $H_2$ for synthesis of CO, methanol and hydrocarbons: challenges and opportunities. Energy Environ. Sci, DOI: 10.1039/C5EE02657A (advance article)

1452. Port of Rotterdam, (undated). Rotterdam energy port. 2-page Factsheet overview, online: https://www.portofrotterdam.com/sites/default/files/Factsheet-Rotterdam-Energy-Port.pdf 1453. Porter, M., (1998). Clusters and the new economics of competition. Harvard Business Review, November-December, 76(6): 77-90.

1454. Powell, D., (2014). East Africa—Disputes, pipelines and wax. Gaffney Cline & Associates slide eck presentation Jun. 18, 2014, online: http://www.gaffney-cline.com/downloads/east_africa_workshop/Disputes%20Pipelines%20%20Wax.pdf 1455. Powerplantccs (undated). Pipeline based transportation. Online: http://www.powerplantccs.com/ccs/tra/tra_pipe.html 1456. Prabowo, B., Susanto, H., Umeki, K., Susanto, H., Yan, M., and Yoshikawa, K., (2015a). Pilot scale autothermal gasification of coconut shell with $CO_2$—$O_2$ mixture. Frontiers in Energy, 9(3): 362-370

1457. Prabowo, B., Aziz, M., Umeki, K., Susanto, H., Yan, M., and Yoshikawa, K., (2015b). Utilization of the rise husk in the $CO_2$-recycling gasification system for the effective implementation of bio-energy with carbon capture and storage (BECCS) technology. Chapter 13, pp. 323-340, in: Advances in $CO_2$ Capture, Sequestration, and Conversion. ACS Symposium Series, v. 1194. ACS.

1458. Prabowo, B., Aziz, M., Umeki, K., Susanto, H., Yan, M., and Yoshikawa, K., (2015c). $CO_2$-recycling biomass gasification system for highly efficient and carbon-negative power generation. In press in: *Advances in $CO_2$ Capture, Separation and Conversion*. ACS 1459. Prabowo, B., Umeki, K., Yan, M., Nakamura, M. R., Castaldi, M. J., and Yoshikawa, K., (2014). $CO_2$-steam mixture for direct and indirect gasification of rice straw in a downdraft gasifier: laboratory-scale experiments and performance prediction. Applied Energy, 1136: 70-679.

1460. Praderio, C., (2015). The ridiculously healthy greens you've never heard of. Feb. 9, 2015. Prevention (magazine), online: http://www.prevention.com/food/healthy-eating-tips/sweet-potato-greens 1461. Prado, J. M. do, Leal, P. F., and Meireles, M. A. de A., (2009). Comparison of manufacturing cost of thyme extract obtained by supercritical fluid extraction and steam distillation. Proc. $9^{th}$ Int. Symp. Supercrit. Fluids, online: http://www.isasf.net/fileadmin/files/Docs/Arcachon/posters/p135-p19%20Prado-Leal-Meireles-Full.pdf 1462. Prakash, G. K. S., (2014). The promise of methanol. Slide deck presentation, USC, Jul. 21, 2014 online: http://dornsife.usc.edu/assets/sites/291/docs/Presentations/Prakash-_USC-July_21_2014-_Prakash-USC .pdf 1463. Prakash, G. K. S., (2013). Developments towards the methanol ecnomy. Potsdam Renewable Energies Symposium, Institute for Advanced Sustainability, Nov. 19-20, 2013, slide deck presentation, online: http://www.iass-potsdam.de/sites/default/files/files/prakash_-_presentation.pdf 1464. Prakash, G. K. S., and Olah, G. A., (2014). The promise of methanol. Slide deck presentation, Jul. 21, 2014 online: http://dornsife.usc.edu/assets/sites/291/docs/Presentations/Prakash-_USC-_July_21_2014-_Prakash-USC.pdf 1465. Prasanna, R., Adak, A., Verma, S., Bidyarani, N., Babu, S., Pal, M., Shivay, Y. S., and Nain, L., (2015). Cyanobacterial inoculation in rice grown under flooded and SRI modes of cultivation elicits differential effects on plant growth and nutrient dynamics. Ecological Eng., 84: 523-541

1466. Praxair, (undated). Economical, efficient, effective: Using carbon dioxide for well fracturing. Brochure, online: http://www.praxair.com/~/media/North%20America/US/Documents/Specification%20Sheets%20and%20Brochures/Industries/Oil%20and%20Gas/P10063C.pdf 1467. Praxair, (undated). Broiler CAS system. Corporate brochure online: http://www.praxair.com/~/media/North%20America/US/Documents/Specification%20Sheets%20and%20Brochures/Industries/Food%20and%20Beverage/P10158B%20Broiler%20CAS%20Systems.pdf 1468. Premier, (undated). Premier Magnesia LLC/Premier CPG Construction Products Group. On-line product sheet: "PreVent-C Admixture: Successful field trial reduced shrinkage cracking by 90-100%, Glen Elder dam and spillway in Glen Elder, Kans." Online: http://www.premiermagnesia.com/userdata/userfiles/file/Articles/glenelder_news %20(2).pdf 1469. Preuss, K., (2008). Role of fluid pressure in the production behavior on enhanced geothermal systems with $CO_2$ as working fluid. Energy Conversion and Management, 49: 1446-1454. (Also: LBNL paper, Lawrence Berkeley National Laboratory, online: http://escholarship.org/uc/item/7rr249rc 1470. Priamo, W. L., Dalmolin, I., Boschetto, D. L., Mezzomo, N., Ferreira, S. R. S., and Oliveira, J. V., (2013). Micronization processes by supercritical fluid technologies: a short review on process design (2008-2012). Acta Scientiarum, 35(4): 695-709.

1471. Priestnall, M., (2014). Decarbonizing flue gas using $CO_2$ mineralization—project experience on ships. Cambridge Carbon Capture slide deck presentation, March 2014, online: http://fe181f76201ce709deld-6f4ab1b22fd15b4eb714da2cdbfadc3a.r62.cf1.rackcdn.com/Michael%20Priestnall.pdf 1472. Priestnall, M., (2013). Making money from mineralization of $CO_2$. Carbon Capture J., February, 2013, online: http://www.carboncapturejournal.com/news/making-money-from-mineralisation-of-co2/3251.aspx 1473. Prigiobbe, V., Hanchen, M., Costa, G., Baciocchi, R., and Mazzotti, M., (2009). Analysis of the effect of temperature, pH, $CO_2$ pressure and salinity on the olivine dissolution kinetics. Energy Procedia, 1: 4881-4884.

1474. Prigiobbe, V., Hanchen, M., Werner, M., Baciocchi, R., and Mazzotti, M., (2009). Mineral carbonation process for $CO_2$ sequestration. Energy Procedia, 1: 4885-4890.

1475. Prigiobbe, V., and Mazzotti, M., (2011). Dissolution of olivine in the presence of oxalate, citrate, and $CO_2$ at 90C and 120C. Chem. Eng. Sci., 66: 6544-6554.

1476. Prigiobbe, V., Negreira, A. S., and Wilcox, J., (2013). Interaction between olivine and water based on density functional theory calculations. J. Phys. Chem. C, 117: 21203-21216.

1477. Prigiobbe, V., Negreira, A. S., Lim, D.-H., and Wilcox, J., (2013). Density functional theory calculations of the interaction of olivine with water. Energy Procedia, 37: 5875-5883.

1478. Prize Capital, LLC, (2011). Author: Matt Peak. *Carbon Capture & Recycling Industry Overview*. Pp. 237. Online: http://www.prizecapital.net/Prize_Capital/Home/Home_files/Prize%20Capital%20CCR%20Industry%20Overview.pdf 1479. Prokofyeva, A., (2014). The German R&D program for $CO_2$ utilization—innovations for a green economy. German Federal Ministry of Research and Education (FONA) slide deck presentation, Bonn, Germany, 21 Oct.

1480. Prokofyeva, A., and Gurtler, C., (2015a). A dream comes true: use of carbon dioxide for the production of plastics. Slide deck presentation, FONA-Forum Green Economy Workshop, 14 Sep. 2015 Online: http://www.fona.de/mediathek/forum/2015/beitrag/c1_prokofyeva_angelina_01_presentation_forum2015.pdf 1481. Prokofyeva, A., and Gurtler, C., (2015b). $CO_2$ as building block for the chemical industry. Bayer Materials Science Nov. 3, 2015 slide deck presentation, online: https://tu-freiberg.de/fakult4/iec/pdf/symposium/$CO_2$-arme_stoffliche_Nutzung_der_Braunkohle_in_Deutschland_1032015.pdf See also Apr. 14, 2015 press release: http://www.press.bayer.com/baynews/baynews.nsf/id/$CO_2$-a-convincing-new-building-block-for-polyurethanes 1482. Pronske, K., (2013). Clean Energy Systems, Inc., Zero-emissions baseload Trigen and load balancing power plants. Slide deck presentation, 28 Feb. 2013, online: http://decarbonizingfires.com/Clean%20Energy%20Systems%20-%20Kimberlina%20-%20 Slide%20Show.pdf 1483. Pruess K., (2006) Enhanced geothermal systems (EGS) using $CO_2$ as working fluid—a novel approach for generating renewable energy with simultaneous sequestration of carbon. Geothermics 2006; 35: p. 351-367.

1484. Prymak, I., Narayana, V., Wohrab, S., and Martin, A., (2015). Continuous synthesis of diethyl carbonate from ethanol and $CO_2$ over Ce—Zr—O catalysts. Catal. Sci. & Technol., 5: 2322-2331.

1485. PU Magazine, (2013). $CO_2$ as a polyol intermediate—the dream becomes a reality. August/September, pp. 236-240, online: http://www.econic-technologies.com/wp-content/uploads/2013/09/PU-Magazine-Aug-Sept-edition-13.pdf 1486. Purchase, R. L., and de Groot, H. J. M., (2016). Biosolar cells: global artificial photosynthesis needs responsive matrices with quantum coherent kinetic control for high yield. Interface Focus, 5: 2015.0014. http://dx.doi.org/10.1098/rsfs.2015.0014

1487. Purchase, R. L., and de Groot, H. J. M., (2015). *Artificial Photosynthesis for the Conversion of Sunlight to Fuel*. Pp. 53, Leiden University, online: http://www.biosolarcells.nl/data/upload/files/bsc-rapporten-en-artikelen/artificial-photosynthesis-webversie.pdf 1488. Puri, V. P., and Mamers, H., (1983). Explosive pretreatment of lignocellulosic residues with high-pressure carbon dioxide for the production of fermentation substrates. Biotechnol. Bioeng., 25(12): 3149-3161.

1489. Qiao, C., Li, L., Johns, R. T., and Xu, J., (2015). Compositional modeling of dissolution-induced injectivity during $CO_2$ flooding in carbonate reservoirs. SPE (Socc. Petrol. Engineers) Journal, 10(1), SPE-170930-PA 1490. Quadrelli, E. A., Centi, G., Duplan, J.-L., and Perathoner, S., (2011). Carbon dioxide recycling: emerging large-scale technologies with industrial potential. ChemSusChem, 4: 1194-1215.

1491. Quercia Bianchi, G., and Brouwers, H. J. H., (2015). Effect of olivine nano-silica additions on cement based systems. Pp. 193-198, in: K. Sobolve and S. P. Shah, (eds.), *Nanotechnology in Construction*. Springer 1492. Qui, Y., Qui, K., Li, J., and Zheng, P., (2015). Preparation of A1203 from nepheline ore on Nanjing county, Sichuan Province of China. Mats. Sci. Forum, 814: 230-234.

1493. Quinn, E. L., and Jones, C. L., (1936). *Carbon Dioxide*. Reinhold Publishing Corporation/

1494. Rabaey, K., and Rozendal, R. A., (2010). Microbial electrosynthesis—revisiting the electrical route for microbial production. Nature Revs. Microbiol., 8: 706-716

1495. Rabaey, K., Girguis, P., and Nielsen, L. K., (2011). Metabolic and practical considerations on microbial electrosynthesis. Curr. Opinion Biotechnol., 22: 1-7

1496. Rabelein, J. G., Hu, Y., and Ribbe, M. W., (2015). Widening the product profile of carbon dioxide reduction by vanadium nitrogenase. ChemBioChem, 16(14): 1993-1996.

1497. Rabelein, J. G., Hu, Y., and Ribbe, M. W., (2014). Differential reduction of $CO_2$ by molybdenum and vanadium nitrogenases. Angew. Chem. Intl., 53(43): 11543-11546.

1498. Radev, D., Peeva, G., and Nenov, V., (2015). pH control during struvite precipitation process of wastewaters. J. Water Resources and Protection, 7: 1399-1408

1499. Radgen, P., (2015). Carbon capture and storage: An industrial perspective. Slide deck presentation, May 4, 2015, online: http://www.spl.ethz.ch/content/dam/ethz/special-interest/mavt/process-engineering/separation-processes-laboratory-dam/documents/education/ccs%20notes/11_CCS-industry-perspective_radgen_FS2015.pdf 1500. Rafidah, J., Sakanishi, K., Miyazawa, T., Mohd Nor, M. Y., Wan Asma, I., Mahanim, S. M. A., Shaharuddin, H., and Paud, E., (2011). Effects of different gasifying agents on syngas production from oil palm trunk. J. Tropical Forest Sci., 23(3): 282-288.

1501. Ragsdale, S. W., and Pierce, E., (2008). Acetogenesis and the Wood-Ljungdahl pathway of $CO_2$ fixation. Biochim. Biophys. Acta, 1784(12): 1873-1898

1502. Rahimi, A., Ulbrich, A., Coon, J. J., and Stahl, S. S., (2014). Formic-acid-induced depolymerization of oxidized lignin to aromatics. Nature, 515: 294-252.

1503. Railsback, L. B., (2006). Degassing of $CO_2$ in caves and precipitation of speleothems. Online 1-page illustrated overview document: http://www.gly.uga.edu/railsback/Fundamentals/1121KarstSpeleoPptn03.pdf, in: L. B. Railsback, (ed.), *Some Fundamental of Mineralogy and Geochemistry*. Online textbook: http://www.gly.uga.edu/railsback/FundamentalsIndex.html 1504. Raloff, J., (undated). Hawaii's hated frogs: tiny invaders raise a big ruckus. Science News Online. Online: http://www.phschool.com/science/science_news/articles/hawaiis_hated_frogs.html 1505. Ramao, I., Gando-Ferreira, L. M., and Zevenhoven, R., (2015). Separation and recovery of valuable metals extracted from serpentine during the production of $Mg(OH)_2$ for $CO_2$ sequestration. Minerals Eng., 77: 25-33.

1506. Ramirez-Torres, A., Gabas, C., Barranquero, C., et al., (2012). *Squalene: Current Knowledge and Potential Therapeutical Uses*. Nova Science Publishers. ISBN: 978-1-61761-404-0

1507. Ramsey, E., Sun, Q., Zhang, Z., Zhang, C., and Gou, W., (2009). Mini-review: Green sustainable processes using supercritical fluid carbon dioxide. J. Environ. Sci., 21: 720-726.

1508. Rana, A., Kabi, S. R., Verma, S. Adak, A., Pal, M., Shivay, Y. S., Prasanna, R., and Nain, L., (2015). Prospecting plant growth promoting bacteria and cyanobacteria as options for enrichment of macro- and micronutrients in grains in rice-wheat cropping sequence. Cogent Food & Agriculture, 1: pared ID: 1037379, online: https://www.researchgate.net/publication/276428946_Prospecting_plant_growth_promoting_bacteria_and_cyanobacteria_as_options_for_enrichment_of_macro-_and_micronutrients_in_grains_in_rice-wheat_cropping_sequence
1509. Randolph, J. B., (2011). Coupling geothermal energy capture with carbon dioxide sequestration in naturally permeable, porous geologic formations—a novel approach for expanding geothermal energy utilization. PhD Thesis, University of Minnesota, online: https://conservancy.umn.edu/handle/11299/116297
1510. Randolph, J. B., and Saar, M. O., (2011a). Coupling carbon dioxide sequestration with geothermal energy capture in naturally permeable, porous geological formations. Energy Procedia, 4: 2206-2213
1511. Randolph, J. B., and Saar, M. O., (2011b). Combining geothermal energy capture with geologic carbon dioxide sequestration. Geophys. Res. Letts., 38: L10401, doi: 10.1029/2011GL047265, 2011
1512. Randolph, J. B., and Saar, M. O., (2011c). Impact of reservoir permeability on the choice of subsurface geothermal heat exchange fluid: $CO_2$ versus water and native brine. Geothermal Resource Council Transactions, 35: 521-526
1513. Randolph, J. B., and Saar, M. O., (2010). Coupling geothermal energy capture with carbon dioxide sequestration in naturally permeable, porous geologic formations: a comparison with enhanced geothermal systems. Geothermal Research Council Transactions, 34: 433-437.
1514. Randolph, J. B., Saar, M. O., Bielicki, J., (2013). Geothermal energy production at geologic $CO_2$ sequestration sites: Impact of thermal drawdown on reservoir pressure. Energy Procedia, 37: 6625-6635.
1515. Raspor, P., and Goranovic, D., (2008). Biotechnological applications of acetic acid bacteria. Crit. Revs. Biotechnol., 28: 101-124
1516. Ravanchi, M. T., and Sahebdelfar, S., (2014). Carbon dioxide capture and utilization in petrochemical industry: potentials and challenges. Appl. Petrochem. Res., 4: 63-77.
1517. Read, A., (2015a). Rotterdam Opslag en Opvang Demonstratieproject (ROAD). ROAD slide deck presentation, Apr. 28, 2015, online: http://www.globalccsinstitute.com/sites/www.globalccsinstitute.com/files/content/media_release/123054/files/ROAD%20presentation%20Andy%20Read%20@MEP%20meeting%20(Strasbourg%2028%20April%202015)%20fina . . . pdf
1518. Read, A., (2015b). Rotterdam Opslag en Opvang Demonstratieproject (ROAD): Creating a Rotterdam $CO_2$ hub for Europe. ROAD slide deck presentation, Jun. 17, 2015, online: http://www.slideshare.net/globalccs/eusew-presentation-by-andy-read-road
1519. Read, A., Tillema, O., Ros, M., Jonker, T., and Hylkema, H., (2014). Update on the ROAD Project and lessons learnt. Energy Procedia, 63: 6079-6095.
1520. Read, D., (2009). Youtube video: "Extracting limonene using liquid carbon dioxide. Online: https://www.youtube.com/watch?v=o2aIUemy9Xw
1521. Reberio, F. C., Borem, F. M., Giomo, G. S., De Lima, R. R., Malta, M. R., and Figueiredo, L. P., (2011). Storage of green coffee in hermetic packaging injected with $CO_2$. J. Stored Products Res., 47: 341-348.
1522. Reda, T., Plugge, C. M., Abram, N. J., and Hirst, J., (2008). Reversible interconversion of carbon dioxide and formate by an electroactive enzyme. PNAS, 105(31): 10654-10658.
1523. Reid, T., and Robinson, H., (1981). Lick Creek Meakin sand unit immiscible $CO_2$ water flood project. J. Petrol. Technol., 33(9): 1723-1729.
1524. Reitan, K. I., (2013). The need for microalgae as a lipid rich resource in future aquafeed. $3^{rd}$ Danish Algae Conference, 9-10 Oct. 2013. Slide deck presentation, online: http://www.algecenterdanmark.dk/media/6676/kjell_inge_reitan_the_need_for_microalgae_as_alipid_rich_resource_for_future_aquafeed.pdf
1525. Relvas, F. M., Morais, A. R. C., and Bogel-Lukasik, (2015). Selective hydrolysis of wheat straw hemicellulose using high-pressure $CO_2$ as catalyst. RSC Advances, 90: DOI: 10.1039/C5RA14632A
1526. Ren, D., Song, Z., Fu, J., and Huo, Z., (2015). Application of diverse hydrogen sources to methanol synthesis from $CO_2$. Chapter 4, pp. 109-122 in: Fangmin Jin et al., ACS Symp. Ser. V. 1194, *Advances in $CO_2$ Capture, Sequestration, and Conversion*. American Chemical Society
1527. Ren, J., Li, F.-F., Lau, J., Gonzalez-Urbina, L., and Licht, S., (2015). One-pot synthesis of carbon nanofibers from $CO_2$. NanoLetters, DOI: 10.1021/acs.nanolett.5bo2427.
1528. Ren, J., Lau, J., Lefler, M., and Licht, S., (2015). The minimum electrolytic energy needed to convert carbon dioxide to carbon by electrolysis in carbonate melts. J. Phys. Chem., 119: 23342-23349.
1529. Renner, M., Weidner, E., Bjorn, J., and Helmut, G., (2012). Free of water tanning using $CO_2$ as process additive—an overview on the process development. J. Supercrit Fluids, 66: 291-296.
1530. Renner, M., Weidner, E., and Brandin, G., (2009). High-pressure carbon dioxide tanning. Chem. Eng. Res. Des., 87: 987-996.
1531. Renuka, N., Prasanna, R., Sood, A., Ahluwalia, A. S., Bansal, R., Babu, S., Singh, R., Shivay, Y. S., and Nain, L., (2015). Exploring the efficacy of wastewater-grown microalgal biomass as a biofertilizer for wheat. Environ. Sci. Pollut. Res., DOI 10.1007/s11356-015-5884-6
1532. Repasky, J. M., Anderson, L. L., Stein, V. E., Armstrong, P. A., and Foster, E. P., (2012). ITM oxygen technology: scale-up toward clean energy applications. Conference paper, International Pittsburgh Coal Conference 2012, Pittsburgh, Pa., Oct. 15-18, 2012, online: http://www.airproducts.com/~/media/files/pdf/industries/itm-oxygen-technology-280-12-058-glb.pdf
1533. Repasky, J., McCarthy, D., Armstrong, P., and Carolan, M., (2014). ITM technology for carbon capture on natural gas and hybrid power systems. Slide deck presentation, Workshop on Technology Pathways Forward for Carbon Capture & Storage on Natural Gas Power Systems, Washington, D.C., Apr. 22, 2014, online: http://slideplayer.com/slide/1723501/ Also: https://www.usea.org/sites/default/files/event-/140417_140422_USEA%20NG%20CCS_WashDC_Repasky%20-no%20backup.pptx
1534. Repasky, J. M., Stein, V. E., Armstrong, P. A., Quintrell, M. S., Maxson, A., and Bartone, L. M., (2013). Ceramic and coal: ITM oxygen and power generation with reduced $CO_2$-emissions, detailed engineering study results. Air Products paper, online: http://www.airproducts.com/~/media/downloads/i/ion-transport-membrane/articles/en-oxygen-paper-2013.pdf?industryItem=industries&subnbdustryItem=Energy&segment=Power&applicationChildItem=Power-Generation&productLevel3=Ion-Transport-Membrane
1535. Reyes, F. A., Mendola, J. A., Ibanez, E., and del Valle, J. M., (2014). Astaxanthin extraction from Haematococcus pluvialis using $CO_2$-expanded ethanol. J. Supercrit. Fluids, 92: 75-83
1536. Rice, M., Baird, C., Stikeleather, L., Morrow, W. E. M., Meyer, R., (2014). Carbon dioxide system for on-farm euthanasia of pigs in small groups. J. Swine Health and Production, September & October, 2014, pp. 248-254, online: https://www.aasv.org/shap/issues/v22n5/v22n5p248.pdf 1537. RiceMate, (undated). Premum Peng La rice. Online: http://www.ricemate.com/media/Co2Peng-Lai_rice_catalog.pdf 1538. Richmond, A., and Hu, Q., (2013). *Handbook of Microalgal Culture*, $2^{nd}$ edition, Wiley-Blackwell, pp. 736.

1539. Ridjan, I., Mathiesen, B., and Connolly, D., (2013a). A review of biomass gasification technologies in Denmark and Sweden. Aarlborg University report, 32pp, online: http://vbn.aau.dk/files/123284438/A_review_of_biomass_gasification_technologies_in_Denmark_and_Sweden.pdf 1540. Ridjan, I., Mathiesen, B., and Connolly, D., (2013b). The feasibility of synthetic fuels in renewable energy systems. Energy, 57: 76-84.

1541. Riduan, S. N., and Zhang, Y., (2011). Recent developments in carbon dioxide utilization under mild conditions. Dalton Trans., 39: 3347-3357.

1542. Rijckaert, A., (2009). Dutch aubergine grower pipes carbon dioxide into greenhouses. The Telegraph, Dec. 14, 2009, online: http://www.telegraph.co.uk/expat/expat-news/6808988/Dutch-aubergine-grower-pipes-carbon-dioxide-into-greenhouses.html 1543. Riman, R., (2012). Utilization of $CO_2$ in high performance building and infrastructure products. USDOE slide deck presentation, Aug. 21-22, 2012, online: http://www.netl.doe.gov/File%20Library/events/2013/carbon%20storage/3-15-Solidia-Tech_FY13_Carbon-Storage-Review Final.pdf 1544. Rivetti, F., Romano, U., and Delledonne, D., (1996). Dimethylcarbonate and its production technology. Chapter 6, pp. 70-80, in: P. T. Anastas and T. C. Williamson (eds.), *Green Chemistry: An Overview*. American Chem. Soc.

1545. Roberts, F. S., Kuhl, K. P., and Nilsson, A., (2015). High selectivity for ethylene from carbon dioxide reduction over copper nanocube electrocatalysts. Angew. Chemie, 17: 5268-5271.

1546. Robledo-Diez, A., (2012). Life-cycle assessment on the conversion of $CO_2$ to formic acid. NTNU Master's thesis, Trondheim, Norway, online: http://brage.bibsys.no/xmlui/handle/11250/234844 and http://www.diva-portal.org/smash/get/diva2:566391/FULLTEXT01.pdf 1547. Rochau, G. E., (2014). Supercritical $CO_2$ Brayton cycle for compact, high efficiency power generation. Sandia National Laboratory, slide deck presentation, Tech Connect World, online: http://www.osti.gov/scitech/biblio/1221555-supercritical-co2-brayton-cycle-compact-high-efficiency-power-generatio 1548. Rochau, G. E., (2011). Supercritical $CO_2$ Brayton cycle: the DOE program. Sandia National Laboratories, Slide deck presentation, $CO_2$ Power Cycle Symposium, May 24-25, 2011, online: http://www.sco2powercyclesymposium.org/resource_center/development_prioritie s/supercritical-co2-brayton-cycle-the-doe-program 1549. Rock, A. J., (1993). The salycilic acid craze, pp. 304-310 in: *The Quiet Revolution: Hermann Kolbe and the Science of Organic Chemistry*. U. California Press. Online: http://ark.cdlib.org/ark:/13030/ft5g500723/

1550. Rodas, B., and Bressani, R., (2009). The oil, fatty acid and squalene content of varieties of raw and processed amaranth grain. Archivos Latinamericanos de Nutricion, 59(1): 82-87.

1551. Rodrigo-Naharro, J., Delgado, A., Herrero, M. J., Granados, A., and Perez del Villar, L., (2013). Current travertines precipitation from $CO_2$-rich groundwaters as an alert of $CO_2$ leakages from a natural $CO_2$ storage at Ganuelas-Mazarron Tertiary Basin (Murcia, Spain). Informes Tecnicos Ciemat, 1279, online: http://www.iaea.org/inis/collection/NCLCollectionStore/_Public/44/039/44039347.pdf 1552. Rodriguez, F., Berenguel, M., Guzman, J. L., and Ramirez-Arias, A., (2015). *Modeling and control of greenhouse crop growth*. Springer.

1553. Rokem, J. S., and Greenblatt, C. L., (2015). Making biofuels competitive: the limitations of biology for fuel production. JSM microbial., 3(2): 1023-1028

1554. Rollin, J. A., del Campo, J. M., Myung, S., Sun, F., You, C., Bakovic, A., Castro, R., Chandrayan, S. K., Wu, C.-H., Adams, M. W. W., Senger, R. S., and Zhang, Y.-H. P., (2015). High-yield hydrogen production from biomass by in vitro metabolic engineering: mixed sugars coutilization and kinetic modeling. PNAS, 112(16): 4964-4969.

1555. Romain, C., and Williams, C. K., (2015). Combining sustainable polymerization routes for the preparation of polyesters, polycarbonates, and copolymers. Chapter 9, pp. 135-146 in: *Green Polymer Chemistry: Biobased Materials and Biocatalysts*. ACS Symp. Ser., v. 1192, American Chem. Soc.

1556. Romanov, V., Soong, Y., Carney, C., Rush, G., Nielsen, B., and O'Connor, W., (2015). Mineralization of carbon dioxide: literature review. ChemBioEng Revs, 2(4): 231-256. Online: http://www.osti.gov/scitech/servlets/purl/1187926

1557. Romero, M., and Steinfeld, (2012). Concentrating solar thermal power and thermochemical fuels. Energy Environ. Sci., 5: 9234-9245.

1558. Ronge, J., Bosserez, T., Martel, D., Nervi, C., Boarino, L., Taulelle, F., Decher, G., Bordiga, S., Martens, J. A., (2014). Monolithic cells for solar fuels. Chem. Soc. Rev., 43: 7963-7981

1559. Ros, M., Read, A., Uilenreef, J., and Limbeek, J., (2014). Start of a $CO_2$ hub in Rotterdam: connecting CCS and CCU. Energy Procedia, 63: 2691-2701.

1560. Rosen, B. A., Salehi-Khojin, A., Thorson, M. R., Zhu, W., Whipple, D. T., Kenis, P. J. A., and Masel, R. I., (2011). Ionic liquid-mediated selective conversion of $CO_2$ to CO at low overpotentials. Science, 334: 643-644.

1561. Rosen, B. A., Haan, J. L., Mukherjee, P., Braunschweig, B., Zhu, W., Salehi-Khojin, A., Dlott, D. D., and Masel, R. I., (2012). In situ spectroscopic examination of a low overpotential pathway for carbon dioxide conversion to carbon monoxide. J. Phys. Chem. C., 116: 15307-15312.

1562. Rosen, J., Hutchings, G. S., Liu, Q., Rivera, S., Zhou, Y., Vlachos, D. G., and Jiao, F., (2015). Mechanistic insights into the electrochemical reduction of $CO_2$ to CO on nanostructured Ag surfaces. ACS Catal., 5(7): 4293-4299.

1563. Rosenthal, D. M., Slattery, R. A., Miller, R. E., Grennan, A. K., Cavagnaro, T. R., Fauquet, C. M., Gleadow, R. M., and Ort, D. R., (2012). Cassava about-FACE: greater than expected yield stimulation of cassava (*Manihot esculenta*) by future $CO_2$ levels. Global Change Biology, 18(8): 2661-2675.

1564. Ross, K. A., (2013a). PhD Thesis (ETH—Zurich). The Effect of Subaquatic Volcanism on the Structure of Lake Kivu in the Albertine Rift, East Africa.

1565. Ross, K. A., (2013b). Slides presented at the November Lake Kivu AVCOR (Active Volcanism & Continental Rifting) meeting.
1566. Ross, K. A., Smets, B., De Batist, M., Hilbe, M., Schmid, M., Anselmetti, F. S., (2014). Lake-level rise in the late Pleistocene and active subaquatic volcanism since the Holocene in Lake Kivu, East African Rift. Geomorphology, 221: 274-285.
1567. Ross, K. A., Gashugi, E., Gafasi, A., Wuest, A., and Schmid, M., (2015a). Characterization of the subaquatic groundwater discharge that maintains the permanent stratification within Lake Kivu; East Africa. PLOS ONE, Mar. 23, 2015. DOI: 10.1371/journal.pone.0121217
1568. Ross, K. A., Schmid, M., Ogorka, S., Muvundja, F. A. and Anselmetti, F. S. (2015b). The history of subaquatic volcanism recorded in the sediments of Lake Kivu: East Africa. J. Paleolimnol. DOI 10.1007/s10933-015-9842-6
1569. Rotterdam Climate Initiative, (2011). $CO_2$ capture and storage in Rotterdam: A network approach. Online: http://www.rotterdamclimateinitiative.nl/documents/CO₂%20capture%20and%20storage%20in%20Rotterdam%20-%20a%20network%20approach%202011.pdf
1570. Rotterdam Climate Initiative, (2012). Rotterdam CCS Cluster Project: Case Study on 'lessons learnt.' Final Report.: http://www.rotterdamclimateinitiative.nl/documenten/Documenten/2012rcicasestudyfinalreport-opt.pdf
1571. Rousu, P., Rousu, P., and Anttila, J., (2002). Sustainable pulp production from agricultural waste. Resources, Conservation and Recycling, 35(1-2): 85-103.
1572. Rowden, R., (2013). The myth of Africa's rise: why the rumors of Africa's explosive growth have been greatly exaggerated. Foreign Policy, Jan. 24, 2013. Online: http://foreignpolicy.com/2013/01/04/the-myth-of-africas-rise/
1573. Royston, K., (2012). Industrial ecology: the integration of environmental concerns with economic development. Slide deck presentation online: http://www.ace-low-carbon-economy.eu/files/Events/ACE%20launch/Hastings%20-%20Industrial%20Ecology.pdf
1574. Riudavets, J., Castene, C., Alomar, O., Pons, M. J., and Gabarra, R., (2009). Modified atmosphere packaging (MAP) as an alternative measure for controlling ten pests that attack processed food products. J. Stored Food Products Res., 45: 91-96.
1575. RSC, (2012). Solar fuels and artificial photosynthesis. Royal Society for Chemistry, online report: http://www.rsc.org/images/Solar-fuels_tcm18-221433.pdf
1576. Rubin, J. B., Carey, J. W., and Taylor, C. M. V., (1997). Enhancement of cemented waste forms by supercritical $CO_2$ carbonation of standard Portland cements. Conference paper, American Nuclear Society, $1^{st}$ Topical Meeting on Decommissioning, Decontamination, & Reutilization of Commercial and Government Facilities, September 7-12, Knoxville, Tenn., USA, online: http://www.osti.gov/scitech/servlets/purl/589871
1577. Rubin, J. B., Taylor, C. M. V., Hartmann, T., and Paviet-Hartmann, P., (2003). Enhancing the properties of Portland cements using supercritical carbon dioxide. Chapter 15, pp. 241-255, in: J. M. DeSimone and W. Tumas (eds.), *Green Chemistry Using Liquid and Supercritical Carbon Dioxide*. Oxford Univ. Press.
1578. Runco, J., (2015). Purification of vanilla from vanilla beans using an SFE-SFC workflow. Application note, Waters Corp., online: http://www.waters.com/webassets/cms/library/docs/720005457en.pdf
1579. Ruschig, U., Muller, U., Willnow, P. and Hopner, T., (1976). $CO_2$ reduction to formate by NADH catalyzed by formate dehydrogenase from *Pseudomonas oxalacticus*. Eur. J. Biochem., 70: 325-330.
1580. Rusli, R., Chang, E. J. T., Pham, H. H. P. L., and Shariff, A. M., (2014). Solid carbon dioxide formation from rapid fluid expansion using integration of computational fluid dynamics and mathematical modeling. CET, Chemical Engineering Transactions, 36: 607-612.
1581. Ryan, R. F., (2008a). Carbon dioxide—the veteran and versatile fumigant. Proc. $8^{th}$ Int. Conf on Controlled Atmosphere and Fumigation in Stored Products, Chengdu, China. Online: http://ftic.co.il/2008ChengduPDF/SESSION%2002%20PAPER%2013.pdf
1582. Ryan, R. F., (2008b). Recycled carbon dioxide—the veteran and versatile pesticide. Proc. Ann. Int'l Conf. on Methyl Bromide Alternatives and Emissions Reductions. Online: http://www.researchgate.net/publication/237526882_RECYCLED_CARBON_DIOXIDE_-_THE_VETERAN_VERSATILE_PESTICIDE
1583. Ryan, R., and Bishop, S., (2003). VAPORMATE: non-flammable ethyl formate/liquid carbon dioxide fumigant mixture. In: E. J. Wright, M. C. Webb and E. Highly, (eds.), pp. 190-192, Proc. Australian Postharvest Technical Conference, Canberra, 25-27 Jun. 2003. CSIRO Stored Grain Research Laboratory, Canberra. Online: http://agronet-service.com/VAPORMATE.pdf
1584. Ryan, R. F., Bishop, S., Chung, B., Folder, I., Krishna, H., and Lemon, A., (undated). Pyrethrum: Nature's pesticide. Online: http://citeseerx.ist.psu.edu/viewdoc/download?doi=10.1.1.197.4324&rep=rep1&type=pdf
1585. Ryan, R. F., Greenhill, M., and Chung, B., (2015). Pyrethrum: the natural choice in pest control. Acta Hort., 1073, February 2015 (Proc. $1^{st}$ Int'l. Symp. On Pyrethrum, the Natural Insecticide and Industrial Developments in the Renewal of a Traditional Industry), pp. 131-135, online: http://www.actahort.org/books/1073/1073_19.htm
1586. Ryde, M. V., (2014). Fuel cells development continuing despite Topsoe closure. DTU Technical University of Denmark news, online: http://www.dtu.dk/english/News/2014/10/Fuel-cells-development-continuing-despite-Topsoe-closure
1587. SAASTA, (2014). "Secret" technology turns farm into green tea extract factory. Public Understanding of Biotechnology, Issue 2, December, 2014, South African Agency for Science & Technology Development, online: http://www.pub.ac.za/newsletter/02-201412/article-1.html
1588. Saavalainen, P., Kabra, S., Turpeinen, E., Oravisjarvi, K., Yadav, G. D., Keiski, R. L., and Pongracz, E., (2015). Sustainability assessment of chemical processes: evaluation of three synthesis routes of DMC. J. Chem., article ID 402315, DIO 10.1155/2015/402315
1589. Saavedra, Y., Dijkxhoorn, Y., Elings, A., Glover-Tay, J., Koomen, I., van der Maden, E., Nkansah, G., and Obeng, P., (2014). Vegetables business opportunities in Ghana: 2014. GhanaVeg Program, Wageningen University, online report: http://www.rvo.nl/sites/default/files/2015/04/Vegetables%20Business%20Opportunities%20in%20Ghana%202014.pdf
1590. Safdarnejad, S. M., Hedengren, J. D., and Baxter, L. L., (2015). Plant-level dynamic optimization of Cryogenic Carbon Capture with conventional and renewable power sources. Appl. Energy, 149: 354-366.
1591. Sage, R. F., and Zhu, X-G., (2011). Exploiting the engine of C4 photosynthesis. J. Experimental Botany, 62(9): 2989-3000.
1592. Sagir, M., Tan, I. M., Mushtaq, M., Pervaiz, M., Tahir, M. S., and Shahzad, K., (2015). $CO_2$ mobility control using CO$_2$ philic surfactant for enhanced oil recovery. J. Petrol. Explor. Prod. Technol., DOI 10.1007/s13202-015-0192-8

1593. Sahin, S., Kalfa, U., Celebioglu, D., Duygu, E., and Lahna, H., (2012). A quarter century of progress in the application of CO$_2$ immiscible EOR project in Bati Raman heavy oil field in Turkey. Society of Petroleum Engineers—SPE Heavy Oil Conf Canada 2012, DOI: 10.2118/157865-MS 1594. Sahin, S., Kalfa, U., and Celebioglu, D., (2007). Bati Raman Field immiscible CO$_2$ application: status quo and future plans. SPE 106575, DOI: 10.2118/106575-MS 1595. Sahu, S., and Cristofaro, N., (2013). Solidia Cement: Part one of a two-part series exploring the chemical properties and performance results of sustainable Solidia Cement and Solidia Concrete. Solidia Technologies website white paper online: http://solidiatech.com/wp-content/uploads/2015/07/Solidia-Purdue-Freeze-Thaw-White-Paper-7-1-15.pdf 1596. Sajilata, M. G., Bajaj, P. R., and Singhal, R. S., (2008). Tea polyphenols as nutraceuticals. Comp. Revs. Food Sci. Food Safety, 7: 229-254.

1597. Sakakura, T., Choi, J.-C., and Yasuda, H., (2007). Transformation of carbon dioxide. Chem. Rev., 107: 2365-2387.

1598. Salehi-Khojin, A., Molly Jhong, H.-R., Rosen, B. A., Zhu, W., Ma, S., Kenis, P. J. A., and Masel, R. I., (2013). Nanoparticle silver catalysts that show enhanced activity for carbon dioxide electrolysis. J. Phys. Chem. C, 117(4): 1627-1632.

1599. Salina, P., (2015). Village Farms presentation slide deck: "Investing in control environment agriculture technologie." Online: http://www.fdcea.com/wp-content/uploads/2015/06/9_salina_investingcea.pdf 1600. Sani, A., Abdullah, W. O., (2014). Extraction, characterization and total phenolic content of local (Malaysian) green sweet potato (*Ipomoea batatas*) leaves. Int. J. Science, Commerce and Humanities, 2(5): 175-182

1601. Sannigrahi, P., and Ragauskas, A. J., (2013). Fundamentals of biomass pretreatment by fractionation. Chapter 10, pp. 201-222, in: C. E. Wyman, (ed.), *Aqueous Pretreatment of Plant Biomass for Biological and Chemical Conversion to Fuels and Chemicals*. John Wiley & Sons, Ltd.

1602. Sanchez-Camargo, A. de P., Mendiola, J. A., Ibanez, E., and Herrero, M., (2014). Supercritical fluid extraction. In: J. Reedijk, (ed.), Elsevier Reference Module in Chemistry, Molecular Science and Chemical Enginering. DOI: 10.1016/B978-0-12-409547-2.10753-X Online: http://digital.csic.es/bitstream/10261/109441/4/Chapter%20SFE-completo.pdf 1603. Sanchez-Camargo, A. P., Meireles, M. A. A., Ferreira, A. L. K., Saito, E., and Cabral, F. A., (2011). Extraction of co-3 fatty acids and astaxanthin from Brazilian red-spotted shrimp waste using supercritical CO$_2$+ethanol mixtures. J. Supercrit. Fluids, 61: 70-77.

1604. Sanchez-Camargo, A. P., Martinez-Correa, H. A., Paviani, L. C., and Cabral, F. A., (2011). Supercritical CO$_2$ extraction of lipids and astaxanthin from Brazilian redspotted shrimp waste (*Farfantepenaeus paulensis*). J. Supercrit. Fluids, 56: 164-173.

1605. Santos, A. L., F., Kawase, K. Y. F., Coelho, G. L. V., (2011). Enzymatic saccharification of lignocellulosic materials after treatment with supercritical carbon dioxide. J. Supercrit. Fluids, 56: 277-282.

1606. Santos, B. A. V., Silva, V. M. T. M., (2014). Review of direct synthesis of dimethyl carbonate. ChemBioEng Revs., 1(5): 214-229.

1607. Santos, B. A. V., Lourieiro, J. M., Robero, A. M., Rodrigues, A., and Cunha, A. F., (2015). Methanol production by bi-reforming. Can. J., Chem. Eng., 93(3): 510-526.

1608. Sanchez-Espana, J., Boehrer, B., and Yusta, I., (2014). Extreme carbon dioxide concentrations in acidic pit lakes provoked by water/rock interaction. Environmental Sci. Technol., 48(8): 4273

1609. Sanna, A., Uibu, M., Caramanna, G., Kuusik, R., and Maroto-Valer, M. M., (2014). A review of mineral carbonation technologies to sequester CO$_2$. Chem. Soc. Rev., 43: 8049-8080.

1610. Santo, I. E., Pedro, A. S., Fialho, R., and Cabral-Albuquerque, E., (2013). Characteristics of lipid micro- and nanoparticles based on supercritical formation for potential pharmaceutical application. Nanoscale Res. Letts., 8(1): 386 (http://www.nanoscalereslett.com/content/8/1/386)

1611. Santos, R. M., (2014). Sustainable valorization of industrial residues via mineral carbonation. Slide deck presentation, 27 May 2014, KU Leuven, online: http://smartpro2.eu/downloadpage.php?id=169

1612. Santos, R. M., Van Audenaerde, A., Chiang, Y. W., Iacobescu, R. I., Knops, P., and Van Gerven, T., (2015). Nickel extraction from olivine: effect of carbonation pre-treatment. Metals, 5: 1620-1644.

1613. Sapphire Energy, (2015). Sapphire Energy, Inc., DOE Bioenergies Technologies Office (BETO) 2015 Project Peer Review. Online: http://energy.gov/sites/prod/files/2015/04/f22/demonstration_market_transformation_moreno_3321.pdf 1614. Sarasota Springs Heritage Area Visitor Center, (2009). Mineral waters: tasting tour of the famous waters of Saratoga. Online: http://www.saratogaspringsvisitorcenter.com/wordpress/wp-content/uploads/2011/07/BROCHURE-Mineral-Waters.pdf 1615. SARF (Scottish Aquaculture Research Foundation), (2014). Use of algae and other non-fish oils in refined edible producrs. Report ISBN: 978-1-907266-59-1 Online: http://www.sarf.org.uk/cms-assets/documents/152960-44386.sarf091.pdf 1616. Sarkar, J., (2012). Transcritical CO$_2$ refrigeration systems: comparison with conventional solutions and applications. Int. J. Air-Cond. Refrig., 20(4). DOI: 10.1142/S2010132

1617. Sarkus, T. A., (2015). Update on the Kemper IGCC with pre-combustion, amd Petro-Nova post-combustion capture projects. NETL slide deck presentation, May 13, 2015, online: http://conference.co2geonet.com/media/1113/european-north-american-14_sarkus.pdf 1618. Sarmento, L. A. V., Machado, R. A. F., Petrus, J. C. C., Tamanini, T. R., and Bolzan, A., (2008). Extraction of polyphenols from cocoa seeds and concentration through polymeric membranes. J. Supercrit. Fluids, 45: 64-69.

1619. Sasaki, T., (2014). Toshiba's energy solution. Toshiba slide deck presentation, Japan-Poland Clean Coal Seminar 2014, 2$^{nd}$ June, 2014, online: http://www.pl.emb-japan.go.jp/keizai/documents/E2_5%20Toshiba%20Sasaki.pdf 1620. Sato, K., Kawaguchi, H., and Kobayashi, H., (2013). Bio-electrochemical conversion of carbon dioxide to methane in geological storage reservoirs. Energy Conversion Management, 66: 343-350

1621. Saus, W., Knittel, D., and Schollmeyer, E., (2003). Dyeing of textiles in supercritical carbon dioxide. Textile Res. J., 63(3): 135-142.
1622. Savile, C. K., and Lalonde, J. J., (2013). Biotechnology for the acceleration of carbon dioxide capture and sequestration. Curr. Opin. Biotech. 22(6): 818-823.
1623. Sawant, H., (2013). Manufacturing innovative materials for $CO_2$ capture and reuse. Carbon Capture J., November-December 2013, pp. 11-12, online: http://b59d35675b007f59b1d7-0196d366fe21fa4c957de1aaf4b3 fb16.r82.cf1.rackcdn.com/CCJ36webhe78w.pdf
1624. Scandola, M., (2015). Polymers from renewable resources: state of the art and perspectives, part 1. University of Bologna slide deck presentation, online: http://www.sinchem.eu/wp-content/uploads/2015/01/15-SCANDOLA-SINCHEM-2015.pdf
1625. Schaeffer, B., Searle, C., Whiley, A. W., and Nissen, R. J., (1996). Effects of atmospheric $CO_2$ enrichment and root restriction on leaf gas exchange and growth of banana (Musa). Physiologia Plantarum, 97(4): 685-693.
1626. Schaeffer, B., Whiley, A. W., and Searle, C., (1999). Atmospheric $CO_2$ enrichment, root restriction, photosynthesis, and dry matter partitioning in subtropical and tropical fruit cycles. HortSci., 34(6): 1033-1037
1627. Schafer, M., (1955). Occurrence and utilization of carbon-dioxide-rich water near Adland, Oreg. The OREBIN, 17(7): 47-51, online: http://www.oregongeology.org/sub/milo/archive/MiningDistricts/JacksonCounty/AshlandDistrict/Gas-IceCorporationClaim/Gas-IceCorporationReports.pdf
1628. Schiermeier, C., (2013). Renewable power: Germany's energy gamble. Nature, 496: 156-158. Online: http://www.nature.com/news/renewable-power-germany-s-energy-gamble-1.12755
1629. Schievano, A., Adani, F., Buessing, L., Botto, A., Casoliba, E. N., Rossoni, M., and Goldfarb, J. L., (2015). An integrated biorefinery concept for olive mill waste management: supercritical $CO_2$ extraction and energy recovery. Green Chem., 17: 2874-2887.
1630. Schlumberger (2014). *Leading the Energy Transition: Hydrogen-Based Energy Conversion. More Than Storage: System Flexibility.* 279pp. SBC (Schlumberger Business Consulting) Energy Institute, online factbook: http://www.slb.com/news/inside_news/2014/2014_0815_more_than_storage.aspx
1631. Schlumberger, (undated). ThermaFOAM CO@ foam system for high temperature wells: The future of high-temperature brownfield $CO_2$ fracturing. Online product sheet: https://www.slb.com/~/media/Files/stimulation/product_sheets/tightgas/thermafoam.pdf
1632. Schmidt, I., Muller, K., and Arlt, W., (2014). Evaluation of formic-acid-based hydrogen storage technologies. Energy & Fuels, 28; 6540-6544.
1633. Schmid, M., Tietze, K., Halbwachs, M. Lorke, A., McGinnis, D., and A. Wiest, A., (2004). How hazardous is the gas accumulation in Lake Kivu? Arguments for a risk assessment in light of the Nyiragongo Volcano eruption of 2002, Acta Vulcanol., 14/15, 115-121.
1634. Schmid M, Halbwachs M, Wehrli B, and Wuest A., (2005). Weak mixing in Lake Kivu: New insights indicate increasing risk of uncontrolled gas eruption. G3 Research Letter 6: Q07009.
1635. Schmid, M., and Wuest, A., (2012). Stratification, mixing and transport processes in Lake Kivu. Pp. 13-28. In: J.-P. Descy et al. (eds), Lake Kivu: Limnology and Biogeochemistry of a Tropical Great Lake. Aquatic Ecology Series 5. Springer.
1636. Schmidt, R., Schulmeyr, J., and Gehrig, M., (undated). Extraction of xanthohumol enriched hop extracts using carbon dioxide as solvent at pressures up to 100 bars. Online: http://www.researchgate.net/publication/228515974_Production_of_xanthohumol_enriched_hop_extract_using_carbon_dioxide_as_solvent_at_pressures_up_to_1000_bars
1637. Schmitz, D. M. and Kufferath, J., (1955). Problemes par la presence de gaz dissous dans les eaux profondes du lac Kivu. Academie Royales des Sciences Coloniales, Bulletin de seances nouvelles serie 1: 326-356.
1638. Schnacke, G., (2015). Carbon capture from oil refining: best practices in enhanced oil recovery. Denbury slide deck presentation, July 2015, online: http://www.pnwer.org/uploads/2/3/2/9/23295822/schnake_[with_edits]_2015-06_co2_eor_(pacific_northwest_erc).pdf
1639. Schoell, M., Tietze, K., Schoberth, S. M., (1988). Origin of methane in Lake Kivu (East-Central Africa). Chem. Geol., 71: 257-265
1640. Schreier, M., Cuvat, L., Giordano, F., Steier, L., Abate, A., Zakeeruddin, S. M., Luo, J., Mayer, M. T., and Gratzel, M., (2015). Efficient photosynthesis of carbon monoxide from $CO_2$ using perovskite photovoltaics. Nature Communications, DOI: 10.1038/ncomms8326
1641. Schrenk, M. O., Brazelton, W. J., and Lang, S. Q., (2013). Serpentinization, carbon and deep life. Revs. Mineralogy & Geochem., 75: 575-606
1642. Schuchmann, K., and Muller, V., (2013). Direct and reversible hydrogenation of $CO_2$ to formate by a bacterial carbon dioxide reductase. Science, 342: 1382-1385.
1643. Schuchmann, K., and Muller, V., (2014). Autotrophy at the thermodynamic limit of life: a model for energy conservation in acetogenic bacteria. Nature Rev. Microbiol., 12(12: 809-821
1644. Schuiling, O., (2014). The green cookery book: recipes against climate change and ocean acidification. Chapter 7, pp. 136-151 in: T. J. Goreau et al., (eds), *Geotherapy: Innovative Methods of Soil Fertility Restoration, Carbon Sequestration and $CO_2$ Decrease.* CRC Press, pp. 630.
1645. Schuiling, R. D., (2013). Olivine: a supergreen fuel. Energy, Sustainability and Society, 3: 18-21.
1646. Schuiling, R. D., (2012). Carbon dioxide sequestration, Weathering approaches to. Pp. 1909-1927, In: *Encyclopedia of Sustainability Science and Technology*. Springer. Also, chapter 7, pp. 141-168 in, T. Lenton and N. Vaughan, (eds.), *Geoengineering Responses to Climate Change, Selected Entries from the Encyclopedia of Sustainability Science and Technology*, online: http://www.homepages.ed.ac.uk/shs/Climatechange/Data%20sources/Lenton%20Vaughan%20book.pdf. Also ("Weathering approaches (enhanced) for carbon dioxide sequestration for mitigation of climate change and ocean acidification") version online: http://www.testunit.nl/wp-content/uploads/2015/02/2013-Springer-Encyclopedia.pdf
1647. Schuiling, R. D., and de Boer, P. L., (2013). Six commercially viable ways to reduce $CO_2$ from the atmosphere and/or reduce $CO_2$ emissions. Environmental Sciences Europe, 25: 35-44, online: http://www.enveurope.com/content/pdf/2190-4715-25-35.pdf
1648. Schuiling, R. D., and de Boer, P. L., (2011). Rolling stones; fast weathering of olivine in shallow seas for cost-effective $CO_2$ capture and mitigation of global warming and ocean acidification. Earth Syst. Dynam. Discuss., 2: 551-578.
1649. Schuiling, R. D., and Krugsman, P., (2006). Enhanced weathering: an effective and cheap tool to sequester $CO_2$. Climatic Change, 74: 349-354.
1650. Schuiling, R. D., Wilson, S. A., and Power, I. M., (2011). Enhanced silicate weathering is not limited by silicic acid saturation. PNAS, 108(12): E41.
1651. Schulz, K. G., Riebesell, U., Rost, B., Thoms, S., and Zeebe, R. E., (2006). Determination of the rate constants for the carbon dioxide the bicarbonate interconversion in pH-buffered seawater systems. Marine Chem., 100: 53-65
1652. Schuwer, T. J. H. S., (2015). Feasibility study of a nuclear-powered passenger aircraft: Heat cycle design for the RECREATE cruiser. PhD Thesis. TU Delft, online: http://www.cruiser-feeder.eu/downloads/feasibility-study-of-a-nuclear-powered-passeng.pdf
1653. Schwedt, G., (2015). *Dynamische Chemie: Schnelle Analysen Mit Teststabchen*. Wiley-VCH
1654. Science News, (2014). Atmospheric carbon dioxide used for energy storage materials. Dec. 2, 2014, online: http://www.sciencedaily.com/releases/2014/12/141202140639.htm
1655. Scotproject (Smart $CO_2$ Transformation), (undated). www.scotproject.org Leaflet: www.greenwin.be/en/event/documents/7
1656. Scott, A., (2006). Down on the plastics farm. Royal Soc. Chem., online: http://www.rsc.org/chemistryworld/Issues/2006/August/DownPlasticsFarm.asp
1657. Scottish Enterprise—SCCS, (undated). Building a $CO_2$ storage hub in the Central North Sea: $SCO_2LAND'S$ blueprint for a carbon-proofed economy. Report, 16 pages, online: http://www.sccs.org.uk/images/expertise/misc/SE-CO$_2$-Hub.pdf
1658. Sears, R., and Feve, J. P., (2014). NeuStream—EOR: Supplying field deployable systems for $CO_2$ and power generation for enhanced oil recovery market. NSG slide deck presentation, July $9^{th}$, 20145 online: https://www.u-wyo.edu/eori/_files/co2conference14/feve.pdf
1659. Segev, R., Hasson, D., and Semiat, R., (2013). Modeling $CaCO_3$ precipitation in a fluidized bed $CO_2$ stripping desalination process. Desalination, 311: 192-197
1660. Segev, R., Hasson, D., and Semiat, R., (2011). Improved high recovery brakish water desalination process based on fluidized bed air stripping. Desalination, 281: 75-79
1661. Semelsberger, T. A., Borup, R. L., and Greene, H. L., (2006). Dimethyl ether (DME) as an alternative fuel. J. Power Sources, 156: 497-511.
1662. SES Innovation, (undated). Website: "Energy storing cryogenic carbon capture." Online: http://www.sesinnovation.com/technology/carbon_capture/ES/
1663. Setapar, S. H. M., Khatoon, A., Ahmad, A., Yunus, M.-A. C., and Zaini, M. A. A., (2014). Use of supercritical $CO_2$ and R134a as a solvent for extraction of β-carotene and α-tocopherols from crude palm oil. Asian J. Chem., 26(18): 5911-5916.
1664. Seyyedi, M., and Sohrabi, M., (2015). Enhancing water imbibition rate and oil recovery by carbonated water in carbonate and sandstone. Energy Fuels, 10.1021/acs.energyfuels.5b02644
1665. SFK Leblanc Company (undated). $CO_2$ stunning system. Corporate brochure information online: http://www.sfkleblanc.com/slaughter-solutions/pig/stunning/co2-stunning/SFK-LEBLANC-CO$_2$-Stunner-specs.pdf/
1666. Shaikh, A. A. G., and Sivaram, S., (1996). Organic carbonates. Chem. Rev., 96: 951-976.
1667. Shainyan, B. A., Danilevich, Y. S., Garmazov, Y. L., Finkelstein, A. L., Aisueva, T. S., Turchaninov, V. K., (2008). Novel technology for chlorination of niobium and tantalum oxides and their low-grade ore concentrates. J. Minerals & Materials Characterization & Eng., 7(2): 163-173.
1668. Shand, M. A., (2006). *The Chemistry and Technology of Magnesia*. Wiley, pp. 266.
1669. Shand, M. A., (2016). *Magnesia Cements: From Formula to Application*. Elsevier, pp. 400.
1670. Shell, (2012). Enhanced oil recovery. Shell Global Solutions International B. V., corporate publication, online: http://www.shell.com/energy-and-innovation/overcoming-technology-challenges/making-the-most-of-our-resources/_jcr_content/par/textimage.file/1444730241753/a06d376ee1310bf908aa8a404f95a6d6/eor-brochure-2012.pdf
1671. Shen, C.-T., Chen, P.-Y., Wu, J.-J., Lee, T.-M., Hsu, T.-M., Chang, C.-M. J., Young, C.-C., and Shieh, C.-J., (2011). Purification of algal anti-tyrosinase zeanthin from *Nannochloropsis oculata* using supercritical anti-solvent precipitation. J. Supercrit. Fluids, 55: 955-962.
1672. Shen, J., Kortlever, R., Kas, R., Birdja, Y. Y., Diaz-Morales, O., Kwon, Y., Ledezma-Yanez, I., Schouten, K. J. P., Mul, G., and Koper, M. T. M., (2015). Electrocatalytic reduction of carbon dioxide to carbon monoxide and methane at an immobilized cobalt protoporphyrin. Nature Comms., DOI: 10.1038/ncomms9177
1673. Sherman, L. M., (2007). Carbon nanotubes lots of potential—if the price is right. Plastics Technology, July 2007, online: http://www.ptonline.com/articles/carbon-nanotubes-lots-of-potentialif-the-price-is-right
1674. Shi, J., Jiang, Y., Jiang, Z., Wang, X., Wang, X., Shang, S., Han, P., and Yang, C., (2015). Enzymatic conversion of carbon dioxide. Chem. Soc. Rev., 44(17): 5981-6000.
1675. Shimada, Y., Kume, T., Ishiguro, K., Kurata, R., Kimura, Y., and Shiina, R., (2010). Large-scale extraction of polyphenolics from sweet potato tops and their characterization. Nippon Shokukin Kagaku Kaiski, 57(4): 143-149 (in Japanese with English title, authors and abstract).
1676. Shin, S.-M., Jung, J.-Y., Park, M.-J., Song, J.-W., and Lee, J.-H., (2015). Catalyst-free hydrogen evolution of Si photocathode by thermovoltage-driven solar water splitting. J. Power Sources, 279: 151-156
1677. Shuai, L., and Luterbacher, J., (2016). Organic solvent effects in biomass conversion reactions. ChemSusChem, 9(2): 133-155
1678. Shuai, L., Questell-Santiago, Y. M., and Luterbacher, J. S., (2016). A mild biomass pretreatment using γ-valerolactone for concentrated sugar production. Green Chem., DOI: 10.1039/c5gc02489g
1679. Siemens and Clean Energy Systems, (2006). Oxyfuel turbine technology development program overview. Siemens, AG corporate slide deck, online: http://www.gas-electricpartnership.com/FB1-SIEMENS%20[Compatibility%20Mode].pdf
1680. Siemens and Clean Energy Systems, (2006). Oxy fuel turbine technology development program overview. Siemens Energy, slide deck presentation, online: http://www.co2conference.net/wp-content/uploads/2012/12/2-5_Ortiz_SIEMENS_Final_OxyFuelTechnology_2010.pdf
1681. Siemens and Clean Energy Systems, (2012). Siemens Oil and Gas: answers for Enhanced Oil Recovery. $6^{th}$ Annual CO$_2$ EOR Conference, Jul. 11-12, 2012, slide deck presentation online: https://www.uwyo.edu/eori/_files/co2conference12/seimens_eor%20answers%20for%20wyoming%20conference.pdf 1682. Sigurbjornsson, O., F., (2013). Exporting Icelandic electricity as fuel: CO$_2$ to Vulcanol. Carbon Recycling International, side deck presentation, Jun. 12, 2013, Rekyjavik, online: http://www.co2-electrofuels.org/Links/~/media/CO$_2$_electrofuels/pdf/6_exportingicelandic.ashx 1683. Sigurdsson, H.; Devine, J. D.; Tchua, F. M.; Presser, F. M.; Pringle, M. K. W.; Evans, W. C. (1987). Origin of the lethal gas burst from Lake Monoun, Cameroon. Journal of Volcanology and Geothermal Research, 31: 1-16.

1684. Silva, C. F., Mendes, M. F., Pessoa, F. L. P., and Queiroz, E. M., (2008). Supercritical carbon dioxide extraction of macademic nuts (*Macademia integrifolia*) nut oil: experiments and modeling. Brazilian J. Chem. Eng., 25(1): 175-181.

1685. Silva, E. K., and Meireles, M. A. A., (2014). Encapsulation of food compounds using supercritical technologies: applications of supercritical carbon dioxide as an antisolvent. Food and Public Health, 4(5): 247-258.

1686. Silverman, G., and Rakita, P. E., (2005). Grignard reactions. Van Nostrand's Encyclopedia of Chemistry.

1687. Singapore Report, (2014). Carbon capture & storage/utilization: Singapore perspectives. https://www-w.nccs.gov.sg/sites/nccs/files/Roadmap_CCSU_20140729.pdf 1688. Singh, L. P., Karade, S. R., Bhattacharyya, S. K., Yousuf, M. M., and Ahalawat, S., (2013). Beneficial role of nanosilica in cement based materials—a review. Constr. Build. Mats., 47: 1069-1077.

1689. Singh, M. R., Clark, E, L., and Bell, A. T., (2015). Thermodynamic and achievable efficiencies for solar-driven electrochemical reduction of carbon dioxide to transportation fuels. PNAS, www.pnas.org/cgi/doi/10.1073/pnas.1519212112

1690. Singh, P., Wani, A. B., Karim, A. A., and Langowski, H.-C., (2011). The use of carbon dioxide in the processing of milk and dairy products: a review. Int. J. Dairy Technol., 65(2): 161-177.

1691. Singh, P., and Haines, M., (2014). A review of existing carbon capture and storage cluster projects and future opportunities. Energy Procedia, 63: 7247-7260.

1692. Sixta, H., (2013). Progress in regenerated cellulose fiber production. Aalto University, Finland slide deck presentation, Dec. 3, 2013, online: http://www.costfp1205.com/en/events/Documents/sixtatroedsson3 dec.pdf 1693. Sloss, L., (2015). Potential for enhanced coalbed methane recovery. Clean Coal Centre, Policy Brief, online: http://www.iea-coal.org.uk/documents/83700/9394/Potential-for-enhanced-coalbed-methane-recovery,-CCC/252; Profile summary note, online: http://www.iea-coal.org.uk/documents/83700/9394/Potential-for-enhanced-coalbed-methane-recovery,-CCC/252; Full report (CCC #252), 41pp.

1694. Smart Stones, (2014). The Olivine Foundation, "Smart Stones" brochure, online: http://alvastbedankt.nl/wp-content/uploads/2014/07/Flyerl.pdf 1695. Smil, V., (2000). *Enriching the Earth: Fritz Haber, Carl Bosch and the Transformation of World Food Production.* MIT Press.

1696. Smil, V., (2013). *Making the Modern World: Materials and Dematerialization.* Wiley, pp. 242.

1697. Smirnov, V., (1996). Alumina production in Russia. Part I: historical background. JOM, 48(8): 24-26.

1698. Smith, R. V., and Evans, M. C. W., (1971). Nitrogenase activity in cell-free extracts of the blue-green alga, *Anabaena cylindrica*. J. Bacteriol., 105(3): 913-917

1699. Smits, E., (2014). E-synergy: local collaboration at agriport. Paper online: http://repository.tudelft.nl/assets/uuid:39ca0212-7339-4c00-90aa-17353ad412c2/Ewout_Smits_1503480_P2_Paper.pdf; Associated presentation slide deck online: http://repository.tudelft.nl/assets/uuid:39ca0212-7339-4c00-90aa-17353ad412c2/Ewout_Smits_1503480_Presentation_P5.pdf 1700. Smock, D., (2015). CO$_2$-based plastics production will begin soon. The Molding Blog, Aug. 6, 2015, online: http://www.themoldingblog.com/2015/08/06/co2-based-plastics-production-begin-soon/

1701. Soh, L., (2014). Carbon dioxide solvent applications in a biorefinery. Chapter 2, pp. 9-35 in: S. O. Obare and R. Luque (eds.), *Green Technologies for the Environment*, ACS Symp. Ser., v. 1186. Amer. Chem. Soc.

1702. Soh, L., and Zimmerman, J., (2011). Biodiesel production: The potential of algal lipids extracted with supercritical carbon dioxide. Green Chem., 13(6): 1422-1429.

1703. Soh, L., and Zimmerman, J., (2012). One-pot algal biodiesel production in supercritical carbon dioxide. $10^{th}$ Int. Symp. On Supercrit. Fluids (ISSF 2012) conference paper, online: http://www.supercriticalfluids.com/wp-content/uploads/AP-133-One-Pot-Algal-Biodiesel-Production-in-Supercritical-Carbon-Dioxide.pdf 1704. Soh, L., Curry, J., Beckman, E. J., Zimmerman, J. B., (2014). Effect of system conditions for biodiesel production via transesterification using carbon dioxide-methanol mixtures in the presence of a heterogeneous catalyst. ACS Sustainable Chem. & Eng., 2(3): 387-395.

1705. Sohrabi, M., (2012). An overview of heavy oil recovery studies. Centre for Enhanced Oil Recovery and CO$_2$ Solutions, Heriot Watt University, slide deck presentation online: http://iea-eor.ptrc.ca/2012/assets/s4/4-%20Sohrabi_Session%204_SLIDES.pdf 1706. Sohrabi, M., (2012). Key developments and challenges of enhanced Oil Recovery techniques and CO$_2$ solutions. Centre for Enhanced Oil Recovery and CO$_2$ Solutions, Heriot Watt University, slide deck presentation online: http://globalenergysystemsconference.com/wp-content/uploads/presentations/GES2013_day1_session2_Mehran_Sohrabi.pdf 1707. Sohrabi, M., Emadi, A., Farzenah, S. A., and Ireland, S., (2015). A thorough investigation of mechanisms of enhanced oil recovery by carbonated water injection. Society of Petroleum Engineers, Conference Paper, 2015, Houston, Tex., SPE-175159-MS, pp. 33.

1708. Sohrabi, M., Riazi, M., Jamiolahmady, M., Kechut, N. I., Ireland, S., and Robertson, G., (2011). Carbonated Water Injection (CWI)—a productive way of using CO$_2$ for oil recovery and CO$_2$ storage. Energy Procedia, 4: 2192-2199.

1709. Solargis, (2011). Global horizontal radiation map (annual average), Africa and Middle East. http://solargis.info/doc/_pics/freemaps/1000px/ghi/SolarGIS-Solar-map-Africa-and-Middle-East-en.png 1710. Sommerfelt, S. T., Davidson, J., and Waldrop, T., (2003). Evaluation of full-scale carbon dioxide stripping columns in a coldwater recirculating system. Aquacultural Engineering, 28: 155-169

1711. Sommerfelt, S. T., Vinci, B. J., and Piedrahita, R. H., (2000). Oxygenation and carbon dioxide control in water reuse systems. Aquacultural Engineering, 22: 87-108

1712. Sommerfelt, S. T., Zuhlke, A., Kolarevic, J., Reiten, B. K. M., Selset, R., Gutierrez, X., and Terjesen, B. F., (2015). Effects of alkalinity on ammonia removal, carbon dioxide stripping, and system pH in semi-commercial scale water recirculating aquaculture systems operated with moving bed bioreactors. Aquacultural Engineering, 65: 46-54

1713. Song, C., (2013). Development of $CO_2$ EOR techniques for unlocking resources in tight oil formations. MSc Thesis, University of Regina, Regina, Saskatchewan, Canada, online: http://ourspace.uregina.ca/handle/10294/5475

1714. Song, C., (2001). Tri-reforming: a new process for reducing $CO_2$ emissions. Chemical Innovation, 31(1): 21-26.

1715. Song, C., (2002). $CO_2$ conversion and utilization: an overview. Chapter 1, pp. 2-30, in: C. Song, A. M. Gaffney, and K. Fujimoto, K., (2002). *$CO_2$ Conversion and Utilization*. ACS Symposium Series (Book 809), American Chemical Society, pp. 440, online: http://pubs.acs.org/doi/pdf/10.1021/bk-2002-0809.ch001

1716. Song, C., (2006). Global challenges and strategies for control, conversion and utilization of $CO_2$ for sustainable development involving energy, catalysis, adsorption and chemical processing. Catal. Today, 115: 2-32.

1717. Song, C., Gaffney, A. M., and Fujimoto, K., (2002). *$CO_2$ Conversion and Utilization*. ACS Symposium Series (Book 809), American Chemical Society, pp. 440

1718. Song, C., and Pan, W., (2004). Tri-reforming of methane: a novel concept for catalytic production of industrially useful synthesis gas with desied $H_2$/CO ratios. Catalysis Today, 98(4): 463-484.

1719. Sonoda, J.-I., Narumi, K., Akio, K., Erisa, T., and Toshir, M., (2015). Green rea catechins—pharmacokinetic properties and health beneficial effects. Pharmaceutica Analytica Acta, 6(2): 2153-2435.

1720. Sorensen, J. A., Braunberger, J. R., Liu, G., Smith, S. A., Klenner, R. C. L., Steadman, E. N., and Harju, J. A., (2014). $CO_2$ storage and utilization in tight hydrocarbon-bearing formations: a case study of the Bakken Formation in the Williston Basin. Energy Procedia, 63: 7852-7860

1721. Sorensen, M., Berge, G. M., Thomassen, M., Ruyter, B., Hatlen, B., and Ytrestoil, T., Ass, T. S., and Asgard, T., (2011). Today's and tomorrow's feed ingredients in Norwegian aquaculture. Nofima Report 52/2011. Online: http://www.nofima.no/filearchive/rapport-52-2011.pdf 1722. Sorlien, P. A., (2014). Novel catalyst development—a Norner Verdandi investment. NornerNews04, p 12, online: http://norner.no/content/download/6604/98910/file/Norner%20News%2004.pdf 1723. Spigarelli, B. P., and Kawatra, S. K., (2013). Opportunities and challenges in carbon dioxide capture. J. $CO_2$ Utilization, 1: 69-87/

1724. Spilling, K., Seppala, J., and Tamminen, T., (2010). Inducing autoflocculation in the diatom *Phaeodactylum tricornatum* through $CO_2$ regulation. J. Appl. Phycol., DOI 10.1007/s10811-010-9616-5

1725. Spanova, M., and Daum, G., (2011). Squalene—biochemistry, molecular biology, process biotechnology, and applications. Eur. J. Lipid Sci. Technol., 113(11): 1299-1320.

1726. Spilimbergo, S., Matthews, M. A., and Cinquemani, C., (2011). Supercritical fluid pasteurization and food safety. Chaper 4, pp. 145-183 in A. Proctor (ed.), *Alternatives to Conventional Food Processing*. Royal Society for Chemistry.

1727. Sponholz, P., Mellmann, D., Cordes, C., Alsabeh, P. G., Li, B., Li, Y., Nielsen, M., Junge, H., Dixneuf, P., and Beller, M., (2014). Efficient and selective hydrogen generation from bioethanol using ruthenium pincer-type complexes. ChemSusChem, 7(9): 2419-2422.

1728. SRI Equity Research, (2015). Liquid Light Inc., Process technology to convert $CO_2$ to major chemicals. (Analyst: Sven Ferguson). Online: http://sriequityresearch.com/sri-equity-research-initiated-coverage-of-liquid-light-inc/

1729. Sridach, W., (2010). The environmentally benign pulping process of non-wood fibers. Suranaree J. Sci. Tech., 17(2): 105-123.

1730. Sridhar, N., Agarwal, A., and Rode, E., (2012). Electrochemical production of chemicals: applicability to $CO_2$ conversion. DNV slide deck presentation, Dec. 10, 2012, online: http://www.arpa-e.energy.gov/sites/default/files/documents/files/3_Narasi_SridharDNV.pdf 1731. Srinivas, K., and King, J. W., (2010). Supercritical carbon dioxide and subcritical water: complimentary agents in the processing of functional foods. Chapter 3, pp. 39-78 in: J. Smith and E. Charter, (eds.), Functional Food Product Development. Wiley-Blackwell.

1732. Stanger, R., Sporl, R., Paneru, M., Grathwohl, S., Weidmann, M., Scheffknecht, G., McDonald, D., Myohanen, K., Ritvanen, J., Rahiala, S., Hyppanen, T., Mletzko, J., Kather, A., and Santos, S., (2015). Oxyfuel combustion for $CO_2$ capture in power plants. Int. J. Greenhouse Gas Control, 40 (September): 55-125.

1733. Starns, T., Martin, C., Hanson, R., Lagarenne, J., Barnett, M., (2015). Integrating liquid air energy storage (LAES) storage technology within industry to provide operational flexibility and other benefits for existing generating assets. ADA-ES slide deck presentation, February, http://www.adaes.com/wp-content/uploads/F8.4-Starns-LAES_EUEC.pdf, 2015, online:

1734. Stavroulias, S., and Panayiotou, C., (2005). Determination of optimum conditions for the extraction of squalene from olive pomace with supercritical $CO_2$. Chem. Biochem. Eng. Q., 19(4): 373-381.

1735. Stempien, J. P., Sun, Q., and Chan, S. H., (2013). Solid oxide electrolyzer cell modeling: a review. J. Power Technologies, 93(4): 216-246.

1736. Stephan, L., and Boussiba, S., (2014). Advances in the production of high-value products by microalgae. Industrial Biotechnology, 10(3): 169-183

1737. Stewart, G., (2003). Dry cleaning with liquid carbon dioxide. Chapter 13, pp. 215-227, in: J. M. DeSimone and W. Tumas (eds.), *Green Chemistry Using Liquid and Supercritical Carbon Dioxide*. Oxford University Press, pp. 288.

1738. Stoddard, S. R., (1895). *Lake George (Illustrated) and Lake Champlain. Saratoga Springs: Its Mineral Waters, Their Medicinal Qualities and Suggestions as to When, How, and Where to Drink Them, With Varioius Other Matters of Interest*. Online: https://catalog.hathitrust.org/Record/009592257

1739. Stolaroff, J. K., and Bourcier, W. L., (2014). Thermodynamic assessment of microencapsulated sodium carbonate slurry for carbon capture. Energy Procedia, 63: 2331-2335.

1740. Stoots, C., (2011). Electrolysis for synthetic fuels production. Idaho National Laboratory, Aug. 25-26, 2011, Topsoe Catalysis Forum, slide deck presentation, online: http://www.topsoe.com/sites/default/files/topsoe_scot_electrolysis_synthetic_fuel_production.pdf 1741. Stossel, E., (2013). Budenheim carbonic acid process. Budenheim corporation slide deck presentation, online: http://re-water-braunschweig.com/wp-content/uploads/stoessel_et_al_budenheim_carbonic_acid_process.pdf 1742. Straathof, A. J. J., (2013). Transformation of biomass into commodity chemicals using enzymes or cells. Chem. Rev., 114(3): 1871-1908

1743. Strahan, R., (2013). Liquid air technologies: a guide to the potential. Center for Low Carbon Futures and the Liquid Air Energy Network, online: http://www.lowcarbonfutures.org/sites/default/files/potential-guide.pdf 1744. Stranberg, T. E., Tilvis, R. S., and Miettinen, T. A., (1990). Metabolic variables of cholesterol during squalene feeding in humans: comparison with cholestyramine treatment. J. Lipid Res., 31: 1637-1643.

1745. Studt, F., Behrens, M., Kunkes, E. L., Thomas, N., Zander, S., Tarasov, A., Schumann, J., Frei, E., Varley, J. B., Abild-Pedersen, Norskov, J. K., and Schlogl, R., (2015). The mechanism of CO and $CO_2$ hydrogenation to methanol over Cu-base catalysts. ChemCatChem, 7(7): 1105-1111.

1746. Studt, F., Sharafutdinov, I., Abild-Pedersen, F., Elkjaer, C. F., Hummelshoj, J. S., Dahl, S., Chorkendorff, I., and Norskov, J. K., (2014). Discovery of a Ni—Ga catalyst for carbon dioxide reduction to methanol. Nature Chemistry, 6, DOI: 10.1038/NCHEM.1873

1747. Stumm, W., and Morgan, J. J., (1996). *Aquatic Chemistry: Chemical Equilibria and Rates in Natural Waters*, $3^{rd}$ Edition, Wiley, pp. 1040

1748. Styring, P., de Coninck, H., and Reith, H., (2011). Carbon capture and utilization in the green economy: Using $CO_2$ to manufacture fuel, chemicals and materials. Online: http://co2chem.co.uk/wp-content/uploads/2012/06/CCU%20in%20the%20green%20economy%20report.pdf 1749. Styring, P., and Quadrelli, E. A., (2014). *Cabon Dioxide Utilization: Closing the Carbon Cycle*. Elsevier, pp, 336.

1750. Su, J., Lu, M., and Lin, H., (2015). High yield production of formate by hydrogenating $CO_2$ derived ammonium carbamate/carbonate at room temperature. Green Chem., 17: 2769-2773.

1751. Su, J., Yang, L., Lu, M., and Lin, H., (2015). Highly efficient hydrogen storage system based on ammonium bicarbonate/formate redox equilibrium over palladium nanocatalysts. ChemSusChem, 8(5): 813-816.

1752. Su, T. M., Qin, Z.-z., Ji, H.-b., Jiang, Y.-x., and Huang, G., (2015). Recent advances in the photocatalytic reduction of carbon dioxide. Environ. Chem. Lett., DOI 10.1007/s10311-015-0528-0.

1753. Suetsugu, T., et al., (2013). Supercritical $CO_2$ extraction of essential oil from Kabosu (*Citrus sphaerocarpa* Tanaka) peel. Flavour, 2: 18-26.

1754. Sugimoto, H., and Inoue, S., (2006). Recent progress in the synthesis of polymers based on carbon dioxide. Pure Appl. Chem., 78(10): 1823-1834. Online: http://pac.iupac.org/publications/pac/pdf/2006/pdf/7810x1823.pdf 1755. Suh, J.-S., Hermawan, D., and Kawai, S., (2000). Manufacture of cement-bonded particleboars from Korean pine and larch by curing of supercritical $CO_2$ fluid. Mokchae Konghak, 28(4): 41-50

1756. Suib, S. L., (2013, editor). *New and Future developments in Catalysis: Activation of Carbon Dioxide*. Elsevier, pp. 658.

1757. Sukenik, A., and Shelef, G., (1984). Algal autoflocculation—verification and proposed mechanisms. Biotechnol. Bioeng., 26: 142-147

1758. Sullivan, B. P., Krist, K., and Guard, H. E., (1993). *Electrochemical and Electrocatalytic Reactions of Carbon Dioxide*. Elsevier, pp. 314.

1759. Sumida, K., Rogow, D. L., Mason, J. A., McDonald, T. M., Bloch, E. D., Herm, Z. R., Bae, T.-H., and Long, J.-R., (2012). Carbob dioxide capture in metal-organic frameworks. Chem. Rev., 112: 724-781.

1760. Sun, H., Mu, T., Xi, L., Zhang, M., and Chen, J., (2014). Sweet potato (*Ipomoea batatas* L.) leaves as nutritional and functional foods. Food Chem., 156: 380-389.

1761. Sun, Y., Lin, L., Deng, H., Peng, H., Li, J., Sun, R., and Liu, S., (2008). Hydrolysis of bamboo fiber cellulose in formic acid. Front. For. China, 3(4): 480-486.

1762. Sunfire GmbH, (2014). Closing the carbon cycle. (Website: www.sunfire.de) Slide deck presentation online: http://www.now-gmbh.de/fileadmin/user_upload/DOWNLOAD/Workshop_Marktplatz_Zulieferer/Mai_Sunfire.pdf Also: http://www.sunfire.de/wp-content/uploads/BILit_FactSheet_POWER-TO-LIQUIDS_EMS_en.pdf 1763. Supaibulwattana, K., Kuntawunginn, W., Cha-um, S., and Kirdmanee, C., (2011). Artemisinin accumulation and enhanced net photosynthetic rate in Qinghao (*Artemisia annua* L.) hardened in vitro in enriched-$CO_2$ photoautotrophic conditions. Plant Omics J. (POJ), 4(2): 75-81.

1764. Surampalli, R. Y., Zhang, T. C., et al., (2015). *Carbon Capture and Storage: Physical, Chemical and Biological Methods*. ASCE (American Society of Civil Engineers, E-book), http://dx.doi.org/10.1061/9780784413678

1765. Suraweera, D. D., Groom, T., and Nicolas, M. E., (2015). Impact of elevated atmospheric carbon dioxide and water deficit on flower development and pyrethrin accumulation in pyrethrum. Procedia Environmental Sci., 29: 5-6.

1766. Sustania 100, (2013). Zero emissions transport refrigeration system: Solutions from Thermo King. online: http://www.sustainia.me/items/zero-emissions-transport-refrigeration-system/

1767. Sustano, S., (2014). Textile dry cleaning using carbon dioxide: process, apparatus and mechanical action. PhD Thesis, Technical University of Delft, online: http://repository.tudelft.nl/assets/uuid:75cbfe8e-561e-4809-93cc-6d1c20e30555/Thesis_Manuscript_-_prom_6_-print.pdf 1768. Sustano, S., Dutschk, V., Mankiewicz, J., van Roosmalen, M., Warmoeskerken, M. M. C. G., and Witkamp, G.-J., (2014a). $CO_2$ dry cleaning: acoustic cavitation and other mechanisms to induce mechanical action. J. Supercrit. Fluids, 89: 1-7.

1769. Sustano, S., van Roosmalen, M., and Witkamp, G.-J., (2014b). Mechanical action in $CO_2$ dry cleaning. J. Supercrit. Fluids, 93: 138-143.

1770. Suzuki, T., Toriumi, M., Sakemi, T., Masui, N., Yano, S., Fujiya, H., and Furukawa, H., (2013). Conceptual design of $CO_2$ transportation system for CCS. Energy Procedia, 37: 2989-2996.

1771. Taherimehr, M., and Pesccarmona, P. P., (2014). Green polycarbonates prepared by copolymerization of $CO_2$ with epoxides. J. Appl. Polym. Sci., DOI: 10.1002/APP.41141

1772. Tahil, W., (2014). The supercritical $CO_2$ closed cycle electric turbofan specific fuel consumption of 0.357 lb/lbf/hr. Meridian International Research, online: https://www.academia.edu/7880039/A Supercritical_CO_2_Closed_Cycle_Turbofan 1773. Takeda, H., Koizumi, H., Okamoto, K., and Ishitani, O., (2014). Photocatalytic $CO_2$ reduction using a Mn complex as a catalyst. Chem. Commun., 50: 1491-1493.

1774. Talling, J. F., (2010). pH, the $CO_2$ system and freshwater science. Freshwater Reviews, 3: 133-146, online: https://www.fba.org.uk/journals/index.php/FRJ/article/viewFile/156/241

1775. Tamura, J., Ono, A., Sugano, Y., Huang, C., Nishizawa, H., and Mikoshiba, S., (2015). Electrochemical reduction of $CO_2$ to ethylene glycol on imidazolium ion-terminated self-assembly monolayer-modified Au electrodes in an aqueous solution. Phy. Chem. Chem. Phys., 17: 26072-26078.

1776. Tanchoux, N., and Leitner, W., (2002). Supercritical carbon dioxide as an environmentally benign medium for chemical synthesis. Chapter 21, pp. 482-501 in J. Clark (ed.), *Handbook of Green Chemistry and Technology*. Blackwell.

1777. Tasin, A., (2005). The greenhouse concept. GE Slide deck presentation online: http://www.understandingchp.com/appguide/DataFiles/GE_CHP_Greenhouses_wCO2.pdf 1778. Tassi, F., Vaselli, O., Tedesco, D., and Montegrossi, G., Darrah, T., Cuoco, E., Mapendano, M. Y., Poreda, R., and Delgado Huertas, A., (2009). Water and gas chemistry at Lake Kivu (DRC): geochemical evidence of vertical and horizontal heterogeneities in a multibasin structure. Geochem. Geophys. Geosystems, 10(2): online: http://onlinelibrary.wiley.com/doi/10.1029/2008GC002191/epdf 1779. Tassou, S. A., Hadawey, A., Ge, Y. T., and Lagroy de Groutte, B., (undated). Carbon dioxide cryogenic transport refrigeration systems. Online: http://www.grimsby.ac.uk/documents/defra/tms-casestudy.pdf 1780. Tata Power, (2012). Clean coal opportunities. Corporate slide deck presentation, Nov. 16, 2015, online: https://www.worldcoal.org/sites/default/files/Address%20by%20 Sydney%20Lobo.pdf 1781. Taub, D. R., (2010). Effects of rising atmospheric concentrations of carbon dioxide on plants. NatureEducation, online: http://www.nature.com/scitable/knowledge/library/effects-of-rising-atmospheric-concentrations-of-carbon-13254108

1782. Taylor, C. M. V., Rubin, J. B., Carey, J. W., Jones, R., Baglin, F. G., (1997). Next generation enhancement of cements by the addition of industrial wastes and subsequent treatment with supercritical $CO_2$. Conference paper, 1997 Green Chemistry and Engineering Conference: Implementing Vision 2020 for the Environment. American Chemical Society, Washington D.C., June 23-25, online: http://www.osti.gov/scitech/servlets/purl/589871

1783. Taylor, D. K., Carbonelli, R., and DeSimone, J. M., (2000). Opportunities for pollution prevention and energy efficiency enabled by the carbon dioxide technology platform. Ann. Rev. Energy Environ., 25: 115-146.

1784. Taylor, I. (2014a). *Is Africa Rising? BRICS—Diversifying Dependency*. James Currey, pp, 208.

1785. Taylor, I., (2014b). The BRICS in Africa: Diversifying Dependency. (Online essay: https://www.codesria.org/IMG/pdf/ian_taylor_the_brics_in_africa_diversifying_dependency.pdf)

1786. TCE News, (2013). 'Impossible material' made by accident. TCE (The Chemical Engineer) News, September 2013, pp. 8, online: https://www.tcetoday.com/~/media/Documents/TCE/Articles/2013/867/867news_complete.pdf 1787. Tchambak, E., Oyeneyin, B., and Oluyemi, G., (2012). Heavy oil recovery: a cold process using $CO_2$-EOR technique. Adv. Msts. Res., 367: 421-429.

1788. TecEco (website sections, undated). History of magnesium in hydraulic cements. Online: http://www.tececo.com/history.magnesium_hydraulic_cements.php; Rosendale cements. Online: http://www.tececo.com/links.cement_rosendale.php 1789. Teir, S., et al., (2010). Potential for carbon capture and storage (CCS) in the Nordic region. VTT Research Notes 2556. Online: http://www.vtt.fi/inf/pdf/tiedotteet/2010/T2556.pdf 1790. Teir, S., Revitzer, H., Eloneva, S., Fogelholm, C.-J., and Zevenhoven, R., (2007). Dissolution of natural serpentinite in mineral and organic acids. Int. J. Miner. Process, 83: 36-46.

1791. Teuner, St. C., Neumann, P., and Von Linde, F., (2001) The Calcor Standard and Calcor Economy Processes. Oil & Gas European Magazine, 3/2001, pp. 44-46. Online: http://www.caloric.com/upload/Products/Caloric_CO2Reforming.pdf 1792. Texiera da Silva, J. A., (2013). Orchids: advances in tissue culture, genetics, phytochemistry and transgenic biotechnology. Floriculture and Ornamental Biotechnology, 7(1): 1-52 Online: http://www.globalsciencebooks.info/JournalsSup/images/Sample/FOB_7(1)1-52o.pdf 1793. Thanh, N. T., Murthy, H. N., and Paek, K. Y., (2014). Optimization of ginseng cell culture in airlift bioreactors and developing the large-scale production system. Industrial Crops and Products, 60: 343-348.

1794. Thauer, R. K., (1972). $CO_2$-reduction to formate by NADPH. The initial step in the total synthesis of acetate from $CO_2$ in *Clostridium thermoaceticum*. FEBS Lett., 27: 111-115.

1795. Thermo King, (undated). Cryo Tech: Single and multi temperature refrigeration system for truck and trailer. Online brochure: http://www.thermoking.no/uploads/2/4/8/5/24859428/cryo.pdf 1796. Theulen, J., (2015a). Turning $CO_2$ into a valuable asset: studies and projects at Heidelberg Cement. Slide deck presentation, 21 May 2015, online: http://www.norcem.no/no/system/files_force/assets/document/5_-_ccu_21_may_2015_hc_jan_theulen.pdf?download=1

1797. Theulen, J., (2015b). $CO_2$ will become a valuable asset. Heidelberg Cement slide deck presentation, May 2015.

1798. Thimsen, D., (2014). Oxy-fuel combustion opportunities for natural gas power systems. EPRI slide deck presentation, USEA Workshop on Technology Pathways Forward for Carbon Capture & Storage on Natural Gas Power Systems, Apr. 22, 2014, online: https://www.usea.org/sites/default/files/event-/Thimsen%202014-04-22%20USEA%20Oxy-Natural%20Gas.pdf 1799. Thomas, D. J., Sullivan, S. L., Price, A. L., and Zimmerman, S. M., (2005). Common freshwater cyanobacteria grow in 100% $CO_2$. Atrobiology, 5(1): 66-74

1800. Thomas, E. R., and Denton, R. D., (1988). Conceptual studies for CO2/natural gas separation using controlled freeze zone (CFZ) process. Gas Separation & Purification, 2(2): 84-89

1801. Thomas, R., (2007). MgO Board. Walls & Ceilings Magazine, November 2007 issue, online: http://magnumbp.com/articles/Walls-Ceilings-Article.pdf 1802. Thorhallsson, S., (1997). Fact-finding and assessment of the CO2 source of Sillunchi. Field Report. Prkustofnun, National Energy Authority (Iceland). Online: http://www.os.is/gogn/Greinargerdir/Grg-OS-1997/STh-97-01.pdf 1803. Thorleifson, L. H., (2011). Potential for implementation of mineral carbonation as a carbon sequestration method in Minnesota. Minnesota Geological Survey Open File Report OFR-11-2, online: http://conservancy.umn.edu/handle/11299//117343

1804. ThyssenKrupp, (undated). Propylene oxide: the Evonik—Uhde HPPO technology. ThyssenKrupp online brochure: http://www.thyssenkrupp-industrial-solutions.com/fileadmin/documents/brochures/uhde_brochures_pdf_en_10000032.pdf 1805. ThyssenKrupp, (undated online brochures). http://www.thyssenkrupp-industrial-solutions.com/fileadmin/documents/brochures/uhde_brochures_pdf_en_2.pdf; http://www.thyssenkrupp-uhdemexico.com/fileadmin/documents/brochures/789570a3-cee9-425e-8549-c161ad7146fa.pdf 1806. Tietze, K., (1978). Geophysikalische Untersuchungen des Kivusees und seiner ungewohnlichen zur Methangaslagerstatte—Schichtung, Dynamik und Gasgehalt des Seewassers. (Doctoral) Dissertation Christian-Albrechts-Universitat Kiel. 149 pp.

1807. Tietze, K., (1980a). The Genesis of the Methane in Lake Kivu (Central Africa). Geologische Rundschau, v. 69(2): 452-472.

1808. Tietze, K., (1980b). The Unique Methane Gas Deposit in Lake Kivu (Central Africa)—Stratification, Dynamics, Genesis and Development. In: Unconventional Gas Recovery Symposium, SPE/DOE8957 (Society of Petroleum Engineers), pp. 275-288.

1809. Tietze, K., (1992). Cyclic gas bursts: are they a "usual" feature of Lake Nyos and other gas-bearing lakes? In: Freeth et al., (eds), Natural Hazards in West and Central Africa. Earth Evolution Series, International Monograph Series on Interdisciplinary Earth Sciences Research and Applications, pp. 97-107.

1810. Tietze, K. (2000). Lake Kivu Gas Development and Promotion-Related Issues: Safe and Environmentally Sound Exploitation. Final Report to the Ministry of Energy, Water and Natural Resources Unit for Promotion and Exploitation of Lake Kivu Gas. (Online available.)

1811. Tietze, K. (2007). Basic plan for monitoring, regulating and steering exploitation of the unique methane gas deposit in Lake Kivu: Safely, Environmentally soundly and with optimal yield. Copyright, PDT GmbH/Dr Klaus Tietze, Celle, Germany. 201 pages.

1812. Tietze, K., Geyh, M., Muller, H., Schroder, L., Stahl, W., and Wehner, H., (1980). The genesis of methane in Lake Kivu (Central Africa). Geol. Rundsch. 69: 452-472.

1813. Tietze, K., and Maier-Reimer, E., (1977). Mathematische-physikalische Untersuchungen zur Erschliessung der Methangaslagerstatte im Kivusee—Zaire. Bundesanstalt fir Geowissenschaften und Rohstoffe (BGR).

1814. Tillema, O., (2015). Rotterdam Opslag en Opvang Demonstratieproject (ROAD): Project update and lessons learnt. ROAD slide deck presentation, May 13, 2015, online: http://conference.co2geonet.com/media/1064/european-north-american-13_tillema.pdf 1815. Timlick, B., (2014). Fumigation with $CO_2$ for stored product insect control. Canadian Grain Commission, online presentation slide deck: http://umanitoba.ca/faculties/engineering/departments/biosystems/pdf/Fumigation with_CO2.pdf 1816. Timmons, M. B., and Ebeling, J. M., (2007, 2010, 2013). *Recirculating Aquaculture*. $1^{st}$ (Cayuga Aqua Ventures), $2^{nd}$ (Northeastern Regional Aquaculture Center), and $3^{rd}$ editions (Ithaca Publishing Co.).

1817. Timmons, M. B., Ebeling, J. M., Wheaton, F. W., Summerfelt, S. T., and Vinci, B. J., (2001, 2002). *Recirculating Aquaculture Systems*. $1^{st}$ (Cayuga Aqua Ventures), and $2^{nd}$ (Cayuga Aqua Ventures) editions 1818. Tisserat, B., (2002). Influence of ultra-high carbon dioxide levels on growth and morphogenesis of Lamiaceae species in soil. J. Herbs, Spices & Medicinal Plants, 9(1): 81-89.

1819. Tisserat, B., and Vaughn, S. F., (2001). Essential oils enhanced by ultra-high carbon dioxide levels from Lamiaceae species grown in vitro and in vivo. Plant Cell Reports, 20: 361-368.

1820. TNO, (2008). K12-B, $CO_2$ storage and enhanced gas recovery. TNO information note, online: https://www.tno.nl/media/1581/357beno.pdf 1821. Todd, D. M., (2013). Innovesca bets on amaranth plants from Rwanda. Pittsburgh Post-Gazette, Sep. 13, 2013, online: http://www.post-gazette.com/business/businessnews/2013/09/13/Innovesca-bets-on-amaranth-plants-from-Rwanda/stories/201309130208

1822. Tolley, W. K., and Tester, L. S., (1989). Supercritical $CO_2$ solubility of TiCl4. Bureau of Mines Report of Investigations RI 9216, online: http://stacks.cdc.gov/view/cdc/10726/cdc_10726_DS1.pdf 1823. Tolley, W. K., Izatt, R. M., and Oscarson, J. L., (1992). Titanium tetrachloride-supercritical carbon dioxide interaction: a solvent extraction and thermodynamic study. Metallurg. Trans. B, 23B: 65-72.

1824. Tomita, K., Machmudah, S., Wahyudiono, Fukuzato, W., Kanada, H., Quitain, A. T., Sasaki, M., and Goto, M., (2014). Extraction of rice bran oil by supercritical carbon dioxide and solubility consideration. Separation and Purification Technol., 125: 319-325.

1825. Torabi, F., Jamaloei, B. Y., Stengler, B. M., and Jackson, D. E., (2012). The evaluation of $CO_2$-based vapour extraction (VAPEX) process for heavy oil recovery. J. Petrol. Prod. Technol., 2: 93-105.

1826. Torella, J. P., Gagliardi, C. J., Chen, J. S., Bediako, D. K., Colon, B., Way, J. C., Silver, P. A., and Nocera, D. G., (2015). Efficient solar-to-fuels production from a hybrid microbial-water-splitting catalyst system. PNAS, 112(8): 2337-2342.

1827. Tornow, C. E., Thorson, M. R., Ma, S., Gewirth, A. A., and Kenis, P. J. A., (2012). Nitrogen-based catalysts for the electrochemical reduction of $CO_2$ to CO. J. A. Chem. Soc., 134(48): 19520-19523.

1828. Toshiba, (2013). The NET power cycle and the combustor and turbine development. Toshiba Corp., slide deck presentation, March 2013, online: http://www.anle-crd.com.au/LiteratureRetrieve.aspx?ID=136064

1829. Toshiba, (2014). Press release: Toshiba supplies a first-of-a-kind supercritical $CO_2$ turbine to new thermal power generation system demonstration plant built in Texas, USA. Online: http://news.toshiba.com/press-release/corporate/toshiba-supplies-first-kind-supercritical-co2-turbine-new-thermal-power-gene 1830. Tran, K.-C., (2011) Recycling carbon dioxide from industrial emissions into renewable methanol. Carbon Recycling International slide deck presentation, online: http://www.iass-potsdam.de/sites/default/files/files/tran_cri_co2torenewablemeoh_0.pdf 1831. Tran, K.-C., (2010). Making renewable fuel by carbon recycling. Carbon Recycling International slide deck presentation, online: http://newenergy.is/gogn/Radstefnur/3mai2010/carbon_recycling_international_cri_overview.pdf 1832. Tremblay, P.-L., and Zhang, T., (2015). Electrifying microbes for the production of chemicals. Frontiers in Microbiology, 6, article 201, DOI: 10.3389/fmicb.2015.00201

1833. Trieb, F., (2013). Power from the desert: DLR studies on the Desertec project. Pp. 110-117 in: R. Wengenmayr and Th. Buhrke (eds.), *Renewable Energy: Sustainable Energy Concepts for the Future*. Wiley-VCH.

1834. Truong, V.-D., McFeeters, R. F., Thompson, R. T., Dean, L. L. and Shofran, B., (2007). Phenolic acid content and composition in leaves and roots of common commercial sweetpotato (*Ipomea batatas* L.) cultivars in the United States. J. Food Sci., 72(6): C343-C349.

1835. Tsuji, Y., and Fujihara, T., (2012). Carbon dioxide as a carbon source in organic transformation: carbon-carbon bond forming reactions by transition-metal catalysts. Chem. Commun., 48: 9956-9964.

1836. Tweddle, G., (2014). Coal & natural gas chemicals. Slide deck presentation, Tecnon OrbiChem marketing seminar at AIPC 2014, Pattaya, 15 May 2014, online: http://www.orbichem.com/userfiles/APIC%202014/APIC2014_02_Gillian_Tweddle.pdf 1837. Tweed, K., (2015). Wind turbines power liquid-air energy storage. IEEE Spectrum, Jul. 14, 2015, Online: http://spectrum.ieee.org/energywise/energy/environment/wind-turbines-power-liquid-air-energy-storage 1838. Tzoganakis, C., (undated). Symposium documents, Institute for Polymer Research 27$^{th}$ Annual Symposium, "Processing of polymers with supercritical $CO_2$," online: https://uwaterloo.ca/institute-polymer-research/sites/ca.institute-polymer-research/files/uploads/files/tzoganakis_costas.pdf 1839. Ueki, T., Nevin, K. P., Woodard, T. L., and Lovley, D. R., (2014). Converting carbon dioxide to butyrate with an engineered strain of *Clostridium ljungdahlii*. mBio, 5(5) e01636-14, online: http://mbio.asm.org/content/5/5/e01636-14.full 1840. Ullah, H., Ahmad, S., Thompson, A. K., Ahmad, W., and Nawaz, M. A., (2010). Storage of ripe mango (*Mangifera indica* L.) CV. Alphonso in controlled atmosphere with elevated $CO_2$. Pak. J. Bot., 42(3): 2077-2084.

1841. UNEP, (2015). Building inclusive green economies in Africa. Experience and lessons learned, 2010-2015, pp 50. Online: http://www.unep.org/greeneconomy/Portals/88/documents/GEI%20Highlights/EC_AFRICA_SYNTREPORT_FINAL_10FEB-c.pdf 1842. UNEP, (2014). Green economy sectoral study on energy—Rwanda. Online: http://www.unep.org/greeneconomy/Portals/88/documents/GEI%20Highlights/Green_Economy_Rwanda_Interieur_Web.pdf 1843. UNIDO/United Nations Industrial Development Organization, (2015). Rwanda, basic information, 2014. http://www.unido.org/Data1/IndStatBrief/Basic_Information.cfm?Country=RWA 1844. UNIDO/United Nations Industrial Development Organization, (2015). Competitive industrial performance report 2014. Authors: S. Upadhyaya and S. M. Yaganeh Online: http://www.unido.or.jp/en/publications/reports/1772/; http://www.researchgate.net/publication/279175722_Competitive_Industrial_Performance_Report_2014

1845. UNIDO/United Nations Industrial Development Organization, (2013). Competitive industrial performance report 2012/2013. Online: https://www.unido.org/fileadmin/user_media/Services/PSD/Competitive_Industrial_Performance_Report_UNIDO_2012_2013.PDF 1846. UNIDO, (undated). Technical notes: structure of the CIP indicators and industrial development scoreboard (IDS) 2007. Online: https://www.unido.org/fileadmin/user_media/Services/Research_and_Statistics/Technical_notes.pdf 1847. Unluer, C., (2015). Development of novel cements with optimized carbon capture capabilities. Slide deck presentation, 2015 International Concrete Sustainability Conference, May 11-13, 2015, Miami, Fla., USA, online: http://mdclips.nrmcaevents.org/?nav=display&file=745

1848. Unluer, C., (2012). Enhancing the carbonation of reactive magnesia cement-based porous blocks. PhD Thesis, University of Cambridge, 1849. Unluer, C., and Al-Tabbaa, A., (2015a). The role of brucite, ground granulated blastfurnace slag, and magnesium silicates in the carbonation and performance of MgO cements. Construction and Building Materials, 94: 629-643.

1850. Unluer, C., and Al-Tabbaa, A., (2015b). Reply to the discussion of the papers "*Impact of hydrated magnesium carbonate additives on the carbonation of reactive MgO cements*" and "*Enhancing the carbonation of MgO cement porous blocks through improved curing conditions*", by S. A. Walling and J. L. Provis. Cement and Concrete Res., 79: 427-430.

1851. Unluer, C., and Al-Tabbaa, A., (2014). Enhancing the carbonation of MgO cement porous blocks through improved curing conditions. Cement and Concrete Res., 59: 55-65.

1852. Unluer, C., and Al-Tabbaa, A., (2013). Impact of hydrated magnesium carbonate additives on the carbonation of reactive MgO cements. Cement and Concrete Res., 54: 87-97.

1853. UOP, (2007). Methanol to olefins (MTO): development of a commercial catalytic process. Corporate slide deck presentation by S. R. Bare, online: http://www.fhi-berlin.mpg.de/acnew/department/pages/teaching/pages/teaching_wintersemester_2007_2008/bare_mto_301107.pdf 1854. UOP, (2013). Advanced MTO: breakthrough technology for the profitable production of light olefins. Corporate slide deck presentation by R. Kempf, online: http://www.wraconferences.com/sites/default/files/day%202%201130%20petchemRick%20Kempf.pdf 1855. UOP, (2014). Methanol to olefins. A pillar of capacity additions in China, but does MTO have a role in India? Corporate slide deck presentation, online: http://www.petrochemconclave.com/presentation/2014/Mr.JGregor.pdf 1856. Upreti, S. R., Lohi, A., Kapadia, R. A., and El-Haj, R., Vapor extraction of heavy oil and bitumen: a review. Energy & Fuels, 21(3): 1562-1574.

1857. Urakawa, A., and Sa, J., (2014). $CO_2$ to fuels. Chapter 3, pp. 93-122, in: Jacinto Sa, (Ed.) *Fuel Production with Heterogeneous Catalysis*. CRC Press 1858. USDOE, (undated). Supercritical $CO_2$ power cycles. US Department of Energy, website section accessed Jan. 27, 2016: http://www.netl.doe.gov/research/coal/energy-systems/turbines/supercritical-co2-power-cycles including Turbines Project Information: http://www.netl.doe.gov/research/coal/energy-systems/turbines/project-information 1859. USEA, (undated). Building consensus on carbon capture, utilization and storage (CCUS) and clean energy systems. United States Energy Association, online information: https://www.usea.org/program/building-consensus-carbon-capture-utilization-and-storage-ccus-and-clean-energy-systems 1860. USEIA, (2015). Global petroleum and other liquids. In: Short-term Energy Outlook, US Energy Information Agency, online: http://www.eia.gov/forecasts/steo/report/global_oil.cfm (Estimate: ~35 billion barrels/yrx~0.136 tonne/barrel=~5 billion tonnes/yr liquid transport fuels production)

1861. USGS, (2015). Bauxite and alumina. US Geological Survey report, online: http://minerals.usgs.gov/minerals/pubs/commodity/bauxite/mcs-2015-bauxi.pdf 1862. USGS, (2015). Iron ore. US Geological Survey report, online: http://minerals.usgs.gov/minerals/pubs/commodity/iron_ore/mcs-2015-feore.pdf 1863. Vale, S. (2008). Megastructures. Online: http://www.royalpride.nl/tomato/images/file/RPH025.PDF 1864. Valigra, L., (2015). Local power: Peregrine Turbine's new approach to distributed energy generation. Mainebiz, Febriary 23, 2015, online: http://www.mainebiz.biz/article/20150223/CURRENTEDITION/302189997/local-power:-peregrine-turbine's-new-approach-to-distributed-energy-generation 1865. Valizadegan, O., Pourmirza, A. A., Safirilizadah, M. H., (2014). The impact of carbon dioxide in stored-product insect treatment with phosphine. African J. Biotech., 11(23): 6377-6382.

1866. van der Assen, N., and Bardow, A., (2014). Life cycle assessment of polyols for polyurethane production using $CO_2$ as feedstock: insights from an industrial case study. Greem Chem., 16: 3272-3280.

1867. van der Ben, C., (2011). Carbon capture and storage: reliable cost effective $CO_2$ shipping through statistical modeling. Rotterdam Climate Initiative slide deck presentation, online: http://www.systemsnavigator.com/DSF2011/looking_back/day_1/VOPAK/Microsoft_PowerPoint_-_Decision_Science_Forummpres_dd_18-10-11.pdf 1868. van der Kraan, M., (2009). Microbial processes in petroleum reservoirs. PhD Thesis, Technical University of Delft, online:

1869. van der Meer, Kreft, E., Geel, C. R., D'Hoore, D., and Hartman, J., (2009). Enhanced gas recovery testing in the K-12-B reservoir by $CO_2$ injection, a reservoir engineering study. $CO_2$—CATO report, online: http://www.co2-cato.org/cato-download/587/20090917_123325_Meer_EGR_k12b.pdf 1870. van der Veen, R., (2012). Diffusion of combined heat and power in Dutch greenhouses—a case study. Project final report, Delft University of Technology, online: http://repository.tudelft.nl/view/ir/uuid:df888718-fa67-4aba-b336-4f06e929b56c 1871. van Eerten-Jansen, M. C. A. A., (2014). Bioelectrochemical methane production from $CO_2$. PhD Thesis, Wageningen University, online: http://library.wur.nl/WebQuery/clc/2066178

1872. van Eerten-Jansen, M. C. A. A., Heijne, A. T., Buisman, C. J. N., and Hamelers, H. V. M., (2012). Microbial electrolysis cells for production of methane from $CO_2$: long-term performance and perspectives. Int. J. Energy Res., 36: 809-819

1873. van Eerten-Jansen, M. C. A. A., Jansen, N. C., Plugge, C. M., de Wilde, V., Buisman, C. J. N., and Heijne, A. T., (2015). Analysis of the mechanisms of bioelectrochemical methane production by mixed cultures. J. Chem. Technol. Biotechnol., 90(5): 963-970

1874. van Eerten-Jansen, M. C. A. A., Veldhoen, A. B., Plugge, C. M., Stams, A. J. M., Buisman, C. J. N., and Heijne, A. T., (2013). Microbial community analysis of a methane-producing biocathode in a bioelectrochemical system. Archea, article ID: 481784, http://dx.doi.org/10.1155/2013/481784

1875. van Ravensway, J. P., Roos, T. H., Surridge-Talbot, A. K. J., Xosa, S., and Sattler, C., (2015). Development of a solar fuels roadmap for South Africa. Energy Procedia, 69: 1838-1848

1876. van Engelenburg, B., (2012). The development of a $CO_2$—hub. Slide deck presentation, Taiwan, 27 Nov. 2012. Online: http://www.2012ccsu.org.tw/DownloadFIle.aspx?F=%2Fdoc%2Fbrief%2F1127_morning%2F5.Joris+Koornneef+Rotterdam+$CO_2$+hub.pdf 1877. van Roosmalen, M. J. E., (2003). Dry-cleaning with high-pressure carbon dioxide. PhD Thesis, Technical University of Delft, online: http://repository.tudelft.nl/view/ir/uuid%3 Acfded0ca-6141-4c5e-ac8b-4c4c70328ba2/

1878. van Roosmalen, M. J. E., van Diggelen, M., Woerlee, G. F., and Witkamp, G.-J., (2003a). Dry-cleaning with high-pressure carbon dioxide—the influence of process conditions and various co-solvents (alcohols) on cleaning-results. J. Supercrit. Fluids, 27(1): 97-108.

1879. van Roosmalen, M. J. E., Woerlee, G., and Witkamp, G.-J., (2003b). Dry-cleaning with high-pressure carbon dioxide—the influence of process conditions and various co-solvents (alcohols) on cleaning-results. J. Supercrit. Fluids, 27(3): 337-344.

1880. van Tongeren, G. J., (2011). Rotterdam Climate Initiative: 50% $CO_2$ reduction; 100% climate proof. RCI slide deck presentation online: http://www.tbm.tudelft.nl/fileadmin/Faculteit/TBM/Over_de_Faculteit/Afdelingen/Afdeling_Infrastructure_Systems_and_Services/Sectie_Economie_van_Infrastructuren/Conferences/Annual_Conference/2011/presentations_27_mei/Ger_van_Tongeren-DELTALINQS.pdf 1881. van Walsum and Shi, H., (2004). Carbonic acid enhancement of hydrolysis in aqueous pretreatment of corn stover. Bioresource Technol., 93: 217-226.

1882. van Walsum, P., Garcia-Gil, M., Chen, S.-F., and Chambliss, K., (2007). Effect of dissolved carbon dioxide on accumulation of organic acids in liquid hot water pretreated biomass hydrolyzates. Appl. Biochem. Biotechnol., 137-140(1-12): 301-311.

1883. van Zyl, P. G., (2007). Recovery of gold from spent matrices using supercritical carbon dioxide. PhD Thesis, North-West University, South Africa, online: http://dspace.nwu.ac.za/bitstream/handle/10394/1487/van-zyl_pietergideon.pdf?sequence=1

1884. Vandeperre, L. J., and Al-Tabbaa, A., (2007). Accelerated carbonation of reactive MgO cements. Adv. Cement Res., 19(2): 67-79.

1885. Vanderveen, J. R., Durelle, J., and Jessop, P. G., (2014). Design and evaluation of switchable-hydrophilicity solvents. Green Chem., 16: 1187-1197

1886. Varelius, E. P., (2014). Optimizing the reaction efficiency of carbon dioxide in a sugar refinery carbonation process. Online: http://www.chemeng.lth.se/exjobb/E712.pdf 1887. Vaselli, A., Tedesco, D., Cuoco, E., and Tassi, F., (2015). Are limnic eruptions in the $CO_2$—$CH_4$-rich gas reservoir of Lake Kivu (Democratic Republic of the Congo and Rwanda) possible? Insights from physicochemical and isotopic data. Chapter 22, p. 489-505, in: D. Rouwet et al., (eds.), *Volcanic Lakes*, Advances in Volcanology, Springer-Verlag.

1888. Velosys website (www.velocys.com); brochure: http://www.velocys.com/resources/Velocys_Booklet.pdf; and slide deck presentations: http://www.velocys.com/press/ppt/ppt141028_Gasification_Technologies_Council.pdf;

http://www.velocys.com/press/ppt/ppt140730_Velocys_GTL%20Technology%20Forum.pdf; http://www.velocys.com/press/ppt/ppt141029_CIS_GasChem.pdf 1889. Venkataraman, G. S., (1981). *Blue-Green Algae for Rice Production: A Manual for its Promotion*, FAO Soils Bulletin No. 46, online: http://www.fao.org/3/a-ar124e.pdf 1890. Verbeke, J., (1957). Recherches ecologiques sur la faune des grandes lacs de l'est du Congo Belge. Exploration Hydrobiologiques des lacs Kivu, Edouard et Albert (1952-54) 3(1). Bussels: Institute Royale des Sciences Naturelles Belgique.

1891. Vilcaez, J., (2015). Numerical modeling and simulation of microbial methanogenesis in geological $CO_2$ storage sites. J. Petroleum Eng., 135: 583-595

1892. Viswanathan, B., (2011/2014). Carbon dioxide to fuels and chemicals. Course materials. National Center for Catalysis Research (India), online: https://nccr.iitm.ac.in/Course%20Material1.pdf; http://www.slideshare.net/HariprasadNarayanan/co2-to-fuels-and-chemicals-course-material-final-version 1893. Volsky, U., (2012). Preparing Russia to meet IPCC 2050 based on dynamic MFA approach for greenhouse gas emissions. MSc Thesis NTNU, Trondheim, Norway, online: http://www.diva-portal.org/smash/get/diva2:566510/FULLTEXT01.pdf 1894. Voormeij, D. A., and Simandi, G. J., (2004). Geological, ocean, and mineral $CO_2$ sequestration options: a technical review. Geoscience Canada, 31(1): 11-22

1895. Wadhwa, V., (2013). Silicon valley can't be copied. MIT Technology Review. Jul. 3, 2013. Online: http://www.technologyreview.com/news/516506/silicon-valley-cant-be-copied/

1896. Wagner, N. S., (1959). Natural sources of carbon dioxide in Oregon. The ORE.-BIN, 21(11): 103-114

1897. Wall, G., Yantovskii, E. I., Lindquist, L., and Tryggstad, J., (1995). A zero emission combustion power plant for enhanced oil recovery. Energy, 20(8): 823-838.

1898. Wallace, M., and Kuuskraa, V., (2014). Near-term projections of $CO_2$ utilization for enhanced oil recovery. Report DOE/NETL-2014/1648, pp. 23. Online: http://www.netl.doe.gov/File%20Library/Research/Energy%20Analysis/Publications/Near-Term-Projections-C2-EOR_april_10_2014.pdf 1899. Walling, S. A., and Provis, J. L., (2015). A discussion of the papers "*Impact of hydrated magnesium carbonate additives on the carbonation of reactive MgO cements*" and "*Enhancing the carbonation of MgO cement porous blocks through improved curing conditions*", by C. Unluer & A. al-Tabbaa. Cement and Concrete Res., in press.

1900. Walsh, J. J., Neri, G., Smith, C. L., and Cowan, A. J., (2014). Electrocatalytic $CO_2$ reduction with a membrane supported manganese catalyst in aqueous solution. Chem. Comm., 50: 12698-12701.

1901. Walter, M. G., Warren, E. L., McKone, J. R., Boettcher, S. W., Mi, Q., Santori, E. A., and Lewis, N. S., (2010). Solar water splitting cells. Chem. Rev., 110: 6446-6473.

1902. Wang, C., Yue, H., Li, C., Liang, B., Zhu, J., and Xie, H., (2014). Mineralization of $CO_2$ using natural K-feldspar and industrial solid waste to produce soluble potassium. Ind. Eng. Chem. Res., 53(19): 7971-7978.

1903. Wang, H., and Ren, Z. J., (2013). A comprehensive review on microbial electrochemical systems as a platform technology. Biotechnol. Adv., 31: 1796-1807

1904. Wang, J., Wang, C., Chen, N., Xiong, Z., Wolfe, D., and Zou, J., (2015). Response of rice production to elevated [$CO_2$] and its interaction with rising temperature or nitrogen supply: a meta-analysis. Climatic Change, 130: 529-543.

1905. Wang, J., Xi, J., and Wang, Y., (2015). Recent advances in the catalytic production of glucose from lignocellulosic biomass. Green Chem., 17: 737-751.

1906. Wang, L., Yao, G., Jing, Z., and Jin, F., (2015). Hydrothermal conversion of $CO_2$ into formic acid with zinc and copper powders under low temperature. Adv. Mats. Res., 1073-6: 39-42.

1907. Wang, L., Yao, G., Chen, F., Jing, Z., and Jin, F., (2015). Ni-enhanced autocatalytic water splitting for the conversion of $CO_2$ to formic acid with Zn. Preprint.

1908. Wang, R., Liu, J., Liu, P., Bi, X., Wang, W., Meng, Y., Ge, X., Chen, M., and Ding, Y., (2014). Ultra-thin layer structured anodes for highly durable low-Pt direct formic acid fuel cells. Nano Res., 7(11): 1569-1580.

1909. Wang, R., Peng, B., and Huang, K., (2015). The research progress of $CO_2$ sequestration by algal biofertilization in China. J. $CO_2$ Utilization, 11: 67-70

1910. Wang, W.-H., Himeda, Y., Muckerman, J. T., Manbeck, G. F., and Fujita, E., (2015). $CO_2$ hydrogenation to formate and methanol as an alternative to photo- and electrochemical $CO_2$ reduction. Chem. Rev., DOI: 10.1021/acs.chemrev.5b00197

1911. Wang, W.-N., Soulis, J., Yang, Y. J., and Biswas, P., (2014). Comparison of $CO_2$ photoreduction systems: a review. Aerosol and Air Quality Research, 14: 533-549.

1912. Wang, W., Tan, K., Xie, E., Liu, J., and Cai, G., (2013). Supercritical $CO_2$ fluid leaching of uranium from sandstone type ores. Adv. Mats. Res, v. 643-648: 3517-3521.

1913. Wang, W., Wang, S., Ma, X., and Gong, J., (2011). Recent advances in catalytic hydrogenation of carbon dioxide. Chem. Soc. Rev., 40: 3703-3727.

1914. Wang, X., Qin, Y., and Wang, F., (2011). Carbon dioxide as a raw material for biodegradable plastics. Bull. Chine Acad. Sci., 25(1): 54-55. Online: http://english.cas.cn/bcas/2011_1/201411/P020141121534311533418.pdf 1915. Wank, L. K., Wu, J. S., Shammas, N. K., and Vaccari, D. A., (2004). Recarbonation and softening. Chapter 6, pp. 199-228, in: L. K. Wang et al., (eds.), *Physicochemical Treatment Processes*, Vol. 3, *Handbook of Environmental Engineering*. Humana Press 1916. WarmCO$_2$, (undated). WarmCO$_2$ (Green Security) Online: http://www.locareproject.eu/dwn 144441

1917. Wasch, L. J., (2014). Geothermal energy—scaling potential with cooling and $CO_2$ degassing. TNO Report, T N O 2013 R11661, online: http://geothermie.nl/fileadmin/user_upload/documents/bestanden/NOPG/TNO_rapport_R11661_TC_Geothermie_Geochemistry_Wasch.pdf 1918. Watkins, J. D., and Bocarsly, A. B., (2014). The direct reduction of carbon dioxide to formate in high gas capacity ionic liquids at post transition metal electrodes. ChemSusChem, 7(1): 284-290.

1919. Wauthier, C., Cayol, V., Kervyn, F., and d'Oreye, N., (2012). Magma sources involved in the 2002 Nyiragongo eruption, as inferred from an InSAR analysis. J. Geophys. Res., Solid Earth 119, B05411 DOI: 10.1029/2011JB008257.

1920. Wauthier, C., Smets, B., and Keir, D., (2015). Diking-induced moderate-magnitude earthquakes on a youthful rift border faulty: the 2002 Nyiragongo-Kahele sequence, D. R. Congo. Geochemistry, Geophysics, Geosystems, 16, DOI: 10.1002/2015GC006110

1921. Wei, N., Li, X., Dahowski, R. T., and Davidson, C. L., (2015). Economic evaluation on $CO_2$-EOR of onshore oil fields in China. Int. J. Greenhouse Gas Control, 37: 170-181.

1922. Weim M., Musie, G. T., Busch, D. H., and Subramanian, B., (2002). $CO_2$-expanded solvents: unique and versatile media for performing homogeneous catalytic oxidations. J. Am. Chem. Soc., 124(11): 2513-2517

1923. Weissman, J. C., and Goebel, R. P., (1987). Design and analysis of microalgal open pond systems for the purpose of producing fuel. SERISTR-231-2840/ DE87001164, Solar Energy Research Institute report, online: http://www.nrel.gov/docs/legosti/old/2840.pdf 1924. Weizmann Magazine (2015). Chaim Weizmann's acetone patent turns 100: a centennial of entrepreneurship. Fall 2015 edition, special section, online: http://www.weizmann.org.uk/pdfs/Acetone%20article.pdf 1925. Wejnerowska, G., Heinrich, P., and Gaca, J., (2013). Separation of squalene and oil from *Amaranthus* seeds by supercritical carbon dioxide. Separ. Purif. Tech., 110: 39-43.

1926. Wen, Y., Zhang, R., Cang, Y., Zhang, J., Liu, L., Guo, X., and Fan, B., (2015). Direct synthesis of dimethyl carbonate and propylene glycol using potassium bicarbonate as catalyst in supercritical $CO_2$. Polish J. Chem. Tech., 17: 62-65.

1927. Wender, N., (1901). Die Kohlensaure Industrie: Eine Darstellung der Entwickelung und des Gegenwartigen Standes Derselben. Verlag von Max Brandt, Berlin, pp. 177

1928. Werner, B. G., and Hotchkiss, J. H., (2006). Continuous flow nonthermal $CO_2$ processing: the lethal effects of subcritical and supercritical $CO_2$ on total microbial populations and bacterial spores in raw milk. J. Dairy Sci., 89: 872-881.

1929. Wesselbaum, S., Hintermair, U., and Leitner, W., (2012). Continuous-flow hydrogenation of carbon dioxide to pure formic acid using an integrated sc$CO_2$ process with immobilized catalyst and base. Angew. Chem. Int. Ed., 51: 8585-8588.

1930. Westerman, D., Santos, R. C. D., Bosley, J. A., Rogers, J. S., and Al-Duri, B., (2006). Extraction of Amaranth seed oil by supercritical carbon dioxide. J. Supercrit. Fluids, 37(1): 38-52.

1931. Whipple, D. T., and Kenis, P. J. A., (2010). Prospects for $CO_2$ utilization via direct heterogeneous electrochemical reduction. J. Phys. Chem. Letts., 1(24): 3451-3458.

1932. Whipple, D. T., Finke, E. C., and Kenis, P. J. A., (2010). Microfluidic reactor for the electrochemical reduction of carbon dioxide: the effect of pH. Electrochem. Solid-State Letts., 13(9): B109-B111.

1933. White, J. L., et al., (2015). Light-driven heterogeneous reduction of carbon dioxide: photocatalysts and photoelectrodes. Chem. Rev., DOI: 10.1021/acs.chemrev.5b00370

1934. White, J. L., Herb, J. T., Kaczur, J. J., Majsztrik, P. W., and Bocarsly, A. B., (2014). Photons to formate: efficient electrochemical solar energy conversion via reduction of carbon dioxide. J. $CO_2$ Utilization, 7: 1-5.

1935. Whited, G. M., Feher, F. J., Benko, D. A., Cervin, M. A., Chotani, G. K., McAuliffe, J. C., LaDuca, R. J., Ben-Shoshan, E. A., and Sanford, K, J., (2010). Development of a gas-phase bioprecoess for isoprene monomer production using metabolic pathway engineering. Industrial Biotechnol., 6(3): 152-163

1936. Whittaker, S., (2015). $CO_2$ EOR and carbon storage. Slide deck presentation, Jun. 1, 2015, Kuala Lumpur, Malaysia, online: http://www.ccop.or.th/ccsm/data/23/docs/CCOP_Whittaker_EOR_June%203_Final.pdf 1937. Wikipedia entry: Eco-Industrial Park. https://en.wikipedia.org/wiki/Eco-industrial_park And, e.g: https://en.wikipedia.org/wiki/KalundborgEco-industrial_Park 1938. Wikipedia entry: Modified atmosphere. https://en.wikipedia.org/wiki/Modified_atmosphere 1939. Wikipedia entry: Natural oil polyols. https://en.wikipedia.org/wiki/Natural_oil_polyols 1940. Wikipedia entry: Power to gas. https://en.wikipedia.org/wiki/Powerto_gas 1941. Wikipedia entry: Solvay process. https://en.wikipedia.org/wiki/Solvay_process 1942. Wilkinson, J. M., (2015). Who is making money from nanomaterials and how? The value chain and business models for nanomaterials. Slide deck presentation. Technology for Industry, LTD., online: http://www.tfi-ltd.co.uk/presentations/Who%20is%20Making%20Money%20from%20Nanomaterials%20and%20How%20-%20The%20Value%20Chain%20and%20Business%20models%20for%20Nanomaterials.pdf 1943. Willauer, H. D., Hardy, D. R., Ndubizu, E. C., Williams, F. W., and Lewis, M. K., (2008). Recovery of $[CO_2]T$ from aqueous bicarbonate using a gas permeable membrane. Naval Research Laboratory, NRL/MR/6180-08-9129

1944. Willauer, H. D., Hardy, D. R., Ndubizu, E. C., Williams, F. W., and Lewis, M. K., (2009a). Recovery of $CO_2$ by phase transition from an aqueous bicarbonate system under pressure by means of multilayer gas permeable membranes. Energy and Fuels, 23(3): 1770-1774

1945. Willauer, H. D., DiMascio, F., Hardy, D. R., Lewis, M. K., and Williams, F. W., (2009b). Extraction of carbon dioxide from seawater by ion exchange resin Part II—using strong base anoin exchange resins. Naval Research Laboratory, NRL/MR/6180-09-9211

1946. Willauer, H. D., DiMascio, F., Hardy, D. R., Lewis, M. K., and Williams, F. W., (2012a). Development of an electrochemical acidification cell for the recovery of $CO_2$ and $H_2$ from seawater. Ind. Eng. Chem. Res., 50(17): 9876-9882

1947. Willauer, H. D., DiMascio, F., Hardy, D. R., Lewis, M. K., and Williams, F. W., (2012b). Development of an electrochemical acidification cell for the recovery of $CO_2$ and $H_2$ from seawater II. Evaluation of the cell by natural seawater. Ind. Eng. Chem. Res., 51(34): 11254-11260

1948. Willauer, H. D., DiMascio, F., Hardy, D. R., and Williams, F. W., (2014). Feasibility of $CO_2$ extraction from seawater and simultaneous hydrogen gas generation using a novel and robust electrolytic cation exchange module based on continuous electrodeionization technology. Ind. Eng. Chem. Res., 53(31): 12192-12200

1949. Willauer, H. D., Hardy, D. R., Lewis, M. K., Ndubizu, E. C., Williams, F. W., (2010a). Effects of pressure on the recovery of $CO_2$ by phase transition from a seawater system by means of multilayer gas permeable membranes. J. Phys. Chem. A, 114(11): 4003-4008

1950. Willauer, H. D., Hardy, D. R., Lewis, M. K., Ndubizu, E. C., Williams, F. W., (2010b). Extraction of $CO_2$ from seawater and aqueous bicarbonate systems by ion-exchange resin processes. Energy and Fuels, 24(12): 6682-6688

1951. Willauer, H. D., DiMascio, F., Hardy, D. R., Lewis, M. K., and Williams, F. W., (2011). Extraction of carbon dioxide from seawater by an electrochemical acidification cell Part II—Laboratory scaling studies. Naval Research Laboratory, NRL/MR/6180-11-9329

1952. Williams Brothers Engineering Company/USAID, (1979). Lake Kivu Methane Phase-I Investigation. USAID Report Online: http://pdf.usaid.gov/pdf_docs/pnaam060.pdf
1953. Williams, C. K., Yi, N., Unruangsri, J., and Shaw, J., (2015 preprint). Carbon dioxide capture and utilization: using dinuclear catalysts to prepare polycarbonates. Royal Society of Chemistry Faraday Discussion meeting paper.
1954. Wilson, S., (2015). Kemper carbon dioxide buyer says plan is still in place. MissippiWatchdog.org, Aug. 18, 2015, online: http://watchdog.org/233524/kemper-project-carbon-dioxide/
1955. Wilson, S., Harrison, A. L., Dipple, G. M., Power, I. M., Barker, S. L. L., Mayer, K. U., Fallon, S. J., Raudsepp, M., and, Southam, G., (2014). Offsetting of $CO_2$ emissions by air capture in mine tailings at the Mount Keith Nickel Mine, Western Australia: rates, controls and prospects for carbon neutral mining. Int. J. Greenhouse Gas Control, 25: 121-140.
1956. Wilson, W., (2001). Eco-friendly fumigant. World-Grain.com, 2/1/2001, online: http://www.world-grain.com/News/Archive/Ecofriendly%20fumigant.aspx?p=1&cck=1
1957. WITT, (undated). Modified Atmosphere Packaging (MAP) in the food industry. Online: http://public.web-il.net/tmi-barak/files/LMMappeUK.pdf
1958. Wittaker, S., Rostron, B., Gardner, C., White, D., Johnson, J., Chalaturnyk, R., and Seeburger, D., (2011). A decade of $CO_2$ injection into depleting oil fields: monitoring and research activities of the IEA GHG Weyburn-Midale $CO_2$ Monitoring and Storage Project. Energy Procedia, 4: 6069-6076.
1959. Wollmann, I., and Moller, K., (2015). Assessment of alternative phosphorus fertilizers for organic farming: sewage precipitation products. IMPROVE-P fact sheet, online: http://www.coreorganic2.org/upload/coreorganic2/document/wollmann2015-Factsheet_Sewage%20precipitation%20products.pdf
1960. Wood, H. G., (1991). Life with CO or $CO_2$ and $H_2$ as a source of carbon and energy. FASEB J., 5(2): 156-163
1961. Wood, H. G., and Ljungdahl, L. G., (1991). Autotrophic character of the acetogenic bacteria. In: L. L. Barton and J. Shivley, (eds.), Variation in Autotrophic Life, pp. 201-250. Academic Press.
1962. Woods, P., (2015). Algenol. Corporate slide deck presentation, 2015 U.S.—China Clean Coal Industry Forum, Billings, Mont., Aug. 29, 2015, online: https://www.usea.org/sites/default/files/event-/Paul%20Woods.pdf
1963. Woolfe, J. A., (1992). Sweet Potato: An Untapped Food Resource. Cambridge Univ. Press.
1964. Worden, R. M., Grethlein, A. J., Jain, M. K., and Datta, R., (1991). Production of butanol and ethanol from synthesis gas via gas fermentation. Fuel, 70: 615-619
1965. World of Chemicals, (2013). SABIC to build carbon dioxide plant in Saudi Arabia. World of Chemicals, Aug. 21, 2013, online: http://www.worldofchemicals.com/media/sabic-to-build-carbon-dioxide-plant-in-saudi-arabia/6271.html
1966. Wright, S., (2012). Mighty mite: a turbine that uses supercritical carbon dioxide can deliver great power in a small package. Mechanical Engineering, January 2012, pp. 40-43 Online: http://www.barber-nichols.com/sites/default/files/wysiwyg/images/supercritical_co2_turbines.pdf
1967. Wright, S. A., Davidson, C. L., and Scammell, W. O., (2014). Bulk energy storage using a supercritical $CO_2$ waste heat recovery power plant. Conference paper, $4^{th}$ International Symposium—Supercritical $CO_2$ Power Cycles, September 9010, Pittsburgh, Pa., USA, online: http://www.swri.org/4org/d18/sCO2/papers2014/system-Concepts/84-Wright.pdf
1968. Wright, S. A., Radel, R. F., Vernon, M. E., Rochau, G. E., and Pickard, P. S., (2010). Operation and analysis of a supercritical $CO_2$ Brayton cycle. Sandia Report SAND2010-0171. Sandia National Laboratories, pp. 101.
1969. WSGA/West Sussex Growers' Association, (undated). Combined horticultural production & energy hubs: A review. Online: http://www.chichester.gov.uk/CHttpHandler.ashx?id=18298&p=0
1970. Wu, B., Gao, Y., Jin, F., Cao, J., Du, Y., and Zhang, Y., (2009). Catalytic conversion of $NaHCO_3$ into formic acid in mild hydrothermal conditions for $CO_2$ utilization. Catalysis Today, 148: 405-410.
1971. Wu, J., Yang, X., He, Z., Mao, X., Hatton, T. A., and Jamison, T. F., (2014). Continuous flow synthesis of ketones from carbon dioxide and organolithium or Grignard reagents. Angew. Chem. Int. Ed., 53(32): 8416-8420.
1972. Wuest, A., Jarc, J., Schmid, M., (2009). Modelling the reinjection of deepwater after methane extraction in Lake Kivu. EAWAG Report (Kastanienbaum, Switzerland) (Available online on Researchgate.)
1973. Wuest, A., Jarc, L., Burgmann, H., Pasche, N. and Schmid, M., (2012). Methane Formation and Future Extraction in Lake Kivu. In: J.-P. Descy et al. (eds.), Lake Kivu: Limnology and Biochemistry of a Tropical Great Lake. Aquatic Ecology Series v. 5. Springer.
1974. Wuppertal Institute, (2015). $CO_2$ reuse NRW: evaluating gas sources, demand and utilization for $CO_2$ and $H_2$ within the North Rhine-Westphalia area with respect to gas qualities. Wuppertal Institute for Climate, Environment and Energy report, online: http://wupperinst.org/fa/redaktion/downloads/projects/$CO_2$_ReUse_summary.pdf; Management summary, online: http://wupperinst.org/fa/redaktion/downloads/projects/$CO_2$_ReUse_summary.pdf
1975. Xi, L., Mu, T., and Sun, H., (2015). Preparative purification of polyphenols from sweet potato (Ipomoea batatas L.) leaves by AB-8 macroporous resins. Food Chem., 172: 166-174.
1976. Xiao, Y., Niu, G., and Kozai, T., (2011). Development and application of photoautotrophic micropropagation plant system. Plant Cell Tiss. Organ. Cult., 105: 149-158.
1977. Xie, H., Wang, Y., Ju, Y., Liang, B., Zhu, J., Zhang, R., Xie, L., Liu, T., Zhou, X., Zeng, H., Li, C., and Lu, H., (2013). Simultaneous mineralization of $CO_2$ and recovery of soluble potassium using earth-abundant potassium feldspar. Chinese Sci. Bull., 58(1): 128-132.
1978. Xie, H., Yue, H., Zhu, J., Liang, B., Li, C., Wang, Y., Xie, L., and Zhou, X., (2015). Scientific and engineering progress in $CO_2$ mineralization using industrial waste and natural minerals. Engineering 2015, 1(1): 150-157.
1979. Xin, M., Shuang, L., and Qinzhu, G., (2015). Effectiveness of gaseous $CO_2$ fertilizer application in China's greenhouses between 1982 and 2010. J. $CO_2$ Utilization, 11: 63-68.
1980. Xing, Z., et al., (2015) Reducing $CO_2$ to dense nanoporous graphene by Mg/Zn for high power electrochemical capacitors. Nano Energy, 11: 600-610.
1981. Xu, A., Indala, S., Hervig, T. A., Pike, R. W., Knopf, F. C., Yaws, C. L., and Hopper, J. R., (2003). Identifying and developing new carbon dioxide consuming processes. AICHE Presentation, 2003 Annual Mtg. Online: http:// www.mpri.lsu.edu/identifying%20and%20developing%20new%20co2%20processes.pdf

1982. Xu, A., Indala, S., Hervig, T. A., Pike, R. W., Knopf, F. C., Yaws, C. L., and Hopper, J. R., (2005). Development and integration of new processes consuming carbon dioxide in multi-plant chemical production complexes. Clean Techn. Environ. Policy, 7: 97-115.

1983. Xu, C., Dowd, P., Li, Q., (2015). Carbon sequestration potential of the Habanero reservoir when carbon dioxide is used as the heat exchange fluid. J. Rock Mechanics and Geotechnical Eng., in press.

1984. Xu, H., Wang, K., and Holmes, D. E., (2014). Bio-electrochemical removal of carbon dioxide ($CO_2$): an innovative method for biogas upgrading. Bioresources Technol., 173: 392-398

1985. Xu, J., Thomsen, M. H., Thomsen, A. B., (2009). Pretreatment on corn stover with low concentration of formic acid. J. Microbiol. Biotechnol., 19(8): 845-850.

1986. Xu, T., Feng, G., Hou, Z., Tian, H., Shi, Y., and Lei, H., (2015). Wellbore-reservoir coupled simulation to study thermal and fluid processes in a $CO_2$-based geothermal system: identifying favorable and unfavorable conditions in comparison with water. Environ. Earth Sci., 73: 6797-6813.

1987. Yakaboylu, O., Harinck, J., Smit, K. G., and de Jong, W., (2015). Supercritical water gasification of biomass: a literature and technology overview. Energies, 8: 859-894.

1988. Yang, C.-J., and Jackson, R. B., (2012). China's growing methanol economy and its implications for energy and the environment. Energy Policy, 41: 878-884.

1989. Yang, J., Fogle, C., and Dalaeli, J., (2005). Polymers from oranges. Slide deck class presentation, online: http://www.ou.edu/class/che-design/a-design/projects-2005/Polymers%20from%20oranges-Presentation.pdf 1990. Yang, Q., (2015). Slide deck presentation, "Plant factory as an essential element in urban area development," online: http://www.fdcea.com/wp-content/uploads/2015/06/5_yang_plantfactory.pdf 1991. Yang, Q., Qin, S., Chen, J., Ni, W., and Xu, Q., (2009). Supercritical carbon dioxide-assisted loosening preparation of dry leather. J. Appl. Polym. Sci., 113: 4015-4022.

1992. Yang, Z.-Y., Moure, V. R., Dean, D. R., and Seefeldt, L. C., (2012). Carbon dioxide reduction to methane and coupling with acetylene to form propylene catalyzed by remodeled nitrogenase. PNAS, 109(48): 19644-19648.

1993. Yang, Z. Z., Song, Z.-Z., and He, L.-N., (2012). *Capture and Utilization of Carbon Dioxide with Polyethylene Glycol*. SpringerBriefs in Green Chemistry for Sustainability 1994. Yang, Z.-Z., He, L.-N., Liu, A.-H., and Li, Y.-N., (2012). Catalytic fixation of carbon dioxide into fuel and chemicals. *Kirk-Othmer Encyclopedia of Chemical Technolgy*. 1-27.

1995. Yang, Z.-Z., Zhao, Y.-N., and He, L.-N., (2011). $CO_2$ chemistry: task-specific ionic liquids for $CO_2$ capture/activation and subsequent conversion. RSC Adv., 1: 545-567

1996. Yantovski, E. I., (2008). Solar energy conversion through seaweed photosynthesis and zero emissions power generation. Surface Engineering and Applied Electrochemistry, 44(2): 138-145 (translation of a Russion text), English version online: http://link.springer.com/article/10.3103%2FS1068375508020117#/page-1

1997. Yantovski, E. I., (2009). Seaweed Ulva photosynthesis and zero emissions power generation. Penn Energy, Aug. 26, 2009, online: http://www.pennenergy.com/articles/pennenergy/2009/08/seaweed-ulva-photosynthesis-and-zero-emissions-power-generation.html 1998. Yantovski, E. I., and McGovern, J., (2006). Solar energy conversion through seaweed photosynthesis with combustion in a Zero-Emission Power Plant. Poster presentation, The $2^{nd}$ International Conference of Renewable Energy in Maritime Island Climates, 26-28 Apr. 2006, Dublin, Ireland, online: http://arrow.dit.ie/engschmecoth/3/

1999. Yantovskii, E. I., Wall, G., Lindquist, L., Tryggstad, J., and Maksutov, R. A., (1993). Oil enhancement Carbon Dioxide Oxygen Power Universal Supply (OCDOPUS project). Energy Convers. Mgmt., 34(9-11): 1219-1227

2000. Yantovsky, E., Gorski, J., and Shokotov, M., (2009). *Zero Emissions Power Cycles*. CRC Press.

2001. Yao, G., Zeng, X., Jin, Y., Zhong, H., Duo, J., and Jin, F., (2015). Hydrogen production by water splitting with Al and in-situ reduction of $CO_2$ into formic acid. Intl. J. Hydrogen Energy, 40: 14248-14289.

2002. Yao, H., Zeng, X., Cheng, M., Yun, J., Jing, Z., and Jin, F., (2012). Catalytic conversion of formic acid to methanol with Cu and Al under hydrothermal conditions. BioResources, 7(1): 972-983.

2003. Yasin, N. H. M., Maeda, T., Hu, A., Yu, C.-P., and Wood, T. K., (2015). $CO_2$ sequestration by methanogens in activated sludge for methane production. Applied Energy, 142: 426-434, online: http://www.che.psu.edu/faculty/wood/group/publications/pdf/228toshiCO2 sequestrationByMethanogensApplEnergy2015.pdf 2004. Yates, Y., (2012). Growing greener tomatoes: first US greenhouse with onsite $CO_2$ fertilization. GE Ecomagination, online: http://www.ecomagination.com/ge-powers-first-co2-capturing-greenhouse-in-us 2005. Ye, L., Yue, H., Wang, Y., Sheng, H., Yuan, B., Lv, L., Li, C., Liang, B., Zhu, J., and Xie, H., (2014). $CO_2$ mineralization of activated K-feldspar-CaCl2 slag to fix carbon and produce soluble potash salt. Ind. Eng. Chem. Res., 53(26): 10557-10565.

2006. Yeh Group, (undated). DryDye™ Fabrics—Exclusively from the Yeg Group. Online: http://www.knitting-industry.com/uploads/l090/drydye-tech-paper-wol.pdf 2007. Yeom, C., Rhim, D.-R., and Lee, J., (2014). Power generation using supercritical $CO_2$. (in Korean) KIC News, 17(1): 51-60.

2008. Yeom, J., Mozsgai, G. Z., Asthana, A., Flachsbart, B. R., Wasczczuk, P., Choban, E. R., Kenis, P. J. A., and Shannon, M. A., (2003). Microfabricated direct formic acid fuel cell. Fuel Cell Sci. Eng. & Technol., Proc., pp. 267-272 (1st International Fuel Cell Science, Engineering and Technology Conference (ASME)

2009. Yesil-Celiktas, O., Gurel, A. and Vadar-Sukan, F., (2010). Large scale cultivation of plant cell and tissue cultures in bioreactors. ISBN: 978-81-474-5, pp 54, online: http://www.trnres.com/ebook/uploads/celiktas/T_1273559071 Celiktas-book.pdf 2010. Yi, Q., Li, W., Feng, J., Xie, K., (2015). Carbon cycle in advanced coal chemical engineering. Chem. Soc. Rev., 44: 5409-5445.

2011. Yi, R., Spiesz, P., and Brouwers, H. J. H., (2014). Effect of nano-silica on the hydration and microstructure development of ultra-high performance concrete (UHPC) with a low binder amount. Construction and Building Mats., 65: 140-150

2012. Yildiz-Ozturk, E., Nalbantsoy, A., Tag, O., and Yesil-Celiktas, O., (2015). A comparative study on extraction processes of *Stevia rebaudiana* leaves with emphasis on antioxidant, cytotoxic and nitric oxide inhibition activities. Ind. Crops Prods., 77: 961-971.
2013. Yimsiri, P., Fiori, L., Sonwai, S., and Guella, G., (2011). Supercritical carbon dioxide extraction of mango butter for cocoa butter replacement. $13^{th}$ Int. Mtg. Supercrit. Fluids conf paper, online: http://www.isasf.net/fileadmin/files/Docs/DenHaag/HtmlDir/Papers/P65.pdf
2014. Yin, H., Mao, X., Tang, D., Xiao, W., Xing, L., Zhu, H., Wang, D., and Sadoway, D. R., (2013). Capture and electrochemical conversion of $CO_2$ to value-added carbon and oxygen by molten salt electrolysis. Energy Environ. Sci., 6: 1538-1545.
2015. Yoda, S. K., Marques, M. O. M., Petenate, A. J., and Meireles, M. A. A., (2003). Supercritical fluid extraction from *Stevia rebaudiana* Bertoni using $CO_2$ and $CO_2+$ water: extraction kinetics and identification of extracted components. J. Food Eng., 57: 125-134.
2016. Yong, J. W. H., Lim, E. Y. C., and Hew, C. S., (1999). Can we use elevated carbon dioxide to increase productivity in the orchid industry? Malayan Orchid Rev., 36: 75-81. Online: http://senseair.se/wp-content/uploads/2011/05/5.pdf
2017. Yoo, J. S., Christensen, R., Vegge, T., Norskov, J. K., and Studt, F., (2015). Theoretical insight into the trends that guide the electrochemical reduction of carbon dioxide to formic acid. ChemSusChem, 10.1002/cssc.201501197
2018. York, J., (2014). From safer chemical design to reduced environmental hazard. York University Center for Green Chemistry slide deck presentation, online: http://www.empa.ch/plugin/template/empa/*/152115
2019. York, A. P. E., Xiao, T-c., and Green, M. L. H., (2007). Methane oxyreforming for synthesis gas production. Catalysis Revs., 49: 511-560
2020. Yoshimoto, M., Kurata, R., Okuno, S., Ishiguro, K., Yamakawa, O., Tsubata, M., Mori, S., and Takagaki, K., (2005). Nutritional value and physiological functions of sweetpotato leaves. Acta Hortic., 703: 107-115.
2021. Young, L. J., (2015). Supercritical carbon dioxide can make electric turbines greener. IEEE Spectrum, Aug. 25, 2015, online: http://spectrum.ieee.org/energywise/energy/the-smarter-grid/supercritical-carbon-dioxide-can-make-electric-turbines-greener
2022. Yousefi, E., (undated). Rekordmaterialet upsalite. SP Process Development, slide deck presentation, online: http://www.spdagen.se/wp-content/themes/stella/assets/pdf/day4/Esmail%20Yousefi,%20SP.pdf
2023. Youssef, N., Elshahed, M. S., and McInerney, M. J., (2009). Microbial processes in oil fields: culprits, problems and opportunities. Chapter 6, pp. 141-251, in: *Advances in Applied Microbiology*, v. 66, Elsevier.
2024. Yuk, H.-G., Geveke, D. J., and Zhang, H. Q., (2010). Efficacy of supercritical carbon dioxide for nonthermal inactivation of *Escherichia coli* K12 in apple cider. Int. J., food Microbiol., 138: 91-99.
2025. Yunus, M. A. C., (2015). Optimisation of squalene from palm oil mesocarp using supercritical carbon dioxide. ASCC $10^{th}$ Asian Control Conf, DIO: 10.1109/ASCC.2015.7244910.
2026. Yver, A. L., Bonnaillie, L. M., Yee, W., McAloon, A., Tomasula, P. M., (2012). Fractionation of whey protein isolate with supercritical carbon dioxide—process modeling and cost estimation. Int. J. Mol. Sci., 13: 240-259.
2027. Zaidul, I. S. M., Norulani, N. A. N., Omar, A. K. M., Sato, Y., and Smith, R. L. Jr., (2007). Separation of palm kernel oil from palm kernel with supercritical carbon dioxide using pressure swing technique. J. Food Engin., 81: 419-428.
2028. Zakkour, (2013). Can industrial $CO_2$ use contribute to climate change mitigation? Carbon Capture Journal, November-December, 2013, pp. 8-11, online: http://rethink.fa.ulisboa.pt/images/repository/carboncapturejournal/pdfs/Carbon_Capture_Journal_36.pdf
2029. Zaybak, Z., Pisciotta, J. M., Tokash, J. C., and Logan, B. E., (2013). Enhanced start-up of anaerobic facultatively autotrophic biocathodes in bioelectrochemical systems. J. Biotechnol., 168: 478-485
2030. Zeebe, R. E., and Wolf-Gladrow, D., (2001). *$CO_2$ in Seawater: Equilibrium, Kinetics, Isotopes*. Elsevier, pp. 360
2031. Zeldes, B. M., Keller, M. W., Loder, A. J., Straub, C. T., Adams, M. W. W., and Kelly, R. M., (2015). Extremely thermophilic microorganisms as metabolic engineering platforms for production of fuels and industrial chemicals. Frontier in Microbiol., 6, Article 1209, DOI: 10.3389/fmicb.2015.01209
2032. Zeller, M. A., Hunt, R., Jones, A., and Sharma, S., (2014). Bioplastics and their thermoplastic blends from *Spirulina* and *Chlorella* microalgae. J. Appl. Polymer Sci., 130(5): 3263-3275.
2033. Zeng, X., Hatakeyama, M., Ogata, K., Liu, J., Wang, Y., Gao, Q., Fuji, K., Fujihara, M., Jin, F., Nakamura, S., (2014). New insights into highly efficient reduction of $CO_2$ to formic acid by using zinc under mild hydrothermal conditions: a joint experimental and theoretical study. Phys. Chem. Chem. Phys., 16: 19836-19840.
2034. Zeng, X., Jin, F., Yao, H.-S., and Cheng, M., (2011). Study of catalytic reduction of formic acid to methanol under mild hydrothermal conditions. Adv. Mats. Res., v 347-353: pp. 3677-3680
2035. ZEP, (2007). Strategic overview. European Technology Platform for Zero Emission Fossil Fuel Power Plants (ZEP). Online report: http://www.zero-emissionplatform.eu/website/docs/ETP%20ZEP/ZEP%20Concepts%20Final%20V2.pdf
2036. ZEP, (2006). A vision for Zero Emission Fossil Fuel Power Plants. European Commission report EUR 22043, online: https://ec.europa.eu/research/energy/pdf/zero_emission_ffpp_en.pdf
2037. $ZeroCO_2$, (undated). Century Plant. $ZeroCO_2$ fact sheet, online: www.zeroco2.no/projects/century-plant
2038. Zhai, Y.-c., Mu, W.-n., Liu, Y., and Xu, Q., (2010). A green process for recovering nickel from nickeliferous laterite ores. Trans, Nonferrous Met. Soc. China, 20: s65-s70.
2039. Zhang, P., de la Torre, T. Z. G., Forsgren, J., Bergstrom, C. A. S., and Stromme, M., (2016). Diffusion-controlled drug release from mesoporous magnesium carbonate Upsalite®. J. Pharmaceutical Sci., 105: 657-663
2040. Zhang, Q. (2002). Devulcanization of recycled tire rubber using supercritical carbon dioxide. PhD Thesis, University of Waterloo, pp. 338.
2041. Zhang, Q., He, D., and Zhu, Q., (2003). Recent progress in direct partial oxidation of methane to methanol. J. Natural Gas Chem., 12: 81-89.
2042. Zhang, Q., Heuberger, C. F., Grossmann, I. E., Sundarmoorthy, A., and Pinto, J. M., (2015b). Air separation with cryogenic energy storage: optimal scheduling considering electric energy and reserve markets. AIChE J., 61(5): 1547-1558.
2043. Zhang, Q., Heuberger, C. F., Grossmann, I. E., Sundarmoorthy, A., and Pinto, J. M., (2015). Optimal scheduling of air separation with cryogenic energy stor- 2044. Zhang, Q., and Tzoganakis, C., (2004). Devulcanization of recycled tire rubber using supercritical carbon dioxide. Conference paper online: http://sperecycling.org/sites/sperecycling.org/files/gpec/GPEC2004/papers/049.pdf 2045. Zhang, R., Lv, W., and Lei, L., (2015). Role of the oxide layer on Sn electrode in electrochemical reduction of $CO_2$ to formate. Appl. Surf. Sci., 356: 24-29.

2046. Zhang, S., Jin, F., Zeng, X., Hu, J., Huo, Z., Wang, Y., Watanabe, N., Hirano, N., and Tsuchiya, N., (2011). Effects of general zero-valent metals powder of Co/W/Ni/Fe on hydrogen production with $H_2S$ as a reductant under hydrothermal conditions. Int. J. Hydrogen Energy, 36: 8878-8884.

2047. Zhang, S., Kang, P., and Meyer, T. J., (2014). Nanostructured tin catalysts for selective electrochemical reduction of carbon dioxide to formate. J. Am. Chem. Soc., 136(5): 1734-1737.

2048. Zhang, S., Kang, P., Ubnoske, S., Brenneman, M. K., Song, N., House, R. L., Glass, J. T., ad Meyer, T. J., (2014). Polyethylenimine-enhanced electrocatalytic reduction of $CO_2$ to formate at nitrogen-doped carbon nanomaterials. J. Am. Chem. Soc., 136: 7845-7848.

2049. Zhang, W., and Cheng, C. Y., (2011). A literature review of titanium metallurgical processes. Hydrometallurgy, 108: 177-188.

2050. Zhang, X., Scholz, C. A., Hecky, R. E., Wood, D. A., Zal, H. J., and Ebinger, C. J., (2014). Climatic control of the late Quaternary turbidite sedimentology of Lake Kivu, East Africa: implications for deep mixing and geologic hazards. Geology, 42(9): 811-814

2051. Zhang Y., (1996) Dynamics of $CO_2$-driven lake eruptions. Nature, 379:57-59

2052. Zhang, Y.-H. P., (2010). Artificial photosynthesis would unify the electro-carbohydrate-hydrogen cycle for sustainability. Nature Proceeedings, online: http://precedings.nature.com/documents/4167/version/1

2053. Zhang, Y.-H. P., (2011). Simpler is better: high-yield and potential low-cost biofuels production through cell-free synthetic pathway biotransformation (SyPaB). ACS Catalysis, 1: 998-1009.

2054. Zhang, Y.-H. P., (2013). Next generation biorefineries will solve the food, biofuels, and next environmental trilemma in the energy-food-water nexus. Energy Sci. & Eng., 1(1): 27-41.

2055. Zhang, Y.-H., P., and Huang, W-D., (2012). Constructing the electricity-carbonate-hydrogen cycle for a sustainability revolution. Trends in Biotechnol., 30(6): 301-306, 2056. Zhang, Y.-H. P., You, C., and Feng, R., (2012). Surpassing photosynthesis: high-efficiency and scalable $CO_2$ utilization through artificial photosynthesis. Chapter 15, pp. 275-292, in: M. Attalla, (ed.), *Recent Advances in Post-Combustion $CO_2$ Capture Chemistry*. ACS Symp. Ser., v. 1097

2057. Zhang Y., and Kling G W (2006) Dynamics of lake eruptions and possible ocean eruptions. Ann. Rev. Earth Planet Sci 34: 32-293.

2058. Zhang, Y., Macintosh, A. D., Wong, J. L., Bielinski, E. A., Williard, P. G., Mercado, B. Q., Hazari, N., and Bernskoetter, W. H., (2015). Iron catalyzed $CO_2$ hydrogenation to formate by Lewis acid co-catalysts. Chem. Sci., 6: 4291-4299.

2059. Zhang, Y., Yin, C., Zhang, Y., and Wu, H., (2013). Synthesis and characterization of cellulose carbamate from wood pulp, assisted by supercritical carbon dioxide. BioResources, 8(1): 1398-1408

2060. Zhang, Y., Zhang, S., and Benson, T., (2015). A conceptual design by integrating dimethyl ether (DME) production with tri-reforming process for $CO_2$ emission reduction. Fuel Processing Technol., 131: 7-13.

2061. Zhao, M., Munnett, A. I., and Harris, A. T., (2013). A review of techno-economic models for the retrofitting of conventional pulverized-coal power plants for post-combustion capture (PCC) of $CO_2$. Energy & Environ. Sci., 6: 25-40.

2062. Zhao, Q., and Frear, C., (2013). Nitrogen and phosphorus recovery from anaerobic digested dairy wastewater. Washington State University slide deck presentation, Aug. 1, 2013, online: https://btc.instructure.com/courses/873594/files/28343587/download 2063. Zhao, S., and Zhang, D., (2014). Supercritical $CO_2$ extraction of *Eucalyptus* leaves oil and comparison with Soxhlet extraction and hydrodistillation methods. Separation Purif. Technol., 133: 443-451.

2064. Zheng, L., Xuehua, C., Mingshu, T., (1991). Hydration and setting time of MgO-type expansive cement. Cement and Concrete Res., 22: 1-5.

2065. Zheng, Y., Lin, H.-M., and Wen, J., (1995). Supercritical carbon dioxide explosion as a pretreatment for cellulose hydrolysis. Biotech. Lett., 17(8): 845-850.

2066. Zheng, Y., Lin, H.-M., and Tsao, G. T., (1998). Pretreatment for cellulose hydrolysis by carbon dioxide explosion. Biotechnol. Prog., 14(6): 890-896.

2067. Zhong, H., Gao, Y., Yao, G., Zeng, X., Li, Q., Huo, Z., and Jin, F., (2015). Highly efficient water splitting and carbon dioxide reduction into formic acid with iron and copper powder. Chem. Eng. J., 280: 215-221.

2068. Zhou, B., (2007). Nano-enabled catalysts for the commercially viable production of $H_2O_2$. Headwaters Technology Innovation, LLC, slide deck presentation, Sep. 26, 2007, online: http://www.epa.gov/oppt/nano/p2docs/casestudy1_zhou.pdf 2069. Zhou, B., (2008). Clean hydrogen peroxide synthesis via a nanocatalyst process. Clean Technology 2008 Conference, proceedings paper, online: www.ct-si.org/publications/proceedings/pdf/2008/70311.pdf 2070. Zhou, L., Bi, Z., Xu, Z., Yang, Y., and Liao, X., (2015). Effects of high-pressure $CO_2$ processing on flavor, texture, and color of foods. Critical Revs. Food Sci. & Nutrition, 55(6): 750-768.

2071. Zhu, Y., Philips, M., Kaczur, J., and Rice, A., (2013). Commercialization of green chemical and fuel technologies: Liquid Light. Aspentech slide deck presentation, Apr. 10, 2013, online: https://www.researchgate.net/publication/283513352_Commercialization_of_Green_Chemical_and_Fuel_Technologies 2072. Zhuang, J., and Li, X., (2012). Hydrolysis of bamboo fiber for production of fermentable sugars in saturated formic acid. Adv. Materials Res., 535-7: 2442-2445.

2073. Zolotov, M. Y., (2014). Formation of brucite and cronstedtite-bearing mineral assemblages on Ceres. Icarus, 228: 13-26

2074. Zosel, K., (1978). Separation with supercritical gases: practical applications. Angw. Chem. Int. Ed. Engl., 17: 702-709. (And associated patent: U.S. Pat. No. 4,260,639, "Process for the decaffeination of coffee.")

2075. Zuo, L., and Benson, S. M., (2013). Exsolution enhanced oil recovery with concurrent $CO_2$ sequestration. Energy Procedia, 37: 6957-6963

What is claimed is:

1. A method for obtaining and utilizing carbon dioxide gas from a body of water containing dissolved carbon dioxide gas and methane gas, said method comprising the steps of:
   (a) extracting water from at least one extraction depth of the body of water to obtain extracted water;
   (b) degassing the extracted water in at least one stage of degassing so as to provide degassed water and extracted gases comprising carbon dioxide gas and methane gas in at least one flow;
   (c) combusting the extracted gases with oxygen to provide an exhaust gas comprising carbon dioxide and water; and
   (d) feeding to a utilization hub the carbon dioxide gas, which is solely from the exhaust gas provided in step (c), wherein the utilization hub is configured to collect the carbon dioxide gas for storage, distribution, processing and/or utilization.

2. The method of claim 1, further comprising utilizing the carbon dioxide collected by the utilization hub to perform at least one process selected from the group consisting of fertilizing growth of plants, fertilizing a biozone of Lake Kivu, lowering a pH of water returned into Lake Kivu, adjusting a pH of water exiting from a vacuum degassing system, adjusting a pH of water fed to an algal growth sector, cultivating algae, supplying a cryogenic energy storage reservoir, heating or cooling a supercritical $CO_2$ power cycle heat engine power generator, delivering pressurized carbon dioxide by pipeline, delivering pressurized carbon dioxide by tanks including by pressurized tank trucks, producing dry ice, storing, producing and distributing refrigerated liquefied and/or solidified carbon dioxide, producing a magnesium-based cement or concrete, producing urea, producing formic acid, producing oxalic acid, producing acetic acid, producing a solvent, producing carbon monoxide, producing a pyrethrum pesticide, producing an asphyxiant, producing a food packaging gas, pasteurizing milk, beer or an agricultural juice, processing an agricultural, food, forest, textile, waste or biofuel product, cleaning a textile, treating leather, extracting geothermal energy, producing a fuel, producing a syngas, producing a chemical via a formate and/or by an oxalic acid platform, producing a chemical by gas fermentation based on a microbial Wood Ljundahl pathway, producing a chemical by a synthetic pathway including carbon dioxide as a reactant, producing a plastic including carbon dioxide as an ingredient, producing carbonic acid, producing a carbonated and/or $CO_2$ pressurized beverage, producing sodium bicarbonate, producing a fracking fluid, producing silicic acid, producing microsilica, producing iron, producing nickel, processing an ore to produce a plant and/or aquatic fertilizer, processing an ore by solution extraction of one or more metals using supercritical carbon dioxide optionally injected into an ore zone, producing an elemental carbon product, producing oxygen gas, and injecting carbon dioxide via drillholes into subterranean strata for geostorage.

3. The method of claim 1, further comprising generation of electrical power.

4. The method of claim 3, further comprising:
   supplying the electrical power to a compression and refrigeration system;
   cooling with the compression and refrigeration system at least one gas to form at least one liquefied gas, wherein the at least one gas is at least one of oxygen, nitrogen, carbon dioxide that has been extracted from the extracted water, carbon dioxide that has been formed in a combustion of associated methane and methane that has been degassed from the extracted water;
   storing the at least one liquefied gas in at least one insulated storage tank;
   releasing from the at least one insulated storage tank a liquid flow of the at least one liquefied gas;
   optionally increasing a pressure of the liquid flow of the at least one liquefied gas;
   heating the liquid flow to form a subcritical gas flow or a supercritical fluid flow, wherein at least a portion of the heating is optionally conducted by heat exchange with a closed system heat engine;
   driving a turbine with a subcritical gas flow or with a supercritical fluid flow to generate electricity; and
   optionally driving a turbine within a closed system heat engine to generate electricity.

5. The method of claim 3, further comprising
   supplying the electrical power to a compression and refrigeration system;
   cooling with the compression and refrigeration system at least one gas to form at least one liquefied gas, wherein the at least one gas is at least one of oxygen, nitrogen, carbon dioxide that has been extracted from the extracted water, carbon dioxide that has been formed in a combustion of associated methane and methane that has been degassed from the extracted water; and
   cooling a server with the at least one liquefied gas.

6. The method of claim 5, further comprising accessing data on the server.

7. The method of claim 1, further comprising extracting from the extracted water at least one product selected from the group consisting of ammonium, ammonia, phosphorous, magnesium and calcium.

8. The method of claim 1, wherein deep gas trapping layers of the body of water possess in their volume average a $CO_2/CH_4$ ratio greater than 4, and more than 98 wt. % of the $CH_4$ dissolved in the water is extracted by the extracting step.

9. The method of claim 8, wherein the body of water is Lake Kivu and the method reduces a risk of a limnic eruption.

10. The method of claim 1, wherein the utilization hub supplies a stream of carbon dioxide into the biozone of Lake Kivu as a carbon fertilizing source supporting photoautotrophic bioproductivity.

11. The method of claim 1, wherein the utilization hub supplies a stream of carbon dioxide which is injected into: (i) post-degassing return flow water containing nutrients that are being diffused into a biozone of Lake Kivu; (ii) de-densified high-pH post-degassing return flow water that is being injected into Lake Kivu underneath the biozone; and/or (iii) post-degassing return flow water for pH control.

12. The method of claim 1, wherein the utilization hub supplies a stream of carbon dioxide to a horticultural greenhouse.

13. The method of claim 1, wherein the utilization hub supplies a stream of carbon dioxide which is injected into algal growth biocultures.

14. The method of claim 1, wherein the utilization hub supplies a stream of carbon dioxide to a compressor to provide compressed carbon dioxide, the compressed carbon dioxide is optionally stored in a storage tank, and the compressed carbon dioxide is distributed through pipelines.

15. The method of claim 1, wherein the utilization hub supplies a stream of carbon dioxide gas to a compression and refrigeration system to provide compressed refrigerated liquid carbon dioxide and/or solid carbon dioxide, and wherein the method optionally comprises at least one of the additional steps of:

(i) storing the compressed refrigerated liquid and/or solid carbon dioxide;
(ii) further cooling the compressed refrigerated liquid carbon dioxide to provide dry ice;
(iii) storing the dry ice;
(iv) using the stored dry ice as cryogenic energy with recovery to generate power; and
(v) distributing the dry ice.

16. The method of claim 1, wherein the degassed water provided in step (b) is transported for water treatment, and the method further comprises the steps of:
(i) photosynthetic treatment of the degassed water by growth of an algal biomass to convert bicarbonate anions to carbon fixed by photosynthesis into biomass and hydroxyl anions in the degassed water, such that the pH of the degassed water is increased and bicarbonate anions are converted into carbonate anions and magnesium and calcium precipitate out of the degassed water onto algal cells to provide de-densified water and flocculated biomass precipitate;
(ii) separating the de-densified water from the flocculated biomass precipitate;
(iii) optionally additionally treating the degassed water by electrochemical methods such that the pH of the degassed water is further increased and additional magnesium and calcium precipitate out of the degassed water to provide further de-densified water and magnesium and calcium precipitate;
(iv) optionally separating the further de-densified water from magnesium and calcium precipitate;
(v) optionally adjusting the pH of the de-densified water or further de-densified water by adding thereto a volume of the carbon dioxide gas collected by the utilization hub from at least one of step (b) and step (c); and
(iv) reinjecting into Lake Kivu a return flow of the de-densified water or further de-densified water separated from the biomass and precipitate, wherein the return flow is reinjected into Lake Kivu at a reinjection depth which is shallower than the extraction depth and which is density matched with the de-densified water or further de-densified water.

17. The method of claim 1, wherein the utilization hub supplies at least one of liquefied natural gas, compressed natural gas and adsorbed natural gas.

18. The method of claim 1, wherein the degassing step is conducted in a water degassing system comprising:
an intake pipe system;
at least one bubble capture unit positioned upwards along a system of degassing pipes;
at least one degassing catalyst unit positioned further upwards along the system of degassing pipes;
a bubbly flow turbine configured to capture and recycle power from jetting foam flow at a top of the system of degassing pipes, wherein the bubbly flow turbine is also configured to function as a foam separator;
at least one vacuum degassing unit positioned at the top of the system of degassing pipes; and
a water flow turbine capturing and recycling power in a downward outflow of degassed water from the vacuum degassing unit.

19. The method of claim 18, wherein the combusting step is conducted in an oxyfuel power generation system in fluid communication with the water degassing system, and the utilization hub is a carbon dioxide utilization hub in fluid communication with the oxyfuel power generation system.

20. The method of claim 19, wherein the oxyfuel power generation system comprises a power generator and an air separation unit configured to provide oxygen for combustion.

21. The method of claim 18, wherein the reinjecting step is conducted in a return flow system which comprises:
an outflow pipe from the water degassing system;
pipe systems connecting flow to at least one water treatment system;
a return flow pipe system and horizontal diffuser to reinject a return flow of degassed water into the body of water at a reinjection depth which is shallower than an extraction depth and which is density matched with the water being reinjected into the body of water; and
flow control valve systems with emergency shut-off capabilities.

22. The method of claim 21, wherein a density of water in the degassed water is decreased and mixed with relatively low density near-surface water from the body of water into the return flow of degassed water for reinjection into the body of water.

23. The method of claim 22, wherein the method is controlled by a control system configured for physical monitoring, system-wide functional integration and emergency response safety assurance.

24. The method of claim 23, wherein the method extracts more than 98 wt. % of $CH_4$ dissolved in a body of water having a $CO_2/CH_4$ ratio greater than 4.

25. The method of claim 1, wherein the utilization hub comprises:
pipes and control valves configured for transferring exhaust gases;
pumps configured for compressing and transferring the exhaust gases into at least one of a storage tank, a gas processing tank and a heat exchange system;
at least two of a storage tank for pressurized gas, a gas dehydration system and a heat exchange system;
at least one compressor for compressing dehydrated carbon dioxide;
at least one storage tank for storing compressed dehydrated carbon dioxide;
at least one dispensing valve for dispensing compressed dehydrated carbon dioxide from at least one storage tank storing compressed dehydrated carbon dioxide;
at least one refrigeration system for compressing and refrigerating dehydrated carbon dioxide gas into liquefied refrigerated carbon dioxide;
at least one of: (i) at least one insulated tank for storing dehydrated liquefied refrigerated carbon dioxide, (ii) at least one insulated tank for storing liquefied refrigerated nitrogen, (iii) at least one insulated tank for storing liquefied refrigerated oxygen, and (iv) at least one dispensing valve for dispensing at least one cryogenic refrigerated liquids selected from the group consisting of carbon dioxide, nitrogen and oxygen;
power generation cryoenergy recovery systems utilizing at least one of the following cryoenergy storing inputs: (i) liquefied refrigerated carbon dioxide, (ii) liquified refrigerated nitrogen and (iii) liquefied refrigerated oxygen;
gas dispensing valves and pipes for transferring and dispensing at least one warmed gas emerging from cryoenergy recovery systems; and
at least one pressurizable reaction chamber configured to provide a mixture of carbon dioxide and water vapor under controlled and time-varying conditions of pressure, mixing ratio, temperature and time and admitting product producing forms containing at least one of the following carbon dioxide and water vapor absorbing substances: magnesium hydroxide, calcium carbonate, hydrated magnesium carbonates, concrete-forming aggregate, pozzolans, steel rebar, microsilica and plant materials.

26. A method for obtaining and utilizing carbon dioxide gas from a body of water containing dissolved carbon dioxide gas and methane gas, said method comprising the steps of:
   (a) extracting water from at least one extraction depth of the body of water to obtain extracted water;
   (b) degassing the extracted water in a first stage of degassing at a first depth so as to provide degassed water and extracted gases comprising carbon dioxide gas and methane gas in at least one flow;
   (c) conveying the degassed water upward to a second stage of degassing at a second depth higher than the first depth wherein an additional amount of carbon dioxide gas is extracted from the degassed water such that the degassed water has a carbon dioxide concentration that is not more than half of an initial concentration of carbon dioxide in the extracted water;
   (d) feeding to a utilization hub the carbon dioxide gas from step (c), wherein the utilization hub is configured to collect the carbon dioxide gas for storage, distribution, processing and/or utilization; and
   (e) utilizing the carbon dioxide collected by the utilization hub to perform at least one process selected from the group consisting of fertilizing growth of plants, fertilizing a biozone of Lake Kivu, lowering a pH of water returned into Lake Kivu, adjusting a pH of water exiting from a vacuum degassing system, adjusting a pH of water fed to an algal growth sector, cultivating algae, supplying a cryogenic energy storage reservoir, heating or cooling a supercritical $CO_2$ power cycle heat engine power generator, delivering pressurized carbon dioxide by pipeline, delivering pressurized carbon dioxide by tanks including by pressurized tank trucks, producing dry ice, storing, producing and distributing refrigerated liquefied and/or solidified carbon dioxide, producing a magnesium-based cement or concrete, producing urea, producing formic acid, producing oxalic acid, producing acetic acid, producing a solvent, producing carbon monoxide, producing a pyrethrum pesticide, producing an asphyxiant, producing a food packaging gas, pasteurizing milk, beer or an agricultural juice, processing an agricultural, food, forest, textile, waste or biofuel product, cleaning a textile, treating leather, extracting geothermal energy, producing a fuel, producing a syngas, producing a chemical via a formate and/or by an oxalic acid platform, producing a chemical by gas fermentation based on a microbial Wood Ljundahl pathway, producing a chemical by a synthetic pathway including carbon dioxide as a reactant, producing a plastic including carbon dioxide as an ingredient, producing carbonic acid, producing a carbonated and/or $CO_2$ pressurized beverage, producing sodium bicarbonate, producing a fracking fluid, producing silicic acid, producing microsilica, producing iron, producing nickel, processing an ore to produce a plant and/or aquatic fertilizer, processing an ore by solution extraction of one or more metals using supercritical carbon dioxide optionally injected into an ore zone, producing an elemental carbon product, producing oxygen gas, and injecting carbon dioxide via drillholes into subterranean strata for geostorage.

* * * * *